(12) United States Patent
Nair et al.

(10) Patent No.: US 12,005,074 B2
(45) Date of Patent: *Jun. 11, 2024

(54) EXTRAHEPATIC DELIVERY

(71) Applicant: ALNYLAM PHARMACEUTICALS, INC., Cambridge, MA (US)

(72) Inventors: Jayaprakash K. Nair, Cambridge, MA (US); Martin Maier, Cambridge, MA (US); Vasant Jadhav, Cambridge, MA (US); Stuart Milstein, Cambridge, MA (US); Kirk Brown, Cambridge, MA (US); Rubina G. Parmar, Cambridge, MA (US); Kallanthottathil G. Rajeev, Cambridge, MA (US); Muthiah Manoharan, Cambridge, MA (US); Alexander V. Kel'In, Cambridge, MA (US); Muthusamy Jayaraman, Cambridge, MA (US); Klaus Charisse, Cambridge, MA (US); Adam Castoreno, Cambridge, MA (US); Christopher S. Theile, Cambridge, MA (US); Kevin Fitzgerald, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,484

(22) Filed: May 3, 2023

(65) Prior Publication Data

US 2024/0009225 A1 Jan. 11, 2024

Related U.S. Application Data

(63) Continuation of application No. 17/052,945, filed as application No. PCT/US2019/031170 on May 7, 2019.

(60) Provisional application No. 62/668,072, filed on May 7, 2018, provisional application No. 62/738,747, filed on Sep. 28, 2018, provisional application No. 62/773,082, filed on Nov. 29, 2018.

(51) Int. Cl.
| | | |
|---|---|---|
| *A61K 31/713* | (2006.01) | |
| *A61K 9/00* | (2006.01) | |
| *A61K 47/54* | (2017.01) | |
| *C12N 15/113* | (2010.01) | |

(52) U.S. Cl.
CPC .......... *A61K 31/713* (2013.01); *A61K 9/0019* (2013.01); *A61K 47/543* (2017.08); *C12N 15/1137* (2013.01); *C12N 15/1138* (2013.01); *C12N 2310/14* (2013.01); *C12N 2310/3515* (2013.01)

(58) Field of Classification Search
CPC .. A61K 31/713; A61K 9/0019; A61K 47/543; C12N 15/1137; C12N 15/1138; C12N 2310/14; C12N 2310/3515
See application file for complete search history.

(56) References Cited

U.S. PATENT DOCUMENTS

| | | |
|---|---|---|
| 4,958,013 A | 9/1990 | Letsinger |
| 5,138,045 A | 8/1992 | Cook et al. |
| 5,218,105 A | 6/1993 | Cook et al. |
| 5,256,775 A | 10/1993 | Froehler |
| 5,411,947 A | 5/1995 | Hostetler et al. |
| 5,416,203 A | 5/1995 | Letsinger |
| 5,420,330 A | 5/1995 | Brush |
| 5,459,255 A | 10/1995 | Cook et al. |
| 5,476,925 A | 12/1995 | Letsinger et al. |
| 5,543,507 A | 8/1996 | Cook et al. |
| 5,578,718 A | 11/1996 | Cook et al. |
| 5,587,471 A | 12/1996 | Cook et al. |
| 5,646,265 A | 7/1997 | McGee |
| 5,698,391 A | 12/1997 | Cook et al. |
| 5,719,271 A | 2/1998 | Cook et al. |
| 5,756,352 A | 5/1998 | Sridhar et al. |
| 5,763,208 A | 6/1998 | Bischofberger et al. |
| 5,852,182 A | 12/1998 | Cook et al. |
| 5,859,221 A | 1/1999 | Cook et al. |
| 5,872,232 A | 2/1999 | Cook et al. |
| 5,936,092 A | 8/1999 | Shen et al. |

(Continued)

FOREIGN PATENT DOCUMENTS

| | | |
|---|---|---|
| CA | 2087818 C | 7/2007 |
| CN | 101824062 A | 9/2010 |

(Continued)

OTHER PUBLICATIONS

Brown et al. Nature Biotechnology (2022) vol. 40, No. 10; pp. 1500-1508. (Year: 2022).*

(Continued)

*Primary Examiner* — J. E. Angell
(74) *Attorney, Agent, or Firm* — Jeffrey N. Townes; Cozen O'Connor

(57) ABSTRACT

One aspect of the present invention relates to a double stranded iRNA agent comprising an antisense strand which is complementary to a target gene; a sense strand which is complementary to said antisense strand; and one or more lipophilic moieties conjugated to one or more internal positions on at least one strand, optionally via a linker or carrier. Another aspect of the invention relates to a method of gene silencing, comprising administering to a cell or a subject in need thereof a therapeutically effective amount of the lipophilic moieties-conjugated double-stranded iRNAs.

28 Claims, 22 Drawing Sheets
Specification includes a Sequence Listing.

(56) References Cited

U.S. PATENT DOCUMENTS

| | | |
|---|---|---|
| 6,001,991 A | 12/1999 | Dean et al. |
| 6,013,639 A | 1/2000 | Peyman et al. |
| 6,111,085 A | 8/2000 | Cook et al. |
| 6,153,737 A | 11/2000 | Manoharan et al. |
| 6,166,239 A | 12/2000 | Manoharan |
| 6,271,358 B1 | 8/2001 | Manoharan et al. |
| 6,335,434 B1 | 1/2002 | Guzaev et al. |
| 6,335,437 B2 | 1/2002 | Manoharan |
| 6,369,209 B1 | 4/2002 | Manoharan et al. |
| 6,448,392 B1 | 9/2002 | Hostetler et al. |
| 6,528,631 B1 | 3/2003 | Cook et al. |
| 6,617,442 B1 | 9/2003 | Crooke et al. |
| 6,656,730 B1 | 12/2003 | Manoharan |
| 6,686,150 B1 | 2/2004 | Blackburn et al. |
| 6,737,236 B1 | 5/2004 | Pieken et al. |
| 6,783,931 B1 | 8/2004 | Cook et al. |
| 7,037,646 B1 | 5/2006 | Cook et al. |
| 7,101,993 B1 | 9/2006 | Cook et al. |
| 7,723,509 B2 | 5/2010 | Manoharan et al. |
| 7,741,472 B2 | 6/2010 | Heindl et al. |
| 7,745,608 B2 | 6/2010 | Manoharan et al. |
| 7,851,615 B2 | 12/2010 | Manoharan et al. |
| 8,110,674 B2 | 2/2012 | Manoharan et al. |
| 8,158,593 B2 | 4/2012 | Abbracchio et al. |
| 8,507,661 B2 | 8/2013 | Manoharan et al. |
| 8,962,580 B2 | 2/2015 | Manoharan et al. |
| 8,975,389 B2 | 3/2015 | Manoharan et al. |
| 8,981,074 B2 | 3/2015 | Kubo et al. |
| 8,993,738 B2 | 3/2015 | Prakash et al. |
| 9,290,760 B2 | 3/2016 | Rajeev et al. |
| 9,982,257 B2 | 5/2018 | Butler et al. |
| 10,087,201 B2 | 10/2018 | Aki et al. |
| 10,815,482 B2 | 10/2020 | Meena et al. |
| 11,208,430 B2 | 12/2021 | Stetsenko et al. |
| 2001/0044528 A1 | 11/2001 | Innis et al. |
| 2002/0121314 A1 | 9/2002 | Tao et al. |
| 2002/0155989 A1 | 10/2002 | Efimov et al. |
| 2003/0096979 A1 | 5/2003 | Manoharan et al. |
| 2003/0191075 A1 | 10/2003 | Cook et al. |
| 2005/0113325 A1 | 5/2005 | Gryaznov et al. |
| 2005/0233342 A1 | 10/2005 | Manoharan et al. |
| 2008/0108801 A1 | 5/2008 | Manoharan et al. |
| 2009/0203132 A1 | 8/2009 | Swayze et al. |
| 2011/0008395 A1 | 1/2011 | Torchilin et al. |
| 2011/0152352 A1 | 6/2011 | Hata et al. |
| 2012/0128761 A1 | 5/2012 | Vagle et al. |
| 2012/0142011 A1 | 6/2012 | Hahn et al. |
| 2013/0295129 A1 | 11/2013 | Irvine et al. |
| 2014/0220573 A1 | 8/2014 | Hrdlicka |
| 2014/0303236 A1 | 10/2014 | van Rooij et al. |
| 2015/0018540 A1 | 1/2015 | Prakash et al. |
| 2015/0275217 A1 | 10/2015 | Goldeck et al. |
| 2016/0376591 A1 | 12/2016 | Manoharan et al. |
| 2017/0114341 A1 | 4/2017 | Bradshaw et al. |
| 2017/0157048 A1 | 6/2017 | Radovic-Moreno et al. |
| 2017/0204408 A9 | 7/2017 | Lewis et al. |
| 2017/0304200 A1 | 10/2017 | Wilner et al. |
| 2018/0216107 A1 | 8/2018 | Frank-Kamenetsky et al. |
| 2018/0327741 A1 | 11/2018 | Daniel et al. |
| 2020/0157545 A1 | 5/2020 | Vargeese et al. |
| 2020/0384010 A1 | 12/2020 | Kugimiya et al. |
| 2021/0062195 A1 | 3/2021 | Libertine et al. |
| 2021/0130825 A1 | 5/2021 | Yokota et al. |

FOREIGN PATENT DOCUMENTS

| | | |
|---|---|---|
| CN | 105194689 A | 12/2015 |
| EP | 2857513 A1 | 4/2015 |
| EP | 3147364 A1 | 3/2017 |
| JP | 2008167739 A | 7/2008 |
| JP | 2008220366 A | 9/2008 |
| JP | 4238381 B2 | 3/2009 |
| JP | 2011-505425 | 2/2011 |
| JP | 2012/526132 A | 10/2012 |
| JP | 2013/520460 A | 6/2013 |
| JP | 2013/523650 A | 6/2013 |
| JP | 2017-534290 A | 11/2017 |
| WO | 1990010448 A2 | 9/1990 |
| WO | 1994002501 A1 | 2/1994 |
| WO | 1995006659 A1 | 3/1995 |
| WO | 1999037819 A2 | 7/1999 |
| WO | 1999057317 A1 | 11/1999 |
| WO | 1999057319 A1 | 11/1999 |
| WO | 2001006016 A2 | 1/2001 |
| WO | 2004080406 A2 | 9/2004 |
| WO | 2004094595 A2 | 11/2004 |
| WO | 2005014782 A2 | 2/2005 |
| WO | 2007031877 A2 | 3/2007 |
| WO | 2009/073809 A2 | 6/2009 |
| WO | 2009073809 A2 | 6/2009 |
| WO | 2009082606 A2 | 7/2009 |
| WO | 2009082607 A2 | 7/2009 |
| WO | 2010011895 A1 | 1/2010 |
| WO | 2010/039548 A2 | 4/2010 |
| WO | 2010101951 A1 | 9/2010 |
| WO | 2011133876 A2 | 10/2011 |
| WO | 2012030683 A2 | 3/2012 |
| WO | 2013013068 A2 | 1/2013 |
| WO | 2013033230 A1 | 3/2013 |
| WO | 2013074974 A2 | 5/2013 |
| WO | 2013/163430 A2 | 10/2013 |
| WO | 2013165816 A2 | 11/2013 |
| WO | 2013166121 A1 | 11/2013 |
| WO | 2014005596 A1 | 1/2014 |
| WO | 2014022739 A2 | 2/2014 |
| WO | 2014/089313 A1 | 6/2014 |
| WO | 2014130607 A1 | 8/2014 |
| WO | 2015006740 A2 | 1/2015 |
| WO | 2015106128 A2 | 7/2015 |
| WO | 2016028649 A1 | 2/2016 |
| WO | 2016057693 A1 | 4/2016 |
| WO | 2016/077349 A1 | 5/2016 |
| WO | 2016100716 A1 | 6/2016 |
| WO | 2017015109 A1 | 1/2017 |
| WO | 2017062862 A2 | 4/2017 |
| WO | 2017189870 A1 | 11/2017 |
| WO | 2017192679 A1 | 11/2017 |
| WO | 2018098328 A1 | 5/2018 |
| WO | 2018127462 A1 | 7/2018 |
| WO | 2018136620 A2 | 7/2018 |
| WO | 2018165541 A1 | 9/2018 |
| WO | 2018220154 A1 | 12/2018 |
| WO | 2018223056 A1 | 12/2018 |
| WO | 2019036612 A1 | 2/2019 |
| WO | 2019126651 A1 | 6/2019 |
| WO | 2019167995 A1 | 9/2019 |
| WO | 2019215333 A1 | 11/2019 |
| WO | 2019217397 A2 | 11/2019 |
| WO | 2019222479 A1 | 11/2019 |
| WO | 2019232255 A1 | 12/2019 |
| WO | 2020010366 A1 | 1/2020 |
| WO | 2020219983 A2 | 10/2020 |

OTHER PUBLICATIONS

Manoharan, M. et al., "Cholesterol Conjugated Uniform and Gapmer Phosphorothioate Oligonucleotides Targeted Against PKC-α and C-raf Gene Expression." Nucleosides & Nucleotides (1997), 16(7-9), 1139-1140.

Manoharan, M. et al., "N-(2-Cyanoethoxycarbonyloxy)succinimide: A New Reagent for Protection of Amino Groups in Oligonucleotides." Journal of Organic Chemistry (1999), 64(17), 6468-6472.

Manoharan, M. et al., "2'—and 3'—cholesterol-conjugated adenosine and cytosine nucleoside building blocks: synthesis of lipidic nucleic acids." Nucleosides & Nucleotides (1997), 16(7-9), 1141-1143.

Manoharan, M. et al., "2'—and 3'-biotin conjugated nucleoside building blocks: synthesis of biotinylated bligonucleotides." Nucleosides & Nucleotides (1997), 16(7-9), 1411-1413.

Manoharan, M. et al., "A 2'-O-thiol tether in the ribose moiety of nucleic acids for conjugation chemistry." Gene (1994), 149(1), 147-56.

(56) References Cited

OTHER PUBLICATIONS

Manoharan, M. et al., "Base-Sequence Dependence of Emission Lifetimes for D141018-30-6NA Oligomers and Duplexes Covalently Labeled with Pyrene: Relative Electron-Transfer Quenching Efficiencies of A, G, C, and T Nucleosides toward Pyrene." Journal of Physical Chemistry (1995), 99(48), 17461-72.

Manoharan, M. et al., "Chemical modifications to improve uptake and bioavailability of antisense oligonucleotides." Ann. N.Y. Acad. Sci. (1992), 660, 306.

Manoharan, M. et al., "Cholic acid-oligonucleotide conjugates for antisense applications." Bioorg. Med. Chem. Let. (1994), 4, 1053.

Krutzfeldt, J. et al., "Silencing of microRNAs in vivo with 'antagomirs'." Nature (2005), 438, 685-689.

Manoharan, M. et al., "Introduction of a lipophilic thioether tether in the minor groove of nucleic acids for antisense applications." Bioorganic & Medicinal Chemistry Letters (1993), 3(12), 2765-70.

Manoharan, M. et al., "Lipidic nucleic acids." Tetrahedron Letters (1995), 36(21), 3651-4.

Manoharan, M. et al., "Oligonucleotide Conjugates: Alteration of the Pharmacokinetic Properties of Antisense Agents." Nucleosides & Nucleotides (1995), 14, 969.

Manoharan, M., "Oligonucleotide conjugates as potential antisense drugs with improved uptake, biodistribution, targeted delivery, and mechanism of action." Antisense and Nucleic Acid Drug Dev. (2002), 12, 103-128.

Mishra, R.K. et al., "Improved leishmanicidal effect of phosphorotioate antisense oligonucleotides by LDL-mediated delivery." Biochim. Biophys. Acta, (1995), 1264, 229.

Nair, J. K. et al., "Impact of enhanced metabolic stability on pharmacokinetics and pharmacodynamics of GalNAc-siRNA conjugates." Nucleic Acids Res. (2017), 45, 10969-10977.

Nair, J. K. et al., "Multivalent N-acetylgalactosamine-conjugated siRNA localizes in hepatocytes and elicits robust RNAi-mediated gene silencing." J. Am. Chem. Soc. (2014), 136, 16958-16961.

Nakamura, M. et al., "Helically Assembled Pyrene Arrays on an RNA Duplex That Exhibit Circularly Polarized Luminescence with Excimer Formation." Chemistry—A European Journal (2016), 22(27), 9121-9124.

Nakamura, M. et al., "Pyrene aromatic arrays on RNA duplexes as helical templates." Organic & Biomolecular Chemistry (2007), 5(12), 1945-1951.

Nikan, M. et al., "Docosahexaenoic acid conjugation enhances distribution and safety of siRNA upon local administration in mouse brain." Mol. Ther. Nucleic Acids (2016), 5, e344.

Nikan, M. et al., "Synthesis and Evaluation of Parenchymal Retention and Efficacy of a Metabolically Stable O- Phosphocholine-N-docosahexaenoyl-l-serine siRNA Conjugate in Mouse Brain." Bioconjugate Chem. (2017), 28, 6, 1758-1766.

Nishina, K. et al., "Efficient In Vivo Delivery of siRNA to the Liver by Conjugation of α-Tocopherol." Mol Therapy (2008), 16(4), 734-740.

Noe, C. R. et al., "Zwitterionic oligonucleotides: A study on binding properties of 2'-O-Aminohexyl modifications." Nucleosides, Nucleotides & Nucleic Acids (2005), 24(8), 1167-1185.

Oberhauser et al., "Effective incorporation of 2'-O-methyl-oligoribonucleotides into liposomes and enhanced cell association through modification with thiocholesterol." Nucl. Acids Res., (1992), 20, 533.

Oliverira, S. et al., "Targeted Delivery of siRNA." BioMed Research International, vol. 2006, Article ID 063675, 9 pages. (2006). https://doi.org/10.1155/JBB/2006/63675.

Osborn, M. F. & Khvorova, A., "Improving siRNA delivery in vivo through lipid conjugation." Nucleic Acid Ther. (2018), 28, 128-136.

Parmar, R. et al., "5'-(E)-vinylphosphonate: a stable phosphate mimic can improve the RNAi activity of siRNA-GalNAc conjugates." ChemBioChem (2016), 17, 985-989.

Perche, P. et al., "Cell-penetrating cationic siRNA and lipophilic derivatives efficient at nanomolar concentrations in the presence of serum and albumin." J. Control. Rel. (2013), 170(1), 92-98.

Petrova, N.S. et al., "Carrier-free cellular uptake and the gene-silencing activity of the lipophilic siRNAs is strongly affected by the length of the linker between siRNA and lipophilic group." Nucleic Acids Research (2012), 40(5), 2330-2344.

Prakash, T. P. et al., "Identification of metabolically stable 5'-phosphate analogs that support single-stranded siRNA activity." Nucleic Acids Research (2015), 43(6), 2993-3011.

Prakash, T. P. et al., "Identification of metabolically stable 5'-phosphate analogs that support single-stranded siRNA activity" [Erratum document]. Nucleic Acids Research (2017), 45(11), 6994.

Rajeev, K.G. et al., "Hepatocyte-specific Delivery of siRNAs Conjugated to Novel Non-nucleosidic Trivalent N- Acetylgalactosamine Elicits Robust Gene Silencing in Vivo." ChemBioChem (2016), 16(6), 903-908.

Ramazeilles, C. et al., "Antisense phosphorothioate oligonucleotides: selective killing of the intracellular parasite Leishmania amazonensis." Proceedings of the National Academy of Sciences of the United States of America (1994), 91(17), 7859-63.

Raouane, M. et al., "Lipid conjugated oligonucleotides: a useful strategy for delivery." Bioconjug. Chem. (2012), 23, 1091-1104.

Roehrig, C. H. et al., "A new strategy for the synthesis of dinucleotides loaded with glycosylated amino acids—Investigations on in vitro non-natural amino acid mutagenesis for glycoprotein synthesis." ChemBioChem (2005), 6(10), 1805-1816.

Saison-Behmoaras, T. et al., "Short modified antisense oligonucleotides directed against Ha-ras point mutation induce selective cleavage of the mRNA and inhibit T24 cells proliferation." EMBO J. (1991), 10, 111.

Sarett, S.M. et al., "Conjugation of palmitic acid improves potency and longevity of siRNA delivered via endosomolytic polymer nanoparticles." Journal of Biomedical Materials Research, Part A (2015), 103(9), 3107-3116.

Sarett, S.M. et al., "Lipophilic siRNA targets albumin in situ and promotes bioavailability, tumor penetration, and carrier-free gene silencing." Proc. Natl. Acad. Sci. USA (2017), 114(32), E6490-E6497.

Sarett, S.M. et al., "Hydrophobic interactions between polymeric carrier and palmitic acid-conjugated siRNA improve PEGylated polyplex stability and enhance in vivo pharmacokinetics and tumor gene silencing." Biomaterials (2016), 97, 122-132.

Schade, M. et al., "Lipophilic nucleic acids—A flexible construction kit for organization and functionalization of surfaces." Adv. Colloid Interface Sci. (2014), 208, 235-251.

Schlegel, M. K. et al. "Chirality dependent potency enhancement and structural impact of glycol nucleic acid modification on siRNA." J. Am. Chem. Soc. (2017), 139, 8537-8546.

Shah, S.S. et al., "Direct Transfection of Fatty Acid Conjugated siRNAs and Knockdown of the Glucose-Regulated Chaperones in Prostate Cancer Cells." Bioconjugate Chemistry (2018), 29(11), 3638-3648.

Shea, R.G. et al., "Synthesis, hybridization properties and antiviral activity of lipid-oligodeoxynucleotide conjugates." Nucl. Acids Res. (1990), 18, 3777.

Soutschek J. et al., "Therapeutic silencing of an endogenous gene by systemic administration of modified siRNAs." Nature (2004), 432(7014), 173-78.

Svinarchuk, F.P. et al., "Inhibition of HIV proliferation in MT-4 cells by antisense oligonucleotide conjugated to lipophilic groups." Biochimie (1993), 75, 49.

Ueno, Y. et al., "Synthesis and silencing properties of siRNAs possessing lipophilic groups at their 3'-termini." Bioorganic & Medicinal Chemistry (2008), 16(16), 7698-7704.

Jeno, Y. et al., "Synthesis and silencing properties of siRNAs possessing lipophilic groups at their 3'-termini." Nucleic Acids Symposium Series (2008), 52(1), 503-504.

Uhlmann & Peyman, "Antisense oligonucleotides: a new therapeutic principle." Chem. Rev. (1990), 90: 543.

Vengut-Climent, E. et al., "Synthesis, RNAi activity and nuclease-resistant properties of apolar carbohydrates siRNA conjugates." Bioorganic & Medicinal Chemistry Letters (2013), 23(14), 4048-4051.

(56) References Cited

OTHER PUBLICATIONS

Werner, D. et al., "Investigations on the influence of 2'-O-alkyl modifications on the base pairing properties of bligonucleotides." Pharmaceutica Acta Helvetiae (1998), 73(1), 3-10.
Whittemore, N. A. et al., "Synthesis and Electrochemistry of Anthraquinone-Oligodeoxynucleotide Conjugates." Bioconjugate Chemistry (1999), 10(2), 261-270.
Winkler, J. et al., "2'-O-lysylaminohexyl oligonucleotides: modifications for antisense and siRNA." ChemMedChem (2008), 3(1), 102-110.
Winkler, J. et al., "2'-O-Lysylaminohexyladenosine modified oligonucleotides." Monatshefte fuer Chemie (2010), 141(7), 809-815.
Wolfrum, C. et al., "Mechanisms and optimization of in vivo delivery of lipophilic siRNAs." Nat. Biotechnol. (2007), 25, 1149-1157.
Wu, S.Y. and McMillan, "Lipidic Systems for In Vivo siRNA Delivery." AAPS J. (2009), 11(4), 639-652.
Wu, Y.-T. et al., "Determination of the optimized conditions for coupling oligonucleotides with 16-mercaptohexadecanoic acid chemically adsorbed upon Au." Bioconjugate Chemistry (2007), 18(6), 1897-1904.
Yamana, K. et al., "2'-Pyrene modified oligonucleotide provides a highly sensitive fluorescent probe of RNA." Nucleic Acids Research (1999), 27(11), 2387-2392.
Yamana, K. et al., "Enhanced fluorescence in the binding of oligonucleotides with a pyrene group in the sugar fragment to complementary polynucleotides." Nucleosides & Nucleotides (1992), 11(2-4), 383-90.
Yamana, K. et al., "Oligonucleotides with pyrene fluorophore at the sugar fragment: synthesis and properties in binding to complementary polynucleotide." Nucleic Acids Symposium Series (1990), 22(Symp. Nucleic Acids Technol.), 103-4.
Yamana, K. et al., "Synthesis of oligonucleotide derivatives with a pyrene group at the sugar fragment." Tetrahedron Letters (1991), 32(44), 6347-50.
Yamana, K. et al., "Synthesis and properties of oligonucleotides containing 2'-pyrenylalkyluridine." Nucleic Acids Symposium Series (1999), 42(1), 113-114.
Yang, J. et al., "Cholesterol-Modified Caged siRNAs for Photoregulating Exogenous and Endogenous Gene Expression." Bioconjugate Chem. (2018), 29(4), 1010-1015.
Yu, C. J. et al., "Electronic detection of single-base mismatches in DNA with ferrocene-modified probes." Journal of the American Chemical Society (2001), 123(45), 11155-11161.
Yu, C. J. et al., "2'-Ribose-ferrocene oligonucleotides for electronic detection of nucleic acids." Journal of Organic Chemistry (2001), 66(9), 2937-2942.
Zhang, S. et al., "Non-viral vectors for the mediation of RNAi." Bioorganic Chemistry (2012), 40, 10-18.
Yamada, Y. et al., "Versatile Site-Specific Conjugation of Small Molecules to siRNA Using Click Chemistry." J. Org. Chem. (2011), 76, 1198-1211.
Li, Q.-J. et al., "miR-181a is an Intrinsic Modulator of T-Cell Sensitivity and Selection." Cell (2007), 129, 147.
Teplova, M. et al., "Crystal Structure and Improved Antisense Properties of 2'-O-(2-methoxyethyl)-RNA." Nat. Structural Biol. (1999), 6, 535.
Pattanayek, R. et al., "Structural Rationalization of a Large Difference in RNA Affinity Despite a Small Difference in Chemistry between Two 2'-O-Modified Nucleic Acid Analogues." J. Am. Chem. Soc. (2004), 126, 15006-15007.
Prakash, T. P. et al., "2'-O-[2-(Amino)-2-oxoethyl]Oligonucleotides." Org. Lett. (2003), 5(4), 403-6.
Prakash, T. P. et al., "Comparing In Vitro and In Vivo Activity of 2'-O-[2-(Methyamino)-2-oxoethyl]- and 2'-O-Methoxyethyl-Modified Antisense Oligonucleotides." J. Med. Chem. (2008), 51, 2766-76.
Parmar, R.G. et al., "Facile Synthesis, Geometry, and 2'-Substituent-Dependent in Vivo Activity of 5'-(E)- and 5'-(Z)-Vinylphosphonate-Modified siRNA Conjugates." J. Med. Chem. (2018), 61, 734-44.
Martin et al., "A New Access to 2'-O-alkylated Ribonucleosides and Properties of 2'-O-Alkylated Oligoribonucleotides," Helv. Chim. Acta (1995), 78, 486-504 (English abstract only).
Peel et al., "Conjugation and Evaluation of Small Hydrophobic Molecules to Triazole-Linked siRNAs," ACS Medical Chemistry Letters 6: 117-122 (2015).
Yamada et al., "Versatile Site-Specific Conjugation of Small Molecules to siRNA Using Click Chemistry," J. Org. Chem. 76: 1198-1211 (2011).
Makimura et al., "Reducing hypothalamic AGRP by RNA interference increases metabolic rate and decreases body weight without influencing food intake," BMC Neuroscience 3: 1-6 (2002).
Peters et al., "RNA inteference in hippocampus demonstrates opposing roles for CREB and PP1α in contextual and temporal long-term memory," Genes, Brain, and Behavior 8: 320-329 (2009).
Shishkina et al., "Attenuation of a2A-Adrenergic Receptor Expression in Neonatal Rat Brain by RNA Interference or Antisense Olignucleotide Reduced Anxiety in Adulthood," Neuroscience 129: 521-528 (2004).
Tan et al., "Gene knockdown with intrathecal siRNA of NMDA receptor NR2B subunit reduces formalin-induced nociception in the rat," Gene Therapy 12: 59-66 (2005).
Thakker et al., "Neurochemical and behavior consequences of widespread gene knockdown in the adult mouse brain by using nonviral RNA interference," PNAS 101: 17270-17275 (2004).
Akaneya et al., "RNAi-Induced Gene Silencing by Local Electroporation in Targeting Brain Region," J Neurophysiol 93: 594-602 (2005).
Chen et al., "REM sleep changes in rates induced by siRNA-mediated orexin knockdown," Eur J Neurosci 24: 2039-2048 (2006).
Dorn et al., "siRNA relieves chronic neuropathic pain," Nucleic Acids Research 32: e49 (2004).
Aaronson, J.G. et al., "Rapid HATU-Mediated Solution Phase siRNA Conjugation." Bioconjugate Chemistry (2011), 22 (8), 1723-1728.
Alterman, J. F. et al., "Hydrophobically modified siRNAs silence Huntingtin mRNA in primary neurons and mouse brain." Mol. Ther. Nucleic Acids 4, e266 (2015).
Barber-Poec'h, I. et al., "Solid phase conjugation chemistry: use of alloc as a protecting group for 2'-amino-linker containing oligonucleotides." Nucleosides & Nucleotides (1997), 16(7-9), 1407-1410.
Bashkin, J. K. et al., "Building Blocks for Ribozyme Mimics: Conjugates of Terpyridine and Bipyridine with Nucleosides." Journal of Organic Chemistry (1996), 61(7), 2314-21.
Biscans, A. et al., "Lipophilic 2'-O-Acetal Ester RNAs: Synthesis, Thermal Duplex Stability, Nuclease Resistance, Cellular Uptake, and siRNA Activity after Spontaneous Naked Delivery." ChemBioChem (2016) 17(21), 2054-2062.
Biscans, A. et al., "Diverse lipid conjugates for functional extra-hepatic siRNA delivery in vivo." Nucleic Acids Res. 47, 1082-1096 (2019).
Byrne, M. et al., "Novel hydrophobically modified asymmetric RNAi compounds (sd-rxRNA) demonstrate robust efficacy in the eye." J. Ocul. Pharmacol. Ther. 29, 855-864 (2013).
Chandela, A. et al., "Synthesis and characterization of small interfering RNAs with haloalkyl groups at their 3'-dangling ends." Bioorganic & Medicinal Chemistry (2019), 27(7), 1341-1349.
Chen, Q. et al., "Lipophilic siRNAs mediate efficient gene silencing in oligodendrocytes with direct CNS delivery." J. Control. Release 144, 227-232 (2010).
Chernikov, I.V. et al., "Cholesterol-Containing Nuclease-Resistant siRNA Accumulates in Tumors in a Carrier-free Mode and Silences MDR1 Gene." Mol. Ther. Nucl. Acids (2017), 6, 209-220.
Cultrara, C.N. et al., "Solid phase synthesis and self-assembly of higher-order siRNAs and their bioconjugates." Chemical Biology & Drug Design (2019), 93(6), 999-1010.
Davis, P. W. et al., "Drug Leads from Combinatorial Phosphodiester Libraries." Journal of Medicinal Chemistry (1995), 38(22), 4363-6.
DeVincenzo, J. et al., "A randomized, double-blind, placebo-controlled study of an RNAi-based therapy directed against respiratory syncytial virus." Proc. Natl Acad. Sci. USA 107, 8800-8805 (2010).

(56) References Cited

OTHER PUBLICATIONS

DiFiglia, M. et al., "Therapeutic silencing of mutant huntingtin with siRNA attenuates striatal and cortical neuropathology and behavioral deficits." Proc. Natl Acad. Sci. USA 104, 17204-17209 (2007).
Dovydenko, I. et al., "Method of carrier-free delivery of therapeutic RNA importable into human mitochondria: Lipophilic conjugates with cleavable bonds." Biomaterials (2016) 76, 408-417.
Foster, D. J. et al., "Advanced siRNA designs further improve in vivo performance of GalNAc-siRNA conjugates." Mol. Ther. 26, 708-717 (2018).
Gauthier, F. et al., "Gymnotic delivery and gene silencing activity of reduction-responsive siRNAs bearing lipophilic disulfide-containing modifications at 2'-position." Bioorg. Med. Chem. (2018) 26(16), 4635-4643.
Gryaznov & Lloyd, "Modulation of oligonucleotide duplex and triplex stability via hydrophobic interactions." Nucleic Acids Research (1993), 21: 5909-5915.
Gvozdeva, O.V. et al., "Modified siRNA effectively silence inducible immunoproteasome subunits in NSO cells." Biochimie (2016), 125, 75-82.
Haraszti, R.A. et al., "Optimized Cholesterol-siRNA Chemistry Improves Productive Loading onto Extracellular Vesicles." Mol. Therapy (2018), 26(8), 1973-1982.
Haraszti, R.A. et al., "5'-Vinylphosphonate improves tissue accumulation and efficacy of conjugated siRNAs in vivo." Nucleic Acids Research, (2017), vol. 45, No. 13 7581-7592.
Hassler, M.R. et al., "Comparison of partially and fully chemically-modified siRNA in conjugate-mediated delivery in vivo." Nucleic Acids Research, (2018) 46(5), 2185-2196.
Hvam, M.L. et al., "Fatty Acid-Modified Gapmer Antisense Oligonucleotide and Serum Albumin Constructs for Pharmacokinetic Modulation." Molecular Therapy (2017), 25(7), 1710-1717.
Imincan, G. et al., "Microenvironmental Effect of 2'-O-(1-Pyrenylmethyl)uridine Modified Fluorescent Oligonucleotide Probes on Sensitive and Selective Detection of Target RNA." Analytical Chemistry (2016), 88(8), 4448-4455.
Iwase, R. et al., "Study on RNA structure by pyrene-labeled 2'-O-methyloligoribonucleotides." Nucleic Acids Symposium Series (1999), 42(1), 115-116.
Iwase, R. et al., "Study of RNA structure by pyrene-labeled oligonucleotides." Nucleic Acids Symposium Series (1997), 37, 205-206.
Jager, A. et al., "Oligonucleotide N-alkylphosphoramidates: synthesis and binding to polynucleotide." Biochemistry (1988), 27, 7237-7246.
Janas, M. M. et al., "Safety evaluation of 2'-deoxy-2'-fluoro nucleotides in GalNAc-siRNA conjugates." Nucleic Acids Res. 47, 3306-3320 (2019).
Janas, M. M. et al., "Selection of GalNAc-conjugated siRNAs with limited off-target-driven rat hepatotoxicity." Nat. Commun. 9, 723 (2018).
Jeong, J.H. et al., "siRNA Conjugate Delivery Systems." Bioconjugate Chem. (2009), 20, 1, 5-14.
Kabanov, A.V. et al., "A new class of antivirals: antisense oligonucleotides combined with a hydrophobic substituent effectively inhibit influenza virus reproduction and synthesis of virus-specific proteins in MDCK cells." FEBS Lett., (1990), 259, 327.
Karmakar, S. et al., "High-Affinity DNA Targeting Using Readily Accessible Mimics of N2'-Functionalized 2'-Amino-α-L-LNA." Journal of Organic Chemistry (2011), 76(17), 7119-7131.
Karmakar, S. et al., "Recognition of double-stranded DNA using energetically activated duplexes with interstrand zippers of 1-, 2- or 4-pyrenyl-functionalized O2'-alkylated RNA monomers." Organic & Biomolecular Chemistry (2014), 12(39), 7758-7773.
Karmakar, S. et al., "Recognition of mixed-sequence DNA duplexes: design guidelines for Invaders based on 2'-O-(Pyren-1-yl)methyl-RNA monomers." Journal of Organic Chemistry (2013), 78(23), 12040-12048.
Kubo, T. et al., "Palmitic acid-conjugated 21-nucleotide siRNA enhances gene-silencing activity." Molecular Pharmaceutics (2011), 8(6), 2193-2203.
Kubo, T. et al., "Amino-Modified and Lipid-Conjugated Dicer-Substrate siRNA Enhances RNAi Efficacy." Bioconjugate Chemistry (2012), 23(2), 164-173.
Kubo, T. et al., "Lipid-conjugated 27-nucleotide double-stranded RNAs with Dicer-substrate potency enhance RNAi-mediated gene silencing." Molecular Pharmaceutics (2012), 9(5), 1374-1383.
Kubo, T. et al., "SiRNAs conjugated with aromatic compounds induce RISC-mediated antisense strand selection and strong gene-silencing activity." Biochemical and Biophysical Research Communications (2012), 426(4), 571-577.
Kubo, T. et al., "Antitumor effect of palmitic acid-conjugated DsiRNA for colon cancer in a mouse subcutaneous tumor model." Chemical Biology & Drug Design (2019), 93(4), 570-581.
Kubo, T. et al., "Gene-silencing potency of symmetric and asymmetric lipid-conjugated siRNAs and its correlation with Dicer recognition." Bioconjugate Chemistry (2013), 24(12), 2045-2057.
Kubo, T. et al., "In Vivo RNAi Efficacy of Palmitic Acid-Conjugated Dicer-Substrate siRNA in a Subcutaneous Tumor Mouse Model." Chemical Biology & Drug Design (2016), 87(6), 811-823.
Laing, B.M. et al., "Properties of Double-Stranded Oligonucleotides Modified with Lipophilic Substituents." Bioconjugate Chem. (2010), 21, 8, 1537-1544.
Letsinger, R.L. et al., "Effects of pendant groups at phosphorus on binding properties of d-ApA analogues." Nucleic Acids Res. (1986), 14, 3487-3499.
Letsinger, R.L. et al., "Cholesteryl-conjugated oligonucleotides: synthesis, properties, and activity as inhibitors of replication of human immunodeficiency virus in cell culture." Proc. Natl. Acad. Sci. USA, (1989), 86, 6553.
Lima, W. F. et al., "Single-Stranded siRNAs Activate RNAi in Animals." Cell (2012), 150(5), 883-894.
Lorenz, C. et al., "Steroid and lipid conjugates of siRNAs to enhance cellular uptake and gene silencing in liver cells." Bioorg. Med. Chem. Lett. (2004), 14(19), 4975-4977.
Ly, S. et al., "Visualization of self-delivering hydrophobically modified siRNA cellular internalization." Nucleic Acids Research (2017), 45(1), 15-25.
Ma, Y. et al., "Annealing novel nucleobase-lipids with oligonucleotides or plasmid DNA based on H-bonding or π-π Interaction: Assemblies and transfections." Biomaterials (2018), 178, 147-157.
Manoharan, M. et al., "2'-O- and 3'-O-pyrimidine amino-tether-containing oligodeoxyribonucleotides: synthesis and conjugation chemistry." Tetrahedron Letters (1995), 36(21), 3647-50.
Manoharan, M. et al., "Conjugated Antisense Oligonucleotides." Nucleosides & Nucleotides (1997), 16(7-9), 1129-1138.
Chen et al., "Efficient downregulation of VEGF in retinal pigment epithelial cells by integrin ligand-labeled liposome-mediated siRNA delivery," International Journal of Nanomedicine 8: 2613-2627 (2013).
Kaczmarek et al., "Synthesis of Nucleosides with 2'-Fixed Lipid Anchors and Their Behavior in Phospholipid Membranes," Eur. J. Org. Chem. 2008: 1917-1928 (2008).

\* cited by examiner

EXTRAHEPATIC DELIVERY

This application is a continuation application of U.S. patent application Ser. No. 17/052,945, filed Nov. 4, 2020; which is a 371 National Stage application of International PCT Application No. PCT/US2019/031170, filed May 7, 2019; which claims benefit of priority to U.S. Provisional Application No. 62/668,072 filed May 7, 2018; U.S. Provisional Application No. 62/738,747 filed Sep. 28, 2018; and U.S. Provisional Application No. 62/773,082 filed Nov. 29, 2018, all of which are herein incorporated by reference in their entirety.

SEQUENCE LISTING

The instant application contains a Sequence Listing which has been submitted via the USPTO patent electronic filing system in XML format and is hereby incorporated by reference in its entirety. Said XML copy, created on May 1, 2023, is named 29520_1501-US-CON__ALN-281-USCON1_SL.xml and is 1,918,969 bytes in size.

BACKGROUND

Efficient delivery of an iRNA agent to cells in vivo requires specific targeting and substantial protection from the extracellular environment, particularly serum proteins. RNAi-based therapeutics show promising clinical data for treatment of liver-associated disorders. However, siRNA delivery into extra-hepatic tissues remains an obstacle, limiting the use of siRNA-based therapies.

One of the factors that limit the experimental and therapeutic application of iRNA agents in vivo is the ability to deliver intact siRNA efficiently. Particular difficulties have been associated with non-viral gene transfer into the retina in vivo. One of the challenges is to overcome the inner limiting membrane, which impedes the transfection of the retina. Additionally, negatively charged sugars of the vitreous have been shown to interact with positive DNA-transfection reagent complexes, promoting their aggregation, which impedes diffusion and cellular uptake.

Delivery of oligonucleotides to the central nervous system (CNS) poses particular problems due to the blood brain barrier (BBB) that free oligonucleotides cannot cross. One means to deliver oligonucleotides into the CNS is by intrathecal delivery. However, the oligonucleotides need also to be efficiently internalized into target cells of the CNS to achieve the desired therapeutic effect. Previous work has typically used delivery reagents such as liposomes, cationic lipids, and nanoparticles forming complexes to aid the intracellular internalization of oligonucleotides into cells of neuronal origin.

Thus, there is a continuing need for new and improved methods for delivering siRNA molecules in vivo, without the use of tissue delivery reagents, to achieve and enhance the therapeutic potential of iRNA agents.

SUMMARY

One aspect of the invention provides a double-stranded iRNA agent comprising: an antisense strand which is complementary to a target gene; a sense strand which is complementary to said antisense strand; and one or more lipophilic moieties conjugated to one or more internal positions on at least one strand, optionally via a linker or carrier.

In some embodiments, the lipophilicity of the lipophilic moiety, measured by octanol-water partition coefficient, log $K_{ow}$, exceeds 0. The lipophilic moiety may possess a log $K_{ow}$ exceeding 1, exceeding 1.5, exceeding 2, exceeding 3, exceeding 4, exceeding 5, or exceeding 10.

In some embodiments, the hydrophobicity of the double-stranded iRNA agent, measured by the unbound fraction in the plasma protein binding assay of the double-stranded iRNA agent, exceeds 0.2. In one embodiment, the plasma protein binding assay determined is an electrophoretic mobility shift assay (EMSA) using human serum albumin protein. The hydrophobicity of the double-stranded iRNA agent, measured by fraction of unbound siRNA in the binding assay, exceeds 0.15, exceeds 0.2, exceeds 0.25, exceeds 0.3, exceeds 0.35, exceeds 0.4, exceeds 0.45, or exceeds 0.5 for an enhanced in vivo delivery of siRNA.

In some embodiments, the lipophilic moiety is an aliphatic, cylic such as alicyclic, or polycyclic such as polyalicyclic compound, such as a steroid (e.g., sterol) or a linear or branched aliphatic hydrocarbon. Exemplary lipophilic moieties are lipid, cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl) lithocholic acid, O3-(oleoyl)cholenic acid, ibuprofen, naproxen, dimethoxytrityl, or phenoxazine.

Suitable lipophilic moieties also include those containing a saturated or unsaturated $C_4$-$C_{30}$ hydrocarbon chain (e.g., $C_4$-$C_{30}$ alkyl or alkenyl), and an optional functional group selected from the group consisting of hydroxyl, amine, carboxylic acid, sulfonate, phosphate, thiol, azide, and alkyne. The functional groups are useful to attach the lipophilic moiety to the iRNA agent. In some embodiments, the lipophilic moiety contains a saturated or unsaturated $C_6$-$C_{18}$ hydrocarbon chain (e.g., a linear $C_6$-$C_{18}$ alkyl or alkenyl). In one embodiment, the lipophilic moiety contains a saturated or unsaturated $C_{16}$ hydrocarbon chain (e.g., a linear $C_{16}$ alkyl or alkenyl).

In some embodiments, the lipophilic moiety is a $C_6$-$C_{30}$ acid (e.g., hexanoic acid, heptanoic acid, octanoic acid, nonanoic acid, decanoic acid, undecanoic acid, dodcanoic acid, tridecanoic acid, tetradecanoic acid, pentadecanoic acid, hexadecanoic acid, heptadecanoic acid, octadecanoic acid, oleic acid, linoleic acid, arachidonic acid, cis-4,7,10,13,16,19-docosahexanoic acid, vitamin A, vitamin E, cholesterol etc.) or a $C_6$-$C_{30}$ alcohol (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

The lipophilic moiety may be conjugated to the iRNA agent via a direct attachment to the ribosugar of the iRNA agent. Alternatively, the lipophilic moiety may be conjugated to the iRNA agent via a linker or a carrier.

In certain embodiments, the lipophilic moiety are conjugated to the iRNA agent via one or more linkers (tethers).

In some embodiments, the lipophilic moiety is conjugated to the double-stranded iRNA agent via a linker a linker containing an ether, thioether, urea, carbonate, amine, amide, maleimide-thioether, disulfide, phosphodiester, sulfonamide linkage, a product of a click reaction (e.g., a triazole from the azide-alkyne cycloaddition), or carbamate.

In some embodiments, at least one of the linkers (tethers) is a redox cleavable linker (such as a reductively cleavable linker; e.g., a disulfide group), an acid cleavable linker (e.g., a hydrazone group, an ester group, an acetal group, or a ketal group), an esterase cleavable linker (e.g., an ester group), a phosphatase cleavable linker (e.g., a phosphate group), or a peptidase cleavable linker (e.g., a peptide bond).

In other embodiments, at least one of the linkers (tethers) is a bio-clevable linker selected from the group consisting of DNA, RNA, disulfide, amide, functionalized monosaccharides or oligosaccharides of galactosamine, glucosamine, glucose, galactose, mannose, and combinations thereof.

In certain embodiments, the lipophilic moiety is conjugated to the double-stranded iRNA agent via a carrier that replaces one or more nucleotide(s). The carrier can be a cyclic group or an acyclic group. In one embodiment, the cyclic group is selected from the group consisting of pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalin. In one embodiment, the acyclic group is a moiety based on a serinol backbone or a diethanolamine backbone.

In some embodiments, the carrier replaces one or more nucleotide(s) in the internal position(s) of the double-stranded iRNA agent.

In other embodiments, the carrier replaces the nucleotides at the terminal end of the sense strand or antisense strand. In one embodiment, the carrier replaces the terminal nucleotide on the 3' end of the sense strand, thereby functioning as an end cap protecting the 3' end of the sense strand. In one embodiment, the carrier is a cyclic group having an amine, for instance, the carrier may be pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, or decalinyl.

In one embodiment, the lipophilic moiety is conjugated to one or more internal positions on at least one strand, which include all positions except the terminal two positions from each end of the strand. In one embodiment, the lipophilic moiety is conjugated to one or more internal positions on at least one strand, which include all positions except the terminal three positions from each end of the strand.

In one embodiment, at least one lipophilic moiety is conjugated to one or more positions of at least one end of the duplex region, which include all positions within the duplex region, but not include the overhang region or the carrier that replaces the terminal nucleotide on the 3' end of the sense strand.

In one embodiment, at least one lipophilic moiety is conjugated on the sense strand within the first five base pairs at the 5'-end of the antisense strand of the duplex region.

In one embodiment, at least one lipophilic moiety is conjugated on the sense strand within the first four base pairs at the 5'-end of the antisense strand of the duplex region.

In one embodiment, at least one lipophilic moiety is conjugated on the sense strand within the first three base pairs at the 5'-end of the antisense strand of the duplex region.

In one embodiment, at least one lipophilic moiety is conjugated on the sense strand within the first two base pairs at the 5'-end of the antisense strand of the duplex region.

In one embodiment, at least one lipophilic moiety is conjugated on the sense strand on the first base pair at the 5'-end of the antisense strand of the duplex region.

In one embodiment, the lipophilic moiety is conjugated to one or more internal positions on at least one strand, which exclude the cleavage site region of the sense strand. For instance, the internal positions exclude positions 9-12 counting from the 5'-end of the sense strand. For example, the internal positions exclude positions 9-11 counting from the 5'-end of the sense strand. Alternatively, the internal positions exclude positions 11-13 counting from the 3'-end of the sense strand.

In one embodiment, the lipophilic moiety is conjugated to one or more internal positions on at least one strand, which exclude the cleavage site region of the antisense strand. For instance, the internal positions exclude positions 12-14 counting from the 5'-end of the antisense strand.

In one embodiment, the lipophilic moiety is conjugated to one or more internal positions on at least one strand, which exclude positions 11-13 on the sense strand, counting from the 3'-end, and positions 12-14 on the antisense strand, counting from the 5'-end.

In one embodiment, one or more lipophilic moieties are conjugated to one or more of the following internal positions: positions 4-8 and 13-18 on the sense strand, and positions 6-10 and 15-18 on the antisense strand, counting from the 5' end of each strand.

In one embodiment, one or more lipophilic moieties are conjugated to one or more of the following internal positions: positions 5, 6, 7, 15, and 17 on the sense strand, and positions 15 and 17 on the antisense strand, counting from the 5' end of each strand.

In some embodiments, the sense and antisense strands of the double-stranded iRNA agent are each 15 to 30 nucleotides in length.

In one embodiment, the sense and antisense strands of a double-stranded iRNA agent are each 19 to 25 nucleotides in length.

In one embodiment, the sense and antisense strands of the double-stranded iRNA agent are each 21 to 23 nucleotides in length.

In some embodiments, the double-stranded iRNA agent comprises a single-stranded overhang on at least one of the termini, e.g., 3' and/or 5' overhang(s) of 1-10 nucleotides in length, for instance, an overhang of 1, 2, 3, 4, 5, or 6 nucleotides. In some embodiments, both strands have at least one stretch of 1-5 (e.g., 1, 2, 3, 4, or 5) single-stranded nucleotides in the double stranded region. In one embodiment, the single-stranded overhang is 1, 2, or 3 nucleotides in length. In some embodiments, the double-stranded iRNA agent may also have a blunt end, located at the 5'-end of the antisense strand (or the 3'-end of the sense strand), or vice versa. In one embodiment, the double-stranded iRNA agent comprises a 3' overhang at the 3'-end of the antisense strand, and optionally a blunt end at the 5'-end of the antisense strand. In one embodiment, the double-stranded iRNA agent has a 5' overhang at the 5'-end of the sense strand, and optionally a blunt end at the 5'-end of the antisense strand. In one embodiment, the double-stranded iRNA agent has two blunt ends at both ends of the iRNA duplex.

In one embodiment, the sense strand of the double-stranded iRNA agent is 21-nucleotides in length, and the antisense strand is 23-nucleotides in length, wherein the strands form a double-stranded region of 21 consecutive base pairs having a 2-nucleotide long single-stranded overhangs at the 3'-end.

In some embodiments, the lipophilic moiety is conjugated to a nucleobase, sugar moiety, or internucleosidic linkage of the double-stranded iRNA agent.

In some embodiments, the double-stranded iRNA agent further comprises a phosphate or phosphate mimic at the 5'-end of the antisense strand. In one embodiment, the phosphate mimic is a 5'-vinyl phosphonate (VP).

In some embodiments, the 5'-end of the antisense strand of the double-stranded iRNA agent does not contain a 5'-vinyl phosphonate (VP).

In some embodiments, the double-stranded iRNA agent further comprises at least one terminal, chiral phosphorus atom.

A site specific, chiral modification to the internucleotide linkage may occur at the 5' end, 3' end, or both the 5' end and 3' end of a strand. This is being referred to herein as a "terminal" chiral modification. The terminal modification may occur at a 3' or 5' terminal position in a terminal region, e.g., at a position on a terminal nucleotide or within the last 2, 3, 4, 5, 6, 7, 8, 9 or 10 nucleotides of a strand. A chiral modification may occur on the sense strand, antisense strand, or both the sense strand and antisense strand. Each of the chiral pure phosphorus atoms may be in either Rp configuration or Sp configuration, and combination thereof. More details regarding chiral modifications and chirally-modified dsRNA agents can be found in PCT/US18/67103, entitled "Chirally-Modified Double-Stranded RNA Agents," filed Dec. 21, 2018, which is incorporated herein by reference in its entirety.

In some embodiments, the double-stranded iRNA agent further comprises a terminal, chiral modification occurring at the first internucleotide linkage at the 3' end of the antisense strand, having the linkage phosphorus atom in Sp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp configuration or Sp configuration.

In one embodiment, the double-stranded iRNA agent further comprises a terminal, chiral modification occurring at the first and second internucleotide linkages at the 3' end of the antisense strand, having the linkage phosphorus atom in Sp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp or Sp configuration.

In one embodiment, the double-stranded iRNA agent further comprises a terminal, chiral modification occurring at the first, second, and third internucleotide linkages at the 3' end of the antisense strand, having the linkage phosphorus atom in Sp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp or Sp configuration.

In one embodiment, the double-stranded iRNA agent further comprises a terminal, chiral modification occurring at the first and second internucleotide linkages at the 3' end of the antisense strand, having the linkage phosphorus atom in Sp configuration; a terminal, chiral modification occurring at the third internucleotide linkages at the 3' end of the antisense strand, having the linkage phosphorus atom in Rp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp or Sp configuration.

In one embodiment, the double-stranded iRNA agent further comprises a terminal, chiral modification occurring at the first and second internucleotide linkages at the 3' end of the antisense strand, having the linkage phosphorus atom in Sp configuration; a terminal, chiral modification occurring at the first, and second internucleotide linkages at the 5' end of the antisense strand, having the linkage phosphorus atom in Rp configuration; and a terminal, chiral modification occurring at the first internucleotide linkage at the 5' end of the sense strand, having the linkage phosphorus atom in either Rp or Sp configuration.

In some embodiments, the double-stranded iRNA agent has at least two phosphorothioate internucleotide linkages at the first five nucleotides on the antisense strand (counting from the 5' end).

In some embodiments, the antisense strand comprises two blocks of one, two, or three phosphorothioate internucleotide linkages separated by 1, 2, 3, 4, 5, 6, 7, 8, 9, 10, 11, 12, 13, 14, 15, 16, 17, or 18 phosphate internucleotide linkages.

In some embodiments, the double-stranded iRNA agent further comprises a targeting ligand that targets a receptor which mediates delivery to a specific CNS tissue. In one embodiment, the targeting ligand is selected from the group consisting of Angiopep-2, lipoprotein receptor related protein (LRP) ligand, bEnd.3 cell binding ligand, transferrin receptor (TfR) ligand, manose receptor ligand, glucose transporter protein, and LDL receptor ligand.

In some embodiments, the double-stranded iRNA agent further comprises a targeting ligand that targets a receptor which mediates delivery to an ocular tissue. In one embodiment, the targeting ligand is selected from the group consisting of trans-retinol, RGD peptide, LDL receptor ligand, and carbohydrate-based ligands. In one embodiment, the targeting ligand is a RGD peptide, such as H-Gly-Arg-Gly-Asp-Ser-Pro-Lys-Cys-OH (SEQ ID NO: 1) or Cyclo(-Arg-Gly-Asp-D-Phe-Cys) (SEQ ID NO: 2).

In some embodiments, the double-stranded iRNA agent further comprises a targeting ligand that targets a liver tissue. In some embodiments, the targeting ligand is a carbohydrate-based ligand. In one embodiment, the targeting ligand is a GalNAc conjugate.

All the above aspects and embodiments would be applicable to an oligonucleotide having one or more lipophilic moieties conjugated to one or more internal positions on the oligonucleotide. In some embodiments, 100%, 95%, 90%, 85%, 80%, 75%, 70%, 65%, 60%, 55%, 50%, 45%, 40%, 35% or 30% of the oligonucleotide is modified. For example, when 50% of the oligonucleotide is modified, 50% of all nucleotides present in the oligonucleotide contain a modification as described herein.

In one embodiment, the oligonucleotide is a double-stranded dsRNA agent, and at least 50% of the nucleotides of the double-stranded dsRNA agent is independently modified with 2'-O-methyl, 2'-O-allyl, 2'-deoxy, or 2'-fluoro.

In one embodiment, the oligonucleotide is an antisense, and at least 50% of the nucleotides of the antisense is independently modified with LNA, CeNA, 2'-methoxyethyl, or 2'-deoxy.

In some embodiments, the double-stranded iRNA agent has less than 12, less than 10, less than 8, less than 6, less than 4, less than 2, or no 2'-F modifications on the sense strand. In some embodiments, the double-stranded iRNA agent has less than 12, less than 10, less than 8, less than 6, less than 4, less than 2, or no 2'-F modifications on the antisense strand.

In some embodiments, the double-stranded iRNA agent has one or more 2'-F modifications on any position of the sense strand or antisense strand.

In some embodiments, the double-stranded iRNA agent has less than 20%, less than 15%, less than 10%, less than 5% non-natural nucleotide, or substantially no non-natural nucleotide. Examples of non-natural nucleotide include acyclic nucleotides, LNA, HNA, CeNA, 2'-O-methoxyalkyl (e.g., 2'-O-methoxymethyl, 2'-O-methoxyethyl, or 2'-O-2-methoxypropanyl), 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), 2'-ara-F, L-nucleoside modification (such as 2'-modified L-nucleoside, e.g., 2'-deoxy-L-nucleoside), BNA abasic sugar, abasic cyclic and open-chain alkyl.

In some embodiments, the double-stranded iRNA agent has greater than 80%, greater than 85%, greater than 90%, greater than 95%, or virtually 100% natural nucleotides. For the purpose of these embodiments, natural nucleotides can include those having 2'-OH, 2'-deoxy, and 2'-OMe.

In one embodiment, the double-stranded iRNA agent comprises a sense strand and antisense strand each having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the double-stranded iRNA agent has less than 20%, less than 15%, less than 10%, less than 5% non-natural nucleotide, or substantially no non-natural nucleotide.

In one embodiment, the double-stranded iRNA agent comprises a sense strand and antisense strand each having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the double-stranded iRNA agent has greater than 80%, greater than 85%, greater than 95%, or virtually 100% natural nucleotides, such as those having 2'-OH, 2'-deoxy, or 2'-OMe.

Another aspect of the invention relates to a method of reducing the expression of a target gene in a cell, comprising contacting said cell with a double-stranded iRNA agent comprising an antisense strand which is complementary to a target gene; a sense strand which is complementary to said antisense strand; and one or more lipophilic moieties conjugated to one or more internal positions on at least one strand, optionally via a linker or carrier.

All the above embodiments relating to the lipophilic moieties and their conjugation to the double-stranded iRNA agent in the first aspect of the invention relating to the double-stranded iRNA agent are suitable in this aspect of the invention relating to a method of reducing the expression of a target gene in a cell.

In one embodiment, the cell is an extraheptic cell.

Another aspect of the invention relates to a method of reducing the expression of a target gene in a subject, comprising administering to the subject a double-stranded iRNA agent comprising contacting said cell with a double-stranded iRNA agent comprising an antisense strand which is complementary to a target gene; a sense strand which is complementary to said antisense strand; and one or more lipophilic moieties conjugated to one or more internal positions on at least one strand, optionally via a linker or carrier.

All the above embodiments relating to the lipophilic moieties and their conjugation to the double-stranded iRNA agent in the first aspect of the invention relating to the double-stranded iRNA agent are suitable in this aspect of the invention relating to a method of reducing the expression of a target gene in a subject.

In some embodiments, the double-stranded iRNA agent is administered extrahepatically.

In one embodiment, the double-stranded iRNA agent is administered intrathecally. By intrathecal administration of the double-stranded iRNA agent, the method can reduce the expression of a target gene in a brain or spine tissue, for instance, cortex, cerebellum, cervical spine, lumbar spine, and thoracic spine.

In some embodiments, exemplary target genes are APP, ATXN2, C9orf72, TARDBP, MAPT (Tau), HTT, SNCA, FUS, ATXN3, ATXN1, SCA1, SCA7, SCA8, MeCP2, PRNP, SOD1, DMPK, and TTR. To reduce the expression of these target genes in the subject, the double-stranded iRNA agent can be administered intravitreally. By intravitreal administration of the double-stranded iRNA agent, the method can reduce the expression of the target gene in an ocular tissue.

Another aspect of the invention relates to a method of treating a subject having a CNS disorder, comprising administering to the subject a therapeutically effective amount of a double-stranded RNAi agent, thereby treating the subject. The double-stranded RNAi agent comprises an antisense strand which is complementary to a target gene; a sense strand which is complementary to said antisense strand; and one or more lipophilic moieties conjugated to one or more internal positions on at least one strand, optionally via a linker or carrier.

All the above embodiments relating to the lipophilic moieties and their conjugation to the double-stranded iRNA agent in the first aspect of the invention relating to the double-stranded iRNA agent are suitable in this aspect of the invention relating to a method of treating a subject having a CNS disorder. Exemplary CNS disorders that can be treated by the method of the invention include alzheimer, amyotrophic lateral sclerosis (ALS), frontotemporal dementia, huntington, Parkinson, spinocerebellar, prion, and lafora.

BRIEF DESCRIPTION OF THE DRAWINGS

FIG. 13A shows the results of SOD1 mRNA silencing by a single intrathecal injection of various exemplary siRNA conjugates in rats in lumbar spine, thoracic spine, and cervical spine regions, respectively. FIG. 13B is a schematic showing of various tissues tested in the CNS of rats. FIG. 13C shows the results of SOD1 mRNA silencing by a single intrathecal injection of various exemplary siRNA conjugates in rats in cerebellum, frontal cortex, and remaining brain regions, respectively.

FIG. 14A shows the results of β-catenin silencing of various exemplary siRNA conjugates in rats in lumbar spine, thoracic spine, and cervical spine regions, respectively. FIG. 14B shows the results of β-catenin silencing of various exemplary siRNA conjugates in rats in cerebellum, frontal cortex, and remaining brain regions, respectively.

FIG. 15A shows the conjugated siRNA levels in CSF, as compared to the unconjugated siRNA levels. FIG. 15B shows the conjugated siRNA levels in brain, as compared to the unconjugated siRNA levels. FIG. 15C shows the conjugated siRNA levels in cerebellum, as compared to the unconjugated siRNA levels and control siRNA levels.

FIG. 16A shows the results of SOD1 silencing in rats in lumbar spine, thoracic spine, and cervical spine regions, respectively. FIG. 16B shows the results of SOD1 silencing in rats in cerebellum, frontal cortex, and remaining brain regions, respectively.

DETAILED DESCRIPTION

Figure 1:
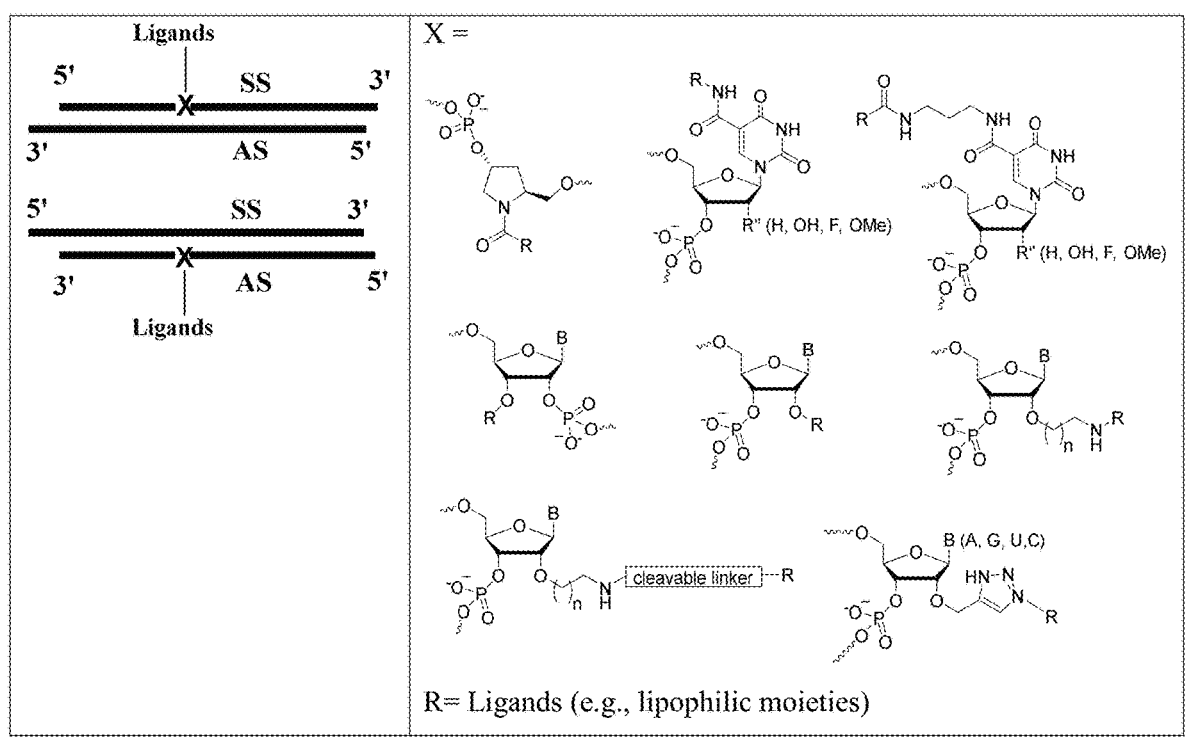
FIG. 1 is a scheme showing ligands, such as lipophilic moieties, that are conjugated to siRNAs at internal positions of the sense or antisense strand (i.e., somewhere within the siRNA sequence).
Figure 2:
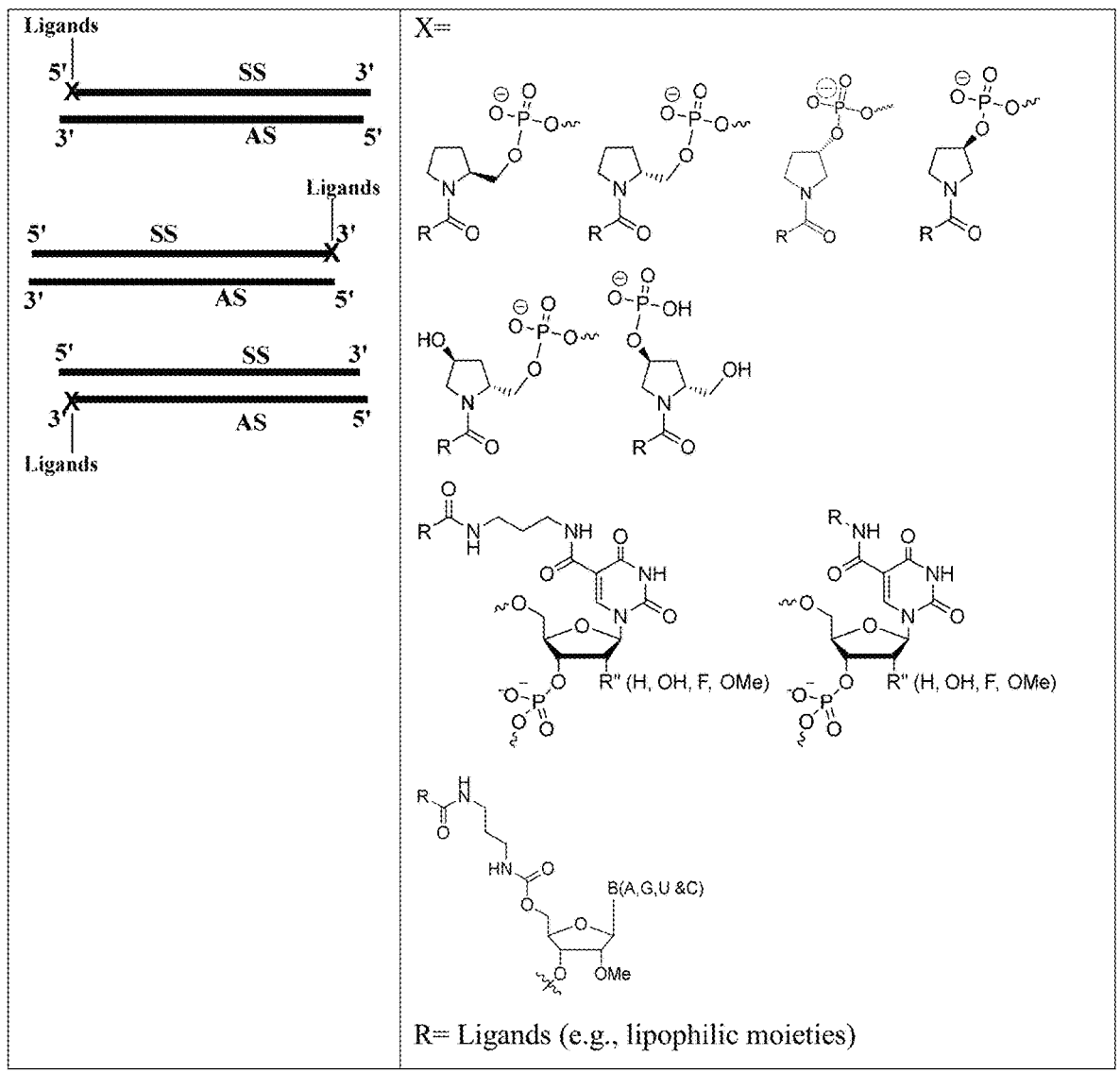
FIG. 2 is a scheme showing ligands, such as lipophilic moieties, that are conjugated to siRNAs through linkers or carriers at the 3'- and/or 5'-ends of the sense or antisense strand.

The inventors have found, inter alia, that conjugating a lipophilic moiety to one or more internal positions on at least one strand of the double-stranded iRNA agent provides surprisingly good results for in vivo intravitreal delivery and intrathecal delivery of the double-stranded iRNAs, resulting in efficient entry of CNS tissues and ocular tissues and are efficiently internalized into cells of the CNS system and ocular system.

One aspect of the invention provides a double-stranded iRNA agent comprising: an antisense strand which is complementary to a target gene; a sense strand which is complementary to said antisense strand; and one or more lipophilic moieties conjugated to one or more internal positions on at least one strand, optionally via a linker or carrier.

The term "lipophile" or "lipophilic moiety" broadly refers to any compound or chemical moiety having an affinity for lipids. One way to characterize the lipophilicity of the lipophilic moiety is by the octanol-water partition coefficient, log $K_{ow}$, where $K_{ow}$ is the ratio of a chemical's concentration in the octanol-phase to its concentration in the aqueous phase of a two-phase system at equilibrium. The octanol-water partition coefficient is a laboratory-measured property of a substance. However, it may also be predicted by using coefficients attributed to the structural components of a chemical which are calculated using first-principle or empirical methods (see, for example, Tetko et al., *J. Chem. Inf Comput. Sci.* 41:1407-21 (2001), which is incorporated herein by reference in its entirety). It provides a thermodynamic measure of the tendency of the substance to prefer a non-aqueous or oily milieu rather than water (i.e. its hydrophilic/lipophilic balance). In principle, a chemical substance is lipophilic in character when its log $K_{ow}$ exceeds 0. Typically, the lipophilic moiety possesses a log $K_{ow}$ exceeding 1, exceeding 1.5, exceeding 2, exceeding 3, exceeding 4, exceeding 5, or exceeding 10. For instance, the log $K_{ow}$ of 6-amino hexanol, for instance, is predicted to be approximately 0.7. Using the same method, the log $K_{ow}$ of cholesteryl N-(hexan-6-ol) carbamate is predicted to be 10.7.

The lipophilicity of a molecule can change with respect to the functional group it carries. For instance, adding a hydroxyl group or amine group to the end of a lipophilic moiety can increase or decrease the partition coefficient (e.g., log $K_{ow}$) value of the lipophilic moiety.

Alternatively, the hydrophobicity of the double-stranded iRNA agent, conjugated to one or more lipophilic moieties, can be measured by its protein binding characteristics. For instance, the unbound fraction in the plasma protein binding assay of the double-stranded iRNA agent can be determined to positively correlate to the relative hydrophobicity of the double-stranded iRNA agent, which can positively correlate to the silencing activity of the double-stranded iRNA agent.

In one embodiment, the plasma protein binding assay determined is an electrophoretic mobility shift assay (EMSA) using human serum albumin protein. An exemplary protocol of this binding assay is illustrated in detail in Example 14. The hydrophobicity of the double-stranded iRNA agent, measured by fraction of unbound siRNA in the binding assay, exceeds 0.15, exceeds 0.2, exceeds 0.25, exceeds 0.3, exceeds 0.35, exceeds 0.4, exceeds 0.45, or exceeds 0.5 for an enhanced in vivo delivery of siRNA.

Accordingly, conjugating the lipophilic moieties to the internal position(s) of the double-stranded iRNA agent provides optimal hydrophobicity for the enhanced in vivo delivery of siRNA.

In certain embodiments, the lipophilic moiety is an aliphatic, cyclic such as alicyclic, or polycyclic such as polyalicyclic compound, such as a steroid (e.g., sterol) or a linear or branched aliphatic hydrocarbon. The lipophilic moiety may generally comprises a hydrocarbon chain, which may be cyclic or acyclic. The hydrocarbon chain may comprise various substituents and/or one or more heteroatoms, such as an oxygen or nitrogen atom. Such lipophilic aliphatic moieties include, without limitation, saturated or unsaturated $C_4$-$C_{30}$ hydrocarbon (e.g., $C_6$-$C_{18}$ hydrocarbon), saturated or unsaturated fatty acids, waxes (e.g., monohydric alcohol esters of fatty acids and fatty diamides), terpenes (e.g., $C_{10}$ terpenes, $C_{15}$ sesquiterpenes, $C_{20}$ diterpenes, $C_{30}$ triterpenes, and $C_{40}$ tetraterpenes), and other polyalicyclic hydrocarbons. For instance, the lipophilic moiety may contain a $C_4$-$C_{30}$ hydrocarbon chain (e.g., $C_4$-$C_{30}$ alkyl or alkenyl). In some embodiment the lipophilic moiety contains a saturated or unsaturated $C_6$-$C_{18}$ hydrocarbon chain (e.g., a linear $C_6$-$C_{18}$ alkyl or alkenyl). In one embodiment, the lipophilic moiety contains a saturated or unsaturated $C_{16}$ hydrocarbon chain (e.g., a linear $C_{16}$ alkyl or alkenyl).

The lipophilic moiety may be attached to the iRNA agent by any method known in the art, including via a functional grouping already present in the lipophilic moiety or introduced into the iRNA agent, such as a hydroxy group (e.g., CO—$CH_2$—OH). The functional groups already present in the lipophilic moiety or introduced into the iRNA agent include, but are not limited to, hydroxyl, amine, carboxylic acid, sulfonate, phosphate, thiol, azide, and alkyne.

Conjugation of the iRNA agent and the lipophilic moiety may occur, for example, through formation of an ether or a carboxylic or carbamoyl ester linkage between the hydroxy and an alkyl group R—, an alkanoyl group RCO— or a substituted carbamoyl group RNHCO—. The alkyl group R may be cyclic (e.g., cyclohexyl) or acyclic (e.g., straight-chained or branched; and saturated or unsaturated). Alkyl group R may be a butyl, pentyl, hexyl, heptyl, octyl, nonyl, decyl, undecyl, dodecyl, tridecyl, tetradecyl, pentadecyl, hexadecyl, heptadecyl or octadecyl group, or the like.

In some embodiments, the lipophilic moiety is conjugated to the double-stranded iRNA agent via a linker a linker containing an ether, thioether, urea, carbonate, amine, amide, maleimide-thioether, disulfide, phosphodiester, sulfonamide linkage, a product of a click reaction (e.g., a triazole from the azide-alkyne cycloaddition), or carbamate.

In another embodiment, the lipophilic moiety is a steroid, such as sterol. Steroids are polycyclic compounds containing a perhydro-1,2-cyclopentanophenanthrene ring system. Steroids include, without limitation, bile acids (e.g., cholic acid, deoxycholic acid and dehydrocholic acid), cortisone, digoxigenin, testosterone, cholesterol, and cationic steroids, such as cortisone. A "cholesterol derivative" refers to a compound derived from cholesterol, for example by substitution, addition or removal of substituents.

In another embodiment, the lipophilic moiety is an aromatic moiety. In this context, the term "aromatic" refers broadly to mono- and polyaromatic hydrocarbons. Aromatic groups include, without limitation, $C_6$-$C_{14}$ aryl moieties comprising one to three aromatic rings, which may be optionally substituted; "aralkyl" or "arylalkyl" groups comprising an aryl group covalently linked to an alkyl group, either of which may independently be optionally substituted or unsubstituted; and "heteroaryl" groups. As used herein, the term "heteroaryl" refers to groups having 5 to 14 ring atoms, preferably 5, 6, 9, or 10 ring atoms; having 6, 10, or 14π electrons shared in a cyclic array, and having, in addition to carbon atoms, between one and about three heteroatoms selected from the group consisting of nitrogen (N), oxygen (O), and sulfur (S).

As employed herein, a "substituted" alkyl, cycloalkyl, aryl, heteroaryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

In some embodiments, the lipophilic moiety is an aralkyl group, e.g., a 2-arylpropanoyl moiety. The structural features of the aralkyl group are selected so that the lipophilic moiety will bind to at least one protein in vivo. In certain embodiments, the structural features of the aralkyl group are selected so that the lipophilic moiety binds to serum, vascular, or cellular proteins. In certain embodiments, the structural features of the aralkyl group promote binding to albumin, an immunoglobulin, a lipoprotein, α-2-macroglubulin, or α-1-glycoprotein.

In certain embodiments, the ligand is naproxen or a structural derivative of naproxen. Procedures for the synthesis of naproxen can be found in U.S. Pat. Nos. 3,904,682 and 4,009,197, which are herein incorporated by reference in their entirety. Naproxen has the chemical name (S)-6-Methoxy-α-methyl-2-naphthaleneacetic acid and the structure is

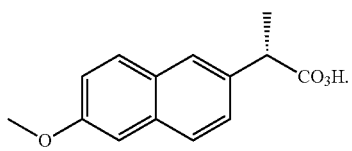

In certain embodiments, the ligand is ibuprofen or a structural derivative of ibuprofen. Procedures for the synthesis of ibuprofen can be found in U.S. Pat. No. 3,228,831, which are herein incorporated by reference in their entirety. The structure of ibuprofen is

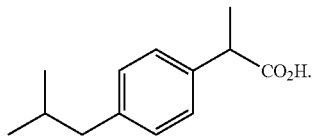

Additional exemplary aralkyl groups are illustrated in U.S. Pat. No. 7,626,014, which is incorporated herein by reference in its entirety.

In another embodiment, suitable lipophilic moieties include lipid, cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, ibuprofen, naproxen, dimethoxytrityl, or phenoxazine.

In some embodiments, the lipophilic moiety is a $C_6$-$C_{30}$ acid (e.g., hexanoic acid, heptanoic acid, octanoic acid, nonanoic acid, decanoic acid, undecanoic acid, dodcanoic acid, tridecanoic acid, tetradecanoic acid, pentadecanoic acid, hexadecanoic acid, heptadecanoic acid, octadecanoic acid, oleic acid, linoleic acid, arachidonic acid, cis-4,7,10, 13,16,19-docosahexanoic acid, vitamin A, vitamin E, cholesterol etc.) or a $C_6$-$C_{30}$ alcohol (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

In certain embodiments, more than one lipophilic moieties can be incorporated into the double-strand iRNA agent, particularly when the lipophilic moiety has a low lipophilicity or hydrophobicity. In one embodiment, two or more lipophilic moieties are incorporated into the same strand of the double-strand iRNA agent. In one embodiment, each strand of the double-strand iRNA agent has one or more lipophilic moieties incorporated. In one embodiment, two or more lipophilic moieties are incorporated into the same position (i.e., the same nucleobase, same sugar moiety, or same internucleosidic linkage) of the double-strand iRNA agent. This can be achieved by, e.g., conjugating the two or more lipophilic moieties via a carrier, and/or conjugating the two or more lipophilic moieties via a branched linker, and/or conjugating the two or more lipophilic moieties via one or more linkers, with one or more linkers linking the lipophilic moieties consecutively.

The lipophilic moiety may be conjugated to the iRNA agent via a direct attachment to the ribosugar of the iRNA agent. Alternatively, the lipophilic moiety may be conjugated to the double-strand iRNA agent via a linker or a carrier.

In certain embodiments, the lipophilic moiety may be conjugated to the iRNA agent via one or more linkers (tethers).

In one embodiment, the lipophilic moiety is conjugated to the double-stranded iRNA agent via a linker containing an ether, thioether, urea, carbonate, amine, amide, maleimide-thioether, disulfide, phosphodiester, sulfonamide linkage, a product of a click reaction (e.g., a triazole from the azide-alkyne cycloaddition), or carbamate. Some exemplary linkages are illustrated in FIG. 1, Examples 2, 3, 5, 6, and 7.

Linkers/Tethers

Linkers/Tethers are connected to the lipophilic moiety at a "tethering attachment point (TAP)." Linkers/Tethers may include any $C_1$-$C_{100}$ carbon-containing moiety, (e.g. $C_1$-$C_{75}$, $C_1$-$C_{50}$, $C_1$-$C_{20}$, $C_1$-$C_{10}$; $C_1$, $C_2$, $C_3$, $C_4$, $C_6$, $C_6$, $C_7$, $C_8$, $C_9$, or $C_{10}$), and may have at least one nitrogen atom. In certain embodiments, the nitrogen atom forms part of a terminal amino or amido (NHC(O)—) group on the linker/tether, which may serve as a connection point for the lipophilic moiety. Non-limited examples of linkers/tethers (underlined) include TAP—$(CH_2)_n$NH—TAP—C(O)$(CH_2)_n$NH—; TAP-NR""$(CH_2)_n$NH—, TAP—C(O)—$(CH_2)_n$—C(O)—; TAP—C(O)—$(CH_2)_n$—C(O)O—; TAP—C(O)—O—; TAP—C(O)—$(CH_2)_n$—NH—C(O)—; TAP—C(O)—$(CH_2)_n$—; TAP—C(O)—NH—; TAP—C(O)—; TAP—$(CH_2)_n$—C(O)—; TAP—$(CH_2)_n$—C(O)O—; TAP—$(CH_2)_n$—; or TAP—$(CH_2)_n$—NH—C(O)—; in which n is 1-20 (e.g., 1, 2, 3, 4, 5, 6, 7, 8, 9, 10, 11, 12, 13, 14, 15, 16, 17, 18, 19, or 20) and R"" is $C_1$-$C_6$ alkyl. Preferably, n is 5, 6, or 11. In other embodiments, the nitrogen may form part of a terminal oxyamino group, e.g., —ONH$_2$, or hydrazino group, —NHNH$_2$. The linker/tether may optionally be substituted, e.g., with hydroxy, alkoxy, perhaloalkyl, and/or optionally inserted with one or more additional heteroatoms, e.g., N, O, or S. Preferred tethered ligands may include, e.g., TAP—$(CH_2)_n$NH(LIGAND); TAP—C(O)$(CH_2)_n$NH(LIGAND); TAP-NR""$(CH_2)_n$NH (LIGAND); TAP—$(CH_2)_n$ONH(LIGAND); TAP—C(O)$(CH_2)_n$ONH(LIGAND); TAP-NR""$(CH_2)_n$ONH(LIGAND); TAP—$(CH_2)_n$NHNH$_2$(LIGAND), TAP—C(O)$(CH_2)_n$NHNH$_2$(LIGAND); TAP-NR""$(CH_2)_n$NHNH$_2$(LIGAND); TAP—C(O)—$(CH_2)_n$—C(O)(LIGAND); TAP—C(O)—$(CH_2)_n$—C(O)O(LIGAND); TAP—C(O)—O(LIGAND); TAP—C(O)—$(CH_2)_n$—NH—C(O)(LIGAND); TAP—C(O)—$(CH_2)_n$(LIGAND); TAP—C(O)—NH(LIGAND); TAP—C(O)(LIGAND); TAP—$(CH_2)_n$—C(O) (LIGAND); TAP—$(CH_2)_n$—C(O)O(LIGAND); TAP—$(CH_2)_n$(LIGAND); or TAP—$(CH_2)_n$—NH—C(O) (LIGAND). In some embodiments, amino terminated linkers/tethers (e.g., NH$_2$, ONH$_2$, NH$_2$NH$_2$) can form an imino bond (i.e., C=N) with the ligand. In some embodiments, amino terminated linkers/tethers (e.g., NH$_2$, ONH$_2$, NH$_2$NH$_2$) can acylated, e.g., with C(O)CF$_3$.

In some embodiments, the linker/tether can terminate with a mercapto group (i.e., SH) or an olefin (e.g., CH=CH$_2$). For example, the tether can be TAP—$(CH_2)_n$—SH, TAP—C(O)$(CH_2)_n$SH, TAP—$(CH_2)_n$—(CH=CH$_2$), or TAP—C(O)(CH$_2$)$_n$(CH=CH$_2$), in which n can be as described elsewhere. The tether may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments, the linker/tether may include an electrophilic moiety, preferably at the terminal position of the linker/tether. Exemplary electrophilic moieties include, e.g., an aldehyde, alkyl halide, mesylate, tosylate, nosylate, or brosylate, or an activated carboxylic acid ester, e.g. an NHS ester, or a pentafluorophenyl ester. Preferred linkers/tethers (underlined) include TAP—(CH$_2$)$_n$CHO; TAP—C(O)(CH$_2$)$_n$CHO; or TAP—NR""(CH$_2$)$_n$CHO, in which n is 1-6 and R"" is C$_1$-C$_6$ alkyl; or TAP—(CH$_2$)$_n$C(O)ONHS; TAP—C(O)(CH$_2$)$_n$C(O)ONHS; or TAP—NR""(CH$_2$)$_n$C(O)ONHS, in which n is 1-6 and R"" is C$_1$-C$_6$ alkyl; TAP—(CH$_2$)$_n$C(O)OC$_6$F$_5$; TAP—C(O)(CH$_2$)$_n$C(O) OC$_6$F$_5$; or TAP—NR""(CH$_2$)$_n$C(O) OC$_6$F$_5$, in which n is 1-11 and R"" is C$_1$-C$_6$ alkyl; or —(CH$_2$)$_n$CH$_2$LG; TAP—C(O)(CH$_2$)$_n$CH$_2$LG; or TAP—NR""(CH$_2$)$_n$CH$_2$LG, in which n can be as described elsewhere and R"" is C$_1$-C$_6$ alkyl (LG can be a leaving group, e.g., halide, mesylate, tosylate, nosylate, brosylate). Tethering can be carried out by coupling a nucleophilic group of a ligand, e.g., a thiol or amino group with an electrophilic group on the tether.

In other embodiments, it can be desirable for the monomer to include a phthalimido group (K) at the terminal position of the linker/tether.

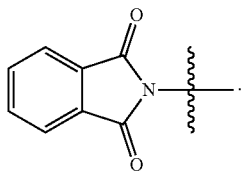

K

In other embodiments, other protected amino groups can be at the terminal position of the linker/tether, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

Any of the linkers/tethers described herein may further include one or more additional linking groups, e.g., —O—(CH$_2$)$_n$—, —(CH$_2$)$_n$—SS—, —(CH$_2$)$_n$—, or —(CH=CH)—.

Cleavable Linkers Tethers

In some embodiments, at least one of the linkers/tethers can be a redox cleavable linker, an acid cleavable linker, an esterase cleavable linker, a phosphatase cleavable linker, or a peptidase cleavable linker.

In one embodiment, at least one of the linkers/tethers can be a reductively cleavable linker (e.g., a disulfide group).

In one embodiment, at least one of the linkers/tethers can be an acid cleavable linker (e.g., a hydrazone group, an ester group, an acetal group, or a ketal group).

In one embodiment, at least one of the linkers/tethers can be an esterase cleavable linker (e.g., an ester group).

In one embodiment, at least one of the linkers/tethers can be a phosphatase cleavable linker (e.g., a phosphate group).

In one embodiment, at least one of the linkers/tethers can be a peptidase cleavable linker (e.g., a peptide bond).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some tethers will have a linkage group that is cleaved at a preferred pH, thereby releasing the iRNA agent from a ligand (e.g., a targeting or cell-permeable ligand, such as cholesterol) inside the cell, or into the desired compartment of the cell.

A chemical junction (e.g., a linking group) that links a ligand to an iRNA agent can include a disulfide bond. When the iRNA agent/ligand complex is taken up into the cell by endocytosis, the acidic environment of the endosome will cause the disulfide bond to be cleaved, thereby releasing the iRNA agent from the ligand (Quintana et al., *Pharm Res.* 19:1310-1316, 2002; Patri et al., *Curr. Opin. Curr. Biol.* 6:466-471, 2002). The ligand can be a targeting ligand or a second therapeutic agent that may complement the therapeutic effects of the iRNA agent.

A tether can include a linking group that is cleavable by a particular enzyme. The type of linking group incorporated into a tether can depend on the cell to be targeted by the iRNA agent. For example, an iRNA agent that targets an mRNA in liver cells can be conjugated to a tether that includes an ester group. Liver cells are rich in esterases, and therefore the tether will be cleaved more efficiently in liver cells than in cell types that are not esterase-rich. Cleavage of the tether releases the iRNA agent from a ligand that is attached to the distal end of the tether, thereby potentially enhancing silencing activity of the iRNA agent. Other cell-types rich in esterases include cells of the lung, renal cortex, and testis.

Tethers that contain peptide bonds can be conjugated to iRNA agents target to cell types rich in peptidases, such as liver cells and synoviocytes. For example, an iRNA agent targeted to synoviocytes, such as for the treatment of an inflammatory disease (e.g., rheumatoid arthritis), can be conjugated to a tether containing a peptide bond.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue, e.g., tissue the iRNA agent would be exposed to when administered to a subject. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, ketals, acetals, esters, and esters of amino acids. Acid cleavable groups can have the general formula C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide cleavable linking groups have the general formula NHCHR$^1$C(O)NHCHR$^2$C(O)—, where R$^1$ and R$^2$ are the R groups of the two adjacent amino acids. These candidates can be evaluated using methods analogous to those described above.

Biocleavable Linkers Tethers

The linkers can also includes biocleavable linkers that are nucleotide and non-nucleotide linkers or combinations thereof that connect two parts of a molecule, for example, one or both strands of two individual siRNA molecule to generate a bis(siRNA). In some embodiments, mere electrostatic or stacking interaction between two individual siRNAs can represent a linker. The non-nucleotide linkers include tethers or linkers derived from monosaccharides, disaccharides, oligosaccharides, and derivatives thereof, aliphatic, alicyclic, heterocyclic, and combinations thereof.

In some embodiments, at least one of the linkers (tethers) is a bio-clevable linker selected from the group consisting of DNA, RNA, disulfide, amide, functionalized monosaccharides or oligosaccharides of galactosamine, glucosamine, glucose, galactose, and mannose, and combinations thereof.

In one embodiment, the bio-cleavable carbohydrate linker may have 1 to 10 saccharide units, which have at least one anomeric linkage capable of connecting two siRNA units. When two or more saccharides are present, these units can be linked via 1-3, 1-4, or 1-6 sugar linkages, or via alkyl chains.

Exemplary bio-cleavable linkers include:
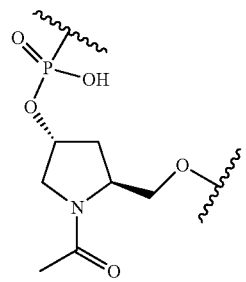
Q198
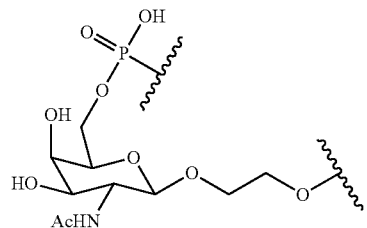
Q303
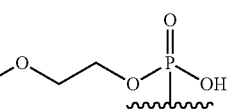
Q48
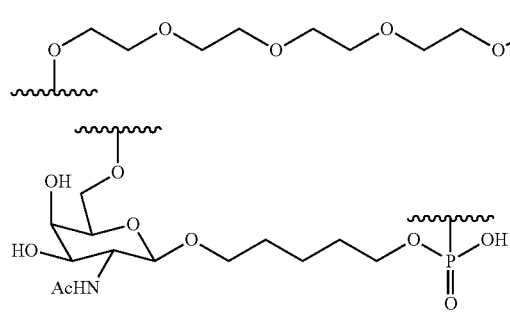
Q304
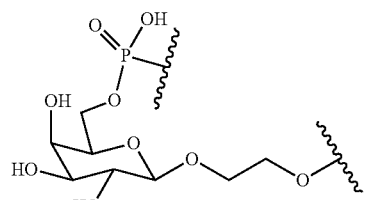
Q305
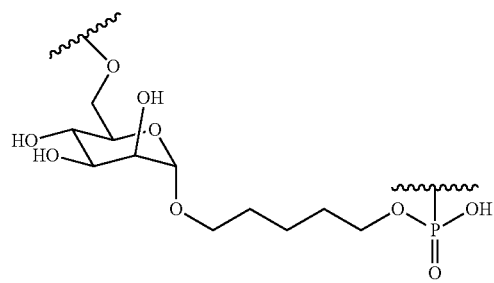
Q306
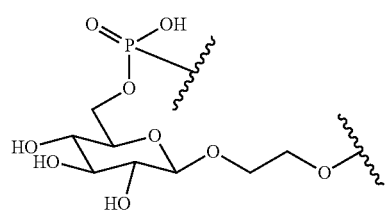
Q312
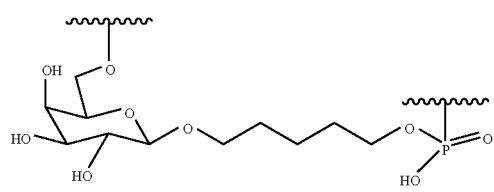
Q313
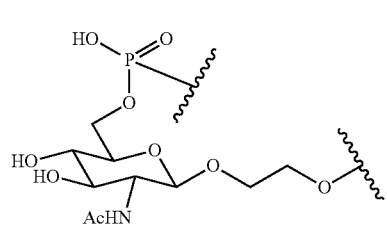
Q314
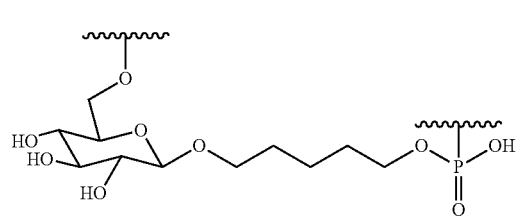
Q315
Q316
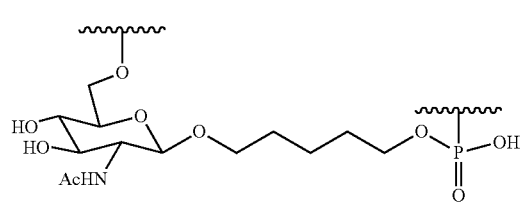
Q317

21
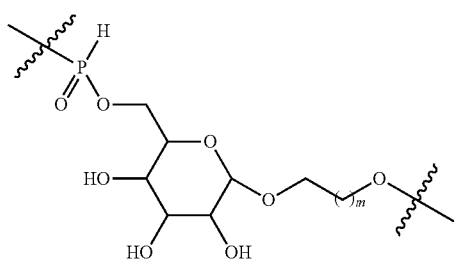
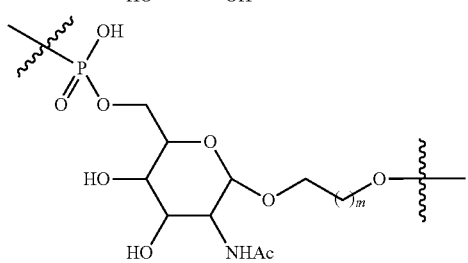
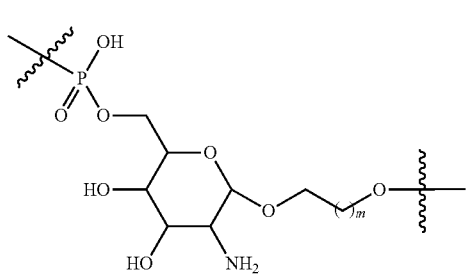
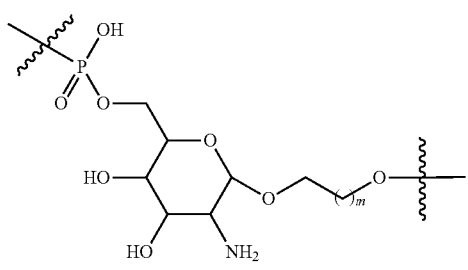
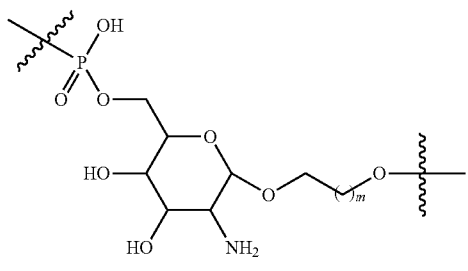
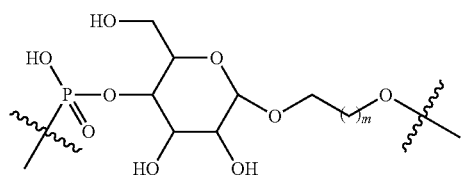
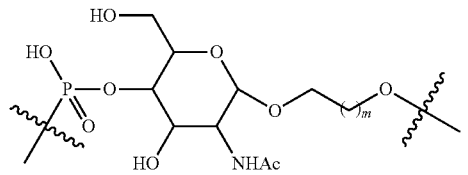
22
-continued
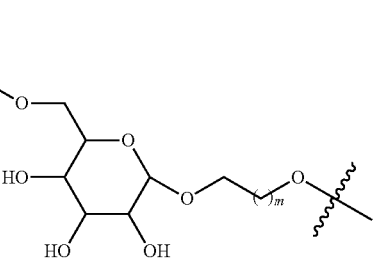
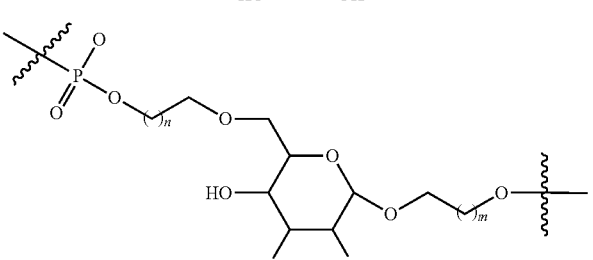
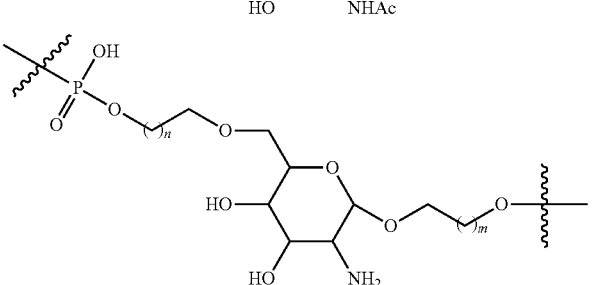
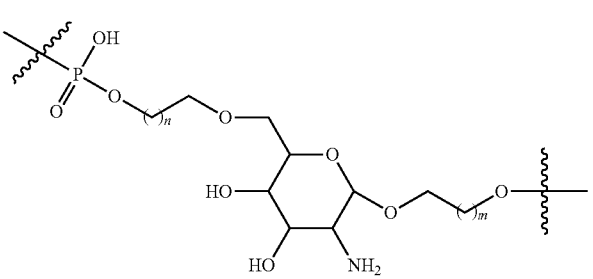
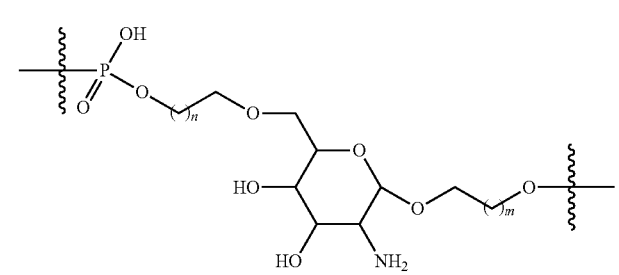
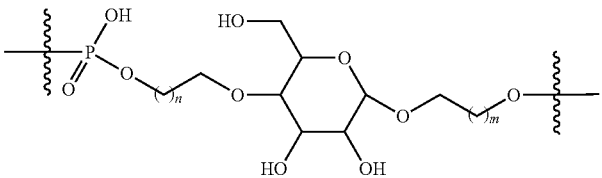
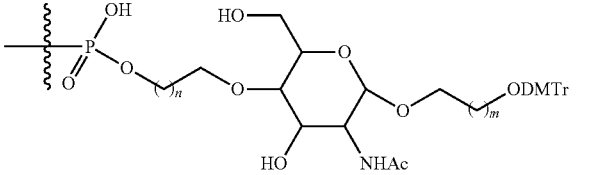

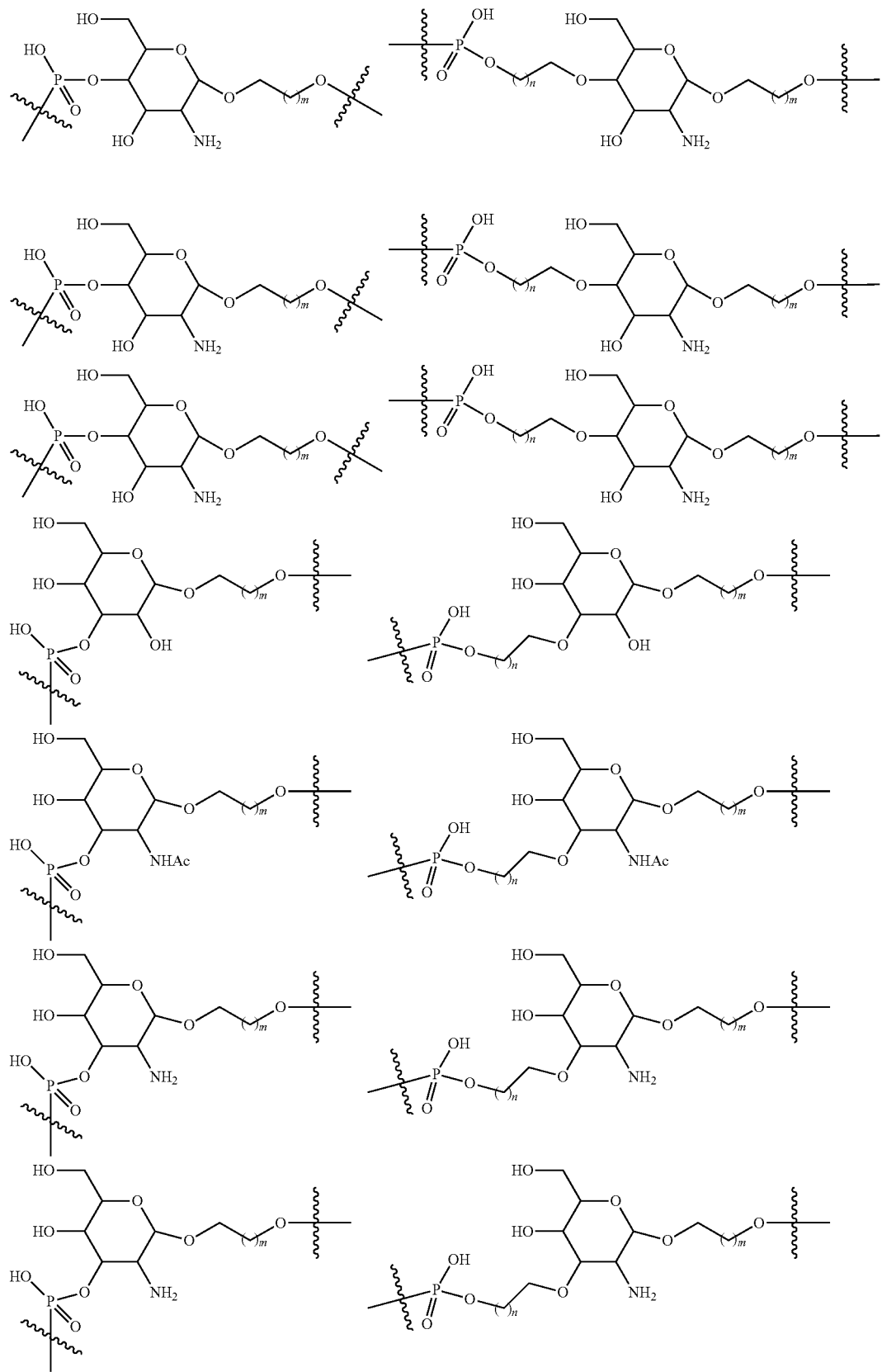

-continued
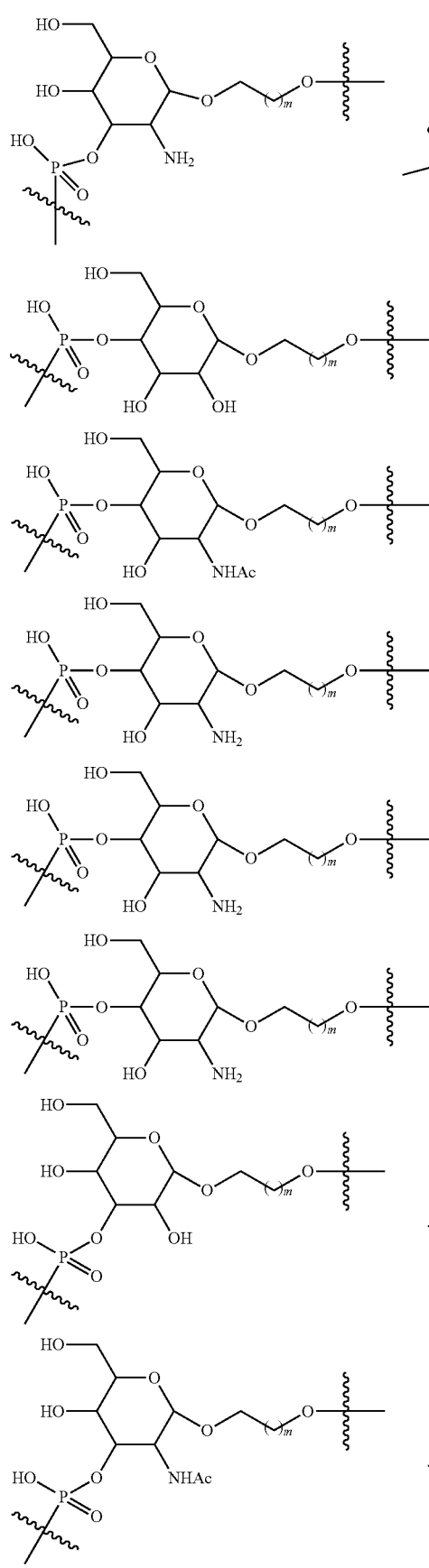
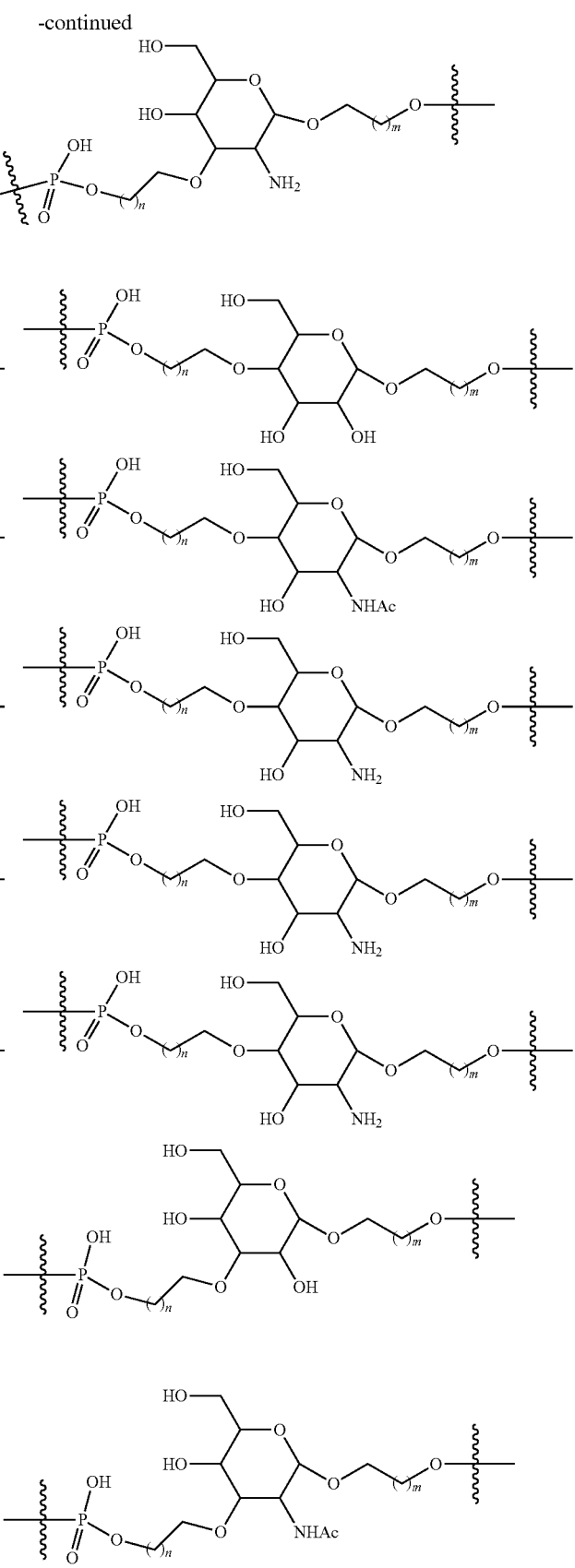

-continued
27
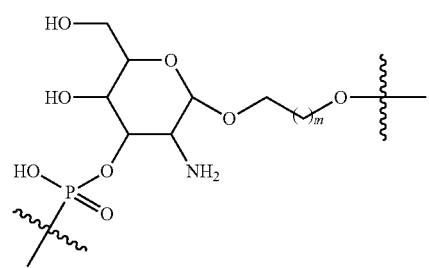
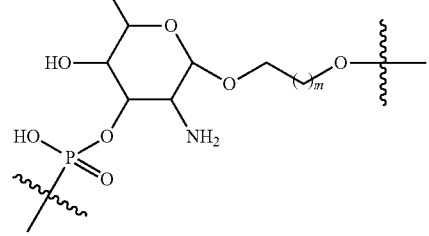
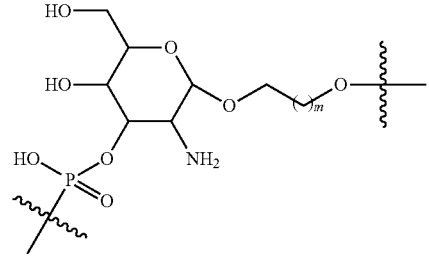
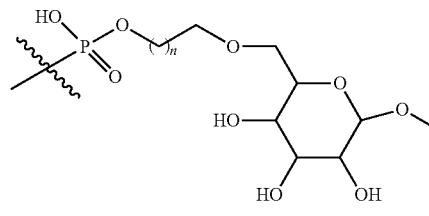

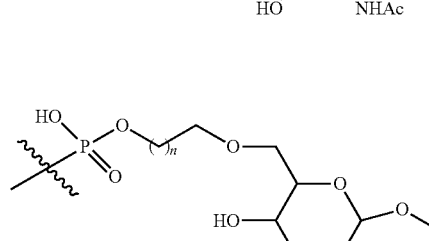
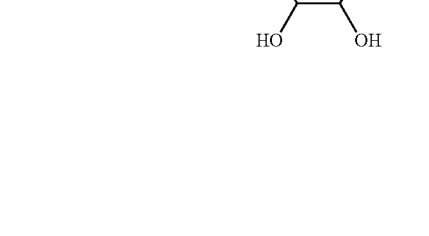
28
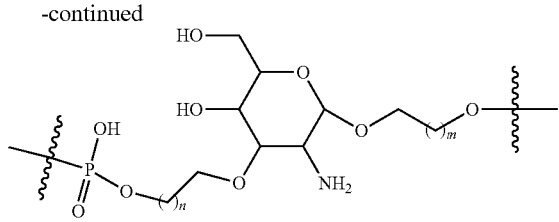
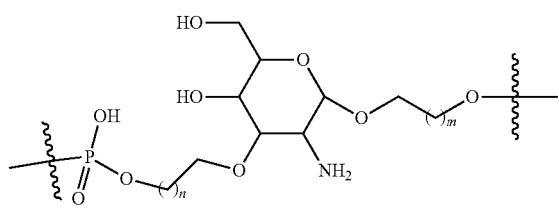
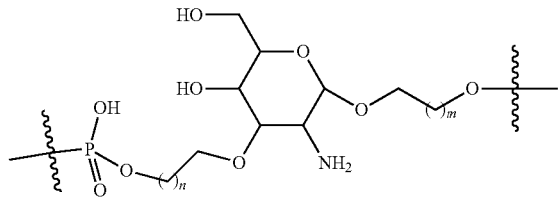
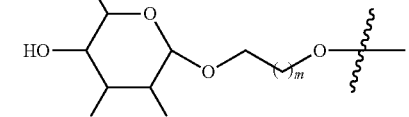
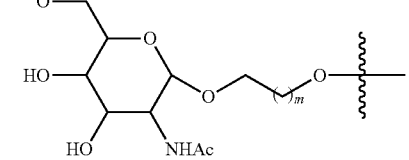
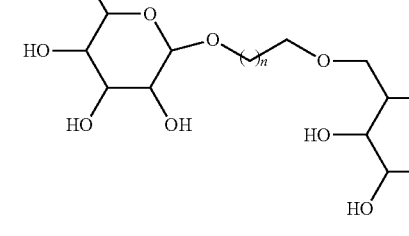

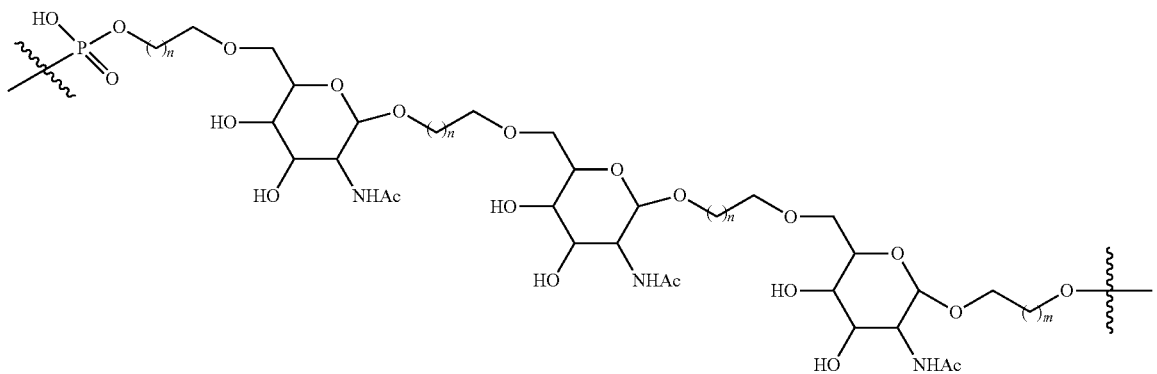
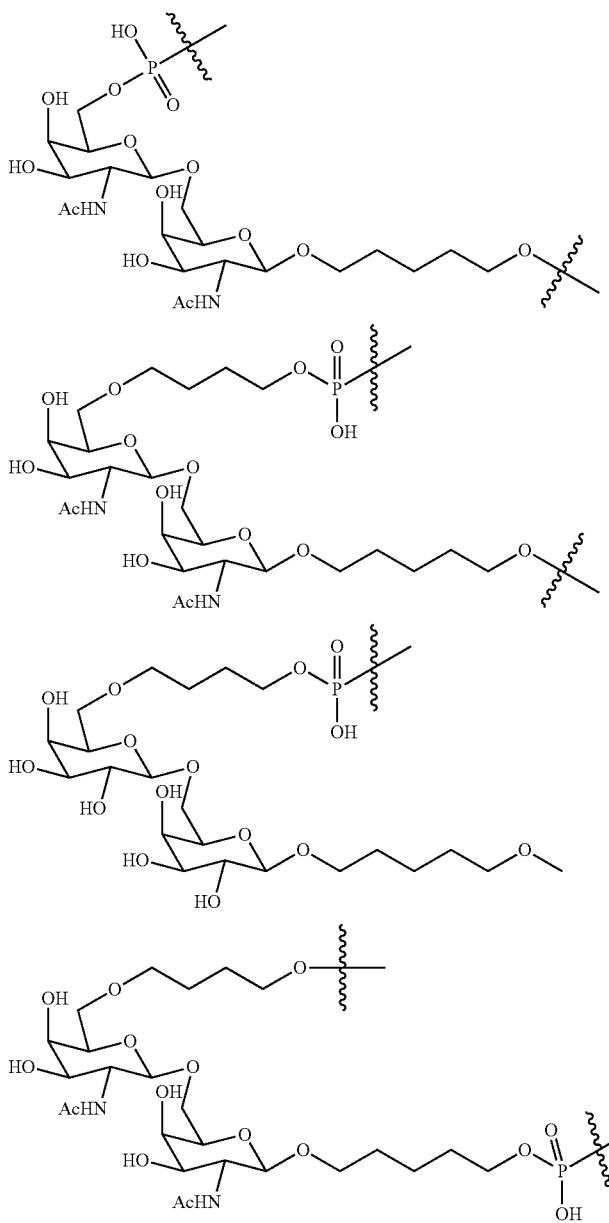

-continued
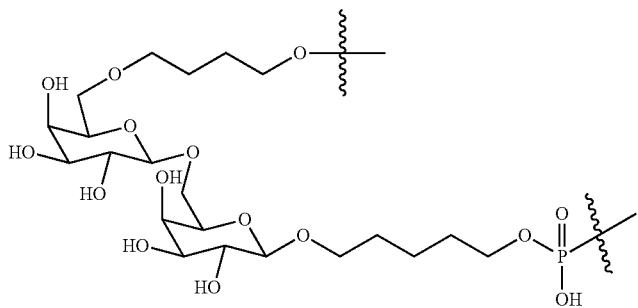
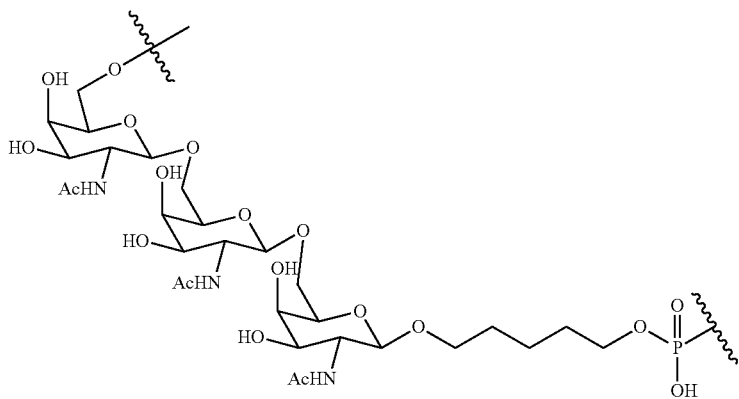
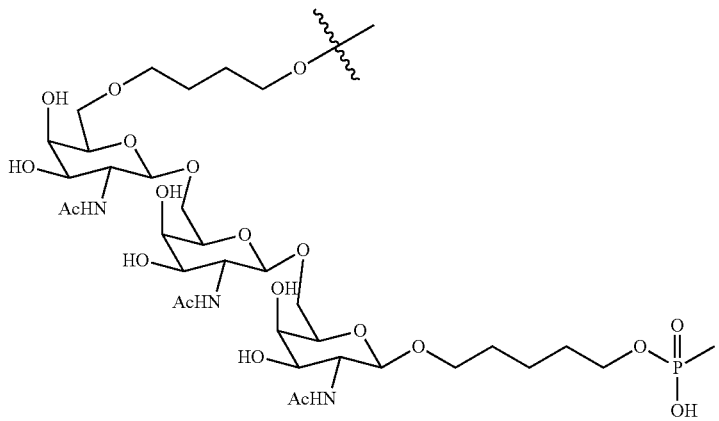
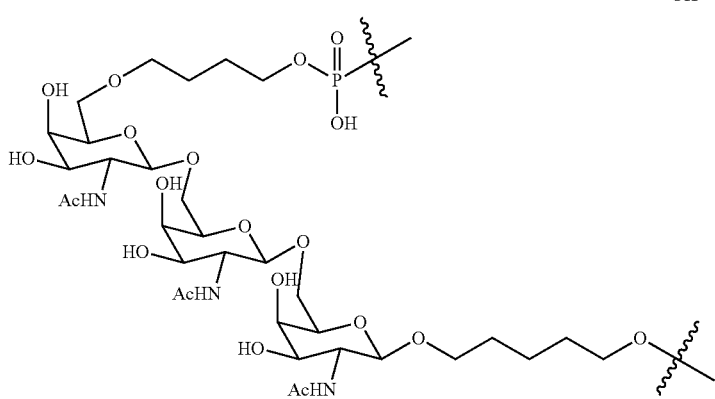

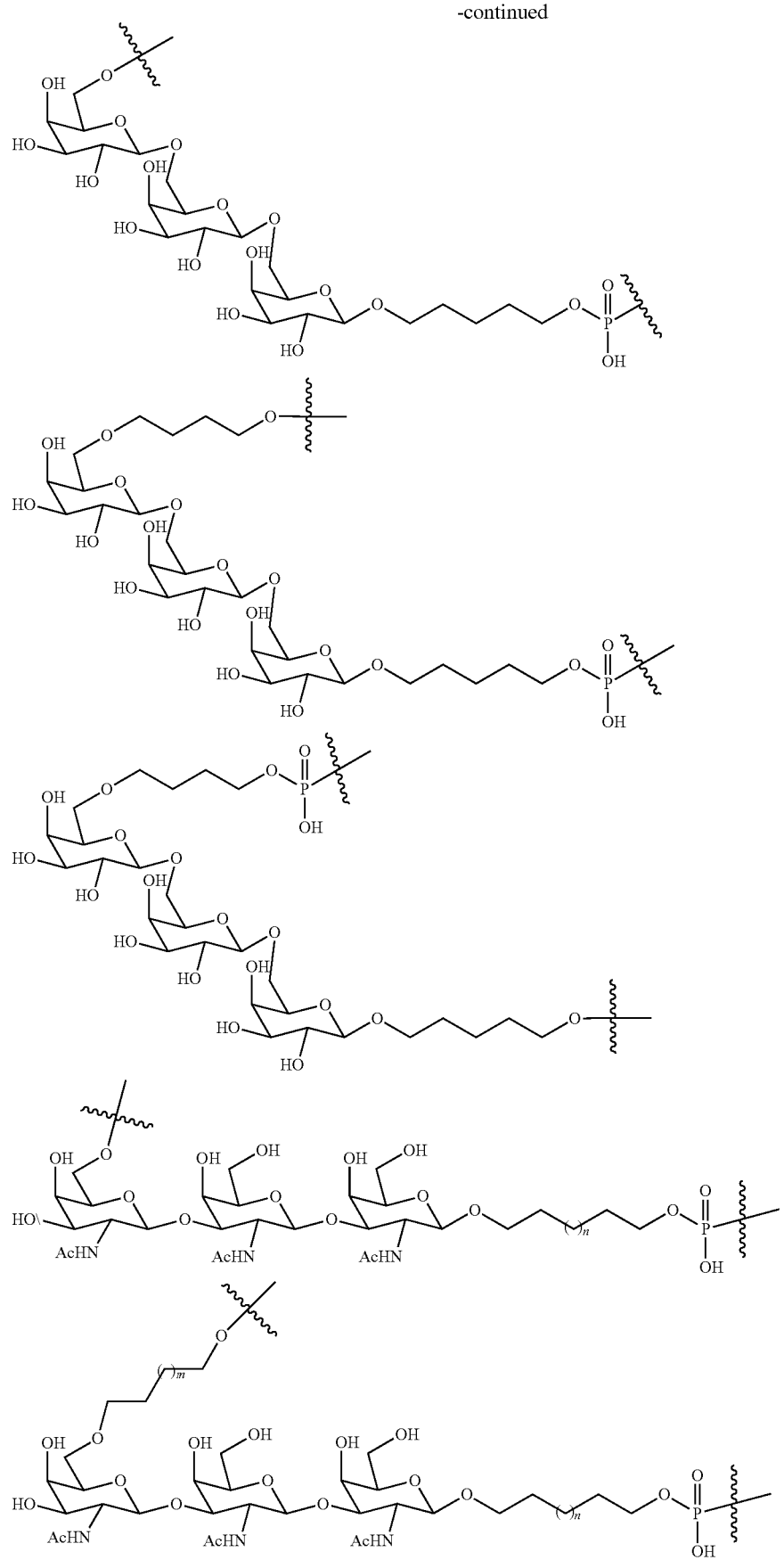

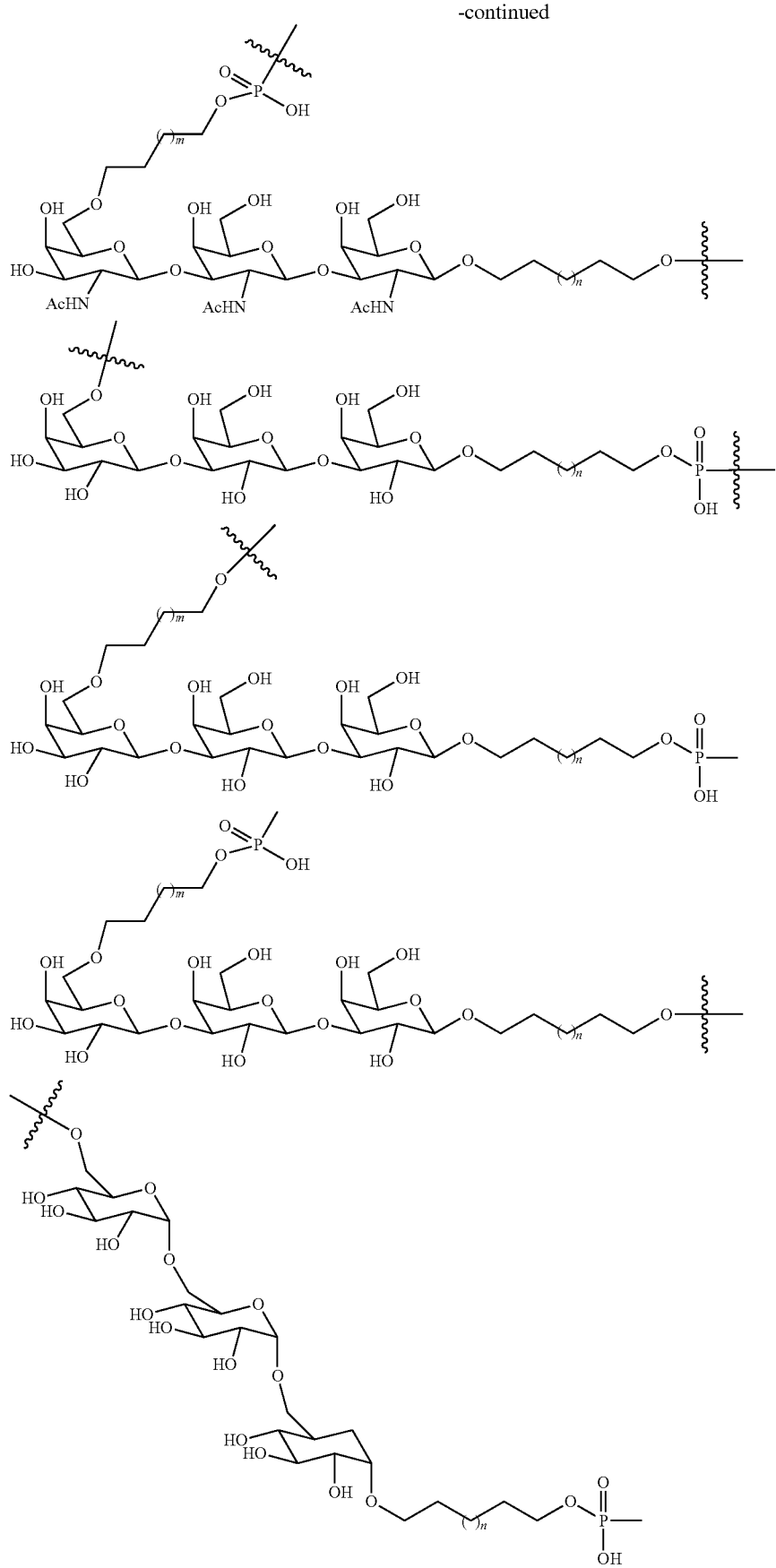

-continued
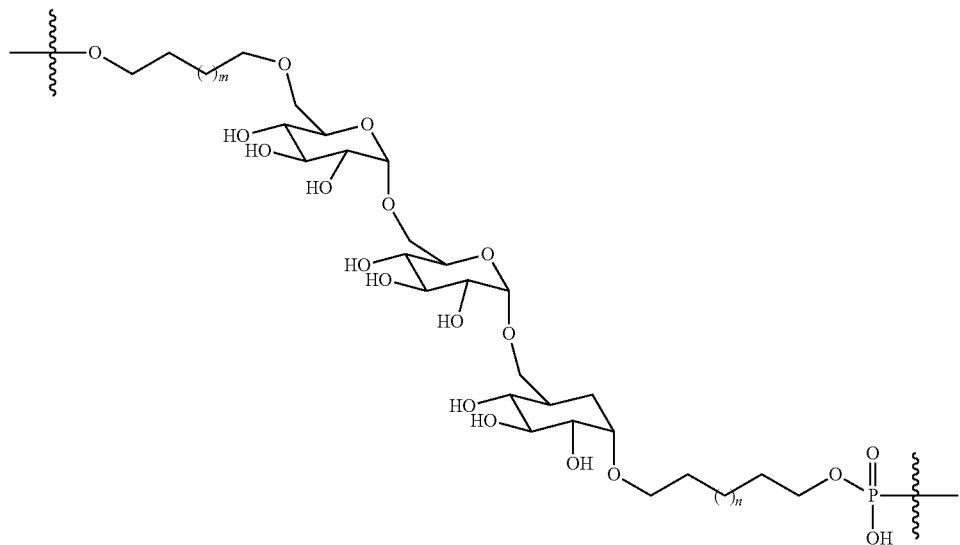
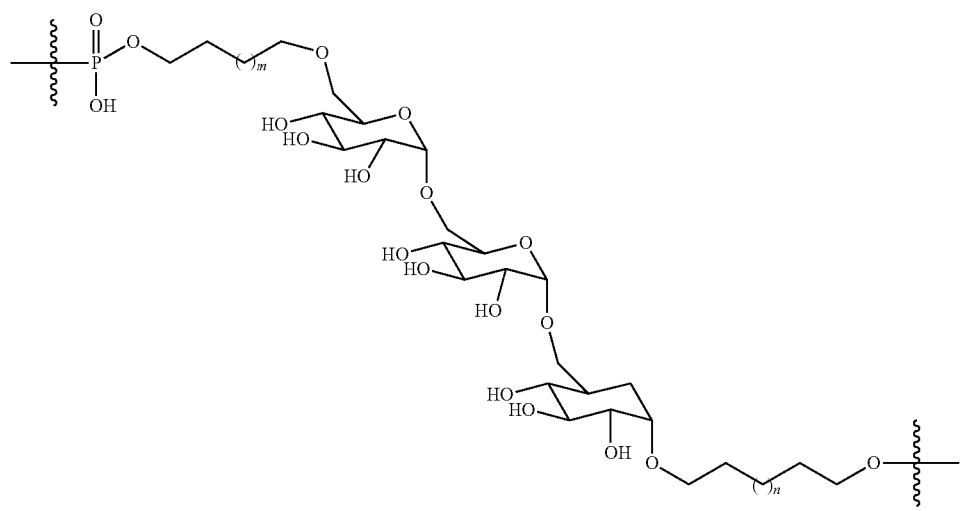
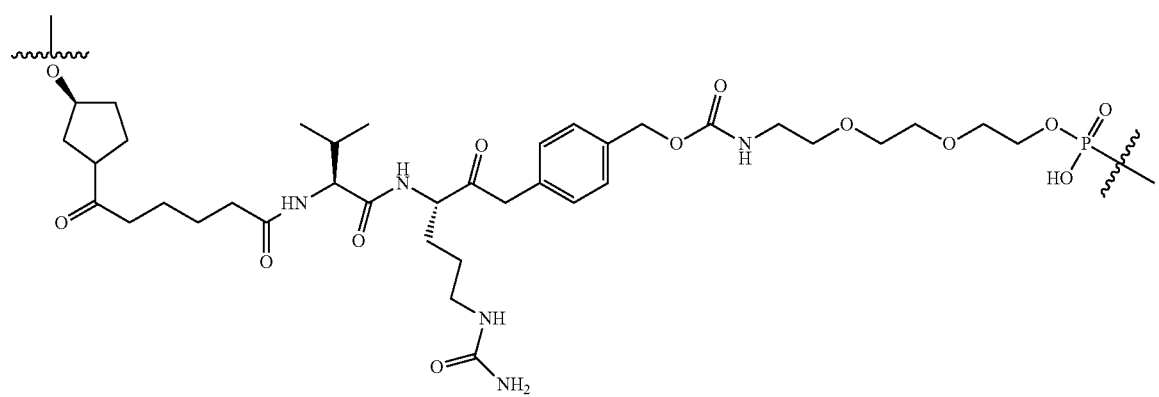
and

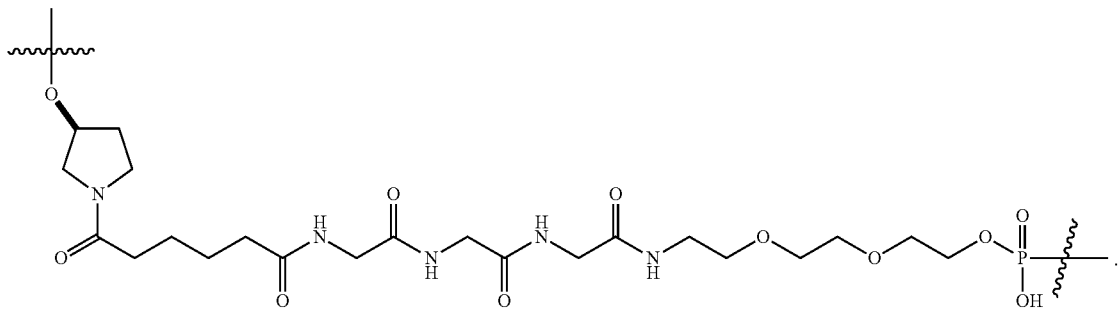

Additional exemplary bio-cleavable linkers are illustrated in Schemes 28-30.

More discussion about the biocleavable linkers may be found in PCT application No. PCT/US18/14213, entitled "Endosomal Cleavable Linkers," filed on Jan. 18, 2018, the content of which is incorporated herein by reference in its entirety.

Carriers

In certain embodiments, the lipophilic moiety is conjugated to the iRNA agent via a carrier that replaces one or more nucleotide(s).

The carrier can be a cyclic group or an acyclic group. In one embodiment, the cyclic group is selected from the group consisting of pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalin. In one embodiment, the acyclic group is a moiety based on a serinol backbone or a diethanolamine backbone.

In some embodiments, the carrier replaces one or more nucleotide(s) in the internal position(s) of the double-stranded iRNA agent.

In other embodiments, the carrier replaces the nucleotides at the terminal end of the sense strand or antisense strand. In one embodiment, the carrier replaces the terminal nucleotide on the 3' end of the sense strand, thereby functioning as an end cap protecting the 3' end of the sense strand. In one embodiment, the carrier is a cyclic group having an amine, for instance, the carrier may be pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, or decalinyl.

A ribonucleotide subunit in which the ribose sugar of the subunit has been so replaced is referred to herein as a ribose replacement modification subunit (RRMS). The carrier can be a cyclic or acyclic moiety and include two "backbone attachment points" (e.g., hydroxyl groups) and a ligand (e.g., the lipophilic moiety). The lipophilic moiety can be directly attached to the carrier or indirectly attached to the carrier by an intervening linker/tether, as described above.

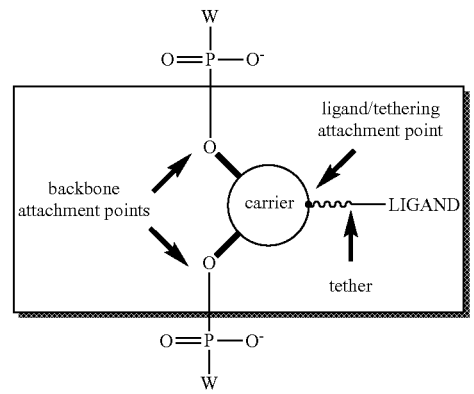

The ligand-conjugated monomer subunit may be the 5' or 3' terminal subunit of the iRNA molecule, i.e., one of the two "W" groups may be a hydroxyl group, and the other "W" group may be a chain of two or more unmodified or modified ribonucleotides. Alternatively, the ligand-conjugated monomer subunit may occupy an internal position, and both "W" groups may be one or more unmodified or modified ribonucleotides. More than one ligand-conjugated monomer subunit may be present in an iRNA agent.

Sugar Replacement-Based Monomers, e.g., Ligand-Conjugated Monomers (Cyclic)

Cyclic sugar replacement-based monomers, e.g., sugar replacement-based ligand-conjugated monomers, are also referred to herein as RRMS monomer compounds. The carriers may have the general formula (LCM-2) provided below (In that structure preferred backbone attachment points can be chosen from $R^1$ or $R^2$; $R^3$ or $R^4$; or $R^9$ and $R^{10}$ if Y is $CR^9R^{10}$ (two positions are chosen to give two backbone attachment points, e.g., $R^1$ and $R^4$, or $R^4$ and $R^9$)). Preferred tethering attachment points include $R^7$; $R^5$ or $R^6$ when X is $CH_2$. The carriers are described below as an entity, which can be incorporated into a strand. Thus, it is understood that the structures also encompass the situations wherein one (in the case of a terminal position) or two (in the case of an internal position) of the attachment points, e.g., $R^1$ or $R^2$; $R^3$ or $R^4$; or $R^9$ or $R^{10}$ (when Y is $CR^9R^{10}$), is connected to the phosphate, or modified phosphate, e.g., sulfur containing, backbone. E.g., one of the above-named R groups can be $—CH_2—$, wherein one bond is connected to the carrier and one to a backbone atom, e.g., a linking oxygen or a central phosphorus atom.

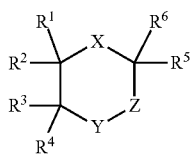

(LCM-2)

wherein:
X is N(CO)R$^7$, NR$^7$ or CH$_2$;
Y is NR$^8$, O, S, CR$^9$R$^{10}$;
Z is CR$^{11}$R$^{12}$ or absent;
Each of R$^1$, R$^2$, R$^3$, R$^4$, R$^9$, and R$^{10}$ is, independently, H, OR$^a$, or (CH$_2$)$_n$OR$^b$, provided that at least two of R$^1$, R$^2$, R$^3$, R$^4$, R$^9$, and R$^{10}$ are OR$^a$ and/or (CH$_2$)$_n$OR$^b$;
Each of R$^5$, R$^6$, R$^{11}$, and R$^{12}$ is, independently, a ligand, H, C$_1$-C$_6$ alkyl optionally substituted with 1-3 R$^{13}$, or C(O)NHR$^7$; or R$^5$ and R$^{11}$ together are C$_3$-C$_8$ cycloalkyl optionally substituted with R$^{14}$;
R$^7$ can be a ligand, e.g., R$^7$ can be R$^d$, or R$^7$ can be a ligand tethered indirectly to the carrier, e.g., through a tethering moiety, e.g., C$_1$-C$_{20}$ alkyl substituted with NR$^c$R$^d$; or C$_1$-C$_{20}$ alkyl substituted with NHC(O)R$^d$;
R$^8$ is H or C$_1$-C$_6$ alkyl;
R$^{13}$ is hydroxy, C$_1$-C$_4$ alkoxy, or halo;
R$^{14}$ is NR$^c$R$^7$;
R$^{15}$ is C$_1$-C$_6$ alkyl optionally substituted with cyano, or C$_2$-C$_6$ alkenyl;
R$^{16}$ is C$_1$-C$_{10}$ alkyl;
R$^{17}$ is a liquid or solid phase support reagent;
L is —C(O)(CH$_2$)$_q$C(O)—, or —C(O)(CH$_2$)$_q$S—;
R$^a$ is a protecting group, e.g., CAr$_3$; (e.g., a dimethoxytrityl group) or Si(X$^{5'}$)(X$^{5''}$)(X$^{5'''}$) in which (X$^{5'}$), (X$^{5''}$), and (X$^{5'''}$) are as described elsewhere.
R$^b$ is P(O)(O$^-$)H, P(OR$^{15}$)N(R$^{16}$)$_2$ or L-R$^{17}$;
R$^c$ is H or C$_1$-C$_6$ alkyl;
R$^d$ is H or a ligand;
Each Ar is, independently, C$_6$-C$_{10}$ aryl optionally substituted with C$_1$-C$_4$ alkoxy;
n is 1-4; and q is 0-4.

Exemplary carriers include those in which, e.g., X is N(CO)R$^7$ or NR$^7$, Y is CR$^9$R$^{10}$, and Z is absent; or X is N(CO)R$^7$ or NR$^7$, Y is CR$^9$R$^{10}$, and Z is CR$^{11}$R$^{12}$; or X is N(CO)R$^7$ or NR$^7$, Y is NR$^8$, and Z is CR$^{11}$R$^{12}$; or X is N(CO)R$^7$ or NR$^7$, Y is O, and Z is CR$^{11}$R$^{12}$; or X is CH$_2$; Y is CR$^9$R$^{10}$; Z is CR$^{11}$R$^{12}$, and R$^5$ and R$^{11}$ together form C$_6$ cycloalkyl (H, z=2), or the indane ring system, e.g., X is CH$_2$; Y is CR$^9$R$^{10}$; Z is CR$^{11}$R$^{12}$, and R$^5$ and R$^{11}$ together form C$_5$ cycloalkyl (H, z=1).

In certain embodiments, the carrier may be based on the pyrroline ring system or the 4-hydroxyproline ring system, e.g., X is N(CO)R$^7$ or NR$^7$, Y is CR$^9$R$^{10}$, and Z is absent (D).

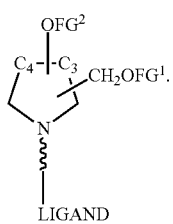

D

OFG$^1$ is preferably attached to a primary carbon, e.g., an exocyclic alkylene group, e.g., a methylene group, connected to one of the carbons in the five-membered ring (—CH$_2$OFG$^1$ in D). OFG$^2$ is preferably attached directly to one of the carbons in the five-membered ring (—OFG$^2$ in D). For the pyrroline-based carriers, —CH$_2$OFG$^1$ may be attached to C-2 and OFG$^2$ may be attached to C-3; or —CH$_2$OFG$^1$ may be attached to C-3 and OFG$^2$ may be attached to C-4. In certain embodiments, CH$_2$OFG$^1$ and OFG$^2$ may be geminally substituted to one of the above-referenced carbons. For the 3-hydroxyproline-based carriers, —CH$_2$OFG$^1$ may be attached to C-2 and OFG$^2$ may be attached to C-4. The pyrroline- and 4-hydroxyproline-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above Accordingly, all cis trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen. Preferred examples of carrier D include the following:

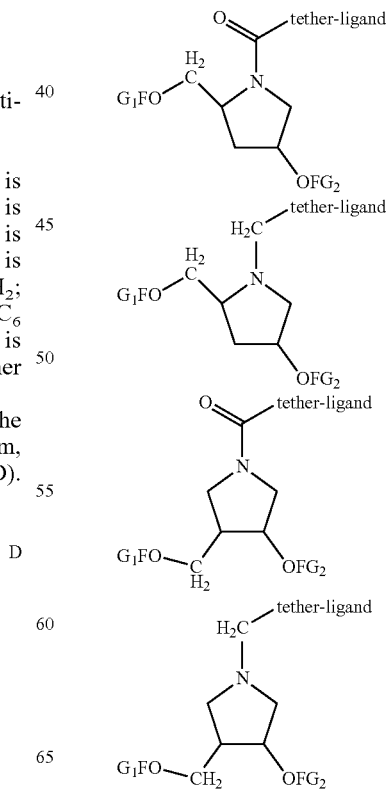

-continued

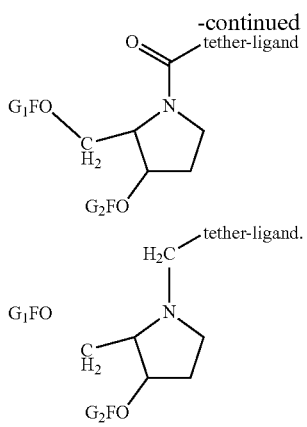

tether-ligand tether-ligand.

In certain embodiments, the carrier may be based on the piperidine ring system (E), e.g., X is N(CO)$R^7$ or $NR^7$, Y is $CR^9R^{10}$, and Z is $CR^{11}R^{12}$.

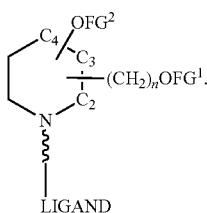

E $OFG^1$ is preferably attached to a primary carbon, e.g., an exocyclic alkylene group, e.g., a methylene group (n=1) or ethylene group (n=2), connected to one of the carbons in the six-membered ring [—$(CH_2)_nOFG^1$ in E]. $OFG^2$ is preferably attached directly to one of the carbons in the six-membered ring (—$OFG^2$ in E). —$(CH_2)_nOFG^1$ and $OFG^2$ may be disposed in a geminal manner on the ring, i.e., both groups may be attached to the same carbon, e.g., at C-2, C-3, or C-4. Alternatively, —$(CH_2)_nOFG^1$ and $OFG^2$ may be disposed in a vicinal manner on the ring, i.e., both groups may be attached to adjacent ring carbon atoms, e.g., —$(CH_2)_nOFG^1$ may be attached to C-2 and $OFG^2$ may be attached to C-3; —$(CH_2)_nOFG^1$ may be attached to C-3 and $OFG^2$ may be attached to C-2; —$(CH_2)_nOFG^1$ may be attached to C-3 and $OFG^2$ may be attached to C-4; or —$(CH_2)_nOFG^1$ may be attached to C-4 and $OFG^2$ may be attached to C-3. The piperidine-based monomers may therefore contain linkages (e.g., carbon-carbon bonds) wherein bond rotation is restricted about that particular linkage, e.g. restriction resulting from the presence of a ring. Thus, —$(CH_2)_nOFG^1$ and $OFG^2$ may be cis or trans with respect to one another in any of the pairings delineated above. Accordingly, all cis trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2OFG^1$ and $OFG^2$ can both have the R configuration; or both have the S configuration; or one center can have the R configuration and the other center can have the S configuration and vice versa). The tethering attachment point is preferably nitrogen.

In certain embodiments, the carrier may be based on the piperazine ring system (F), e.g., X is N(CO)$R^7$ or $NR^7$, Y is $NR^8$, and Z is $CR^{11}R^{12}$, or the morpholine ring system (G), e.g., X is N(CO)$R^7$ or $NR^7$, Y is O, and Z is $CR^{11}R^{12}$.

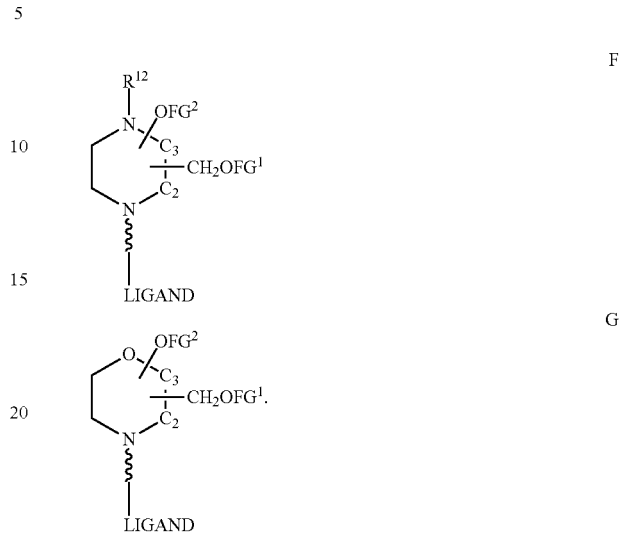

$OFG^1$ is preferably attached to a primary carbon, e.g., an exocyclic alkylene group, e.g., a methylene group, connected to one of the carbons in the six-membered ring (—$CH_2OFG^1$ in F or G). $OFG^2$ is preferably attached directly to one of the carbons in the six-membered rings (—$OFG^2$ in F or G). For both F and G, —$CH_2OFG^1$ may be attached to C-2 and $OFG^2$ may be attached to C-3; or vice versa. In certain embodiments, $CH_2OFG^1$ and $OFG^2$ may be geminally substituted to one of the above-referenced carbons. The piperazine- and morpholine-based monomers may therefore contain linkages (e.g., carbon-carbon bonds) wherein bond rotation is restricted about that particular linkage, e.g. restriction resulting from the presence of a ring. Thus, $CH_2OFG^1$ and $OFG^2$ may be cis or trans with respect to one another in any of the pairings delineated above. Accordingly, all cis trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2OFG^1$ and $OFG^2$ can both have the R configuration; or both have the S configuration; or one center can have the R configuration and the other center can have the S configuration and vice versa). $R'''$ can be, e.g., $C_1$-$C_6$ alkyl, preferably $CH_3$. The tethering attachment point is preferably nitrogen in both F and G.

In certain embodiments, the carrier may be based on the decalin ring system, e.g., X is $CH_2$; Y is $CR^9R^{10}$; Z is $CR^{11}R^{12}$, and $R^5$ and $R^{11}$ together form $C_6$ cycloalkyl (H, z=2), or the indane ring system, e.g., X is $CH_2$; Y is $CR^9R^{10}$; Z is $CR^{11}R^{12}$, and $R^5$ and $R^{11}$ together form $C_5$ cycloalkyl (H, z=1).

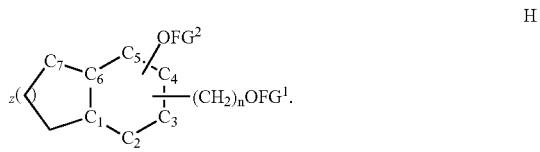

H

OFG$^1$ is preferably attached to a primary carbon, e.g., an exocyclic methylene group (n=1) or ethylene group (n=2) connected to one of C-2, C-3, C-4, or C-5 [—(CH$_2$)$_n$OFG$^1$ in H]. OFG$^2$ is preferably attached directly to one of C-2, C-3, C-4, or C-5 (—OFG$^2$ in H). —(CH$_2$)$_n$OFG$^1$ and OFG$^2$ may be disposed in a geminal manner on the ring, i.e., both groups may be attached to the same carbon, e.g., at C-2, C-3, C-4, or C-5. Alternatively, —(CH$_2$)$_n$OFG$^1$ and OFG$^2$ may be disposed in a vicinal manner on the ring, i.e., both groups may be attached to adjacent ring carbon atoms, e.g., —(CH$_2$)$_n$OFG$^1$ may be attached to C-2 and OFG$^2$ may be attached to C-3; —(CH$_2$)$_n$OFG$^1$ may be attached to C-3 and OFG$^2$ may be attached to C-2; —(CH$_2$)$_n$OFG$^1$ may be attached to C-3 and OFG$^2$ may be attached to C-4; or —(CH$_2$)$_n$OFG$^1$ may be attached to C-4 and OFG$^2$ may be attached to C-3; —(CH$_2$)$_n$OFG$^1$ may be attached to C-4 and OFG$^2$ may be attached to C-5; or —(CH$_2$)$_n$OFG$^1$ may be attached to C-5 and OFG$^2$ may be attached to C-4. The decalin or indane-based monomers may therefore contain linkages (e.g., carbon-carbon bonds) wherein bond rotation is restricted about that particular linkage, e.g. restriction resulting from the presence of a ring. Thus, —(CH$_2$)$_n$OFG$^1$ and OFG$^2$ may be cis or trans with respect to one another in any of the pairings delineated above. Accordingly, all cis trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). In a preferred embodiment, the substituents at C-1 and C-6 are trans with respect to one another. The tethering attachment point is preferably C-6 or C-7.

Other carriers may include those based on 3-hydroxyproline (J).

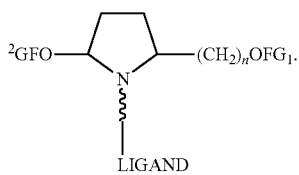

Thus, —(CH$_2$)$_n$OFG$^1$ and OFG$^2$ may be cis or trans with respect to one another. Accordingly, all cis trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen.

Details about more representative cyclic, sugar replacement-based carriers can be found in U.S. Pat. Nos. 7,745,608 and 8,017,762, which are herein incorporated by reference in their entireties.

Sugar Replacement-Based Monomers (Acyclic)

Acyclic sugar replacement-based monomers, e.g., sugar replacement-based ligand-conjugated monomers, are also referred to herein as ribose replacement monomer subunit (RRMS) monomer compounds. Preferred acyclic carriers can have formula LCM-3 or LCM-4:

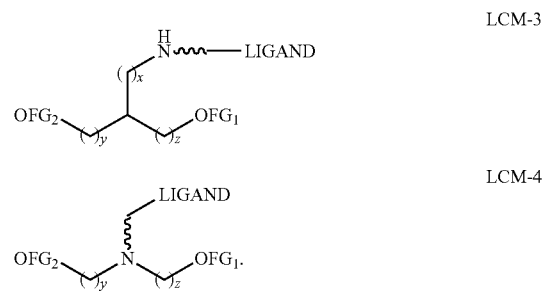

In some embodiments, each of x, y, and z can be, independently of one another, 0, 1, 2, or 3. In formula LCM-3, when y and z are different, then the tertiary carbon can have either the R or S configuration. In preferred embodiments, x is zero and y and z are each 1 in formula LCM-3 (e.g., based on serinol), and y and z are each 1 in formula LCM-3. Each of formula LCM-3 or LCM-4 below can optionally be substituted, e.g., with hydroxy, alkoxy, perhaloalkyl.

Details about more representative acyclic, sugar replacement-based carriers can be found in U.S. Pat. Nos. 7,745,608 and 8,017,762, which are herein incorporated by reference in their entireties.

In some embodiments, the double stranded iRNA agent comprises one or more lipophilic moieties conjugated to the 5' end of the sense strand or the 5' end of the antisense strand.

In certain embodiments, the lipophilic moiety is conjugated to the 5'-end of a strand via a carrier and/or linker. In one embodiment, the lipophilic moiety is conjugated to the 5'-end of a strand via a carrier of a formula:

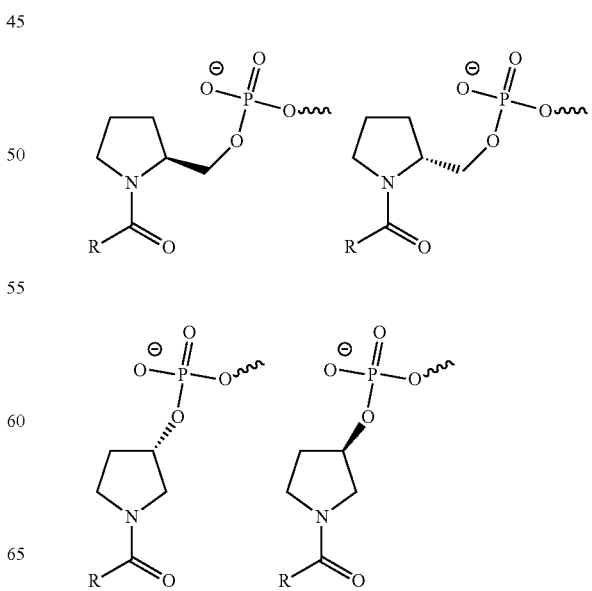

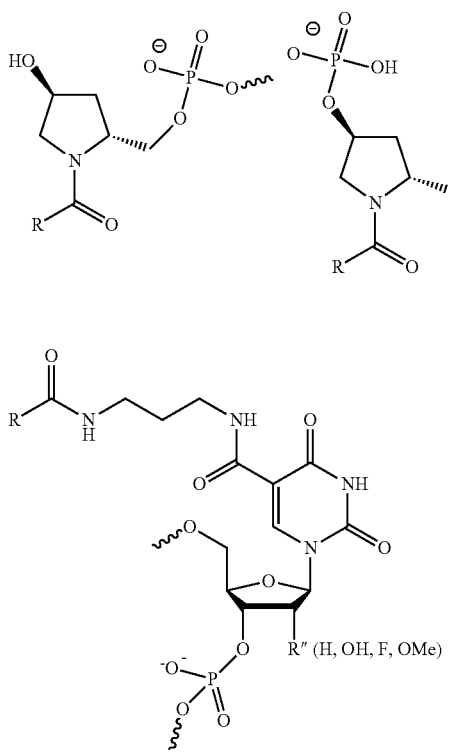

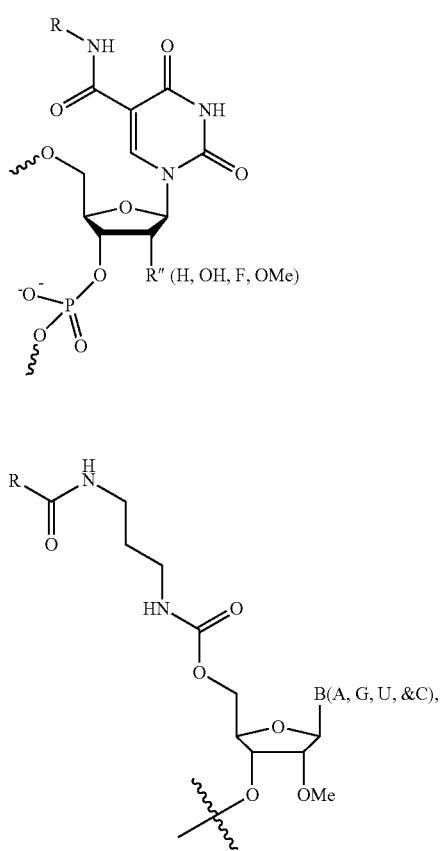

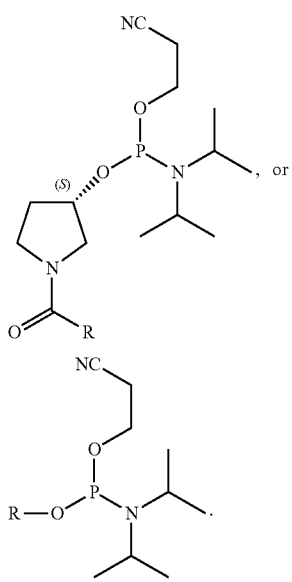

R is a ligand such as the lipophilic moiety.

In some embodiments, the double stranded iRNA agent comprises one or more lipophilic moieties conjugated to the 3' end of the sense strand or the 3' end of the antisense strand.

In certain embodiments, the lipophilic moiety is conjugated to the 3'-end of a strand via a carrier and/or linker. In one embodiment, the lipophilic moiety is conjugated to the 3'-end of a strand via a carrier of a formula:

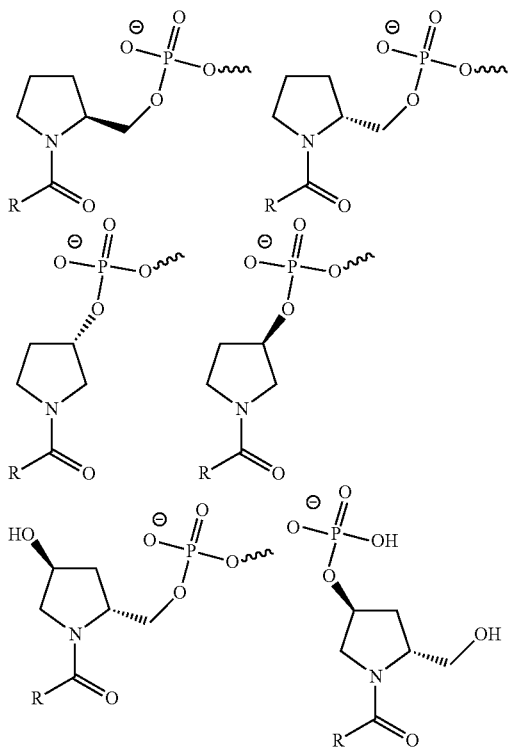

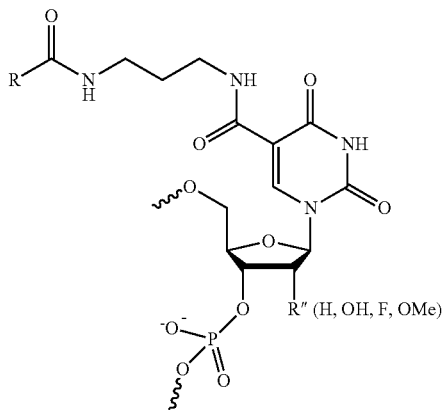

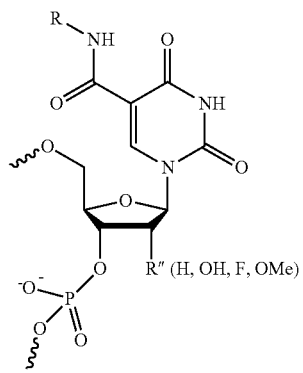

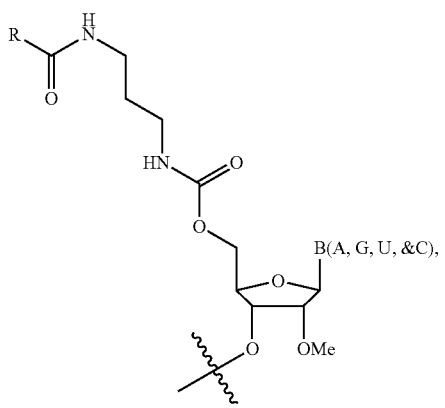

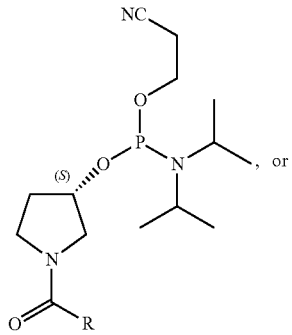

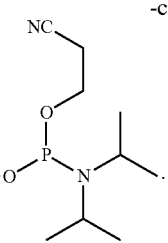, or

R is a ligand such as the lipophilic moiety.

In some embodiments, the double stranded iRNA agent comprises one or more lipophilic moieties conjugated to both ends of the sense strand.

In some embodiments, the double stranded iRNA agent comprises one or more lipophilic moieties conjugated to both ends of the antisense strand.

In some embodiments, the double stranded iRNA agent comprises one or more lipophilic moieties conjugated to the 5' end or 3' end of the sense strand, and one or more lipophilic moieties conjugated to the 5' end or 3' end of the antisense strand, In some embodiments, the lipophilic moiety is conjugated to the terminal end of a strand via one or more linkers (tethers) and/or a carrier.

In one embodiment, the lipophilic moiety is conjugated to the terminal end of a strand via one or more linkers (tethers).

In one embodiment, the lipophilic moiety is conjugated to the 5' end of the sense strand or antisense strand via a cyclic carrier, optionally via one or more intervening linkers (tethers).

In some embodiments, the lipophilic moiety is conjugated to one or more internal positions on at least one strand. Internal positions of a strand refers to the nucleotide on any position of the strand, except the terminal position from the 3' end and 5' end of the strand (e.g., excluding 2 positions: position 1 counting from the 3' end and position 1 counting from the 5' end).

In one embodiment, the lipophilic moiety is conjugated to one or more internal positions on at least one strand, which include all positions except the terminal two positions from each end of the strand (e.g., excluding 4 positions: positions 1 and 2 counting from the 3' end and positions 1 and 2 counting from the 5' end). In one embodiment, the lipophilic moiety is conjugated to one or more internal positions on at least one strand, which include all positions except the terminal three positions from each end of the strand (e.g., excluding 6 positions: positions 1, 2, and 3 counting from the 3' end and positions 1, 2, and 3 counting from the 5' end).

In one embodiment, the lipophilic moiety is conjugated to one or more internal positions on at least one strand, except the cleavage site region of the sense strand, for instance, the lipophilic moiety is not conjugated to positions 9-12 counting from the 5'-end of the sense strand, for example, the lipophilic moiety is not conjugated to positions 9-11 counting from the 5'-end of the sense strand. Alternatively, the internal positions exclude positions 11-13 counting from the 3'-end of the sense strand.

In one embodiment, the lipophilic moiety is conjugated to one or more internal positions on at least one strand, which exclude the cleavage site region of the antisense strand. For instance, the internal positions exclude positions 12-14 counting from the 5'-end of the antisense strand.

In one embodiment, the lipophilic moiety is conjugated to one or more internal positions on at least one strand, which exclude positions 11-13 on the sense strand, counting from the 3'-end, and positions 12-14 on the antisense strand, counting from the 5'-end.

In one embodiment, one or more lipophilic moieties are conjugated to one or more of the following internal positions: positions 4-8 and 13-18 on the sense strand, and positions 6-10 and 15-18 on the antisense strand, counting from the 5' end of each strand.

In one embodiment, one or more lipophilic moieties are conjugated to one or more of the following internal positions: positions 5, 6, 7, 15, and 17 on the sense strand, and positions 15 and 17 on the antisense strand, counting from the 5' end of each strand.

In some embodiments, the lipophilic moiety is conjugated to a nucleobase, sugar moiety, or internucleosidic linkage of the double-stranded iRNA agent.

Definitions

Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "target nucleic acid" refers to any nucleic acid molecule the expression or activity of which is capable of being modulated by an siRNA compound. Target nucleic acids include, but are not limited to, RNA (including, but not limited to pre-mRNA and mRNA or portions thereof) transcribed from DNA encoding a target protein, and also cDNA derived from such RNA, and miRNA. For example, the target nucleic acid can be a cellular gene (or mRNA transcribed from the gene) whose expression is associated with a particular disorder or disease state. In some embodiments, a target nucleic acid can be a nucleic acid molecule from an infectious agent.

As used herein, the term "iRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, RNAi agent, or iRNA agent, herein. Thus, these terms can be used interchangeably herein. As used herein, the term iRNA includes microRNAs and pre-microRNAs. Moreover, the "compound" or "compounds" of the invention as used herein, also refers to the iRNA agent, and can be used interchangeably with the iRNA agent.

The iRNA agent should include a region of sufficient homology to the target gene, and be of sufficient length in terms of nucleotides, such that the iRNA agent, or a fragment thereof, can mediate downregulation of the target gene. (For ease of exposition the term nucleotide or ribonucleotide is sometimes used herein in reference to one or more monomeric subunits of an iRNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired some embodiments can include, particularly in the antisense strand, one or more, or for example, 6, 5, 4, 3, 2, or fewer mismatches (with respect to the target RNA). The sense strand need only be sufficiently complementary with the antisense strand to maintain the over all double stranded character of the molecule.

iRNA agents include: molecules that are long enough to trigger the interferon response (which can be cleaved by Dicer (Bernstein et al. 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA agents herein. "siRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60, 50, 40, or 30 nucleotide pairs. The siRNA agent, or a cleavage product thereof, can down regulate a target gene, e.g., by inducing RNAi with respect to a target RNA, wherein the target may comprise an endogenous or pathogen target RNA.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents may be antisense with regard to the target molecule. A single strand iRNA agent may be sufficiently long that it can enter the RISC and participate in RISC mediated cleavage of a target mRNA. A single strand iRNA agent is at least 14, and in other embodiments at least 15, 20, 25, 29, 35, 40, or 50 nucleotides in length. In certain embodiments, it is less than 200, 100, or 60 nucleotides in length.

A loop refers to a region of an iRNA strand that is unpaired with the opposing nucleotide in the duplex when a section of the iRNA strand forms base pairs with another strand or with another section of the same strand.

Hairpin iRNA agents will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region, in some embodiments at the 3', and in certain embodiments on the antisense side of the hairpin. In some embodiments, the overhangs are 2-3 nucleotides in length.

A "double stranded (ds) iRNA agent" as used herein, is an iRNA agent which includes more than one, and in some cases two, strands in which interchain hybridization can form a region of duplex structure.

As used herein, the terms "siRNA activity" and "RNAi activity" refer to gene silencing by an siRNA.

As used herein, "gene silencing" by a RNA interference molecule refers to a decrease in the mRNA level in a cell for a target gene by at least about 5%, at least about 10%, at least about 20%, at least about 30%, at least about 40%, at least about 50%, at least about 60%, at least about 70%, at least about 80%, at least about 90%, at least about 95%, at least about 99% up to and including 100%, and any integer in between of the mRNA level found in the cell without the presence of the miRNA or RNA interference molecule. In one preferred embodiment, the mRNA levels are decreased by at least about 70%, at least about 80%, at least about 90%, at least about 95%, at least about 99%, up to and including 100% and any integer in between 5% and 100%."

As used herein the term "modulate gene expression" means that expression of the gene, or level of RNA molecule or equivalent RNA molecules encoding one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is at least 5%, 10%, 20%, 30%, 40%, 50%, 60%, 70%, 80%, 90%, 100%, 2-fold, 3-fold, 4-fold, 5-fold or more different from that observed in the absence of the siRNA, e.g., RNAi agent. The % and/or fold difference can be calculated relative to the control or the non-control, for example, $$\% \text{ difference} = \frac{[\text{expression with } siRNA - \text{expression without } siRNA]}{\text{expression without } siRNA}$$

or $$\% \text{ difference} = \frac{[\text{expression with } siRNA - \text{expression without } siRNA]}{\text{expression without } siRNA}$$

As used herein, the term "inhibit", "down-regulate", or "reduce" in relation to gene expression, means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, or level of RNA molecules or equivalent RNA molecules encoding one or more proteins or protein subunits, or activity of one or more proteins or protein subunits, is reduced at least 10% lower relative to a corresponding non-modulated control, and preferably at least 10%, 20%, 30%, 40%, 50%, 60%, 70%, 80%, 90%, 95%, 98%, 99% or most preferably, 100% (i.e., no gene expression).

As used herein, the term "increase" or "up-regulate" in relation to gene expression means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, or level of RNA molecules or equivalent RNA molecules encoding one or more proteins or protein subunits, or activity of one or more proteins or protein subunits, is increased at least 10% relative to a corresponding non-modulated control, and preferably at least 10%, 20%, 30%, 40%, 50%, 60%, 70%, 80%, 90%, 95%, 98%, 100%, 1.1-fold, 1.25-fold, 1.5-fold, 1.75-fold, 2-fold, 3-fold, 4-fold, 5-fold, 10-fold, 50-fold, 100-fold or more.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The double-stranded iRNAs comprise two oligonucleotide strands that are sufficiently complementary to hybridize to form a duplex structure. Generally, the duplex structure is between 15 and 30, more generally between 18 and 25, yet more generally between 19 and 24, and most generally between 19 and 21 base pairs in length. In some embodiments, longer double-stranded iRNAs of between 25 and 30 base pairs in length are preferred. In some embodiments, shorter double-stranded iRNAs of between 10 and 15 base pairs in length are preferred. In another embodiment, the double-stranded iRNA is at least 21 nucleotides long.

In some embodiments, the double-stranded iRNA comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length.

The phrase "antisense strand" as used herein, refers to an oligomeric compound that is substantially or 100% complementary to a target sequence of interest. The phrase "antisense strand" includes the antisense region of both oligomeric compounds that are formed from two separate strands, as well as unimolecular oligomeric compounds that are capable of forming hairpin or dumbbell type structures. The terms "antisense strand" and "guide strand" are used interchangeably herein.

The phrase "sense strand" refers to an oligomeric compound that has the same nucleoside sequence, in whole or in part, as a target sequence such as a messenger RNA or a sequence of DNA. The terms "sense strand" and "passenger strand" are used interchangeably herein.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol.* LII pp. 123-133; Frier et al., 1986, *Proc. Nat. Acad. Sci.* USA 83:9373-9377; Turner et al., 1987, *I. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In some embodiments, the double-stranded region of a double-stranded iRNA agent is equal to or at least, 10, 11, 12, 13, 14, 15, 16, 17, 18, 19, 20, 21, 22, 23, 23, 24, 25, 26, 27, 28, 29, 30 or more nucleotide pairs in length.

In some embodiments, the antisense strand of a double-stranded iRNA agent is equal to or at least 14, 15, 16, 17, 18, 19, 20, 21, 22, 23, 23, 24, 25, 26, 27, 28, 29, or 30 nucleotides in length.

In some embodiments, the sense strand of a double-stranded iRNA agent is equal to or at least 10, 11, 12, 13, 14, 15, 16, 17, 18, 19, 20, 21, 22, 23, 23, 24, 25, 26, 27, 28, 29, or 30 nucleotides in length.

In one embodiment, the sense and antisense strands of the double-stranded iRNA agent are each 15 to 30 nucleotides in length.

In one embodiment, the sense and antisense strands of the double-stranded iRNA agent are each 19 to 25 nucleotides in length.

In one embodiment, the sense and antisense strands of the double-stranded iRNA agent are each 21 to 23 nucleotides in length.

In some embodiments, one strand has at least one stretch of 1-5 single-stranded nucleotides in the double-stranded region. By "stretch of single-stranded nucleotides in the double-stranded region" is meant that there is present at least one nucleotide base pair at both ends of the single-stranded stretch. In some embodiments, both strands have at least one stretch of 1-5 (e.g., 1, 2, 3, 4, or 5) single-stranded nucleotides in the double stranded region. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no single-stranded nucleotides opposite to the single-stranded iRNAs of the first strand and vice versa (e.g., a single-stranded loop). In some embodiments, the single-stranded nucleotides are present within 8 nucleotides from either end, for example 8, 7, 6, 5, 4, 3, or 2 nucleotide from either the 5' or 3' end of the region of complementarity between the two strands.

In one embodiment, the double-stranded iRNA agent comprises a single-stranded overhang on at least one of the termini. In one embodiment, the single-stranded overhang is 1, 2, or 3 nucleotides in length.

In one embodiment, the sense strand of the iRNA agent is 21-nucleotides in length, and the antisense strand is 23-nucleotides in length, wherein the strands form a double-stranded region of 21 consecutive base pairs having a 2-nucleotide long single-stranded overhangs at the 3'-end.

In some embodiments, each strand of the double-stranded iRNA has a ZXY structure, such as is described in PCT Publication No. 2004080406, which is hereby incorporated by reference in its entirety.

In certain embodiment, the two strands of double-stranded oligomeric compound can be linked together. The two strands can be linked to each other at both ends, or at one end only. By linking at one end is meant that 5'-end of first strand is linked to the 3'-end of the second strand or 3'-end of first strand is linked to 5'-end of the second strand. When the two strands are linked to each other at both ends, 5'-end of first strand is linked to 3'-end of second strand and 3'-end of first strand is linked to 5'-end of second strand. The two strands can be linked together by an oligonucleotide linker including, but not limited to, $(N)_n$; wherein N is independently a modified or unmodified nucleotide and n is 3-23. In some embodiments, n is 3-10, e.g., 3, 4, 5, 6, 7, 8, 9, or 10. In some embodiments, the oligonucleotide linker is selected from the group consisting of GNRA, $(G)_4$, $(U)_4$, and $(dT)_4$, wherein N is a modified or unmodified nucleotide and R is a modified or unmodified purine nucleotide. Some of the nucleotides in the linker can be involved in base-pair interactions with other nucleotides in the linker. The two strands can also be linked together by a non-nucleosidic linker, e.g. a linker described herein. It will be appreciated by one of skill in the art that any oligonucleotide chemical modifications or variations describe herein can be used in the oligonucleotide linker.

Hairpin and dumbbell type oligomeric compounds will have a duplex region equal to or at least 14, 15, 15, 16, 17, 18, 19, 29, 21, 22, 23, 24, or 25 nucleotide pairs. The duplex region can be equal to or less than 200, 100, or 50, in length. In some embodiments, ranges for the duplex region are 15-30, 17 to 23, 19 to 23, and 19 to 21 nucleotides pairs in length.

The hairpin oligomeric compounds can have a single strand overhang or terminal unpaired region, in some embodiments at the 3', and in some embodiments on the antisense side of the hairpin. In some embodiments, the overhangs are 1-4, more generally 2-3 nucleotides in length. The hairpin oligomeric compounds that can induce RNA interference are also referred to as "shRNA" herein.

In certain embodiments, two oligomeric strands specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

siRNA Design

In one embodiment, the iRNA agent of the invention is a double ended bluntmer of 19 nt in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5' end.

In one embodiment, the iRNA agent of the invention is a double ended bluntmer of 20 nt in length, wherein the sense strand contains at least one motif of three 2'-F modifications on three consecutive nucleotides at positions 8, 9, 10 from the 5' end. The antisense strand contains at least one motif of three 2'-O-methyl modifications on three consecutive nucleotides at positions 11, 12, 13 from the 5' end.

In one embodiment, the iRNA agent of the invention is a double ended bluntmer of 21 nt in length, wherein the sense strand contains at least one motif of three 2'-F modifications on three consecutive nucleotides at positions 9, 10, 11 from the 5' end. The antisense strand contains at least one motif of three 2'-O-methyl modifications on three consecutive nucleotides at positions 11, 12, 13 from the 5' end.

In one embodiment, the iRNA agent of the invention comprises a 21 nucleotides (nt) sense strand and a 23 nucleotides (nt) antisense, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the iRNA is blunt, while the other end is comprises a 2 nt overhang. Preferably, the 2 nt overhang is at the 3'-end of the antisense. Optionally, the iRNA agent further comprises a ligand (e.g., GalNAc$_3$).

In one embodiment, the iRNA agent of the invention comprises a sense and antisense strands, wherein: the sense strand is 25-30 nucleotide residues in length, wherein starting from the 5' terminal nucleotide (position 1) positions 1 to 23 of said first strand comprise at least 8 ribonucleotides; antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the iRNA agent of the invention comprises a sense and antisense strands, wherein said iRNA agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein said 3' end of said first strand and said 5' end of said second strand form a blunt end and said second strand is 1-4 nucleotides longer at its 3' end than the first strand, wherein the duplex region which is at least 25 nucleotides in length, and said second strand is sufficiently complementary to a target mRNA along at least 19 nt of said second strand length to reduce target gene expression when said iRNA agent is introduced into a mammalian cell, and wherein dicer cleavage of said iRNA preferentially results in an siRNA comprising said 3' end of said second strand, thereby reducing expression of the target gene in the mammal. Optionally, the iRNA agent further comprises a ligand (e.g., GalNAc$_3$).

In one embodiment, the sense strand of the iRNA agent contains at least one motif of three identical modifications on three consecutive nucleotides, where one of the motifs occurs at the cleavage site in the sense strand. For instance, the sense strand can contain at least one motif of three 2'-F modifications on three consecutive nucleotides within 7-15 positions from the 5' end.

In one embodiment, the antisense strand of the iRNA agent can also contain at least one motif of three identical modifications on three consecutive nucleotides, where one of the motifs occurs at or near the cleavage site in the antisense strand. For instance, the antisense strand can contain at least one motif of three 2'-O-methyl modifications on three consecutive nucleotides within 9-15 positions from the 5' end.

For iRNA agent having a duplex region of 17-23 nt in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the 1$^{st}$ nucleotide from the 5'-end of the antisense strand, or, the count starting from the 1$^{st}$ paired nucleotide within the duplex region from the 5'-end of the antisense strand. The cleavage site in the antisense strand may also change according to the length of the duplex region of the iRNA from the 5'-end.

In some embodiments, the iRNA agent comprises a sense strand and antisense strand each having 14 to 30 nucleotides, wherein the sense strand contains at least two motifs of three identical modifications on three consecutive nucleotides, where at least one of the motifs occurs at or near the cleavage site within the strand and at least one of the motifs occurs at another portion of the strand that is separated from the motif at the cleavage site by at least one nucleotide. In one embodiment, the antisense strand also contains at least one motif of three identical modifications on three consecutive nucleotides, where at least one of the motifs occurs at or near the cleavage site within the strand. The modification in the motif occurring at or near the cleavage site in the sense strand is different than the modification in the motif occurring at or near the cleavage site in the antisense strand.

In some embodiments, the iRNA agent comprises a sense strand and antisense strand each having 14 to 30 nucleotides, wherein the sense strand contains at least one motif of three 2'-F modifications on three consecutive nucleotides, where at least one of the motifs occurs at or near the cleavage site in the strand. In one embodiment, the antisense strand also contains at least one motif of three 2'-O-methyl modifications on three consecutive nucleotides at or near the cleavage site.

In some embodiments, the iRNA agent comprises a sense strand and antisense strand each having 14 to 30 nucleotides, wherein the sense strand contains at least one motif of three 2'-F modifications on three consecutive nucleotides at positions 9, 10, 11 from the 5' end, and wherein the antisense strand contains at least one motif of three 2'-O-methyl modifications on three consecutive nucleotides at positions 11, 12, 13 from the 5' end.

In one embodiment, the iRNA agent of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the iRNA agent of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In one aspect, the invention relates to a double-stranded RNA (dsRNA) agent for inhibiting the expression of a target gene. The dsRNA agent comprises a sense strand and an antisense strand, each strand having 14 to 40 nucleotides. The dsRNA agent is represented by formula (I):

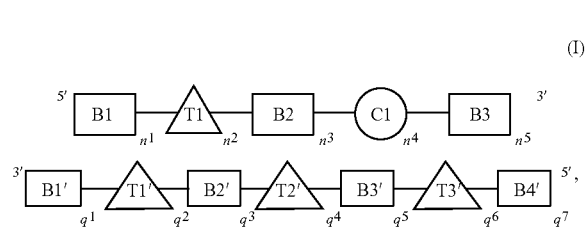

(I)

In formula (I), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications. In one embodiment, B1, B2, B3, B1', B2', B3', and B4' each contain 2'-OMe or 2'-F modifications. In one embodiment, at least one of B1, B2, B3, B1', B2', B3', and B4' contain 2'-O—N-methylacetamido (2'-O-NMA) modification.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. In one example, C1 is at position 15 from the 5'-end of the sense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

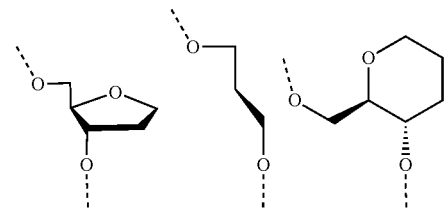

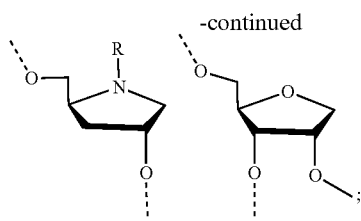

and iii) sugar modification selected from the group consisting of:

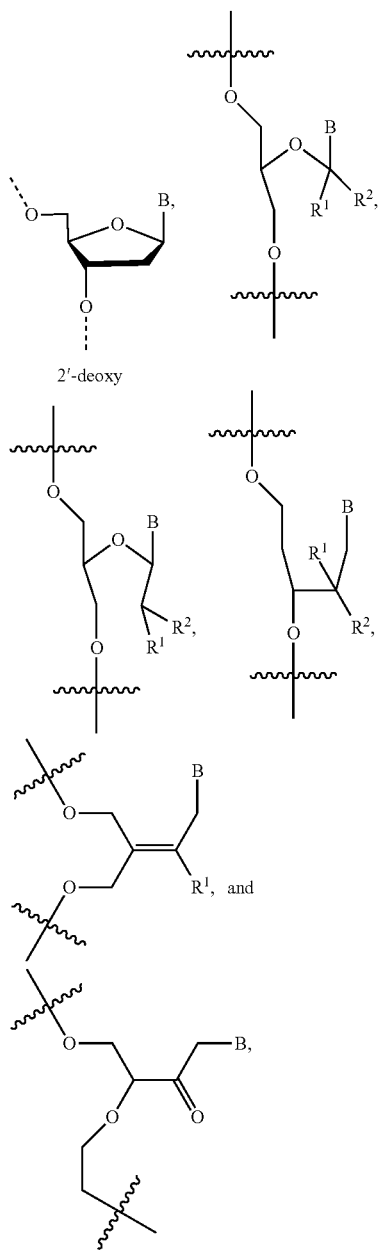

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

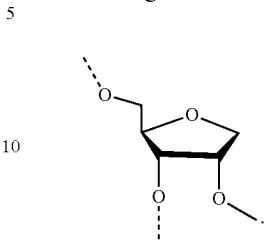

T1, T1', T2', and T3' each independently represent a nucleotide comprising a modification providing the nucleotide a steric bulk that is less or equal to the steric bulk of a 2'-OMe modification. A steric bulk refers to the sum of steric effects of a modification. Methods for determining steric effects of a modification of a nucleotide are known to one skilled in the art. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length; alternatively, $n^4$ is 0.

$q^5$ is independently 0-10 nucleotide(s) in length.

$n^2$ and $q^4$ are independently 0-3 nucleotide(s) in length. Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.

In one embodiment, $n^2$, $n^4$, $q^2$, $q^4$, and $q^6$ are each 1.

In one embodiment, C1 is at position 14-17 of the 5'-end of the sense strand, when the sense strand is 19-22 nucleotides in length, and $n^4$ is 1. In one embodiment, C1 is at position 15 of the 5'-end of the sense strand In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1.

In an exemplary embodiment, T3' starts from position 2 from the 5' end of the antisense strand and T1' starts from position 14 from the 5' end of the antisense strand. In one example, T3' starts from position 2 from the 5' end of the antisense strand and $q^6$ is equal to 1 and T1' starts from position 14 from the 5' end of the antisense strand and $q^2$ is equal to 1.

In one embodiment, T1' and T3' are separated by 11 nucleotides in length (i.e. not counting the T1' and T3' nucleotides).

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at the cleavage site of the sense strand. In one example, T1 is at position 11 from the 5' end of the sense strand, when the sense strand is 19-22 nucleotides in length, and $n^2$ is 1. In an exemplary embodiment, T1 is at the cleavage site of the sense strand at position 11 from the 5' end of the sense strand, when the sense strand is 19-22 nucleotides in length, and $n^2$ is 1, In one embodiment, T2' starts at position 6 from the 5' end of the antisense strand. In one example, T2' is at positions 6-10 from the 5' end of the antisense strand, and $q^4$ is 1. In an exemplary embodiment, T1 is at the cleavage site of the sense strand, for instance, at position 11 from the 5' end of the sense strand, when the sense strand is 19-22 nucleotides in length, and $n^2$ is 1; T1' is at position 14 from the 5' end of the antisense strand, and $q^2$ is equal to 1, and the modification to T1' is at the 2' position of a ribose sugar or at positions in a non-ribose, acyclic or backbone that provide less steric bulk than a 2'-OMe ribose; T2' is at positions 6-10 from the 5' end of the antisense strand, and $q^4$ is 1; and T3' is at position 2 from the 5' end of the antisense strand, and $q^6$ is equal to 1, and the modification to T3' is at the 2' position or at positions in a non-ribose, acyclic or backbone that provide less than or equal to steric bulk than a 2'-OMe ribose.

In one embodiment, T2' starts at position 8 from the 5' end of the antisense strand. In one example, T2' starts at position 8 from the 5' end of the antisense strand, and $q^4$ is 2. In one embodiment, T2' starts at position 9 from the 5' end of the antisense strand. In one example, T2' is at position 9 from the 5' end of the antisense strand, and $q^4$ is 1. In one embodiment, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate inter-nucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1;

optionally with at least 2 additional TT at the 3'-end of the antisense strand; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within positions 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

The dsRNA agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-PS$_2$), 5'-end vinylphosphonate (5'-VP), 5'-end methylphosphonate (MePhos), or 5'-deoxy-5'-C-malonyl (

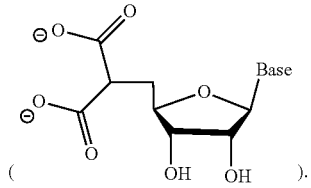

).

When the 5'-end phosphorus-containing group is 5'-end vinylphosphonate (5'-VP), the 5'-VP can be either 5'-E-VP isomer (i.e., trans-vinylphosphate,

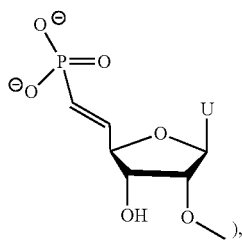

),

5'-Z-VP isomer (i.e., cis-vinylphosphate,

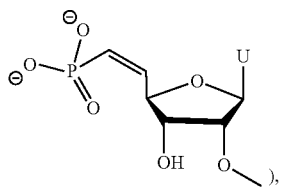

), or mixtures thereof.

In one embodiment, the dsRNA agent comprises a phosphorus-containing group at the 5'-end of the sense strand. In one embodiment, the dsRNA agent comprises a phosphorus-containing group at the 5'-end of the antisense strand.

In one embodiment, the dsRNA agent comprises a 5'-P. In one embodiment, the dsRNA agent comprises a 5'-P in the antisense strand.

In one embodiment, the dsRNA agent comprises a 5'-PS. In one embodiment, the dsRNA agent comprises a 5'-PS in the antisense strand.

In one embodiment, the dsRNA agent comprises a 5'-VP. In one embodiment, the dsRNA agent comprises a 5'-VP in the antisense strand. In one embodiment, the dsRNA agent comprises a 5'-E-VP in the antisense strand. In one embodiment, the dsRNA agent comprises a 5'-Z-VP in the antisense strand.

In one embodiment, the dsRNA agent comprises a 5'-PS$_2$. In one embodiment, the dsRNA agent comprises a 5'-PS$_2$ in the antisense strand.

In one embodiment, the dsRNA agent comprises a 5'-PS$_2$. In one embodiment, the dsRNA agent comprises a 5'-deoxy-5'-C-malonyl in the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The dsRNA agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The dsRNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The dsRNA agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-deoxy-5'-C-malonyl.

In one embodiment, 100%, 95%, 90%, 85%, 80%, 75%, 70%, 65%, 60%, 55%, 50%, 45%, 40%, 35% or 30% of the dsRNA agent of the invention is modified. For example, when 50% of the dsRNA agent is modified, 50% of all nucleotides present in the dsRNA agent contain a modification as described herein.

In one embodiment, each of the sense and antisense strands of the dsRNA agent is independently modified with acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or 2'-ara-F.

In one embodiment, each of the sense and antisense strands of the dsRNA agent contains at least two different modifications.

In one embodiment, the dsRNA agent of Formula (I) further comprises 3' and/or 5' overhang(s) of 1-10 nucleotides in length. In one example, dsRNA agent of formula (I) comprises a 3' overhang at the 3'-end of the antisense strand and a blunt end at the 5'-end of the antisense strand. In another example, the dsRNA agent has a 5' overhang at the 5'-end of the sense strand.

In one embodiment, the dsRNA agent of the invention does not contain any 2'-F modification.

In one embodiment, the sense strand and/or antisense strand of the dsRNA agent comprises one or more blocks of phosphorothioate or methylphosphonate internucleotide linkages. In one example, the sense strand comprises one block of two phosphorothioate or methylphosphonate internucleotide linkages. In one example, the antisense strand comprises two blocks of two phosphorothioate or methylphosphonate internucleotide linkages. For example, the two blocks of phosphorothioate or methylphosphonate internucleotide linkages are separated by 16-18 phosphate internucleotide linkages.

In one embodiment, each of the sense and antisense strands of the dsRNA agent has 15-30 nucleotides. In one example, the sense strand has 19-22 nucleotides, and the antisense strand has 19-25 nucleotides. In another example, the sense strand has 21 nucleotides, and the antisense strand has 23 nucleotides.

In one embodiment, the nucleotide at position 1 of the 5'-end of the antisense strand in the duplex is selected from the group consisting of A, dA, dU, U, and dT. In one embodiment, at least one of the first, second, and third base pair from the 5'-end of the antisense strand is an AU base pair.

In one embodiment, the antisense strand of the dsRNA agent of the invention is 100% complementary to a target RNA to hybridize thereto and inhibits its expression through RNA interference. In another embodiment, the antisense strand of the dsRNA agent of the invention is at least 95%, at least 90%, at least 85%, at least 80%, at least 75%, at least 70%, at least 65%, at least 60%, at least 55%, or at least 50% complementary to a target RNA.

In one aspect, the invention relates to a dsRNA agent as defined herein capable of inhibiting the expression of a target gene. The dsRNA agent comprises a sense strand and an antisense strand, each strand having 14 to 40 nucleotides. The sense strand contains at least one thermally destabilizing nucleotide, wherein at least one of said thermally destabilizing nucleotide occurs at or near the site that is opposite to the seed region of the antisense strand (i.e. at position 2-8 of the 5'-end of the antisense strand). Each of the embodiments and aspects described in this specification relating to the dsRNA represented by formula (I) can also apply to the dsRNA containing the thermally destabilizing nucleotide.

The thermally destabilizing nucleotide can occur, for example, between positions 14-17 of the 5'-end of the sense strand when the sense strand is 21 nucleotides in length. The antisense strand contains at least two modified nucleic acids that are smaller than a sterically demanding 2'-OMe modification. Preferably, the two modified nucleic acids that are smaller than a sterically demanding 2'-OMe are separated by 11 nucleotides in length. For example, the two modified nucleic acids are at positions 2 and 14 of the 5' end of the antisense strand.

In one embodiment, the dsRNA agent further comprises at least one ASGPR ligand. For example, the ASGPR ligand is one or more GalNAc derivatives attached through a bivalent or trivalent branched linker, such as:

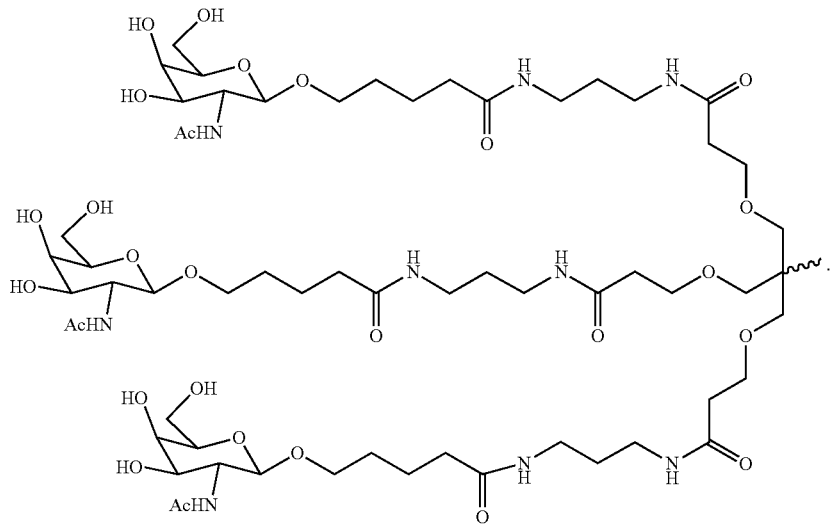 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one example, the ASGPR ligand is attached to the 3' end of the sense strand.

For example, the dsRNA agent as defined herein can comprise i) a phosphorus-containing group at the 5'-end of the sense strand or antisense strand; ii) with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand); and iii) a ligand, such as a ASGPR ligand (e.g., one or more GalNAc derivatives) at 5'-end or 3'-end of the sense strand or antisense strand. For instance, the ligand may be at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-VP (e.g., a 5'-E-VP, 5'-Z-VP, or combination thereof), and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The dsRNA agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The dsRNA agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In a particular embodiment, the dsRNA agents of the present invention comprise:

(a) a sense strand having:
  (i) a length of 21 nucleotides;
  (ii) optionally an ASGPR ligand attached to the 3'-end, wherein said ASGPR ligand comprises three GalNAc derivatives attached through a trivalent branched linker; and
  (iii) 2'-F modifications at positions 1, 3, 5, 7, 9 to 11, 13, 17, 19, and 21, and 2'-OMe modifications at positions 2, 4, 6, 8, 12, 14 to 16, 18, and 20 (counting from the 5' end);
and
(b) an antisense strand having:
  (i) a length of 23 nucleotides;
  (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
  (iii) phosphorothioate internucleotide linkages between nucleotide positions 21 and 22, and between nucleotide positions 22 and 23 (counting from the 5' end);
    wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) optionally an ASGPR ligand attached to the 3'-end, wherein said ASGPR ligand comprises three GalNAc derivatives attached through a trivalent branched linker;
  (iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) optionally an ASGPR ligand attached to the 3'-end, wherein said ASGPR ligand comprises three GalNAc derivatives attached through a trivalent branched linker;
  (iii) 2'-OMe modifications at positions 1 to 6, 8, 10, and 12 to 21, 2'-F modifications at positions 7, and 9, and a desoxy-nucleotide (e.g. dT) at position 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) optionally an ASGPR ligand attached to the 3'-end, wherein said ASGPR ligand comprises three GalNAc derivatives attached through a trivalent branched linker;
  (iii) 2'-OMe modifications at positions 1 to 6, 8, 10, 12, 14, and 16 to 21, and 2'-F modifications at positions 7, 9, 11, 13, and 15; and (iv) phosphorothioate internucleotide linkages between nucleotide positions 1 and 2, and between nucleotide positions 2 and 3 (counting from the 5' end); and (b) an antisense strand having:
(i) a length of 23 nucleotides;
(ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:
(a) a sense strand having:
(i) a length of 21 nucleotides;
(ii) optionally an ASGPR ligand attached to the 3'-end, wherein said ASGPR ligand comprises three GalNAc derivatives attached through a trivalent branched linker;
(iii) 2'-OMe modifications at positions 1 to 9, and 12 to 21, and 2'-F modifications at positions 10, and 11; and
(iv) phosphorothioate internucleotide linkages between nucleotide positions 1 and 2, and between nucleotide positions 2 and 3 (counting from the 5' end); and (b) an antisense strand having:
(i) a length of 23 nucleotides;
(ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:
(a) a sense strand having:
(i) a length of 21 nucleotides;
(ii) optionally an ASGPR ligand attached to the 3'-end, wherein said ASGPR ligand comprises three GalNAc derivatives attached through a trivalent branched linker;
(iii) 2'-F modifications at positions 1, 3, 5, 7, 9 to 11, and 13, and 2'-OMe modifications at positions 2, 4, 6, 8, 12, and 14 to 21; and
(iv) phosphorothioate internucleotide linkages between nucleotide positions 1 and 2, and between nucleotide positions 2 and 3 (counting from the 5' end); and (b) an antisense strand having:
(i) a length of 23 nucleotides;
(ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:
(a) a sense strand having:
(i) a length of 21 nucleotides;
(ii) optionally an ASGPR ligand attached to the 3'-end, wherein said ASGPR ligand comprises three GalNAc derivatives attached through a trivalent branched linker;
(iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
(iv) phosphorothioate internucleotide linkages between nucleotide positions 1 and 2, and between nucleotide positions 2 and 3 (counting from the 5' end); and (b) an antisense strand having:
(i) a length of 25 nucleotides;
(ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxynucleotides (e.g. dT) at positions 24 and 25 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a four nucleotide overhang at the 3'-end of the antisense strand, and a blunt end at the 5'-end of the antisense strand.

In another particular embodiment, the dsRNA agents of the present invention comprise:
(a) a sense strand having:
(i) a length of 21 nucleotides;
(ii) optionally an ASGPR ligand attached to the 3'-end, wherein said ASGPR ligand comprises three GalNAc derivatives attached through a trivalent branched linker;
(iii) 2'-OMe modifications at positions 1 to 6, 8, and 12 to 21, and 2'-F modifications at positions 7, and 9 to 11; and
(iv) phosphorothioate internucleotide linkages between nucleotide positions 1 and 2, and between nucleotide positions 2 and 3 (counting from the 5' end); and (b) an antisense strand having:
(i) a length of 23 nucleotides;
(ii) 2'-OMe modifications at positions 1, 3 to 5, 7, 8, 10 to 13, 15, and 17 to 23, and 2'-F modifications at positions 2, 6, 9, 14, and 16 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:
(a) a sense strand having:
  (i) a length of 21 nucleotides;
  (ii) optionally an ASGPR ligand attached to the 3'-end, wherein said ASGPR ligand comprises three Gal-NAc derivatives attached through a trivalent branched linker;
  (iii) 2'-OMe modifications at positions 1 to 6, 8, and 12 to 21, and 2'-F modifications at positions 7, and 9 to 11; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-OMe modifications at positions 1, 3 to 5, 7, 10 to 13, 15, and 17 to 23, and 2'-F modifications at positions 2, 6, 8, 9, 14, and 16 (counting from the 5' end); and
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the dsRNA agents have a two nucleotide overhang at the 3'-end of the antisense strand, and a blunt end at the 5'-end of the antisense strand.

In another particular embodiment, the dsRNA agents of the present invention comprise:
(a) a sense strand having:
  (i) a length of 19 nucleotides;
  (ii) optionally an ASGPR ligand attached to the 3'-end, wherein said ASGPR ligand comprises three Gal-NAc derivatives attached through a trivalent branched linker;
  (iii) 2'-OMe modifications at positions 1 to 4, 6, and 10 to 19, and 2'-F modifications at positions 5, and 7 to 9; and
  (iv) phosphorothioate internucleotide linkages between nucleotide positions 1 and 2, and between nucleotide positions 2 and 3 (counting from the 5' end); and
(b) an antisense strand having:
  (i) a length of 21 nucleotides;
  (ii) 2'-OMe modifications at positions 1, 3 to 5, 7, 10 to 13, 15, and 17 to 21, and 2'-F modifications at positions 2, 6, 8, 9, 14, and 16 (counting from the 5' end); and
  (iii) phosphorothioate internucleotide linkages between nucleotide positions 1 and 2, between nucleotide positions 2 and 3, between nucleotide positions 19 and 20, and between nucleotide positions 20 and 21 (counting from the 5' end);
wherein the dsRNA agents have a two nucleotide overhang at the 3'-end of the antisense strand, and a blunt end at the 5'-end of the antisense strand.

In one embodiment, the dsRNA agents of the present invention comprise:
(a) a sense strand having:
  (i) a length of 18-23 nucleotides;
  (ii) three consecutive 2'-F modifications at positions 7-15; and
(b) an antisense strand having:
  (i) a length of 18-23 nucleotides;
  (ii) at least 2'-F modifications anywhere on the strand; and
  (iii) at least two phosphorothioate internucleotide linkages at the first five nucleotides (counting from the 5' end);
wherein the dsRNA agents have one or more lipophilic moieties conjugated to one or more positions on at least one strand; and either have two nucleotides overhang at the 3'-end of the antisense strand, and a blunt end at the 5'-end of the antisense strand; or blunt end both ends of the duplex.

In one embodiment, the dsRNA agents of the present invention comprise:
(a) a sense strand having:
  (i) a length of 18-23 nucleotides;
  (ii) less than four 2'-F modifications;
(b) an antisense strand having:
  (i) a length of 18-23 nucleotides;
  (ii) at less than twelve 2'-F modification; and
  (iii) at least two phosphorothioate internucleotide linkages at the first five nucleotides (counting from the 5' end);
wherein the dsRNA agents have one or more lipophilic moieties conjugated to one or more positions on at least one strand; and either have two nucleotides overhang at the 3'-end of the antisense strand, and a blunt end at the 5'-end of the antisense strand; or blunt end both ends of the duplex.

In one embodiment, the dsRNA agents of the present invention comprise:
(a) a sense strand having:
  (i) a length of 19-35 nucleotides;
  (ii) less than four 2'-F modifications;
(b) an antisense strand having:
  (i) a length of 19-35 nucleotides;
  (ii) at less than twelve 2'-F modification; and
  (iii) at least two phosphorothioate internucleotide linkages at the first five nucleotides (counting from the 5' end);
wherein the duplex region is between 19 to 25 base pairs (preferably 19, 20, 21 or 22); and wherein the dsRNA agents have one or more lipophilic moieties conjugated to one or more positions on at least one strand; and either have two nucleotides overhang at the 3'-end of the antisense strand, and a blunt end at the 5'-end of the antisense strand; or blunt end both ends of the duplex.

In one embodiment, the dsRNA agents of the present invention comprise a sense strand and antisense strands having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the dsRNA agents have one or more lipophilic moieties conjugated to one or more positions on at least one strand; and wherein the dsRNA agents have less than 20%, less than 15% and less than 10% non-natural nucleotide.

Examples of non-natural nucleotide includes acyclic nucleotides, LNA, HNA, CeNA, 2'-methoxyethyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or 2'-ara-F, and others.

In one embodiment, the dsRNA agents of the present invention comprise a sense strand and antisense strands having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the dsRNA agents have one or more lipophilic moieties conjugated to one or more positions on at least one strand; and wherein the dsRNA agents have greater than 80%, greater than 85% and greater than 90% natural nucleotide, such as 2'-OH, 2'-deoxy and 2'-OMe are natural nucleotides.

In one embodiment, the dsRNA agents of the present invention comprise a sense strand and antisense strands having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the dsRNA agents have one or more lipophilic moieties conjugated to one or more positions on at least one strand; and wherein the dsRNA agents have 100% natural nucleotide, such as 2'-OH, 2'-deoxy and 2'-OMe are natural nucleotides.

Examples of lipophilic moieties include, but not limited to, lipid (a saturated or unsaturated C4-C30 hydrocarbon chain, and an optional functional group selected from the group consisting of hydroxyl, amine, carboxylic acid, sulfonate, phosphate, thiol, azide, and alkyne), cholesterol, retinoic acid, cholic acid, adamantane acetic acid, 1-pyrene butyric acid, dihydrotestosterone, 1,3-bis-O(hexadecyl) glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

In some embodiments, the lipophilic moiety is a $C_6$-$C_{30}$ acid (e.g., hexanoic acid, heptanoic acid, octanoic acid, nonanoic acid, decanoic acid, undecanoic acid, dodcanoic acid, tridecanoic acid, tetradecanoic acid, pentadecanoic acid, hexadecanoic acid, heptadecanoic acid, octadecanoic acid, oleic acid, linoleic acid, arachidonic acid, cis-4,7,10, 13,16,19-docosahexanoic acid, vitamin A, vitamin E, cholesterol etc.) or a $C_6$-$C_{30}$ alcohol (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

In one example, the lipophilic moiety is a saturated or unsaturated C6-C18 hydrocarbon chain.

In one example, the lipophilic moiety is docosahexaenoic acid.

In one embodiment, the dsRNA agents of the present invention a sense strand and an antisense strand, each strand having 14 to 30 nucleotides, wherein the sense strand sequence is represented by formula (I):

$$5'n_p\text{-}N_a\text{—}(XXX)_i\text{-}N_b\text{-}YYY\text{-}N_b\text{—}(ZZZ)_j\text{-}N_a\text{-}n_q3' \quad (I)$$

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 1, 2, 3, 4, 5, or 6 modified nucleotides;
each $n_p$ and $n_q$ independently represent an overhang nucleotide;

wherein $N_b$ and Y do not have the same modification;
wherein XXX, YYY and ZZZ each independently represent one motif of three identical modifications on three consecutive nucleotides;
wherein the dsRNA agents have one or more lipophilic moieties conjugated to one or more positions on at least one strand; and
wherein the antisense strand of the dsRNA comprises two blocks of one, two or three phosphorothioate internucleotide linkages separated by 1, 2, 3, 4, 5, 6, 7, 8, 9, 10, 11, 12, 13, 14, 15, 16, 17, or 18 phosphate internucleotide linkages.

Various publications described multimeric siRNA and can all be used with the iRNA of the invention. Such publications include WO2007/091269, U.S. Pat. No. 7,858,769, WO2010/141511, WO2007/117686, WO2009/014887 and WO2011/031520, which are hereby incorporated by reference in their entirety.

In some embodiments, 100%, 95%, 90%, 85%, 80%, 75%, 70%, 65%, 60%, 55%, 50%, 45%, 40%, 35% or 30% of the iRNA agent of the invention is modified.

In some embodiments, each of the sense and antisense strands of the iRNA agent is independently modified with acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or 2'-ara-F.

In some embodiments, each of the sense and antisense strands of the iRNA agent contains at least two different modifications.

In some embodiments, the double-stranded iRNA agent of the invention of the invention does not contain any 2'-F modification.

In some embodiments, the double-stranded iRNA agent of the invention contains one, two, three, four, five, six, seven, eight, nine, ten, eleven or twelve 2'-F modification(s). In one example, double-stranded iRNA agent of the invention contains nine or ten 2'-F modifications.

The iRNA agent of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the iRNA comprises the phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand and/or antisense strand of the iRNA agent comprises one or more blocks of phosphorothioate or methylphosphonate internucleotide linkages. In one example, the sense strand comprises one block of two phosphorothioate or methylphosphonate internucleotide linkages. In one example, the antisense strand comprises two blocks of two phosphorothioate or methylphosphonate internucleotide linkages. For example, the two blocks of phosphorothioate or methylphosphonate internucleotide linkages are separated by 16-18 phosphate internucleotide linkages.

In some embodiments, the antisense strand of the iRNA agent of the invention is 100% complementary to a target RNA to hybridize thereto and inhibits its expression through RNA interference. In another embodiment, the antisense strand of the iRNA agent of the invention is at least 95%, at least 90%, at least 85%, at least 80%, at least 75%, at least 70%, at least 65%, at least 60%, at least 55%, or at least 50% complementary to a target RNA.

In one aspect, the invention relates to a iRNA agent capable of inhibiting the expression of a target gene. The iRNA agent comprises a sense strand and an antisense strand, each strand having 14 to 40 nucleotides. The sense strand contains at least one thermally destabilizing nucleotide, wherein at least one said thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand when the sense strand is 21 nucleotides in length. The antisense strand contains at least two modified nucleic acids that are smaller than a sterically demanding 2'-OMe modification. Preferably, the two modified nucleic acids that is smaller than a sterically demanding 2'-OMe are separated by 11 nucleotides in length. For example, the two modified nucleic acids are at positions 2 and 14 of the 5' end of the antisense strand.

In some embodiments, the compound of the invention disclosed herein is a miRNA mimic. In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded iRNAs. In some embodiments, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

In some embodiments, the compound of the invention disclosed herein is an antimir. In some embodiments, compound of the invention comprises at least two antimirs covalently linked to each other via a nucleotide-based or non-nucleotide-based linker, for example a linker described in the disclosure, or non-covalently linked to each other. The terms "antimir" "microRNA inhibitor" or "miR inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

In some embodiments, compound of the invention disclosed herein is an antagomir. In some embodiments, the compound of the invention comprises at least two antagomirs covalently linked to each other via a nucleotide-based or non-nucleotide-based linker, for example a linker described in the disclosure, or non-covalently linked to each other. Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate intersugar linkage and, for example, a cholesterol-moiety at 3'-end. In a preferred embodiment, antagomir comprises a 2'-O-methyl modification at all nucleotides, a cholesterol moiety at 3'-end, two phosphorothioate intersugar linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

Recent studies have found that dsRNA can also activate gene expression, a mechanism that has been termed "small RNA-induced gene activation" or RNAa (activating RNA). See for example Li, L. C. et al. *Proc Natl Acad Sci USA*. (2006), 103(46):17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites. In some embodiments, the RNA activator can increase the expression of a gene. In some embodiments, increased gene expression inhibits viability, growth development, and/or reproduction.

Accordingly, in some embodiments compound of the invention disclosed herein is activating RNA. In some embodiments, the compound of the invention comprises at least two activating RNAs covalently linked to each other via a nucleotide-based or non-nucleotide-based linker, for example a linker described in the disclosure, or non-covalently linked to each other.

Accordingly, in some embodiments, compound of the invention disclosed herein is a triplex forming oligonucleotide (TFO). In some embodiments, the compound of the invention comprises at least two TFOs covalently linked to each other via a nucleotide-based or non-nucleotide-based linker, for example a linker described in the disclosure, or non-covalently linked to each other. Recent studies have shown that triplex forming oligonucleotides can be designed which can recognize and bind to polypurine/polypyrimidine regions in double-stranded helical DNA in a sequence-specific manner. These recognition rules are outline by Maher III, L. J., et al., Science (1989) vol. 245, pp 725-730; Moser, H. E., et al., Science (1987) vol. 238, pp 645-630; Beal, P. A., et al., Science (1992) vol. 251, pp 1360-1363; Conney, M., et al., Science (1988) vol. 241, pp 456-459 and Hogan, M. E., et al., EP Publication 375408. Modification of the oligonucleotides, such as the introduction of intercalators and intersugar linkage substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 1 12:487-94). In general, the triplex-forming oligonucleotide has the sequence correspondence:

oligo 3'-A G G T
duplex 5'-A G C T
duplex 3'-T C G A

However, it has been shown that the A-AT and G-GC triplets have the greatest triple helical stability (Reither and Jeltsch, BMC Biochem, 2002, Sept12, Epub). The same authors have demonstrated that TFOs designed according to the A-AT and G-GC rule do not form non-specific triplexes, indicating that the triplex formation is indeed sequence specific.

Thus for any given sequence a triplex forming sequence can be devised. Triplex-forming oligonucleotides preferably are at least 15, more preferably 25, still more preferably 30 or more nucleotides in length, up to 50 or 100 nucleotides.

Formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFGl and endogenous HPRT genes in mammalian cells (Vasquez et al., Nucl Acids Res. 1999; 27: 1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-I gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94). Detailed description of the design, synthesis and administration of effective TFOs can be found in U.S. Pat. App. Nos. 2003 017068 and 2003 0096980 to Froehler et al, and 2002 0128218 and 2002 0123476 to Emanuele et al, and U.S. Pat. No. 5,721,138 to Lawn, contents of which are herein incorporated in their entireties.

Nucleic Acid Modifications

In some embodiments, the double-stranded iRNA agent of the invention comprises at least one nucleic acid modification described herein. For example, at least one modification selected from the group consisting of modified internucleoside linkage, modified nucleobase, modified sugar, and any combinations thereof. Without limitations, such a modification can be present anywhere in the double-stranded iRNA agent of the invention. For example, the modification can be present in one of the RNA molecules.

Nucleic Acid Modifications (Nucleobases)

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleoside backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The unmodified or natural nucleobases can be modified or replaced to provide iRNAs having improved properties. For example, nuclease resistant oligonucleotides can be prepared with these bases or with synthetic and natural nucleobases (e.g., inosine, xanthine, hypoxanthine, nubularine, isoguanosine, or tubercidine) and any one of the oligomer modifications described herein. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

An oligomeric compound described herein can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Exemplary modified nucleobases include, but are not limited to, other synthetic and natural nucleobases such as inosine, xanthine, hypoxanthine, nubularine, isoguanosine, tubercidine, 2-(halo)adenine, 2-(alkyl)adenine, 2-(propyl)adenine, 2-(amino)adenine, 2-(aminoalkyl)adenine, 2-(aminopropyl) adenine, 2-(methylthio)-$N^6$-(isopentenyl)adenine, 6-(alkyl) adenine, 6-(methyl)adenine, 7-(deaza)adenine, 8-(alkenyl) adenine, 8-(alkyl)adenine, 8-(alkynyl)adenine, 8-(amino) adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, $N^3$-(methyl)uracil, 5-uracil (i.e., pseudouracil), 2-(thio)pseudouracil, 4-(thio)pseudouracil, 2,4-(dithio)pseudouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanosine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed.

As used herein, a universal nucleobase is any nucleobase that can base pair with all of the four naturally occurring nucleobases without substantially affecting the melting behavior, recognition by intracellular enzymes or activity of the iRNA duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, Nucleic Acids Research, 29, 2437-2447).

Further nucleobases include those disclosed in U.S. Pat. No. 3,687,808; those disclosed in International Application No. PCT/US09/038425, filed Mar. 26, 2009; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P.Ed. Wiley- VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Nucleic Acid Modifications (Sugar)

Double-stranded iRNA agent of the inventions provided herein can comprise one or more (e.g., 1, 2, 3, 4, 5, 6, 7, 8, 9, 10, 11, 12, 13, 14, 15 or more) monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a locked nucleic acid or bicyclic nucleic acid. In certain embodiments, oligomeric compounds comprise one or more (e.g., 1, 2, 3, 4, 5, 6, 7, 8, 9, 10, 11, 12, 13, 14, 15 or more) monomers that are LNA.

In some embodiments of a locked nucleic acid, the 2' position of furanosyl is connected to the 4' position by a linker selected independently from —[C(R1)(R2)]$_n$—, —[C(R1)(R2)]$_n$—O—, —[C(R1)(R2)]$_n$—N(R1)-, —[C(R1)(R2)]$_n$—N(R1)-O—, —[C(R1R2)]$_n$—O—N(R1)-, —C(R1)=C(R2)-O—, —C(R1)=N—, —C(R1)=N—O—, —C(=NR1)-, —C(=NR1)-O—, —C(=O)—, —C(=O)O—, —C(=S)—, —C(=S)O—, —C(=S)S—, —O—, —Si(R1)2-, —S(=O)$_x$— and —N(R1)-;

wherein:

x is 0, 1, or 2;

n is 1, 2, 3, or 4;

each R1 and R2 is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, N3, COOJ1, acyl (C(=O)—H), substituted acyl, CN, sulfonyl (S(=O) 2-J1), or sulfoxyl (S(=O)-J1); and each J1 and J2 is, independently, H, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl or a protecting group.

In some embodiments, each of the linkers of the LNA compounds is, independently, —[C(R1)(R2)]n-, —[C(R1)(R2)]n-O—, —C(R1R2)-N(R1)-O— or —C(R1R2)-O—N(R1)-. In another embodiment, each of said linkers is, independently, 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R1)-2' and 4'-CH$_2$—N(R1)-O-2'- wherein each R1 is, independently, H, a protecting group or C1-C12 alkyl.

Certain LNA's have been prepared and disclosed in the patent literature as well as in scientific literature (Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039; Examples of issued US patents and published applications that disclose LNA s include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are LNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term methyleneoxy (4'-CH$_2$—O-2') LNA is used for the bicyclic moiety; in the case of an ethylene group in this position, the term ethyleneoxy (4'-CH$_2$CH$_2$—O-2') LNA is used (Singh et al., Chem. Commun., 1998, 4, 455-456: Morita et al., Bioorganic Medicinal Chemistry, 2003, 11, 2211-2226). Methyleneoxy (4'-CH$_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., Proc. Natl. Acad. Sci. U.S.A., 2000, 97, 5633-5638).

An isomer of methyleneoxy (4'-CH$_2$—O-2') LNA that has also been discussed is alpha-L-methyleneoxy (4'-CH$_2$—O-2') LNA which has been shown to have superior stability against a 3'-exonuclease. The alpha-L-methyleneoxy (4'-CH$_2$—O-2') LNA's were incorporated into antisense gapmers and chimeras that showed potent antisense activity (Frieden et al., Nucleic Acids Research, 2003, 21, 6365-6372).

The synthesis and preparation of the methyleneoxy (4'-CH$_2$—O-2') LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-CH$_2$—O-2') LNA, phosphorothioate-methyleneoxy (4'-CH$_2$—O-2') LNA and 2'-thio-LNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Modified sugar moieties are well known and can be used to alter, typically increase, the affinity of the antisense compound for its target and/or increase nuclease resistance. A representative list of preferred modified sugars includes but is not limited to bicyclic modified sugars, including methyleneoxy (4'-CH$_2$—O-2') LNA and ethyleneoxy (4'-(CH$_2$)$_2$—O-2' bridge) ENA; substituted sugars, especially 2'-substituted sugars having a 2'-F, 2'-OCH₃ or a 2'-O(CH₂)₂—OCH₃ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH₂CH₂O)ₙCH₂CH₂OR, n=1-50; "locked" nucleic acids (LNA) in which the furanose portion of the nucleoside includes a bridge connecting two carbon atoms on the furanose ring, thereby forming a bicyclic ring system; O-AMINE or O—(CH₂)ₙAMINE (n=1-10, AMINE=NH₂; alkylamino, dialkylamino, heterocyclyl, arylamino, diaryl amino, heteroaryl amino, diheteroaryl amino, ethylene diamine or polyamino); and O—CH₂CH₂(NCH₂CH₂NMe₂)₂.

"Deoxy" modifications include hydrogen (i.e. deoxyribose sugars, which are of particular relevance to the single-strand overhangs); halo (e.g., fluoro); amino (e.g. NH₂; alkylamino, dialkylamino, heterocyclyl, arylamino, diaryl amino, heteroaryl amino, diheteroaryl amino, or amino acid); NH(CH₂CH₂NH)ₙCH₂CH₂-AMINE (AMINE=NH₂; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thioalkyl; thioalkoxy; thioalkyl; alkyl; cycloalkyl; aryl; alkenyl and alkynyl, which can be optionally substituted with e.g., an amino functionality.

Other suitable 2'-modifications, e.g., modified MOE, are described in U.S. Patent Application Publication No. 20130130378, contents of which are herein incorporated by reference.

A modification at the 2' position can be present in the arabinose configuration The term "arabinose configuration" refers to the placement of a substituent on the C2' of ribose in the same configuration as the 2'-OH is in the arabinose.

The sugar can comprise two different modifications at the same carbon in the sugar, e.g., gem modification. The sugar group can also contain one or more carbons that possess the opposite stereochemical configuration than that of the corresponding carbon in ribose. Thus, an oligomeric compound can include one or more monomers containing e.g., arabinose, as the sugar. The monomer can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

Double-stranded iRNA agent of the inventions disclosed herein can also include abasic sugars, i.e., a sugar which lack a nucleobase at C-1' or has other chemical groups in place of a nucleobase at C1'. See for example U.S. Pat. No. 5,998,203, content of which is herein incorporated in its entirety. These abasic sugars can also be further containing modifications at one or more of the constituent sugar atoms. Double-stranded iRNA agent of the inventions can also contain one or more sugars that are the L isomer, e.g. L-nucleosides. Modification to the sugar group can also include replacement of the 4'-O with a sulfur, optionally substituted nitrogen or CH₂ group. In some embodiments, linkage between C1' and nucleobase is in a configuration.

Sugar modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide. In some embodiments, acyclic nucleotide is

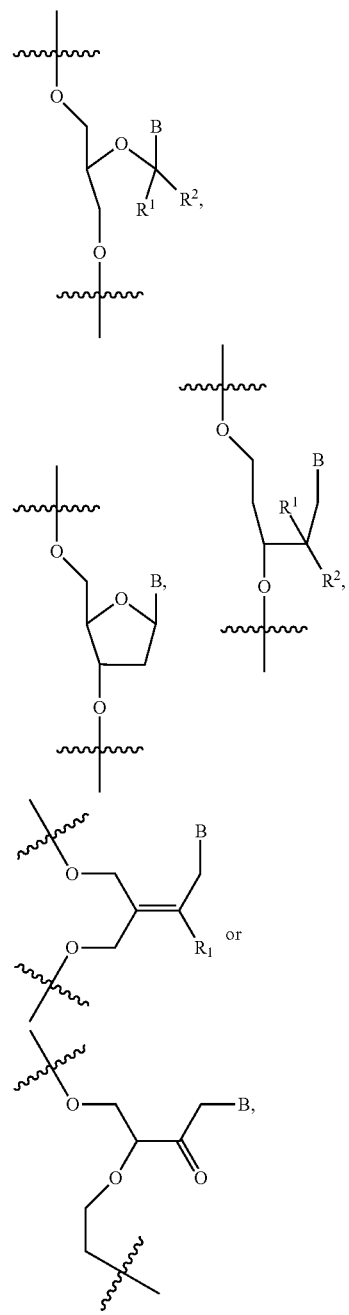

wherein B is a modified or unmodified nucleobase, R₁ and R₂ independently are H, halogen, OR₃, or alkyl; and R₃ is H, alkyl, cycloalkyl, aryl, aralkyl, heteroaryl or sugar).

In some embodiments, sugar modifications are selected from the group consisting of 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE) and gem 2'-OMe/2'F with 2'-O-Me in the arabinose configuration.

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of O, S, S(O), SO$_2$, N(R'), C(O), N(R')C(O)O, OC(O)N(R'), CH(Z'), phosphorous containing linkage, optionally substituted aryl, optionally substituted heteroaryl, optionally substituted heterocyclic or optionally substituted cycloalkyl, where R' is hydrogen, acyl or optionally substituted aliphatic, Z' is selected from the group consisting of OR$_{11}$, COR$_{11}$, CO$_2$R$_{11}$,

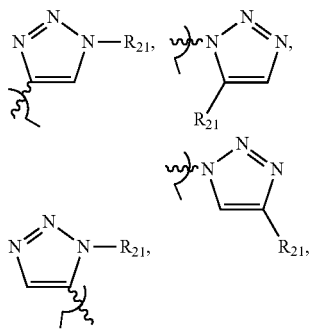

NR$_{21}$R$_{31}$, CONR$_{21}$R$_{31}$, CON(H)NR$_{21}$R$_{31}$, ONR$_{21}$R$_{31}$, CON(H)N=CR$_{41}$R$_{51}$, N(R$_{21}$)C(=NR$_{31}$)NR$_{21}$R$_{31}$, N(R$_{21}$)C(O)NR$_{21}$R$_{31}$, N(R$_{21}$)C(S)NR$_{21}$R$_{31}$, OC(O)NR$_{21}$R$_{31}$, SC(O)NR$_{21}$R$_{31}$, N(R$_{21}$)C(S)OR$_{11}$, N(R$_{21}$)C(O)OR$_{11}$, N(R$_{21}$)C(O)SR$_{11}$, N(R$_{21}$)N=CR$_{41}$R$_{51}$, ON=CR$_{41}$R$_{51}$, SO$_2$R$_{11}$, SOR$_{11}$, SR$_{11}$, and substituted or unsubstituted heterocyclic; R$_{21}$ and R$_{31}$ for each occurrence are independently hydrogen, acyl, unsubstituted or substituted aliphatic, aryl, heteroaryl, heterocyclic, OR$_{11}$, COR$_{11}$, CO$_2$R$_{11}$, or NR$_{11}$R$_{11'}$; or R$_{21}$ and R$_{31}$, taken together with the atoms to which they are attached, form a heterocyclic ring; R$_{41}$ and R$_{51}$ for each occurrence are independently hydrogen, acyl, unsubstituted or substituted aliphatic, aryl, heteroaryl, heterocyclic, OR$_{11}$, COR$_{11}$, or CO$_2$R$_{11}$, or NR$_{11}$R$_{11'}$; and R$_{11}$ and R$_{11'}$ are independently hydrogen, aliphatic, substituted aliphatic, aryl, heteroaryl, or heterocyclic. In some embodiments, the hydrogen attached to the C4' of the 5' terminal nucleotide is replaced.

In some embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the iRNA.

In certain embodiments, LNA's include bicyclic nucleoside having the formula:

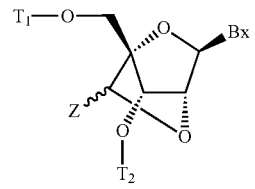

wherein:
Bx is a heterocyclic base moiety;
T$_1$ is H or a hydroxyl protecting group;
T$_2$ is H, a hydroxyl protecting group or a reactive phosphorus group;
Z is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, or substituted amide.

In some embodiments, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C$_1$-C$_6$ alkyl, and X is O, S or NJ1.

In certain such embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H, C$_1$-C$_6$ alkyl, or substituted C$_1$-C$_6$ alkyl and X is 0 or NJ1.

In certain embodiments, the Z group is C$_1$-C$_6$ alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C$_1$-C$_6$ alkyl, and X is O, S or NJ1. In another embodiment, the Z group is C$_1$-C$_6$ alkyl substituted with one or more Xx, wherein each Xx is independently halo (e.g., fluoro), hydroxyl, alkoxy (e.g., CH$_3$O—), substituted alkoxy or azido.

In certain embodiments, the Z group is —CH$_2$Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C$_1$-C$_6$ alkyl, and X is O, S or NJ1. In another embodiment, the Z group is CH$_2$Xx, wherein Xx is halo (e.g., fluoro), hydroxyl, alkoxy (e.g., CH$_3$O—) or azido.

In certain such embodiments, the Z group is in the (R)-configuration:

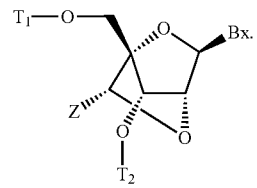

In certain such embodiments, the Z group is in the (S)-configuration:

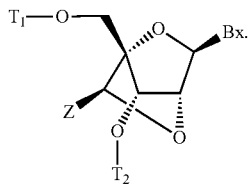

In certain embodiments, each $T_1$ and $T_2$ is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, $T_1$ is a hydroxyl protecting group selected from acetyl, benzyl, t-butyldimethylsilyl, t-butyldiphenylsilyl and dimethoxytrityl wherein a more preferred hydroxyl protecting group is $T_1$ is 4,4'-dimethoxytrityl.

In certain embodiments, $T_2$ is a reactive phosphorus group wherein preferred reactive phosphorus groups include diisopropylcyanoethoxy phosphoramidite and H-phosphonate. In certain embodiments $T_1$ is 4,4'-dimethoxytrityl and $T_2$ is diisopropylcyanoethoxy phosphoramidite.

In certain embodiments, the compounds of the invention comprise at least one monomer of the formula:

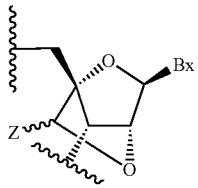

or of the formula:

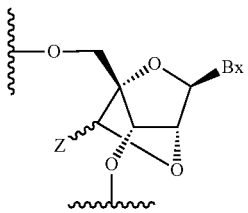

or of the formula:

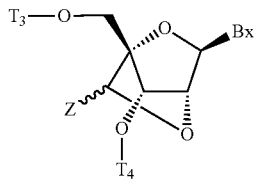

wherein
Bx is a heterocyclic base moiety;
$T_3$ is H, a hydroxyl protecting group, a linked conjugate group or an internucleoside linking group attached to a nucleoside, a nucleotide, an oligonucleoside, an oligonucleotide, a monomeric subunit or an oligomeric compound;

$T_4$ is H, a hydroxyl protecting group, a linked conjugate group or an internucleoside linking group attached to a nucleoside, a nucleotide, an oligonucleoside, an oligonucleotide, a monomeric subunit or an oligomeric compound;

wherein at least one of $T_3$ and $T_4$ is an internucleoside linking group attached to a nucleoside, a nucleotide, an oligonucleoside, an oligonucleotide, a monomeric subunit or an oligomeric compound; and Z is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, or substituted amide.

In some embodiments, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In some embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H or $C_1$-$C_6$ alkyl, and X is O or NJ1.

In certain such embodiments, at least one Z is $C_1$-$C_6$ alkyl or substituted $C_1$-$C_6$ alkyl. In certain embodiments, each Z is, independently, $C_1$-$C_6$ alkyl or substituted $C_1$-$C_6$ alkyl. In certain embodiments, at least one Z is $C_1$-$C_6$ alkyl. In certain embodiments, each Z is, independently, $C_1$-$C_6$ alkyl. In certain embodiments, at least one Z is methyl. In certain embodiments, each Z is methyl. In certain embodiments, at least one Z is ethyl. In certain embodiments, each Z is ethyl. In certain embodiments, at least one Z is substituted $C_1$-$C_6$ alkyl. In certain embodiments, each Z is, independently, substituted $C_1$-$C_6$ alkyl. In certain embodiments, at least one Z is substituted methyl. In certain embodiments, each Z is substituted methyl. In certain embodiments, at least one Z is substituted ethyl. In certain embodiments, each Z is substituted ethyl.

In certain embodiments, at least one substituent group is $C_1$-$C_6$ alkoxy (e.g., at least one Z is $C_1$-$C_6$ alkyl substituted with one or more $C_1$-$C_6$ alkoxy). In another embodiment, each substituent group is, independently, $C_1$-$C_6$ alkoxy (e.g., each Z is, independently, $C_1$-$C_6$ alkyl substituted with one or more $C_1$-$C_6$ alkoxy).

In certain embodiments, at least one $C_1$-$C_6$ alkoxy substituent group is $CH_3O$— (e.g., at least one Z is $CH_3OCH_2$—). In another embodiment, each $C_1$-$C_6$ alkoxy substituent group is $CH_3O$ (e.g., each Z is $CH_3OCH_2$—).

In certain embodiments, at least one substituent group is halogen (e.g., at least one Z is $C_1$-$C_6$ alkyl substituted with one or more halogen). In certain embodiments, each substituent group is, independently, halogen (e.g., each Z is, independently, $C_1$-$C_6$ alkyl substituted with one or more halogen). In certain embodiments, at least one halogen substituent group is fluoro (e.g., at least one Z is $CH_2FCH_2$—, $CHF_2CH_2$— or $CF_3CH_2$—). In certain embodiments, each halo substituent group is fluoro (e.g., each Z is, independently, $CH_2FCH_2$—, $CHF_2CH_2$— or $CF_3CH_2$—).

In certain embodiments, at least one substituent group is hydroxyl (e.g., at least one Z is C1-C6 alkyl substituted with one or more hydroxyl). In certain embodiments, each substituent group is, independently, hydroxyl (e.g., each Z is, independently, $C_1$-$C_6$ alkyl substituted with one or more hydroxyl). In certain embodiments, at least one Z is $HOCH_2$—. In another embodiment, each Z is $HOCH_2$—.

In certain embodiments, at least one Z is $CH_3$—, $CH_3CH_2$—, $CH_2OCH_3$—, $CH_2F$— or $HOCH_2$—. In certain embodiments, each Z is, independently, $CH_3$—, $CH_3CH_2$—, $CH_2OCH_3$—, $CH_2F$— or $HOCH_2$—.

In certain embodiments, at least one Z group is $C_1$-$C_6$ alkyl substituted with one or more Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or $C_1$-$C_6$ alkyl, and X is O, S or NJ1. In another embodiment, at least one Z group is $C_1$-$C_6$ alkyl substituted with one or more Xx, wherein each Xx is, independently, halo (e.g., fluoro), hydroxyl, alkoxy (e.g., $CH_3O$—) or azido.

In certain embodiments, each Z group is, independently, $C_1$-$C_6$ alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or $C_1$-$C_6$ alkyl, and X is O, S or NJ1. In another embodiment, each Z group is, independently, $C_1$-$C_6$ alkyl substituted with one or more Xx, wherein each Xx is independently halo (e.g., fluoro), hydroxyl, alkoxy (e.g., $CH_3O$—) or azido.

In certain embodiments, at least one Z group is —$CH_2Xx$, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or $C_1$-$C_6$ alkyl, and X is O, S or NJ1 In certain embodiments, at least one Z group is —$CH_2Xx$, wherein Xx is halo (e.g., fluoro), hydroxyl, alkoxy (e.g., $CH_3O$—) or azido.

In certain embodiments, each Z group is, independently, $CH_2Xx$, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or $C_1$-$C_6$ alkyl, and X is O, S or NJ1. In another embodiment, each Z group is, independently, —$CH_2Xx$, wherein each Xx is, independently, halo (e.g., fluoro), hydroxyl, alkoxy (e.g., $CH_3O$—) or azido.

In certain embodiments, at least one Z is $CH_3$—. In another embodiment, each Z is, $CH_3$—.

In certain embodiments, the Z group of at least one monomer is in the (R) configuration represented by the formula:

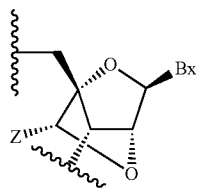

or the formula:

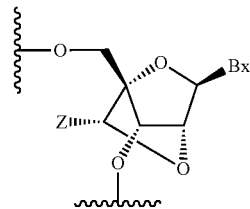

or the formula:

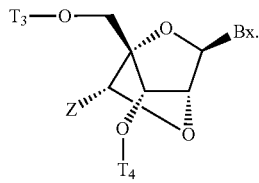

IN certain embodiments, the Z group of each monomer of the formula is in the (R)-configuration.

In certain embodiments, the Z group of at least one monomer is in the (S)-configuration represented by the formula:

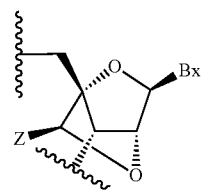

or the formula:

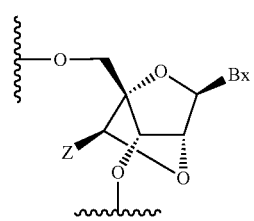

or the formula:

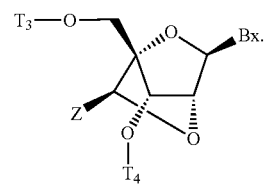

In certain embodiments, the Z group of each monomer of the formula is in the (S)-configuration.

In certain embodiments, $T_3$ is H or a hydroxyl protecting group. In certain embodiments, $T_4$ is H or a hydroxyl protecting group. In a further embodiment $T_3$ is an internucleoside linking group attached to a nucleoside, a nucleotide or a monomeric subunit. In certain embodiments, $T_4$ is an internucleoside linking group attached to a nucleoside, a nucleotide or a monomeric subunit. In certain embodiments, $T_3$ is an internucleoside linking group attached to an oligonucleoside or an oligonucleotide. In certain embodiments, $T_4$ is an internucleoside linking group attached to an oligonucleoside or an oligonucleotide. In certain embodiments, $T_3$ is an internucleoside linking group attached to an oligomeric compound. In certain embodiments, $T_4$ is an internucleoside linking group attached to an oligomeric compound. In certain embodiments, at least one of $T_3$ and $T_4$ comprises an internucleoside linking group selected from phosphodiester or phosphorothioate.

In certain embodiments, double-stranded iRNA agent of the invention comprise at least one region of at least two contiguous monomers of the formula:

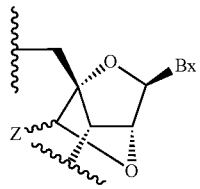

or of the formula:

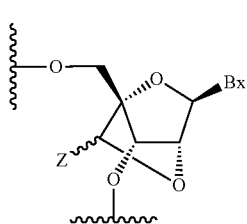

or of the formula:

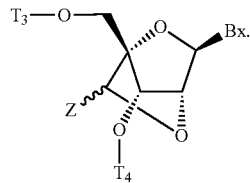

In certain such embodiments, LNAs include, but are not limited to, (A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$-O-2') LNA, (D) Aminooxy (4'-CH$_2$—O—N(R)-2') LNA and (E) Oxyamino (4'-CH$_2$—N(R)—O-2') LNA, as depicted below:

(A)

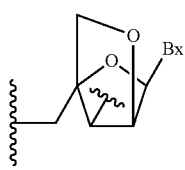

-continued (B)

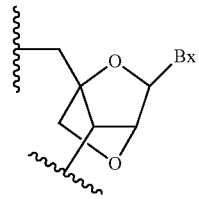

(C)

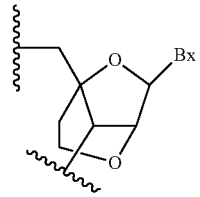

(D)

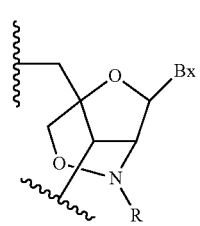

(E)

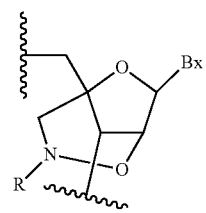

In certain embodiments, the double-stranded iRNA agent of the invention comprises at least two regions of at least two contiguous monomers of the above formula. In certain embodiments, the double-stranded iRNA agent of the invention comprises a gapped motif. In certain embodiments, the double-stranded iRNA agent of the invention comprises at least one region of from about 8 to about 14 contiguous β-D-2'-deoxyribofuranosyl nucleosides. In certain embodiments, the Double-stranded iRNA agent of the invention comprises at least one region of from about 9 to about 12 contiguous β-D-2'-deoxyribofuranosyl nucleosides.

In certain embodiments, the double-stranded iRNA agent of the invention comprises at least one (e.g., 1, 2, 3, 4, 5, 6, 7, 8, 9, 10, 11, 12, 13, 14, 15 or more) comprises at least one (S)-cEt monomer of the formula:

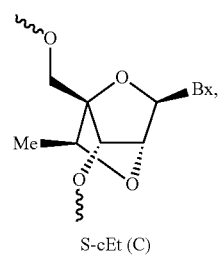

S-cEt (C)

wherein Bx is heterocyclic base moiety.

In certain embodiments, monomers include sugar mimetics. In certain such embodiments, a mimetic is used in place of the sugar or sugar-internucleoside linkage combination, and the nucleobase is maintained for hybridization to a selected target. Representative examples of a sugar mimetics include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

Nucleic Acid Modifications (Intersugar Linkage)

Described herein are linking groups that link monomers (including, but not limited to, modified and unmodified nucleosides and nucleotides) together, thereby forming an oligomeric compound, e.g., an oligonucleotide. Such linking groups are also referred to as intersugar linkage. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—$CH_2$—N($CH_3$)—O—CH2-), thiodiester (—O—C(O)—S—), thionocarbamate (—O—C(O)(NH)—S—); siloxane (—O—Si(H)$_2$—O—); and N,N'-dimethylhydrazine ($CH_2$—N($CH_3$)—N($CH_3$)—). Modified linkages, compared to natural phosphodiester linkages, can be used to alter, typically increase, nuclease resistance of the oligonucleotides. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The phosphate group in the linking group can be modified by replacing one of the oxygens with a different substituent. One result of this modification can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the linkage can be replaced by any of the following: S, Se, $BR_3$ (R is hydrogen, alkyl, aryl), C (i.e. an alkyl group, an aryl group, etc. . . . ), H, $NR_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the sugar of the monomer), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

In certain embodiments, the phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-$CH_2$—C(=O)—N(H)-5') and amide-4 (3'-$CH_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide, sulfonate, sulfonamide, sulfonate ester, thioformacetal (3'-S—$CH_2$—O-5'), formacetyl (3'-O—$CH_2$—O-5'), oxime, methyleneimino, methylenecarbonylamino, methylenemethylimino (MMI, 3'-$CH_2$—N($CH_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—$CH_2$—S—C5', C3'-O—P(O)—O—SS—C5', C3'-$CH_2$—NH—NH—C5', 3'-NHP(O)(OCH$_3$)—O-5' and 3'-NHP(O)(OCH$_3$)—O-5' and nonionic linkages containing mixed N, O, S and $CH_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phosphotriesters, aminoalkylphosphotriesters, alkylphosphonates (e.g., methyl-phosphonate), selenophosphates, phosphoramidates (e.g., N-alkylphosphoramidate), and boranophosphonates.

In some embodiments, the double-stranded iRNA agent of the invention comprises at least one (e.g., 1, 2, 3, 4, 5, 6, 7, 8, 9, 10, 11, 12, 13, 14, 15 or more and up to including all) modified or nonphosphodiester linkages. In some embodiments, the double-stranded iRNA agent of the invention comprises at least one (e.g., 1, 2, 3, 4, 5, 6, 7, 8, 9, 10, 11, 12, 13, 14, 15 or more and up to including all) phosphorothioate linkages.

The double-stranded iRNA agent of the inventions can also be constructed wherein the phosphate linker and the sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. A preferred surrogate is a PNA surrogate.

The double-stranded iRNA agent of the inventions described herein can contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the double-stranded iRNA agent of the inventions provided herein are all such possible isomers, as well as their racemic and optically pure forms.

Nucleic Acid Modifications (Terminal Modifications

In some embodiments, the double-stranded iRNA agent further comprises a phosphate or phosphate mimic at the 5'-end of the antisense strand. In one embodiment, the phosphate mimic is a 5'-vinyl phosphonate (VP).

In some embodiments, the 5'-end of the antisense strand of the double-stranded iRNA agent does not contain a 5'-vinyl phosphonate (VP).

Ends of the iRNA agent of the invention can be modified. Such modifications can be at one end or both ends. For example, the 3' and/or 5' ends of an iRNA can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a double stranded oligomeric compound, this array can substitute for a hairpin loop in a hairpin-type oligomeric compound.

Terminal modifications useful for modulating activity include modification of the 5' end of iRNAs with phosphate or phosphate analogs. In certain embodiments, the 5' end of an iRNA is phosphorylated or includes a phosphoryl analog. Exemplary 5'-phosphate modifications include those which are compatible with RISC mediated gene silencing. Modifications at the 5'-terminal end can also be useful in stimulating or inhibiting the immune system of a subject. In some embodiments, the 5'-end of the oligomeric compound comprises the modification

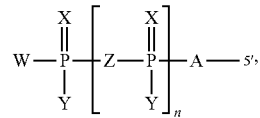

wherein W, X and Y are each independently selected from the group consisting of O, OR (R is hydrogen, alkyl, aryl), S, Se, BR$_3$ (R is hydrogen, alkyl, aryl), BH$_3^-$, C (i.e. an alkyl group, an aryl group, etc. . . . ), H, NR$_2$ (R is hydrogen, alkyl, aryl), or OR (R is hydrogen, alkyl or aryl); A and Z are each independently for each occurrence absent, O, S, CH$_2$, NR (R is hydrogen, alkyl, aryl), or optionally substituted alkylene, wherein backbone of the alkylene can comprise one or more of O, S, SS and NR (R is hydrogen, alkyl, aryl) internally and/or at the end; and n is 0-2. In some embodiments, n is 1 or 2. It is understood that A is replacing the oxygen linked to 5' carbon of sugar. When n is 0, W and Y together with the P to which they are attached can form an optionally substituted 5-8 membered heterocyclic, wherein W an Y are each independently O, S, NR' or alkylene. Preferably the heterocyclic is substituted with an aryl or heteroaryl. In some embodiments, one or both hydrogen on C5' of the 5'-terminal nucleotides are replaced with a halogen, e.g., F.

Exemplary 5'-modifications include, but are not limited to, 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ((HO)$_2$(O)P—NH—5', (HO)(NH$_2$)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH$_2$OMe), ethoxymethyl, etc. . . . ). Other exemplary 5'-modifications include where Z is optionally substituted alkyl at least once, e.g., ((HO)$_2$(X)P—O[—CH$_2$)$_a$—O—P(X)(OH)—O]$_b$-5', ((HO)$_2$(X)P—O[—(CH$_2$)$_a$—P(X)(OH)—O]$_b$-5', ((HO)$_2$(X)P—[—(CH$_2$)$_a$—O—P(X)(OH)—O]$_b$-5'; dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[—(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[—(CH$_2$)$_a$—P(X)(OH)—O]$_b$-5', Me$_2$N[—(CH$_2$)$_a$—P(X)(OH)—O]$_b$-5', wherein a and b are each independently 1-10. Other embodiments, include replacement of oxygen and/or sulfur with BH$_3$, BH$_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Thermally Destabilizing Modifications

The compounds of the invention, such as iRNAs or dsRNA agents, can be optimized for RNA interference by increasing the propensity of the iRNA duplex to disassociate or melt (decreasing the free energy of duplex association) by introducing a thermally destabilizing modification in the sense strand at a site opposite to the seed region of the antisense strand (i.e., at positions 2-8 of the 5'-end of the antisense strand). This modification can increase the propensity of the duplex to disassociate or melt in the seed region of the antisense strand.

The thermally destabilizing modifications can include abasic modification; mismatch with the opposing nucleotide in the opposing strand; and sugar modification such as 2'-deoxy modification or acyclic nucleotide, e.g., unlocked nucleic acids (UNA) or glycerol nucleic acid (GNA).

Exemplified abasic modifications are:

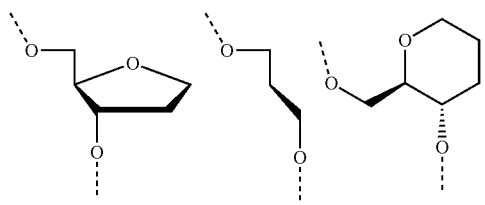

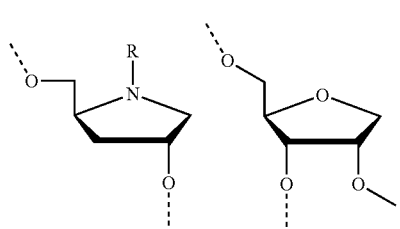

Exemplified sugar modifications are:

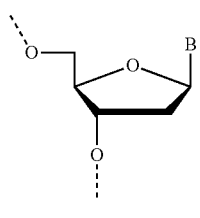

2'-deoxy

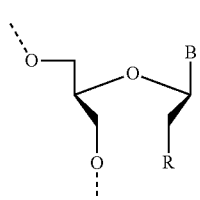

unlocked nucleic acid
R = H, OH, O-alkyl

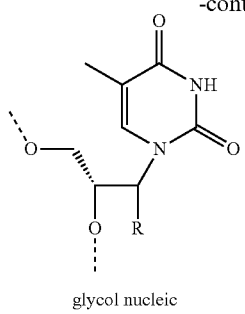

glycol nucleic acid
R = H, OH, O-alkyl

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent and/or at least one of ribose carbons or oxygen (e.g., C1', C2', C3', C4' or O4') are independently or in combination absent from the nucleotide. In some embodiments, acyclic nucleotide is

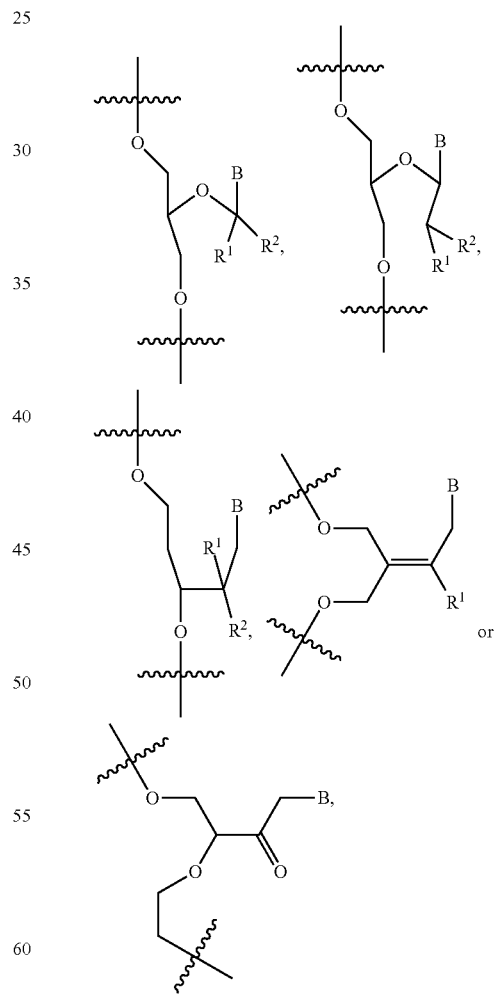

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

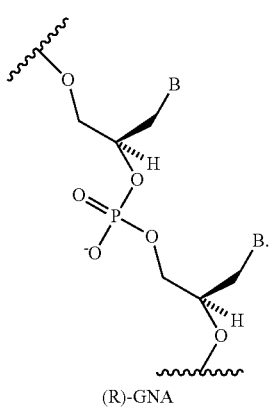

(R)-GNA

The thermally destabilizing modification can be mismatches (i.e., noncomplementary base pairs) between the thermally destabilizing nucleotide and the opposing nucleotide in the opposite strand within the dsRNA duplex. Exemplary mismatch basepairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the compounds of the invention, such as siRNA or iRNA agent, contains at least one nucleobase in the mismatch pairing that is a 2'-deoxy nucleobase; e.g., the 2'-deoxy nucleobase is in the sense strand.

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

Nucleobase modifications with impaired or completely abolished capability to form hydrogen bonds with bases in the opposite strand have been evaluated for destabilization of the central region of the dsRNA duplex as described in WO 2010/0011895, which is herein incorporated by reference in its entirety. Exemplary nucleobase modifications are:

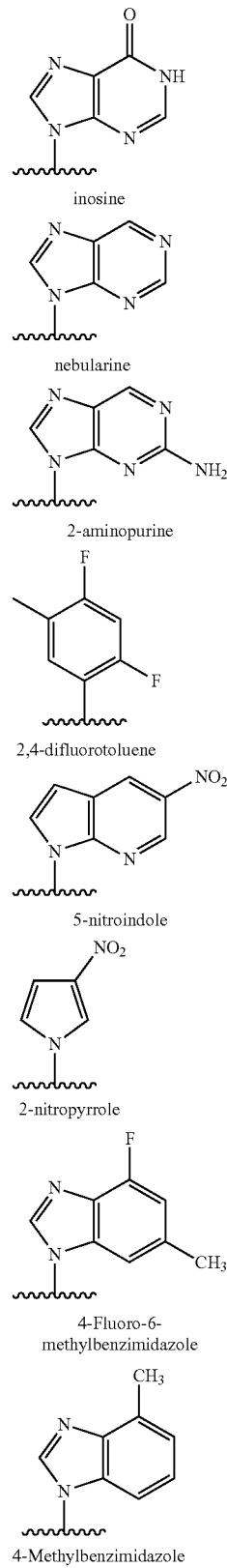

inosine nebularine 2-aminopurine 2,4-difluorotoluene 5-nitroindole 2-nitropyrrole 4-Fluoro-6-methylbenzimidazole 4-Methylbenzimidazole Exemplary phosphate modifications known to decrease the thermal stability of dsRNA duplexes compared to natural phosphodiester linkages are:

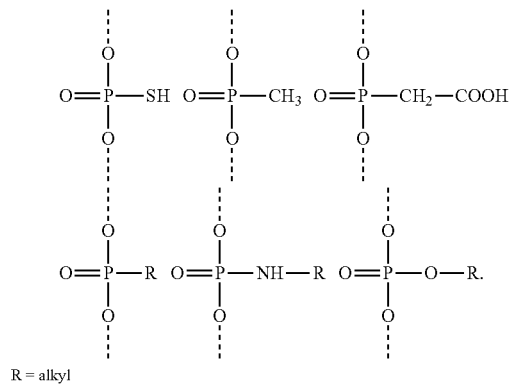

R = alkyl

In some embodiments, compounds of the invention can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, compounds of the invention can comprise L sugars (e.g., L ribose, L-arabinose with 2'-H, 2'-OH and 2'-OMe). For example, these L sugar modifications can be used to promote nuclease resistance or to inhibit binding of the sense to the antisense strand, or can be used at the 5' end of the sense strand to avoid sense strand activation by RISC.

In one embodiment the iRNA agent of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In some embodiments, at least one strand of the iRNA agent of the invention disclosed herein is 5' phosphorylated or includes a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), (OH)$_2$(O)P-5'-CH$_2$—), 5'-alkyletherphosphonates (R=alkylether=methoxymethyl (MeOCH2-), ethoxymethyl, etc., e.g. RP(OH)(O)—O-5'-).

Target Genes

Without limitations, target genes for siRNAs include, but are not limited to genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Specific exemplary target genes for the siRNAs include, but are not limited to, PCSK-9, ApoC3, AT3, AGT, ALAS1, TMPR, HAO1, AGT, C5, CCR-5, PDGF beta gene; Erb-B gene, Src gene; CRK gene; GRB2 gene; RAS gene; MEKK gene; JNK gene; RAF gene; Erk1/2 gene; PCNA (p21) gene; MYB gene; c-MYC gene; JUN gene; FOS gene; BCL-2 gene; Cyclin D gene; VEGF gene; EGFR gene; Cyclin A gene; Cyclin E gene; WNT-1 gene; beta-catenin gene; c-MET gene; PKC gene; NFKB gene; STAT3 gene; survivin gene; Her2/Neu gene; topoisomerase I gene; topoisomerase II alpha gene; p73 gene; p21 (WAF1/CIP1) gene, p27 (KIP1) gene; PPM1D gene; caveolin I gene; MIB I gene; MTAI gene; M68 gene; tumor suppressor genes; p53 gene; DN-p63 gene; pRb tumor suppressor gene; APC1 tumor suppressor gene; BRCA1 tumor suppressor gene; PTEN tumor suppressor gene; MLL fusion genes, e.g., MLL-AF9, BCR/ABL fusion gene; TEL/AML1 fusion gene; EWS/FLI1 fusion gene; TLS/FUS1 fusion gene; PAX3/FKHR fusion gene; AML1/ETO fusion gene; alpha v-integrin gene; Flt-1 receptor gene; tubulin gene; Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, plasmodium gene, a gene that is required for plasmodium gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in loss of heterozygosity (LOH) cells, one allele gene of a polymorphic gene and combinations thereof.

The loss of heterozygosity (LOH) can result in homozygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in duploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific modulation of one allele of an essential gene with a composition of the invention.

In certain embodiments, the invention provides a double-stranded iRNA agent of the invention that modulates a micro-RNA.

Targeting CNS

In some embodiments, the invention provides a double-stranded iRNA agent that targets APP for Early Onset Familial Alzheimer Disease, ATXN2 for Spinocerebellar Ataxia 2 and ALS, and C9orf72 for Amyotrophic Lateral Sclerosis and Frontotemporal Dementia.

In some embodiments, the invention provides a double-stranded iRNA agent that targets TARDBP for ALS, MAPT (Tau) for Frontotemporal Dementia, and HTT for Huntington Disease.

In some embodiments, the invention provides a double-stranded iRNA agent that targets SNCA for Parkinson Disease, FUS for ALS, ATXN3 for Spinocerebellar Ataxia 3, ATXN1 for SCA1, genes for SCA7 and SCA8, ATN1 for DRPLA, MeCP2 for XLMR, PRNP for Prion Diseases, recessive CNS disorders: Lafora Disease, DMPK for DM1 (CNS and Skeletal Muscle), and TTR for hATTR (CNS, ocular and systemic).

Spinocerebellar ataxia is an inherited brain-function disorder. Dominantly inherited forms of spinocerebellar ataxias, such as SCA1-8, are devastating disorders with no disease-modifying therapy. Exemplary targets include SCA2, SCA3, and SCA1.

Targeting ATXN2 for SCA2

Spinocerebellar Ataxia 2 (SCA2), a progressive ataxia, is the second most common SCA. Another disease associated with this target is amyotrophic lateral sclerosis (ALS). These diseases are debilitating and ultimately lethal diseases with no disease-modifying therapy. The prevalence of SCA is 2-6 per 100,000 people; ATXN2 causes 15% of SCA population worldwide and much more SCA populations in some countries, especially in Cuba (40 per 100,000 people). Targeting ATXN2 can be excellent via human molecular genetics, e.g., coding CAG repeat expansion in ATXN2 was discovered in familial and sporadic SCA and ALS, in tissues such as spinal cord, brainstem, or cerebellum. The mechanism of this targeting may be because autosomal dominant coding CAG expansion of ATXN2 causes expression of toxic, misfolded protein and Purkinje cell and neuronal death. The efficacy has been shown by 70% knockdown (KD) of ATXN2 mRNA; and mATXN2 mice KD POC has been demonstrated. With respect to safety, mATXN2 knockout (KO) mice have been reported healthy. Possible diagnosis includes family history; genetic testing; or early symptoms. Biomarkers that can be used include, e.g., CSF CAG mRNA and peptide repeat proteins Targeting ATXA3 for SCA3

Spinocerebellar Ataxia 3 (SCA3), a progressive ataxia, is the most common SCA worldwide. This disease is debilitating and ultimately lethal disease with no disease-modifying therapy. It is the most common cause of SCA and the prevalence of SCA is 2-6 per 100,000 people; ATXN3 causes 21% of SCA population in US and much more in Europe, especially in Portugal. Targeting ATXN3 can be excellent via human molecular genetics, e.g., coding CAG repeat expansion in ATXN3 was discovered in familial and sporadic SCA, in tissues such as spinal cord, brainstem, or cerebellum. The mechanism of this targeting may be because autosomal dominant coding CAG expansion of ATXN3 causes expression of toxic, misfolded protein, Purkinje cell and neuron death. The efficacy has been shown by 70% KD of ATXN3 mRNA; and mATXN3 KD mice POC has been demonstrated. With respect to safety, mATXN3 KO mice have been reported healthy. Possible diagnosis includes family history; genetic testing; or early symptoms. Biomarkers that can be used include, e.g., CSF CAG mRNA and peptide repeat proteins.

Targeting ATXA1 for SCA1

Spinocerebellar Ataxia 1 (SCA1), a progressive ataxia, is the first SCA gene discovered in 1993. This disease is debilitating and ultimately lethal disease with no disease-modifying therapy. The prevalence of SCA is 2-6 per 100,000 people; ATXN1 causes 6% of SCA population in US and worldwide, and much more in some countries (25% in Japan), especially in Poland (64%) and Siberia (100%). Targeting ATXN1 can be excellent via human molecular genetics, e.g., coding CAG repeat expansion in ATXN1 was discovered in familial and sporadic SCA, in tissues such as spinal cord, brainstem, or cerebellum. The mechanism of this targeting may be because autosomal dominant coding CAG expansion of ATXN1 causes expression of toxic, misfolded protein, Purkinje cell and neuronal death. The efficacy has been shown by 70% KD of ATXN1 mRNA; and mATXN1 mice POC has been demonstrated. With respect to safety, mATXN1 KO mice have been reported healthy. Possible diagnosis includes family history; genetic testing; or early symptoms. Biomarkers that can be used include, e.g., CSF CAG mRNA and peptide repeat proteins.

Targeting ATXA7 for SCA7

Spinocerebellar Ataxia 7 (SCA7) causes progressive ataxia and retinal degeneration. This disease is debilitating and ultimately lethal retinal and cerebellar disorder with no disease-modifying therapy. The prevalence of SCA is 2-6 per 100,000 people; ATXN7 causes 5% of SCA population worldwide, and much more in some countries, especially in South Africa. Targeting ATXN7 can be excellent via human molecular genetics, e.g., coding CAG repeat expansion in ATXN7 discovered in familial and sporadic SCA, in tissues such as spinal cord, brainstem, cerebellum, or retina. The mechanism of this targeting may be because autosomal dominant coding CAG expansion of ATXN1 causes expression of toxic, misfolded protein, inciting cone and rod dystrophy, Purkinje cell and neuronal lethality. The efficacy has been shown by 70% KD of ATXN1 mRNA, via intrathecal (IT) and intravitreal (IVT) administrations. Possible diagnosis includes family history; genetic testing; or early symptoms. Biomarkers that can be used include, e.g., CSF CAG mRNA and peptide repeat proteins.

Targeting ATXA8 for SCA8

Spinocerebellar Ataxia 8 (SCA8), a progressive neurodegenerative ataxia is caused by CTG repeat expansion in ATXN8. This disease is debilitating and ultimately lethal disease with no disease-modifying therapy. The prevalence: SCA is 2-6 per 100,000 people; ATXN8 causes 3% of SCA population worldwide, and much more in some countries, especially in Finland. Targeting ATXN8 can be excellent via human molecular genetics, e.g., coding CTG repeat expansion in ATXN8 was discovered in familial and sporadic SCA, in tissues such as spinal cord, brainstem, or cerebellum. The mechanism of this targeting may be because autosomal dominant coding CTG expansion of ATXN8 causes expression of toxic, misfolded protein, inciting Purkinje cell and neuronal lethality. The efficacy has been shown by 70% KD of ATXN8 mRNA. Possible diagnosis includes family history; genetic testing; or early symptoms. Biomarkers that can be used include, e.g., CSF CTG mRNA and peptide repeat proteins.

Targeting CACNA1A for SCA6

Spinocerebellar ataxia 6 (SCA6) is a progressive ataxia. This disease is debilitating and ultimately lethal disease with no disease-modifying therapy. The prevalence of SCA is 2-6 per 100,000 people; and CACNA1A causes 15% of SCA population worldwide. Targeting CACNA1A can be excellent via human molecular genetics, e.g., coding CAG repeat expansion in CACNA1A was discovered in familial and sporadic SCA, in tissues such as spinal cord, brainstem, or cerebellum. The mechanism of this targeting may be because autosomal dominant coding CAG expansion of CACNA1A causes expression of toxic, misfolded protein and Purkinje cell and neuronal death. The efficacy has been shown by 70% KD of CACNA1A CAG expansion. Possible diagnosis includes family history; genetic testing; or early symptoms. Biomarkers that can be used include, e.g., CSF CAG mRNA and peptide repeat proteins.

Exemplary target for inherited polyglutamine disorders includes huntington disease (HD).

Targeting HTT for Huntington Disease

Huntington mutations causes HD, a progressive CNS degenerative disease. This disease is debilitating and ultimately lethal disease with no disease-modifying therapy. The prevalence of HD is 5-10 per 100,000 people worldwide, and much more common in certain countries, especially in Venezuela. Targeting HTT can be excellent via human molecular genetics, e.g., coding CAG repeat expansion in HTT discovered in familial and sporadic HD, in tissues such as striatum, or cortex. The mechanism of this targeting may be because autosomal dominant coding CAG expansion of HTT causes expression of toxic, misfolded protein and neuronal death. The efficacy has been shown by 70% KD of HTT CAG expansion only; and murine POC has been demonstrated. With respect to safety, KO of HTT in mice can be lethal; KD in humans has been demonstrated. Possible diagnosis includes family history; genetic testing; early symptoms. Biomarkers that can be used include, e.g., CSF mRNA and peptide repeat proteins.

Targeting ATN1 for DRPLA

Atrophin 1 mutations causes dentatorubral-pallidoluysian atrophy (DRPLA), which is a progressive spinocerebellar disorder similar to HD. This disease is debilitating and ultimately lethal disease with no disease-modifying therapy. The prevalence of DRPLA is 2-7 per 1,000,000 people in Japan. Targeting ATN1 can be excellent via human molecular genetics, e.g., coding CAG repeat expansion in ATN1 was discovered in familial and sporadic SCA, in tissues such as spinal cord, brainstem, cerebellum, or cortex. The mechanism of this targeting may be because autosomal dominant coding CAG expansion of ATN1 causes expression of toxic, misfolded protein and neuronal death. The efficacy has been shown by 70% KD of ATN1. With respect to safety, ATN1 KO mice have been reported healthy. Possible diagnosis includes family history; genetic testing; or early symptoms. Biomarkers that can be used include, e.g., CSF CAG mRNA and peptide repeat proteins.

Targeting AR for Spinal and Bulbar Muscular Atrophy

Androgen receptor mutations causes spinal and bulbar muscular atrophy (SBMA, Kennedy disease), a progressive muscle wasting disease, and other diseases. This disease is debilitating and ultimately lethal disease with no disease-modifying therapy. The prevalence of SBMA is 2 per 100,000 males; females have a mild phenotype. Targeting AR can be excellent via human molecular genetics, e.g., coding CAG repeat expansion in AR discovered in familial SBMA, in tissues such as spinal cord, or brainstem. The mechanism of this targeting may be because X-linked coding CAG expansion of AR causes toxic gain-or-function and motor neuron lethality. The efficacy has been shown by 70% KD of AR. Possible diagnosis includes family history; genetic testing; or early symptoms. Biomarkers that can be used include, e.g., CSF CAG mRNA and peptide repeat proteins.

Targeting FXN for Friedrich Ataxia

Recessive loss of function GAA expansion of FXN causes friedrich ataxia (FA), a progressive degenerative ataxia. This disease is debilitating and ultimately lethal disease with no disease-modifying therapy. The prevalence of FA is 2 per 100,000 people worldwide. Targeting FXN can be excellent via human molecular genetics, e.g., intron GAA repeat expansion in FXN was discovered in familial FA, in tissues such as spinal cord, cerebellum, or perhaps retina and heart. The mechanism of this targeting may be because autosomal recessive non-coding FAA expansion of FXN causes deceased expression of FXN, an important mitochondrial protein. The efficacy has been shown by 70% KD of FXN intron GAS expansion. With respect to safety, KD of intron GAA is safe and effective in mice. Possible diagnosis includes family history; genetic testing; or early symptoms. Biomarkers that can be used include, e.g., CSF mRNA and peptide repeat proteins.

Targeting FMR1 for FXTAS

Fragile X-associated tremor/ataxia syndrome (FXTAS), a progressive disorder of ataxia and cognitive loss in adults caused by FMR1 overexpression. This disease is debilitating disease with no disease-modifying therapy. The prevalence of FMR1 permutation is 1 in 500 males. Targeting FMR1 can be excellent via human molecular genetics, e.g., coding CCG repeat expansion pre-mutations in FMR1 was discovered in FXTAS, in tissues such as spinal cord, cerebellum, or cortex. The mechanism of this targeting may be because X-linked coding CCG expansion of FMR1 causes toxic mRNA. The efficacy has been shown by 70% KD of toxic mRNA. Possible diagnosis includes family history; genetic testing; or early symptoms. Biomarkers that can be used include, e.g., CSF mRNA and peptide repeat proteins.

Targeting Upstream of FMR1 for Fragile X Syndrome

Fragile X syndrome (FRAXA), a progressive disorder of mental retardation, may be treated by targeting upstream mRNA of FMR1. This disease is debilitating disease with no disease-modifying therapy. The prevalence of FRAXA is 1 per 4,000 males and 1 per 8,000 females. Targeting FMR1 can be excellent via human molecular genetics, e.g., coding CCG repeat expansion in FMR1 was discovered in FRAXA, in tissues such as CNS. The mechanism of this targeting may be because X-linked coding CCG expansion of FMR1 causes LOF; and normal FMR1 functions to transport specific mRNAs from nucleus. The efficacy has been shown by 70% KD of toxic mRNA. Possible diagnosis includes family history; genetic testing; or early symptoms. Biomarkers that can be used include, e.g., CSF mRNA and peptide repeat proteins.

Dominant Inherited Amyotrophic Lateral Sclerosis is a devastating disorders with no disease-modifying therapy. Exemplary targets include C9orf72, ATXN2 (also causes SCA2), and MAPT.

Targeting C9orf72 for ALS

C9orf72 is the most common cause of Amyotrophic Lateral Sclerosis (ALS) and Frontotemporal Dementia (FTD). These diseases are lethal disorders of motor neurons with no disease-modifying therapy. The prevalence of ALS is 2-5 per 100,000 people (10% is familial); C9orf72 causes 39% of familial ALS in US and Europe and 7% of sporadic ALS. Targeting C9orf72 can be excellent via human molecular genetics, e.g., hexa-nucleotide expansion was discovered in familial and sporadic ALS, in tissues such as upper and lower motor neurons (for ALS); or cortex (for FTD). The mechanism of this targeting may be because autosomal dominant hexa-nucleotide expansion causes repeat-associated non-AUG-dependent translation of toxic dipeptide repeat proteins and neuron lethality. The efficacy has been shown by 70% KD of C9orf72. With respect to safety, heterozygous LOF mutations of C9orf72 appear to be safe in humans and mice. Possible diagnosis includes family history; genetic testing; or early symptoms. Biomarkers that can be used include, e.g., CSF hexa-nucleotide repeat mRNAs and dipeptide repeat proteins.

Targeting TARDBP for ALS

TARDBP mutations causes ALS and Frontotemporal Dementia (FTD). These diseases are lethal disorders of motor neurons with no disease-modifying therapy. The prevalence of ALS is 2-5 per 100,000 people (10% is familial); TARDBP causes 5% of familial ALS and 1.5% of sporadic ALS. Targeting TARDBP can be excellent via human molecular genetics, e.g., mutations were discovered in familial and sporadic ALS, in tissues such as upper and lower motor neurons (for ALS); or cortex (for FTD). The mechanism of this targeting may be because autosomal dominant TRDBP mutations cause toxic TRDBP protein and neuron lethality. The efficacy has been shown by 70% KD of TARDBP mutant alleles. Possible diagnosis includes family history; genetic testing; or early symptoms. Biomarkers that can be used include, e.g., CSF proteins.

Targeting FUS for ALS

FUS mutations causes ALS and FTD. These diseases are lethal disorder of motor neurons with no disease-modifying therapy. The prevalence of ALS is 2-5 per 100,000 people (10% is familial); FUS causes 5% of familial ALS; FUS inclusions are often found in sporadic ALS. Targeting FUS can be excellent via human molecular genetics, e.g., mutations were discovered in familial ALS, in tissues such as upper and lower motor neurons for ALS. The mechanism of this targeting may be because autosomal dominant FUS mutations cause abnormal protein folding and neuron lethality. The efficacy has been shown by 70% KD of FUS mutant alleles. With respect to safety, KO mice struggle but survive and have an ADHD phenotype. Possible diagnosis includes family history; genetic testing; or early symptoms. Biomarkers that can be used include, e.g., CSF proteins.

Targeting SOD1 for ALS

Dominant and recessive mutations of SOD1 cause ALS. This disease is lethal disorder of motor neurons with no disease-modifying therapy. The prevalence of ALS is 2-5 per 100,000 people (10% is familial); SOD1 causes 5-20% of familial ALS. Target SOD1 can be excellent via human molecular genetics, e.g., many SOD1 mutations associate with AD and AR ALS in families, in tissues such as upper and lower motor neurons for ALS. The efficacy of this targeting may need mutation-specific KD. Possible diagnosis includes family history; genetic testing; or early symptoms. Biomarkers may be mutation-specific.

Dominant Inherited Frontotemporal Dementia and Progressive Supra-nuclear Palsy. The targets include MAPT because it may be important for AD, or C9orf72.

Targeting Microtubule-Associated Protein Tau for FTD-17 and PSP

Familial Frontotemporal Dementia 17 (FTD-17), a familial form of FTD lined to chromosome 17, and Familial Progressive Supra-nuclear Palsy may be caused by MAPT mutations, which may also cause rare forms of Progressive Supra-nuclear Palsy, Corticobasal Degeneration, Tauopathy with Respiratory Failure, Dementia with Seizures. These diseases are lethal neurodegenerative disorders with no disease-modifying therapy. The prevalence of FTD is 15-22 per 100,000 people; the prevalence of FTD-17 in Netherlands is 1 in 1,000,000 population. Targeting MAPT can be excellent via human molecular genetics, e.g., GOF point and splice site mutations of MAPT were discovered in familial and sporadic FTD, in tissues such as frontal or temporal cortex. The mechanism of this targeting may be because autosomal dominant GOF mutations of MAPT lead to toxic Tau peptides and neuronal death. The efficacy has been shown by 70% KD of MAPT. With respect to safety, MAPT KO mice have been reported healthy. Possible diagnosis includes family history; genetic testing; early symptoms. Biomarkers that can be used include, e.g., CSF Tau mRNAs and proteins.

Targeting Sequestosome 1 for FTD and ALS

Sporadic FTD/ALS associate with dominant SQSTM1 mutations. This disease is lethal neurodegenerative disorder with no disease-modifying therapy. This is a very rare disease. Targeting Sequestosome 1 is reasonable via human molecular genetic association in sporadic cases, in tissues such as frontal and temporal cortex, or cerebellum and spinal cord. Possible diagnosis includes genetic testing; early symptoms.

Dominant Inherited Parkinson Disease is a devastating disorders with no disease-modifying therapy. The targets include SNCA.

Targeting SNCA for Parkinson Disease

Alpha Synuclein mutations causes familial Parkinson disease (PD) and Lewy body dementia. These diseases are lethal neurodegenerative disorders with no disease-modifying therapy. The prevalence of PD is 4 million worldwide; ⅓ of PD is familial; 1% of fPD is caused by SNCA. Targeting SNCA can be excellent via human molecular genetics, e.g., SNCA point mutations and duplications cause familial PD, in tissues such as medulla oblongata; or substantia nigra of the midbrain. The mechanism of this targeting may be because overexpression or expression of abnormal SNCA protein leads to toxic peptides and neuronal death. The efficacy has been shown by 70% KD of SNCA. With respect to safety, SNCA KO mice are healthy. Possible diagnosis includes family history; genetic testing; or early symptoms. Biomarkers that can be used include, e.g., CSF SNCA mRNAs and proteins.

Targeting LRRK2 for Parkinson Disease

Leucine-rich repeat kinase 2 mutations causes familial Parkinson disease. This disease is lethal neurodegenerative disorder with no disease-modifying therapy. The prevalence of PD is 4 million worldwide; ⅓ of PD is familial; 3-7% of fPD is caused by LRRK2. Targeting LRRK2 can be excellent via human molecular genetics, e.g., LRRK2 point mutations cause familial PD, in tissues such as medulla oblongata; or substantia nigra of the midbrain. Possible diagnosis includes family history; genetic testing; early symptoms. Biomarkers that can be used include, e.g., CSF mRNAs and proteins.

Targeting GARS for Spinal Muscular Atrophy V

Autosomal dominant Glycyl-tRNA Synthetase mutations causes spinal muscular atrophy V (SMAV) or distal hereditary motor neuropathy Va. These diseases are neurodegenerative disorders with no disease-modifying therapy. These are very rare diseases. Targeting GARs can be good via human molecular genetics, e.g., GARS point mutations cause familial SMA, in tissues such as spinal cord. Possible diagnosis includes family history; genetic testing; early symptoms.

Targeting Seipin for Spinal Muscular Atrophy

Autosomal dominant Seipin mutations causes spinal muscular atrophy (SMA) or distal hereditary motor neuropathy. These diseases are neurodegenerative disorders with no disease-modifying therapy. These are very rare diseases. Targeting Seipin can be good via human molecular genetics, e.g., Seipin point mutations cause familial SMA, in tissues such as spinal cord. The mechanism of this targeting is probably GOF and toxic peptides. The efficacy has been shown by 50% KD. With respect to safety, recessive LOF mutations cause progressive encephalopathy with or without lipodystrophy. Possible diagnosis includes family history; genetic testing; or early symptoms.

Dominant Inherited Alzheimer Disease is a devastating disorders with no disease-modifying therapy. The targets include APP because of central mechanistic role in familial disease and possible role in common AD.

Targeting APP for Alzheimer Disease

Amyloid precursor protein mutations causes early onset familial Alzheimer disease (EOFAD); AD in down syndrome; or AD. These diseases are lethal neurodegenerative disorders with no disease-modifying therapy. The prevalence of EOFAD-APP is 1% AD; the prevalence of Trisomy 21 is 1% AD; and the prevalence of AD is about 2.5-5 million in US. Targeting APP can be excellent via human molecular genetics, e.g., APP duplications and point mutations cause EOFAD, in tissues such as cerebral cortex or hippocampus. The mechanism of this targeting may be because APP overexpression or expression of toxic metabolites cause progressive neuronal death. The efficacy has been shown by 70% KD of APP. With respect to safety, KD mice have been reported healthy with some behavioral abnormalities; KD mice have been reported healthy with some spatial memory effects. Possible diagnosis includes family history; genetic testing; early symptoms; or MRI. Biomarkers that can be used include, e.g., CSF APP mRNA and peptides.

Targeting PSEN1 for Alzheimer Disease

Presenilin 1 mutations causes early onset familial Alzheimer disease (EOFAD); or AD. These diseases are lethal neurodegenerative disorder with no disease-modifying therapy. Targeting PSEN1 can be excellent via human molecular genetics, e.g., PSEN1 point mutations cause EOFAD, in tissues such as cerebral cortex; or hippocampus. The mechanism of this targeting may be because autosomal dominant mutations of PSEN1 cause abnormal APP metabolism and toxic peptides cause progressive neuronal death. The efficacy has been shown by APP KD may obviate need for PSEN1-specific therapy. Possible diagnosis includes family history; genetic testing; early symptoms; or MRI. Biomarkers that can be used include, e.g., CSF PSEN1 and APP peptides.

Targeting PSEN2 for Alzheimer Disease

Presenilin 2 mutations causes early onset familial Alzheimer disease (EOFAD); or AD. These diseases are lethal neurodegenerative disorder with no disease-modifying therapy. Targeting PSEN2 can be excellent via human molecular genetics, e.g., PSEN2 point mutations cause EOFAD, in tissues such as cerebral cortex or hippocampus. The mechanism of this targeting may be because autosomal dominant mutations of PSEN2 cause abnormal APP metabolism and toxic peptides cause progressive neuronal death. Possible diagnosis includes family history; genetic testing; early symptoms; or MRI. Biomarkers that can be used include, e.g., CSF PSEN2 and APP peptides.

Targeting Apo E for Alzheimer Disease

Apolipoprotein E4 is associated with sporadic AD in the elderly. This disease is lethal neurodegenerative disorder with no disease-modifying therapy. The prevalence of AD is 2.5-5 million in US. Targeting Apo E may be effective because genomic evidence supporting the association between ApoE4 and AD is excellent in many populations. The target tissue may be cerebral cortex. It is not yet clear if Apo E4 contributes to the pathogenesis of AD despite the strong association in many populations. Thus far, data indicate that Apo E4 homozygosity indicates increased risk of AD in the elderly but is not sufficient for causing AD, even in the elderly. With respect to safety, KD of Apo E in CNS may be safe as human LOF mutations in Apo E are not associated with obvious neurologic defects, although systemic exposure may cause hyperlipoproteinemia type III. Possible diagnosis includes clinical diagnosis of AD; exclusion of EOFAD mutation; genetic testing for the Apo E4 genotype. Biomarkers that can be used include, e.g., CSF APP, Tau mRNA and peptides.

CNS Gene Duplication Disorders. Consistent KD by half may ameliorate these disorders. The targets include MeCP2.

Targeting MeCP2 for X-Linked Mental Retardation

Methyl CpG Binding Protein 2 gene duplication causes X-linked Mental Retardation (XLMR). This disease is lethal cognitive disorder with no disease-modifying therapy. 1-15% of X-linked MR is caused by MeCP2 duplication; 2-3% of population has MR. Targeting MeCP2 can be excellent via human molecular genetics, e.g., MeCP2 duplication causes XLMR, in tissues such as cerebral cortex. The mechanism of this targeting may be because MeCP2 overexpression cause dysregulation of other gene and neurodegeneration. The efficacy has been shown by 50% KD of MeCP2; and ASO KD in mouse models reverse phenotype. With respect to safety, MeCP2 LOF mutations may cause Rett syndrome. Possible diagnosis includes family history; genetic testing; or early symptoms. Biomarkers that can be used include, e.g., CSF MeCP2 mRNA and peptides.

Dominant Inherited Cerebral Amyloid Angiopathy is a devastating disorder with no disease-modifying therapy. The targets include TTR.

Targeting TTR for hATTR CAA

This targeting may be a low risk introduction to CNS siRNA. Cerebral Amyloid Angiopathy (CAA) and Meningeal Amyloid are lethal disorders with no disease-modifying therapy. Targeting TTR can be excellent via human genetics and pharmacology. The target tissues can be CNS vascular system, or CNS. The mechanism of this targeting may be because Mutant protein accumulates in vascular adventitia, causing CNS bleeds. The efficacy has been shown by 70% KD of TTR. Possible diagnosis includes family history; genetic testing; or early symptoms. Biomarkers that can be used include, e.g., CSF mRNA and protein.

Targeting ITM2B for CAA

Integral Membrane Protein 2B mutations causes Cerebral Amyloid Angiopathy (CAA), British Type or Familial British Dementia (FBD). Specific mutation may also cause dominant retinal degeneration. This disease is lethal disorder with no disease-modifying therapy. This is a rare disease. Targeting ITM2B can be excellent via human molecular genetics. The target tissues can be CNS vascular system, or CNS. The mechanism of this targeting probably involves GOF mutations. The efficacy has been shown by 70% KD of ITM2B mutant allele. Possible diagnosis includes family history; genetic testing; or early symptoms. Biomarkers that can be used include, e.g., CSF mRNA and protein possible.

Targeting CST3 for CAA

Cystatin C mutations causes familial cerebral amyloid angiopathy, Icelandic type. This disease is lethal disorder with no disease-modifying therapy. This is a rare disease, except in Iceland and Denmark. Targeting CST3 can be excellent via human genetics. The target tissue can be CNS vascular system. The mechanism of this targeting may be because mutant protein accumulates in vascular adventitia, causing CNS bleeds. The efficacy has been shown by Possibly 70% KD of mutant allele. With respect to safety, CST3 KO mice may have risk of arthritis. Possible diagnosis includes family history; genetic testing; or early symptoms. Biomarkers that can be used include, e.g., CSF mRNA and protein possible.

Targeting SPAST for Spastic Paraplegia

SPASTIN mutations causes Spastic Paraplegia (SP) 4 with cognitive loss. This disease is lower motor neurodegenerative disorder with no disease-modifying therapy. The prevalence of SP is 5 per 100,000 population; SP4 is 45% of dominant SP. Targeting SPAST can be excellent via human molecular genetics, e.g., SPAST trinucleotide mutations causes familial SP, in tissues such as spinal cord; or CNS. The mechanism of this targeting may be because nonsense and probable dominant-negative mutations cause abnormal microtubule metabolism and neurodegeneration. Possible diagnosis includes family history; genetic testing; or early symptoms. Biomarkers that can be used include, e.g., CSF SPAST mRNAs and proteins possible.

Targeting KIF5A for Spastic Paraplegia

Kinesin Family Member 5A mutations causes Spastic Paraplegia (SP) 10 with peripheral neuropathy and other disorders. This disease is lower motor neurodegenerative disorder with no disease-modifying therapy. The prevalence of SP is 5 per 100,000 people; SP10 is 1 per 1,000,000 people. Targeting KIF5A can be excellent via human molecular genetics, e.g., KIF5A amino terminal missense mutations cause SP10; and KIF5A is expressed in the CNS and encodes a microtubule motor protein. The target tissue may be spinal cord. The mechanism of this targeting may be because autosomal dominant missense mutations cause SP10 possibly affect microtubule binding to the motor. The efficacy may be provided by possibly KD of mutant alleles. With respect to safety, KIF5A frameshift mutations cause Neonatal intractable myoclonus and splice site mutations are associated with familial ALS, possibly through LOF mechanisms. Possible diagnosis includes family history; genetic testing; or early symptoms. Biomarkers that can be used include, e.g., CSF mRNAs and proteins possible.

Targeting ATL1 for Spastic Paraplegia

Atlastin mutations causes Spastic Paraplegia 3A and Sensory Neuropathy 1D, Hereditary Sensory Neuropathy (HSN). This disease is a lower motor neurodegenerative disorder with no disease-modifying therapy. The prevalence of SP is 5 per 100,000 people; SP3A is a rare dominant form. Targeting ATL1 can be excellent via human molecular genetics, e.g., ATL1 point mutations cause familial SP. The target tissue may be spinal cord. The mechanism of this targeting may be because autosomal dominant expression of dominant-negative ATL1 protein causes SP3A; however, LOF mutations causes Sensory Neuropathy 1D. The efficacy has been shown by 70% KD of specific ATL1 allele. With respect to safety, ATL1 heterozygous LOF mutations causes HSN1D. Possible diagnosis includes family history; genetic testing; or early symptoms. Biomarkers that can be used include, e.g., CSF ATL1 mRNAs and proteins.

Targeting NIPA1 for Spastic Paraplegia

LOF NIPA1 mutations cause Spastic Paraplegia 6 with epilepsy and seizures. This disease is lower motor neurodegenerative disorder with no disease-modifying therapy. The prevalence of SP is 5 per 100,000 people; SP6 is a rare dominant form. Targeting NIPA1 can be excellent via human molecular genetics, e.g., NIPA1 point mutations cause familial SP. The target tissues can be spinal cord; or CNS. The mechanism of this targeting may be because autosomal dominant expression of defective membrane protein causes SP3A; and possibly LOF. Possible diagnosis includes family history; genetic testing; or early symptoms. Biomarkers that can be used include, e.g., CSF mRNAs and proteins possible.

Dominant Inherited Myotonic Dystrophy is a disorder of CNS, Skeletal Muscle and Cardiac Muscle Requiring CNS and Systemic Therapy. The targets include MPK for DM1.

Targeting DMPK for Myotonic Dystrophy 1

CNS and systemic therapy needed for effective therapy targeting dystrophia Myotonica Protein Kinase. Myotonic dystrophy 1 (DM1) is a degenerative disorder of muscle and CNS. It is a lethal disorder with no disease-modifying therapy. The prevalence of DM1 is 1 per 8,000 people worldwide. Targeting DMPK can be excellent via human molecular genetics, e.g., DMPK CTG repeat expansion causes familial DM1. The target tissues may be skeletal muscle, cardiac muscle, or CNS. The mechanism of this targeting may be because autosomal dominant non-coding CTG repeat causes abnormal RNA processing and dominant negative effect; anticipation from extreme expansion causes early onset disease. The efficacy has been shown by 70% of DMPK; and ASO efficacy have been demonstrated in mice. The safety has been demonstrated in mice with KO and ASO KD. Possible diagnosis includes family history; genetic testing; or early symptoms. Biomarkers that can be used include, e.g., Blood and CSF mRNAs and proteins.

Targeting ZNF9 for Myotonic Dystrophy 2

Zinc Finger Protein 9 mutations causes Myotonic dystrophy 2 (DM2), a degenerative disorder of skeletal muscle. This is a serious disorder with no disease-modifying therapy. The prevalence of DM2 is 1 per 8,000 people worldwide; it is the most common muscular dystrophy in adults. Targeting ZNF9 can be excellent via human molecular genetics, e.g., ZNF9 CTTG repeat expansion in intron 1 causes familial DM2. The target tissues can be skeletal muscle, or cardiac muscle. The mechanism of this targeting may be because autosomal dominant CTTG repeat expansion in intron 1 causes abnormal RNA metabolism and dominant negative effects. The efficacy has been shown by 70% of ZNF9. Safe KD in mice has been demonstrated. Possible diagnosis includes family history; genetic testing; or early symptoms. Biomarkers that can be used include, e.g., Blood mRNAs and proteins.

Dominant Inherited Prion Diseases are inherited, sporadic and transmissible PRNP disorders. The targets include PRNP.

Targeting PRNP for Myotonic Prion Diseases

Myotonic prion diseases are dominant inherited Prion diseases, including PRNP-Related Cerebral Amyloid Angiopathy, Gerstmann-Straussler Disease (GSD), Creutzfeldt-Jakob Disease (CJD), Fatal Familial Insomnia (FFI), Huntington Disease-Like 1 (HDL1), and Kuru susceptibility. These diseases are lethal neurodegenerative disorders with no disease-modifying therapy. The prevalence of this type of diseases is 1 per 1,000,000 people. Targeting PRNP can be excellent via human molecular genetics, e.g., PRNP mutations causes familial and sporadic Prion disease. The target tissue can be CNS. The mechanism of this targeting may be because autosomal dominant protein mid-folding causes neurotoxicity. The efficacy has been shown by 70% of PRNP KD; and PRNP polymorphisms appear protective for Kuru. With respect to safety, PRNP KO mice have been reported healthy. Possible diagnosis includes family history; genetic testing; or early symptoms. Biomarkers that can be used include, e.g., CSF mRNAs and proteins.

Targeting Glycogen Synthase for Myoclonic Epilepsy of Lafora

Laforin (EPM2A) gene mutations causes AR Myoclonic Epilepsy, an inherited progressive seizure disorder. This disease is a lethal disorder of seizures and cognitive decline with no disease-modifying therapy. The prevalence of this disease is 4 per 1,000,000 people. Targeting Glycogen Synthase can be excellent via human molecular genetics, e.g., mutations causes AR familial Myoclonic Epilepsy of Lafora. The target tissue may be CNS. The mechanism of this targeting may be because autosomal recessive dysfunction of Laforin causes misfolding of glycogen and foci for seizures. The efficacy has been shown by 70% KD of Glycogen synthase GYS1. With respect to safety, GYS1 deficiency causes skeletal and cardiac muscle glycogen deficiency; GYS1 mice that survive have muscle defects. Possible diagnosis includes family history; genetic testing; or early symptoms. Biomarkers that can be used include, e.g., CSF mRNAs and protein.

In some embodiments, the invention provides a double-stranded iRNA agent that target genes for diseases including, but are not limited to, age-related macular degeneration (AMD) (dry and wet), birdshot chorioretinopathy, dominant retinitis pigmentosa 4, Fuch's dystrophy, hATTR amyloidosis, hereditary and sporadic glaucoma, and stargardt's disease.

In some embodiments, the invention provides a double-stranded iRNA agent that targets VEGF for wet (or exudative) AMD.

In some embodiments, the invention provides a double-stranded iRNA agent that targets C3 for dry (or nonexudative) AMD.

In some embodiments, the invention provides a double-stranded iRNA agent that targets CFB for dry (or nonexudative) AMD.

In some embodiments, the invention provides a double-stranded iRNA agent that targets MYOC for glaucoma.

In some embodiments, the invention provides a double-stranded iRNA agent that targets ROCK2 for glaucoma.

In some embodiments, the invention provides a double-stranded iRNA agent that targets ADRB2 for glaucoma.

In some embodiments, the invention provides a double-stranded iRNA agent that targets CA2 for glaucoma.

In some embodiments, the invention provides a double-stranded iRNA agent that targets CRYGC for cataract.

In some embodiments, the invention provides a double-stranded iRNA agent that targets PPP3CB for dry eye syndrome.

Ligands

In certain embodiments, the double-stranded iRNA agent of the invention is further modified by covalent attachment of one or more conjugate groups. In general, conjugate groups modify one or more properties of the attached double-stranded iRNA agent of the invention including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In some embodiments, the double-stranded iRNA agent further comprises a targeting ligand that targets a receptor which mediates delivery to a specific CNS tissue. These targeting ligands can be conjugated in combination with the lipophilic moiety to enable specific intrathecal and systemic delivery.

Exemplary targeting ligands that targets the receptor mediated delivery to a CNS tissue are peptide ligands such as Angiopep-2, lipoprotein receptor related protein (LRP) ligand, bEnd.3 cell binding ligand; transferrin receptor (TfR) ligand (which can utilize iron transport system in brain and cargo transport into the brain parenchyma); manose receptor ligand (which targets olfactory ensheathing cells, glial cells), glucose transporter protein, and LDL receptor ligand.

In some embodiments, the double-stranded iRNA agent further comprises a targeting ligand that targets a receptor which mediates delivery to a specific ocular tissue. These targeting ligands can be conjugated in combination with the lipophilic moiety to enable specific intravitreal and systemic delivery. Exemplary targeting ligands that targets the receptor mediated delivery to a ocular tissue are lipophilic ligands such as all-trans retinol (which targets the retinoic acid receptor); RGD peptide (which targets retinal pigment epithelial cells), such as H-Gly-Arg-Gly-Asp-Ser-Pro-Lys-Cys-OH or Cyclo(-Arg-Gly-Asp-D-Phe-Cys; LDL receptor ligands; and carbohydrate based ligands (which targets endothelial cells in posterior eye).

Preferred conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Generally, a wide variety of entities, e.g., ligands, can be coupled to the oligomeric compounds described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacrylic acid), N-isopropylacrylamide polymers, polyphosphazene, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, H$_2$A peptides, *Xenopus* peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), Golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to,

AALEALAEALEALAEALEALAEAAAAGGC (GALA); (SEQ ID NO: 3)

AALAEALAEALAEALAEALAEALAAAAGGC (EALA); (SEQ ID NO: 4)

ALEALAEALEALAEA; (SEQ ID NO: 5)

GLFEAIEGFIENGWEGMIWDYG (INF-7); (SEQ ID NO: 6)

GLFGAIAGFIENGWEGMIDGWYG (Inf HA-2); (SEQ ID NO: 7)

GLFEAIEGFIENGWEGMIDGWYGCGLFEAIEGFIENGWEGMID GWYGC (diINF-7); (SEQ ID NO: 8)

GLFEAIEGFIENGWEGMIDGGCGLFEAIEGFIENGWEGMIDGGC (diINF-3); (SEQ ID NO: 9)

GLFGALAEALAEALAEHLAEALAEALEALAAGGSC (GLF); (SEQ ID NO: 10)

GLFEAIEGFIENGWEGLAEALAEALEALAAGGSC (GALA-INF3); (SEQ ID NO: 11)

GLF EAI EGFI ENGW EGnI DG K GLF EAI EGFI ENGW EGnI DG (INF-5, n is norleucine); (SEQ ID NO: 12)

LFEALLELLESLWELLLEA (JTS-1); (SEQ ID NO: 13)

GLFKALLKLLKSLWKLLLKA (ppTG1); (SEQ ID NO: 14)

GLFRALLRLLRSLWRLLLRA (ppTG20); (SEQ ID NO: 15)

WEAKLAKALAKALAKHLAKALAKALKACEA (KALA); (SEQ ID NO: 16)

GLFFEAIAEFIEGGWEGLIEGC (HA); (SEQ ID NO: 17)

GIGAVLKVLTTGLPALISWIKRKRQQ (Melittin); (SEQ ID NO: 18)

H5WYG; and (SEQ ID NO: 19)

CHK6HC. (SEQ ID NO: 20)

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-01 (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (also referred to as XTC herein).

Synthetic polymers with endosomolytic activity amenable to the present invention are described in U.S. Pat. App. Pub. Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Exemplary cell permeation peptides include, but are not limited to, RQIKIWFQNRRMKWKK (penetratin) (SEQ ID NO: 21); GRKKRRQRRRPPQC (Tat fragment 48-60) (SEQ ID NO: 22); GALFLGWL-GAAGSTMGAWSQPKKKRKV (signal sequence based peptide) (SEQ ID NO: 23); LLIILRRRIRKQAHAHSK (PVEC) (SEQ ID NO: 24); GWTLNSAGYLLKINLKA-LAALAKKIL (transportan) (SEQ ID NO: 25); KLALKLA-LKALKAALKLA (amphiphilic model peptide) (SEQ ID NO: 26); RRRRRRRRR (Arg9) (SEQ ID NO: 27); KFFKFFKFFK (Bacterial cell wall permeating peptide) (SEQ ID NO: 28); LLGDFFRK-SKEKIGKEFKRIVQRIKDFLRNLVPRTES (LL-37) (SEQ ID NO: 29); SWLSKTAKKLENSAKKRISEGIAIAI-QGGPR (cecropin P1) (SEQ ID NO: 30); ACYCRIPA-CIAGERRYGTCIYQGRLWAFCC (α-defensin) (SEQ ID NO: 31); DHYNCVSSGGQCLYSACPIFTKIQGT-CYRGKAKCCK (β-defensin) (SEQ ID NO: 32); RRRPRP-PYLPRPRPPPFFPPRLPPRIPPGFPPRFPPRFPGKR-NH2 (PR-39) (SEQ ID NO: 33); ILPWKWPWWPWRR-NH2 (indolicidin) (SEQ ID NO: 34); AAVALLPAVLLALLAP (RFGF) (SEQ ID NO: 35); AALLPVLLAAP (RFGF analogue) (SEQ ID NO: 36); and RKCRIVVIRVCR (bactenecin) (SEQ ID NO: 37).

Exemplary cationic groups include, but are not limited to, protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); and NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactosamine (GalNAc), multivalent GalNAc, e.g. GalNAc$_2$ and GalNAc$_3$ (GalNAc and multivalent GalNAc are collectively referred to herein as GalNAc conjugates); D-mannose, multivalent mannose, multivalent lactose, N-acetyl-glucosamine, Glucose, multivalent Glucose, multivalent fucose, glycosylated polyaminoacids and lectins.

The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2, 4, 6-triiodophenol and flufenamic acid). Oligomeric compounds that comprise a number of phosphorothioate intersugar linkages are also known to bind to serum protein, thus short oligomeric compounds, e.g. oligonucleotides of comprising from about 5 to 30 nucleotides (e.g., 5 to 25 nucleotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

The ligand or tethered ligand can be present on a monomer when said monomer is incorporated into a component of the double-stranded iRNA agent of the invention (e.g., a double-stranded iRNA agent of the invention or linker). In some embodiments, the ligand can be incorporated via coupling to a "precursor" monomer after said "precursor" monomer has been incorporated into a component of the double-stranded iRNA agent of the invention (e.g., a double-stranded iRNA agent of the invention or linker). For example, a monomer having, e.g., an amino-terminated tether (i.e., having no associated ligand), e.g., monomer-linker-NH$_2$ can be incorporated into a component of the compounds of the invention (e.g., a double-stranded iRNA agent of the invention or linker). In a subsequent operation, i.e., after incorporation of the precursor monomer into a component of the compounds of the invention (e.g., a double-stranded iRNA agent of the invention or linker), a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

In some embodiments, ligand can be conjugated to nucleobases, sugar moieties, or internucleosidic linkages of the double-stranded iRNA agent of the invention. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonuclotides. Generally, an oligonucleotide is attached to a conjugate moiety by contacting a reactive group (e.g., OH, SH, amine, carboxyl, aldehyde, and the like) on the oligonucleotide with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

The ligand can be attached to the double-stranded iRNA agent of the inventions via a linker or a carrier monomer, e.g., a ligand carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier monomer into the backbone, e.g., the phosphate, or modified phosphate, e.g., sulfur containing, backbone, of an oligonucleotide. A "tethering attachment point" (TAP) in refers to an atom of the carrier monomer, e.g., a carbon atom or a heteroatom (distinct from an atom which provides a backbone attachment point), that connects a selected moiety. The selected moiety can be, e.g., a carbohydrate, e.g. monosaccharide, disaccharide, trisaccharide, tetrasaccharide, oligosaccharide and polysaccharide. Optionally, the selected moiety is connected by an intervening tether to the carrier monomer. Thus, the carrier will often include a functional group, e.g., an amino group, or generally, provide a bond, that is suitable for incorporation or tethering of another chemical entity, e.g., a ligand to the constituent atom.

Representative U.S. patents that teach the preparation of conjugates of nucleic acids include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,149,782; 5,214,136; 5,245,022; 5,254, 469; 5,258,506; 5,262,536; 5,272,250; 5,292,873; 5,317,098; 5,371,241, 5,391,723; 5,416,203, 5,451,463; 5,510, 475; 5,512,667; 5,514,785; 5,565,552; 5,567,810; 5,574, 142; 5,585,481; 5,587,371; 5,595,726; 5,597,696; 5,599, 923; 5,599,928; 5,672,662; 5,688,941; 5,714,166; 6,153, 737; 6,172,208; 6,300,319; 6,335,434; 6,335,437; 6,395, 437; 6,444,806; 6,486,308; 6,525,031; 6,528,631; 6,559, 279; contents of which are herein incorporated in their entireties by reference.

In some embodiments, the double-stranded iRNA agent further comprises a targeting ligand that targets a liver tissue. In some embodiments, the targeting ligand is a carbohydrate-based ligand. In one embodiment, the targeting ligand is a GalNAc conjugate.

In certain embodiments, the double-stranded iRNA agent of the invention further comprises a ligand having a structure shown below:

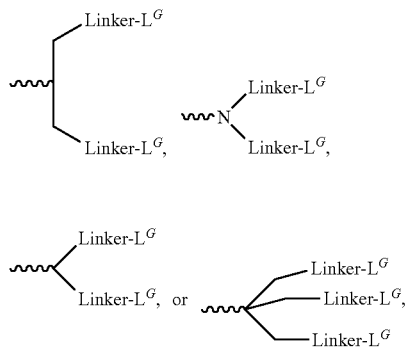

wherein:
L$^G$ is independently for each occurrence a ligand, e.g., carbohydrate, e.g. monosaccharide, disaccharide, trisaccharide, tetrasaccharide, polysaccharide; and
Z', Z", Z''' and Z'''' are each independently for each occurrence O or S.

In certain embodiments, the double-stranded iRNA agent of the invention comprises a ligand of Formula (II), (III), (IV) or (V):

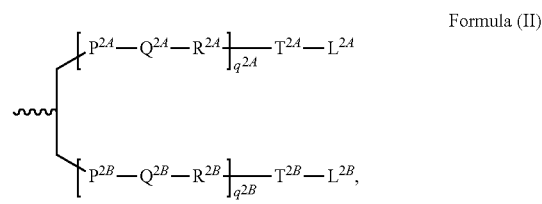

Formula (II)

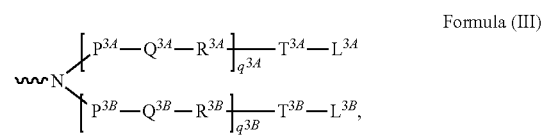

Formula (III)

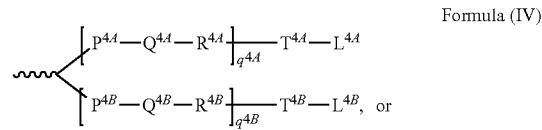

Formula (IV)

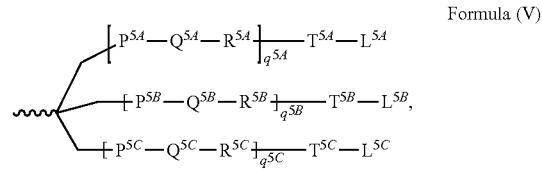

Formula (V)

wherein:
q$^{2A}$, q$^{2B}$, q$^{3A}$, q$^{3B}$, q$^{4A}$, q$^{4B}$, q$^{5A}$, q$^{5B}$ and q$^{5C}$ represent independently for each occurrence 0-20 and wherein the repeating unit can be the same or different;

Q and Q' are independently for each occurrence is absent, —(P$^7$-Q$^7$-R$^7$)$_p$-T$^7$- or -T$^7$-Q$^7$-T$^{7'}$-B-T$^{8'}$-Q$^8$-T$^8$ P$^{2A}$, P$^{2B}$, P$^{3A}$, P$^{3B}$, P$^{4A}$, P$^{4B}$, P$^{5A}$, P$^{5B}$, P$^{5C}$, P$^7$, T$^{2A}$, T$^{2B}$, T$^{3A}$, T$^{3B}$, T$^{4A}$, T$^{4B}$, T$^{4A}$, T$^{5B}$, T$^{5C}$, T$^7$, T$^{7'}$, T$^8$ and T$^{8'}$ are each independently for each occurrence absent, CO, NH, O, S, OC(O), NHC(O), CH$_2$, CH$_2$NH or CH$_2$O;

B is —CH$_2$—N(B$^L$)—CH$_2$—;

B$^L$ is -T$^B$-Q$^B$-T$^{B'}$-R$^x$;

Q$^{2A}$, Q$^{2B}$, Q$^{3A}$, Q$^{3B}$, Q$^{4A}$, Q$^{4B}$, Q$^{5A}$, Q$^{5B}$, Q$^{5C}$, Q$^7$, Q$^8$, and Q$^B$ are independently for each occurrence absent, alkylene, substituted alkylene and wherein one or more methylenes can be interrupted or terminated by one or more of O, S, S(O), SO$_2$, N(R$^N$), C(R')=C(R'), C≡C or C(O);

T$^B$ and T$^{B'}$ are each independently for each occurrence absent, CO, NH, O, S, OC(O), OC(O)O, NHC(O), NHC(O)NH, NHC(O)O, CH$_2$, CH$_2$NH or CH$_2$O;

R$^x$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecogenin, diosgenin), a terpene (e.g., triterpene, e.g., sarsasapogenin, Friedelin, epifriedelanol derivatized lithocholic acid), or a cationic lipid;

$R^1$, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^7$ are each independently for each occurrence absent, NH, O, S, CH$_2$, C(O)O, C(O)NH, NHCH($R^a$)C(O), —C(O)—CH($R^a$)—NH—, CO,

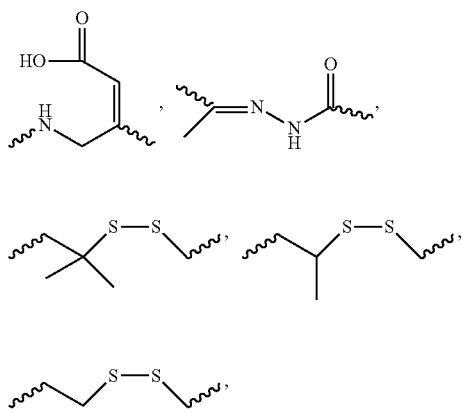

or heterocyclyl;

$L^1$, $L^{2A}$, $L^{2B}$, $L^{3A}$, $L^{3B}$, $L^{4A}$, $L^{4B}$, $L^{5A}$, $L^{5B}$ and $L^{5C}$ are each independently for each occurrence a carbohydrate, e.g., monosaccharide, disaccharide, trisaccharide, tetrasaccharide, oligosaccharide and polysaccharide;

R' and R" are each independently H, $C_1$-$C_6$ alkyl, OH, SH, or N($R^N$)$_2$;

$R^N$ is independently for each occurrence H, methyl, ethyl, propyl, isopropyl, butyl or benzyl;

$R^a$ is H or amino acid side chain;

Z', Z", Z''' and Z"" are each independently for each occurrence O or S;

p represent independently for each occurrence 0-20.

As discussed above, because the ligand can be conjugated to the iRNA agent via a linker or carrier, and because the linker or carrier can contain a branched linker, the iRNA agent can then contain multiple ligands via the same or different backbone attachment points to the carrier, or via the branched linker(s). For instance, the branchpoint of the branched linker may be a bivalent, trivalent, tetravalent, pentavalent, or hexavalent atom, or a group presenting such multiple valencies. In certain embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or glycerol derivative.

In certain embodiments, the double-stranded iRNA agent of the invention comprises a ligand of structure:

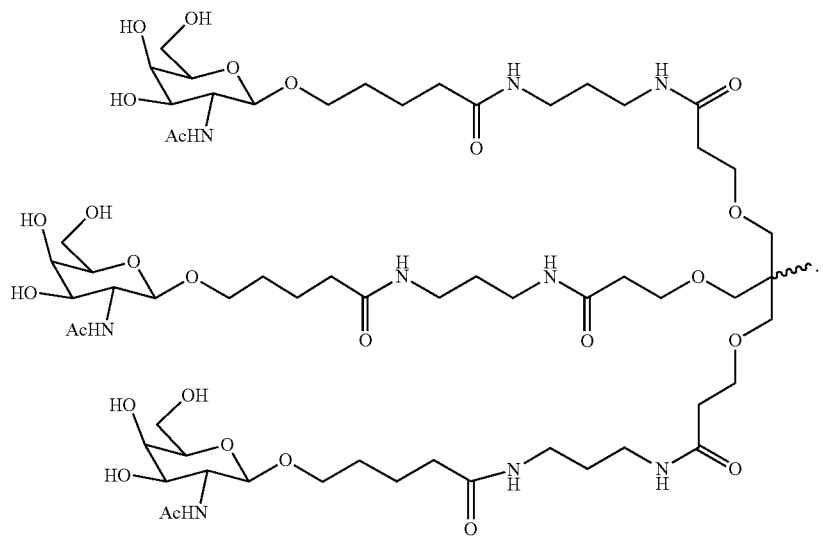 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the double-stranded iRNA agent of the invention comprises a ligand of structure:

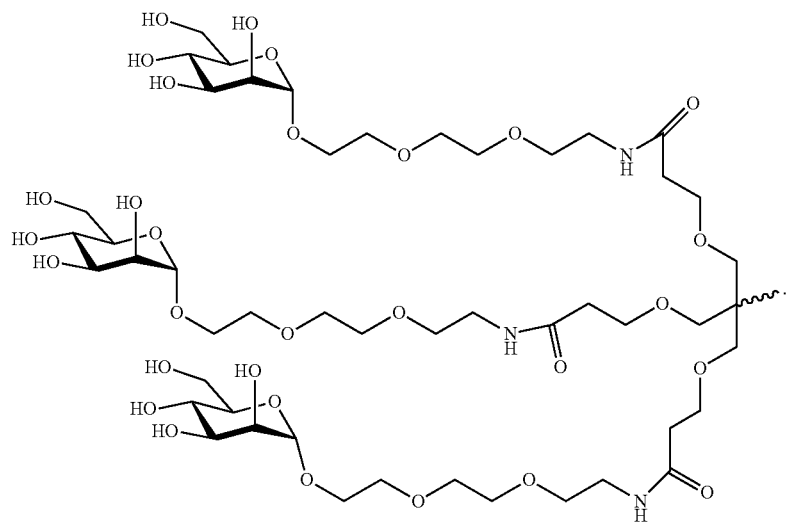

In certain embodiments, the double-stranded iRNA agent of the invention comprises a ligand of structure:

In certain embodiments, the double-stranded iRNA agent of the invention comprises a ligand of structure:

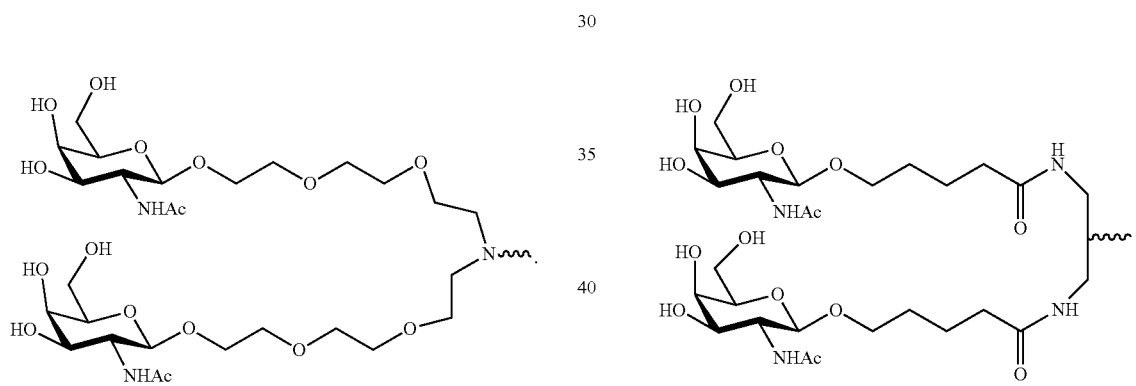

In certain embodiments, the double-stranded iRNA agent of the invention comprises a ligand of structure:

In certain embodiments, the double-stranded iRNA agent of the invention comprises a ligand of structure:

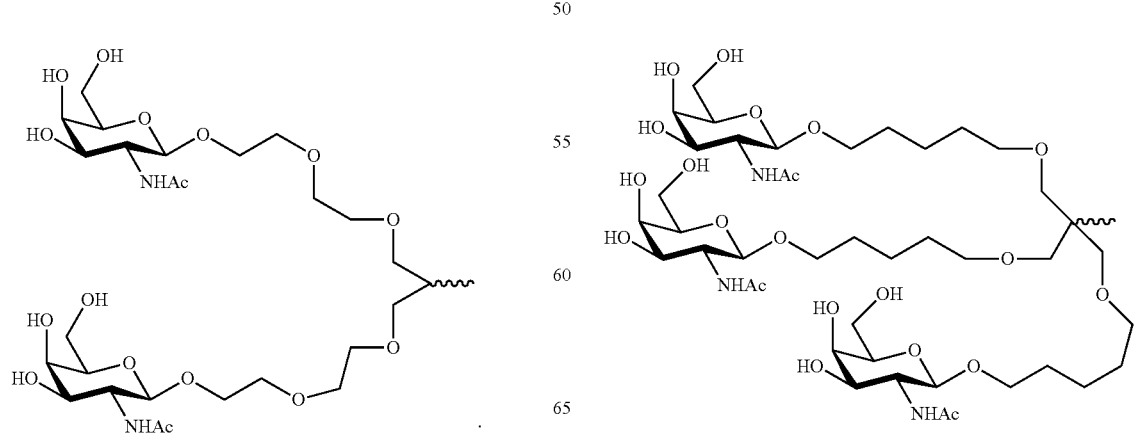

In certain embodiments, the double-stranded iRNA agent of the invention comprises a ligand of structure:
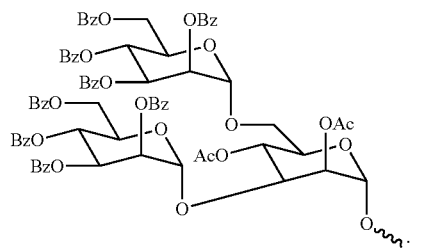
In certain embodiments, the double-stranded iRNA agent of the invention comprises a ligand of structure:
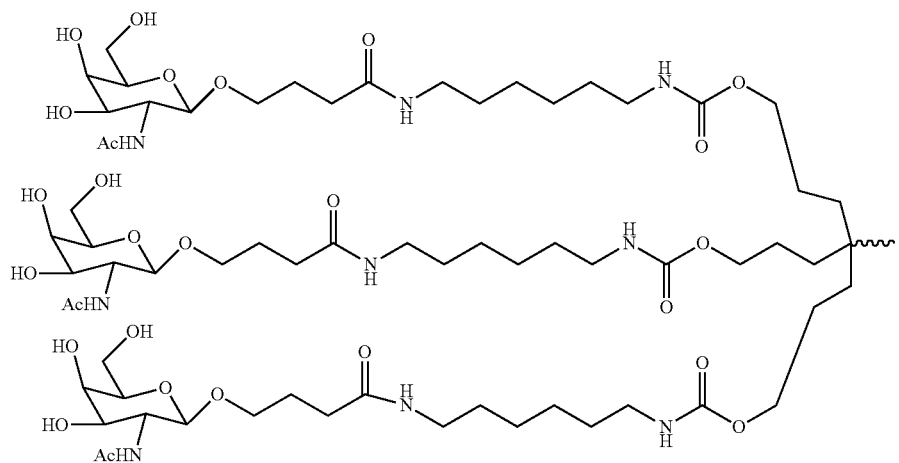 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]
In certain embodiments, the double-stranded iRNA agent of the invention comprises a ligand of structure:
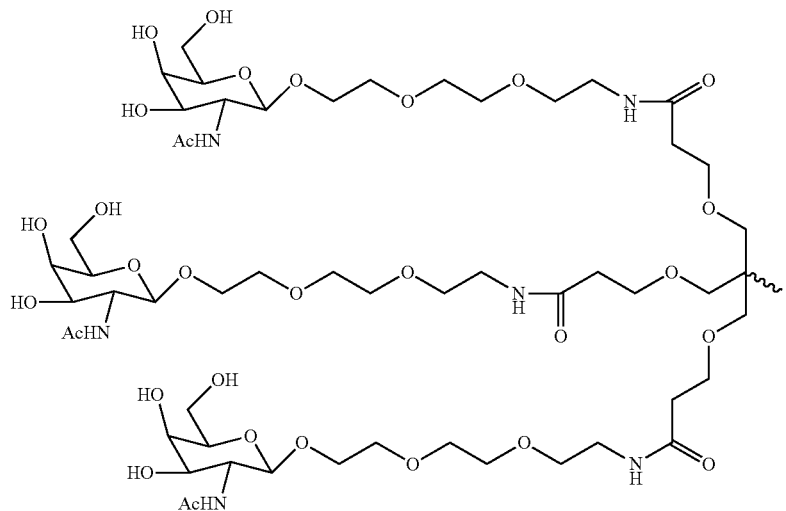 [SMILES: CC(=O)NC1C(OCCOCCOCCNC(=O)CCOCC(C)(COCCC(=O)NCCOCCOCCOC2OC(CO)C(O)C(O)C2NC(C)=O)COCCC(=O)NCCOCCOCCOC2OC(CO)C(O)C(O)C2NC(C)=O)OC(CO)C(O)C1O]

In certain embodiments, the double-stranded iRNA agent of the invention comprises a ligand of structure:
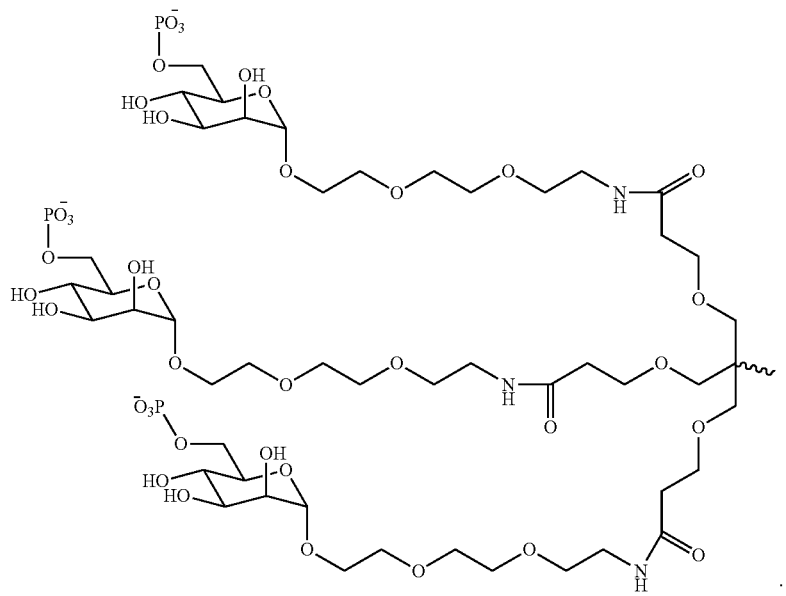
In certain embodiments, the double-stranded iRNA agent of the invention comprises a ligand of structure:
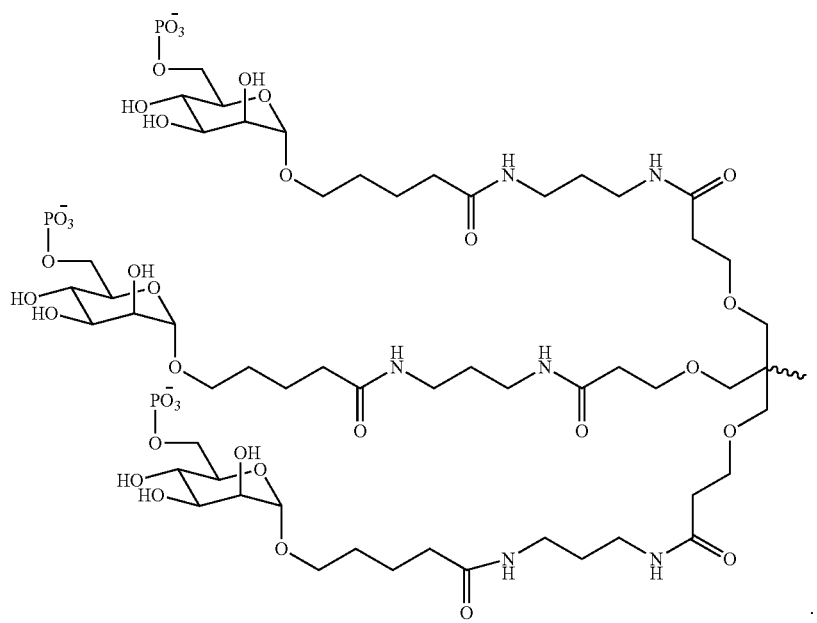

In certain embodiments, the double-stranded iRNA agent of the invention comprises a monomer of structure:
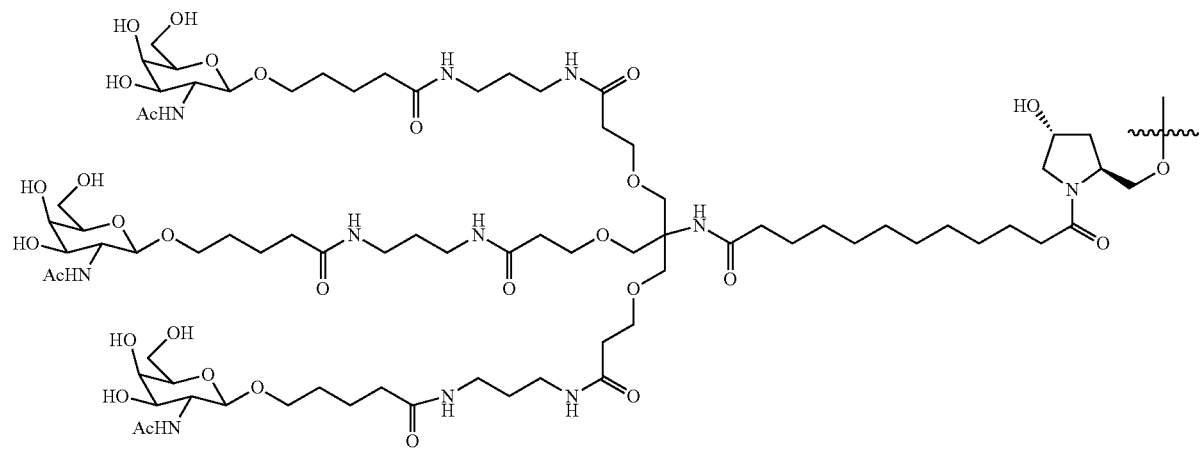 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]
In certain embodiments, the double-stranded iRNA agent of the invention comprises a ligand of structure:
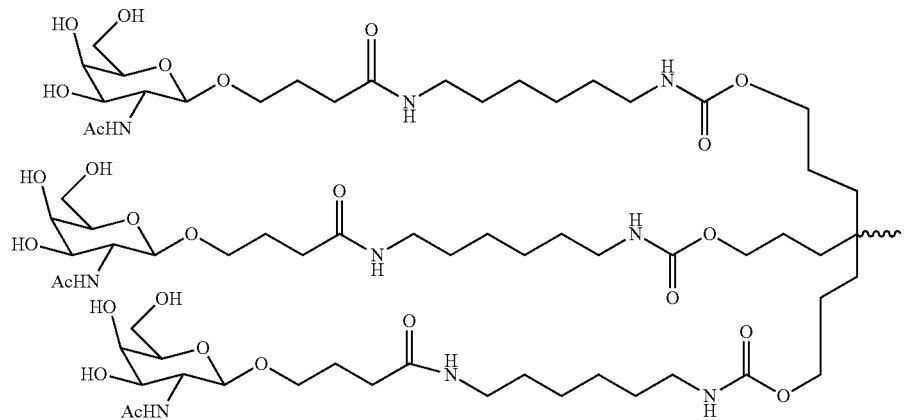 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]
Exemplary Ligand Monomers
In certain embodiments, the double-stranded iRNA agent of the invention comprises a monomer of structure:
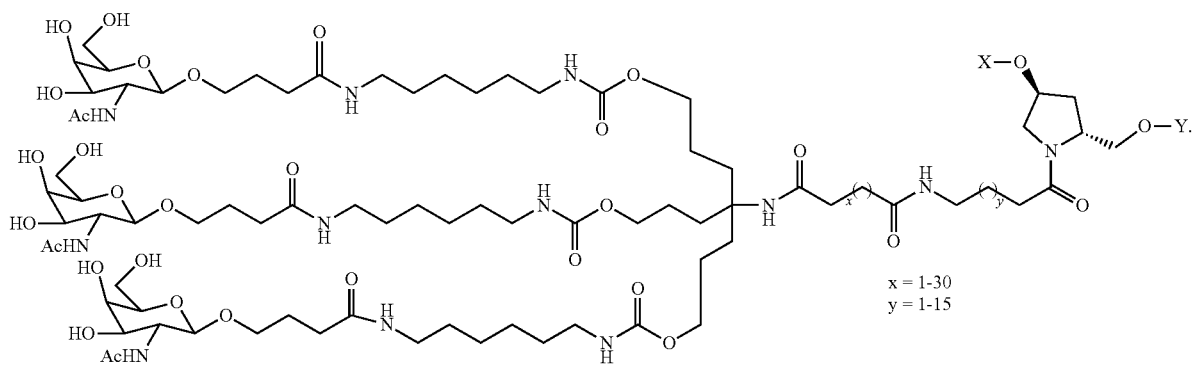
x = 1-30
y = 1-15

In certain embodiments, the double-stranded iRNA agent of the invention comprises a monomer of structure:
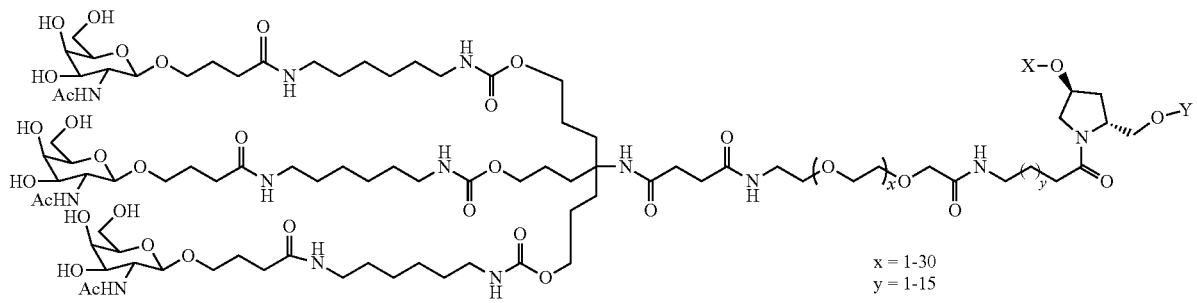
x = 1-30
y = 1-15
In certain embodiments, the double-stranded iRNA agent of the invention comprises a monomer of structure:
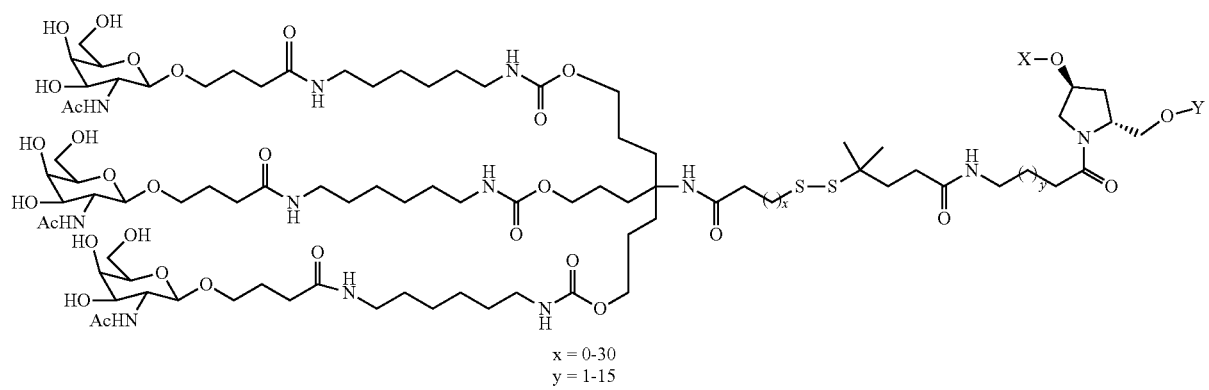
x = 0-30
y = 1-15
In certain embodiments, the double-stranded iRNA agent of the invention comprises a monomer of structure:
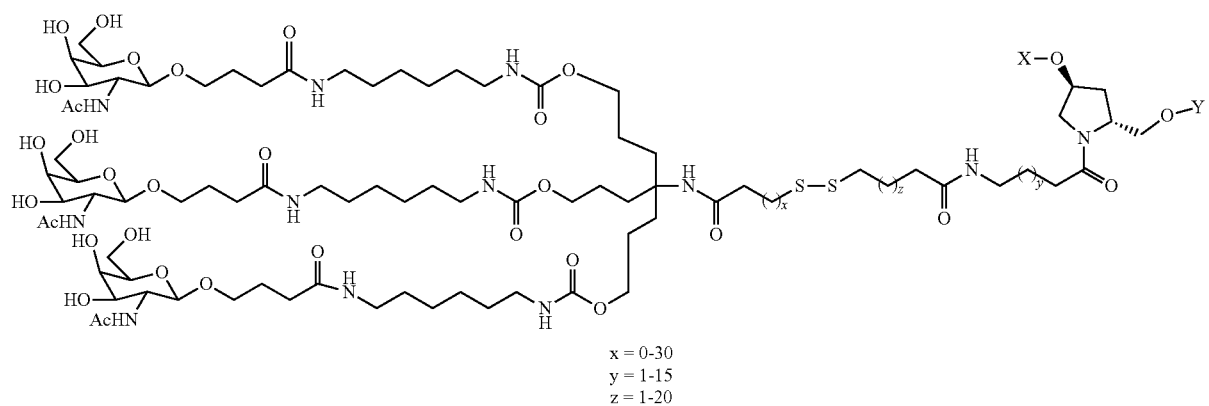
x = 0-30
y = 1-15
z = 1-20

In certain embodiments, the double-stranded iRNA agent of the invention comprises a monomer of structure:

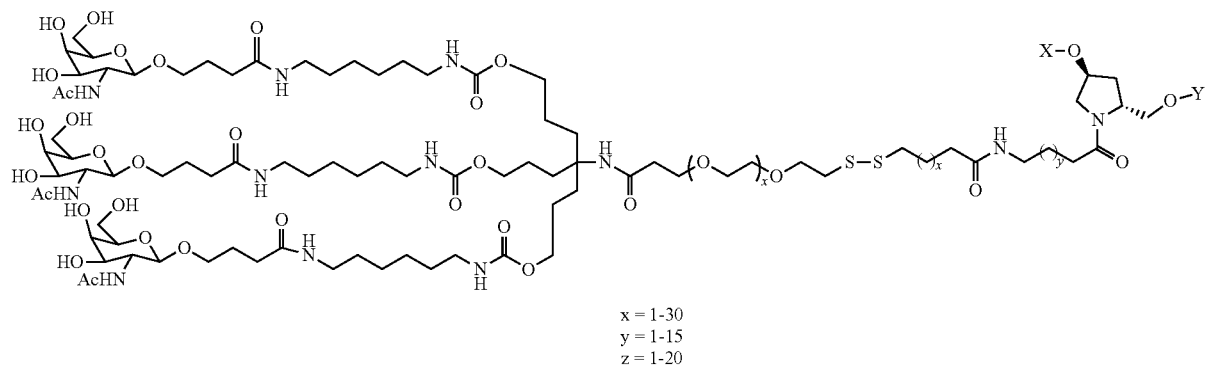

x = 1-30
y = 1-15
z = 1-20

In certain embodiments, the double-stranded iRNA agent of the invention comprises a monomer of structure:

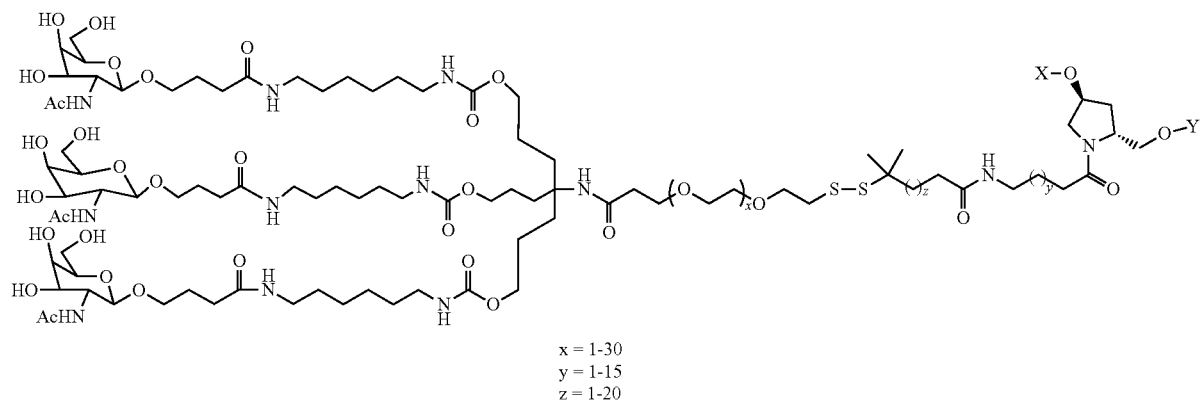

x = 1-30
y = 1-15
z = 1-20

In certain embodiments, the double-stranded iRNA agent of the invention comprises a ligand of structure:

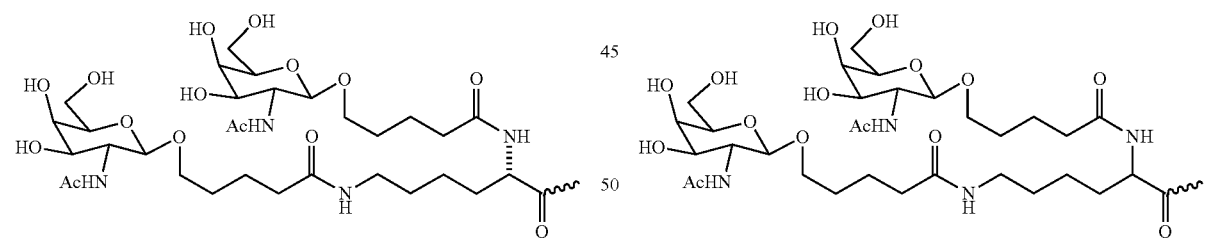

In certain embodiments, the double-stranded iRNA agent of the invention comprises a ligand of structure:

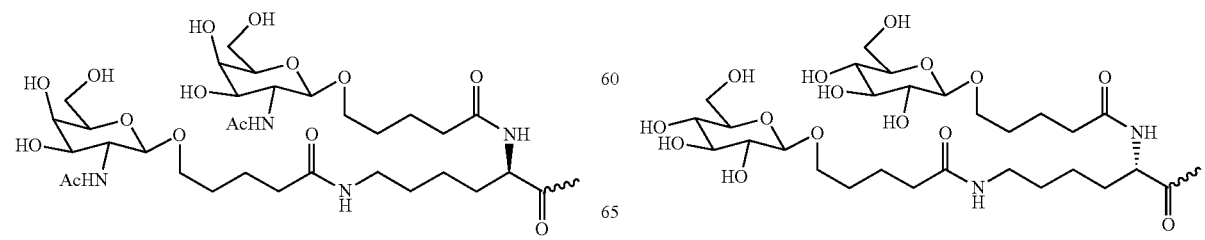

In certain embodiments, the double-stranded iRNA agent of the invention comprises a ligand of structure:

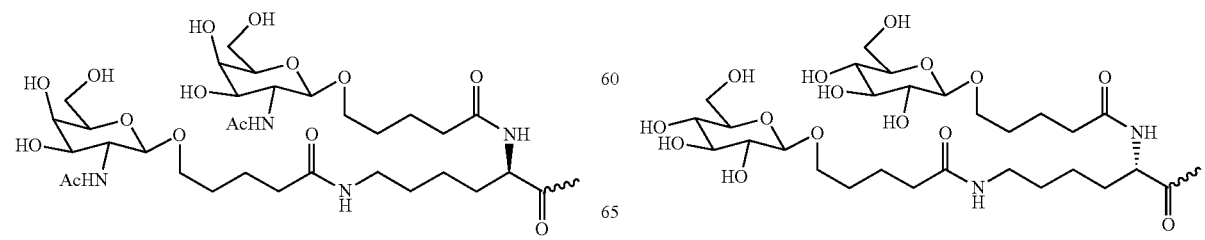

In certain embodiments, the double-stranded iRNA agent of the invention comprises a ligand of structure:

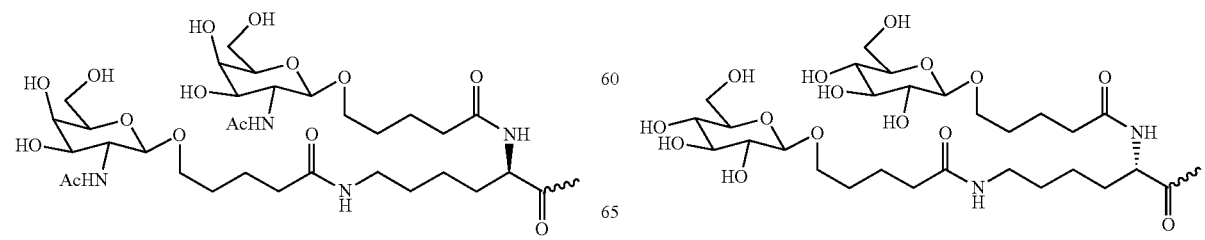

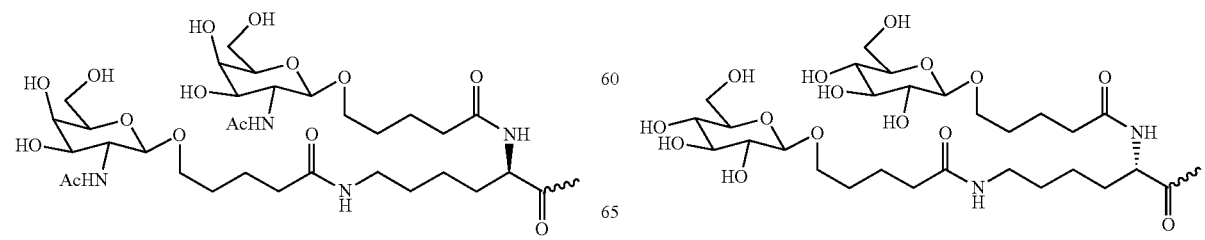

In certain embodiments, the double-stranded iRNA agent of the invention comprises a ligand of structure:

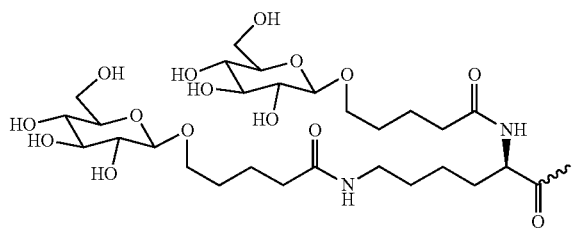

In certain embodiments, the double-stranded iRNA agent of the invention comprises a ligand of structure:

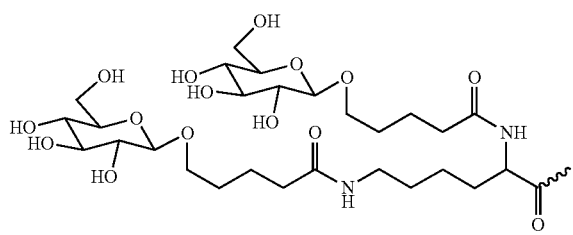

In certain embodiments, the double-stranded iRNA agent of the invention comprises a ligand of structure:

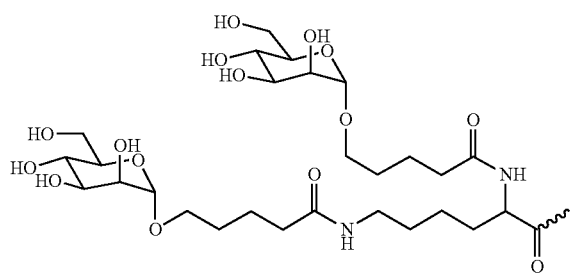

In certain embodiments, the double-stranded iRNA agent of the invention comprises a ligand of structure:

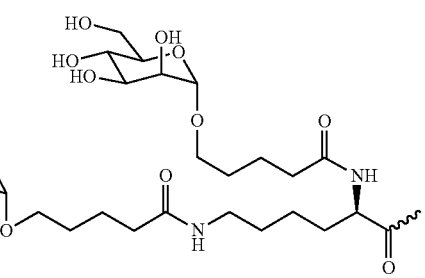

In certain embodiments, the double-stranded iRNA agent of the invention comprises a ligand of structure:

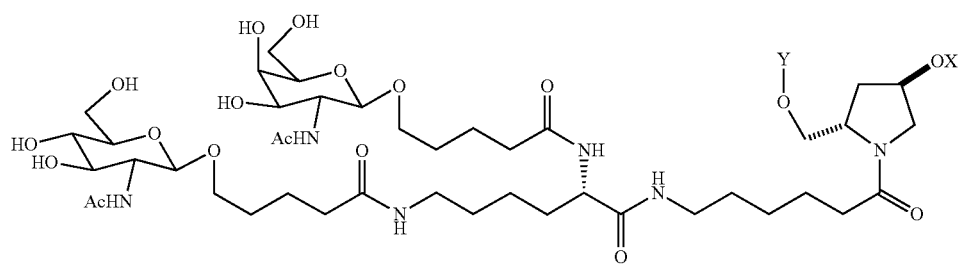

In certain embodiments, the double-stranded iRNA agent of the invention comprises a monomer of structure:

In certain embodiments, the double-stranded iRNA agent of the invention comprises a monomer of structure:

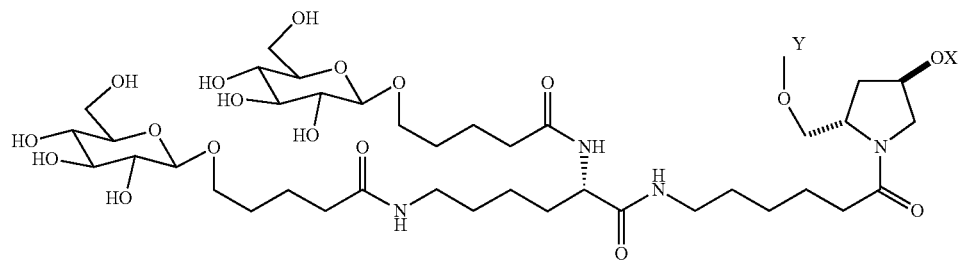

In certain embodiments, the double-stranded iRNA agent of the invention comprises a monomer of structure:

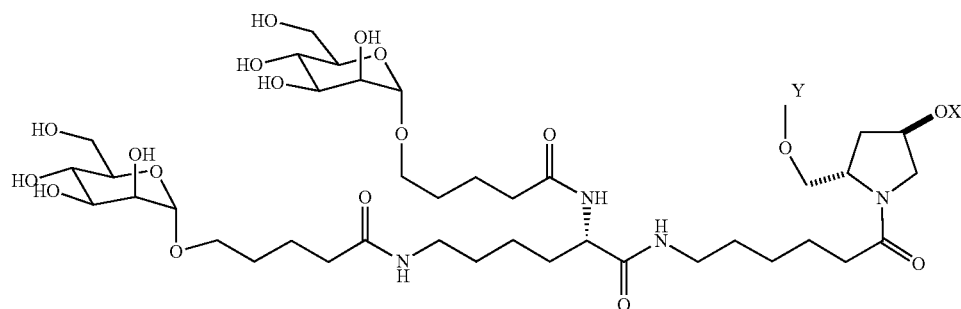

In certain embodiments, the double-stranded iRNA agent of the invention comprises a monomer of structure:

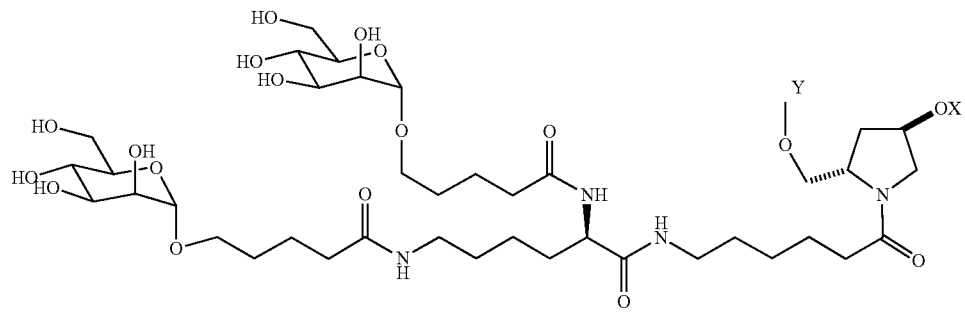

In certain embodiments, the double-stranded iRNA agent of the invention comprises a monomer of structure:

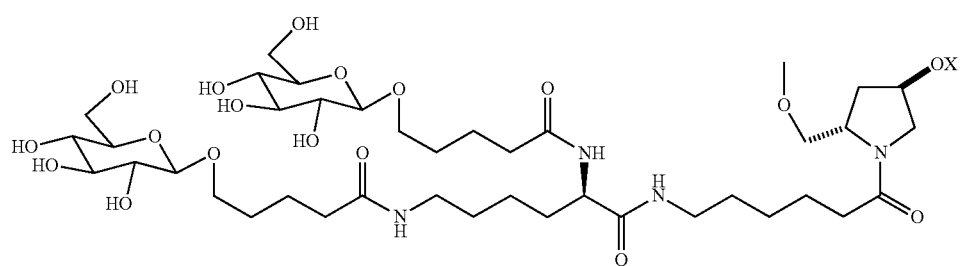

In certain embodiments, the double-stranded iRNA agent of the invention comprises a monomer of structure:

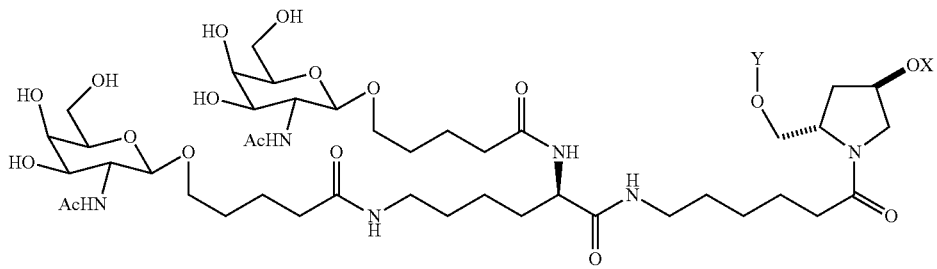

In some embodiments both $L^{2A}$ and $L^{2B}$ are different.

In some preferred embodiments both $L^{3A}$ and $L^{3B}$ are the same.

In some embodiments both $L^{3A}$ and $L^{3B}$ are different.

In some preferred embodiments both $L^{4A}$ and $L^{4B}$ are the same.

In some embodiments both $L^{4A}$ and $L^{4B}$ are different.

In some preferred embodiments all of $L^{5A}$, $L^{5B}$ and $L^{5C}$ are the same.

In some embodiments two of $L^{5A}$, $L^{5B}$ and $L^{5C}$ are the same.

In some embodiments $L^{5A}$ and $L^{5B}$ are the same.

In some embodiments $L^{5A}$ and $L^{5C}$ are the same.

In some embodiments $L^5B$ and $L^{5C}$ are the same.

In certain embodiments, the double-stranded iRNA agent of the invention comprises a monomer of structure:

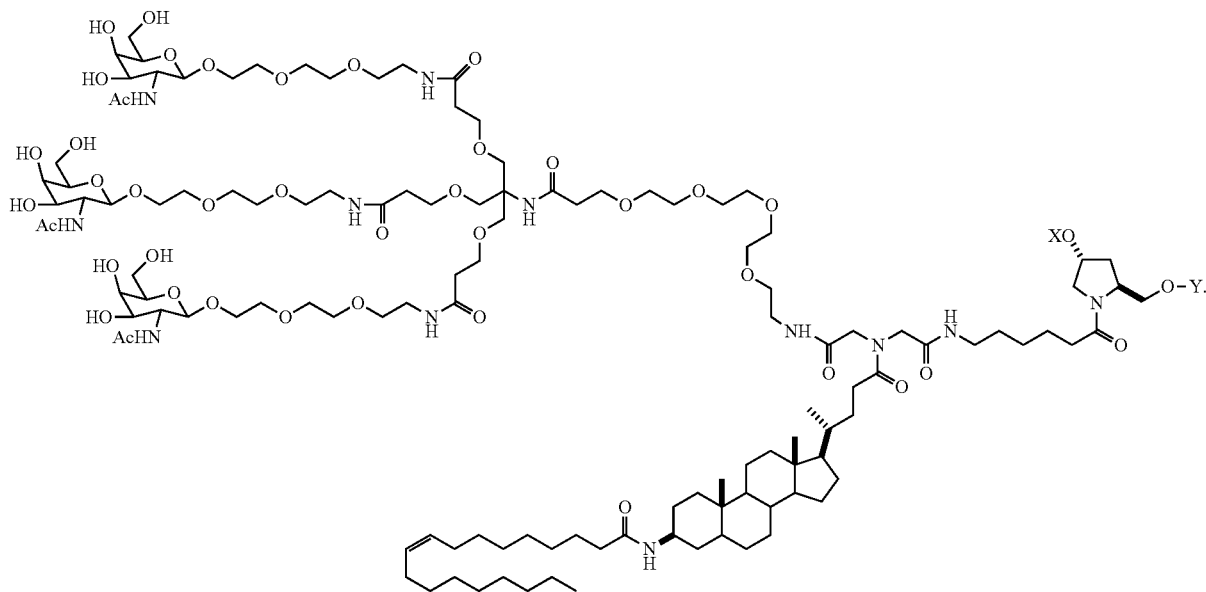

In certain embodiments, the double-stranded iRNA agent of the invention comprises a monomer of structure:

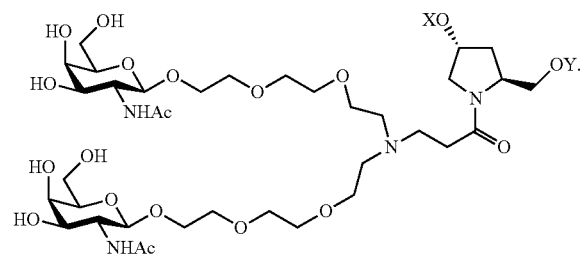

In certain embodiments, the double-stranded iRNA agent of the invention comprises a monomer of structure:

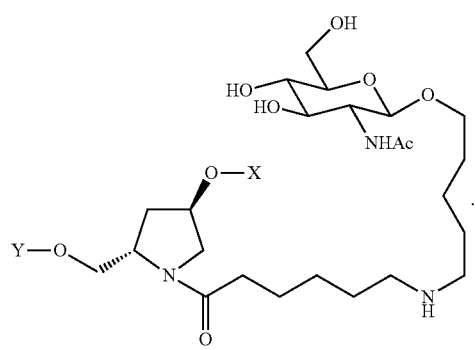

In certain embodiments, the double-stranded iRNA agent of the invention comprises a monomer of structure:

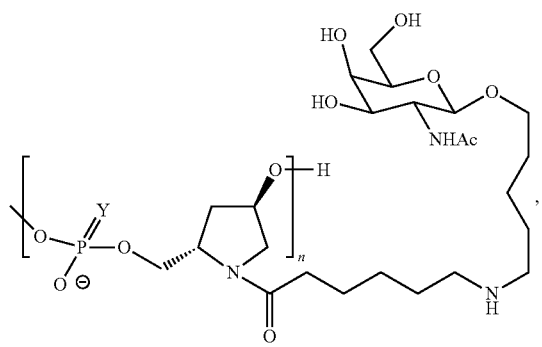

wherein Y is O or S, and n is 1-6.

In certain embodiments, the double-stranded iRNA agent of the invention comprises a monomer of structure:

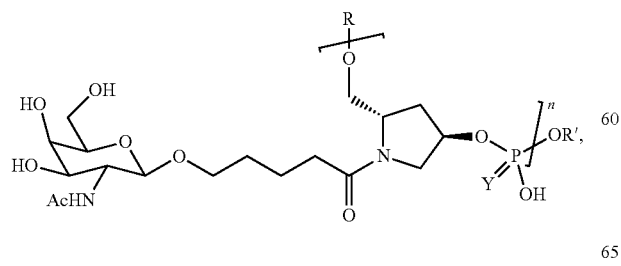

wherein Y is O or S, n is 1-6, R is hydrogen or nucleic acid, and R' is nucleic acid.

In certain embodiments, the double-stranded iRNA agent of the invention comprises a monomer of structure:

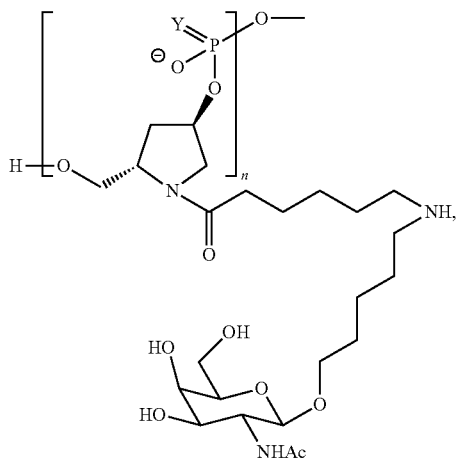

wherein Y is O or S, and n is 1-6.

In certain embodiments, the oligomeric compound described herein, including but not limited to double-stranded iRNA agent of the inventions, comprises a monomer of structure:

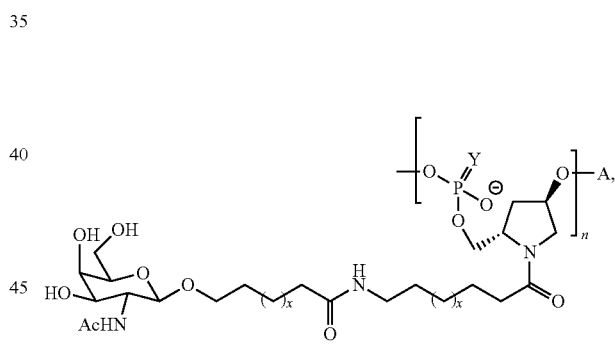

wherein Y is O or S, n is 2-6, x is 1-6, and A is H or a phosphate linkage.

In certain embodiments, the double-stranded iRNA agent of the invention comprises at least 1, 2, 3 or 4 monomer of structure:

In certain embodiments, the double-stranded iRNA agent of the invention comprises a monomer of structure:
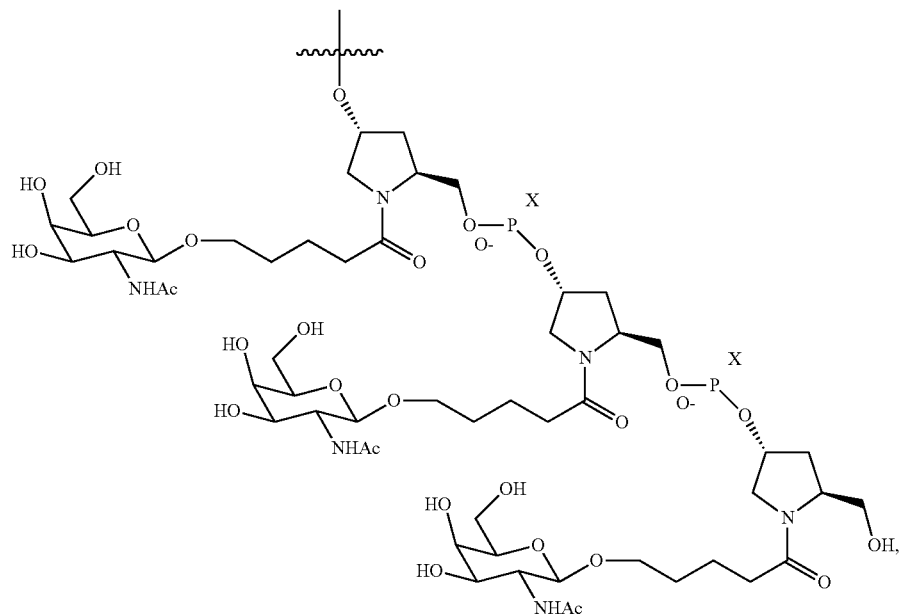
wherein X is O or S.
In certain embodiments, the oligomeric compound described herein, including but not limited to double-stranded iRNA agent of the inventions, comprises a monomer of structure:
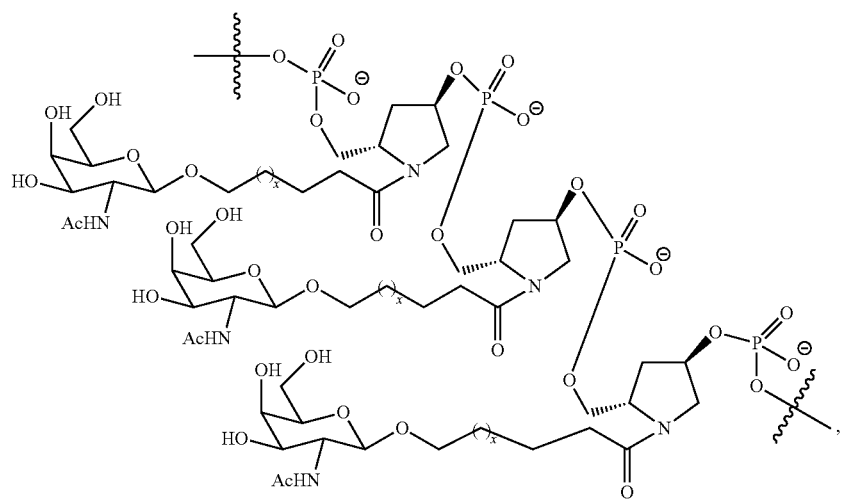
wherein x is 1-12.

In certain embodiments, the double-stranded iRNA agent of the invention comprises a monomer of structure:

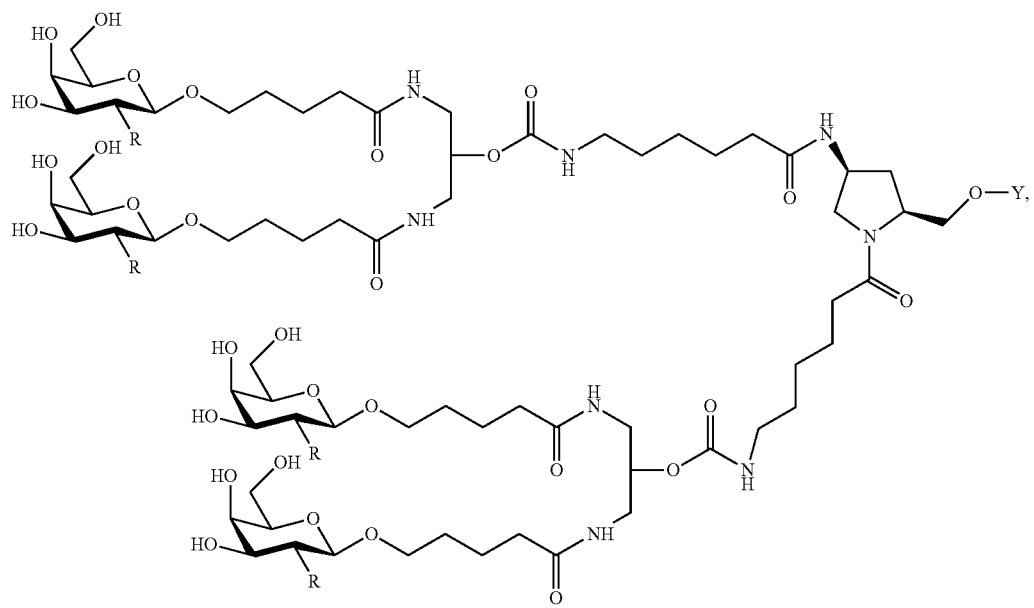

wherein R is OH or NHCOCH$_3$.

In certain embodiments, the double-stranded iRNA agent of the invention comprises a monomer of structure:

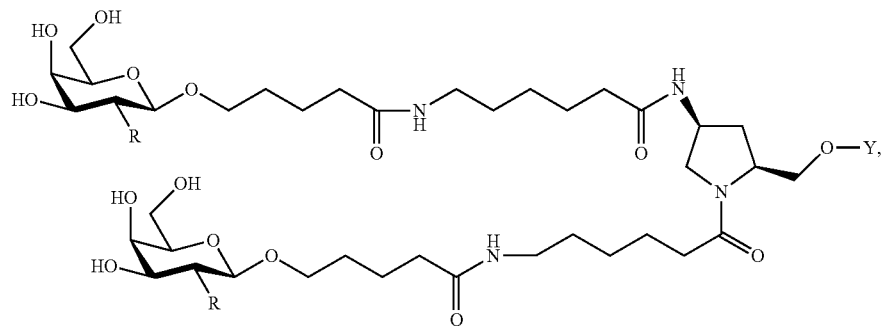

wherein R is OH or NHCOCH$_3$.

In certain embodiments, the double-stranded iRNA agent of the invention comprises a monomer of structure:

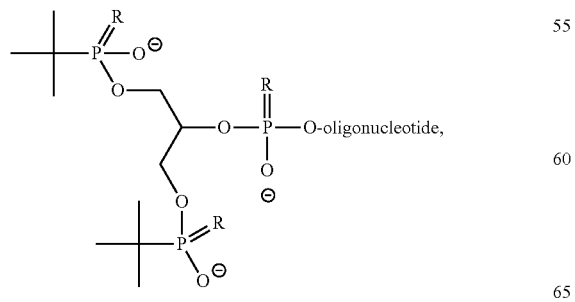

Formula (VII)

wherein R is O or S.

In certain embodiments, the double-stranded iRNA agent of the invention comprises a monomer of structure:

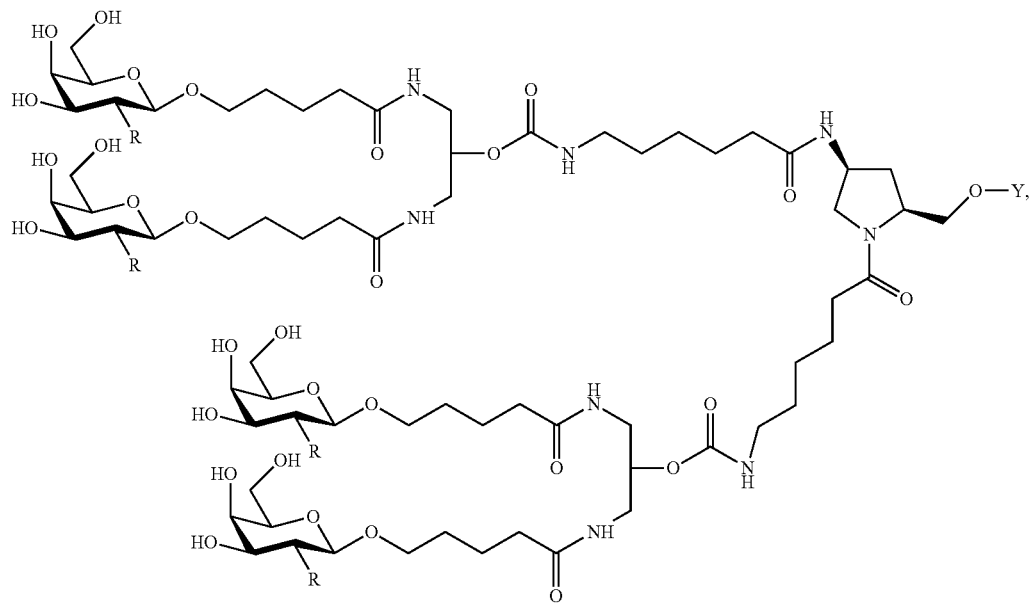

wherein R is OH or NHCOCH$_3$.

In certain embodiments, the double-stranded iRNA agent of the invention comprises a monomer of structure:

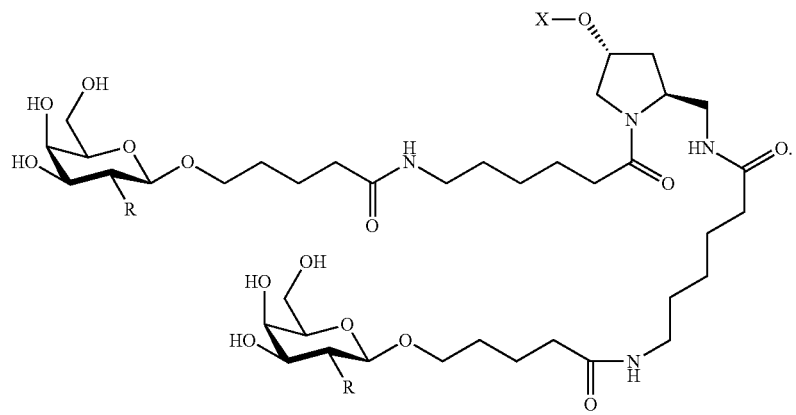

In certain embodiments, the double-stranded iRNA agent of the invention comprises a monomer of structure:

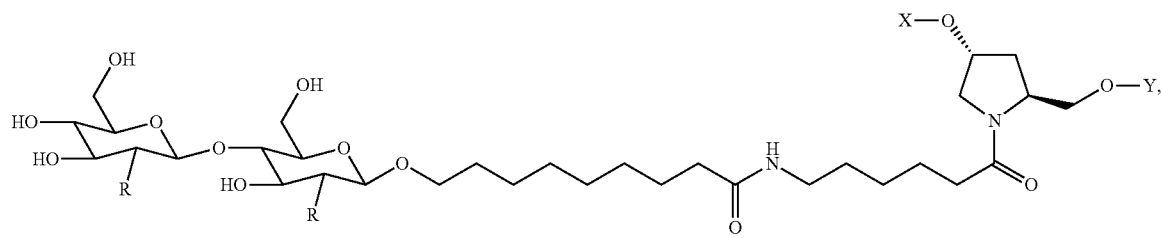

wherein R is OH or NHCOCH$_3$.

In certain embodiments, the double-stranded iRNA agent of the invention comprises a monomer of structure:

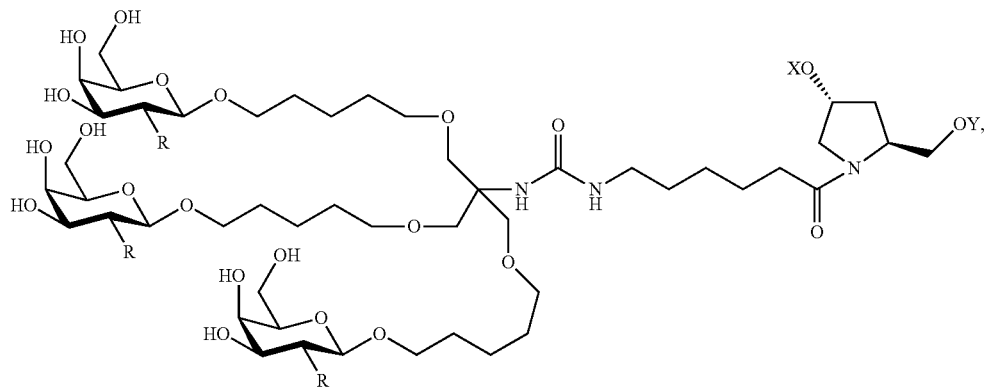

wherein R is OH or NHCOCH₃.

In certain embodiments, the double-stranded iRNA agent of the invention comprises a monomer of structure:

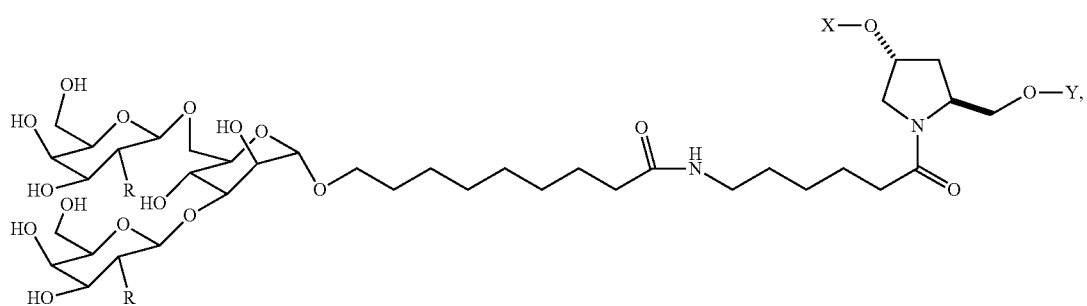

wherein R is OH or NHCOCH₃.

In certain embodiments, the double-stranded iRNA agent of the invention comprises a monomer of structure:

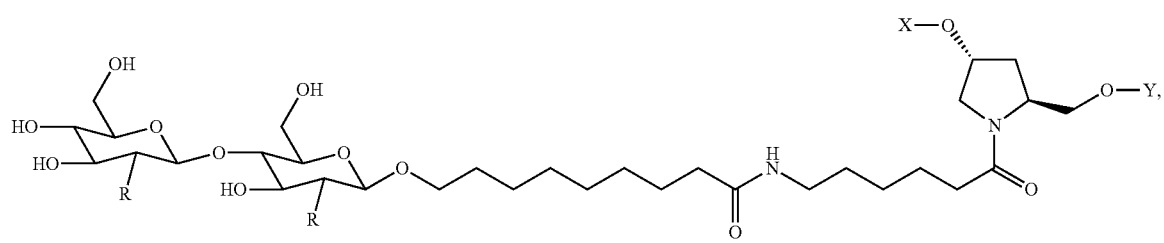

wherein R is OH or NHCOCH₃.

In certain embodiments, the double-stranded iRNA agent of the invention comprises a monomer of structure:

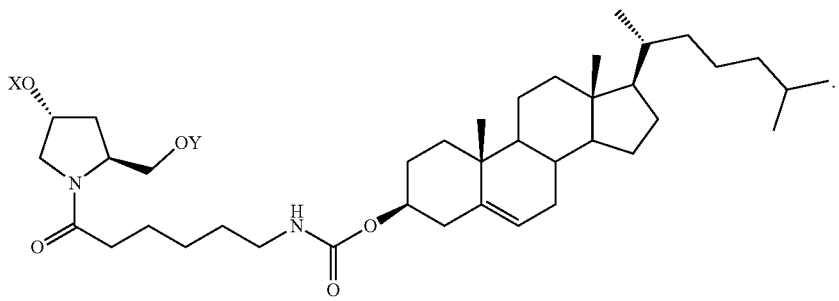

In the above described monomers, X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, a nucleoside, or an oligonucleotide; and Z' and Z" are each independently for each occurrence O or S.

In certain embodiments, the double-stranded iRNA agent of the invention is conjugated with a ligand of structure:

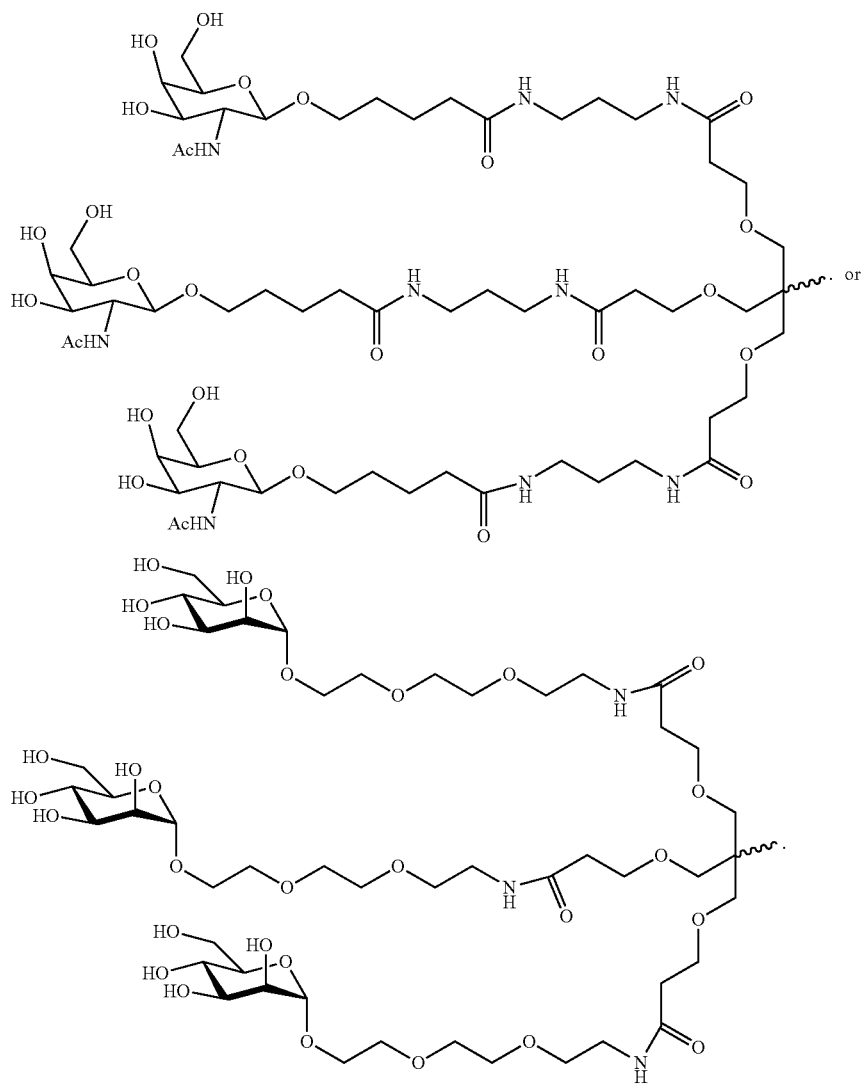

In certain embodiments, the double-stranded iRNA agent of the invention comprises a ligand of structure:
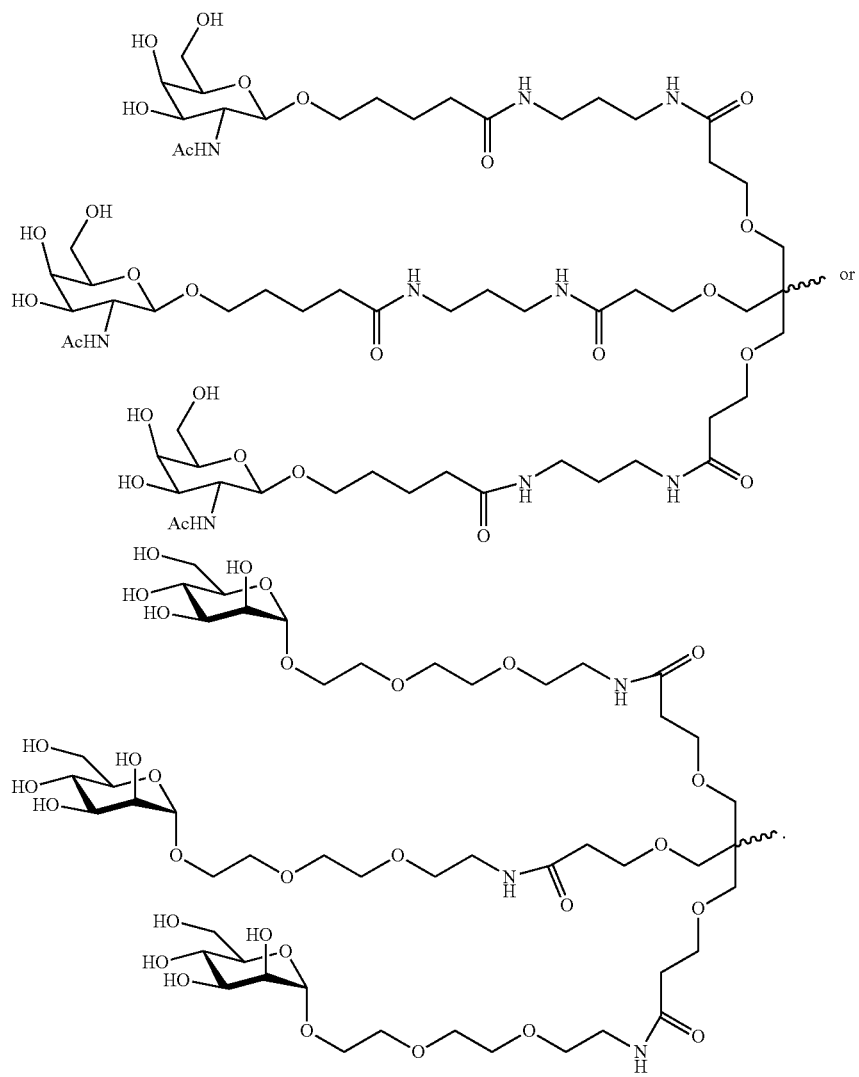
In certain embodiments, the double-stranded iRNA agent of the invention comprises a monomer of structure:
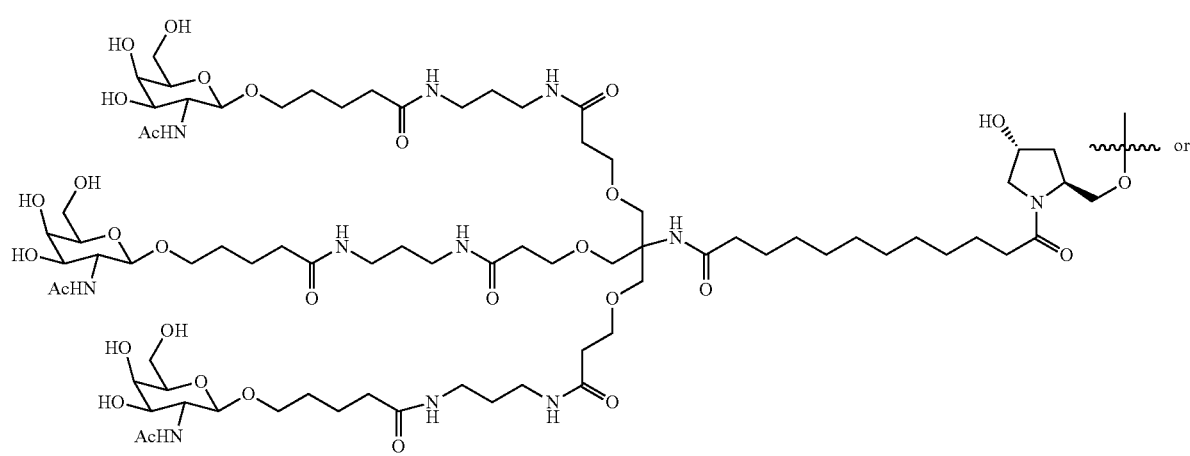

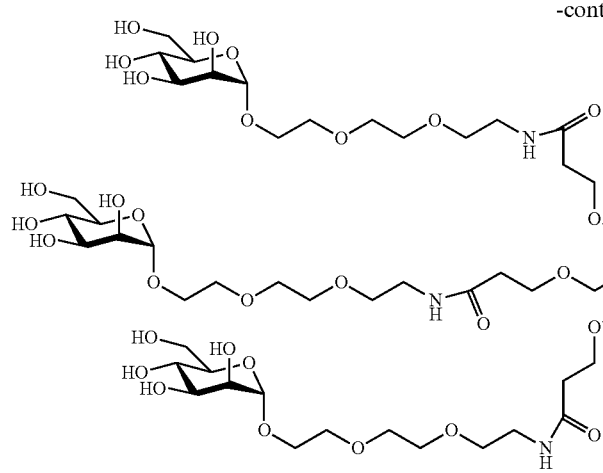 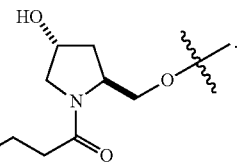

Synthesis of above described ligands and monomers is described, for example, in U.S. Pat. No. 8,106,022, content of which is incorporated herein by reference in its entirety.

Evaluation of Candidate iRNAs

One can evaluate a candidate iRNA agent, e.g., a modified RNA, for a selected property by exposing the agent or modified molecule and a control molecule to the appropriate conditions and evaluating for the presence of the selected property. For example, resistance to a degradant can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dssiRNA compounds.

In an alternative functional assay, a candidate dssiRNA compound homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dssiRNA compound would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added and/or cells in which a non-modified RNA is added.

Physiological Effects

The siRNA compounds described herein can be designed such that determining therapeutic toxicity is made easier by the complementarity of the siRNA with both a human and a non-human animal sequence. By these methods, an siRNA can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, *Pan paniscus, Pan troglodytes, Macaca* mulatto, or *Cynomolgus* monkey. The sequence of the siRNA compound could be complementary to sequences within homologous genes, e.g., oncogenes or tumor suppressor genes, of the non-human mammal and the human. By determining the toxicity of the siRNA compound in the non-human mammal, one can extrapolate the toxicity of the siRNA compound in a human. For a more strenuous toxicity test, the siRNA can be complementary to a human and more than one, e.g., two or three or more, non-human animals.

The methods described herein can be used to correlate any physiological effect of an siRNA compound on a human, e.g., any unwanted effect, such as a toxic effect, or any positive, or desired effect.

Increasing Cellular Uptake of siRNAs

Described herein are various siRNA compositions that contain covalently attached conjugates that increase cellular uptake and/or intracellular targeting of the siRNAs.

Additionally provided are methods of the invention that include administering an siRNA compound and a drug that affects the uptake of the siRNA into the cell. The drug can be administered before, after, or at the same time that the siRNA compound is administered. The drug can be covalently or non-covalently linked to the siRNA compound. The drug can be, for example, a lipopolysaccharide, an activator of p38 MAP kinase, or an activator of NF-κB. The drug can have a transient effect on the cell. The drug can increase the uptake of the siRNA compound into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The drug can also increase the uptake of the siRNA compound into a given cell or tissue by activating an inflammatory response, for example. Exemplary drugs that would have such an effect include tumor necrosis factor alpha (TNFalpha), interleukin-1 beta, a CpG motif, gamma interferon or more generally an agent that activates a toll-like receptor.

siRNA Production

An siRNA can be produced, e.g., in bulk, by a variety of methods. Exemplary methods include: organic synthesis and RNA cleavage, e.g., in vitro cleavage.

Organic Synthesis. An siRNA can be made by separately synthesizing a single stranded RNA molecule, or each respective strand of a double-stranded RNA molecule, after which the component strands can then be annealed.

A large bioreactor, e.g., the OligoPilot II from Pharmacia Biotec AB (Uppsala Sweden), can be used to produce a large amount of a particular RNA strand for a given siRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the siRNA. Typically, the two complementary strands are produced separately and then annealed, e.g., after release from the solid support and deprotection.

Organic synthesis can be used to produce a discrete siRNA species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsiRNA Cleavage. siRNAs can also be made by cleaving a larger siRNA. The cleavage can be mediated in vitro or in vivo. For example, to produce iRNAs by cleavage in vitro, the following method can be used:

In vitro transcription. dsiRNA is produced by transcribing a nucleic acid (DNA) segment in both directions. For example, the HiScribe™ RNAi transcription kit (New England Biolabs) provides a vector and a method for producing a dsiRNA for a nucleic acid segment that is cloned into the vector at a position flanked on either side by a T7 promoter. Separate templates are generated for T7 transcription of the two complementary strands for the dsiRNA. The templates are transcribed in vitro by addition of T7 RNA polymerase and dsiRNA is produced. Similar methods using PCR and/or other RNA polymerases (e.g., T3 or SP6 polymerase) can also be dotoxins that may contaminate preparations of the recombinant enzymes.

In Vitro Cleavage. In one embodiment, RNA generated by this method is carefully purified to remove endsiRNA is cleaved in vitro into siRNAs, for example, using a Dicer or comparable RNAse III-based activity. For example, the dsiRNA can be incubated in an in vitro extract from *Drosophila* or using purified components, e.g., a purified RNAse or RISC complex (RNA-induced silencing complex). See, e.g., Ketting et al. *Genes Dev* 2001 Oct. 15; 15(20):2654-9. and Hammond *Science* 2001 Aug. 10; 293(5532):1146-50.

dsiRNA cleavage generally produces a plurality of siRNA species, each being a particular 21 to 23 nt fragment of a source dsiRNA molecule. For example, siRNAs that include sequences complementary to overlapping regions and adjacent regions of a source dsiRNA molecule may be present.

Regardless of the method of synthesis, the siRNA preparation can be prepared in a solution (e.g., an aqueous and/or organic solution) that is appropriate for formulation. For example, the siRNA preparation can be precipitated and redissolved in pure double-distilled water, and lyophilized. The dried siRNA can then be resuspended in a solution appropriate for the intended formulation process.

Making Double-Stranded iRNA Agents Conjugated to a Lipophilic Moiety

In some embodiments, the lipophilic moiety is conjugated to the double-stranded iRNA agent via a nucleobase, sugar moiety, or internucleosidic linkage.

Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a lipophilic moiety is conjugated to a nucleobase, the preferred position is one that does not interfere with hybridization, i.e., does not interfere with the hydrogen bonding interactions needed for base pairing. In one embodiment, the lipophilic moieties may be conjugated to a nucleobase via a linker containing an alkyl, alkenyl or amide linkage. Exemplary conjugations of the lipophilic moieties to the nucleobase are illustrated in FIG. 1 and Example 7.

Conjugation to sugar moieties of nucleosides can occur at any carbon atom. Exemplary carbon atoms of a sugar moiety that a lipophilic moiety can be attached to include the 2', 3', and 5' carbon atoms. A lipophilic moiety can also be attached to the 1' position, such as in an abasic residue. In one embodiment, the lipophilic moieties may be conjugated to a sugar moiety, via a 2'-O modification, with or without a linker. Exemplary conjugations of the lipophilic moieties to the sugar moiety (via a 2'-O modification) are illustrated in FIG. 1 and Examples 1, 2, 3, and 6.

Internucleosidic linkages can also bear lipophilic moieties. For phosphorus-containing linkages (e.g., phosphodiester, phosphorothioate, phosphorodithioate, phosphoroamidate, and the like), the lipophilic moiety can be attached directly to the phosphorus atom or to an O, N, or S atom bound to the phosphorus atom. For amine- or amide-containing internucleosidic linkages (e.g., PNA), the lipophilic moiety can be attached to the nitrogen atom of the amine or amide or to an adjacent carbon atom.

There are numerous methods for preparing conjugates of oligonucleotides. Generally, an oligonucleotide is attached to a conjugate moiety by contacting a reactive group (e.g., OH, SH, amine, carboxyl, aldehyde, and the like) on the oligonucleotide with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

In one embodiment, a first (complementary) RNA strand and a second (sense) RNA strand can be synthesized separately, wherein one of the RNA strands comprises a pendant lipophilic moiety, and the first and second RNA strands can be mixed to form a dsRNA. The step of synthesizing the RNA strand preferably involves solid-phase synthesis, wherein individual nucleotides are joined end to end through the formation of internucleotide 3'-5' phosphodiester bonds in consecutive synthesis cycles.

In one embodiment, a lipophilic molecule having a phosphoramidite group is coupled to the 3'-end or 5'-end of either the first (complementary) or second (sense) RNA strand in the last synthesis cycle. In the solid-phase synthesis of an RNA, the nucleotides are initially in the form of nucleoside phosphoramidites. In each synthesis cycle, a further nucleoside phosphoramidite is linked to the —OH group of the previously incorporated nucleotide. If the lipophilic molecule has a phosphoramidite group, it can be coupled in a manner similar to a nucleoside phosphoramidite to the free OH end of the RNA synthesized previously in the solid-phase synthesis. The synthesis can take place in an automated and standardized manner using a conventional RNA synthesizer. Synthesis of the lipophilic molecule having the phosphoramidite group may include phosphitylation of a free hydroxyl to generate the phosphoramidite group.

Synthesis procedures of lipophilic moiety-conjugated phosphoramidites are exemplified in Examples 1, 2, 4, 5, 6, and 7. Examples of procedures of post-synthesis conjugation of lipophilic moieties or other ligands are illustrated in Example 3.

In general, the oligonucleotides can be synthesized using protocols known in the art, for example, as described in Caruthers et al., Methods in Enzymology (1992) 211:3-19; WO 99/54459; Wincott et al., Nucl. Acids Res. (1995) 23:2677-2684; Wincott et al., Methods Mol. Bio., (1997) 74:59; Brennan et al., Biotechnol. Bioeng. (1998) 61:33-45; and U.S. Pat. No. 6,001,311; each of which is hereby incorporated by reference in its entirety. In general, the synthesis of oligonucleotides involves conventional nucleic acid protecting and coupling groups, such as dimethoxytrityl at the 5'-end, and phosphoramidites at the 3'-end. In a non-limiting example, small scale syntheses are conducted on a Expedite 8909 RNA synthesizer sold by Applied Biosystems, Inc. (Weiterstadt, Germany), using ribonucleoside phosphoramidites sold by ChemGenes Corporation (Ashland, Mass.). Alternatively, syntheses can be performed on a 96-well plate synthesizer, such as the instrument produced by Protogene (Palo Alto, Calif.), or by methods such as those described in Usman et al., J. Am. Chem. Soc. (1987) 109:7845; Scaringe, et al., Nucl. Acids Res. (1990) 18:5433; Wincott, et al., Nucl. Acids Res. (1990) 23:2677-2684; and Wincott, et al., Methods Mol. Bio. (1997) 74:59, each of which is hereby incorporated by reference in its entirety.

The nucleic acid molecules of the present invention may be synthesized separately and joined together post-synthetically, for example, by ligation (Moore et al., Science (1992) 256:9923; WO 93/23569; Shabarova et al., Nucl. Acids Res. (1991) 19:4247; Bellon et al., Nucleosides & Nucleotides (1997) 16:951; Bellon et al., Bioconjugate Chem. (1997) 8:204; or by hybridization following synthesis and/or deprotection. The nucleic acid molecules can be purified by gel electrophoresis using conventional methods or can be purified by high pressure liquid chromatography (HPLC; see Wincott et al., supra, the totality of which is hereby incorporated herein by reference) and re-suspended in water.

Pharmaceutical Compostions

In one aspect, the invention features a pharmaceutical composition that includes an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) including a nucleotide sequence complementary to a target RNA, e.g., substantially and/or exactly complementary. The target RNA can be a transcript of an endogenous human gene. In one embodiment, the siRNA compound (a) is 19-25 nucleotides long, for example, 21-23 nucleotides, (b) is complementary to an endogenous target RNA, and, optionally, (c) includes at least one 3' overhang 1-5 nt long. In one embodiment, the pharmaceutical composition can be an emulsion, microemulsion, cream, jelly, or liposome.

In one example the pharmaceutical composition includes an siRNA compound mixed with a topical delivery agent. The topical delivery agent can be a plurality of microscopic vesicles. The microscopic vesicles can be liposomes. In some embodiments the liposomes are cationic liposomes.

In another aspect, the pharmaceutical composition includes an siRNA compound, e.g., a double-stranded siRNA compound, or ssiRNA compound (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) admixed with a topical penetration enhancer. In one embodiment, the topical penetration enhancer is a fatty acid. The fatty acid can be arachidonic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester, monoglyceride, diglyceride or pharmaceutically acceptable salt thereof.

In another embodiment, the topical penetration enhancer is a bile salt. The bile salt can be cholic acid, dehydrocholic acid, deoxycholic acid, glucholic acid, glycholic acid, glycodeoxycholic acid, taurocholic acid, taurodeoxycholic acid, chenodeoxycholic acid, ursodeoxycholic acid, sodium tauro-24,25-dihydro-fusidate, sodium glycodihydrofusidate, polyoxyethylene-9-lauryl ether or a pharmaceutically acceptable salt thereof.

In another embodiment, the penetration enhancer is a chelating agent. The chelating agent can be EDTA, citric acid, a salicylate, a N-acyl derivative of collagen, laureth-9, an N-amino acyl derivative of a beta-diketone or a mixture thereof.

In another embodiment, the penetration enhancer is a surfactant, e.g., an ionic or nonionic surfactant. The surfactant can be sodium lauryl sulfate, polyoxyethylene-9-lauryl ether, polyoxyethylene-20-cetyl ether, a perfluorochemical emulsion or mixture thereof.

In another embodiment, the penetration enhancer can be selected from a group consisting of unsaturated cyclic ureas, 1-alkyl-alkones, 1-alkenylazacyclo-alakanones, steroidal anti-inflammatory agents and mixtures thereof. In yet another embodiment the penetration enhancer can be a glycol, a pyrrol, an azone, or a terpenes.

In one aspect, the invention features a pharmaceutical composition including an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) in a form suitable for oral delivery. In one embodiment, oral delivery can be used to deliver an siRNA compound composition to a cell or a region of the gastrointestinal tract, e.g., small intestine, colon (e.g., to treat a colon cancer), and so forth. The oral delivery form can be tablets, capsules or gel capsules. In one embodiment, the siRNA compound of the pharmaceutical composition modulates expression of a cellular adhesion protein, modulates a rate of cellular proliferation, or has biological activity against eukaryotic pathogens or retroviruses. In another embodiment, the pharmaceutical composition includes an enteric material that substantially prevents dissolution of the tablets, capsules or gel capsules in a mammalian stomach. In some embodiments the enteric material is a coating. The coating can be acetate phthalate, propylene glycol, sorbitan monoleate, cellulose acetate trimellitate, hydroxy propyl methylcellulose phthalate or cellulose acetate phthalate.

In another embodiment, the oral dosage form of the pharmaceutical composition includes a penetration enhancer. The penetration enhancer can be a bile salt or a fatty acid. The bile salt can be ursodeoxycholic acid, chenodeoxycholic acid, and salts thereof. The fatty acid can be capric acid, lauric acid, and salts thereof.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an siRNA compound and a delivery vehicle. In one embodiment, the siRNA compound is (a) is 19-25 nucleotides long, for example, 21-23 nucleotides, (b) is complementary to an endogenous target RNA, and, optionally, (c) includes at least one 3' overhang 1-5 nucleotides long.

In one embodiment, the delivery vehicle can deliver an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) to a cell by a topical route of administration. The delivery vehicle can be microscopic vesicles. In one example the microscopic vesicles are liposomes. In some embodiments the liposomes are cationic liposomes. In another example the microscopic vesicles are micelles. In one aspect, the invention features a pharmaceutical composition including an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) in an injectable dosage form. In one embodiment, the injectable dosage form of the pharmaceutical composition includes sterile aqueous solutions or dispersions and sterile powders. In some embodiments the sterile solution can include a diluent such as water; saline solution; fixed oils, polyethylene glycols, glycerin, or propylene glycol.

In one aspect, the invention features a pharmaceutical composition including an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) in oral dosage form. In one embodiment, the oral dosage form is selected from the group consisting of tablets, capsules and gel capsules. In another embodiment, the pharmaceutical composition includes an enteric material that substantially prevents dissolution of the tablets, capsules or gel capsules in a mammalian stomach. In some embodiments the enteric material is a coating. The coating can be acetate phthalate, propylene glycol, sorbitan monoleate, cellulose acetate trimellitate, hydroxy propyl methyl cellulose phthalate or cellulose acetate phthalate. In one embodiment, the oral dosage form of the pharmaceutical composition includes a penetration enhancer, e.g., a penetration enhancer described herein.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) in a rectal dosage form. In one embodiment, the rectal dosage form is an enema. In another embodiment, the rectal dosage form is a suppository.

In one aspect, the invention features a pharmaceutical composition including an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) in a vaginal dosage form. In one embodiment, the vaginal dosage form is a suppository. In another embodiment, the vaginal dosage form is a foam, cream, or gel.

In one aspect, the invention features a pharmaceutical composition including an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) in a pulmonary or nasal dosage form. In one embodiment, the siRNA compound is incorporated into a particle, e.g., a macroparticle, e.g., a microsphere. The particle can be produced by spray drying, lyophilization, evaporation, fluid bed drying, vacuum drying, or a combination thereof. The microsphere can be formulated as a suspension, a powder, or an implantable solid.

Treatment Methods and Routes of Delivery

Another aspect of the invention relates to a method of reducing the expression of a target gene in a cell, comprising contacting said cell with the double-stranded iRNA agent of the invention. In one embodiment, the cell is an extraheptic cell.

Another aspect of the invention relates to a method of reducing the expression of a target gene in a subject, comprising administering to the subject the double-stranded iRNA agent of the invention.

Another aspect of the invention relates to a method of treating a subject having a CNS disorder, comprising administering to the subject a therapeutically effective amount of the double-stranded RNAi agent of the invention, thereby treating the subject. Exemplary CNS disorders that can be treated by the method of the invention include alzheimer, amyotrophic lateral sclerosis (ALS), frontotemporal dementia, huntington, Parkinson, spinocerebellar, prion, and lafora.

The double-stranded iRNA agent of the invention can be delivered to a subject by a variety of routes, depending on the type of genes targeted and the type of disorders to be treated. In some embodiments, the double-stranded iRNA agent is administered extrahepatically, such as an ocular administration (e.g., intravitreal administration) or an intrathecal administration.

In one embodiment, the double-stranded iRNA agent is administered intrathecally. By intrathecal administration of the double-stranded iRNA agent, the method can reduce the expression of a target gene in a brain or spine tissue, for instance, cortex, cerebellum, cervical spine, lumbar spine, and thoracic spine.

In some embodiments, exemplary target genes are APP, ATXN2, C9orf72, TARDBP, MAPT(Tau), HTT, SNCA, FUS, ATXN3, ATXN1, SCA1, SCA7, SCA8, MeCP2, PRNP, SOD1, DMPK, and TTR. To reduce the expression of these target genes in the subject, the double-stranded iRNA agent can be administered intravitreally. By intravitreal administration of the double-stranded iRNA agent, the method can reduce the expression of the target gene in an ocular tissue.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the invention. A composition that includes a iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes may be controlled to render the preparation isotonic.

For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

In one embodiment, the administration of the siRNA compound, e.g., a double-stranded siRNA compound, or ssiRNA compound, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

Intrathecal Administration. In one embodiment, the double-stranded iRNA agent is delivered by intrathecal injection (i.e. injection into the spinal fluid which bathes the brain and spinal chord tissue). Intrathecal injection of iRNA agents into the spinal fluid can be performed as a bolus injection or via minipumps which can be implanted beneath the skin, providing a regular and constant delivery of siRNA into the spinal fluid. The circulation of the spinal fluid from the choroid plexus, where it is produced, down around the spinal chord and dorsal root ganglia and subsequently up past the cerebellum and over the cortex to the arachnoid granulations, where the fluid can exit the CNS, that, depending upon size, stability, and solubility of the compounds injected, molecules delivered intrathecally could hit targets throughout the entire CNS.

In some embodiments, the intrathecal administration is via a pump. The pump may be a surgically implanted osmotic pump. In one embodiment, the osmotic pump is implanted into the subarachnoid space of the spinal canal to facilitate intrathecal administration.

In some embodiments, the intrathecal administration is via an intrathecal delivery system for a pharmaceutical including a reservoir containing a volume of the pharmaceutical agent, and a pump configured to deliver a portion of the pharmaceutical agent contained in the reservoir. More details about this intrathecal delivery system may be found in PCT/US2015/013253, filed on Jan. 28, 2015, which is incorporated by reference in its entirety.

The amount of intrathecally injected iRNA agents may vary from one target gene to another target gene and the appropriate amount that has to be applied may have to be determined individually for each target gene. Typically, this amount ranges between 10 µg to 2 mg, preferably 50 µg to 1500 kg, more preferably 100 µg to 1000 µg.

Rectal Administration. The invention also provides methods, compositions, and kits, for rectal administration or delivery of siRNA compounds described herein.

Accordingly, an siRNA compound, e.g., a double-stranded siRNA compound, or ssiRNA compound, (e.g., a precursor, e.g., a larger siRNA compound which can be processed into a ssiRNA compound, or a DNA which encodes a an siRNA compound, e.g., a double-stranded siRNA compound, or ssiRNA compound, or precursor thereof) described herein, e.g., a therapeutically effective amount of a siRNA compound described herein, e.g., a siRNA compound having a double stranded region of less than 40, and, for example, less than 30 nucleotides and having one or two 1-3 nucleotide single strand 3' overhangs can be administered rectally, e.g., introduced through the rectum into the lower or upper colon. This approach is particularly useful in the treatment of, inflammatory disorders, disorders characterized by unwanted cell proliferation, e.g., polyps, or colon cancer.

The medication can be delivered to a site in the colon by introducing a dispensing device, e.g., a flexible, camera-guided device similar to that used for inspection of the colon or removal of polyps, which includes means for delivery of the medication.

The rectal administration of the siRNA compound is by means of an enema. The siRNA compound of the enema can be dissolved in a saline or buffered solution. The rectal administration can also by means of a suppository, which can include other ingredients, e.g., an excipient, e.g., cocoa butter or hydropropyl methylcellulose.

Ocular Delivery. The iRNA agents described herein can be administered to an ocular tissue. For example, the medications can be applied to the surface of the eye or nearby tissue, e.g., the inside of the eyelid. They can be applied topically, e.g., by spraying, in drops, as an eyewash, or an ointment. Administration can be provided by the subject or by another person, e.g., a health care provider. The medication can be provided in measured doses or in a dispenser which delivers a metered dose. The medication can also be administered to the interior of the eye, and can be introduced by a needle or other delivery device which can introduce it to a selected area or structure. Ocular treatment is particularly desirable for treating inflammation of the eye or nearby tissue.

In certain embodiments, the double-stranded iRNA agents may be delivered directly to the eye by ocular tissue injection such as periocular, conjunctival, subtenon, intracameral, intravitreal, intraocular, anterior or posterior juxtascleral, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

In one embodiment, the double-stranded iRNA agents may be administered into the eye, for example the vitreous chamber of the eye, by intravitreal injection, such as with pre-filled syringes in ready-to-inject form for use by medical personnel.

For ophthalmic delivery, the double-stranded iRNA agents may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the conjugate in a physiologically acceptable isotonic aqueous buffer. Further, the solution may include an acceptable surfactant to assist in dissolving the double-stranded iRNA agents. Viscosity building agents, such as hydroxymethyl cellulose, hydroxyethyl cellulose, methylcellulose, polyvinylpyrrolidone, or the like may be added to the pharmaceutical compositions to improve the retention of the double-stranded iRNA agents.

To prepare a sterile ophthalmic ointment formulation, the double-stranded iRNA agents is combined with a preservative in an appropriate vehicle, such as mineral oil, liquid lanolin, or white petrolatum. Sterile ophthalmic gel formulations may be prepared by suspending the double-stranded iRNA agents in a hydrophilic base prepared from the combination of, for example, CARBOPOL®-940 (BF Goodrich, Charlotte, N.C.), or the like, according to methods known in the art.

Topical Delivery. Any of the siRNA compounds described herein can be administered directly to the skin. For example, the medication can be applied topically or delivered in a layer of the skin, e.g., by the use of a microneedle or a battery of microneedles which penetrate into the skin, but, for example, not into the underlying muscle tissue. Administration of the siRNA compound composition can be topical. Topical applications can, for example, deliver the composition to the dermis or epidermis of a subject. Topical administration can be in the form of transdermal patches, ointments, lotions, creams, gels, drops, suppositories, sprays, liquids or powders. A composition for topical administration can be formulated as a liposome, micelle, emulsion, or other lipophilic molecular assembly. The transdermal administration can be applied with at least one penetration enhancer, such as iontophoresis, phonophoresis, and sonophoresis.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the invention. In some embodiments, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) is delivered to a subject via topical administration. "Topical administration" refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 □m and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations that provide seals to further enhance the skins permeability barrier.

The permeability barrier provided by the skin is such that it is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose position and retention at the site of administration (Lee et al., Critical Reviews in Therapeutic Drug Carrier Systems, 1991, p. 168) may be useful methods for enhancing the transport of topically applied compositions across skin and mucosal sites.

The compositions and methods provided may also be used to examine the function of various proteins and genes in vitro in cultured or preserved dermal tissues and in animals. The invention can be thus applied to examine the function of any gene. The methods of the invention can also be used therapeutically or prophylactically. For example, for the treatment of animals that are known or suspected to suffer from diseases such as psoriasis, lichen planus, toxic epidermal necrolysis, erythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

Pulmonary Delivery. Any of the siRNA compounds described herein can be administered to the pulmonary system. Pulmonary administration can be achieved by inhalation or by the introduction of a delivery device into the pulmonary system, e.g., by introducing a delivery device which can dispense the medication. Certain embodiments may use a method of pulmonary delivery by inhalation. The medication can be provided in a dispenser which delivers the medication, e.g., wet or dry, in a form sufficiently small such that it can be inhaled. The device can deliver a metered dose of medication. The subject, or another person, can administer the medication. Pulmonary delivery is effective not only for disorders which directly affect pulmonary tissue, but also for disorders which affect other tissue. siRNA compounds can be formulated as a liquid or nonliquid, e.g., a powder, crystal, or aerosol for pulmonary delivery.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the invention. A composition that includes an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) can be administered to a subject by pulmonary delivery. Pulmonary delivery compositions can be delivered by inhalation by the patient of a dispersion so that the composition, for example, iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are may be used. One of the benefits of using an atomizer or inhaler is that the potential for contamination is minimized because the devices are self contained. Dry powder dispersion devices, for example, deliver drugs that may be readily formulated as dry powders. A iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." For example, the average particle size is less than about 10 µm in diameter with a relatively uniform spheroidal shape distribution. In some embodiments, the diameter is less than about 7.5 µm and in some embodiments less than about 5.0 µm. Usually the particle size distribution is between about 0.1 µm and about 5 µm in diameter, sometimes about 0.3 µm to about 5 µm.

The term "dry" means that the composition has a moisture content below about 10% by weight (% w) water, usually below about 5% w and in some cases less it than about 3% w. A dry composition can be such that the particles are readily dispersible in an inhalation device to form an aerosol.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A group of carbohydrates may include lactose, trehalose, raffinose maltodextrins, and mannitol. Suitable polypeptides include aspartame. Amino acids include alanine and glycine, with glycine being used in some embodiments.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate may be used in some embodiments.

Pulmonary administration of a micellar iRNA formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Oral or Nasal Delivery. Any of the siRNA compounds described herein can be administered orally, e.g., in the form of tablets, capsules, gel capsules, lozenges, troches or liquid syrups. Further, the composition can be applied topically to a surface of the oral cavity.

Any of the siRNA compounds described herein can be administered nasally. Nasal administration can be achieved by introduction of a delivery device into the nose, e.g., by introducing a delivery device which can dispense the medication. Methods of nasal delivery include spray, aerosol, liquid, e.g., by drops, or by topical administration to a surface of the nasal cavity. The medication can be provided in a dispenser with delivery of the medication, e.g., wet or dry, in a form sufficiently small such that it can be inhaled. The device can deliver a metered dose of medication. The subject, or another person, can administer the medication.

Nasal delivery is effective not only for disorders which directly affect nasal tissue, but also for disorders which affect other tissue siRNA compounds can be formulated as a liquid or nonliquid, e.g., a powder, crystal, or for nasal delivery. As used herein, the term "crystalline" describes a solid having the structure or characteristics of a crystal, i.e., particles of three-dimensional structure in which the plane faces intersect at definite angles and in which there is a regular internal structure. The compositions of the invention may have different crystalline forms. Crystalline forms can be prepared by a variety of methods, including, for example, spray drying.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the invention. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many drugs. Further, the sublingual mucosa is convenient, acceptable and easily accessible.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

A pharmaceutical composition of iRNA may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity. For example, the medication can be sprayed into the buccal cavity or applied directly, e.g., in a liquid, solid, or gel form to a surface in the buccal cavity. This administration is particularly desirable for the treatment of inflammations of the buccal cavity, e.g., the gums or tongue, e.g., in one embodiment, the buccal administration is by spraying into the cavity, e.g., without inhalation, from a dispenser, e.g., a metered dose spray dispenser that dispenses the pharmaceutical composition and a propellant.

An aspect of the invention also relates to a method of delivering an oligonucleotide into the CNS by intrathecal delivery or into an ocular tissue by intravitreally.

Some embodiments relates to a method of reducing the expression of a target gene in a cell, comprising contacting said cell with an oligonucleotide having one or more lipophilic moieties conjugated to oligonucleotide, optionally via a linker or carrier. In one embodiment, the cell is a cell in the CNS system. In one embodiment, the cell is an ocular cell.

Some embodiments relates to a method of reducing the expression of a target gene in a subject, comprising administering to the subject an oligonucleotide having one or more lipophilic moieties conjugated to oligonucleotide, optionally via a linker or carrier. In one embodiment, the oligonucleotide conjugate is administered intrathecally (to reduce the expression of a target gene in a brain or spine tissue). In one embodiment, the oligonucleotide conjugate is administered intravitreally (to reduce the expression of a target gene in an ocular tissue).

In some embodiments, the oligonucleotide is double-stranded. In one embodiment, the oligonucleotide is a double-stranded iRNA agent comprising an antisense strand which is complementary to a target gene and a sense strand which is complementary to said antisense strand.

In some embodiments, the oligonucleotide is single-stranded. In one embodiment, the oligonucleotide is an antisense.

In some embodiments, the lipophilic moiety is conjugated to one or more internal positions on at least one strand of the oligonucleotide. In some embodiments, the lipophilic moiety is conjugated to one or more terminal positions on at least one strand of the oligonucleotide.

Kits

In certain other aspects, the invention provides kits that include a suitable container containing a pharmaceutical formulation of an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof). In certain embodiments the individual components of the pharmaceutical formulation may be provided in one container. Alternatively, it may be desirable to provide the components of the pharmaceutical formulation separately in two or more containers, e.g., one container for an siRNA compound preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The invention is further illustrated by the following examples, which should not be construed as further limiting. The contents of all references, pending patent applications and published patents, cited throughout this application are hereby expressly incorporated by reference.

EXAMPLES

The invention now being generally described, it will be more readily understood by reference to the following examples which are included merely for purposes of illustration of certain aspects and embodiments of the present invention, and are not intended to limit the invention.

Example 1: Synthesis of Nucleoside Phosphoramidites for the Synthesis of Lipophilic Conjugates Scheme 1

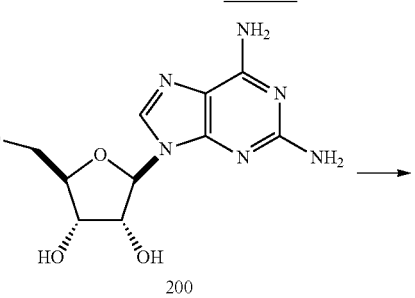

200

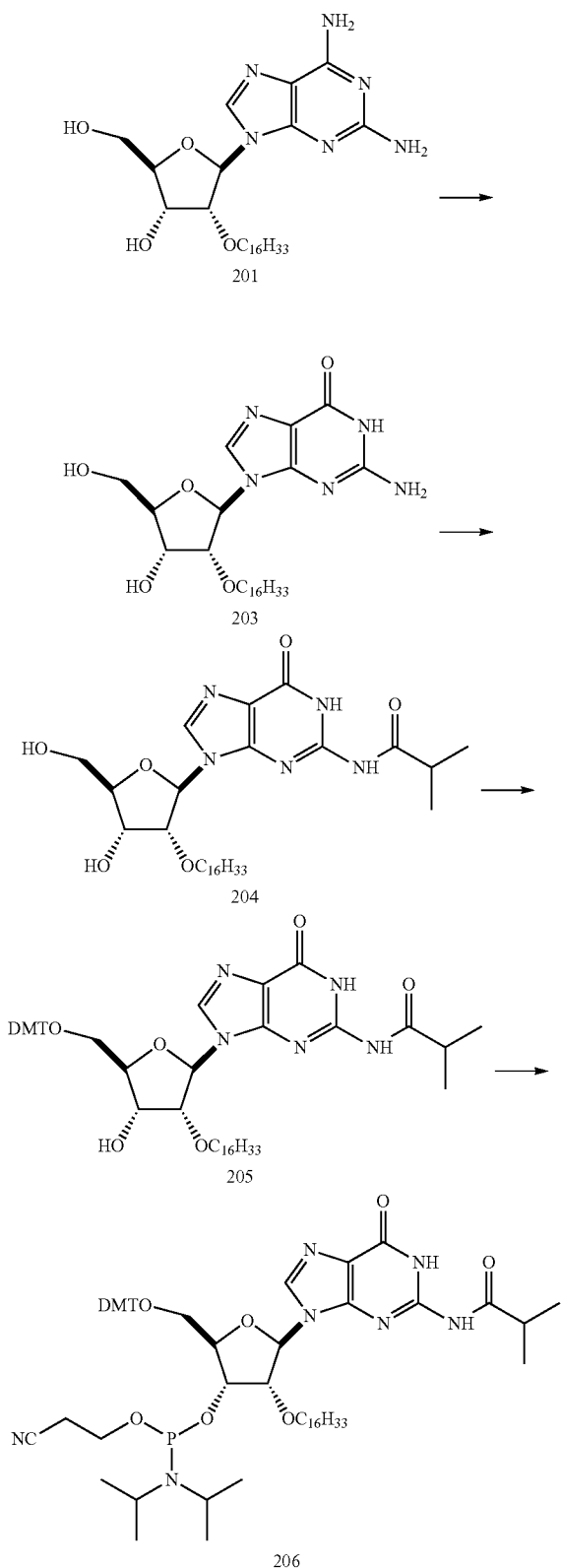

Synthesis of Compound 201: Sodium hydride (NaH) (21 g) was added to 2,6-diamino 9-(β-D-ribofuranosyl)purine 200 (105 g) in dry dimethyl formamide (DMF) (1500 ml). After stirring for 30 minutes, 1-bromohexadecane (150 ml) was added. The solution was stirred overnight at room temperature and then quenched by the addition of ethanol (EtOH) (50 ml). The reaction mixture was evaporated in vacuo, and the residue was suspended in methylene chloride and purified by silica gel chromatography using 5-10% MeOH/CH$_2$Cl$_2$ as the eluent. The product-containing fractions were pooled and the solvent was stripped to yield a crude foam 201 (95 g).

Synthesis of compound 203: The above foam (95 g) and adenosine deaminase (2000 mg, Sigma Chemicals Type II) were stirred at room temperature overnight in 0.1 M tris buffer (1500 ml, pH 7.4), DMSO (1000 ml), and 0.1 M sodium phosphate buffer (100 ml). A further aliquot of adenosine deaminase (140 mg) in 0.1 M phosphate buffer (30 ml) and DMSO (20 ml) was added and the reaction was stirred for 10 days. The solvent was evaporated in vacuo and the residue was flash chromatographed on silica gel using 0-10% MeOH/CH$_2$Cl$_2$. The product-containing fractions were evaporated in vacuo to give a solid 203 (35 g).

Synthesis of compound 204: The above solid (35 g) in pyridine (500 ml) was cooled in an ice bath and trimethylsilyl chloride (84 ml) was added. The reaction mixture was stirred for 30 minutes and isobutyryl chloride (58 ml) was added. The solution was stirred for 4 hours to reach room temperature. The solution was cooled, with H$_2$O being added (100 ml), and the solution was stirred for an additional 30 minutes. Concentrated NH$_4$—OH (100 ml) was added and the solution was evaporated in vacuo. The residue was purified by silica gel chromatography using 0-5% MeOH/DCM to elute the product. The product-containing fractions were evaporated to yield 25 g of product as a foam 204.

Synthesis of compound 205: N2-Isobutyryl-2'-O-hexadecylguanosine 204 (25 g) was co-evaporated with pyridine and then solubilized in pyridine (180 ml). Dimethoxytrityl chloride (20 g) and dimethylaminopyridine (50 mg) were added with stirring at room temperature. The reaction mixture was stirred overnight and evaporated in vacuo. The residue was partitioned between CH$_2$Cl$_2$/aqueous NaHCO$_3$. The organic phase was dried (MgSO$_4$) and evaporated. The residue was purified by silica gel chromatography (1:1 EtOAc/hexane) to yield 30 g of product 205.

Synthesis of compound 206: The above solid 205 (30 g), bis-(N,N-diisopropylamino)-2-cyanoethylphosphite (20 g), and N,N-diisopropylammonium tetrazolide (10 g) were stirred at room temperature overnight. The solution was partitioned against aqueous NaHCO$_3$ and dried over MgSO$_4$. The solvent was evaporated in vacuo and the residue was purified by silica gel chromatography (1% TEA in EtOAc) to yield 29 g of product 206 as a foam. $^1$H NMR (500 MHz, Acetonitrile-d3) δ 7.84 (d, J=11.1 Hz, 1H), 7.45 (dd, J=7.7, 5.7 Hz, 2H), 7.33 (dd, J=9.0, 7.1 Hz, 4H), 7.27 (m, 2H), 7.22 (dd, J=8.5, 6.0 Hz, 1H), 6.83 (m, 4H), 5.89 (t, J=5.7 Hz, 1H), 4.64 (m, 1H), 4.47 (m, 1H), 4.27 (m, 1H), 3.92-3.77 (m, 1H), 3.75 (d, J=2.3 Hz, 6H), 3.72-3.66 (m, 1H), 3.62 (m, 3H), 3.49 (m, 1H), 3.37 (d, J=3.9 Hz, 1H), 3.33 (d, J=4.0 Hz, 1H), 2.67 (d, J=3.9 Hz, 1H), 2.58-2.41 (m, 2H), 1.48 (m, 2H), 1.34-1.14 (m, 35H), 1.14-1.02 (m, 9H), 0.88 (t, J=6.7 Hz, 3H). $^{31}$P NMR (202 MHz, Acetonitrile-d3) δ 151.11, 150.93.

Scheme 2

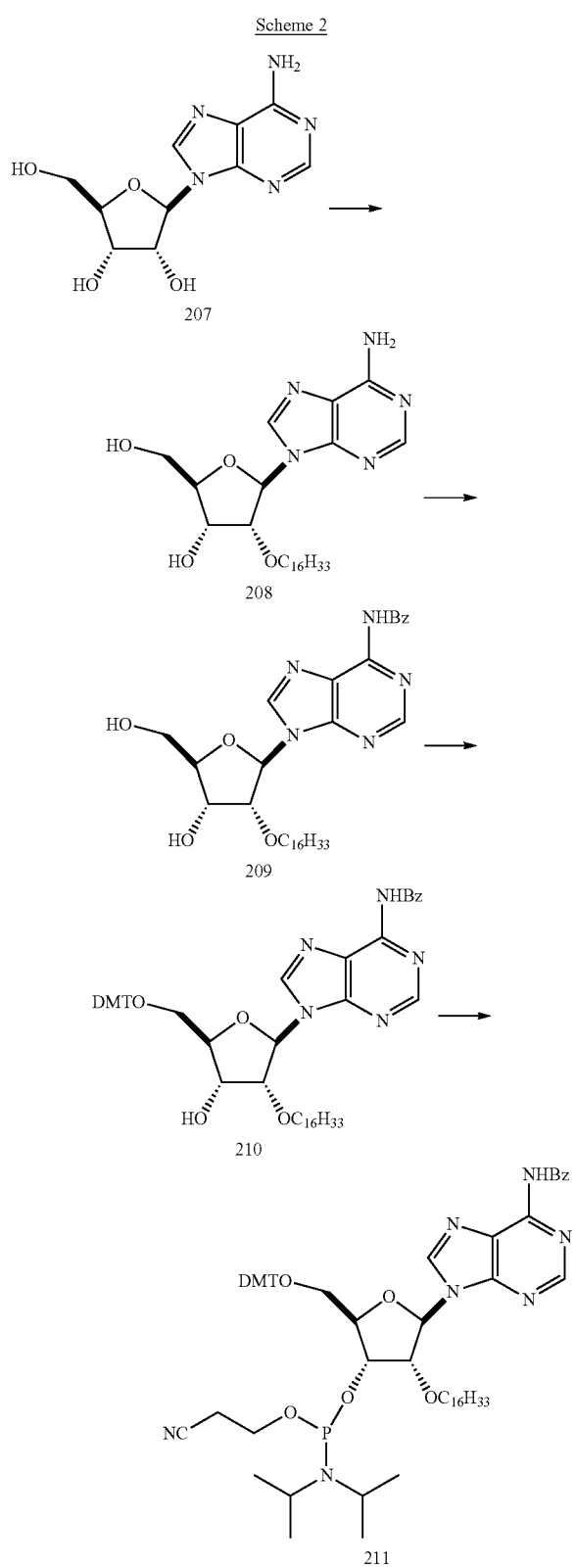

Synthesis of compound 208: Sodium hydride (NaH) (25 g) was added to 2,6-diamino 9-(β-D-ribofuranosyl)purine 207 (125 g) in dry dimethyl formamide (DMF) (1500 ml). After stirring for 30 minutes, 1-bromohexadecane (180 gl) was added. The solution was stirred overnight at room temperature and then quenched by the addition of ethanol (EtOH) (50 ml). The reaction mixture was evaporated in vacuo, and the residue was suspended in methylene chloride and purified by silica gel chromatography using 0-10% MeOH/CH$_2$Cl$_2$ as the eluent. The product-containing fractions were pooled and the solvent was stripped to yield the product 208 as a foam (36 g).

Synthesis of compound 209: The above solid 208 (36 g) in pyridine (500 ml) was cooled in an ice bath and trimethylsilyl chloride (30 ml) was added. The reaction mixture was stirred for 30 minutes and benzoyl chloride (20 ml) was added. The solution was stirred for 4 hours to reach room temperature. The solution was cooled, with H$_2$O being added (100 ml), and the solution was stirred for an additional 30 minutes. Concentrated NH$_4$—OH (100 ml) was added and the solution was evaporated in vacuo. The residue was purified by silica gel chromatography using 0-5% MeOH/CH$_2$Cl$_2$ to elute the product. The product-containing fractions were evaporated to yield 32 g of product 209 as a foam.

Synthesis of compound 210: N2-Benzoyl-2'-O-hexadecyladenosine 209 (32 g) was co-evaporated with pyridine and then solubilized in pyridine (180 ml). Dimethoxytrityl chloride (20 g) and dimethylaminopyridine (50 mg) were added with stirring at room temperature. The reaction mixture was stirred overnight and evaporated in vacuo. The residue was partitioned between DCM/aqueous NaHCO$_3$. The organic phase was dried (MgSO$_4$) and evaporated. The residue was purified by silica gel chromatography (1:1 EtOAc/hexane) to yield 35 g of product 210.

Synthesis of compound 211: The above solid 210 (35 g), bis-(N,N-diisopropylamino)-2-cyanoethylphosphite (20 g) and N,N-diisopropylammonium tetrazolide (10 g) were stirred at room temperature overnight. The solution was partitioned against aqueous NaHCO$_3$ and dried over MgSO$_4$. The solvent was evaporated in vacuo and the residue was purified by silica gel chromatography (1:1 EtOAc/hexane) to yield 37 g of product 211 as a foam. $^1$H NMR (500 MHz, Acetonitrile-d3) δ 9.37 (s, 1H), 8.57 (d, J=9.4 Hz, 1H), 8.27 (d, J=10.3 Hz, 1H), 7.99 (d, J=7.6 Hz, 2H), 7.61 (d, J=7.4 Hz, 1H), 7.52 (t, J=7.6 Hz, 2H), 7.42 (t, J=7.3 Hz, 2H), 7.34-7.16 (m, 7H), 6.85-6.77 (m, 4H), 6.11 (dd, J=5.0, 2.5 Hz, 1H), 4.80 (m, 1H), 4.69 (m, 1H), 4.32 (m, 1H), 3.97-3.78 (m, 1H), 3.74 (d, J=3.1 Hz, 7H), 3.64 (m, 4H), 3.56-3.40 (m, 2H), 3.33 (m, 1H), 2.73-2.59 (m, 1H), 2.50 (t, J=6.0 Hz, 1H), 1.52-1.45 (m, 2H), 1.33-1.12 (m, 37H), 1.09 (d, J=6.8 Hz, 3H), 0.87 (t, J=6.8 Hz, 3H). $^{31}$P NMR (202 MHz, Acetonitrile-d3) δ 151.19, 150.78.

Scheme 3

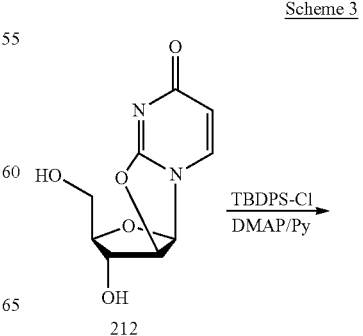

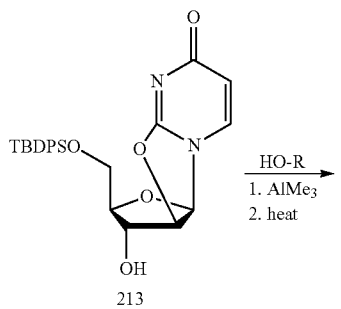

213

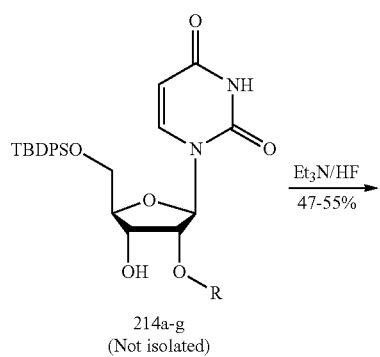

214a-g
(Not isolated)

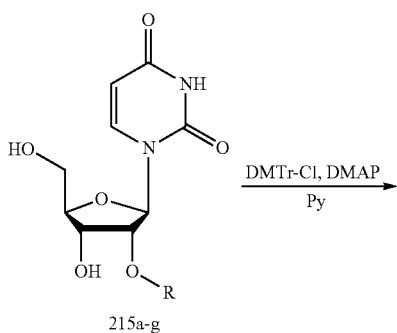

215a-g

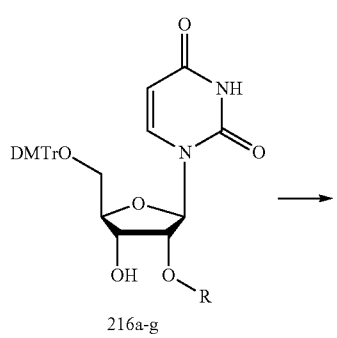

216a-g

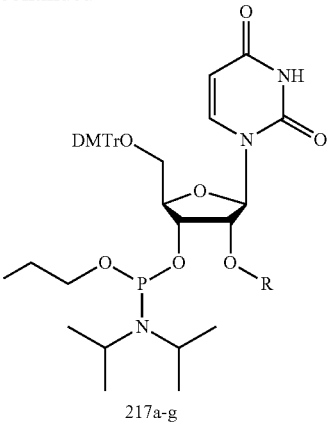

217a-g

R = $C_6H_{13}$, $C_8H_{17}$, $C_{10}H_{21}$, $C_{12}H_{25}$, $C_{14}H_{39}$, $C_{16}H_{33}$ and $C_{18}H_{35}$ Synthesis of 213: To a solution of anhydro-compound 212 (24.0 g, 0.1 mol) and DMAP (0.16 g, 1.3 mmol) in anhydrous pyridine (120 mL) under argon atmosphere, TBDPSCl (28 mL, 0.11 mol) was added. The mixture was stirred at room temperature for 24 hours after which time no notable amount of starting material 212 could be observed by TLC (chloroform:methanol 5:1). Pyridine was removed under the reduced pressure, and the residue was partitioned between ethyl acetate and 10% phosphoric acid. The organic phase was separated, washed consecutively with 5% aqueous NaCl and saturated NaCl, and dried over anhydrous sodium sulfate. Once crystallization started during aqueous washings, limited amount of DCM was added to dissolve the solids. After filtration of sodium sulfate, the solution was evaporated, and the residue was stirred with 800 mL of diethyl ether for 2 days. The white precipitate was filtered, washed once with diethyl ether, and dried to afford 40.8 g (85%) of 213 as white crystalline solid.

Synthesis of Compound 215f and 215 g: 0.36 mol of hexadecane-1-ol or oleyl alcohol was dried under high vacuum for ~40 minutes in a round bottom flask fitted with a magnetic bar, gas inlet, reflux condenser, oil heating bath, addition funnel, and a bubbler atop of the condenser, with the flask being filled with Ar. Anhydrous diglyme (65 mL) was added, followed by dropwise addition of 2M solution of $AlMe_3$ in heptane (55 mL, 0.11 mmol). The mixture was heated to 110° C. and the completeness of the reaction was monitored by the end of methane evolution. The mixture was cooled to room temperature under Ar, then anhydro-nucleoside 213 (23.2 g, 50 mmol) was added, and the oil bath was heated at 145° C. overnight. The mixture was cooled to room temperature under Ar and partitioned between 10% $H_3PO_4$ (500 mL) and ethyl acetate (250 mL). The organic layer was separated, washed consecutively with aqeuous NaCl (5%) and saturated NaCl, and dried over anhydrous $Na_2SO_4$. The solvents were removed in vacuum, and the residue was dissolved in THF (200 mL) and treated with triethylamine trihydrofluoride (33 mL, 0.2 mol). The mixture was stirred under Ar for 3 days and partitioned between 5% aqueous NaCl (300 mL) and ethylacetate (300 mL). The organic phase was separated, washed with saturated aqueous NaCl, and the solvent was evaporated. The residue was dissolved in hexanes (800 mL), and extracted with 90% aqueous MeOH (2×800 mL). The combined methanol extracts were evaporated, and the residue was partitioned between ethylacetate and saturated aqueous NaCl. The organic phase was separated and dried over anhydrous Na₂SO₄. The solvent was evaporated and the residue was purified by column chromatography on silica gel with gradient 3%-10% of methanol in DCM to afford 10.9 g (47%) of 215f (R=$C_{16}H_{33}$), or 13.7 g (55%) of 215g (R=$C_{18}H_{35}$, oleyl).

Synthesis of compound 216f: To a solution of anhydrocompound 215f (10.61 g, 22.6 mmol), DMAP (0.550 g, 4.4 mmol), and DMTrCl (9.76 g, 29 mmol) in anhydrous pyridine (70 mL) under argon atmosphere, triethylamine (4.1 mL, 29 mmol) was added. The mixture was stirred at room temperature overnight, quenched by addition of 1 mL of MeOH. Pyridine was removed in vacuum, and the residue was partitioned between ethyl acetate and 5% aqueous NaCl. The organic phase was separated, washed with saturated NaCl, and dried over anhydrous sodium sulfate. The solvent was evaporated in vacuum, and the product was isolated by chromatography of the residue over a column of silica gel with gradient (35 to 60%) of ethyl acetate in hexanes to afford 14.89 g (86%) of 216f as yellowish amorphous foam.

Synthesis of compound 217f: Compound 216f (25 g), bis-(N,N-diisopropylamino)-2-cyanoethylphosphite (15 g), and N,N-diisopropylammonium tetrazolide (7.5 g) were stirred at room temperature overnight. The solution was partitioned against aqueous NaHCO₃ and dried over MgSO₄. The solvent was evaporated in vacuo and the residue was purified by silica gel chromatography (1:1 EtOAc/hexane) to yield 27 g of product as a foam. ¹H NMR (500 MHz, Acetonitrile-d3) δ 9.02 (s, 1H), 7.77 (dd, J=43.4, 8.1 Hz, 1H), 7.49-7.40 (m, 2H), 7.36-7.29 (m, 6H), 7.26 (m, 1H), 6.88 (dd, J=8.7, 6.4 Hz, 4H), 5.85 (dd, J=7.5, 3.4 Hz, 1H), 5.22 (t, J=7.6 Hz, 1H), 4.44 (m, 1H), 4.14 (m, 1H), 4.07-3.99 (m, 1H), 3.86 (m, 1H), 3.77 (d, J=3.1 Hz, 7H), 3.63 (m, 5H), 3.45-3.33 (m, 2H), 2.66 (m, 1H), 2.52 (d, J=5.9 Hz, 1H), 1.55 (m, 2H), 1.26 (s, 26H), 1.16 (dd, J=11.0, 6.7 Hz, 9H), 1.05 (d, J=6.8 Hz, 3H), 0.88 (t, J=6.8 Hz, 3H). ³¹P NMR (202 MHz, Acetonitrile-d3) δ 151.01, 150.61.

Synthesis of compound 216a: Using the procedure described for 216f, compound 216a was synthesized. ¹H NMR (400 MHz, DMSO-d6) δ 11.37 (d, J=2.3 Hz, 1H), 7.71 (d, J=8.1 Hz, 1H), 7.39-7.34 (m, 2H), 7.31 (t, J=7.6 Hz, 2H), 7.28-7.20 (m, 5H), 6.94-6.83 (m, 4H), 5.28 (dd, J=8.1, 2.2 Hz, 1H), 5.11 (d, J=6.5 Hz, 1H), 4.16 (m, 1H), 4.01-3.92 (m, 1H), 3.89 (t, J=4.6 Hz, 1H), 3.73 (s, 6H), 3.55 (m, 2H), 3.30-3.18 (m, 2H), 1.54-1.43 (m, 2H), 1.33-1.15 (m, 6H), 0.83 (t, J=6.7 Hz, 3H).

Synthesis of Compound 217a: Compound 216a (4.0 g, 6.35 mmol) was added to a reaction flask, evacuated, and purged with argon. The starting material was dissolved in dichloromethane, and diisopropylethylamine (2.21 ml, 12.7 mmol) was added via syringe. 2-cyanoethyl N,N-diisopropylchlorophosphoramidite (2.12 ml, 9.53 mmol) was added and stirred at room temperature for 3 hours. The reaction was checked by TLC (70% EtOAc/hexane) and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (30% to 100% EtOAc/hexane), and the product fractions were combined and concentrated on reduced pressure to yield (3.42 g, 65%) of 216a. ¹H NMR (400 MHz, Acetonitrile-d3) δ 8.98 (s, 1H), 7.86-7.66 (m, 1H), 7.49-7.39 (m, 2H), 7.39-7.21 (m, 7H), 6.93-6.83 (m, 4H), 5.85 (dd, J=6.2, 3.5 Hz, 1H), 5.22 (dd, J=8.2, 6.3 Hz, 1H), 4.44 (m, 1H), 4.20-3.98 (m, 2H), 3.93-3.82 (m, 1H), 3.77 (d, J=2.4 Hz, 7H), 3.71-3.55 (m, 5H), 3.47-3.32 (m, 2H), 2.72-2.61 (m, 1H), 2.52 (t, J=6.0 Hz, 1H), 1.62-1.49 (m, 2H), 1.41-1.23 (m, 6H), 1.17 (dd, J=8.8, 6.8 Hz, 9H), 1.05 (d, J=6.8 Hz, 3H), 0.88 (m, 3H). 31P NMR (202 MHz, Acetonitrile-d3) δ 149.63, 149.26.

Synthesis of compound 216b: Using the procedure described for 216f, compound 216b was synthesized. ¹H NMR (400 MHz, DMSO-d6) δ 11.36 (d, J=2.2 Hz, 1H), 7.71 (d, J=8.1 Hz, 1H), 7.41-7.35 (m, 2H), 7.31 (t, J=7.6 Hz, 2H), 7.23 (m, 5H), 6.94-6.82 (m, 4H), 5.79 (d, J=3.9 Hz, 1H), 5.28 (dd, J=8.1, 2.2 Hz, 1H), 5.11 (d, J=6.5 Hz, 1H), 4.16 (m, 1H), 3.99-3.92 (m, 1H), 3.89 (m, 1H), 3.73 (s, 6H), 3.55 (m, 2H), 3.30-3.17 (m, 2H), 1.49 (t, J=6.9 Hz, 2H), 1.30-1.19 (m, 10H), 0.89-0.79 (m, 3H).

Synthesis of compound 217b: Compound 216b (4.0 g, 6.08 mmol) was added to a reaction flask, evacuated, and purged with argon. The starting material was dissolved in dichloromethane, and diisopropylethylamine (2.12 ml, 12.16 mmol) was added via syringe. 2-cyanoethyl N,N-diisopropylchlorophosphoramidite (2.03 ml, 9.12 mmol) was added and stirred at room temperature for 2.5 hours. The reaction was checked by TLC (70% EtOAc/hexane) and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (30% to 100% EtOAc/hexane), and the product fractions were combined and concentrated on reduced pressure to yield (3.55 g, 68%) of 217b. ¹H NMR (500 MHz, Acetonitrile-d3) δ 9.12 (d, J=4.5 Hz, 1H), 7.85-7.68 (m, 1H), 7.44 (m, 2H), 7.37-7.28 (m, 6H), 7.26 (m, 1H), 6.93-6.83 (m, 4H), 5.88-5.80 (m, 1H), 5.29-5.20 (m, 1H), 4.45 (m, 1H), 4.15 (m, 1H), 4.09-4.01 (m, 1H), 3.99-3.82 (m, 1H), 3.83-3.71 (m, 8H), 3.73-3.55 (m, 5H), 3.46-3.33 (m, 2H), 2.66 (m, 1H), 2.52 (t, J=6.0 Hz, 1H), 1.97 (s, 1H), 1.56 (m, 2H), 1.39-1.24 (m, 10H), 1.24-1.10 (m, 9H), 1.06 (d, J=6.7 Hz, 3H), 0.91-0.84 (m, 3H). ³¹P NMR (202 MHz, Acetonitrile-d3) δ 149.64, 149.25.

Synthesis of compound 216c: Using the procedure described for 216f, compound 216c was synthesized. ¹H NMR (400 MHz, DMSO-d6) δ 11.36 (d, J=2.2 Hz, 1H), 7.71 (d, J=8.1 Hz, 1H), 7.41-7.35 (m, 2H), 7.31 (t, J=7.6 Hz, 2H), 7.27-7.19 (m, 5H), 6.92-6.86 (m, 4H), 5.79 (d, J=3.9 Hz, 1H), 5.28 (dd, J=8.1, 2.1 Hz, 1H), 5.11 (d, J=6.5 Hz, 1H), 4.16 (m, 1H), 3.95 (m, 1H), 3.89 (m, 1H), 3.73 (s, 6H), 3.55 (m, 2H), 3.30-3.18 (m, 2H), 1.49 (t, J=6.9 Hz, 2H), 1.23 (d, J=7.0 Hz, 13H), 0.83 (t, J=6.6 Hz, 3H).

Synthesis of compound 217c: Compound 216c (4.0 g, 5.83 mmol) was added to a reaction flask, evacuated, and purged with argon. The starting material was dissolved in dichloromethane, and diisopropylethylamine (2.04 ml, 11.66 mmol) was added via syringe. 2-cyanoethyl N,N-diisopropylchlorophosphoramidite (1.95 ml, 8.75 mmol) was added and stirred at room temperature for 4 hours. The reaction was checked by TLC (70% EtOAc/hexane) and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (30% to 100% EtOAc/hexane), and the product fractions were combined and concentrated on reduced pressure to yield (4.20 g, 81%) of 217c. $^1$H NMR (400 MHz, Acetonitrile-d3) δ 9.02 (s, 1H), 7.77 (dd, J=35.4, 8.2 Hz, 1H), 7.49-7.39 (m, 2H), 7.39-7.21 (m, 7H), 6.93-6.83 (m, 4H), 5.85 (dd, J=6.1, 3.5 Hz, 1H), 5.22 (dd, J=8.2, 6.3 Hz, 1H), 4.15 (m, 1H), 4.03 (m, 1H), 3.77 (d, J=2.4 Hz, 7H), 3.69-3.53 (m, 4H), 3.47-3.32 (m, 2H), 2.71-2.61 (m, 1H), 2.52 (t, J=6.0 Hz, 1H), 1.56 (m, 2H), 1.38-1.24 (m, 14H), 1.16 (dd, J=8.8, 6.8 Hz, 9H), 1.05 (d, J=6.7 Hz, 3H), 0.92-0.83 (m, 3H). $^{31}$P NMR (202 MHz, Acetonitrile-d3) δ 149.63, 149.25.

Synthesis of compound 216d: Using the procedure described for 216f, compound 216d was synthesized. $^1$H NMR (400 MHz, DMSO-d6) δ 11.36 (d, J=2.2 Hz, 1H), 7.71 (d, J=8.1 Hz, 1H), 7.41-7.34 (m, 2H), 7.31 (t, J=7.6 Hz, 2H), 7.28-7.19 (m, 5H), 6.94-6.81 (m, 4H), 5.79 (d, J=3.9 Hz, 1H), 5.28 (dd, J=8.1, 2.2 Hz, 1H), 5.11 (d, J=6.5 Hz, 1H), 4.16 (m, 1H), 3.95 (m, 1H), 3.89 (m, 1H), 3.73 (s, 7H), 3.55 (m, 2H), 3.30-3.17 (m, 2H), 1.49 (t, J=6.8 Hz, 2H), 1.22 (s, 19H), 0.88-0.79 (m, 3H).

Synthesis of Compound 217d: Compound 216d (5.0 g, 6.99 mmol) was added to a reaction flask, evacuated, and purged with argon. The starting material was dissolved in dichloromethane, and diisopropylethylamine (2.44 ml, 14 mmol) was added via syringe. 2-cyanoethyl N,N-diisopropylchlorophosphoramidite (2.34 ml, 10.50 mmol) was added and the reaction stirred at room temperature for 3 hours. The reaction was checked by TLC (70% EtOAc/hexane) and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (30% to 100% EtOAc/hexane), and the product fractions were combined and concentrated on reduced pressure to yield (4.54 g, 73%) of 217d. $^1$H NMR (500 MHz, Chloroform-d) δ 8.15 (s, 1H), 8.01 (dd, J=44.6, 8.2 Hz, 1H), 7.43-7.34 (m, 2H), 7.34-7.21 (m, 7H), 6.84 (m, 3H), 5.95 (dd, J=21.0, 2.6 Hz, 1H), 5.21 (t, J=7.5 Hz, 1H), 4.29-4.17 (m, 1H), 4.00 (m, 1H), 3.97-3.86 (m, 1H), 3.80 (d, J=3.5 Hz, 6H), 3.77-3.64 (m, 2H), 3.65-3.52 (m, 4H), 3.44 (m, 1H), 2.63 (m, 1H), 2.42 (t, J=6.3 Hz, 1H), 1.60 (dd, J=7.2, 4.5 Hz, 2H), 1.39-1.21 (m, 17H), 1.21-1.12 (m, 8H), 1.04 (d, J=6.8 Hz, 3H), 0.87 (t, J=6.8 Hz, 2H). $^{31}$P NMR (202 MHz, Chloroform-d) δ 150.102, 150.07.

Synthesis of compound 216e: Using the procedure described for 216f, compound 216e was synthesized. $^1$H NMR (400 MHz, DMSO-d6) δ 11.36 (d, J=2.2 Hz, 1H), 7.71 (d, J=8.1 Hz, 1H), 7.37 (d, J=7.3 Hz, 2H), 7.31 (t, J=7.5 Hz, 2H), 7.27-7.20 (m, 5H), 6.93-6.82 (m, 4H), 5.79 (d, J=3.8 Hz, 1H), 5.27 (dd, J=8.1, 2.1 Hz, 1H), 5.11 (d, J=6.5 Hz, 1H), 4.16 (m, 1H), 3.95 (m, 1H), 3.89 (m, 1H), 3.73 (s, 6H), 3.55 (m, 2H), 3.30-3.18 (m, 2H), 1.49 (t, J=6.9 Hz, 2H), 1.21 (s, 22H), 0.83 (t, J=6.6 Hz, 3H).

Synthesis of compound 217e: Compound 216e (5.0 g, 6.73 mmol) was added to a reaction flask, evacuated, and purged with argon. The starting material was dissolved in dichloromethane, and diisopropylethylamine (2.35 ml, 13.46 mmol) was added via syringe. 2-cyanoethyl N,N-diisopropylchlorophosphoramidite (2.25 ml, 10.10 mmol) was added and the reaction stirred at room temperature for 3 hours. The reaction was checked by TLC (70% EtOAc/hexane), and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (30% to 100% EtOAc/hexane), and the product fractions were combined and concentrated on reduced pressure to yield (4.86 g, 77%) of 217e. $^1$H NMR (500 MHz, Chloroform-d) δ 8.49 (s, 1H), 8.01 (dd, J=45.8, 8.2 Hz, 1H), 7.39 (dd, J=17.7, 7.3 Hz, 2H), 7.34-7.21 (m, 8H), 6.88-6.79 (m, 4H), 5.96 (dd, J=21.6, 2.5 Hz, 1H), 5.22 (dd, J=8.2, 6.2 Hz, 1H), 4.29-4.17 (m, 1H), 4.04-3.87 (m, 2H), 3.80 (dd, J=3.6, 1.4 Hz, 8H), 3.76-3.64 (m, 2H), 3.64-3.53 (m, 5H), 3.45 (m, 1H), 2.63 (m, 1H), 2.42 (s, 1H), 1.59 (m, 3H), 1.40-1.29 (m, 4H), 1.25 (s, 21H), 1.22-1.10 (m, 11H), 1.04 (d, J=6.8 Hz, 4H), 0.88 (t, J=6.9 Hz, 3H). $^{31}$P NMR (202 MHz, Chloroform-d) δ 150.13, 150.06.

Synthesis of compound 216g: Using the procedure described for 216f, compound 216g was synthesized. $^1$H NMR (400 MHz, DMSO-d6) δ 11.36 (d, J=2.2 Hz, 1H), 7.71 (d, J=8.1 Hz, 1H), 7.40-7.29 (m, 4H), 7.23 (m, 5H), 6.93-6.85 (m, 4H), 5.78 (d, J=3.8 Hz, 1H), 5.35-5.23 (m, 3H), 5.10 (d, J=6.5 Hz, 1H), 4.15 (m, 1H), 3.95 (m, 1H), 3.88 (t, J=4.5 Hz, 1H), 3.73 (s, 6H), 3.54 (m, 2H), 3.30-3.16 (m, 2H), 1.96 (m, 4H), 1.49 (t, J=6.8 Hz, 2H), 1.32-1.15 (m, 21H), 0.87-0.79 (m, 3H).

Synthesis of compound 217g: Compound 216g (5.0 g, 6.28 mmol) was added to a reaction flask, evacuated, and purged with argon. The starting material was dissolved in dichloromethane, and diisopropylethylamine (2.19 ml, 12.56 mmol) was added via syringe. 2-cyanoethyl N,N-diisopropylchlorophosphoramidite (2.09 ml, 9.42 mmol) was added and the reaction was stirred at room temperature for 3 hours. The reaction was checked by TLC (70% EtOAc/hexane) and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (30% to 100% EtOAc/Hexane), and the product fractions were combined and concentrated on reduced pressure to yield (4.83 g, 77.1%) of 217g. $^1$H NMR (400 MHz, Chloroform-d) δ 8.38 (s, 1H), 8.02 (dd, J=35.6, 8.1 Hz, 1H), 7.44-7.35 (m, 2H), 7.28 (m, 7H), 6.84 (m, 4H), 5.95 (dd, J=16.6, 2.5 Hz, 1H), 5.34 (t, J=4.9 Hz, 2H), 5.21 (dd, J=8.1, 5.5 Hz, 1H), 4.30-4.17 (m, 1H), 4.00 (m, 1H), 3.80 (d, J=2.5 Hz, 6H), 3.77-3.65 (m, 2H), 3.59 (m, 4H), 3.45 (m, 1H), 2.63 (m, 1H), 2.42 (s, 1H), 2.00 (m, 4H), 1.59 (m, 3H), 1.30 (dd, J=22.5, 8.3 Hz, 21H), 1.22-1.13 (m, 8H), 1.04 (d, J=6.8 Hz, 3H), 0.88 (t, J=6.7 Hz, 3H). $^{31}$P NMR (202 MHz, Chloroform-d) δ 150.12, 150.07.

Scheme 4

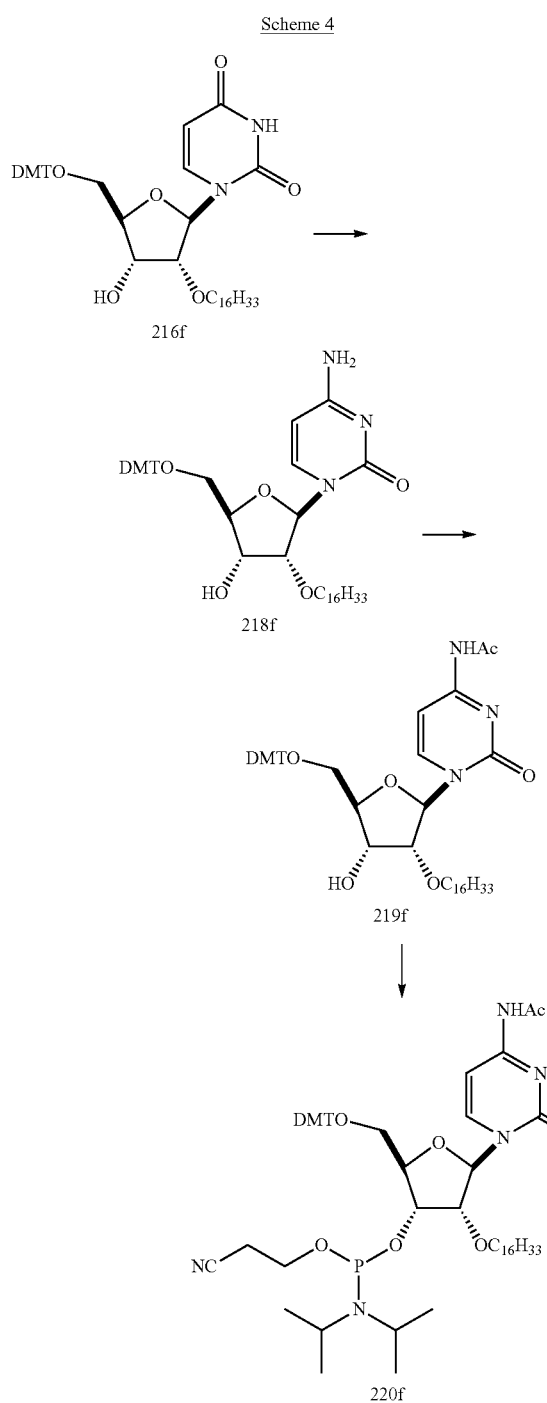

Synthesis of compound 218f: The DMT nucleoside 217f (30 g) was dissolved in anhydrous pyridine (300 ml). Trimethylsilyl chloride (20 ml) was added and the mixture was stirred for 30 minutes. Triazole (30 g) and triethylamine (80 ml) were added and cooled to 0° C. POCl$_3$ (9 ml) was added and the mixture was stirred for 2 hours at 0° C. Concentrated ammonia (100 ml) was added and stirred for 1 hour. Water 500 ml was added and the mixture was extracted with CH$_2$Cl$_2$ (2×500 ml). The combined organic layer was evaporated and the residue was purified on silica gel chromatography. The desired product 218f was eluted with Methanol/CH$_2$Cl$_2$ (0-5%). Yield: 24 g.

Synthesis of compound 219f: The above solid 218f (24 g) was dissolved in DMF (200 ml) and acetic anhydride (6 ml) was added. The solution was stirred for 24 hours. Water (500 ml) was added and the mixture was extracted with dichloromethane (500 ml). The organic layer was evaporated and the residue was purified on silica gel chromatography. The desired product 219f was eluted with Methanol/CH$_2$Cl$_2$ (0-5%). Yield: 21 g.

Synthesis of compound 220f: The above compound 219f (21 g), bis-(N,N-diisopropylamino)-2-cyanoethylphosphite (14 g), and N,N-diisopropylammonium tetrazolide (7 g) were stirred at room temperature overnight. The solution was partitioned against aqueous NaHCO$_3$ and dried over MgSO$_4$. The solvent was evaporated in vacuo and the residue was purified by silica gel chromatography (1:1 EtOAc/hexane) to yield 22 g of product as a foam. $^1$H NMR (500 MHz, Acetonitrile-d3) δ 9.15 (s, 1H), 8.46 (dd, J=45.6, 7.5 Hz, 1H), 7.95 (d, J=7.6 Hz, 2H), 7.63 (t, J=7.5 Hz, 1H), 7.57-7.41 (m, 5H), 7.41-7.31 (m, 6H), 7.28 (m, 1H), 7.04 (d, J=15.8 Hz, 1H), 6.90 (t, J=7.9 Hz, 4H), 5.90 (d, J=7.8 Hz, 1H), 4.51 (m, 1H), 4.20 (dd, J=10.6, 8.1 Hz, 1H), 4.04 (dd, J=31.3, 4.6 Hz, 1H), 3.91-3.81 (m, 2H), 3.79 (d, J=3.1 Hz, 6H), 3.74 (m, 2H), 3.69-3.41 (m, 6H), 2.67-2.59 (m, 1H), 2.54-2.48 (m, 1H), 1.58 (m, 2H), 1.36 (m, 2H), 1.25 (d, J=4.7 Hz, 26H), 1.21-1.09 (m, 10H), 1.04 (d, J=6.8 Hz, 3H), 0.87 (t, J=6.8 Hz, 3H). $^{31}$P NMR (202 MHz, Acetonitrile-d3) δ 151.10, 150.19.

Example 2: Synthesis of Nucleoside Phosphoramidites Used as Precursors to Introduce Lipophilic Conjugates Post Oligonucleotide Synthesis

Scheme 5

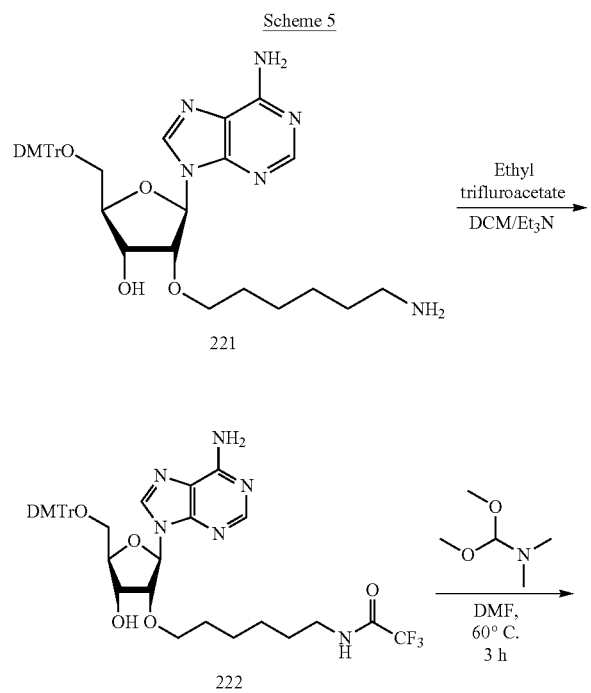

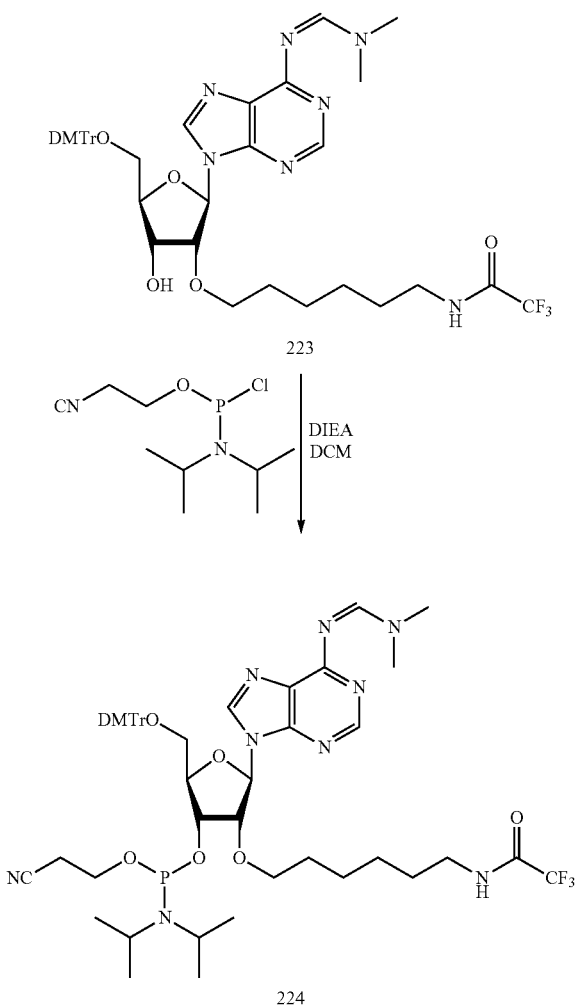

Compound 222: Compound 221 (6 g, 8.98 mmol) was added to a reaction flask and dissolved in DCM. The reaction was stirred and trimethylamine (4.89 ml, 35.92 mmol) was added via syringe. Ethyl trifluoracetate (3.19 g, 22.45 mmol) was added dropwise to the reaction. The reaction was checked by TLC (5% MeOH/DCM), developed using phosphomolybdic acid, and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off, and the mother liquor was concentrated, and put on high vacuum to yield (4.96 g 72%) of 222. $^1$H NMR (400 MHz, DMSO-d6) δ 9.36 (s, 1H), 8.26 (s, 1H), 8.09 (s, 1H), 7.41-7.33 (m, 2H), 7.31 (s, 2H), 7.24 (m, 6.8 Hz, 7H), 6.88-6.79 (m, 4H), 6.01 (d, J=5.0 Hz, 1H), 5.18 (d, J=6.0 Hz, 1H), 4.57 (t, J=5.0 Hz, 1H), 4.38 (m, 1H), 4.07 (m, 1H), 3.73 (s, 6H), 3.58 (m, 1H), 3.43 (m, 1H), 3.24 (d, J=4.7 Hz, 2H), 3.12 (m, 2H), 1.41 (m, 4H), 1.18 (d, J=5.5 Hz, 4H). Mass calculation for C39H43F3N6O7: 764.80, found: 765.3 (M+H).

Compound 223: Compound 222 (4.96 g, 6.49 mmol) was added into a reaction flask. The starting material was dissolved in dimethylformamide, and N,N-dimethylformamide dimethyl acetal (4.31 ml, 32.45 mmol) was added via syringe. The reaction was heated to 60° C. in an oil bath for 3 hours. The reaction was checked by TLC (5% MeOH/DCM), concentrated under reduced pressure, and dried on high vacuum overnight. The residue was purified by flash chromatography on silica gel (0% to 10% MeOH/DCM), and the product fractions were combined and concentrated on reduced pressure to yield (5.21 g, 98%) of 223. $^1$H NMR (400 MHz, DMSO-d6) δ 9.35 (t, J=5.5 Hz, 1H), 8.91 (s, 1H), 8.37 (d, J=4.8 Hz, 2H), 7.41-7.33 (m, 2H), 7.31-7.16 (m, 7H), 6.89-6.78 (m, 4H), 6.07 (d, J=5.1 Hz, 1H), 5.20 (d, J=6.0 Hz, 1H), 4.61 (t, J=5.1 Hz, 1H), 4.39 (m, 1H), 4.09 (m, 1H), 3.73 (d, J=1.3 Hz, 6H), 3.58 (m, 1H), 3.43 (m, 1H), 3.25 (d, J=4.7 Hz, 2H), 3.20 (s, 3H), 3.13 (s, 3H), 3.10 (m, 2H), 1.41 (m, 4H), 1.17 (m, 4H). Mass calculation for C42H48F3N7O7: 819.88, found: 820.4 (M+H).

Compound 224: Compound 223 (5.21 g, 6.36 mmol) was added to a reaction flask, evacuated, and purged with argon. The starting material was dissolved in dichloromethane and diisopropylethylamine (2.21 ml, 12.72 mmol) was added via syringe. 2-cyanoethyl N,N-diisopropylchlorophosphoramidite (2.12 ml, 9.54 mmol) was added and the reaction stirred at room temperature for 1 hour. The reaction was checked by TLC (100% EtOAc) and the reaction was concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (10% to 100% EtOAc/hexane), and the product fractions were combined and concentrated on reduced pressure to yield (5.02 g, 77%) of 224. $^1$H NMR (400 MHz, Acetonitrile-d3) δ 8.89 (d, J=1.9 Hz, 1H), 8.35 (d, J=8.3 Hz, 1H), 8.10 (d, J=9.2 Hz, 1H), 7.57 (s, 1H), 7.42 (m, 2H), 7.34-7.15 (m, 7H), 6.81 (m, 4H), 6.09-6.01 (m, 1H), 4.83-4.62 (m, 2H), 4.28 (m, J=16.1, 4.2 Hz, 1H), 4.15-3.98 (m, 1H), 3.94-3.77 (m, 2H), 3.75 (d, J=2.6 Hz, 6H), 3.69-3.55 (m, 4H), 3.55-3.37 (m, 3H), 3.30 (m, 1H), 3.16 (d, J=9.9 Hz, 7H), 2.75 (t, J=6.0 Hz, 1H), 2.72-2.63 (m, 1H), 2.50 (s, 1H), 1.47 (m, 2H), 1.38 (s, 1H), 1.27-1.11 (m, 19H), 1.08 (d, J=6.7 Hz, 4H). $^{31}$P NMR (202 MHz, Acetonitrile-d3) δ 151.08, 150.72 $^{19}$F NMR (376 MHz, Acetonitrile-d3) δ −77.04 (d, J=2.7 Hz).

Scheme 6

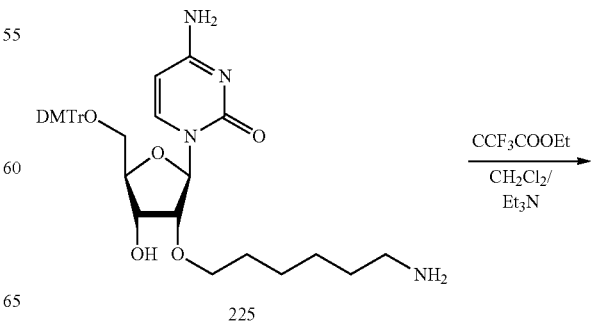

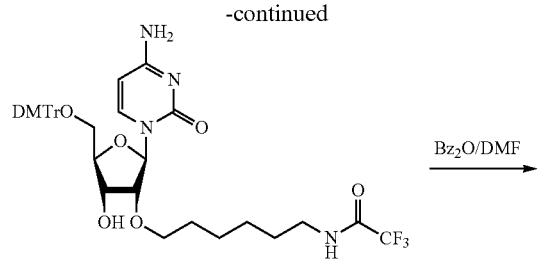

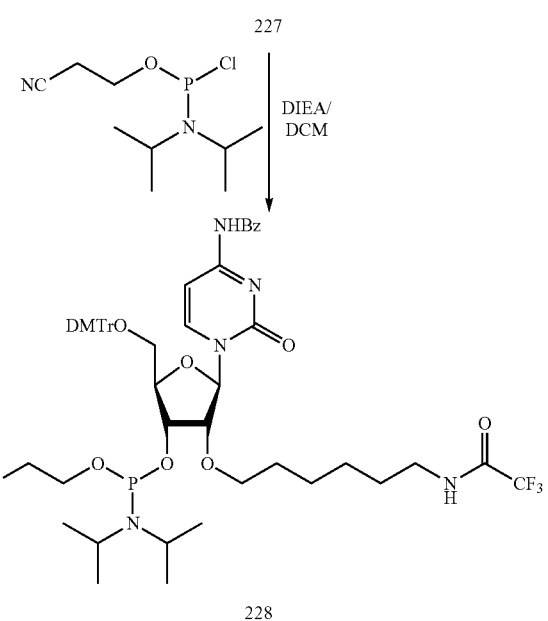

Compound 226: Compound 225 (6 g, 9.31 mmol) was added to a reaction flask. The starting material was dissolved in dichloromethane and trimethylamine (5.08 ml, 37.24 mmol) was added via syringe. Ethyl trifluoracetate (3.31 g, 23.28 mmol) was added dropwise to the reaction. The reaction was checked by TLC (100% ethyl acetate), developed using phosphomolybdic acid, and concentrated under reduced pressure. The residue was dissolved in dichloromethane, added to separation funnel, and the organic layer was washed with saturated sodium bicarbonate solution. The organic layer was separated and washed with a brine solution. The organic layer was then separated and dried with sodium sulfate. The solid was filtered off and the mother liquor was concentrated. The residue was purified by flash chromatography on silica gel (10% to 100% EtOAc/hexane), and the product fractions were combined and concentrated on reduced pressure to yield (4.22 g, 61.2%) of 226. $^1$H NMR (400 MHz, DMSO-d6) δ 9.40 (t, J=5.5 Hz, 1H), 7.79 (d, J=7.5 Hz, 1H), 7.43-7.37 (m, 2H), 7.33 (t, J=7.5 Hz, 2H), 7.30-7.23 (m, 5H), 7.18 (d, J=16.4 Hz, 2H), 6.95-6.86 (m, 4H), 5.82 (d, J=2.6 Hz, 1H), 5.50 (d, J=7.5 Hz, 1H), 5.01 (d, J=7.0 Hz, 1H), 4.17 (m, 1H), 3.96 (dd, J=7.2, 3.4 Hz, 1H), 3.75 (s, 6H), 3.73 (dd, J=5.0, 2.6 Hz, 1H), 3.62 (m, 2H), 3.27 (d, J=3.4 Hz, 2H), 3.17 (m, 2H), 1.50 (m, 4H), 1.29 (m, 4H). Mass calculation for C38H43F3N4O8: 740.78, found: 739.2 (M−H).

Compound 227: Compound 226 (4.22 g, 5.7 mmol) was added to a reaction flask. The starting material was dissolved in dimethylformamide and benzoic anhydride (1.42 g, 6.27 mmol) was added. The reaction was stirred at room temperature overnight. The reaction was checked by TLC (5% MeOH/DCM), developed using phosphomolybdic acid, and concentrated under reduced pressure. The residue was dissolved in dichloromethane, added to separation funnel, and the organic layer was washed with saturated sodium bicarbonate solution. The organic layer was separated and washed with a brine solution. The organic layer was separated and dried with sodium sulfate. The solid was filtered off and the mother liquor was concentrated. The residue was purified by flash chromatography on silica gel (0% to 10% MeOH/DCM) and the product fractions were combined and concentrated on reduced pressure to yield (3.41 g, 71%) of 227. $^1$H NMR (400 MHz, DMSO-d6) δ 11.29 (s, 1H), 9.40 (t, J=5.4 Hz, 1H), 8.41 (d, J=7.5 Hz, 1H), 8.04-7.93 (m, 2H), 7.68-7.59 (m, 1H), 7.52 (dd, J=8.3, 7.0 Hz, 2H), 7.45-7.39 (m, 2H), 7.35 (t, J=7.7 Hz, 2H), 7.29 (dd, J=7.8, 5.4 Hz, 5H), 7.16 (d, J=7.5 Hz, 1H), 6.98-6.89 (m, 4H), 5.84 (d, J=1.4 Hz, 1H), 5.11 (d, J=7.3 Hz, 1H), 4.29 (m, 1H), 4.06 (m, 1H), 3.89-3.82 (m, 1H), 3.77 (s, 7H), 3.72-3.61 (m, 1H), 3.38 (m, 2H), 3.18 (m, 2H), 1.53 (m, 4H), 1.33 (m, 4H). Mass calculation for C45H47F3N4O9: 844.89, found: 843.3 (M−H).

Compound 228: Compound 227 (3.41 g, 4.04 mmol) was added to a reaction flask, evacuated, and purged with argon. The starting material was dissolved in dichloromethane, and diisopropylethylamine (1.4 ml, 8.08 mmol) was added via syringe. 2-cyanoethyl N,N-diisopropylchlorophosphoramidite (1.35 ml, 6.06 mmol) was added and the reaction stirred at room temperature for 1 hour. The reaction was checked by TLC (2/1 EtOAc/hexane) and concentrated under reduced pressure. The residue was dissolved in dichloromethane, added to separation funnel, and the organic layer was washed with saturated sodium bicarbonate solution. The organic layer was separated and washed with a brine solution. The organic layer was separated and dried with sodium sulfate. The solid was then filtered off and the mother liquor was concentrated. The residue was purified by flash chromatography on silica gel (10% to 100% EtOAc/hexane) and the product fractions were combined and concentrated on reduced pressure to yield (3.81 g, 90.3%) of 228. $^1$H NMR (400 MHz, Acetonitrile-d3) δ 9.15 (s, 1H), 8.48 (dd, J=35.8, 7.5 Hz, 1H), 7.98-7.90 (m, 2H), 7.62 (m, 2H), 7.56-7.42 (m, 5H), 7.41-7.23 (m, 8H), 7.04 (s, 1H), 6.94-6.85 (m, 4H), 5.90 (dd, J=6.4, 1.2 Hz, 1H), 4.52 (m, 1H), 4.24-3.97 (m, 4H), 3.92-3.81 (m, 2H), 3.81-3.77 (m, 6H), 3.77-3.66 (m, 3H), 3.66-3.41 (m, 6H), 3.25 (m, 2H), 2.75 (t, J=5.9 Hz, 1H), 2.64 (m, 1H), 2.56 (s, 1H), 2.50 (d, J=1.8 Hz, OH), 2.16 (s, 2H), 1.97 (s, OH), 1.56 (m, 5H), 1.37 (m, 5H), 1.29-1.09 (m, 16H), 1.03 (d, J=6.8 Hz, 4H). $^{31}$P NMR (202 MHz, Acetonitrile-d3) δ 151.16, 150.18. $^{19}$F NMR (376 MHz, Acetonitrile-d3) δ −77.04 (d, J=2.7 Hz).

Scheme 7

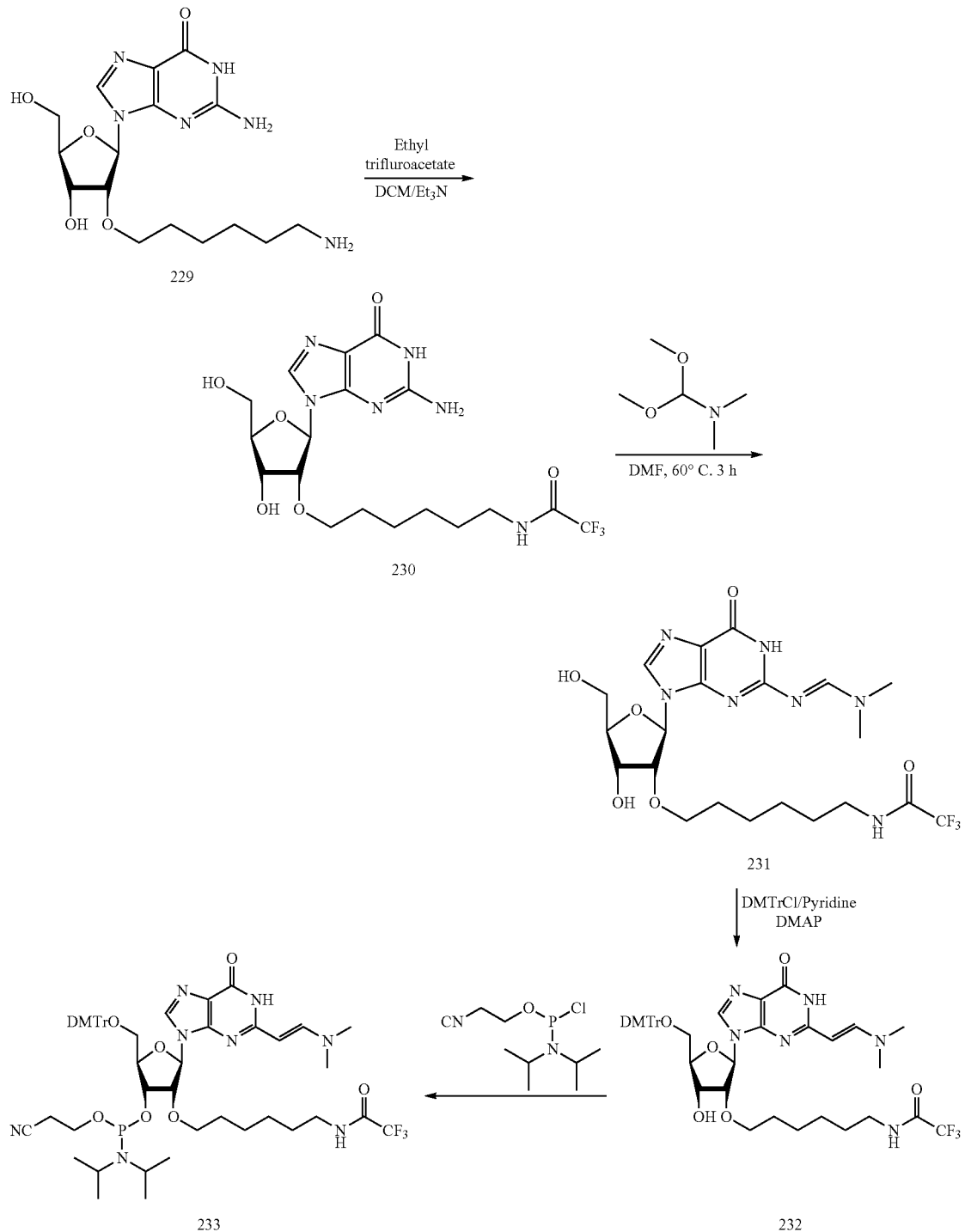

Compound 230: Compound 229 (2.5 g, 6.54 mmol) was added to a reaction flask, dissolved in minimal water, and diluted with methanol. The reaction was cooled to 0° C., and trimethylamine (14.27 ml, 104.64 mmol) was added via syringe. Ethyl trifluoracetate (9.3 g, 65.4 mmol) was added, the pH was monitored and adjusted to ~pH 9, and the reaction was stirred for 3 days. The reaction was checked by TLC (15% MeOH/DCM), developed using Hessian stain, and concentrated under reduced pressure. The residue was purified by reverse phase prep-HPLC, using a method of 5% to 35% ACN/H2O over 45 minutes. The product eluted around 25 minutes. The product fractions were combined, concentrated on reduced pressure, and lyophilized to yield (0.661 g, 21.1%) of 230. $^1$H NMR (400 MHz, DMSO-d6) δ 10.64 (s, 1H), 9.36 (t, J=5.8 Hz, 1H), 7.96 (s, 1H), 6.45 (s, 2H), 5.77 (d, J=6.4 Hz, 1H), 5.14-5.04 (m, 2H), 4.23 (m, 2H), 3.88 (m, 1H), 3.53 (m, 2H), 3.34 (m, 3H), 3.10 (m, 2H), 1.39 (m, 4H), 1.16 (m, 4H). Mass calculation for C18H25F3N6O6: 478.43, found: 479.2 (M+H).

Compound 231: Compound 230 (0.65 g, 1.36 mmol) was added into a reaction flask. The starting material was dissolved in dimethylformamide, and N,N-dimethylformamide dimethyl acetal (0.903 ml, 6.8 mmol) was added via syringe. The reaction was heated to 60° C. in an oil bath for 2.5 hours. The reaction was checked by TLC (7% MeOH/DCM), concentrated under reduced pressure, and dried on high vacuum overnight. The residue was purified by flash chromatography on silica gel (0% to 10% MeOH/DCM) and the product fractions were combined and concentrated on reduced pressure to yield (0.504 g, 69.5%) of 231. $^1$H NMR (400 MHz, DMSO-d6) δ 11.37 (s, 1H), 9.36 (t, J=5.8 Hz, 1H), 8.52 (s, 1H), 8.08 (s, 1H), 5.87 (d, J=6.1 Hz, 1H), 5.15 (d, J=5.0 Hz, 1H), 5.07 (t, J=5.5 Hz, 1H), 4.35-4.20 (m, 2H), 3.91 (m, 1H), 3.68-3.49 (m, 3H), 3.37 (m, 1H), 3.14 (s, 3H), 3.10 (m, 2H), 3.02 (s, 3H), 1.39 (m, 4H), 1.16 (dd, J=8.7, 5.0 Hz, 4H). Mass calculation for C21H30F3N7O6: 533.51, found: 534.3 (M+H).

Compound 232: Compound 231 (0.5 g, 0.938 mmol) and 5 ml of anhydrous pyridine were added to a reaction flask. Pyridine was stripped off under reduced pressure. This was repeated for three times and reaction mixture was dried under high vacuum overnight. The next day, 4-(dimethylamino)pyridine (0.011 g, 0.094 mmol) and anhydrous pyridine were added to the reaction flask. The reaction was cooled to 0° C. using an ice bath. The reaction flask was evacuated and purged with argon. 4,4'-dimethoxytrityl chloride (0.352 g, 1.04 mmol) was dissolved in anhydrous pyridine and the resulting solution was added via syringe to the reaction flask. The reaction was allowed to reach to room temperature and was stirred overnight. The reaction was checked by TLC (5% MeOH/DCM) and developed using Hanessian stain. Methanol was added to quench the reaction and the reaction mixture was concentrated under reduced pressure. The residue was dissolved in dichloromethane, added to separation funnel, and the organic layer was washed with saturated sodium bicarbonate. The organic layer was separated and washed with a brine solution. The organic layer was separated and dried with sodium sulfate. The solid was filtered off and the mother liquor was concentrated. The residue was purified by flash chromatography on silica gel (0% to 10% MeOH/DCM) and the product fractions were combined and concentrated on reduced pressure to yield (0.621 g, 79%) of 232. $^1$H NMR (400 MHz, DMSO-d6) δ 11.40 (s, 1H), 9.37 (t, J=5.7 Hz, 1H), 8.48 (s, 1H), 7.93 (s, 1H), 7.39-7.31 (m, 2H), 7.30-7.16 (m, 7H), 6.88-6.78 (m, 4H), 5.92 (d, J=5.0 Hz, 1H), 5.19 (d, J=5.7 Hz, 1H), 4.30 (m, 2H), 4.01 (m, 1H), 3.72 (s, 6H), 3.57 (m, 1H), 3.45 (m, 1H), 3.25 (dd, J=10.5, 6.0 Hz, 1H), 3.17-3.10 (m, 2H), 3.09 (d, J=5.5 Hz, 4H), 3.01 (s, 3H), 1.41 (m, 4H), 1.19 (d, J=6.5 Hz, 3H). Mass calculation for C42H48F3N7O8: 835.88, found: 836.4 (M+H).

Compound 233: Compound 232 (1.20 g, 1.44 mmol) was added to a reaction flask, evacuated, and purged with argon. The starting material was dissolved in dichloromethane, and diisopropylethylamine (0.5 ml, 2.88 mmol) was added via syringe. 2-cyanoethyl N,N-diisopropylchlorophosphoramidite (0.385 ml, 1.73 mmol) was added and the reaction was stirred at room temperature for 3 hours. The reaction was checked by TLC (100% EtOAc) and concentrated under reduced pressure. The residue was dissolved in dichloromethane, added to separation funnel, and the organic layer was washed with saturated sodium bicarbonate. The organic layer was separated and washed with a brine solution. The organic layer was then separated and dried with sodium sulfate. The solid was filtered off and the mother liquor was concentrated. The residue was purified by flash chromatography on silica gel (10% to 100% EtOAc/hexane) and the product fractions were combined and concentrated on reduced pressure to yield (1.21 g, 81.2%) of 233. $^1$H NMR (400 MHz, Acetonitrile-d3) δ 9.36 (s, 1H), 8.49 (s, 1H), 7.73 (d, J=10.7 Hz, 1H), 7.64 (d, J=13.4 Hz, 1H), 7.47-7.37 (m, 2H), 7.35-7.16 (m, 7H), 6.83 (m, 4H), 5.97 (dd, J=5.4, 2.5 Hz, 1H), 4.61-4.44 (m, 2H), 4.30-4.18 (m, 1H), 4.15-3.98 (m, 2H), 3.76 (d, J=3.2 Hz, 6H), 3.71-3.55 (m, 4H), 3.55-3.41 (m, 2H), 3.38-3.28 (m, 2H), 3.18 (m, 2H), 3.08-3.01 (m, 5H), 2.75 (t, J=5.9 Hz, 1H), 2.65 (m, 1H), 2.46 (s, 1H), 1.52-1.34 (m, 4H), 1.27-1.11 (m, 18H), 1.03 (d, J=6.8 Hz, 4H). $^{31}$P NMR (202 MHz, Acetonitrile-d3) δ 150.95. $^{19}$F NMR (376 MHz, Acetonitrile-d3) δ −77.04.

Scheme 8

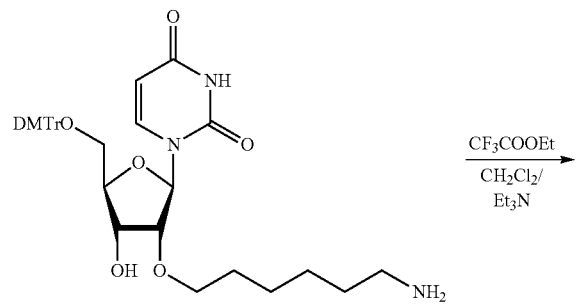

234

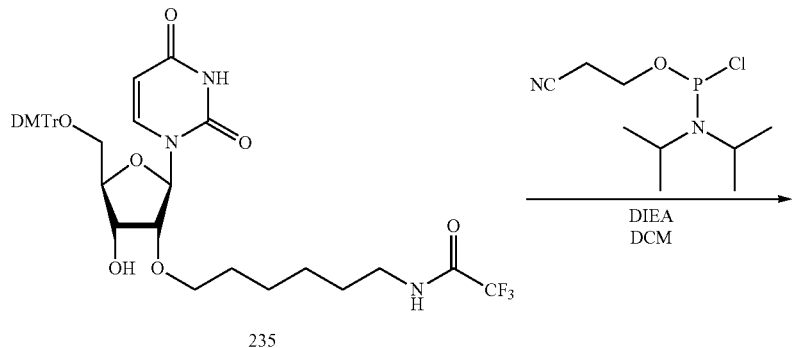

235

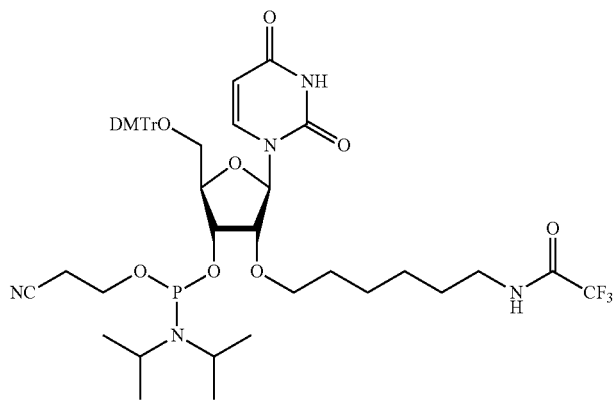

236

Compound 235: Compound 234 (5 g, 7.75 mmol) was added to a reaction flask. The starting material was dissolved in dichloromethane, and trimethylamine (4.23 ml, 31 mmol) was added via syringe. Ethyl trifluoracetate (2.75 g, 19.38 mmol) was added dropwise to the reaction. The reaction was checked by TLC (5% MeOH/DCM), developed using phosphomolybdic acid, and concentrated under reduced pressure. The residue was dissolved in dichloromethane, added to separation funnel, and the organic layer was washed with saturated sodium bicarbonate. The organic layer was separated and washed with a brine solution. The organic layer was then separated and dried with sodium sulfate. The solid was filtered off and the mother liquor was concentrated and put on high vacuum to yield (4.32 g 75%) of 235. $^1$H NMR (500 MHz, DMSO-d6) δ 11.36 (d, J=2.6 Hz, 2H), 9.36 (s, 1H), 7.71 (d, J=8.1 Hz, 2H), 7.36 (d, J=8.4 Hz, 4H), 7.31 (t, J=7.6 Hz, 4H), 7.27-7.20 (m, 10H), 6.89 (d, J=8.5 Hz, 8H), 5.78 (d, J=3.6 Hz, 2H), 5.27 (dd, J=8.1, 2.1 Hz, 2H), 5.10 (dd, J=6.7, 2.7 Hz, 2H), 4.16 (m, 2H), 3.95 (m, 2H), 3.88 (m, 2H), 3.73 (s, 13H), 3.55 (m, 4H), 3.36 (m, 1H), 3.28 (d, J=4.4 Hz, 1H), 3.22 (dd, J=10.9, 2.8 Hz, 2H), 3.14 (m, 3H), 2.11 (s, 2H), 1.48 (m, 8H), 1.36-1.19 (m, 8H). Mass calculation for C38H42F3N3O9: 741.76, found: 740.2 (M−H).

Compound 236: Compound 235 (4.3 g, 5.8 mmol) was added to a reaction flask, evacuated, and purged with argon. The starting material was dissolved in dichloromethane, and diisopropylethylamine (2.02 ml, 11.6 mmol) was added via syringe. 2-cyanoethyl N,N-diisopropylchlorophosphoramidite (1.93 ml, 8.7 mmol) was added and the reaction was stirred at room temperature for 1 to 2 hours. The reaction was checked by TLC (75% EtOAc/hexane) and concentrated under reduced pressure. The residue was dissolved in ethyl acetate, added to separation funnel, and the organic layer was washed with saturated sodium bicarbonate. The organic layer was separated and washed with a brine solution. The organic layer was then separated and dried with sodium sulfate. The solid was filtered off and the mother liquor was concentrated. The residue was purified by flash chromatography on silica gel (10% to 100% EtOAc/hexane) and the product fractions were combined and concentrated on reduced pressure to yield (4.62 g, 85%) of 236. $^1$H NMR (400 MHz, Acetonitrile-d3) δ 9.06 (s, 1H), 7.74 (d, J=8.1 Hz, 1H), 7.49-7.39 (m, 2H), 7.39-7.21 (m, 7H), 6.93-6.83 (m, 4H), 5.84 (dd, J=7.0, 3.2 Hz, 1H), 5.21 (m, 1H), 4.45 (m, 1H), 4.20-3.97 (m, 3H), 3.91-3.79 (m, 1H), 3.77 (d, J=2.4 Hz, 7H), 3.63 (m, 4H), 3.48-3.31 (m, 3H), 3.23 (m, 1H), 2.67 (m, 1H), 2.52 (t, J=6.0 Hz, 1H), 2.08 (d, J=1.9 Hz, 1H), 1.64-1.45 (m, 4H), 1.42-1.28 (m, 4H), 1.27-1.09 (m, 9H), 1.05 (d, J=6.7 Hz, 3H). $^{31}$P NMR (162 MHz, Acetonitrile-d3) δ 149.53, 149.06. $^{19}$F NMR (376 MHz, Acetonitrile-d3) δ −83.43, −83.89 (d, J=2.4 Hz).

Example 3: Post-Synthetic Conjugation of Ligands (e.g., Lipophilic Moities) to siRNA
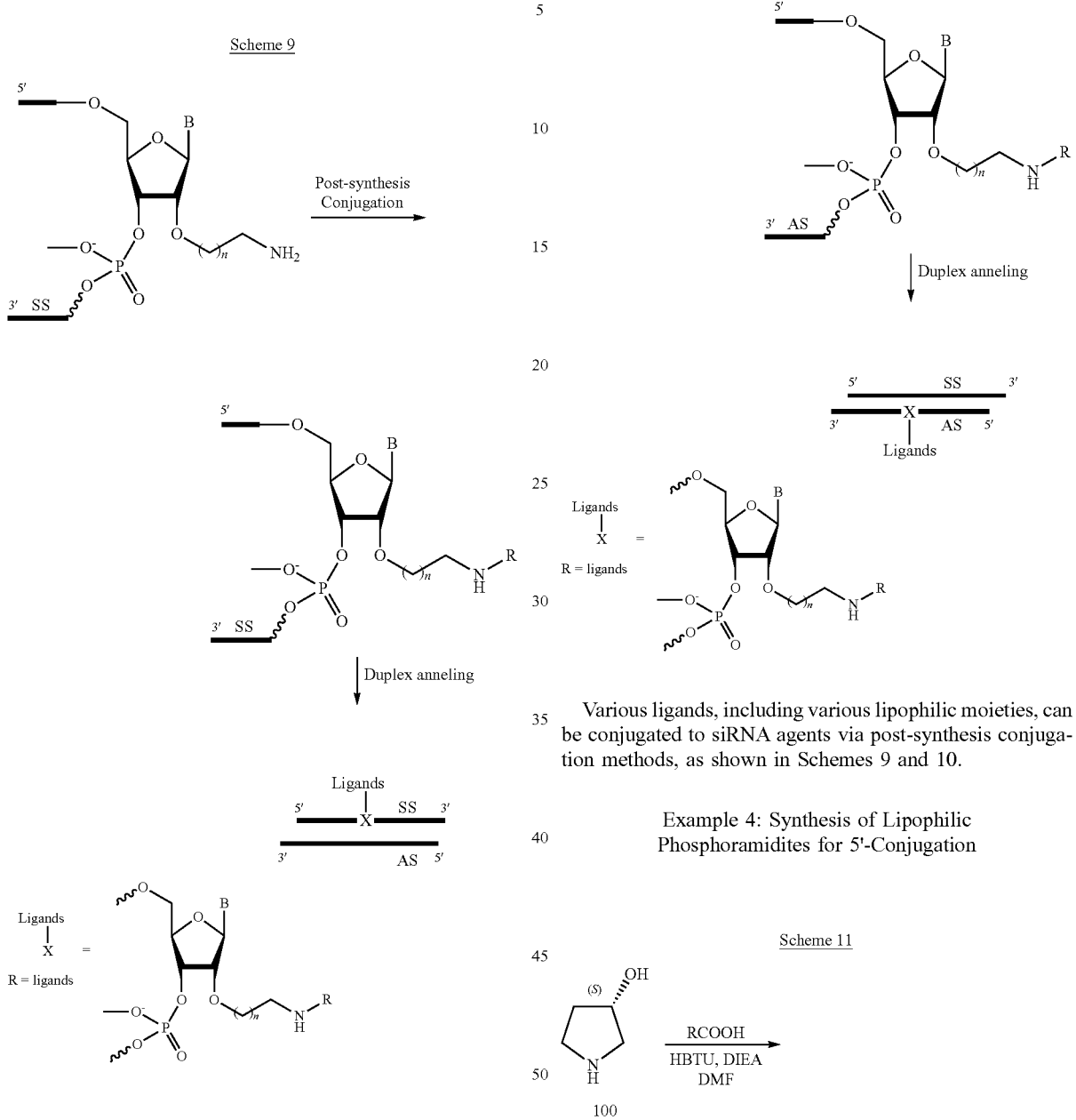
Various ligands, including various lipophilic moieties, can be conjugated to siRNA agents via post-synthesis conjugation methods, as shown in Schemes 9 and 10.
Example 4: Synthesis of Lipophilic Phosphoramidites for 5'-Conjugation
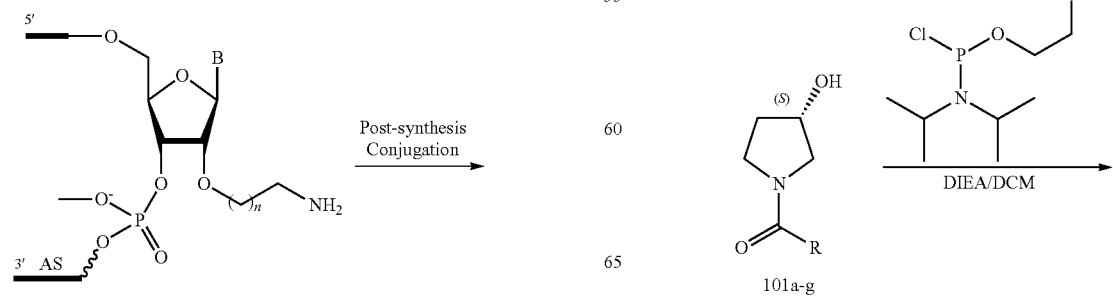

211

-continued

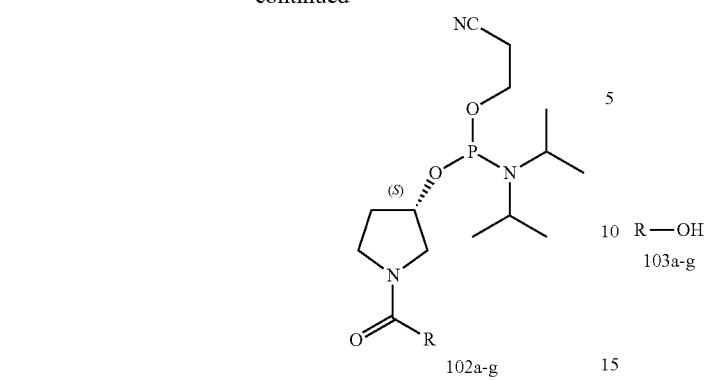

102a-g

R = $C_6H_{13}$, $C_8H_{17}$, $C_{10}H_{21}$, $C_{12}H_{25}$, $C_{14}H_{29}$, $C_{16}H_{33}$ and $C_{18}H_{35}$ Compound 101a-g: Compound 100 (1 g) was treated with alkyl carboxylic acids under peptide coupling conditions. Alkyl carboxylic acids were taken in dichloromethane and treated with HBTU and DIEA for few minutes. Amine was added to the reaction mixture and stirred for 2 hours. The reaction was monitored by TLC, washed with aqueous bicarbonate solution and brine. The organic layer was dried over sodium sulfate and the crude product was purified by silica gel chromatography to obtain compounds 101a-g. The phosphoramidites of these molecules were made by treating it with amidite reagent in presence of DIEA as illustrated in Example 1 (Scheme 4) to generate compound 102a-g.

212

Scheme 12

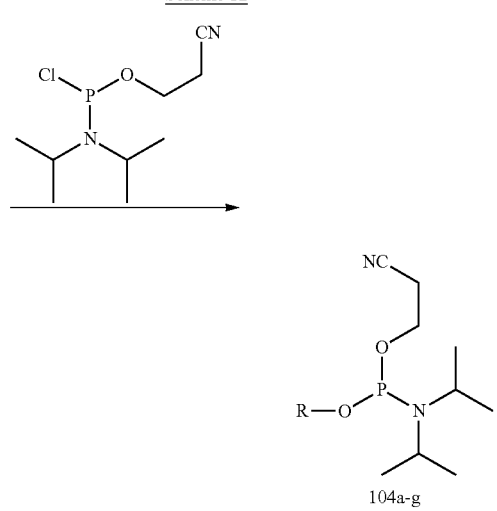

104a-g

R = $C_6H_{13}$, $C_8H_{17}$, $C_{10}H_{21}$, $C_{12}H_{25}$, $C_{14}H_{29}$, $C_{16}H_{33}$ and $C_{18}H_{35}$ As shown in Scheme 12, the phosphoramidites were prepared by treating the alcohol with phosphoramidite reagent as illustrated in Example 1 to generate compound 104a-g:

Example 5: Synthesis of Thiocholesterol Amidite and CPG

Scheme 13. Synthesis of 4-hydroxy-L-prolinol-thiocholesterol phosphoramidite

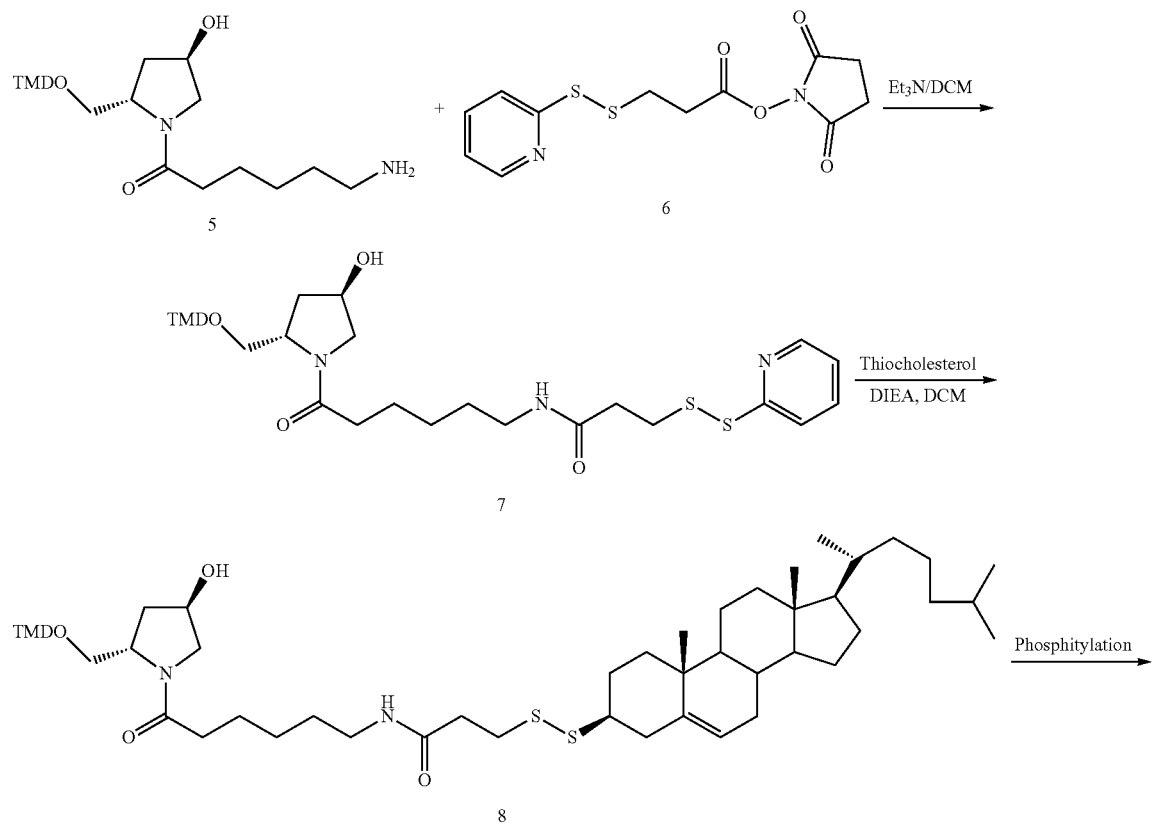

-continued

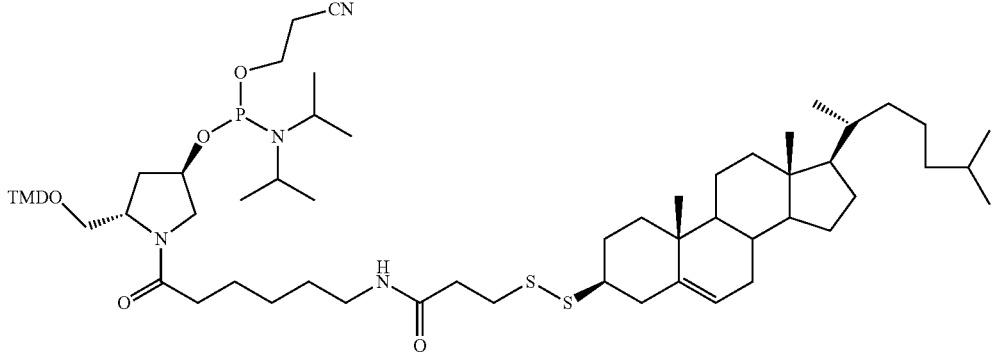

9

N-(6-{2-[Bis-(4-methoxy-phenyl)-phenyl-methoxymethyl]-4-hydroxy-pyrrolidin-1-yl}-6-oxo-hexyl)-3-(pyridin-2-yldisulfanyl)-propionamide (7)

As shown in Scheme 13, amine 5 (7.7 g, 14.5 mmol) was dissolved in anhydrous dichloromethane (40 mL) and cooled to 0° C. To the solution were added triethylamine (3.0 g, 4.2 mL, 30 mmol) and 3-(Pyridin-2-yldisulfanyl)-propionic succinate ester 6 (SPDP) (4.5 g, 14.4 mmol) successively. The reaction temperature was brought to ambient temperature and stirred further for 16 hours. The completion of the reaction was ascertained by TLC (10% MeOH/CHCl$_3$, R$_f$=0.6). The reaction mixture was diluted with dichloromethane and washed with saturated NaHCO$_3$, water, and followed by brine. The organic layer was dried over sodium sulfate, filtered, and concentrated under vacuum to afford the crude product. Compound 7 (10.58 g, 78%) was obtained as a white foamy solid after column chromatography over silica gel. $^1$H NMR (400 MHz, DMSO-d$_6$): δ 8.45 (d, 1H), 7.9 (m, 1H), 7.8 (m, 1H), 7.76 (m, 1H), 7.3 (m, 4H), 7.18 (m, 5H), 6.86 (m, 4H), 4.98 (d, —OH, 1H), 4.38 (m, 1H), 4.1 (m, 1H) (s, 6H), 3.56 (m, 1H), 3.46 (m, 1H), 3.21-3.34 (m, 3H), 3.14 (m, 1H), 3 (m, 2H), 2.48 (m, 2H), 2.2 (m, 2H), 1.8-2.02 (m, 2H), 1.1-1.5 (4H). $^{13}$C NMR (100 MHz, DMSO-d$_6$): δ.171.32, 169.97, 159.36, 158.31, 158.18, 149.80, 145.27, 138.08, 136.1, 135.9, 129.8, 128.0, 127.7, 121.4, 119.3, 113.3, 85.338, 68.7, 55.3, 34.75, 34.28, 29.1, 26.3, 24.36.

4-Hydroxy-L-prolinol-thiocholesterol-DMT-Alcohol (8)

Compound 7 (7.5 g, 10.28 mmol) was dissolved in anhydrous dichloromethane (75 mL) under argon and cooled to 0° C. To this solution diisopropylethyl amine (2.71 g, 3.66 mL, 21 mmol) was added, followed by addition of thiocholesterol (4.145 g, 10.28 mmol). The reaction mixture was brought to ambient temperature and stirred further for 16 hours. The completion of the reaction was ascertained by TLC (100% ethyl acetate, R$_f$=0.6). The reaction mixture was concentrated under reduced pressure and the residue was subjected to column chromatography on silica gel. After eluting with 4 L of ethyl acetate, the column was eluted with 5% MeOH/dichloromethane (2 L) to obtain compound 8 as white foamy solid (8 g, 76%). $^1$H NMR (400 MHz, DMSO-d$_6$): δ 7.88 (m, 1H), 7.3 (m, 4H), 7.17 (m, 5H), 6.84 (m, 4H), 5.3 (bs, 1H), 4.89 (d, —OH), 4.38 (m, 1H), 4.1 (m, 1H), 3.72 (s, 6H), 3.56 (m, 1H), 3.32 (m, 1H), 3.14 (m, 1H), 3 (m, 3H), 2.84 (m, 2H), 2.64 (m, 1H), 2.42 (m, 2H), 2.2 (m, 3H), 1.8-2.0 (m, 7H), 0.8-1.54 (m, 35H), 0.62 (s, 3H). $^{13}$C NMR (100 MHz, DMSO-d$_6$): δ 170.8, 158.0, 157.9, 155.6, 145.0, 139.7, 135.8, 135.7, 129.5, 127.7, 127.5, 121.7, 113.1, 113.0, 85.7, 85.1, 72.7, 68.5, 63.3, 60.72, 56.1, 55.5, 55.28, 54.9, 49.4, 41.8, 36.5, 35.2, 31.3, 30.35, 27.7, 27.3, 26.0, 24.1, 23.8, 23.2, 22.6, 22.3, 21.11, 20.5, 19.43, 18.9, 18.5, 14.4, 11.6.

4-hydroxy-L-prolinol-thiocholesterol phosphoramidite (9)

Compound 8 (5.7 g, 5.58 mmol) was coevaporated with anhydrous toluene (50 mL). To the residue N,N-tetraisopropylammonium tetrazolide (0.315 g, 2.79 mmol) was added and the mixture was dried over P$_2$O$_5$ in a vacuum oven for overnight at 40° C. The reaction mixture was dissolved in dichloromethane (20 mL), and 2-cyanoethyl-N,N,N',N'-tetraisopropylphosphoramidite (2.48 g, 2.72 mL, 8.25 mmol) was added. The reaction mixture was stirred at ambient temperature for overnight. The completion of the reaction was ascertained by TLC (R$_f$=0.9 in ethyl acetate). The reaction mixture was diluted with dichloromethane (50 mL) and washed with 5% NaHCO$_3$ (50 mL) and brine (50 mL). The organic layer was dried over anhydrous Na$_2$SO$_4$, filtered, and concentrated under reduced pressure. The residue was purified over silica gel (50:49:1, EtOAc:hexane:triethlyamine) to afford 9 as white foamy solid (6.1 g, 89%). $^1$H NMR (400 MHz, C$_6$D$_6$): δ 7.62 (m, 2H), 7.45 (m, 5H), 7.24 (m, 2H), 7.1 (m, 1H), 6.82 (m, 4H), 5.64 (m, 1H), 5.38 (m, 1H), 4.7 (m, 1H), 4.54 (m, 2H), 3.78 (m, 2H), 3.5 (m, 3H), 3.36 (m, 9H), 3.22 (m, 4H), 3.06 (m, 3H), 2.72 (m, 1H), 2.32-2.54 (m, 5H), 1.8-2.2 (m, 10H), 1.08-1.74 (m, 28H), 1.3 (m, 6H), 0.94 (m, 12H), 0.67 (s, 3H). $^{31}$P NMR (161.82 MHz, C$_6$D$_6$): δ 146.05, 145.91, 145.66, 145.16 $^{13}$C NMR (100 MHz, C$_6$D$_6$): δ 171.43, 171.25, 169.87, 159.25, 159.11, 146.08, 141.59, 136.66, 136.6, 130.62, 130.54, 128.63, 127.53, 127.02, 121.53, 117.73, 117.57, 113.66, 113.57, 86.59, 86.54, 64.36, 58.56, 58.37, 58.30, 56.96, 56.51, 56.07, 54.86, 54.77, 50.57, 50.27, 43.48, 43.35, 42.55, 40.13, 39.9, 39.75, 39.56, 38.70, 36.94, 36.64, 36.29, 36.19, 35.90, 34.58, 32.24, 32.08, 29.48, 29.03, 28.98, 28.6, 28.38, 26.54, 24.68, 24.61, 24.54, 23.6, 23.0, 22.74, 21.26, 20.03, 19.9, 19.38, 19.01, 12.06.

Scheme 14. Synthesis of polymer support immobilized with thiocholesterol

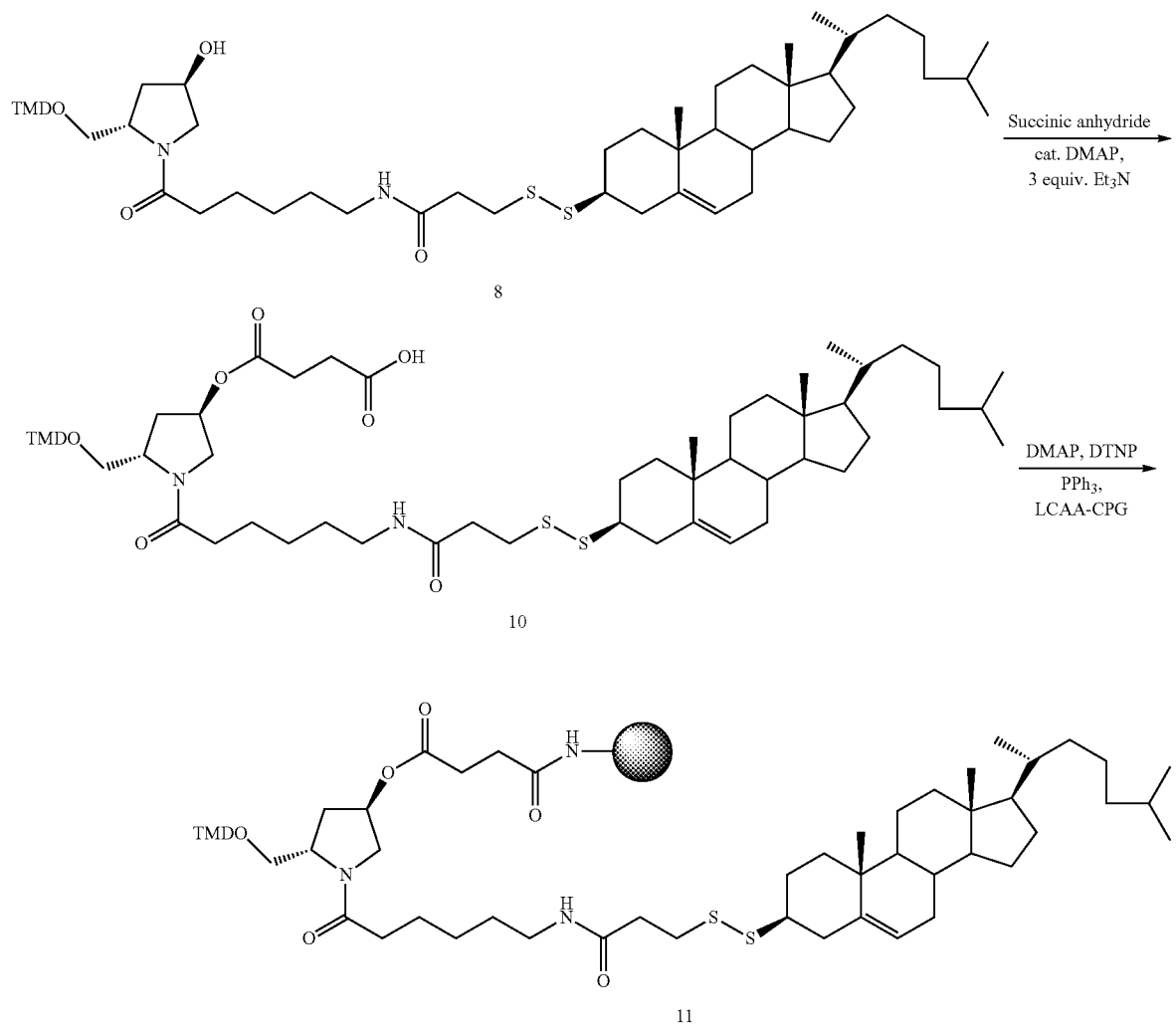

4-Hydroxy-L-prolinol-thiocholesterol-succinate (10)

As shown in Scheme 14, Compound 8 (2.2 g, 2.15 mmol) was mixed with succinic anhydride (0.323 g, 3.23 mmol) and DMAP (0.026 g, 0.215 mmol), and dried under vacuum at 40° C. overnight. The mixture was dissolved in anhydrous dichloromethane (10 mL). Then triethylamine (0.708 g, 0.976 mL, 7 mmol) was added and the solution was stirred at room temperature under argon atmosphere for 16 hours. It was then diluted with dichloromethane (50 mL) and washed with ice cold aqueous citric acid (5% wt., 25 mL) and water (2×25 mL). The organic phase was dried over anhydrous sodium sulfate and concentrated to dryness. The crude product was purified by flash silica gel column chromatography to afford compound 10 as white foamy solid (2.2 g, 92% yield; $R_f$=0.6 s in 10% MeOH/CHCl$_3$). $^1$H NMR (400 MHz, DMSO-d$_6$): δ 12.22 (bs, 1H), 7.84 (m, 1H), 7.25 (m, 4H), 7.2 (m, 5H), 6.86 (m, 4H), 5.36 (m, 2H), 4.18 (bs, 1H), 3.72 (s, 6H), 3.4-3.6 (m, 2H), 3.2 (m, 1H), 3.0 (m, 4H), 2.84 (m, 2H), 2.64 (m, 2H), 2.4-2.52 (m, 12H), 2.2 (m, 6H), 1.9 (m, 8H), 0.8-1.52 (m, 28H), 0.65 (s, 3H). $^{13}$C NMR (100 MHz, DMSO-d$_6$): δ 173.35, 171.94, 170.63, 169.64, 157.99, 144.96, 141.02, 135.72, 129.61, 127.81, 127.55, 113.12, 56.15, 54.99, 52.28, 49.58, 49.06, 41.82, 36.17, 34.97, 33.41, 33.09, 31.32, 27.39, 23.16, 22.68, 22.39, 20.56, 18.95, 18.54, 11.66, 6.02, 5.0

Solid Support with Immobilized Thiocholesterol (11)

Succinate 10 (2.1 g, 1.9 mmol) was dissolved in dichloroethane (8 mL). To that solution DMAP (0.228 g, 1.9 mmol) was added. 2,2'-dithio-bis(5-nitropyridine) (0.58 g, 1.9 mmol) in acetonitrile/dichloroethane (3:1, 8 mL) was added successively. To the resulting solution triphenylphosphine (0.49 g, 1.9 mmol) in acetonitrile (4 ml) was added. The reaction mixture turned bright orange in color. The solution was agitated briefly using wrist-action shaker (5 mins). Long chain alkyl amine-CPG (LCAA-CPG) (12 g, 1860 μmoles, 155 μm/g) was added. The suspension was agitated for 4 hours. The CPG was filtered through a sintered funnel and washed with acetonitrile, dichloromethane, and ether successively. Unreacted amino groups were masked using acetic anhydride/pyridine. The loading capacity of the CPG 11 was measured by taking UV measurement. (57 μM/g).

Example 6: Synthesis of 2'-O Lipophilic Conjugates by Click Chemistry

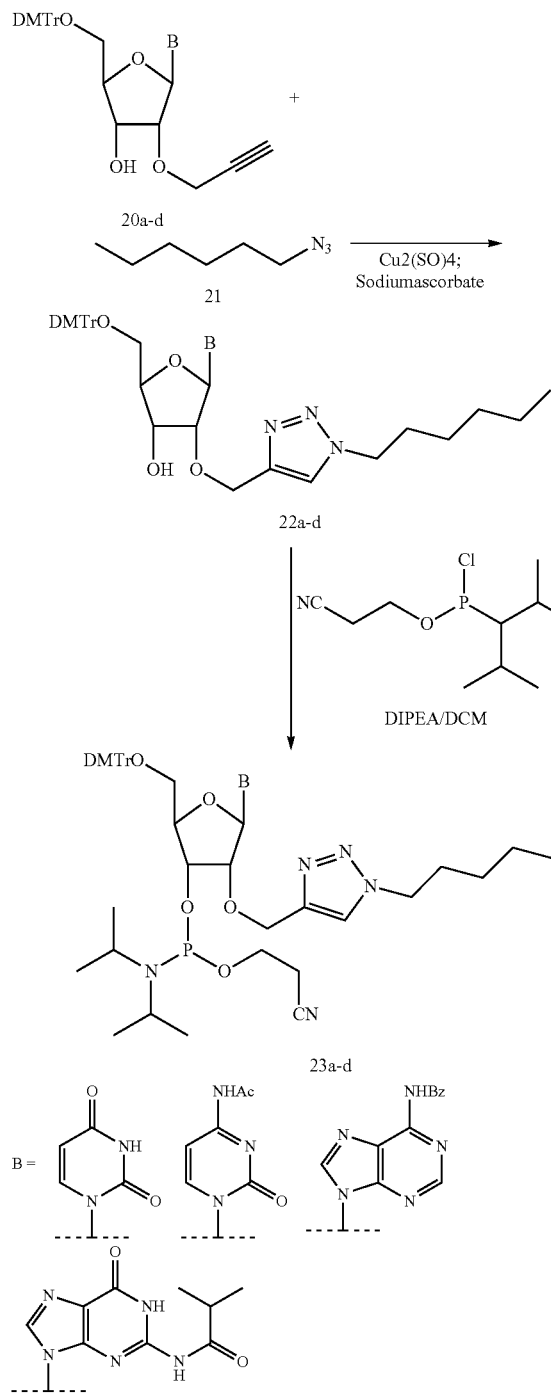

Synthesis of compound 22a: The commercially available propargyl U 20a (5.8 g, 10 mmol) was dissolved in THF (40 mL), and tert-butanol (40 mL) was added followed by copper sulfate (1 g). To this mixture an aqueous solution of sodium ascorbate was added followed by hexyl azide. The mixture was stirred at room temperature overnight. The TLC of the reaction showed the completion the next day and the reaction was concentrated in a rotary evaporator. The residue was dissolved in dichloromethane (100 mL) and the solution was filtered through celite and the filtrate after concentration and column purification provided the pure product 22a (6.99 g, 96%) as a white solid.

Synthesis of compound 22b: Using a similar procedure used for U, propargyl C 20b (6.2 g, 10 mmol) was converted to the corresponding click product 22b (5.9 g, 78%) as a white solid.

Synthesis of compound 22c: Using a similar procedure used for U, propargyl A 20c (7.1 g, 10 mmol) was converted to the corresponding click product 22c (7.9 g, 96%) as a white solid.

Synthesis of compound 22d: Using a similar procedure described for U, propargyl G 22d (6.9 g, 10 mmol) was converted to the corresponding click product 22d (7.9 g, 96%) as a off white powder.

Synthesis of Phophoramidites 23a-d: Compounds 22a-d were treated with phosphoramidite reagent in presence of DIEA to generate 23a-d.

Example 7: Synthesis of Nucleobase Modified Conjugates (Pyrimidines)

1. Synthesis of 5-iodouridine Derivatives

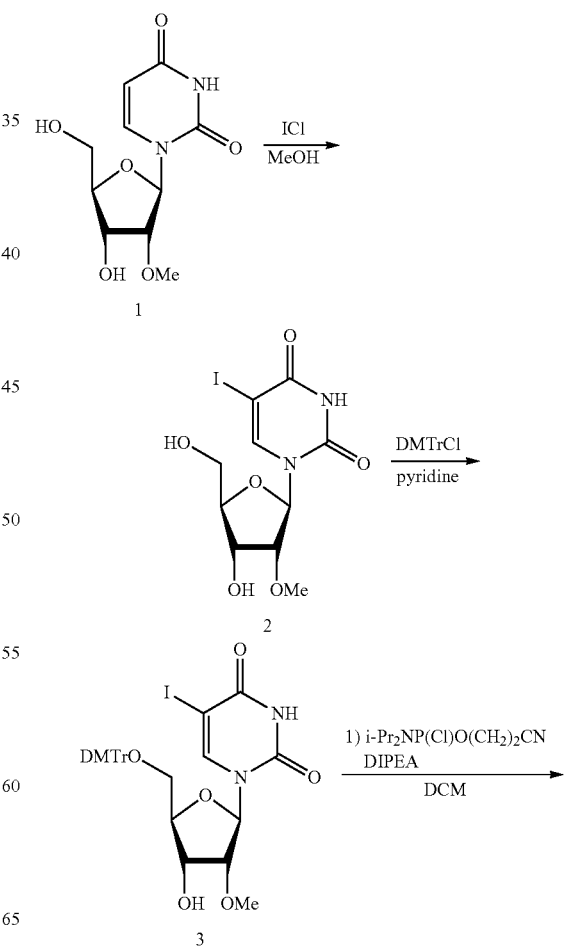

Scheme 16. Synthesis of 2'-O-methyl-5-iodouridine phosphoramidite (4)

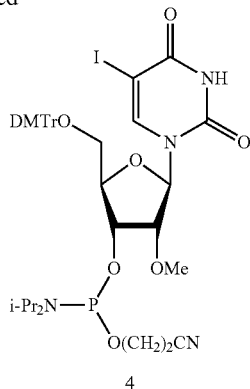

2'-O-Methyl-5-iodouridine (2)

ICl (8.6 mL, 174 mmol) was added to a solution of 2'-O-methyluridine 1 (25.0 g, 96.8 mmol) in MeOH (400 mL) at room temperature. The reaction mixture was refluxed for 15 hours. The resulting mixture was concentrated in vacuo. DCM (200 mL) was added to the obtained crude residue (58.1 g), then the precipitation was collected by filtration and washed with DCM to obtain compound 2 (36.7 g, 99%) as a white powder. $^1$H NMR (400 MHz, DMSO-$d_6$) δ: 3.31 (s, 2H), 3.37 (s, 3H), 3.53-3.59 (m, 1H), 3.67-3.72 (m, 1H), 3.78 (t, J=4.5 Hz, 1H), 3.85 (qu, J=3.0 Hz, 1H), 4.10 (q, J=6.0 Hz, 1H), 5.12 (d, J=6.0 Hz, 1H), 5.30 (t, J=6.0 Hz, 1H), 5.78 (d, J=4.0 Hz, 1H), 8.52 (s, 1H), 11.69 (s, 1H).

5'-O-(4,4'-Dimethoxytrityl)-2'-O-methyl-5-iodouridine (3)

Under Ar atmosphere, DMTrCl (33.9 g, 100 mmol) was added to a solution of compound 3 (36.6 g, 95.3 mmol) in anhydrous pyridine (400 mL) at 0° C. The reaction mixture was stirred at room temperature for 14 hours. Then, the reaction was quenched with MeOH and diluted with EtOAc. The organic layer was washed with water and brine, dried over Na$_2$SO$_4$, and concentrated in vacuo. The crude residue (108 g) was purified by column chromatography (0-50% EtOAc in n-hexane) to give compound 3 (53.4 g, 82%) as a white foam. v$^1$H NMR (400 MHz, DMSO-$d_6$) δ: 3.17 (dd, J=3.0, 10.5 Hz, 1H), 3.17 (dd, J=5.0, 10.5 Hz, 1H), 3.39 (s, 3H), 3.73 (s, 6H), 3.91-3.97 (m, 2H), 4.15 (q, J=6.5 Hz, 1H), 5.19 (d, J=6.5 Hz, 1H), 5.78 (d, J=4.0 Hz, 1H), 6.87-7.41 (m, 13H), 7.99 (s, 1H), 11.77 (s, 1H).

3'-O-[2-Cyanoethoxy(diisopropylamino)phosphino]-5'-O-(4,4'-dimethoxytrityl)-2'-O-methyl-5-iodouridine (4)

Under Ar atmosphere, DIPEA (1.2 mL, 7.30 mmol) and i-Pr$_2$NP(Cl)O(CH$_2$)$_2$CN (0.39 mL, 1.75 mmol) were added to a solution of compound 3 (1.00 g, 1.46 mmol) in anhydrous DCM (15 mL) at 0° C. The reaction mixture was stirred at room temperature for 2 hours. The reaction then was quenched with sat NaHCO$_3$ and extracted with EtOAc. The combined organic layer was washed with water and brine, dried over Na$_2$SO$_4$, and concentrated in vacuo. The crude residue (1.46 g) was purified by column chromatography (60% EtOAc in n-hexane) to give compound 4 (841 mg, 65%) as a white foam.

Scheme 17.
Synthesis of 2'-deoxy-2'-(R)-fluoro-5-iodouridine phosphoramidite (8)

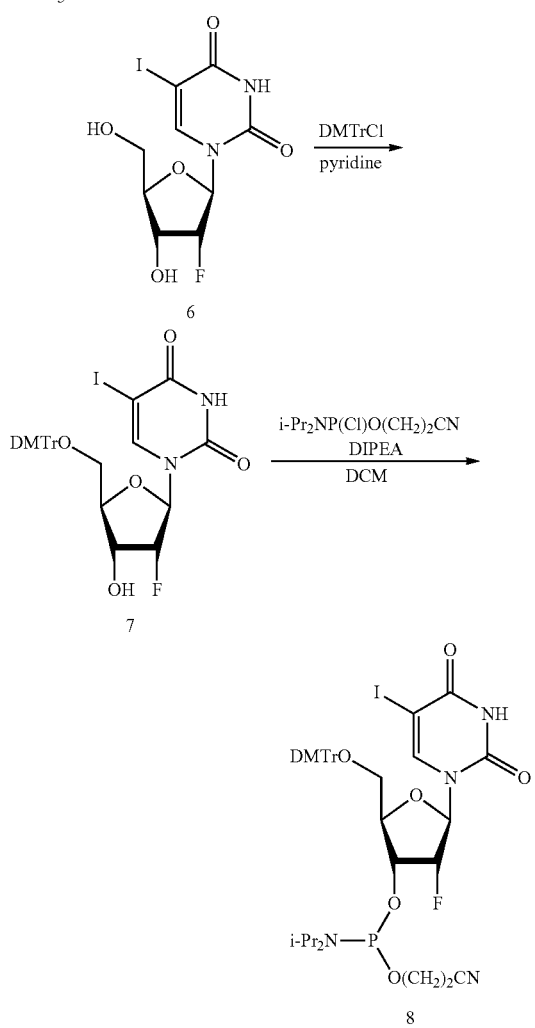

2'-Deoxy-2'-(R)-fluoro-5-iodouridine (6)

ICl (7.3 mL, 146 mmol) was added to a solution of 2'-deoxy-2'-fluorouridine 5 (20.0 g, 81.2 mmol) in MeOH (400 mL) at room temperature. The reaction mixture was refluxed for 17 hours. The resulting mixture was concentrated in vacuo. DCM (200 mL) was added to the obtained crude residue (49.1 g), then the precipitation was collected by filtration and washed with DCM to obtain compound 6 (29.6 g, 97%) as a white powder. $^1$H NMR (400 MHz, DMSO-$d_6$) δ: 3.56-3.61 (m, 1H), 3.77-3.82 (m, 1H), 3.86-3.89 (m, 1H), 4.09-4.21 (m, 1H), 5.01 (ddd, J=1.5, 5.0, 53.0 Hz, 1H), 5.37 (t, J=4.5 Hz, 1H), 5.58 (d, J=6.5 Hz, 1H), 5.84 (dd, J=1.5, 17.0 Hz, 1H), 8.51 (s, 1H), 11.71 (s, 1H).

2'-Deoxy-5'-O-(4,4'-dimethoxytrityl)-2'-(R)-fluoro-5-iodouridine (7)

Under Ar atmosphere, DMTrCl (28.1 g, 83.0 mmol) was added to a solution of compound 6 (29.4 g, 79.0 mmol) in anhydrous pyridine (400 mL) at 0° C. The reaction mixture was stirred at room temperature for 2 hours. Then, the reaction was quenched with MeOH and diluted with EtOAc. The organic layer was washed with water and brine, dried over $Na_2SO_4$, and concentrated in vacuo. The crude residue (98.8 g) was purified by column chromatography (0-50% EtOAc in n-hexane) to give compound 7 (49.5 g, 93%) as a yellow foam. $^1$H NMR (400 MHz, DMSO-$d_6$) δ: 3.20-3.25 (m, 2H), 3.72 (s, 6H), 3.97-4.01 (m, 1H), 4.26-4.36 (m, 1H), 5.16 (dd, J=4.5, 53.0 Hz, 1H), 5.60 (d, J=7.0 Hz, 1H), 5.82 (d, J=20.5 Hz, 1H), 6.85-7.41 (m, 13H), 8.06 (s, 1H), 11.81 (s, 1H); $^{13}$C NMR (100 MHz, DMSO-$d_6$) δ: 55.0, 62.4, 68.1 (d, J=13.0 Hz), 69.7, 81.3, 85.6, 89.4 (d, J=28.0 Hz), 93.3 (d, J=146 Hz), 113.2, 126.7, 127.6, 127.9, 129.7, 135.3, 135.4, 144.7, 145.0, 149.8, 158.0, 158.1, 160.6; HRMS calculated for $C_{30}H_{29}FIN_2O_7$ (MH$^+$) 675.0998.

3'-O-[2-Cyanoethoxy(diisopropylamino)phosphino]-2'-deoxy-5'-O-(4,4'-dimethoxytrityl)-2'-(R)-fluoro-5-iodouridine (8)

Under Ar atmosphere, DIPEA (1.5 mL, 8.90 mmol) and i-Pr$_2$NP(Cl)O(CH$_2$)$_2$CN (0.48 mL, 2.14 mmol) were added to a solution of compound 7 (1.20 g, 1.78 mmol) in anhydrous DCM (15 mL) at 0° C. The reaction mixture was stirred at room temperature for 2 hours. The reaction then was quenched with saturated NaHCO$_3$ and extracted with EtOAc. The combined organic layer was washed with water and brine, dried over Na$_2$SO$_4$, and concentrated in vacuo. The crude residue (1.71 g) was purified by column chromatography (60% EtOAc in n-hexane) to give compound 8 (1.29 g, 83%) as a white foam.

Scheme 18. Synthesis of LNA-5-iodouridine phosphoramidite 12

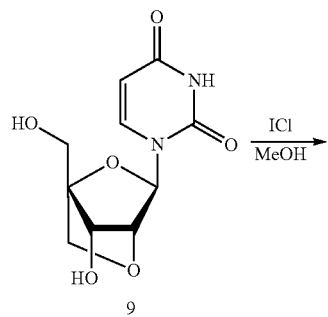

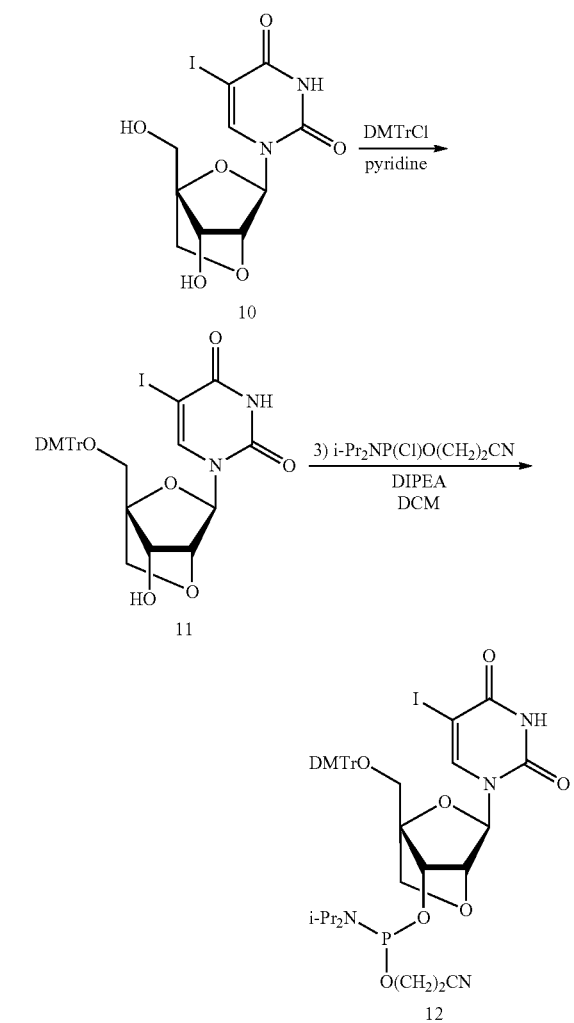

Synthesis of compound 12: Compound 12 (LNA derivative) was synthesized via a similar procedure as compound 8 in Scheme 2

2. Synthesis of 5-iodocytidine Derivatives

Scheme 19. Synthesis of 2'-O-methyl-5-iodocytidine phosphoramidite (15)

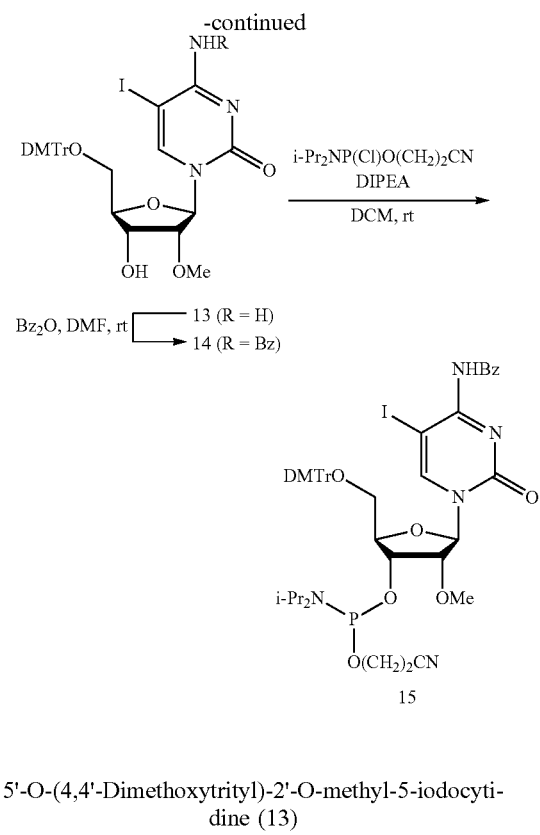

5'-O-(4,4'-Dimethoxytrityl)-2'-O-methyl-5-iodocytidine (13)

Under Ar atmosphere, Et₃N (8.1 mL, 58.2 mmol) and TMSCl (1.8 mL, 14.6 mmol) were added to a solution of 3 (5.00 g, 7.28 mmol) in anhydrous MeCN (50 mL) at 0° C. The reaction mixture was stirred at room temperature for 18 hours. The reaction mixture was then concentrated under reduced pressure. The residue was dissolved in DCM and washed with water and brine, and dried over Na₂SO₄. Evaporation of the solvent formed a foam (6.21 g), which was dissolved in anhydrous MeCN (50 mL) under Ar atmosphere. Then, Et₃N (15.3 mL, 110 mmol), 1,2,4-triazole (5.04 g, 73.0 mmol), and POCl₃ (1.3 mL, 14.6 mmol) were added to this solution at −40° C. The reaction mixture was stirred at 0° C. for 3 hours, quenched with saturated NaHCO₃, and extracted with EtOAc. The organic layer was washed with H₂O and brine, dried over Na₂SO₄, and concentrated in vacuo. Then, 28% aqueous NH3 (3.0 mL) was added to a solution of obtained crude material (6.32 g) in THE (18 mL) at room temperature. The reaction mixture was stirred at room temperature for 15 hours. The reaction mixture was dissolved in DCM. The organic layer was washed with water and brine, dried over Na₂SO₄, and concentrated in vacuo. The crude residue (6.10 g) was purified by column chromatography (0-10% MeOH in DCM) to give compound 13 (3.29 g, 66% for 3 steps) as a white foam.

N4-Benzoyl-5'-O-(4,4'-dimethoxytrityl)-2'-O-methyl-5-iodocytidine (14)

Under Ar atmosphere, Bz₂O (1.02 g, 4.49 mmol) was added to a solution of compound 13 (2.80 g, 4.08 mmol) in anhydrous DMF (10 mL) at room temperature. The reaction mixture was stirred at room temperature for 15 hours. Then, the reaction mixture was concentrated in vacuo. The crude residue (4.14 g) was purified by column chromatography (30-50% EtOAc in n-hexane) to give compound 14 (1.84 g, 57%) as a yellow foam.

N4-Benzoyl-3'-O-[2-cyanoethoxy(diisopropylamino)phosphino]-5'-O-(4,4'-dimethoxytrityl)-2'-O-methyl-5-iodocytidine (15)

Under Ar atmosphere, DIPEA (0.54 mL, 3.17 mmol) and i-Pr₂NP(Cl)O(CH₂)₂CN (0.17 mL, 0.769 mmol) were added to a solution of compound 14 (500 mg, 0.633 mmol) in anhydrous DCM (5.0 mL) at 0° C. The reaction mixture was stirred at room temperature for 3 hours. The reaction then was quenched with saturated NaHCO₃ and extracted with EtOAc. The combined organic layer was washed water and brine, dried over Na₂SO₄, and concentrated in vacuo. The crude residue (677 mg) was purified by column chromatography (20-40% EtOAc in n-hexane) to give compound 15 (400 mg, 64%) as a white foam.

Scheme 20. Synthesis of 2'-deoxy-2'-(R)-fluoro-5-iodocytidine phosphoramidite (18)

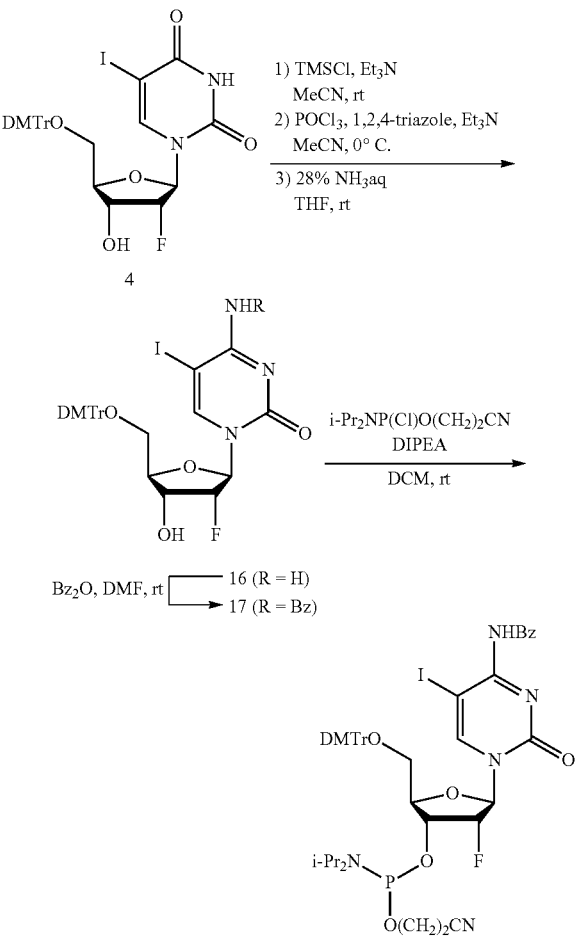

2'-Deoxy-5'-O-(4,4'-dimethoxytrityl)-2'-(R)-fluoro-5-iodocytidine (16)

Under Ar atmosphere, Et₃N (3.5 mL, 24.9 mmol) and TMSCl (0.79 mL, 6.23 mmol) were added to a solution of 7 (2.10 g, 3.11 mmol) in anhydrous MeCN (20 mL) at 0° C. The reaction mixture was stirred at room temperature for 15 hours. The reaction mixture was then concentrated under reduced pressure. The residue was dissolved in DCM, washed with water and brine, and dried over Na$_2$SO$_4$. Evaporation of the solvent formed a foam (2.50 g), which was dissolved in anhydrous MeCN (20 mL) under Ar atmosphere. Then, Et$_3$N (6.5 mL, 46.7 mmol), 1,2,4-triazole (2.15 g, 31.1 mmol) and POCl$_3$ (0.57 mL, 6.23 mmol) were added to this solution at −40° C. The reaction mixture was stirred at 0° C. for 3 hours, quenched with saturated NaHCO$_3$, and extracted with EtOAc. The organic layer was washed with H$_2$O and brine, dried over Na$_2$SO$_4$, and concentrated in vacuo. Then, 28% aqueous NH$_3$ (1.5 mL) was added to a solution of obtained crude material (2.49 g) in THF (9.0 mL) at room temperature. The reaction mixture was stirred at room temperature for 15 hours. The reaction mixture was dissolved in DCM. The organic layer was washed with water and brine, dried over Na$_2$SO$_4$, and concentrated in vacuo. The crude residue (2.88 g) was purified by column chromatography (0-10% MeOH in DCM) to give compound 16 (1.48 g, 70% for 3 steps) as a brown foam.

N4-Benzoyl-2'-deoxy-5'-O-(4,4'-dimethoxytrityl)-2'-(R)-fluoro-5-iodocytidine (17)

Under Ar atmosphere, Bz$_2$O (480 mg, 2.12 mmol) was added to a solution of compound 16 (1.30 g, 1.93 mmol) in anhydrous DMF (8.0 mL) at room temperature. The reaction mixture was stirred at room temperature for 15 hours. Then, the reaction mixture was concentrated in vacuo. The crude residue (2.00 g) was purified by column chromatography (30-50% EtOAc in n-hexane) to give compound 17 as a yellow foam (889 mg, 59%).

N4-Benzoyl-3'-O-[2-cyanoethoxy(diisopropylamino)phosphino]-2'-deoxy-5'-O-(4,4'-dimethoxytrityl)-2'-(R)-fluoro-5-iodo-cytidine (18)

Under Ar atmosphere, DIPEA (0.29 mL, 1.67 mmol) and i-Pr$_2$NP(Cl)O(CH$_2$)$_2$CN (90 µL, 0.401 mmol) were added to a solution of compound 17 (260 mg, 0.334 mmol) in anhydrous DCM (5.0 mL) at 0° C. The reaction mixture was stirred at room temperature for 3 hours. The reaction then was quenched with sat NaHCO$_3$ and extracted with EtOAc. The combined organic layer was washed water and brine, dried over Na$_2$SO$_4$, and concentrated in vacuo. The crude residue (375 mg) was purified by column chromatography (20-40% EtOAc in n-hexane) to give compound 18 (280 mg, 86%) as a white foam.

Scheme 21. Synthesis of LNA-5-iodocytidine phosphoramidite (21)

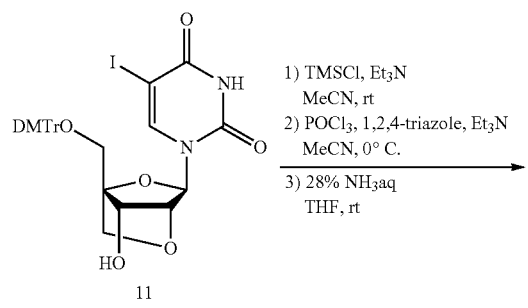

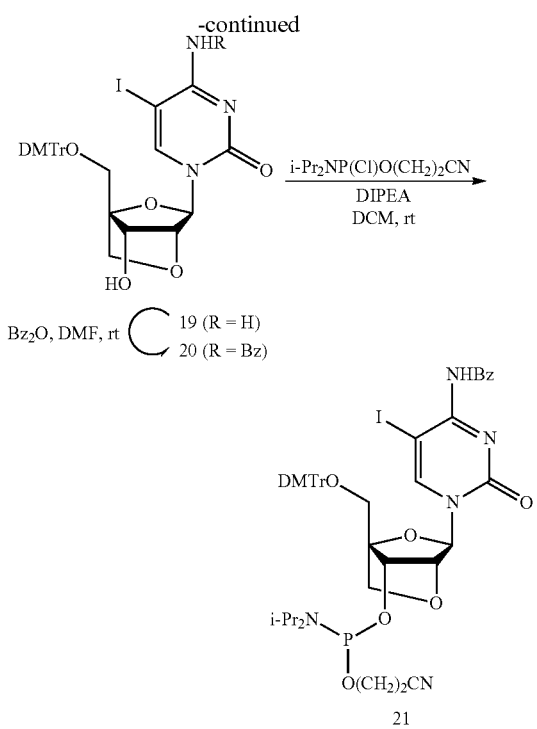

Synthesis of compound 21: Compound 21 was synthesized using a similar procedure as compound 18 in Scheme 20.

3. Synthesis of Ligand-Conjugated Boronic Acid Ester

Scheme 22

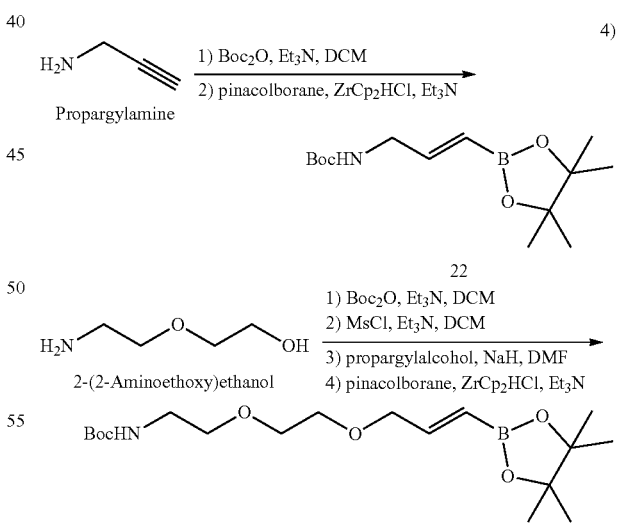

(E)-tert-Butyl 3-(4,4,5,5-tetramethyl-1,3,2-dioxaborolan-2-yl)allylcarbamate (22)

Under Ar atmosphere, propargylamine (5.0 g, 90.8 mmol) in anhydrous DCM (100 mL) was added to a solution of Et$_3$N (25.3 mL, 182 mmol) and di-tert-butyl dicarbonate (22.9 mL, 99.9 mmol) in anhydrous DCM (200 mL) at 0° C. The reaction mixture was stirred at room temperature for 3 hours. The reaction was then quenched with saturated NH$_4$Cl and diluted with EtOAc. The organic layer was washed with saturated NH$_4$Cl and brine, dried over Na$_2$SO$_4$, and concentrated in vacuo to obtain crude N-Boc-propargylamine (12.6 g) as a brown oil. Then, under Ar atmosphere, pinacol borane (17.8 mL, 123 mmol), Et$_3$N (1.1 mL, 8.18 mmol), and ZrCp$_2$HCl (2.11 g, 8.18 mmol) were added to this crude material at room temperature. The reaction mixture was refluxed for 15 hours. The reaction was then quenched with saturated NH$_4$Cl at 0° C., and this resulting mixture was diluted with EtOAc. The organic layer was washed with sat NH$_4$Cl and brine, dried over Na$_2$SO$_4$, and concentrated in vacuo. The crude residue (35.9 g) was purified by column chromatography (10-20% EtOAc in n-hexane) to give compound 22 (14.0 g, 54% for 2 steps) as a yellow oil.

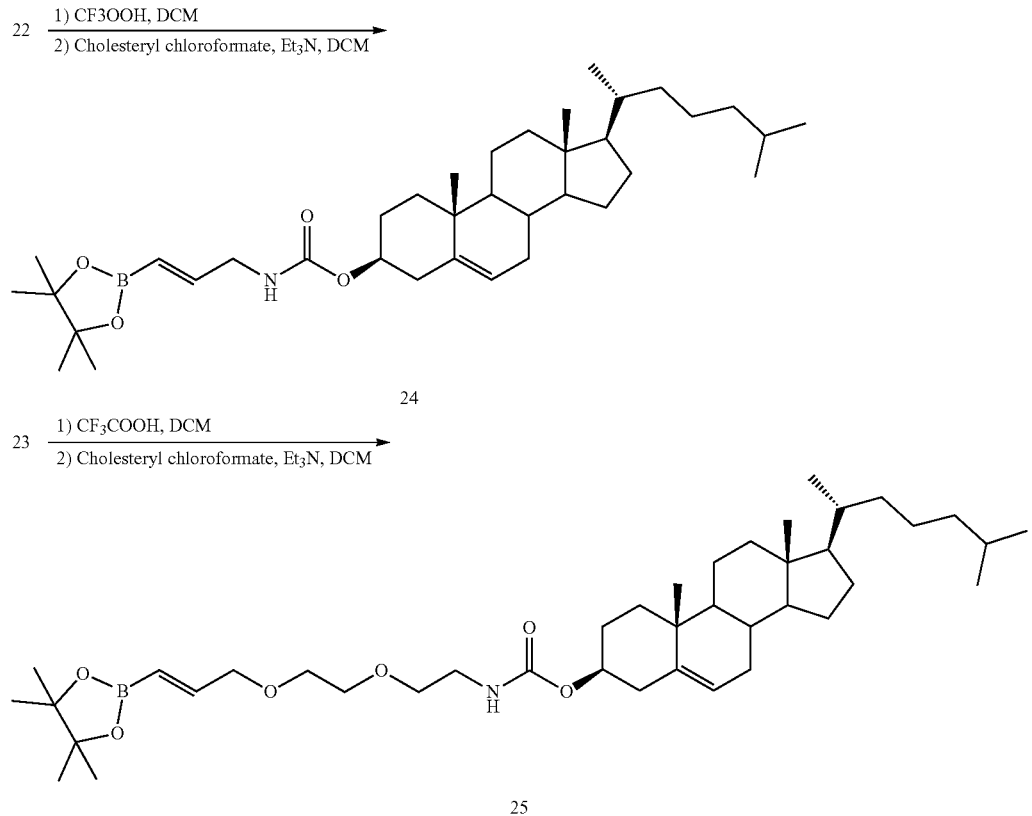

(E)-Cholesteryl 3-(4,4,5,5-tetramethyl-1,3,2-dioxaborolan-2-yl)allylcarbamate (24)

Compound 22 (2.60 g, 9.18 mmol) was dissolved in CF$_3$COOH/DCM (9:1, 100 mL) and stirred at room temperature for 3 hours. The resulting mixture was then concentrated in vacuo and remaining CF$_3$COOH was removed by coevaporation (3× toluene, 3×DCM) to obtain crude TFA ammonium salt (3.01 g) as a brown oil. Under Ar atmosphere, Et$_3$N (3.8 mL, 27.5 mmol) and cholesteryl chloroformate (4.33 g, 9.64 mmol) were added to a solution of this crude amine in anhydrous DCM (50 mL) at room temperature. The reaction mixture was stirred at room temperature for 3 hours. The reaction was then quenched with saturated NaHCO$_3$. The organic layer was washed with brine, dried over Na$_2$SO$_4$, and concentrated in vacuo. The crude residue (6.90 g) was purified by column chromatography (silica 100 g; solvent: 10-20% EtOAc in n-hexane) to give compound 24 as a white foam (4.76 g, 87% for 2 steps).

Scheme 24
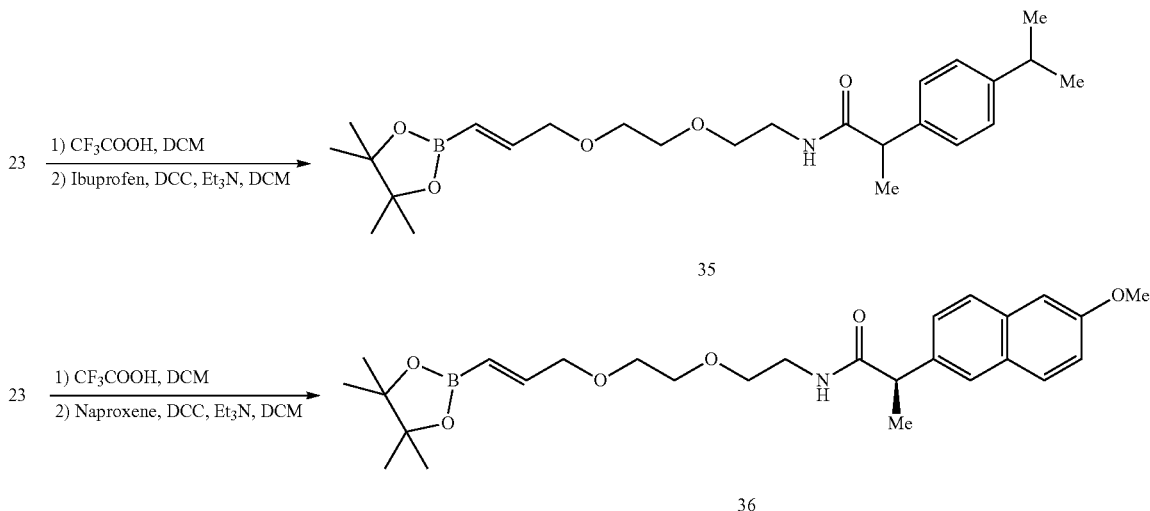
4. Conjugation by Suzuki-Miyaura Cross-Coupling
Scheme 25
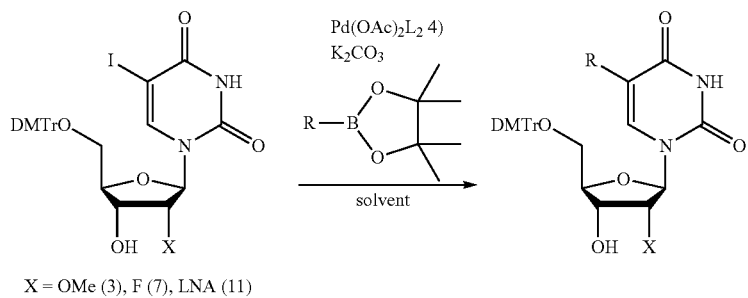
X = OMe (3), F (7), LNA (11)
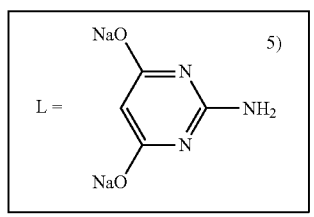
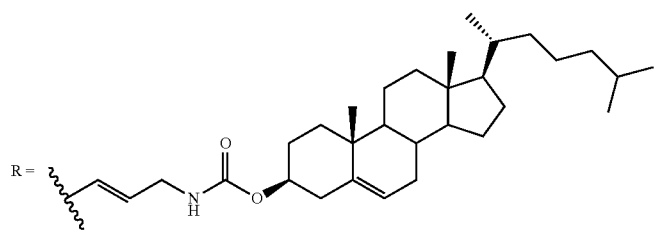
X = OMe (40), F (41), LNA (42)

-continued
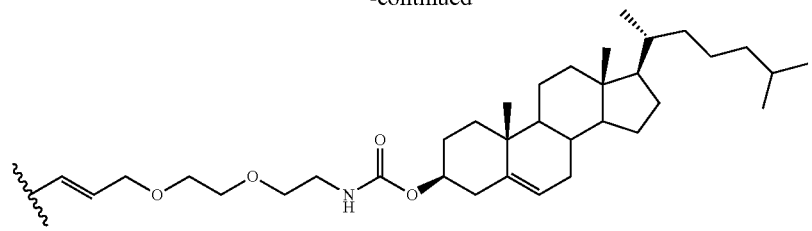
X = OMe (43), F (44), LNA (45)
Scheme 26
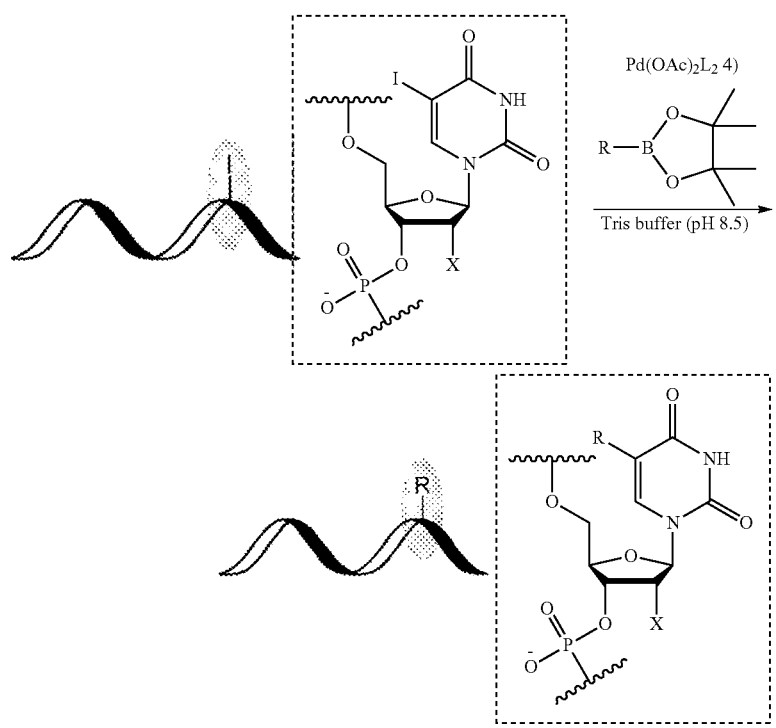
X = OMe (ON-1), F (ON-2), LNA (ON-3)
R =
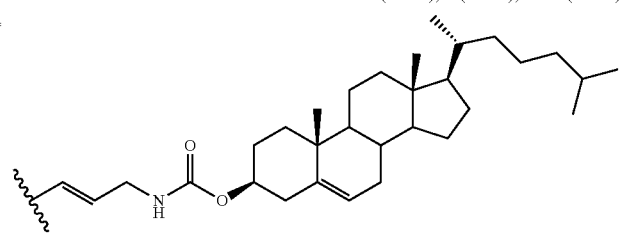
X = OMe (ON-1), F (ON-2), LNA (ON-3)
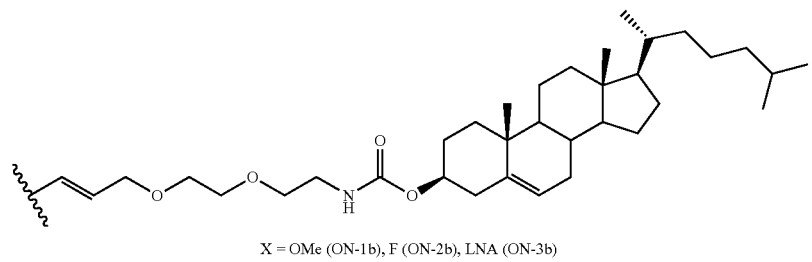
X = OMe (ON-1b), F (ON-2b), LNA (ON-3b)

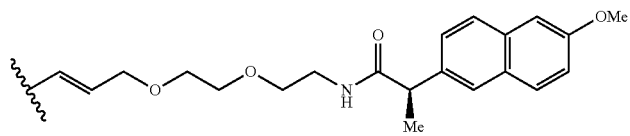

X = OMe (ON-1g), F (ON-2g), LNA (ON-3g)

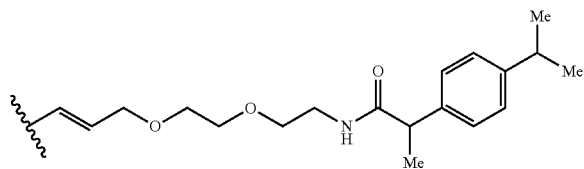

X = OMe (ON-1f), F (ON-2f), LNA (ON-3f)

As shown in Schemes 25-26, a single stranded of an oligonucleotide was conjugated to a ligand (such as a lipophilic moiety), the product was purified, followed by hybridization to complementary strands, giving siRNA conjugates.

Scheme 27. Conjugation on CPG

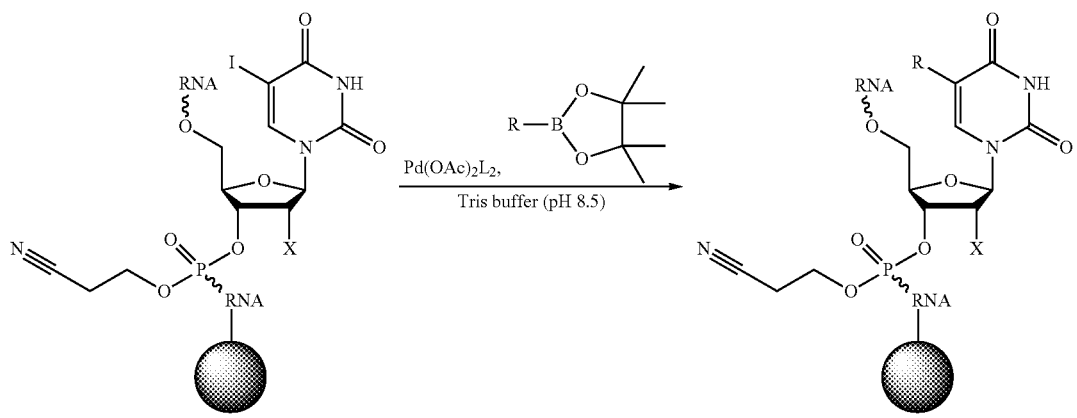

X = OMe (ON-4), F (ON-5), LNA (ON-6)

R =

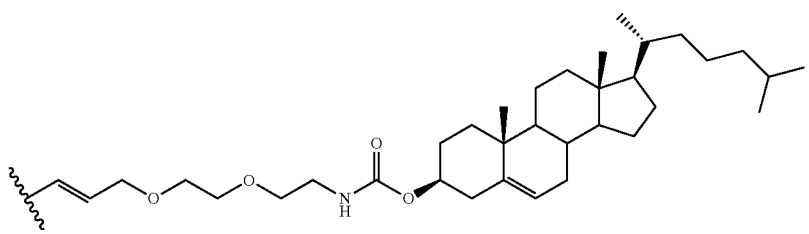

X = OMe (ON-4a), F (ON-5a), LNA (ON-6a)

Schemes 27 illustrates a procedure of conjugating a ligand (such as a lipophilic moiety) to a RNA attached to a CPG.

Example 8: Functionalized Bio-Cleavable Linkers and Phosphoramidites
Scheme 28.
Various carbohydrates
(galactose, galactosamine, glucose, glucosamine, mannose, mannosamine derivatives or pentose derivatives).
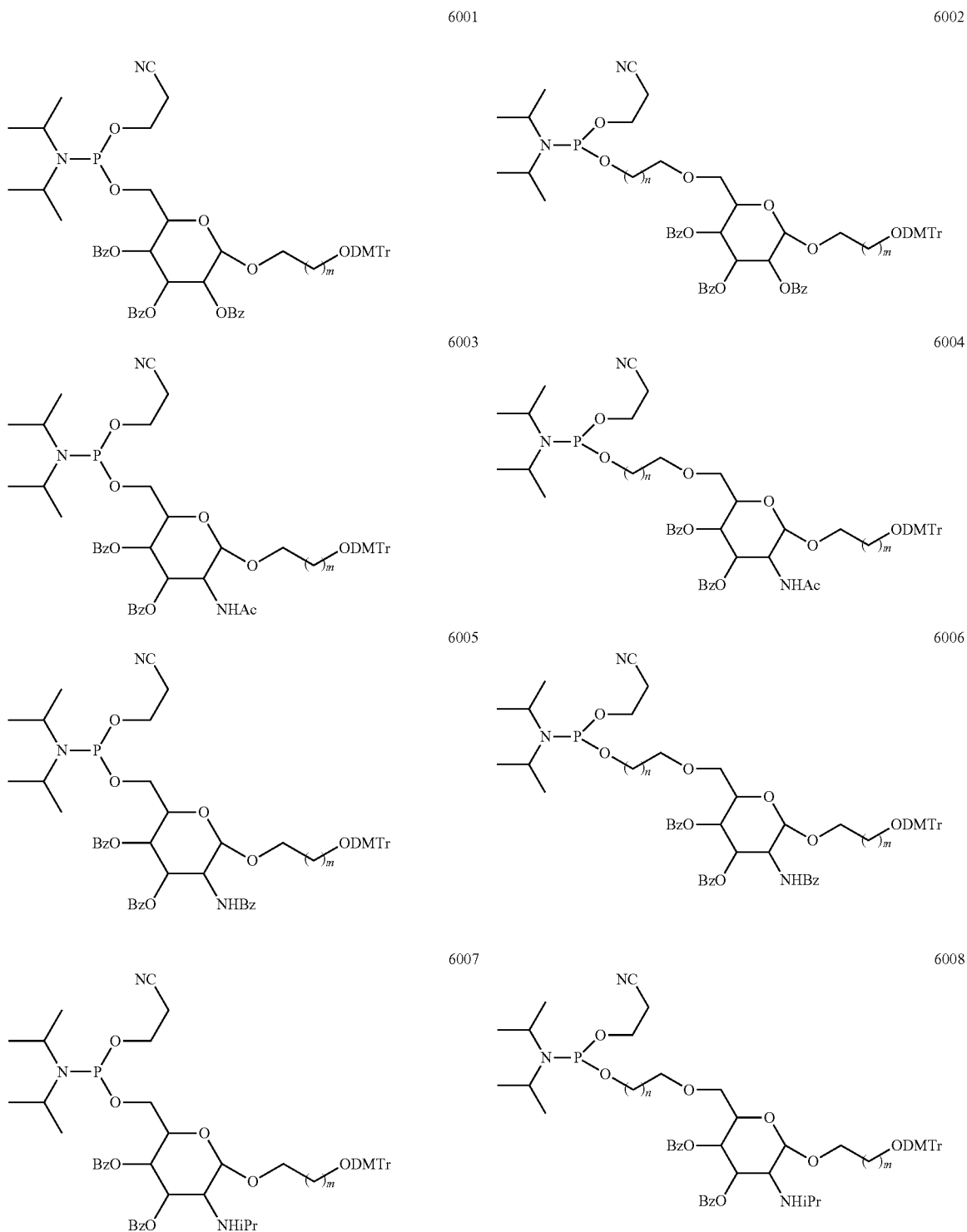

-continued
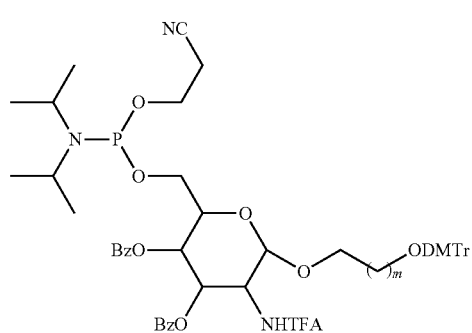
6009
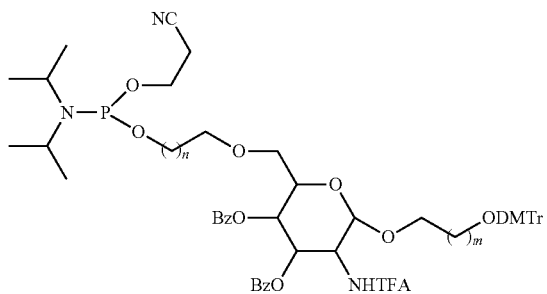
6010
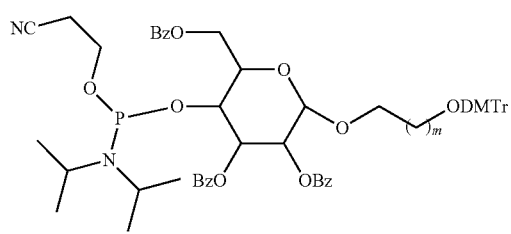
6011
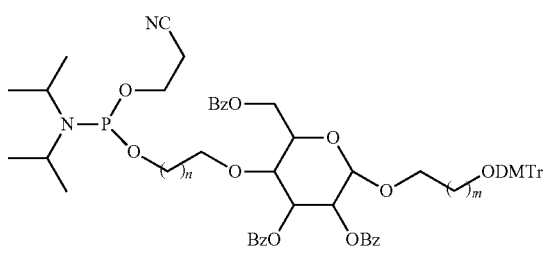
6012
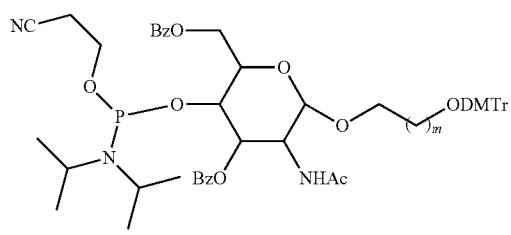
6013
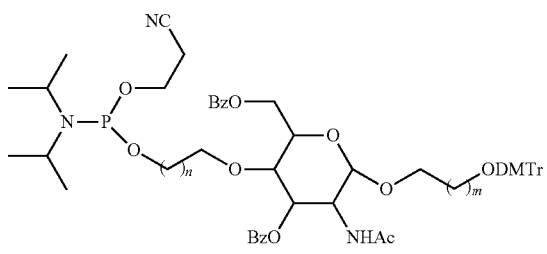
6014
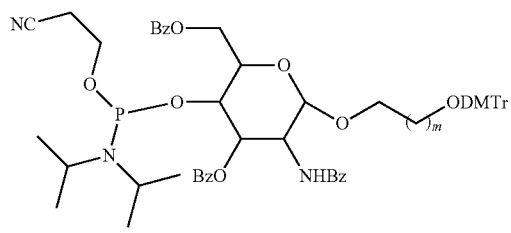
6015
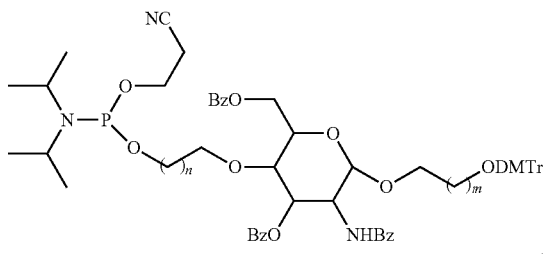
6016
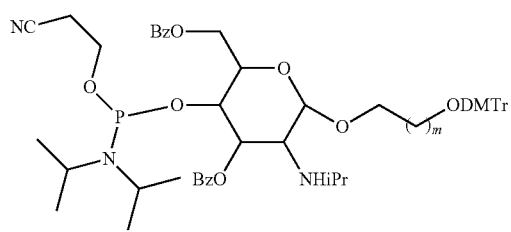
6017
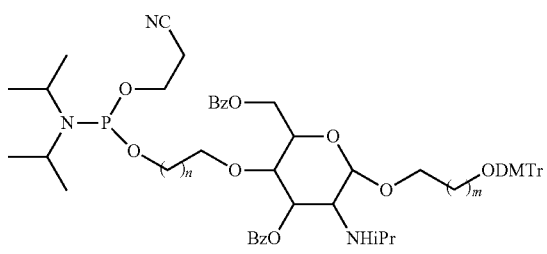
6018

6019
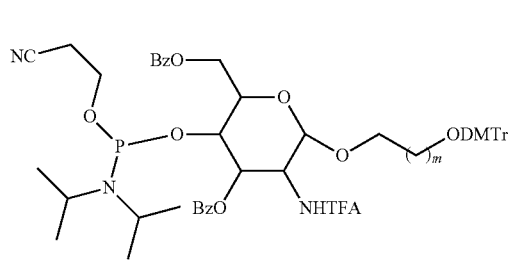
6020
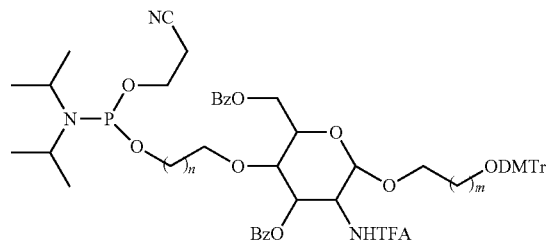
6021
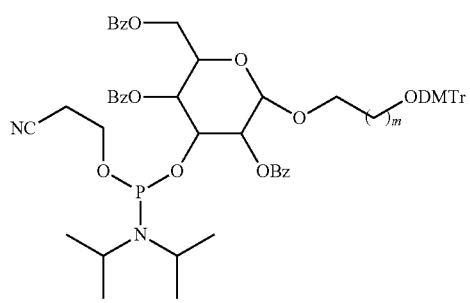
6022
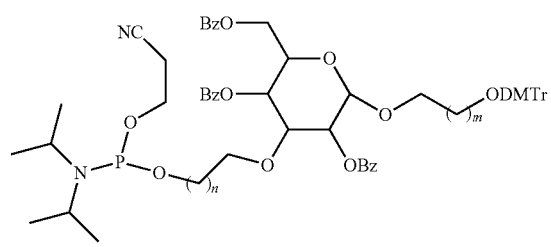
6023
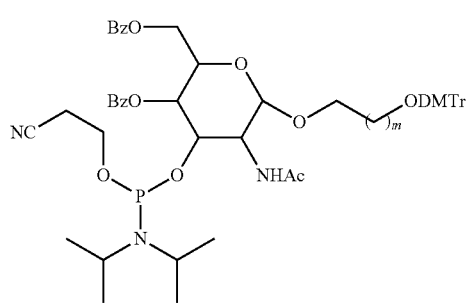
6024
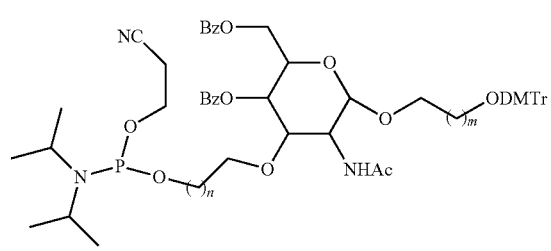
6025
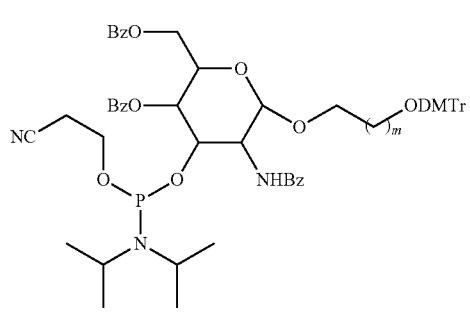
6026
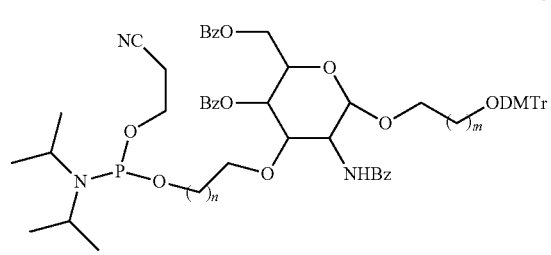
6027
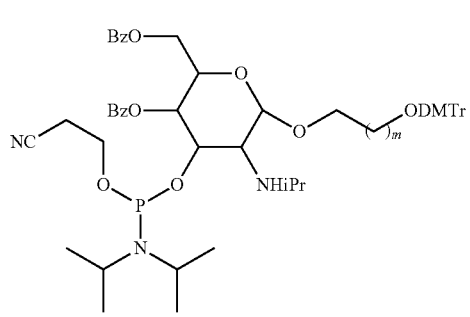
6028
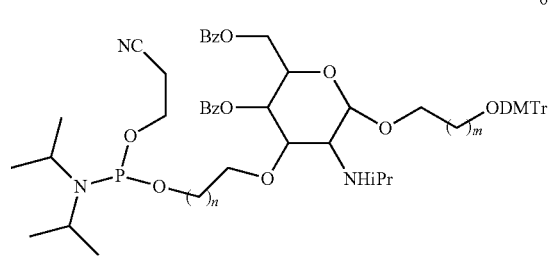

-continued
6029
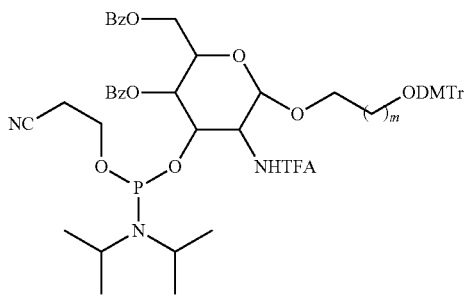
6030
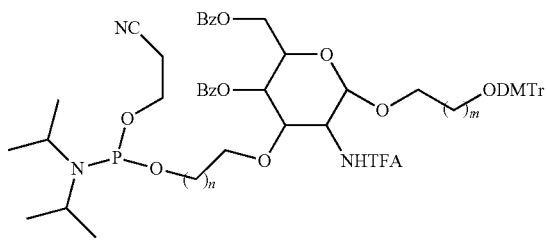
6031
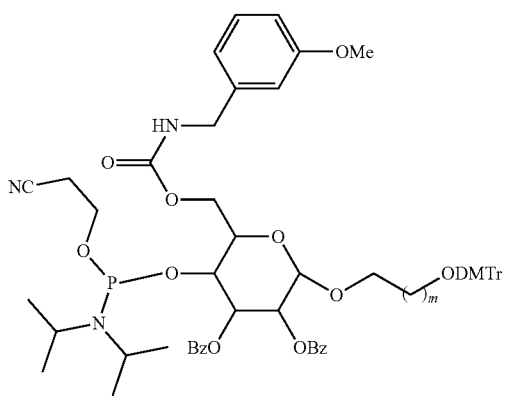
6032
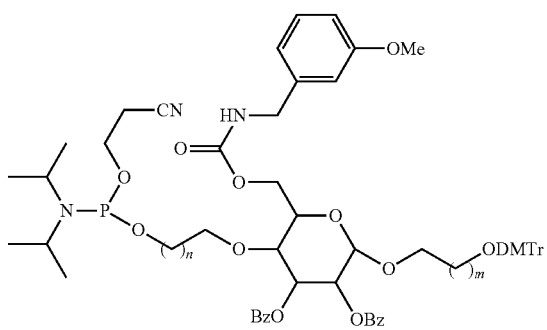
6033
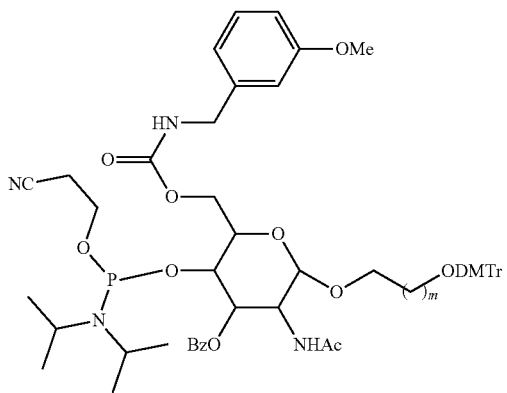
6034
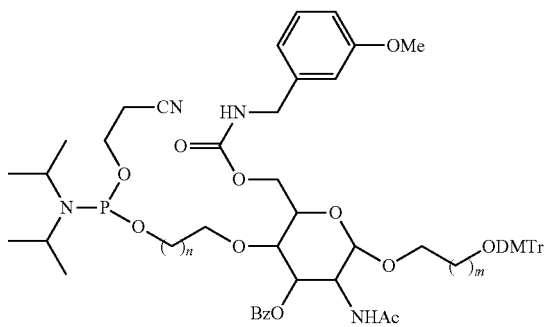
6035
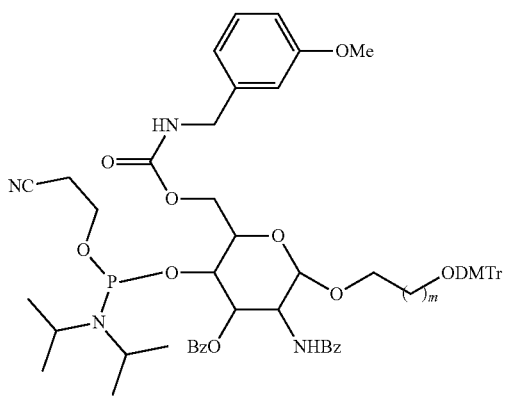
6036
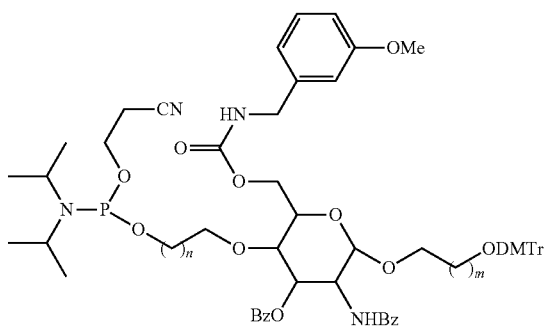

-continued
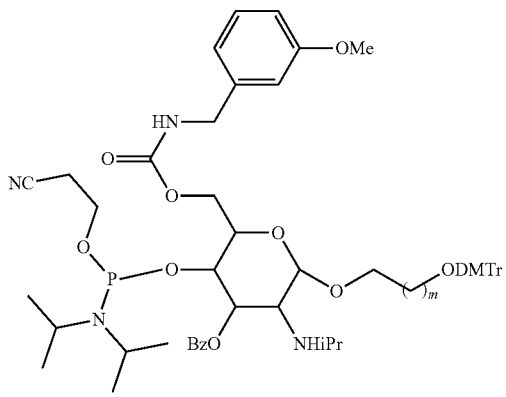
6037
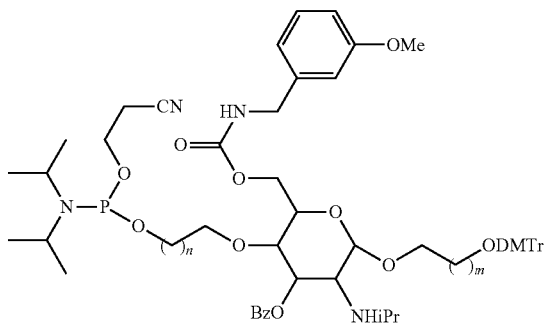
6038
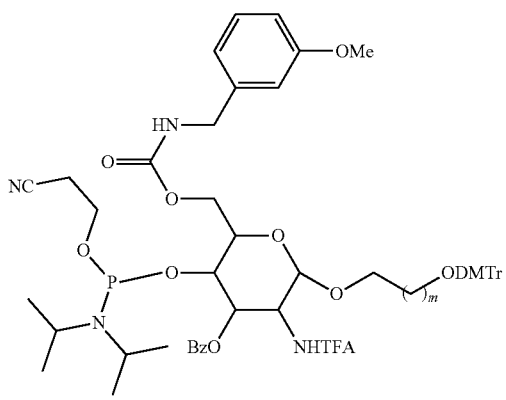
6039
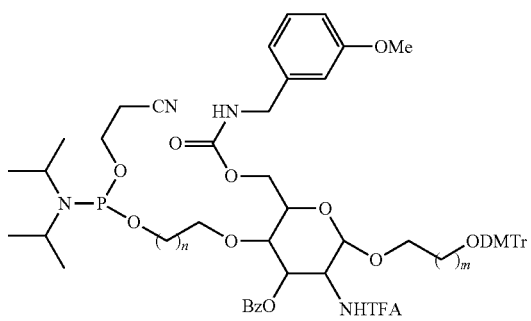
6040
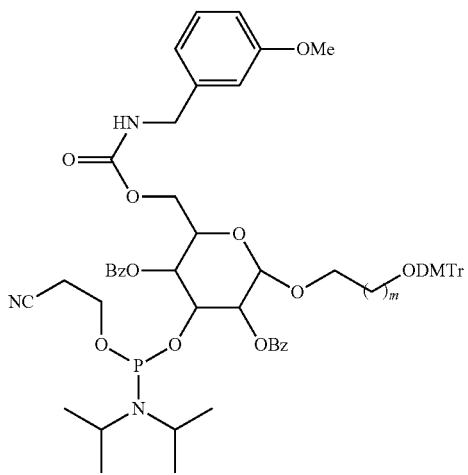
6041
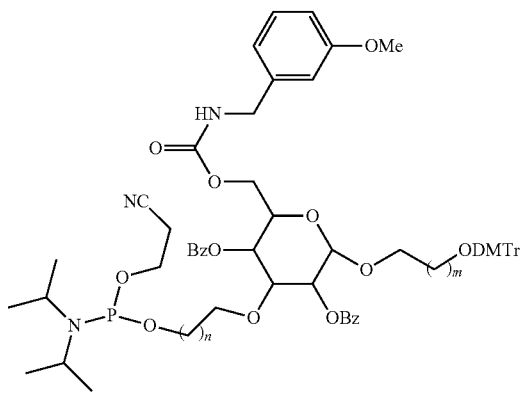
6042

-continued
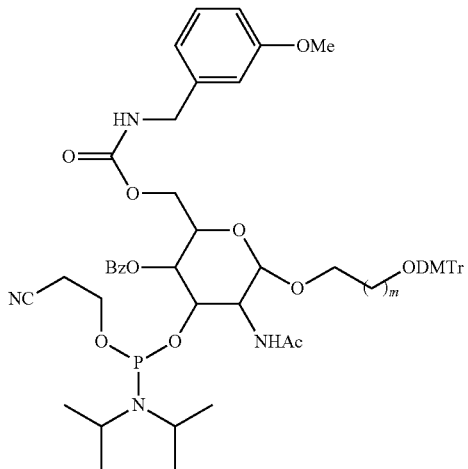
6043
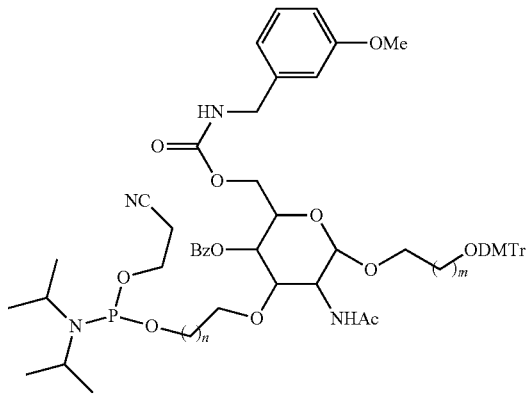
6044
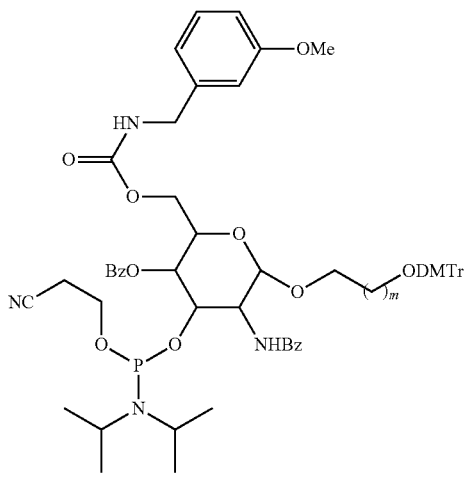
6045
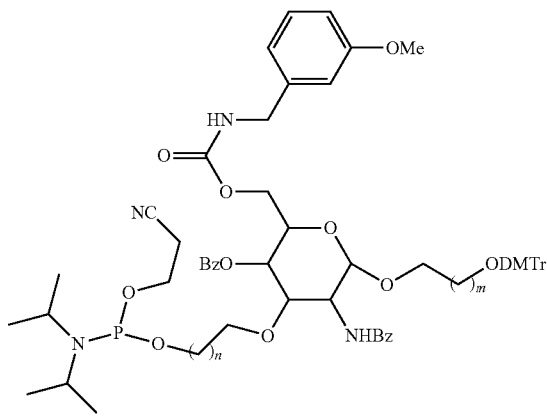
6046
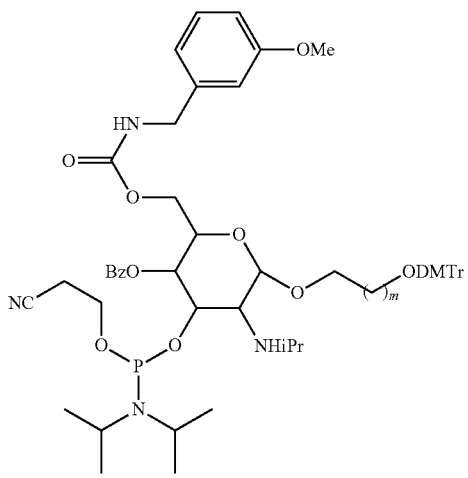
6047
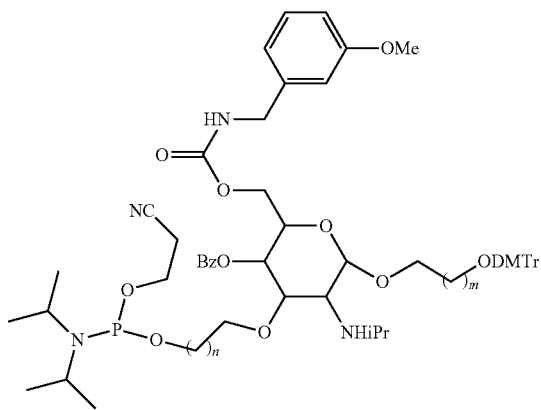
6048

-continued
247
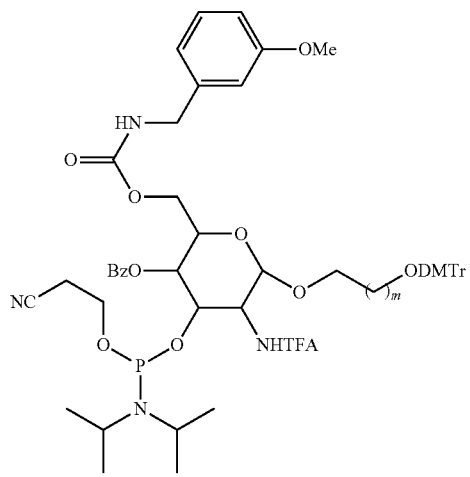
6049
248
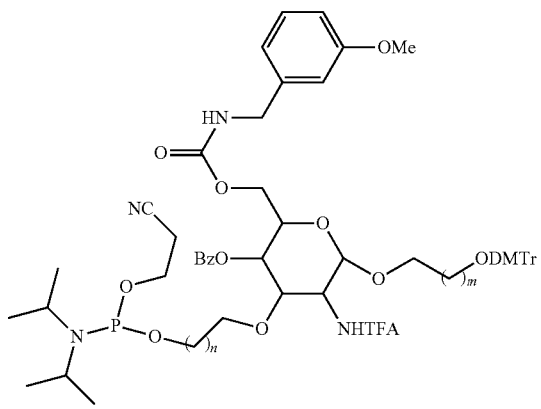
6050
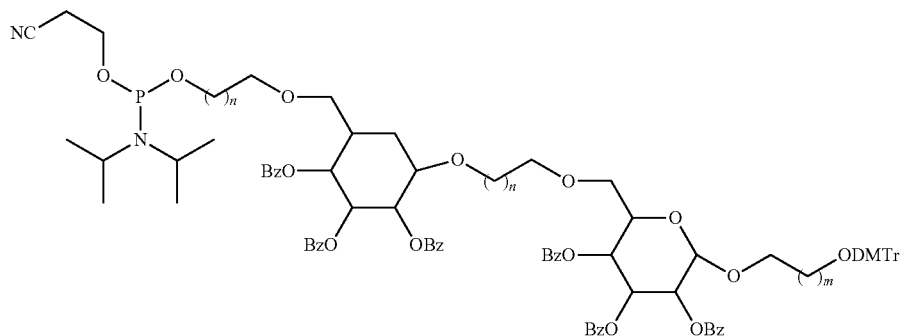
6051
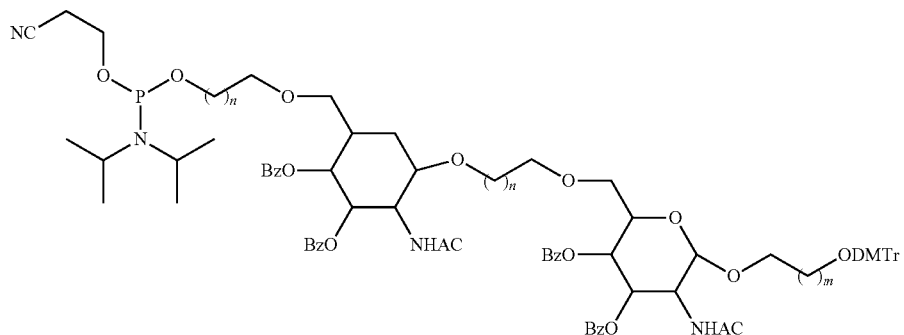
6052
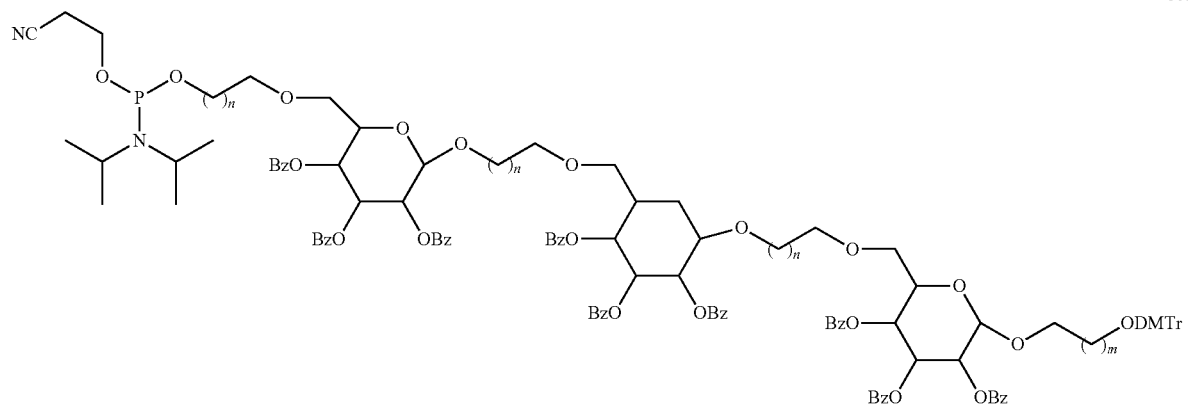
6053

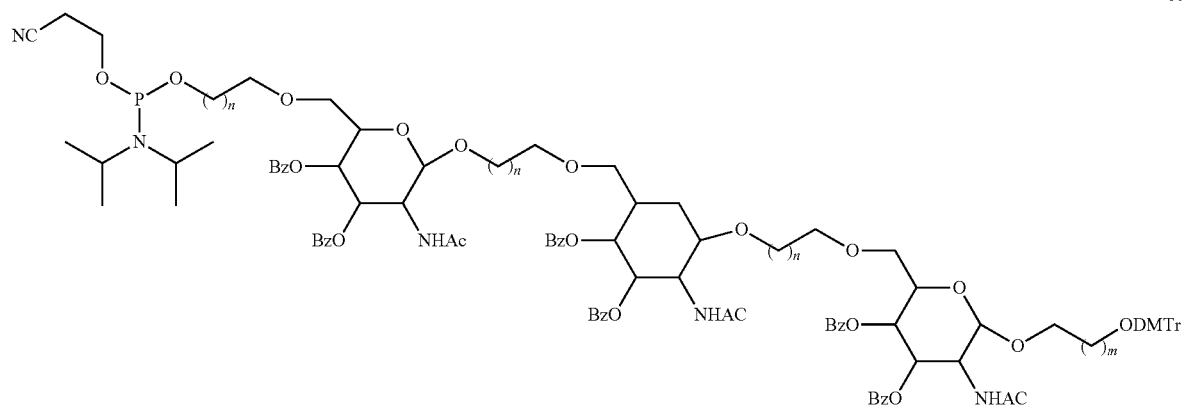

6054 n = 1-12 and m = 1-12

Figure 3:
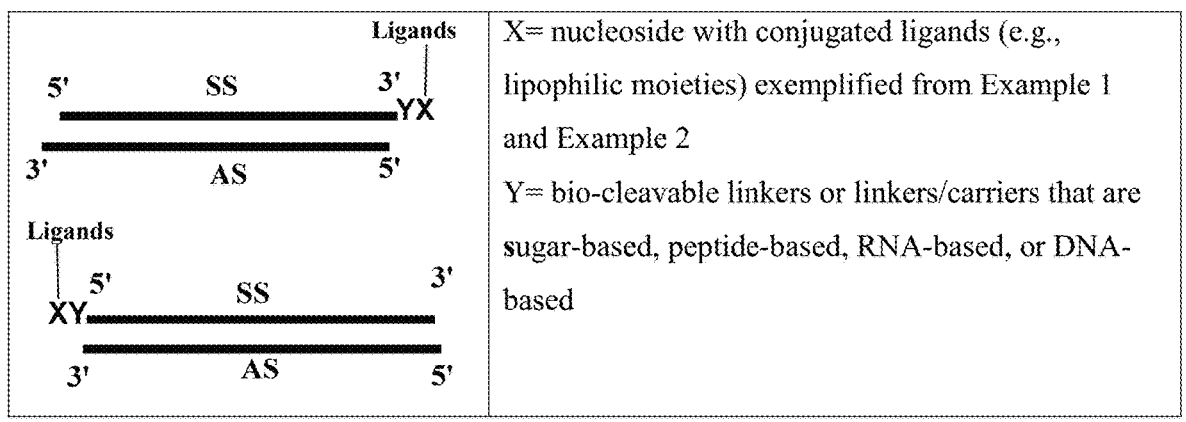
FIG. 3 is a scheme showing ligands, such as lipophilic moieties, that are conjugated to siRNAs via bio-cleavable linkers.

The siRNA conjugate was synthesized on the solid support with consecutive addition of one or more of the cleavable linkers illustrated in Scheme 28, and followed by hybridization to complementary strands, as shown in FIG. 3.

Example 9. Functionalized Cleavable Linkers and Phosphoramidites

Scheme 29. Various modified carbohydrates (di or tri sacchaides of galactose, galactosamine, glucose, glucosamine, mannose, mannoseamine derivatives)

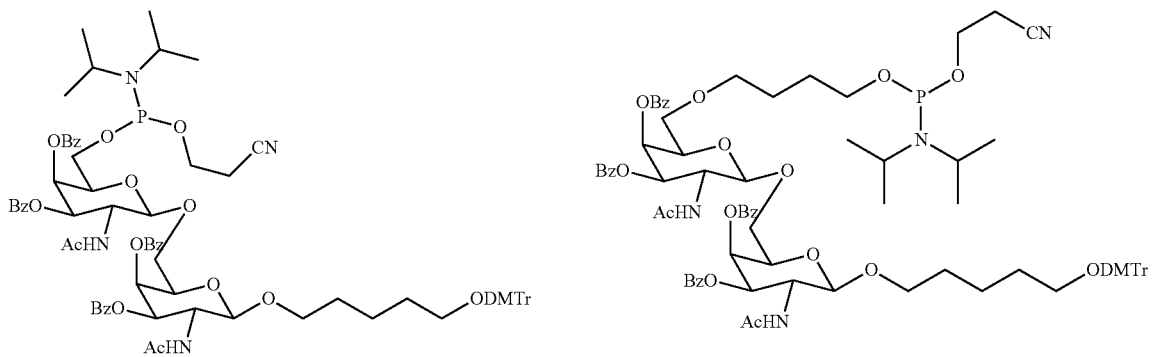

6055　6056

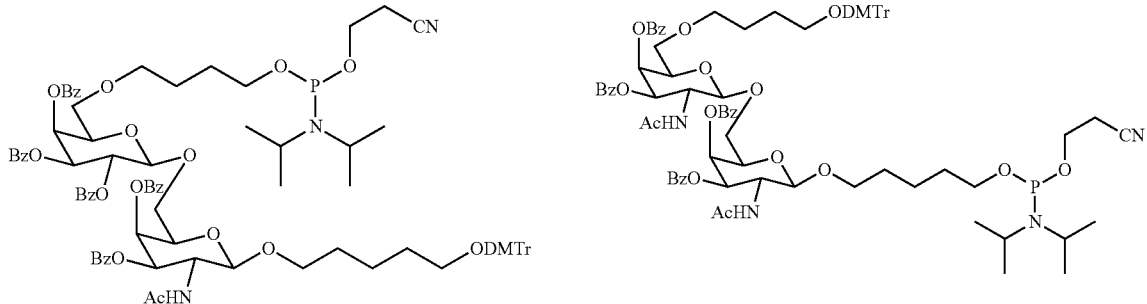

6057　6058

251 252
-continued
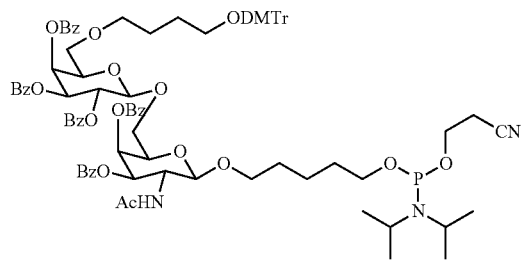
6059
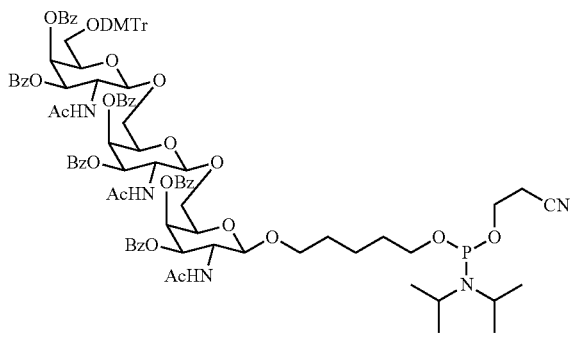
6060
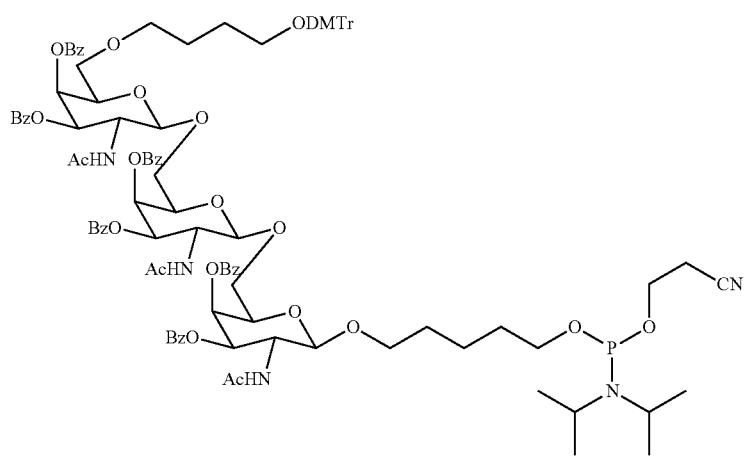
6061
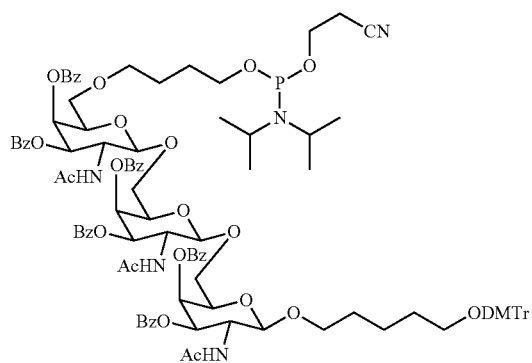
6062
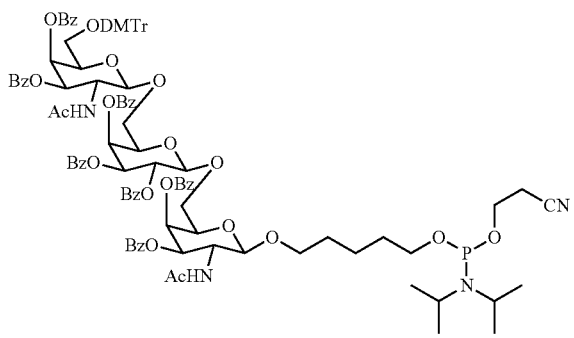
6063
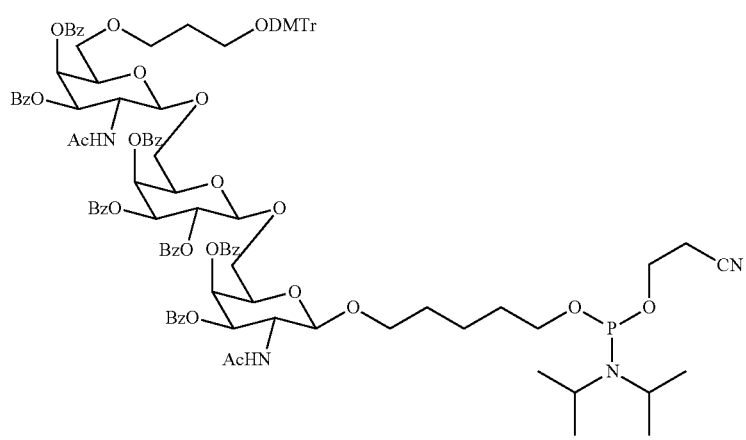
6064

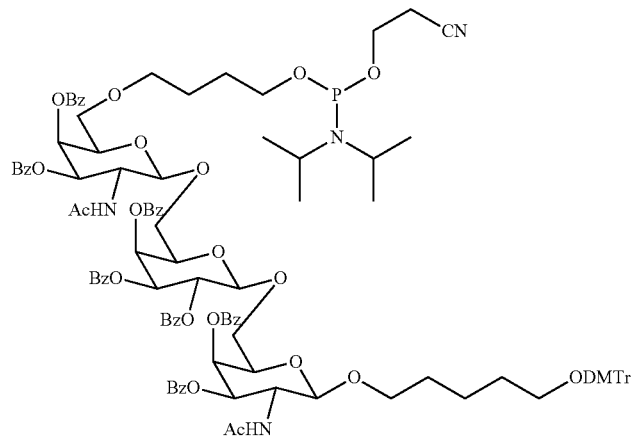
6065
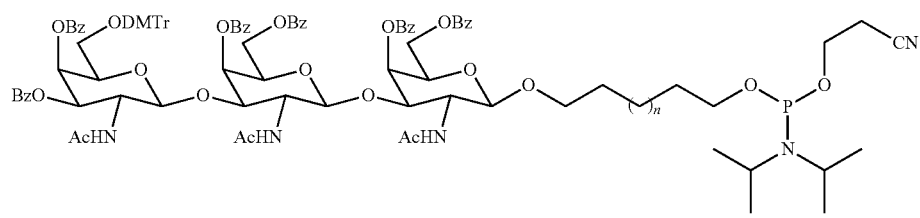
6066
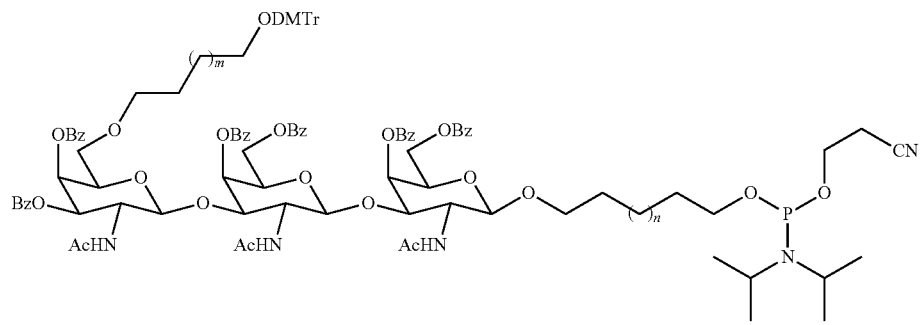
6067
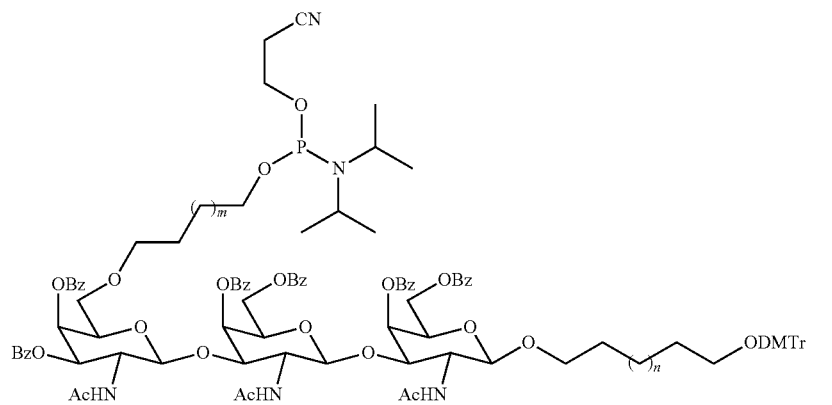
6068
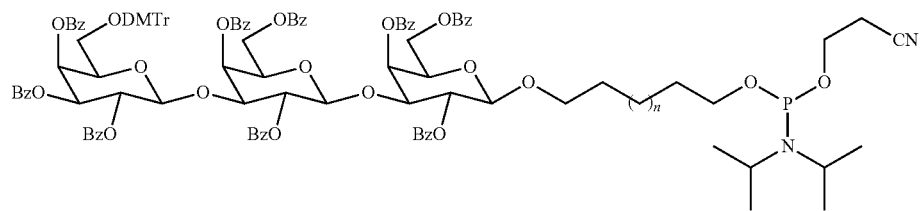
6069

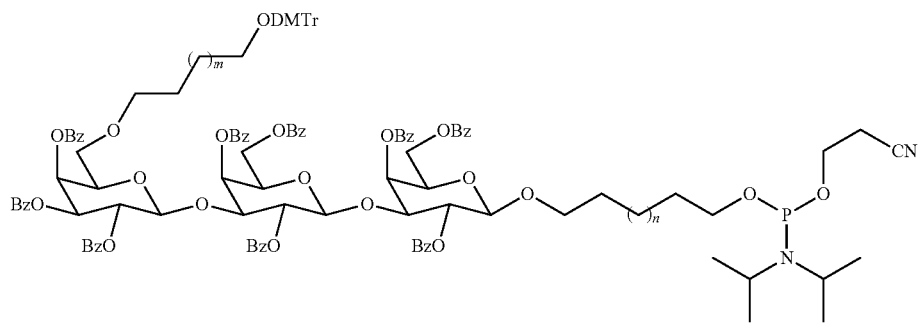
6070
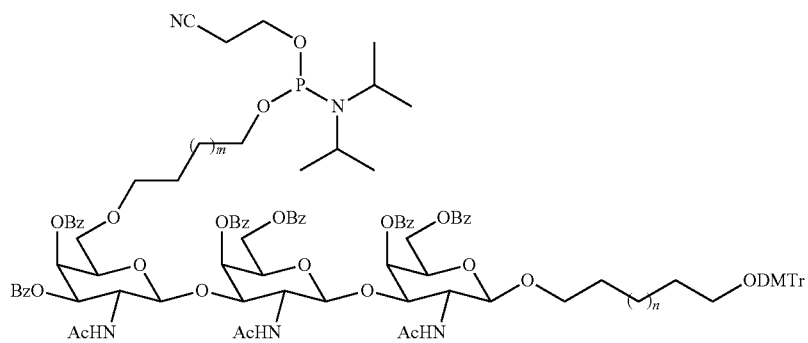
6071
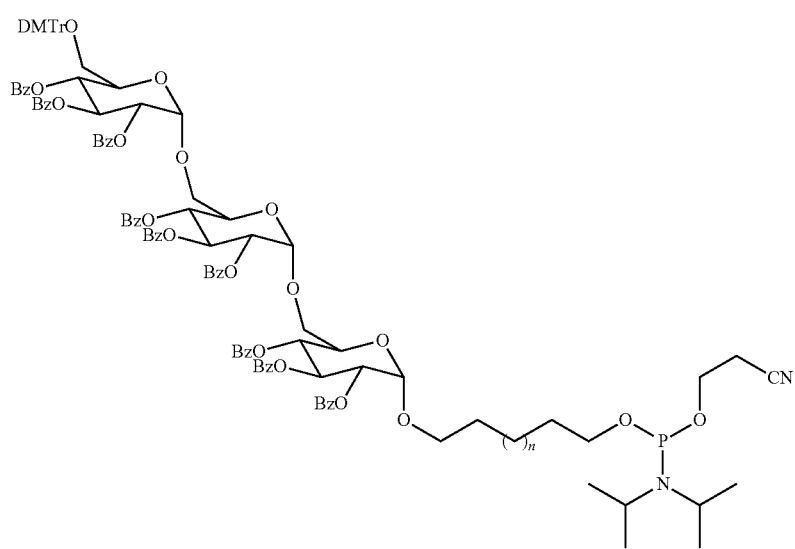
6072

-continued
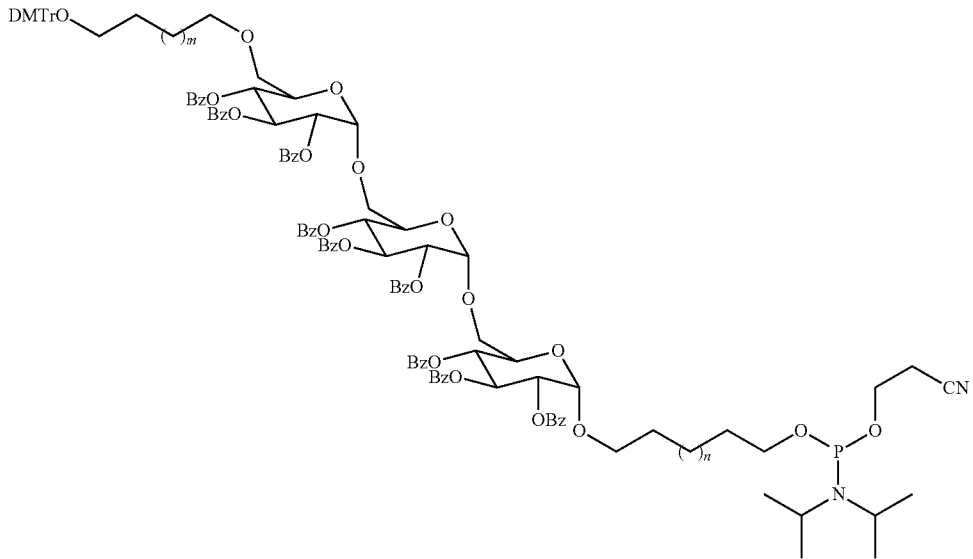
6073
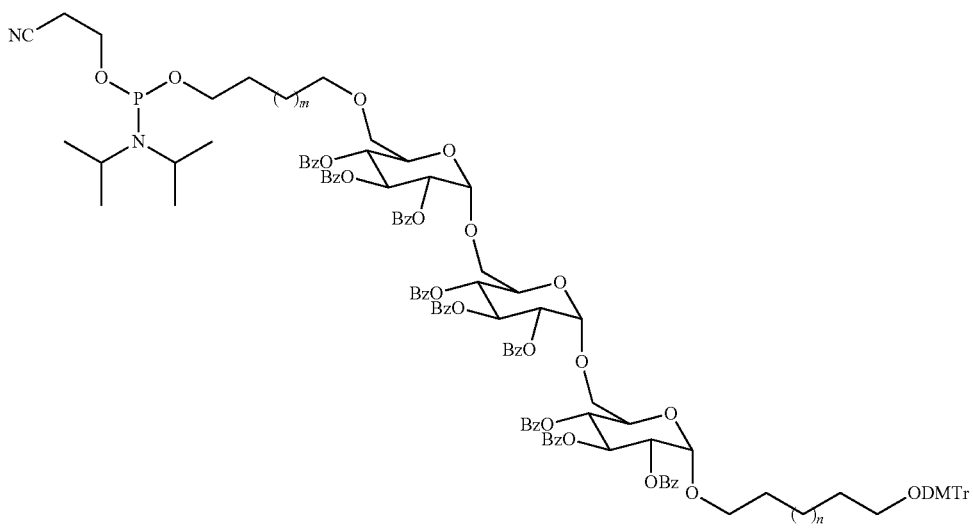
6074
n = 1-12 and m = 1-12
The siRNA conjugate was synthesized on the solid support with consecutive addition of one or more of the cleavable linkers illustrated in Scheme 29, and followed by hybridization to complementary strands, as shown in FIG. 3.
Example 10: Functionalized Protease Cleavable Linkers and Phosphoramidites Scheme 30
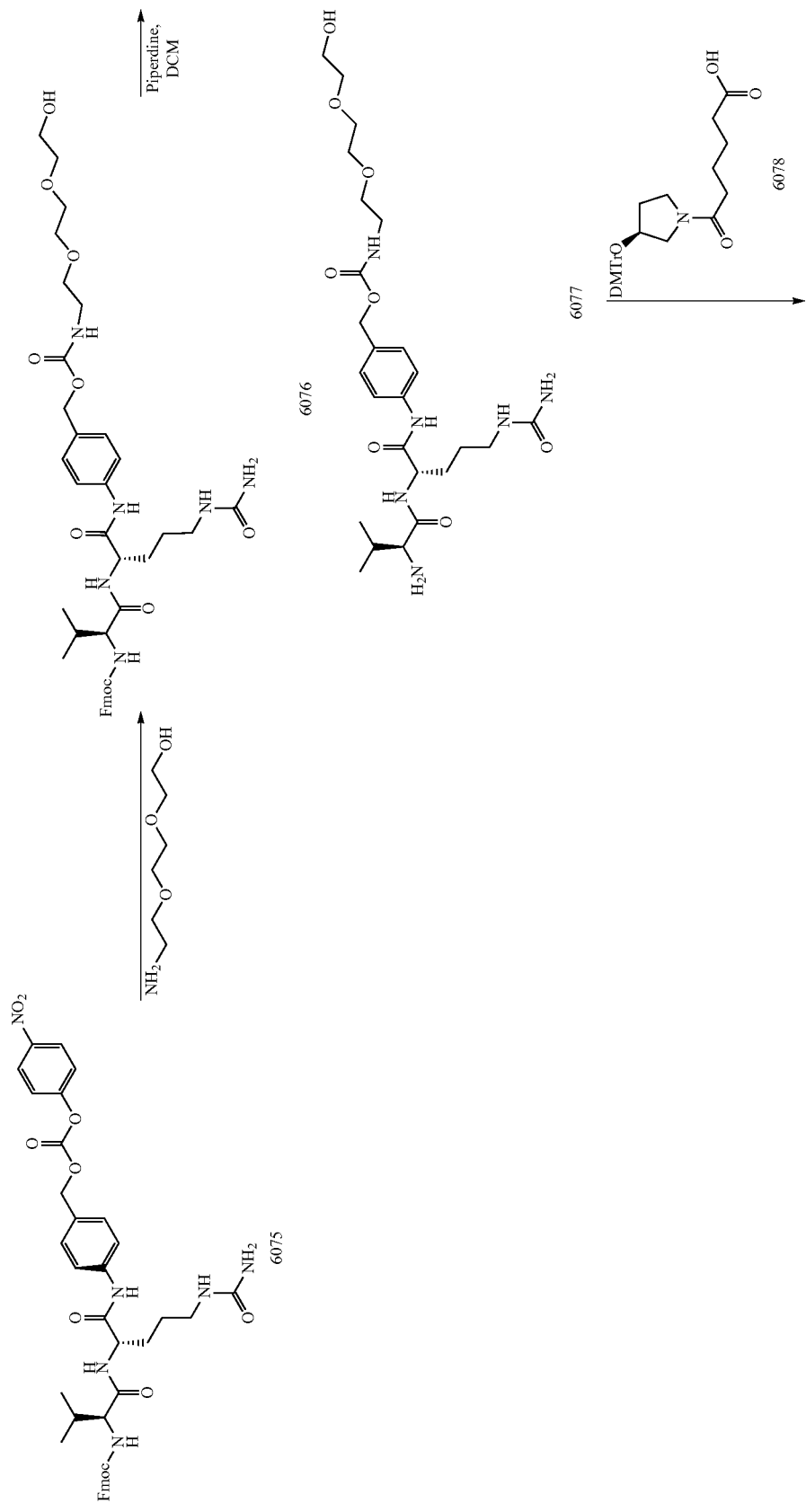

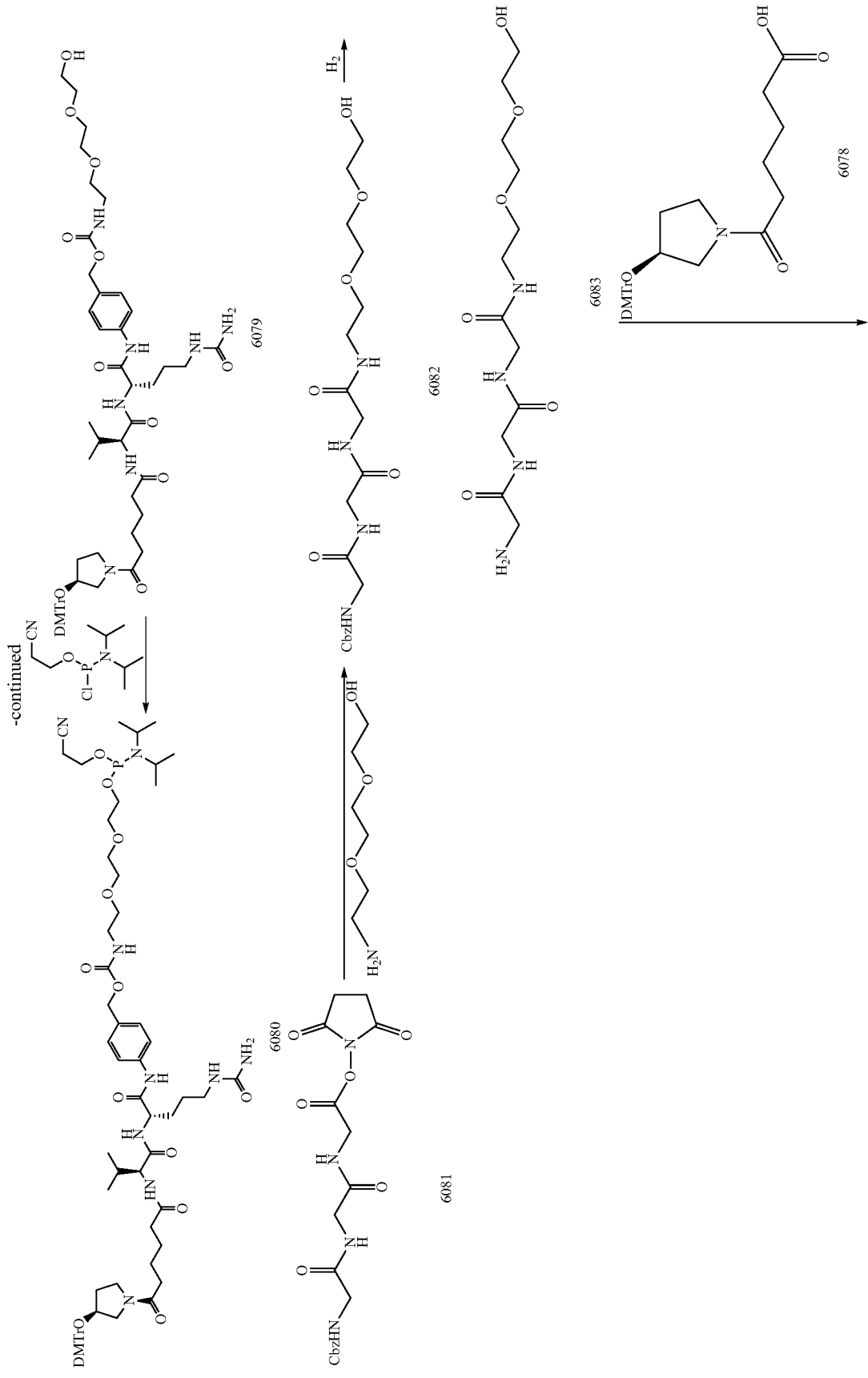

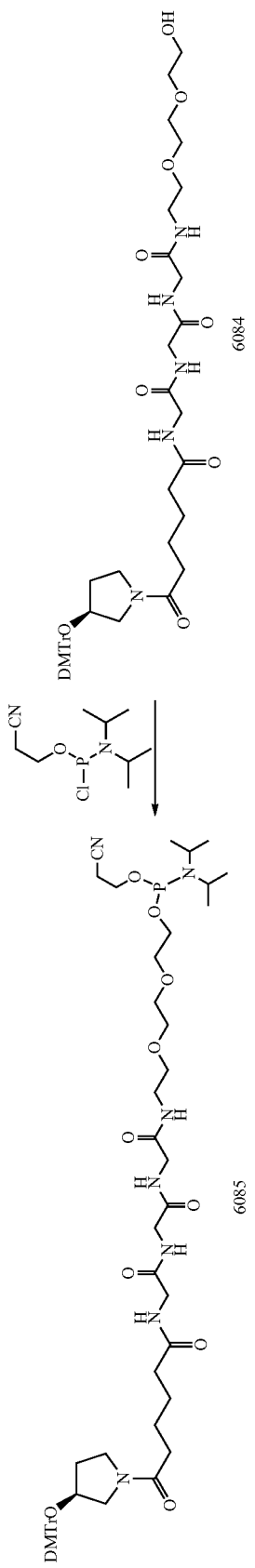

The siRNA conjugate was synthesized on the solid support with consecutive addition of one or more of the cleavable linkers illustrated in Scheme 30, and followed by hybridization to complementary strands, as shown in FIG. 3.

Example 11: mRNA Knockdown in Mouse Eyes

Figure 4:
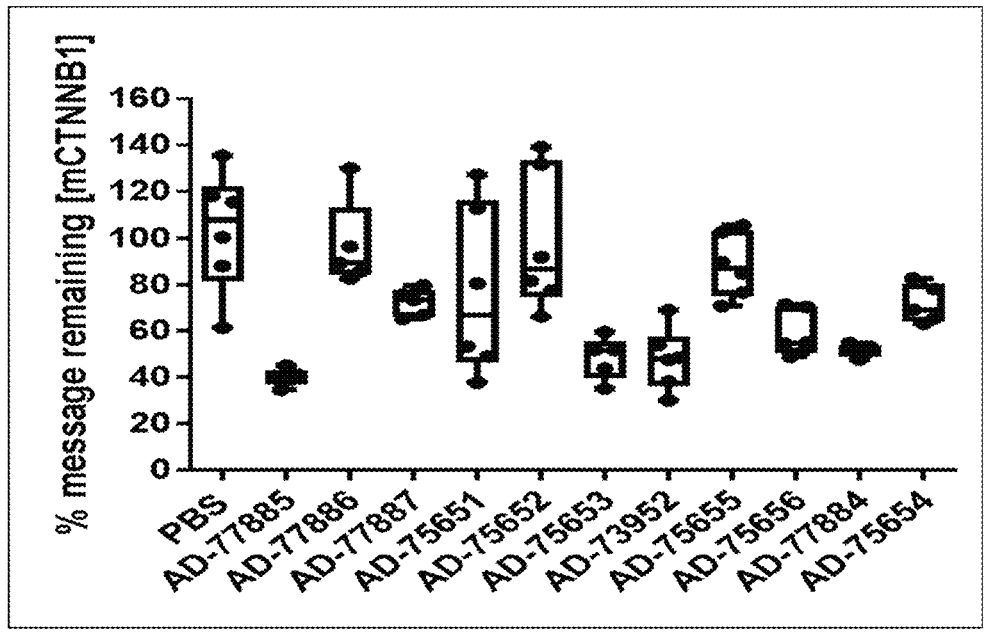
FIG. 4 is a graph showing the results of beta catenin gene (ocular CTNNB1) silencing by an intravitreal injection of various exemplary siRNA conjugates in mice.

Beta catenin gene silencing was studied with siRNA conjugates listed in Table 1a in wild type C57BL/6 mice (n=5) followed by an intravitreal injection at 7.5 µg/eye (1.5 µL), with the mice sacrificed on day 14. The results are shown in FIG. 4.

TABLE 1a siRNA duplex used in intravitreal injection in mice.

| Duplex Name | Oligo Name | Target | SEQ ID NO: | strand | oligoSeq | Calc. Mass | Found MW | Conjugation |
|---|---|---|---|---|---|---|---|---|
| AD-77885.1 | A-154945.1 | CTNNB1 | 38 | sense | usascuguUfgGfAfUfugauucgaasadTdTL10 | 8306.91 | 8302.61 | Hyp-C6-Chol |
|  | A-147656.2 | CTNNB1 | 39 | antis | VP(Tams)UfsucgAfaUfCfaaucCfaAfcaguasgsc | 7738.13 | 7733.17 |  |
| AD-77886.1 | A-155621.1 | CTNNB1 | 40 | sense | usascuguUfgGfAfUfugauucgaaaQ197L245 | 8164.95 | 8160.73 | Hyp-C6-Ibuprofen |
|  | A-147656.2 | CTNNB1 | 39 | antis | VP(Tams)UfsucgAfaUfCfaaucCfaAfcaguasgsc | 7738.13 | 7733.17 |  |
| AD-77887.1 | A-156183.1 | CTNNB1 | 41 | sense | usascuguUfgGfAfUfugauucgaaaL262 | 7508.23 | 7504.43 | Hyp-C6-C16 |
|  | A-147656.2 | CTNNB1 | 39 | antis | VP(Tams)UfsucgAfaUfCfaaucCfaAfcaguasgsc | 7738.13 | 7733.17 |  |
| AD-75651.1 | A-148043.1 | CTNNB1 | 42 | sense | usascuguUfgGfAfUfugauucgaaaL52 | 7452.11 | 7448.37 | Hyp-C6-C12 |
|  | A-147656.2 | CTNNB1 | 39 | antis | VP(Tams)UfsucgAfaUfCfaaucCfaAfcaguasgsc | 7738.13 | 7733.17 |  |
| AD-75652.2 | A-148044.1 | CTNNB1 | 43 | sense | usascuguUfgGfAfUfugauucgaaaL55 | 7532.24 | 7528.43 | Hyp-C6-Linoleyl |
|  | A-147656.2 | CTNNB1 | 39 | antis | VP(Tams)UfsucgAfaUfCfaaucCfaAfcaguasgsc | 7738.13 | 7733.17 |  |
| AD-75653.2 | A-148045.1 | CTNNB1 | 44 | sense | usascuguUfgGfAfUfugauucgaaaL57 | 7536.27 | 7532.46 | Hyp-C6-C18 |
|  | A-147656.2 | CTNNB1 | 39 | antis | VP(Tams)UfsucgAfaUfCfaaucCfaAfcaguasgsc | 7738.13 | 7733.17 |  |
| AD-73952.3 | A-147655.3 | CTNNB1 | 45 | sense | usascuguUfgGfAfUfugauucgaaaL10 | 7682.46 | 7678.54 | Hyp-C6-Chol |
|  | A-147656.2 | CTNNB1 | 39 | antis | VP(Tams)UfsucgAfaUfCfaaucCfaAfcaguasgsc | 7738.13 | 7733.17 |  |
| AD-75655.1 | A-148047.1 | CTNNB1 | 46 | sense | usascuguUfgGfAfUfugauucgaaaL8 | 7269.81 | 7266.2 | Hyp-C6-NH2 |
|  | A-147656.2 | CTNNB1 | 39 | antis | VP(Tams)UfsucgAfaUfCfaaucCfaAfcaguasgsc | 7738.13 | 7733.17 |  |
| AD-75656.2 | A-151280.1 | CTNNB1 | 47 | sense | usascuguUfgGfAfUfugauucgaaaL252 | 7580.3 | 7576.43 | Hyp-C6-DHA |
|  | A-147656.2 | CTNNB1 | 39 | antis | VP(Tams)UfsucgAfaUfCfaaucCfaAfcaguasgsc | 7738.13 | 7733.17 |  |
| AD-77884.1 | A-152960.2 | NA | 48 | sense | usascuguUfgGfAfUfugau(Uhd)cgasasa | 7220.07 | 7216.27 | C16@N6 |
|  | A-147656.2 | CTNNB1 | 39 | antis | VP(Tams)UfsucgAfaUfCfaaucCfaAfcaguasgsc | 7738.13 | 7733.17 |  |
| AD-75654.3 | A-148046.2 | CTNNB1 | 49 | sense | usascuguUfgGfAfUfugauucgaaaL148 | 7888.83 | 7884.76 |  |
|  | A-147656.2 | CTNNB1 | 39 | antis | VP(Tams)UfsucgAfaUfCfaaucCfaAfcaguasgsc | 7738.13 | 7733.17 |  |

* Upper and lower case letters in italics indicate 2'-deoxy-2'-fluoro (2'-F), and 2'-O-methyl (2'-OMe) sugar modifications, respectively, to adenosine, cytidine, guanosine and uridine; s indicates phosphorothioate (PS) linkage; VP-Vinyl phosphonate; Uhd, 2'-O-hexadecyl uridine; Tam, 2'-O-(N-methylacetamide) thymidine

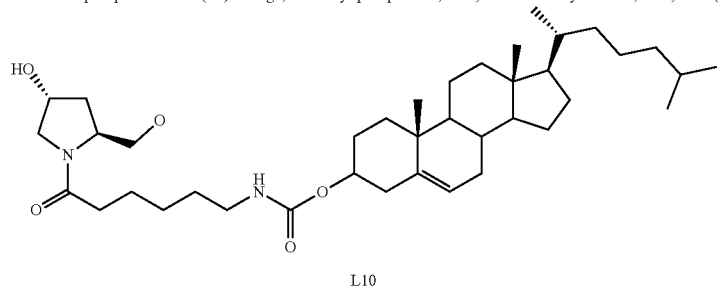

L10

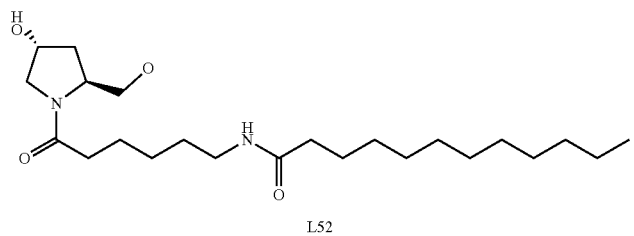

L52

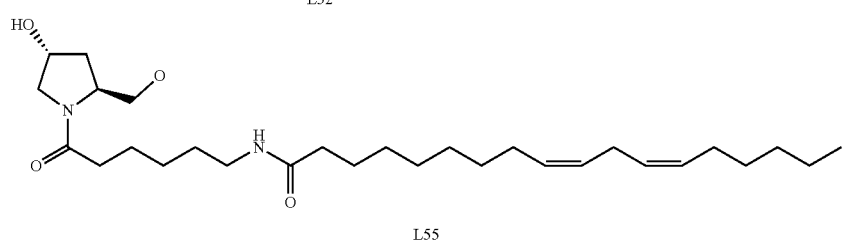

L55

TABLE 1a-continued siRNA duplex used in intraviteal injection in mice.

| Duplex Name | Oligo Name | Target | SEQ ID NO: | strand | oligoSeq | Calc. Mass | Found MW | Conjugation |
|---|---|---|---|---|---|---|---|---|

L262

L8

L252

L148

L57

(Uhd)

TABLE 1a-continued siRNA duplex used in intraviteal injection in mice.

| Duplex Name | Oligo Name | Target | SEQ ID NO: | strand | oligoSeq | Calc. Mass | Found MW | Conjugation |
|---|---|---|---|---|---|---|---|---|

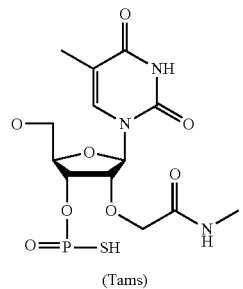

(Tams)

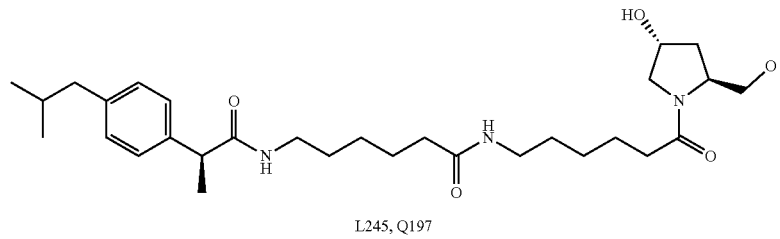

L245, Q197

TABLE 1b

Brief descriptions of sense strand modifictions for siRNA duplex listed in Table 1a.

| Duplex Name | Sense strand modifications |
|---|---|
| AD-77885.1 | 3' end Cholesterol with cleavable dTdT linker |
| AD-77886.1 | 3' end with 2 × ibuprofen |
| AD-77887.1 | 3' end with C16 |
| AD-75651.1 | 3' end with C12 |
| AD-75652.2 | 3' end with C18:2 |
| AD-75653.2 | 3' end with C18 |
| AD-73952.3 | 3' end with cholesterol |
| AD-75655.1 | 3' end C6 amino linker control |

TABLE 1b-continued

Brief descriptions of sense strand modifictions for siRNA duplex listed in Table 1a.

| Duplex Name | Sense strand modifications |
|---|---|
| AD-75656.2 | 3' end with DHA (C22:6) |
| AD-77884.1 | internal C16 |
| AD-75654.3 | 3' end with 2 × C18:1 |

Example 12: mRNA Knockdown in CNS

TABLE 2 siRNA duplexes used for intrathecal injection in the CNS study

| Duplex ID (Target) | Single strand ID | SEQ ID NO: | Strand | Sequence 5'-3' | MW calc (g/mol) | MW obs (g/mol) |
|---|---|---|---|---|---|---|
| AD-135778 | A-268861 | 50 | S | csasuuuuAfaUfCfCfucacucuaaaL96 | 8585.99 | 8587.20 |
| (SOD1) | A-268862 | 51 | AS | usUfsuagAfgUfGfaggaUfuAfaaaugsasg | 7771.18 | 7772.91 |
| AD-224937 | A-444399 | 52 | S | csasuuuuAfaUfCfCfucacucuaaaL10 | 7502.52 | 7503.10 |
| (SOD1) | A-268862 | 51 | AS | usUfsuagAfgUfGfaggaUfuAfaaaugsasg | 7771.18 | 7772.91 |
| AD-224938 | A-444400 | 53 | S | csasuuu(Uhd)AfaUfCfCfucacucuaaa | 7008.30 | 7009.33 |
| (SOD1) | A-268862 | 51 | AS | usUfsuagAfgUfGfaggaUfuAfaaaugsasg | 7771.18 | 7772.91 |
| AD-224939 | A-444401 | 54 | S | csasuuuuAfaUfCfCfucacucuaaa | 6798.07 | 6799.15 |
| (SOD1) | A-268862 | 51 | AS | usUfsuagAfgUfGfaggaUfuAfaaaugsasg | 7771.18 | 7772.91 |

TABLE 2-continued siRNA duplexes used for intrathecal injection in the CNS study

| Duplex ID (Target) | Single strand ID | SEQ ID NO: | Strand | Sequence 5'-3' | MW calc (g/mol) | MW obs (g/mol) |
|---|---|---|---|---|---|---|
| AD-77884 (b-cat) | A-152960 | 48 | S | usascuguUfgGfAfUfugau(Uhd)cgasasa | 7216.27 | 7218.29 |
|  | A-147656 | 39 | AS | VP(Tams)UfsucgAfaUfCfaaucCfaAfcaguasgsc | 7733.17 | 7734.01 |

Nf indicates 2'-deoxy-2'-fluoro (2'-F), lower case indicates 2'-O-methyl (2'-OMe) nucleotide; s indicates phosphorothioate (PS) linkage; VP, vinyl phosphonate; Uhd, 2'-O-hexadecyl uridine'; Tam, 2'-O-(N-methylacetamide) thymidine; Target gene transcripts: SOD1, superoxide dismutase 1; b-cat, beta-catenin.

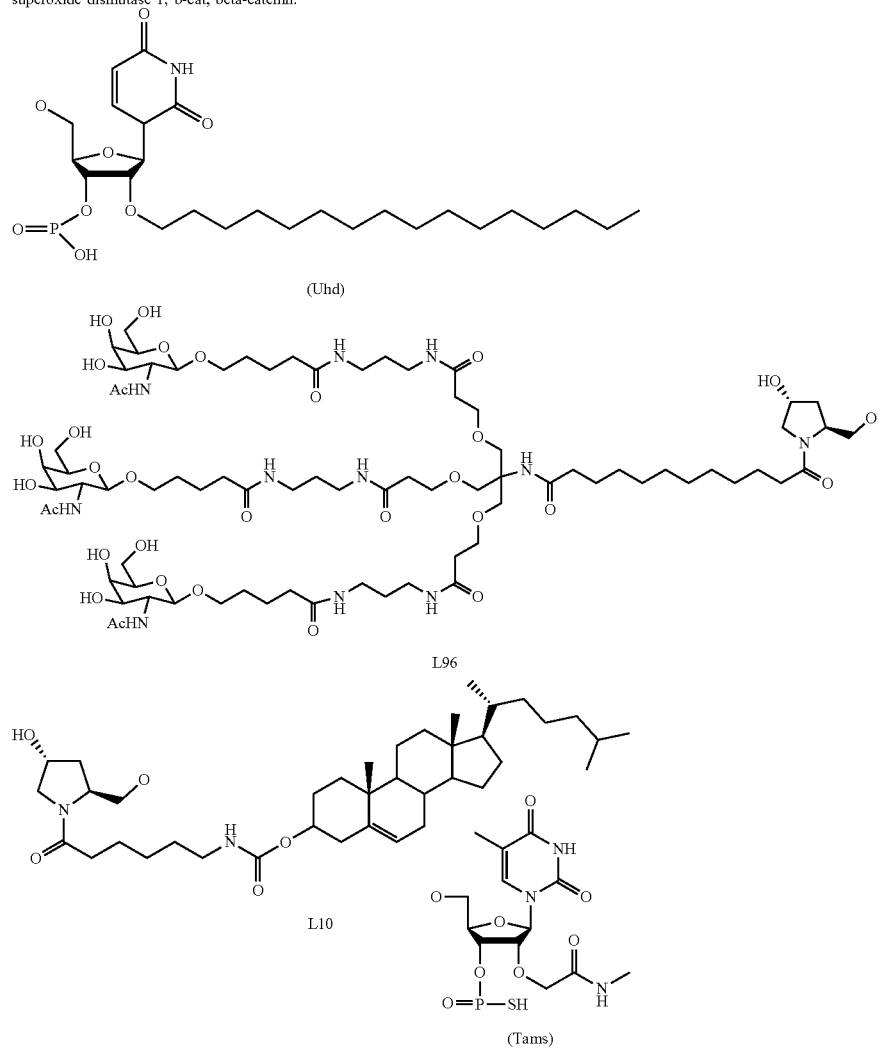

Figure 5:
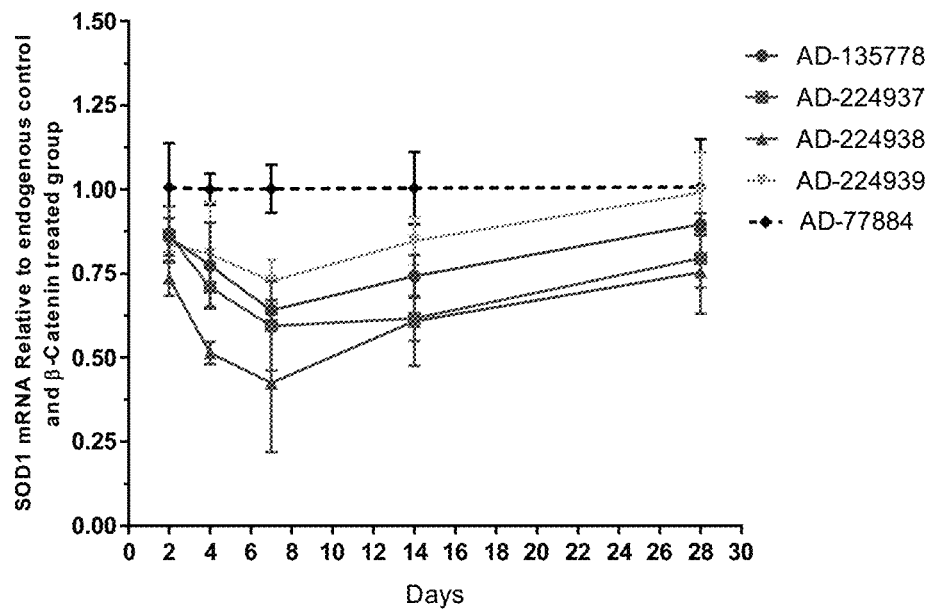
FIG. 5 is a graph showing the results of SOD1 mRNA silencing by a single intrathecal injection of various exemplary siRNA conjugates in Cortex of Sprague Dawley Rats.

Gene silencing of SOD1 mRNA (Mean±SD levels) in Cortex of Sprague Dawley Rats was studied with siRNA conjugates listed in Table 2, after a single intrathecal injection at 0.9 mg dose, as compared to endogenous control and beta catenin treated group. The results are shown in FIG. 5.

Figure 6:
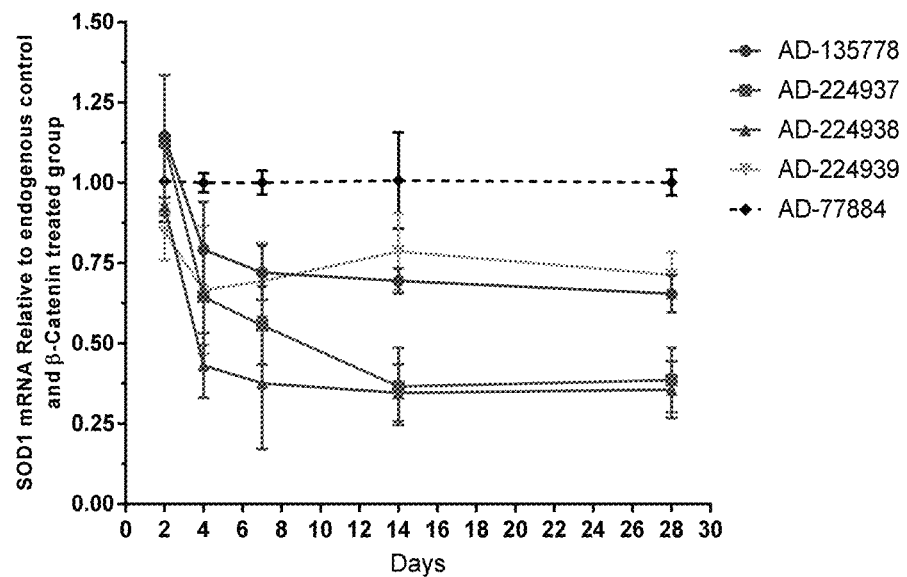
FIG. 6 is a graph showing the results of SOD1 mRNA silencing by a single intrathecal injection of various exemplary siRNA conjugates in Cerebellum of Sprague Dawley Rats.

Gene silencing of SOD1 mRNA (Mean±SD levels) in Cerebellum of Sprague Dawley Rats was studied with siRNA conjugates listed in Table 2, after a single intrathecal injection at 0.9 mg dose, as compared to endogenous control and beta catenin treated group. The results are shown in FIG. 6.

Figure 7:
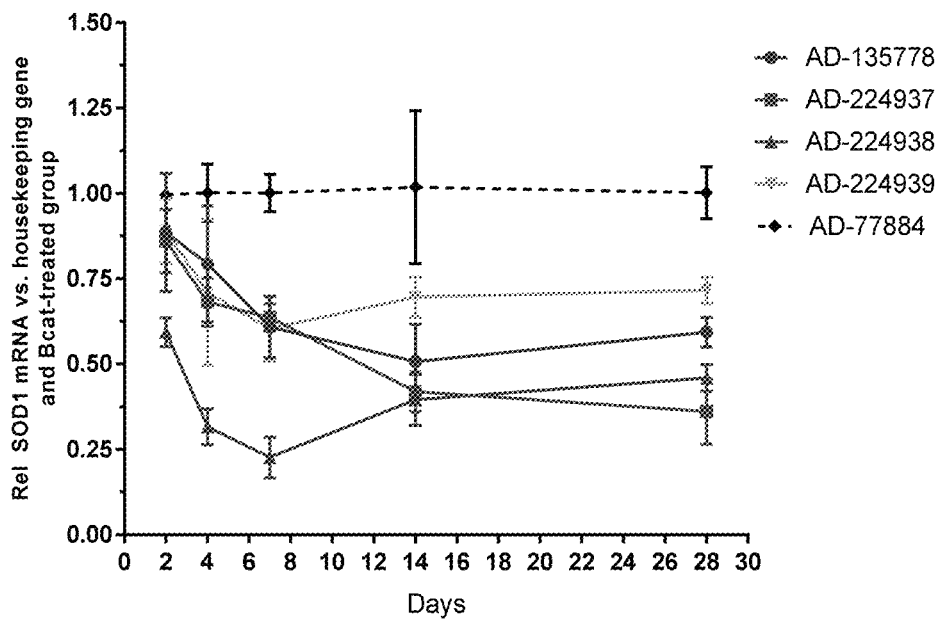
FIG. 7 is a graph showing the results of SOD1 mRNA silencing by a single intrathecal injection of various exemplary siRNA conjugates in Cervical Spine of Sprague Dawley Rats.

Gene silencing of SOD1 mRNA (Mean±SD levels) in Cervical Spine of Sprague Dawley Rats was studied with siRNA conjugates listed in Table 2, after a single intrathecal injection at 0.9 mg dose, as compared to endogenous control and beta catenin treated group. The results are shown in FIG. 7.

Figure 8:
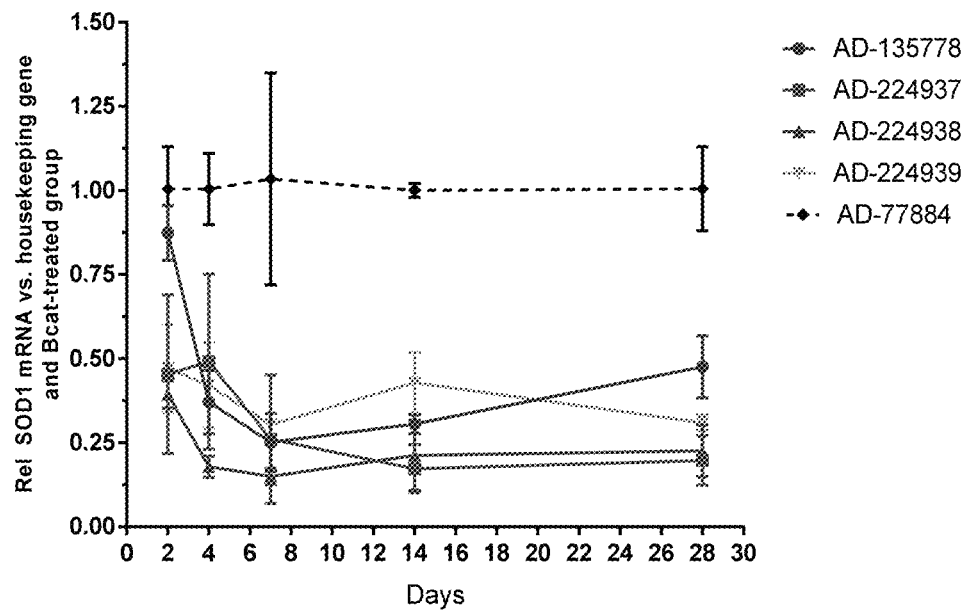
FIG. 8 is a graph showing the results of SOD1 mRNA silencing by a single intrathecal injection of various exemplary siRNA conjugates in Lumbar Spine of Sprague Dawley Rats.

Gene silencing of SOD1 mRNA (Mean±SD levels) in Lumbar Spine of Sprague Dawley Rats was studied with siRNA conjugates listed in Table 2, after a single intrathecal injection of at 0.9 mg dose, as compared to endogenous control and beta catenin treated group. The results are shown in FIG. 8.

Figure 9:
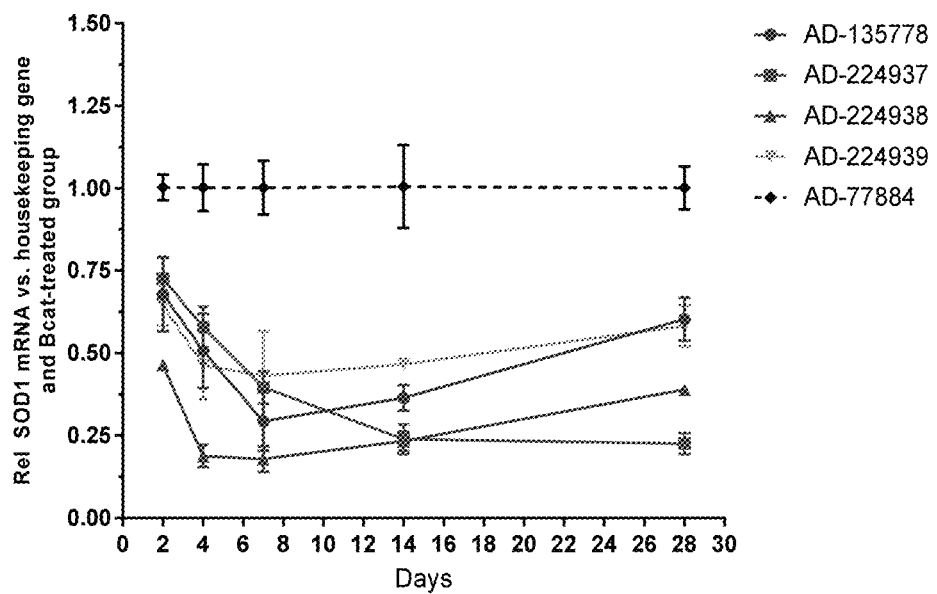
FIG. 9 is a graph showing the results of SOD1 mRNA silencing by a single intrathecal injection of various exemplary siRNA conjugates in Thoracic Spine of Sprague Dawley Rats.

Gene silencing of SOD1 mRNA (Mean±SD levels) in Thoracic Spine of Sprague Dawley Rats was studied with siRNA conjugates listed in Table 2, after a single intrathecal injection of at 0.9 mg dose, as compared to endogenous control and beta catenin treated group. The results are shown in FIG. 9.

Figure 10:
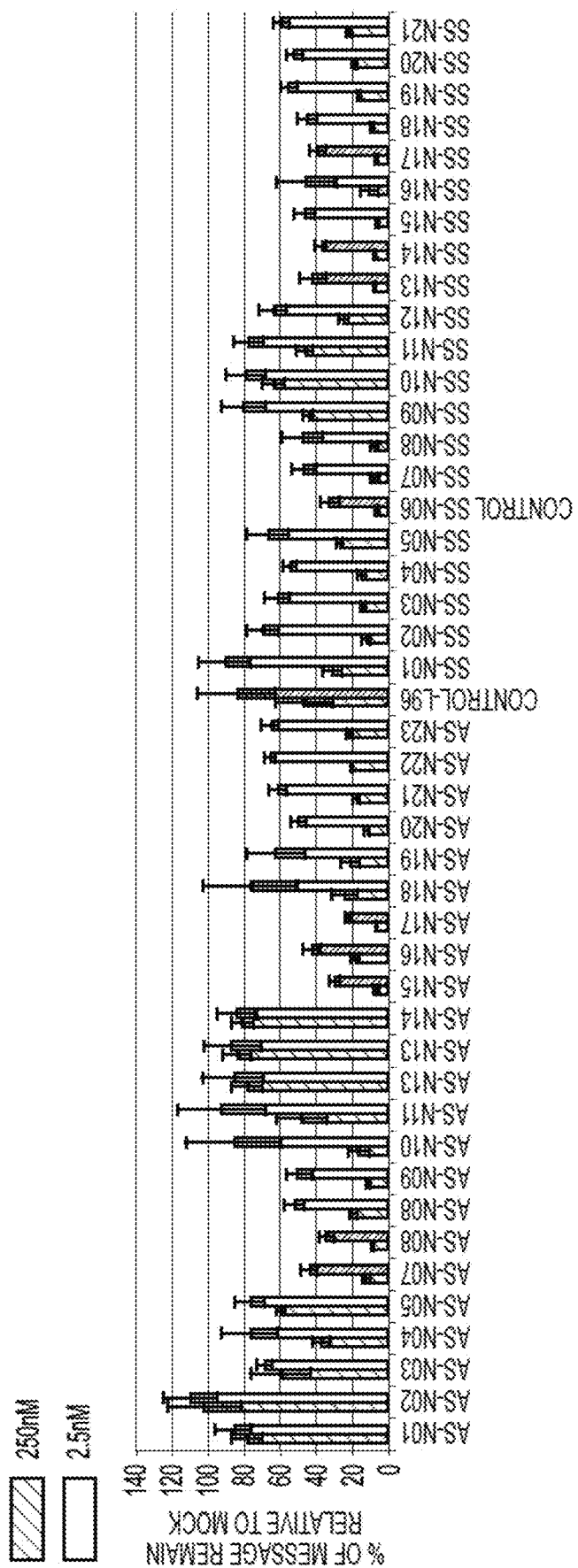
FIG. 10 shows the results of primay cyno hepatocyte (PCH) free uptake (without transfection agent) for cells incubated with a F12 siRNA, modified by conjugating a lipophilic moiety (C16) at each position of the antisense strand and sense strand, at 2.5 and 250 nM concentrations by measuring F12 mRNA levels after 24 hours using RT-qPCR.
Figure 11:
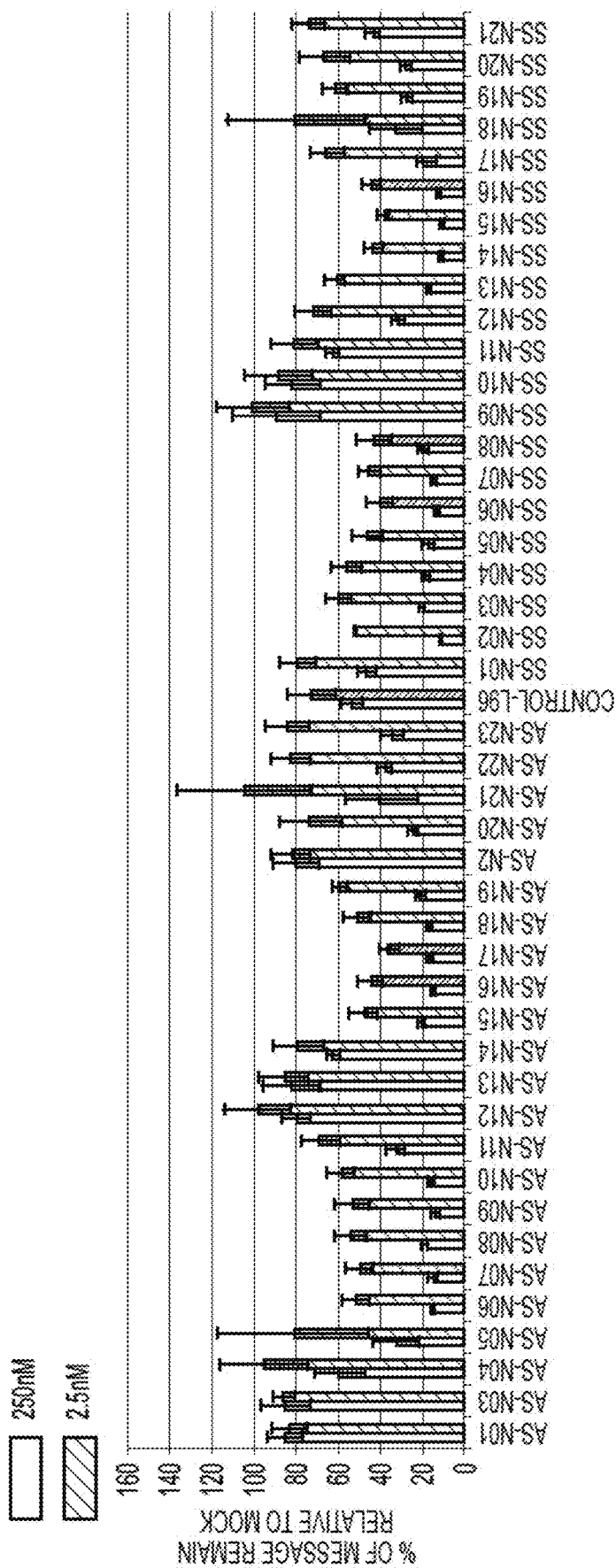
FIG. 11 shows the results of primay cyno hepatocyte (PCH) free uptake (without transfection agent) for cells incubated with a F12 siRNA, modified by conjugating a lipophilic moiety (C16) at each position of the antisense strand and sense strand, at 2.5 and 250 nM concentrations by measuring F12 mRNA levels after 24 hours using RT-qPCR.

Example 13: Positional Impact of Lipophilic Modification (C16) Across the siRNA Sequence The effect of the position of the lipophilic modification across the entire siRNA sequence on both sense and antisense strands was evaluated in mouse hepatocytes using GalNAc conjugates (based two F12 sequences, shown in Table 3). Cells were incubated with each siRNA conjugate (listed in Table 3) at 2.5 and 250 nM concentrations for free uptake (without transfection agent) and F12 mRNA was measured after 24 hours by RT-qPCR (as shown in FIG. 10 and FIG. 11). 2.5 μL of each siRNA's from Table 3 per well were added to 40 μL of William's E Medium (Life Technology) containing ~5×10³ PMH cells in a 384-well-plate. Cells were incubated at 37° C. at 5% $CO_2$ for 24 hours prior to RNA purification. Values are plotted as a fraction of untreated control cells. Each sample was run in technical duplicate, and each point represents the mean of 2 biological samples±% error. GAPDH served as the internal control and the values of remaining F12 mRNA's were plotted relative to untreated controls. In vitro activity of F12 siRNA's having a C16 modification in one of the internal positions in primary cyno hepatocytes showed that there are regions in siRNA duplexes where the C16-conjugate is tolerated and all positions are not equally active.

TABLE 3 siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|
| AD-75869.5 | A-152253.6 | F12 | 55 | sense | gsasaacuCfaAfUfAfaag(Uhd)gcuuuaL96 | 8966.96 | 8962.29 |
| | A-148543.78 | F12 | 56 | antis | usAfsaagCfacuuuauUfgAfguuucsusg | 7610.04 | 7606.12 |
| AD-75868.17 | A-151278.15 | F12 | 57 | sense | gsasaac(Uhd)CfaAfUfAfaagugcuuuaL96 | 8966.96 | 8962.29 |
| | A-148543.69 | F12 | 56 | antis | usAfsaagCfacuuuauUfgAfguuucsusg | 7610.04 | 7606.12 |
| AD-148062.1 | A-147454.151 | F12 | 58 | sense | gsasaacuCfaAfUfAfaagucuuuaL96 | 8756.56 | 8752.06 |
| | A-293109.1 | F12 | 59 | antis | usAfsaagCfacuuuauUf(Ghd)Afguuucsusg | 7820.44 | 7816.35 |
| AD-148064.1 | A-147454.153 | F12 | 58 | sense | gsasaacuCfaAfUfAfaagucuuuaL96 | 8756.56 | 8752.06 |
| | A-293111.1 | F12 | 60 | antis | usAfsaagCfacuuuauUfgAf(Ghd)uuucsusg | 7820.44 | 7816.35 |
| AD-84861.2 | A-168581.2 | F12 | 61 | sense | gsasaacuCfaAfUfAfaagug(Chd)uuuaL96 | 8966.95 | 8962.29 |
| | A-148543.80 | F12 | 56 | antis | usAfsaagCfacuuuauUfgAfguuucsusg | 7610.04 | 7606.12 |
| AD-148045.1 | A-293092.1 | F12 | 62 | sense | gsasaacuCfaAfUfAfa(Ahd)gugcuuuaL96 | 8966.97 | 8962.29 |
| | A-148543.76 | F12 | 56 | antis | usAfsaagCfacuuuauUfgAfguuucsusg | 7610.04 | 7606.12 |
| AD-148046.1 | A-293093.1 | F12 | 63 | sense | gsasaacuCfaAfUfAfaa(Ghd)ugcuuuaL96 | 8966.97 | 8962.29 |
| | A-148543.77 | F12 | 56 | antis | usAfsaagCfacuuuauUfgAfguuucsusg | 7610.04 | 7606.12 |
| AD-84859.2 | A-168579.2 | F12 | 64 | sense | gsasaacu(Chd)aAfUfAfaagugcuuuaL96 | 8978.99 | 8974.31 |
| | A-148543.70 | F12 | 56 | antis | usAfsaagCfacuuuauUfgAfguuucsusg | 7610.04 | 7606.12 |
| AD-148041.1 | A-293088.1 | F12 | 65 | sense | gsasaacuCf(Ahd)AfUfAfaagugcuuuaL96 | 8966.97 | 8962.29 |
| | A-148543.71 | F12 | 56 | antis | usAfsaagCfacuuuauUfgAfguuucsusg | 7610.04 | 7606.12 |
| AD-148056.1 | A-147454.144 | F12 | 58 | sense | gsasaacuCfaAfUfAfaagucuuuaL96 | 8756.56 | 8752.06 |
| | A-293103.1 | F12 | 66 | antis | usAfsaagCfa(Chd)uuuauUfgAfguuucsusg | 7820.43 | 7816.35 |
| AD-84862.2 | A-168582.2 | F12 | 67 | sense | gsasaacuCfaAfUfAfaaguc(Uhd)uuaL96 | 8966.96 | 8962.29 |
| | A-148543.81 | F12 | 56 | antis | usAfsaagCfacuuuauUfgAfguuucsusg | 7610.04 | 7606.12 |
| AD-148047.1 | A-293094.1 | F12 | 68 | sense | gsasaacuCfaAfUfAfaagu(Ghd)cuuuaL96 | 8966.97 | 8962.29 |
| | A-148543.79 | F12 | 56 | antis | usAfsaagCfacuuuauUfgAfguuucsusg | 7610.04 | 7606.12 |
| AD-148057.1 | A-147454.145 | F12 | 58 | sense | gsasaacuCfaAfUfAfaagucuuuaL96 | 8756.56 | 8752.06 |
| | A-293104.1 | F12 | 69 | antis | usAfsaagCfac(Uhd)uuauUfgAfguuucsusg | 7820.43 | 7816.35 |

TABLE 3-continued siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|
| AD-148084.1 | A-293131.1 | F12 | 70 | sense | gsasacucAfaUfAfAfagu(Ghd)cuuugaL96 | 8982.97 | 8978.29 |
| | A-170430.18 | F12 | 71 | antis | usCfsaaaGfcAfCfuuuaUfuGfaguucscsu | 7544.96 | 7541.09 |
| AD-148071.1 | A-293118.1 | F12 | 72 | sense | gs(Ahds)acucAfaUfAfAfagugcuuugaL96 | 8982.96 | 8978.29 |
| | A-170430.5 | F12 | 71 | antis | usCfsaaaGfcAfCfuuuaUfuGfaguucscsu | 7544.96 | 7541.09 |
| AD-148083.1 | A-293130.1 | F12 | 73 | sense | gsasacucAfaUfAfAfag(Uhd)gcuuugaL96 | 8982.96 | 8978.29 |
| | A-170430.17 | F12 | 71 | antis | usCfsaaaGfcAfCfuuuaUfuGfaguucscsu | 7544.96 | 7541.09 |
| AD-148067.1 | A-147454.156 | F12 | 58 | sense | gsasaacuCfaAfUfAfaagugcuuuaL96 | 8756.56 | 8752.06 |
| | A-293114.1 | F12 | 74 | antis | usAfsaagCfacuuuauUfgAfguu(Uhd)csusg | 7820.43 | 7816.35 |
| AD-148037.1 | A-293084.1 | F12 | 75 | sense | gs(Ahds)aacuCfaAfUfAfaagugcuuuaL96 | 8966.96 | 8962.29 |
| | A-148543.65 | F12 | 56 | antis | usAfsaagCfacuuuauUfgAfguuucsusg | 7610.04 | 7606.12 |
| AD-148085.1 | A-293132.1 | F12 | 76 | sense | gsasacucAfaUfAfAfagug(Chd)uuugaL96 | 8982.95 | 8978.29 |
| | A-170430.19 | F12 | 71 | antis | usCfsaaaGfcAfCfuuuaUfuGfaguucscsu | 7544.96 | 7541.09 |
| AD-148055.1 | A-147454.143 | F12 | 58 | sense | gsasaacuCfaAfUfAfaagugcuuuaL96 | 8756.56 | 8752.06 |
| | A-293102.1 | F12 | 77 | antis | usAfsaagCf(Ahd)cuuuauUfgAfguuucsusg | 7820.44 | 7816.35 |
| AD-148075.1 | A-293122.1 | F12 | 78 | sense | gsasacu(Chd)AfaUfAfAfagugcuuugaL96 | 8982.95 | 8978.29 |
| | A-170430.9 | F12 | 71 | antis | usCfsaaaGfcAfCfuuuaUfuGfaguucscsu | 7544.96 | 7541.09 |
| AD-148038.1 | A-293085.1 | F12 | 79 | sense | gsas(Ahd)acuCfaAfUfAfaagugcuuuaL96 | 8966.97 | 8962.29 |
| | A-148543.66 | F12 | 56 | antis | usAfsaagCfacuuuauUfgAfguuucsusg | 7610.04 | 7606.12 |
| AD-148099.1 | A-170194.18 | F12 | 80 | sense | gsasacucAfaUfAfAfagugcuuugaL96 | 8772.56 | 8768.05 |
| | A-293146.1 | F12 | 81 | antis | usCfsaaaGfcAf(Chd)uuuaUfuGfaguucscsu | 7767.38 | 7763.34 |
| AD-148076.1 | A-293123.1 | F12 | 82 | sense | gsasacuc(Ahd)aUfAfAfagugcuuugaL96 | 8995 | 8990.3 |
| | A-170430.10 | F12 | 71 | antis | usCfsaaaGfcAfCfuuuaUfuGfaguucscsu | 7544.96 | 7541.09 |
| AD-148039.1 | A-293086.1 | F12 | 83 | sense | gsasa(Ahd)cuCfaAfUfAfaagugcuuuaL96 | 8966.97 | 8962.29 |
| | A-148543.67 | F12 | 56 | antis | usAfsaagCfacuuuauUfgAfguuucsusg | 7610.04 | 7606.12 |
| AD-148106.1 | A-170194.25 | F12 | 80 | sense | gsasacucAfaUfAfAfagugcuuugaL96 | 8772.56 | 8768.05 |
| | A-293153.1 | F12 | 84 | antis | usCfsaaaGfcAfCfuuuaUfu(Ghd)aguucscsu | 7767.4 | 7763.34 |
| AD-148097.1 | A-170194.16 | F12 | 80 | sense | gsasacucAfaUfAfAfagugcuuugaL96 | 8772.56 | 8768.05 |
| | A-293144.1 | F12 | 85 | antis | usCfsaaaGf(Chd)AfCfuuuaUfuGfaguucscsu | 7755.35 | 7751.32 |
| AD-148096.1 | A-170194.15 | F12 | 80 | sense | gsasacucAfaUfAfAfagugcuuugaL96 | 8772.56 | 8768.05 |
| | A-293143.1 | F12 | 86 | antis | usCfsaaa(Ghd)cAfCfuuuaUfuGfaguucscsu | 7767.4 | 7763.34 |
| AD-84864.2 | A-168584.2 | F12 | 87 | sense | gsasaacuCfaAfUfAfaagucuu(Uhd)aL96 | 8966.96 | 8962.29 |
| | A-148543.83 | F12 | 56 | antis | usAfsaagCfacuuuauUfgAfguuucsusg | 7610.04 | 7606.12 |
| AD-148058.1 | A-147454.146 | F12 | 58 | sense | gsasaacuCfaAfUfAfaagugcuuuaL96 | 8756.56 | 8752.06 |
| | A-293105.1 | F12 | 88 | antis | usAfsaagCfacu(Uhd)uauUfgAfguuucsusg | 7820.43 | 7816.35 |
| AD-148107.1 | A-170194.26 | F12 | 80 | sense | gsasacucAfaUfAfAfagugcuuugaL96 | 8772.56 | 8768.05 |
| | A-293154.1 | F12 | 89 | antis | usCfsaaaGfcAfCfuuuaUfuGf(Ahd)guucscsu | 7755.36 | 7751.32 |

TABLE 3-continued siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|
| AD-148108.1 | A-170194.27 | F12 | 80 | sense | gsasacucAfaUfAfAfagugcuuugaL96 | 8772.56 | 8768.05 |
| | A-293155.1 | F12 | 90 | antis | usCfsaaaGfcAfCfuuuaUfuGfa(Ghd)uucscsu | 7755.36 | 7751.32 |
| AD-148100.1 | A-170194.19 | F12 | 80 | sense | gsasacucAfaUfAfAfagugcuuugaL96 | 8772.56 | 8768.05 |
| | A-293147.1 | F12 | 91 | antis | usCfsaaaGfcAfCf(Uhd)uuaUfuGfaguucscsu | 7755.35 | 7751.32 |
| AD-148082.1 | A-293129.1 | F12 | 92 | sense | gsasacucAfaUfAfAfa(Ghd)ugcuuugaL96 | 8982.97 | 8978.29 |
| | A-170430.16 | F12 | 71 | antis | usCfsaaaGfcAfCfuuuaUfuGfaguucscsu | 7544.96 | 7541.09 |
| AD-148074.1 | A-293121.1 | F12 | 93 | sense | gsasac(Uhd)cAfaUfAfAfagugcuuugaL96 | 8982.96 | 8978.29 |
| | A-170430.8 | F12 | 71 | antis | usCfsaaaGfcAfCfuuuaUfuGfaguucscsu | 7544.96 | 7541.09 |
| AD-79643.2 | A-147454.157 | F12 | 58 | sense | gsasaacuCfaAfUfAfaagugcuuuaL96 | 8756.56 | 8752.06 |
| | A-157363.2 | F12 | 94 | antis | usAfsaagCfacuuuauUfgAfguuu(Chds)usg | 7820.36 | 7816.35 |
| AD-84863.2 | A-168583.2 | F12 | 95 | sense | gsasaacuCfaAfUfAfaagugcu(Uhd)uaL96 | 8966.96 | 8962.29 |
| | A-148543.82 | F12 | 56 | antis | usAfsaagCfacuuuauUfgAfguuucsusg | 7610.04 | 7606.12 |
| AD-148063.1 | A-147454.152 | F12 | 58 | sense | gsasaacuCfaAfUfAfaagugcuuuaL96 | 8756.56 | 8752.06 |
| | A-293110.1 | F12 | 96 | antis | usAfsaagCfacuuuauUfg(Ahd)guuucsusg | 7832.48 | 7828.37 |
| AD-148073.1 | A-293120.1 | F12 | 97 | sense | gsasa(Chd)ucAfaUfAfAfagugcuuugaL96 | 8982.95 | 8978.29 |
| | A-170430.7 | F12 | 71 | antis | usCfsaaaGfcAfCfuuuaUfuGfaguucscsu | 7544.96 | 7541.09 |
| AD-148086.1 | A-293133.1 | F12 | 98 | sense | gsasacucAfaUfAfAfagugc(Uhd)uugaL96 | 8982.96 | 8978.29 |
| | A-170430.20 | F12 | 71 | antis | usCfsaaaGfcAfCfuuuaUfuGfaguucscsu | 7544.96 | 7541.09 |
| AD-148098.1 | A-170194.17 | F12 | 80 | sense | gsasacucAfaUfAfAfagugcuuugaL96 | 8772.56 | 8768.05 |
| | A-293145.1 | F12 | 99 | antis | usCfsaaaGfc(Ahd)CfuuuaUfuGfaguucscsu | 7767.4 | 7763.34 |
| AD-148054.1 | A-147454.142 | F12 | 58 | sense | gsasaacuCfaAfUfAfaagugcuuuaL96 | 8756.56 | 8752.06 |
| | A-293101.1 | F12 | 100 | antis | usAfsaag(Chd)acuuuauUfgAfguuucsusg | 7832.47 | 7828.37 |
| AD-148077.1 | A-293124.1 | F12 | 101 | sense | gsasacucAf(Ahd)UfAfAfagugcuuugaL96 | 8982.97 | 8978.28 |
| | A-170430.11 | F12 | 71 | antis | usCfsaaaGfcAfCfuuuaUfuGfaguucscsu | 7544.96 | 7541.09 |
| AD-148068.1 | A-147454.158 | F12 | 58 | sense | gsasaacuCfaAfUfAfaagugcuuuaL96 | 8756.56 | 8752.06 |
| | A-293115.1 | F12 | 102 | antis | usAfsaagCfacuuuauUfgAfguuucs(Uhds)g | 7820.37 | 7816.35 |
| AD-148072.1 | A-293119.1 | F12 | 103 | sense | gsas(Ahd)cucAfaUfAfAfagugcuuugaL96 | 8982.97 | 8978.28 |
| | A-170430.6 | F12 | 71 | antis | usCfsaaaGfcAfCfuuuaUfuGfaguucscsu | 7544.96 | 7541.09 |
| AD-148105.1 | A-170194.24 | F12 | 80 | sense | gsasacucAfaUfAfAfagugcuuugaL96 | 8772.56 | 8768.05 |
| | A-293152.1 | F12 | 104 | antis | usCfsaaaGfcAfCfuuuaUf(Uhd)Gfaguucscsu | 7755.35 | 7751.32 |
| AD-148066.1 | A-147454.155 | F12 | 58 | sense | gsasaacuCfaAfUfAfaagugcuuuaL96 | 8756.56 | 8752.06 |
| | A-293113.1 | F12 | 105 | antis | usAfsaagCfacuuuauUfgAfgu(Uhd)ucsusg | 7820.43 | 7816.35 |
| AD-148069.1 | A-147454.159 | F12 | 58 | sense | gsasaacuCfaAfUfAfaagugcuuuaL96 | 8756.56 | 8752.06 |
| | A-293116.1 | F12 | 106 | antis | usAfsaagCfacuuuauUfgAfguuucsus(Ghd) | 7820.44 | 7816.35 |
| AD-148109.1 | A-170194.28 | F12 | 80 | sense | gsasacucAfaUfAfAfagugcuuugaL96 | 8772.56 | 8768.05 |
| | A-293156.1 | F12 | 107 | antis | usCfsaaaGfcAfCfuuuaUfuGfag(Uhd)ucscsu | 7755.35 | 7751.32 |
| AD-148048.1 | A-293095.1 | F12 | 108 | sense | gsasaacuCfaAfUfAfaagugcuuu(Ahd)L96 | 8966.97 | 8962.29 |

TABLE 3-continued siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|
|  | A-148543.84 | F12 | 56 | antis | usAfsaagCfacuuuauUfgAfguuucsusg | 7610.04 | 7606.12 |
| AD-148065.1 | A-147454.154 | F12 | 58 | sense | gsasaacuCfaAfUfAfaagugcuuuaL96 | 8756.56 | 8752.06 |
|  | A-293112.1 | F12 | 109 | antis | usAfsaagCfacuuuauUfgAfg(Uhd)uucsusg | 7820.43 | 7816.35 |
| AD-148044.1 | A-293091.1 | F12 | 110 | sense | gsasaacuCfaAfUfAf(Ahd)agugcuuuaL96 | 8966.97 | 8962.29 |
|  | A-148543.75 | F12 | 56 | antis | usAfsaagCfacuuuauUfgAfguuucsusg | 7610.04 | 7606.12 |
| AD-148110.1 | A-170194.29 | F12 | 80 | sense | gsasacucAfaUfAfagugcuuugaL96 | 8772.56 | 8768.05 |
|  | A-293157.1 | F12 | 111 | antis | usCfsaaaGfcAfCfuuuaUfuGfagu(Uhd)cscsu | 7755.35 | 7751.32 |
| AD-148040.1 | A-293087.1 | F12 | 112 | sense | gsasaa(Chd)cuCfaAfUfAfaagugcuuuaL96 | 9286.16 | 9281.35 |
|  | A-148543.68 | F12 | 56 | antis | usAfsaagCfacuuuauUfgAfguuucsusg | 7610.04 | 7606.12 |
| AD-148088.1 | A-293135.1 | F12 | 113 | sense | gsasacucAfaUfAfAfagugcuu(Uhd)gaL96 | 8982.96 | 8978.29 |
|  | A-170430.22 | F12 | 71 | antis | usCfsaaaGfcAfCfuuuaUfuGfaguucscsu | 7544.96 | 7541.09 |
| AD-148089.1 | A-293136.1 | F12 | 114 | sense | gsasacucAfaUfAfAfagugcuuu(Ghd)aL96 | 8982.97 | 8978.29 |
|  | A-170430.23 | F12 | 71 | antis | usCfsaaaGfcAfCfuuuaUfuGfaguucscsu | 7544.96 | 7541.09 |
| AD-148036.1 | A-293083.1 | F12 | 115 | sense | (Ghds)asaacuCfaAfUfAfaagugcuuuaL96 | 8966.96 | 8962.29 |
|  | A-148543.64 | F12 | 56 | antis | usAfsaagCfacuuuauUfgAfguuucsusg | 7610.04 | 7606.12 |
| AD-148081.1 | A-293128.1 | F12 | 116 | sense | gsasacucAfaUfAfAf(Ahd)gugcuuugaL96 | 8982.97 | 8978.28 |
|  | A-170430.15 | F12 | 71 | antis | usCfsaaaGfcAfCfuuuaUfuGfaguucscsu | 7544.96 | 7541.09 |
| AD-148095.1 | A-170194.14 | F12 | 80 | sense | gsasacucAfaUfAfAfagugcuuugaL96 | 8772.56 | 8768.05 |
|  | A-293142.1 | F12 | 117 | antis | usCfsaa(Ahd)GfcAfCfuuuaUfuGfaguucscsu | 7755.36 | 7751.32 |
| AD-148087.1 | A-293134.1 | F12 | 118 | sense | gsasacucAfaUfAfAfagugcu(Uhd)ugaL96 | 8982.96 | 8978.29 |
|  | A-170430.21 | F12 | 71 | antis | usCfsaaaGfcAfCfuuuaUfuGfaguucscsu | 7544.96 | 7541.09 |
| AD-148101.1 | A-170194.20 | F12 | 80 | sense | gsasacucAfaUfAfAfagugcuuugaL96 | 8772.56 | 8768.05 |
|  | A-293148.1 | F12 | 119 | antis | usCfsaaaGfcAfCfu(Uhd)uaUfuGfaguucscsu | 7755.35 | 7751.32 |
| AD-148113.1 | A-170194.32 | F12 | 80 | sense | gsasacucAfaUfAfAfagugcuuugaL96 | 8772.56 | 8768.05 |
|  | A-293160.1 | F12 | 120 | antis | usCfsaaaGfcAfCfuuuaUfuGfaguucscs(Uhd) | 7755.35 | 7751.32 |
| AD-148052.1 | A-147454.140 | F12 | 58 | sense | gsasaacuCfaAfUfAfaagugcuuuaL96 | 8756.56 | 8752.06 |
|  | A-293099.1 | F12 | 121 | antis | usAfsa(Ahd)gCfacuuuauUfgAfguuucsusg | 7820.44 | 7816.35 |
| AD-148112.1 | A-170194.31 | F12 | 80 | sense | gsasacucAfaUfAfAfagugcuuugaL96 | 8772.56 | 8768.05 |
|  | A-293159.1 | F12 | 122 | antis | usCfsaaaGfcAfCfuuuaUfuGfaguucs(Chds)u | 7755.28 | 7751.32 |
| AD-148111.1 | A-170194.30 | F12 | 80 | sense | gsasacucAfaUfAfAfagugcuuugaL96 | 8772.56 | 8768.05 |
|  | A-293158.1 | F12 | 123 | antis | usCfsaaaGfcAfCfuuuaUfuGfaguu(Chds)csu | 7755.28 | 7751.32 |
| AD-148042.1 | A-293089.1 | F12 | 124 | sense | gsasaacuCfa(Ahd)UfAfaagugcuuuaL96 | 8979 | 8974.31 |
|  | A-148543.72 | F12 | 56 | antis | usAfsaagCfacuuuauUfgAfguuucsusg | 7610.04 | 7606.12 |
| AD-148090.1 | A-293137.1 | F12 | 125 | sense | gsasacucAfaUfAfAfagugcuuug(Ahd)L96 | 8982.97 | 8978.28 |
|  | A-170430.24 | F12 | 71 | antis | usCfsaaaGfcAfCfuuuaUfuGfaguucscsu | 7544.96 | 7541.09 |
| AD-148043.1 | A-293090.1 | F12 | 126 | sense | gsasaacuCfaAfUf(Ahd)aagugcuuuaL96 | 8979 | 8974.31 |
|  | A-148543.74 | F12 | 56 | antis | usAfsaagCfacuuuauUfgAfguuucsusg | 7610.04 | 7606.12 |

TABLE 3-continued siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|
| AD-74210.29 | A-147454.136 | F12 | 58 | sense | gsasaacuCfaAfUfAfaagugcuuuaL96 | 8756.56 | 8752.06 |
| | A-148543.63 | F12 | 56 | antis | usAfsaagCfacuuuauUfgAfguuucsusg | 7610.04 | 7606.12 |
| AD-148070.1 | A-293117.1 | F12 | 127 | sense | (Ghds)asacucAfaUfAfAfagugcuuugaL96 | 8982.96 | 8978.28 |
| | A-170430.4 | F12 | 71 | antis | usCfsaaaGfcAfCfuuuaUfuGfaguucscsu | 7544.96 | 7541.09 |
| AD-148059.1 | A-147454.147 | F12 | 58 | sense | gsasaacuCfaAfUfAfaagugcuuuaL96 | 8756.56 | 8752.06 |
| | A-293106.1 | F12 | 128 | antis | usAfsaagCfacuu(Uhd)auUfgAfguuucsusg | 7820.43 | 7816.35 |
| AD-85402.4 | A-170194.9 | F12 | 80 | sense | gsasacucAfaUfAfAfagugcuuugaL96 | 8772.56 | 8768.05 |
| | A-170430.3 | F12 | 71 | antis | usCfsaaaGfcAfCfuuuaUfuGfaguucscsu | 7544.96 | 7541.09 |
| AD-148053.1 | A-147454.141 | F12 | 58 | sense | gsasaacuCfaAfUfAfaagugcuuuaL96 | 8756.56 | 8752.06 |
| | A-293100.1 | F12 | 129 | antis | usAfsaa(Ghd)CfacuuuauUfgAfguuucsusg | 7820.44 | 7816.35 |
| AD-148051.1 | A-147454.139 | F12 | 58 | sense | gsasaacuCfaAfUfAfaagugcuuuaL96 | 8756.56 | 8752.06 |
| | A-293098.1 | F12 | 130 | antis | usAfs(Ahd)agCfacuuuauUfgAfguuucsusg | 7820.44 | 7816.35 |
| AD-148094.1 | A-170194.13 | F12 | 80 | sense | gsasacucAfaUfAfAfagugcuuugaL96 | 8772.56 | 8768.05 |
| | A-293141.1 | F12 | 131 | antis | usCfsa(Ahd)aGfcAfCfuuuaUfuGfaguucscsu | 7755.36 | 7751.32 |
| AD-148080.1 | A-293127.1 | F12 | 132 | sense | gsasacucAfaUfAfAf(Ahd)agugcuuugaL96 | 8995 | 8990.3 |
| | A-170430.14 | F12 | 71 | antis | usCfsaaaGfcAfCfuuuaUfuGfaguucscsu | 7544.96 | 7541.09 |
| AD-148104.1 | A-170194.23 | F12 | 80 | sense | gsasacucAfaUfAfAfagugcuuugaL96 | 8772.56 | 8768.05 |
| | A-293151.1 | F12 | 133 | antis | usCfsaaaGfcAfCfuuua(Uhd)uGfaguucscsu | 7767.39 | 7763.34 |
| AD-84860.2 | A-168580.2 | F12 | 134 | sense | gsasaacuCfaAf(Uhd)AfaagugcuuuaL96 | 8978.99 | 8974.31 |
| | A-148543.73 | F12 | 56 | antis | usAfsaagCfacuuuauUfgAfguuucsusg | 7610.04 | 7606.12 |
| AD-148049.1 | A-147454.137 | F12 | 58 | sense | gsasaacuCfaAfUfAfaagugcuuuaL96 | 8756.56 | 8752.06 |
| | A-293096.1 | F12 | 135 | antis | (Uhds)AfsaagCfacuuuauUfgAfguuucsusg | 7820.37 | 7816.35 |
| AD-148060.1 | A-147454.148 | F12 | 58 | sense | gsasaacuCfaAfUfAfaagugcuuuaL96 | 8756.56 | 8752.06 |
| | A-293107.1 | F12 | 136 | antis | usAfsaagCfacuuu(Ahd)uUfgAfguuucsusg | 7820.44 | 7816.35 |
| AD-148102.1 | A-170194.21 | F12 | 80 | sense | gsasacucAfaUfAfAfagugcuuugaL96 | 8772.56 | 8768.05 |
| | A-293149.1 | F12 | 137 | antis | usCfsaaaGfcAfCfuu(Uhd)aUfuGfaguucscsu | 7755.35 | 7751.32 |
| AD-148092.1 | A-170194.11 | F12 | 80 | sense | gsasacucAfaUfAfAfagugcuuugaL96 | 8772.56 | 8768.05 |
| | A-293139.1 | F12 | 138 | antis | us(Chds)aaaGfcAfCfuuuaUfuGfaguucscsu | 7767.32 | 7763.34 |
| AD-148061.1 | A-147454.150 | F12 | 58 | sense | gsasaacuCfaAfUfAfaagugcuuuaL96 | 8756.56 | 8752.06 |
| | A-293108.1 | F12 | 139 | antis | usAfsaagCfacuuuau(Uhd)gAfguuucsusg | 7832.47 | 7828.37 |
| AD-148079.1 | A-293126.1 | F12 | 140 | sense | gsasacucAfaUf(Ahd)AfagugcuuugaL96 | 8995 | 8990.3 |
| | A-170430.13 | F12 | 71 | antis | usCfsaaaGfcAfCfuuuaUfuGfaguucscsu | 7544.96 | 7541.09 |
| AD-148103.1 | A-170194.22 | F12 | 80 | sense | gsasacucAfaUfAfAfagugcuuugaL96 | 8772.56 | 8768.05 |
| | A-293150.1 | F12 | 141 | antis | usCfsaaaGfcAfCfuuu(Ahd)UfuGfaguucscsu | 7755.36 | 7751.32 |
| AD-79644.2 | A-147454.149 | F12 | 58 | sense | gsasaacuCfaAfUfAfaagugcuuuaL96 | 8756.56 | 8752.06 |
| | A-157364.2 | F12 | 142 | antis | usAfsaagCfacuuua(Uhd)UfgAfguuucsusg | 7820.43 | 7816.35 |
| AD-148093.1 | A-170194.12 | F12 | 80 | sense | gsasacucAfaUfAfAfagugcuuugaL96 | 8772.56 | 8768.05 |

TABLE 3-continued siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|
|  | A-293140.1 | F12 | 143 | antis | usCfs(Ahd)aaaGfcAfCfuuuaUfuGfaguucscsu | 8098.6 | 8094.39 |
| AD-148091.1 | A-170194.10 | F12 | 80 | sense | gsasacucAfaUfAfAfagugcuuugaL96 | 8772.56 | 8768.05 |
|  | A-293138.1 | F12 | 144 | antis | (Uhds)CfsaaaGfcAfCfuuuaUfuGfaguucscsu | 7755.29 | 7751.32 |
| AD-148078.1 | A-293125.1 | F12 | 145 | sense | gsasacucAfa(Uhd)AfAfagugcuuugaL96 | 8994.99 | 8990.31 |
|  | A-170430.12 | F12 | 71 | antis | usCfsaaaGfcAfCfuuuaUfuGfaguucscsu | 7544.96 | 7541.09 |
| AD-148050.1 | A-147454.138 | F12 | 58 | sense | gsasaacuCfaAfUfAfaagugcuuuaL96 | 8756.56 | 8752.06 |
|  | A-293097.1 | F12 | 146 | antis | us(Ahds)aagCfacuuuauUfgAfguuucsusg | 7832.47 | 7828.37 |

\* Upper and lower case letters in italics indicate 2'-deoxy-2'-fluoro (2'-F), and 2'-O-methyl (2'-OMe) sugar modifications, respectively, to adenosine, cytidine, guanosine and uridine; s indicates phosphorothioate (PS) linkage; VP-Vinyl phosphonate vinyl phosphonate; Nhd, 2'-O-hexadecyl; Tam, 2'-O-(N-methylacetamide) thymidine.

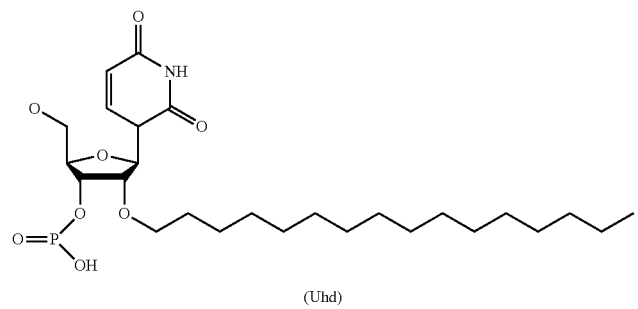

(Uhd)

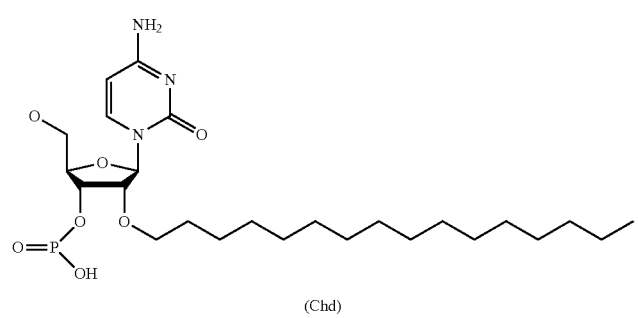

(Chd)

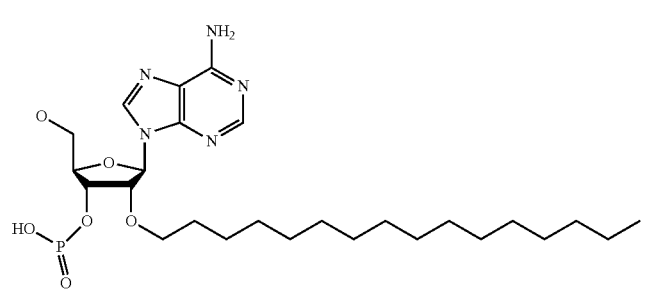

(Ahd)

TABLE 3-continued siRNAs used for positional impact of lipophilic modification (C16) across the siRNA sequences (F12)

| Duplex Name | Oligo Name | target | SEQ ID NO: | strand | oligoSeq | calc Mass | Fount MW |
|---|---|---|---|---|---|---|---|

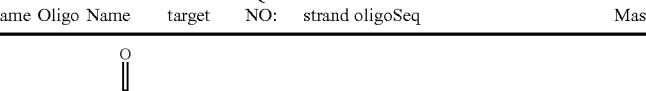

(Ghd)

Example 14. Plasma Protein Binding of C16 siRNA Conjugates

Figure 12:
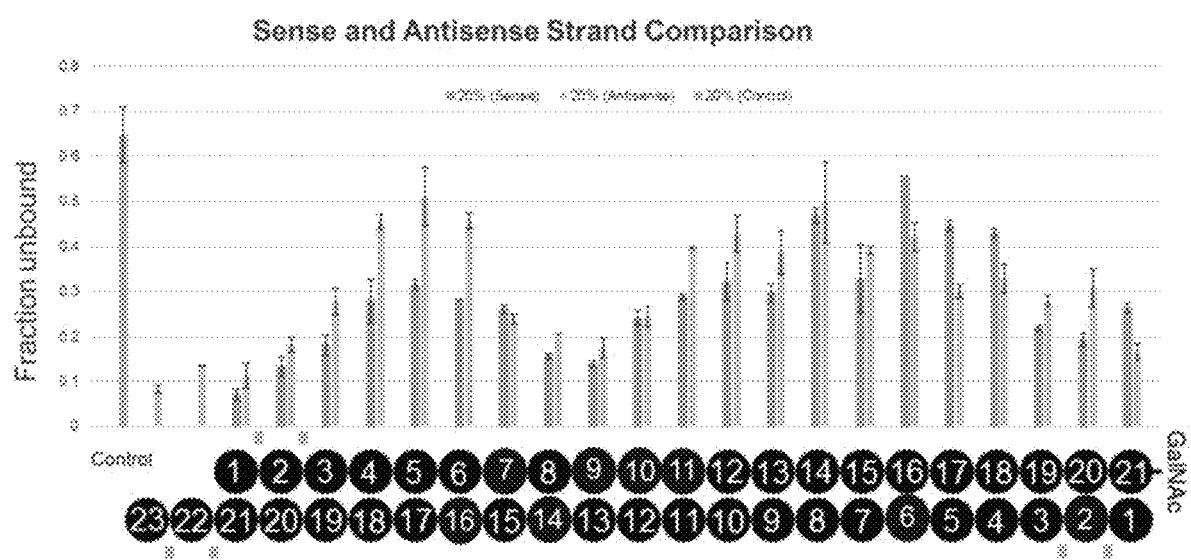
FIG. 12 shows the results of relative hydrophobicity for each position of the antisence strand and sense strand of an siRNA duplex, modified by conjugating a lipophilic moiety (C16) at each position of the antisence strand and sense strand, determined by measuring the unbound fraction using an electrophoretic mobility shift assay after each siRNA conjugate was incubated with human serum albumin.

Protein (using human serum albumin) binding characteristics of siRNA duplexes having lipophilic modifications were determined using an electrophoretic mobility shift assay (EMSA). Duplexes were incubated with human serum albumin and the unbound fraction was determined. Details about the protocols are as follows. Duplexes at a stock concentration of 10 µM were diluted to a final concentration of 0.5 µM (20 µL total volume) containing 0, 20, or 90% serum in 1×PBS. The samples were mixed, centrifuged for 30 seconds, and subsequently incubated at room temperature for 10 minutes. Once incubation was complete, 4 µL of 6×EMSA Gel-loading solution was added to each sample, centrifuged for 30 seconds, and 12 µL of each sample was loaded onto a 26 well BioRad 10% PAGE (polyacrylamide gel electrophoresis). The gel was run for 1 hour at 100 volts. After completion of the run, the gel was removed from the casing and washed in 50 mL of 10% TBE (Tris base, boric acid and EDTA). Once washing was complete, 5 µL of SYBR Gold was added to the gel, allowed to incubate at room temperature for 10 minutes, and the gel-washed again in 50 mL of 10% TBE. A Gel Doc XR+ gel documentation system was used to read the gel using the following parameters: the imaging application was set to SYBR Gold, the size was set to Bio-Rad criterion gel, the exposure was set to automatic for intense bands, the highlight saturated pixels where turned one and the color was set to gray. The detection, molecular weight analysis, and output were all disabled. Once a clean photo of the gel was obtained Image Lab 5.2 was used to process the image. The lanes and bands where manually set to measure band intensity. Band intensities of each sample where normalized to PBS to obtain the fraction of unbound siRNA. From this measurement relative hydrophobicity was determined and was plotted in FIG. 12. Some regions of the duplexes displayed medium protein binding and this translated to better activity in vitro (see Example 13)

Example 15: Determination of Kd Values for Plasma Protein Binding (Correlation to Hydrophobicity)—Lower Number Indicates Tight Binding Procedure for Kd Determination to Human Serum Albumin to Oligonucleotides:

BioRad 10% TBE gel was pre-run at 100 volts for 20 minutes. Duplexes at a stock concentration of 10 µM were diluted to a final concentration of 0.5 µM (20 µL total volume) containing various concentrations of Human Serum Albumin (0 µM to 1000 µM in increments of 100). The samples were mixed, centrifuged for 30 seconds, and subsequently incubated at room temperature for 10 minutes. Once incubation was complete, 4 µL of 6×EMSA Gel-loading solution was added to each sample, centrifuged for 30 seconds, and 12 µL of each sample was loaded onto a 26 well BioRad 10% TBE gel. The gel was run at 50 volts for roughly 20 minutes to allow the entire sample to be loaded on the gel. Once samples were fully loaded the gel was run for 1 hour at 100 volts. After completion of the run, the gel was removed from the casing and washed in 50 mL of 10% TBE. Once washing was complete, 5 µL of SYBR Gold was added to the gel, allowed to incubate at room temperature for 10 minutes, and the gel-washed again in 50 mL of 10% TBE. A Gel Doc XR+ gel documentation system was used to read the gel using the following parameters: the imaging application was set to SYBR Gold, the size was set to Bio-Rad criterion gel, the exposure was set to automatic for intense bands, the highlight saturated pixels where turned one and the color was set to gray. The detection, molecular weight analysis, and output were all disabled. Once a clean photo of the gel was obtained Image Lab 5.2 was used to process the image. The lanes and bands were manually set to measure band intensity. Band intensities of each sample where normalized to that of the duplex without HSA to obtain the fraction of bound siRNA relative to the concentration of HSA. The results are shown in Tables 4-5.

TABLE 4

| ID | Kd values for HSA binding |
|---|---|
| AD-64228 | NA |
| AD-74957 | 8.94 µm |
| AD-74954 | 155 µm |
| A-131350 | 266.4 |
| A-150425 | 353.4 |

TABLE 5

| Duplex Name | Oligo Name | target | SEQ ID NO: | strand | oligoSeq | Exact MW | |
|---|---|---|---|---|---|---|---|
| AD-64228.1 | A-128009.1 | None | 147 | sense | asascaguGfuUfCfUfugcucuauaaL96 | 8681.99 | None |
| | A-128003.8 | mTTR | 148 | antis | usUfsauaGfaGfCfaagaAfcAfcuguususu | 7628.13 | |
| AD-74957.1 | A-150196.1 | mrTTR | 149 | sense | Q11asascaguGfuUfCfUfugcucuauaaL96 | 9387.45 | Chol-@5'end |
| | A-128003.40 | mTTR | 148 | antis | usUfsauaGfaGfCfaagaAfcAfcuguususu | 7628.13 | |
| AD-74954.1 | A-150193.1 | mrTTR | 150 | sense | asascag(Uhd)GfuUfCfUfugcucuauaaL96 | 8892.23 | C16-@N6 |
| | A-128003.37 | mTTR | 148 | antis | usUfsauaGfaGfCfaagaAfcAfcuguususu | 7628.13 | |
| | A-131350.1 | TTR-ASO | 151 | antis | (Teos)(m5Ceos)(Teos)(Teos)(Geos)dGsdTsdTsdAs(m5dCs)dAsdTsdGsdAsdAs(Aeos)(Teos)(m5Ceos)(m5Ceos)(m5Ceos)dAL96 | 9295.01 | ASO |
| | A-150425.1 | NA | 152 | antis | (Teos)(Teos)(Aeos)(Teos)(Aeos)dGsdAsdGs(m5dCs)dAsdAsdGsdAsdAs(m5dCs)(Aeos)(m5Ceos)(Teos)(Geos)(Teo)dAL96 | 9333.04 | ASO |

Example 16: Intrathecal Delivery (IT) of siRNA Conjugates—Single Dose Time Course in Rat FIG. 27. The protocol and siRNA duplexes used for intrathecal injection in the CNS study (FIG. 27 discloses SEQ ID NOS 153-156, respectively, in order).

Figure 27:
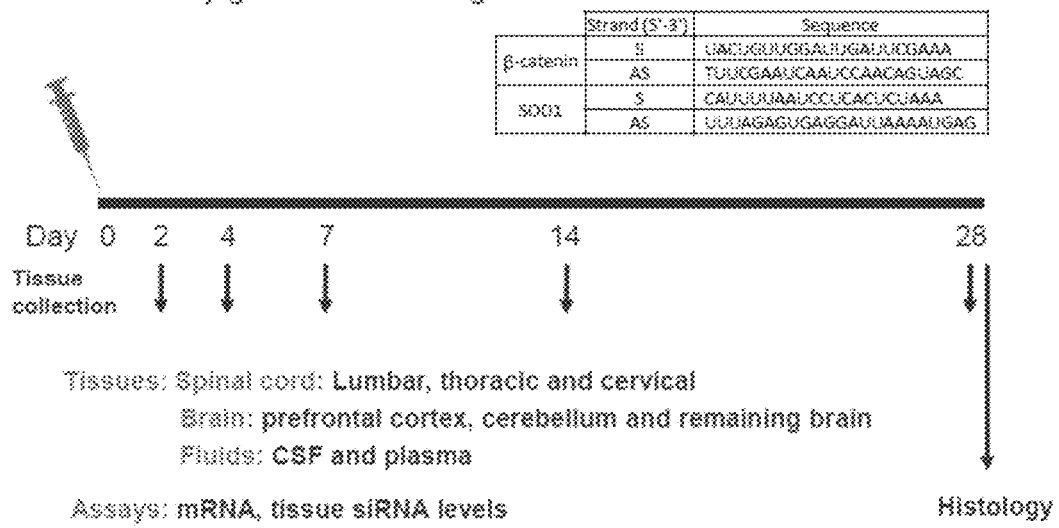
FIG. 27 is a scheme showing the protocol and siRNA duplexes used for intrathecal injection in the CNS study (FIG. 27 discloses SEQ ID NOS 153-156, respectively, in order). SOD1 gene silencing and beta-catenin gene-silencing in rats were studied with siRNA conjugates listed in the table shown in FIG. 27, after a single intrathecal injection at 0.9 mg dose.

SOD1 gene silencing and beta-catenin gene-silencing in rats were studied with siRNA conjugates listed in the table shown in FIG. 27, after a single intrathecal injection at 0.9 mg dose. The results are shown in FIGS. 13-15.

Figure 13A:
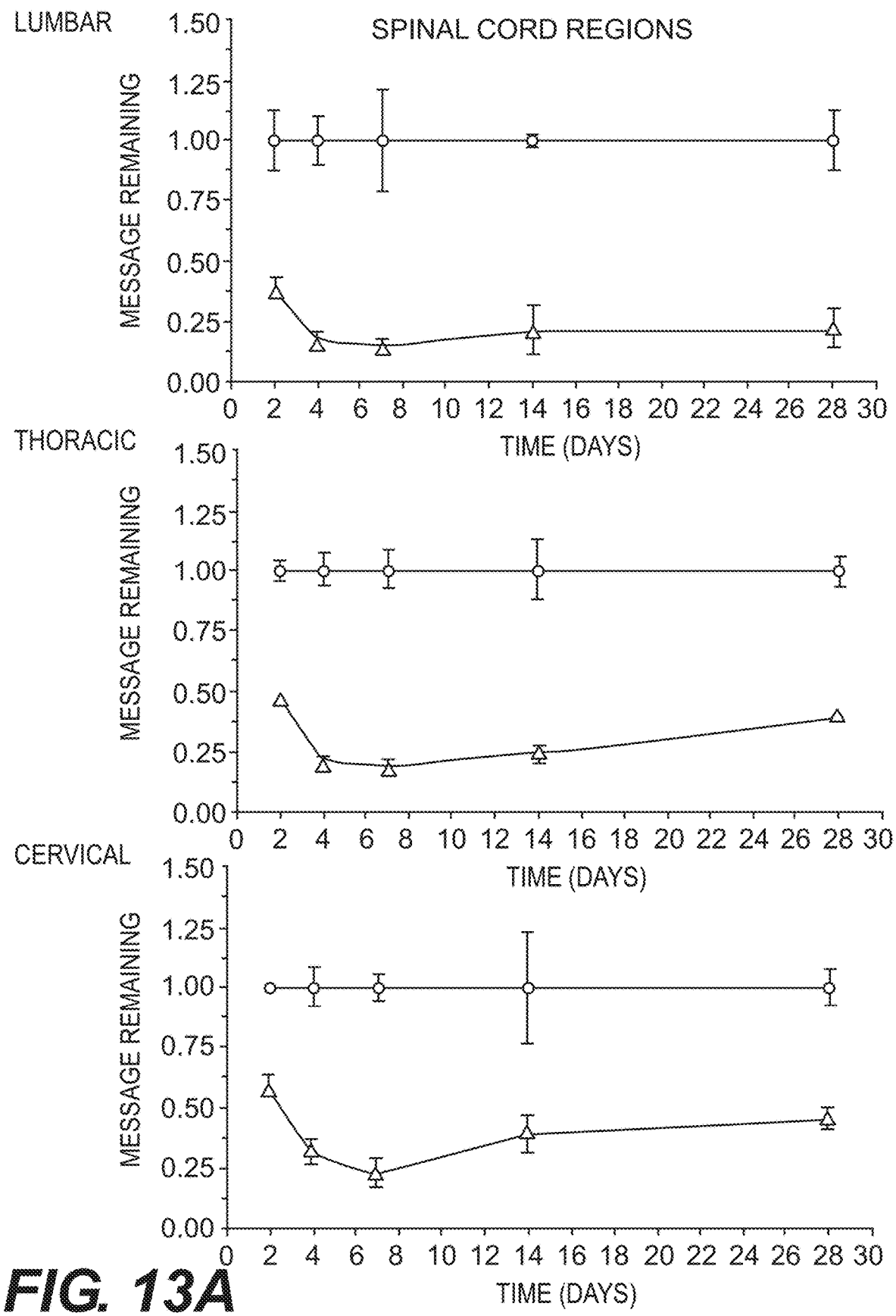
FIGS. 13A-13C show that durable SOD1 mRNA silencing is seen in all regions of the brain and spinal cord tested.
Figure 13B:
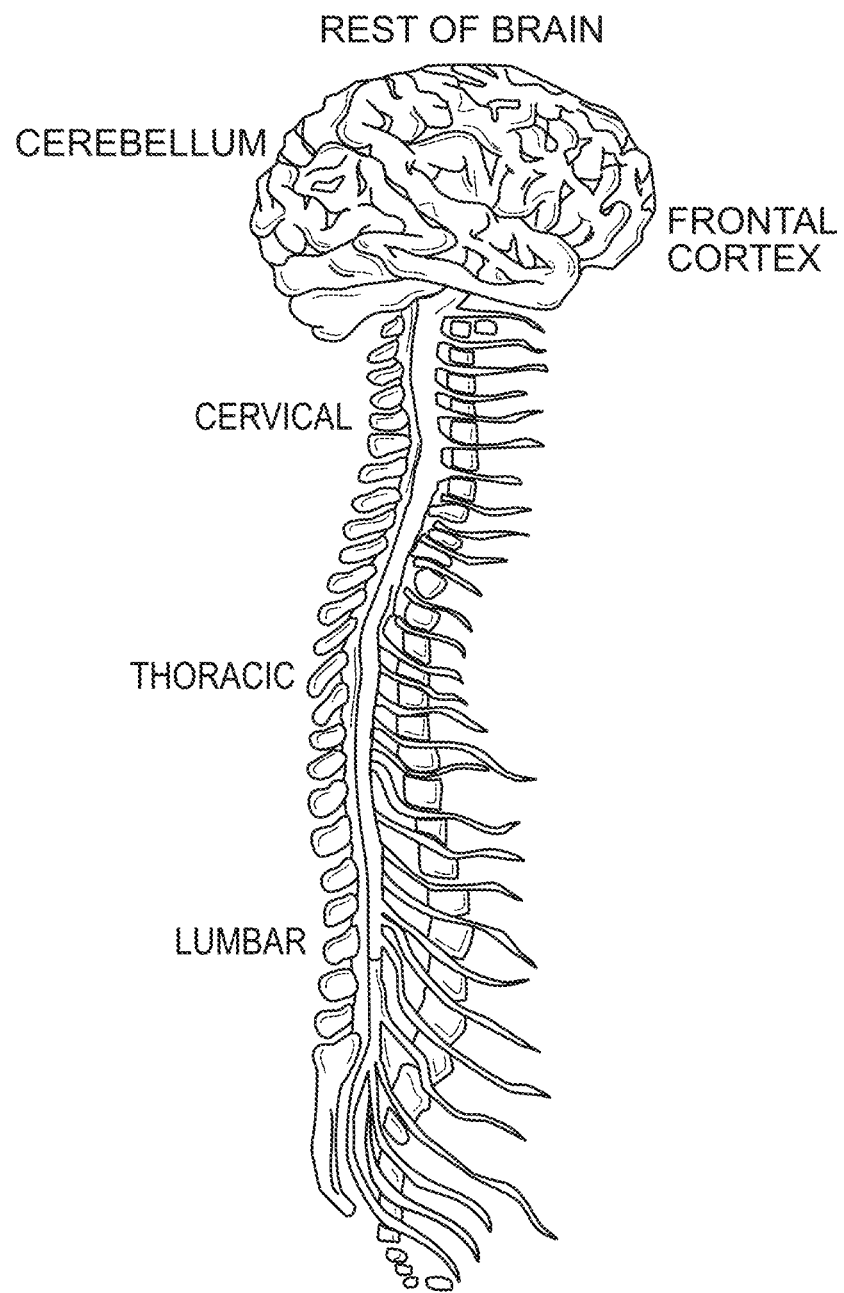
Figure 13C:
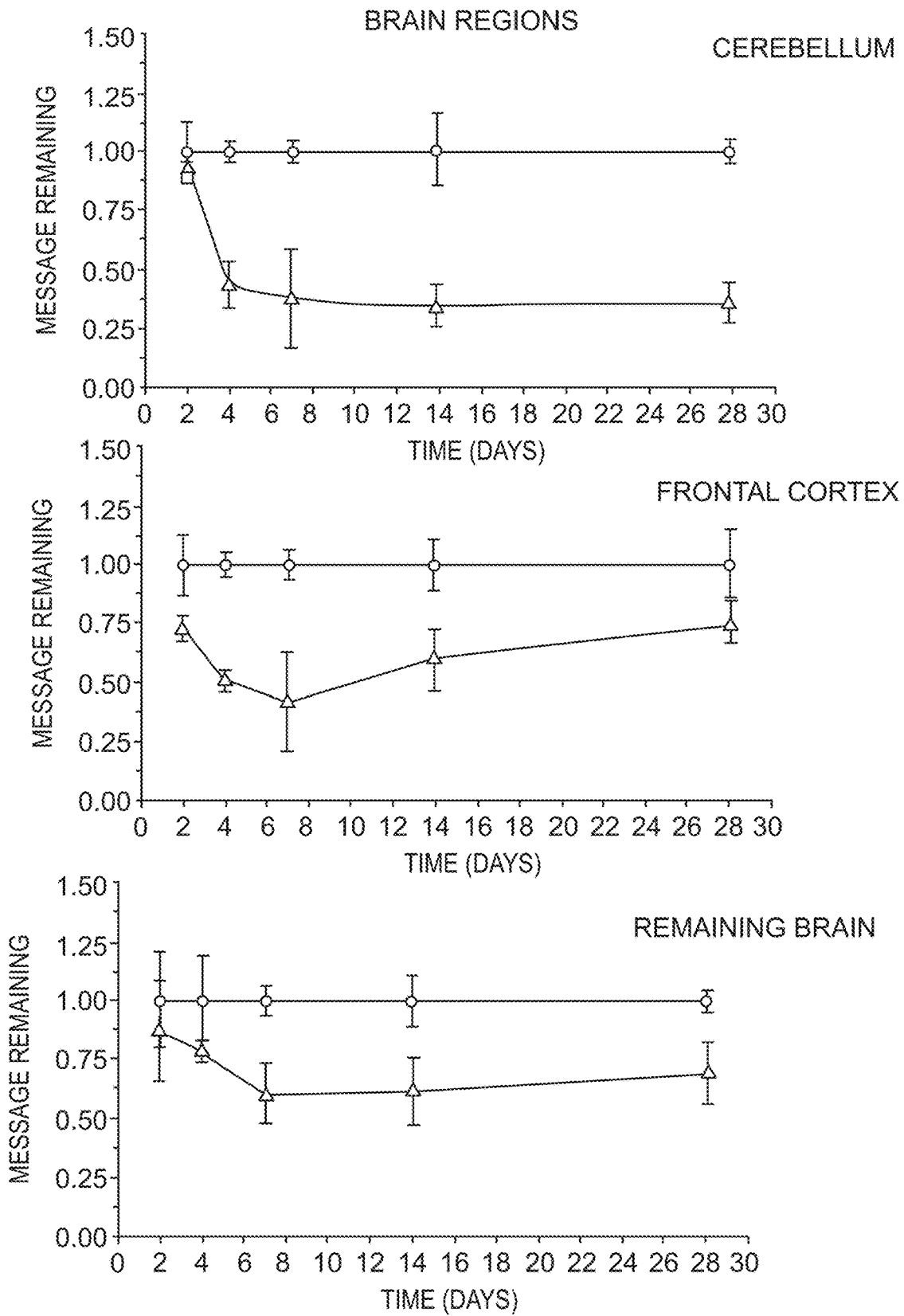
Figure 14A:
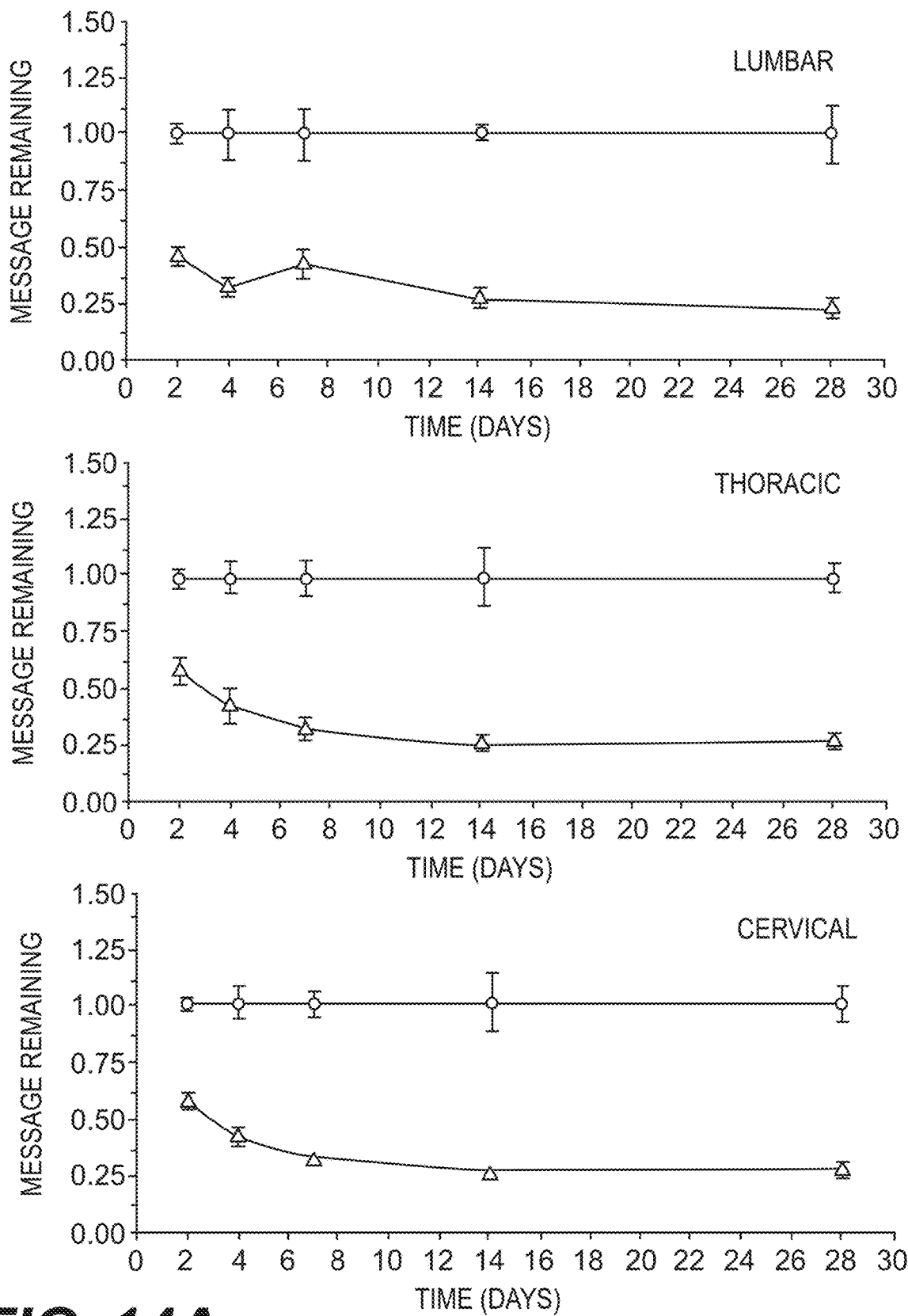
FIGS. 14A-14B show the results of silencing of β-catenin following a single intrathecal dose.
Figure 14B:
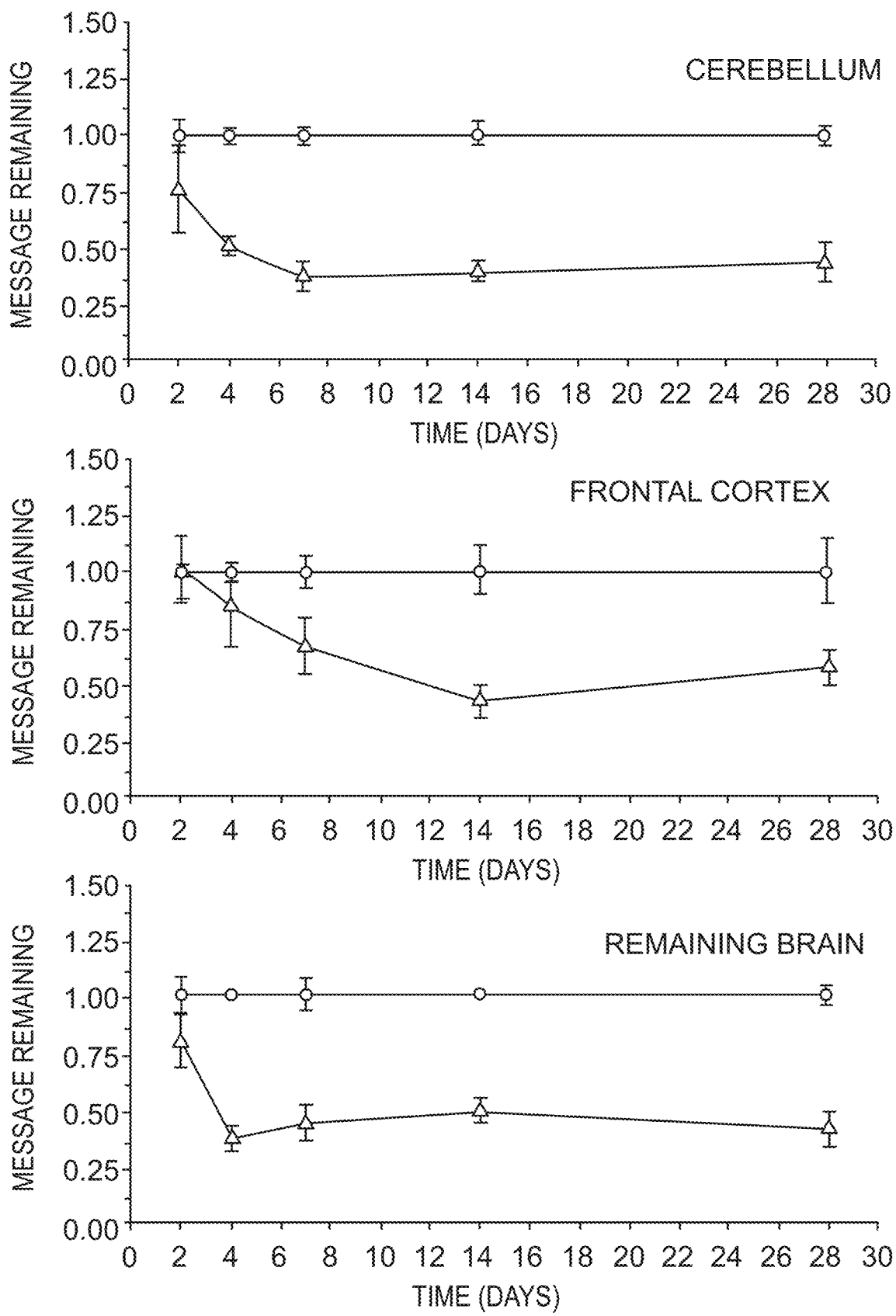
Figure 15A:
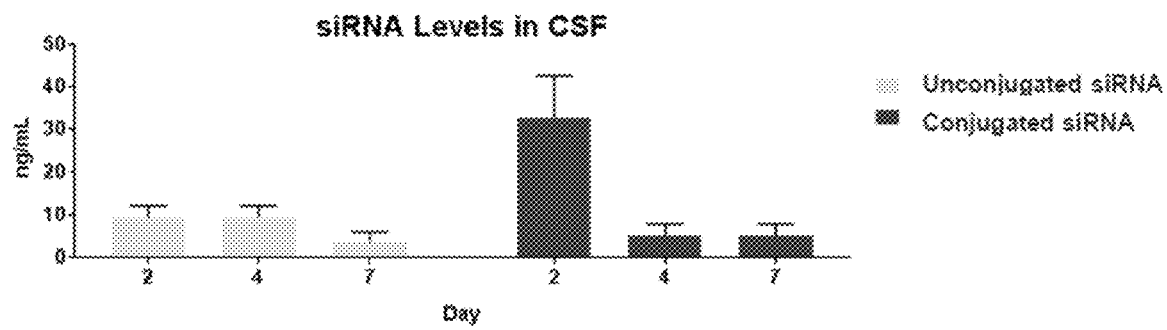
FIGS. 15A-15C show the results of silencing of SOD1 following a single intrathecal dosing of exemplary siRNA duplexes in rats, indicating higher drug levels and robust silencing observed in brain with SOD1 siRNA conjugate.
Figure 15B:
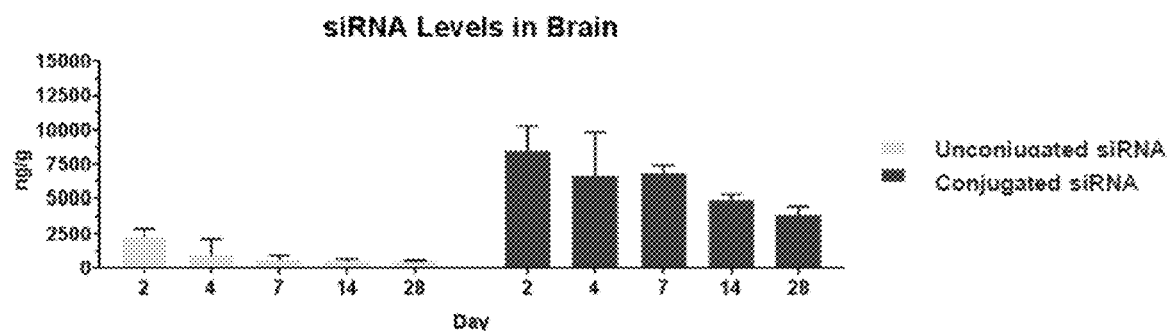
Figure 15C:
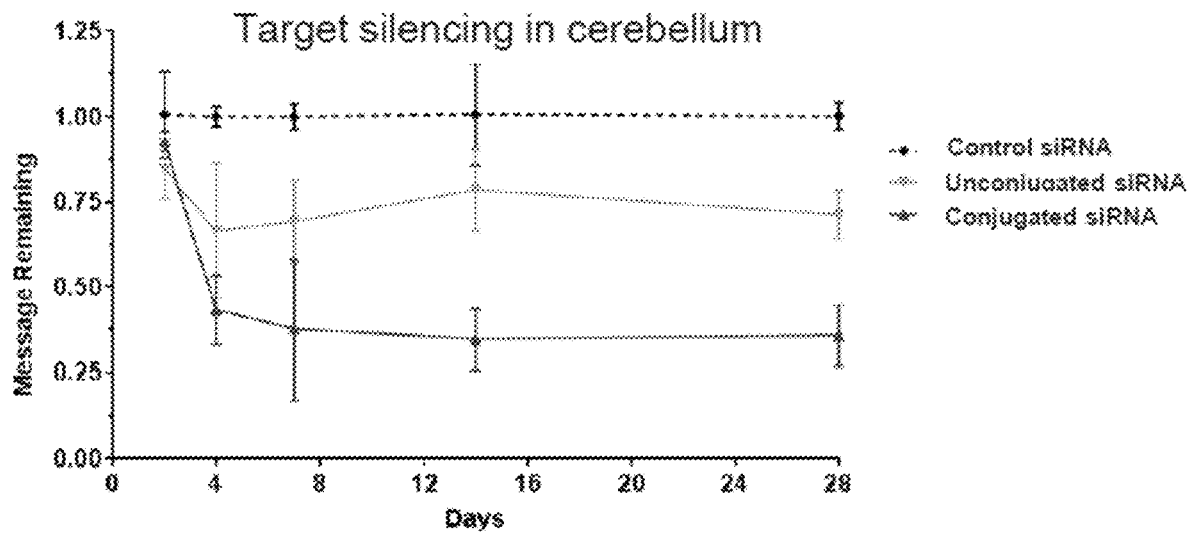

FIG. 13B shows all the regions of the brain and spinal cord tested. FIGS. 13A and 13C show the results of silencing of SOD1 following a single IT dosing of the siRNA duplexes in rats in various regions illustrated in FIG. 13B. As shown in FIGS. 13A and 13C, durable SOD1 mRNA silencing is seen in all regions of the brain and spinal cord tested. FIGS. 14A-14B show the results of silencing of β-catenin following a single IT dosing. As shown in FIGS. 14A-14B, durable β-catenin silencing is seen in all regions of the brain and spinal cord tested. FIG. 15 shows the results of silencing of SOD1 following a single IT dosing of the siRNA duplexes in rats in various regions. FIG. 15A shows the conjugated siRNA levels in CSF, as compared to the unconjugated siRNA levels. As shown in the figure, rapid siRNA clearance from CSF is seen for conjugated siRNA. FIG. 15B shows the conjugated siRNA levels in brain, as compared to the unconjugated siRNA levels. As shown in the figure, conjugated siRNA is seen to have superior uptake and stability in brain over unconjugated siRNA. FIG. 15C shows the conjugated siRNA levels in cerebellum, as compared to the unconjugated siRNA levels and control siRNA levels. As shown in the figure, the increased uptake in brain of conjugated siRNA resulted in substantial improvement in mRNA knockdown, indicating a targeted silencing. FIGS. 15A-15C illustrate higher drug levels and robust silencing observed in brain with SOD1 siRNA conjugate.

Example 17: Further Refining of SOD1 siRNA

TABLE 6

| Duplex Id | Oligo Id | strand | target | SEQ ID NO: | oligoSeq | Molecular Weight | MW found |
|---|---|---|---|---|---|---|---|
| AD-401824 (SOD1 modified) | A-637448 | sense | SOD1 | 157 | csasuuu(Uhd)AfaUfCfCfucacucuasasa | 7043.976 | 7040.254 |
| | A-444402 | Antis | SOD1 | 158 | VPusUfsuagAfgUfGfaggaUfuAfaaaugsasg | 7851.156 | 7847.154 |
| AD-401825 (SOD1 parent) | A-637448 | sense | SOD1 | 157 | csasuuu(Uhd)AfaUfCfCfucacucuasasa | 7043.976 | 7040.254 |
| | A-268862 | Antis | SOD1 | 51 | usUfsuagAfgUfGfaggaUfuAfaaaugsasg | 7775.157 | 7771.175 |

Figure 16A:
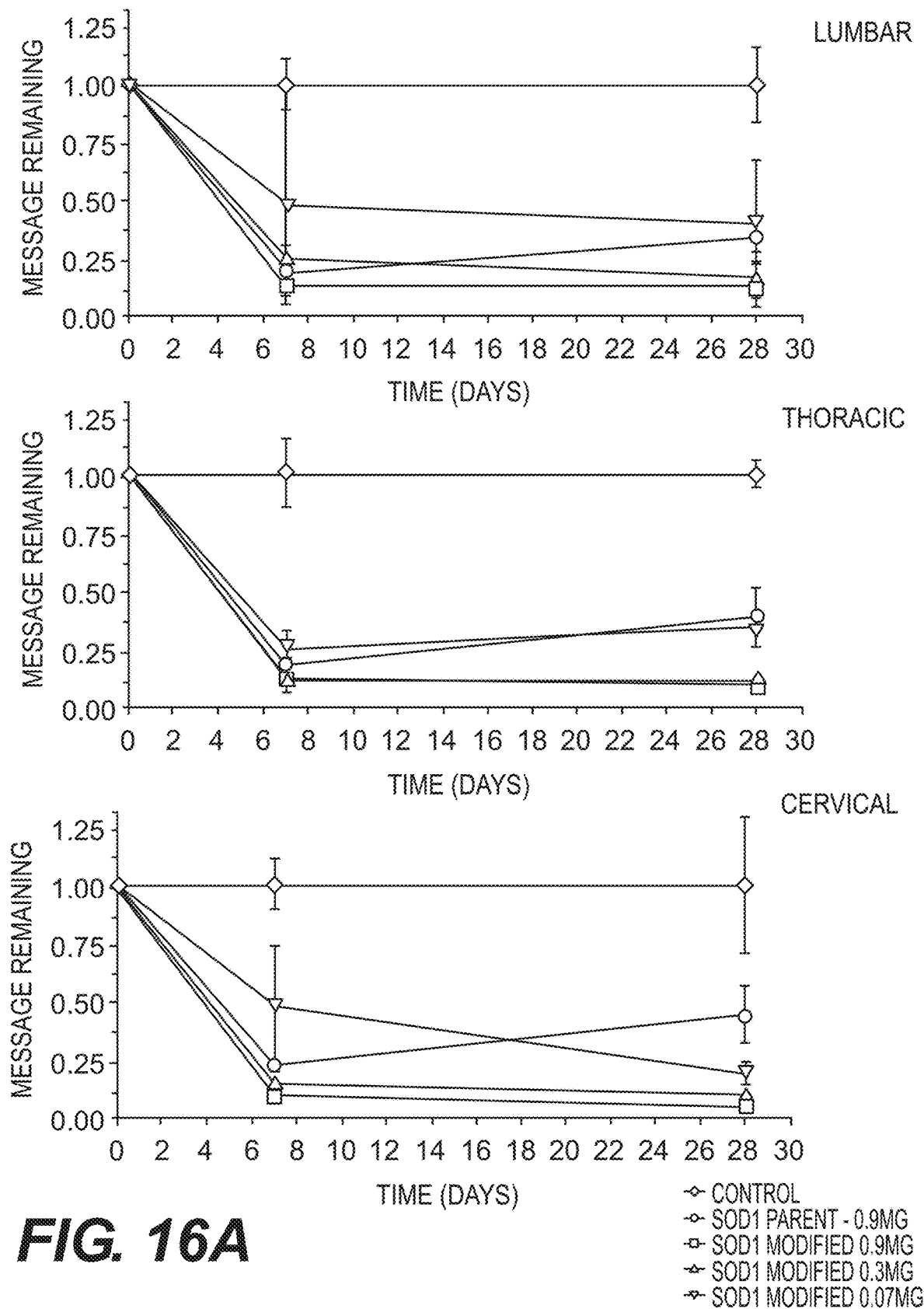
FIGS. 16A-16B show the results of silencing of SOD1 with different chemistry modifications at various doses.
Figure 16B:
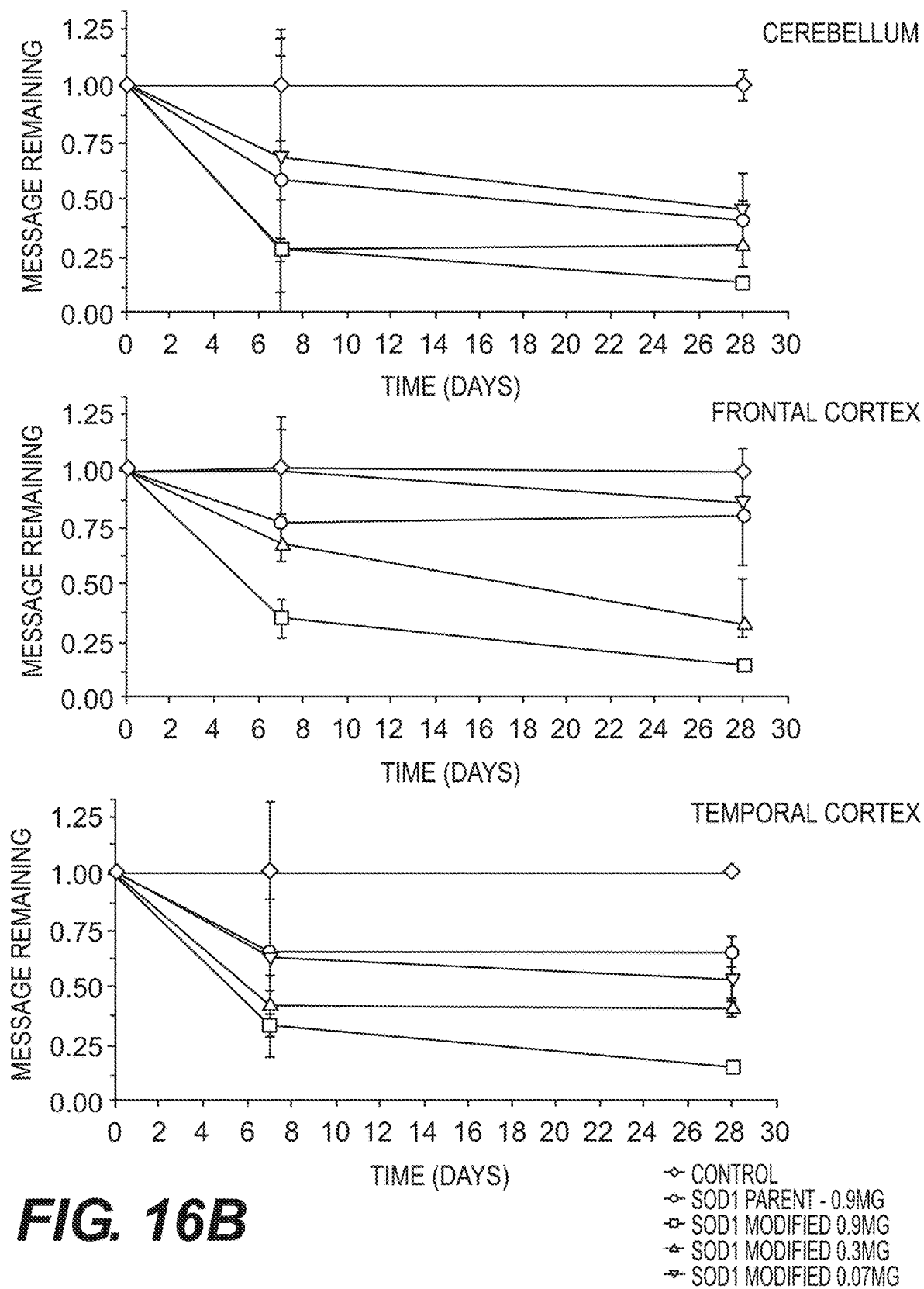

Table 6 shows the SOD1 siRNAs modified with different chemistry. Control is aCSF. FIGS. 16A-16B show the results of silencing of SOD1 with SOD1 siRNAs modified with different chemistry at various doses. As shown in the FIGS. 16A-16B, superior silencing was achieved with modified SOD1 siRNAs as compared to parent SOD1 siRNA, at the dosage level of 10-fold lower.

Example 18: Evaluating Translation of CNS siRNA Conjugate Delivery to Non-Human Primate (NHP)- Single does NHP Design FIG. 28. The protocol and siRNA duplexes used for intrathecal injection in the CNS study (FIG. 28 discloses SEQ ID NOS 153-154, respectively, in order).

Figure 28:
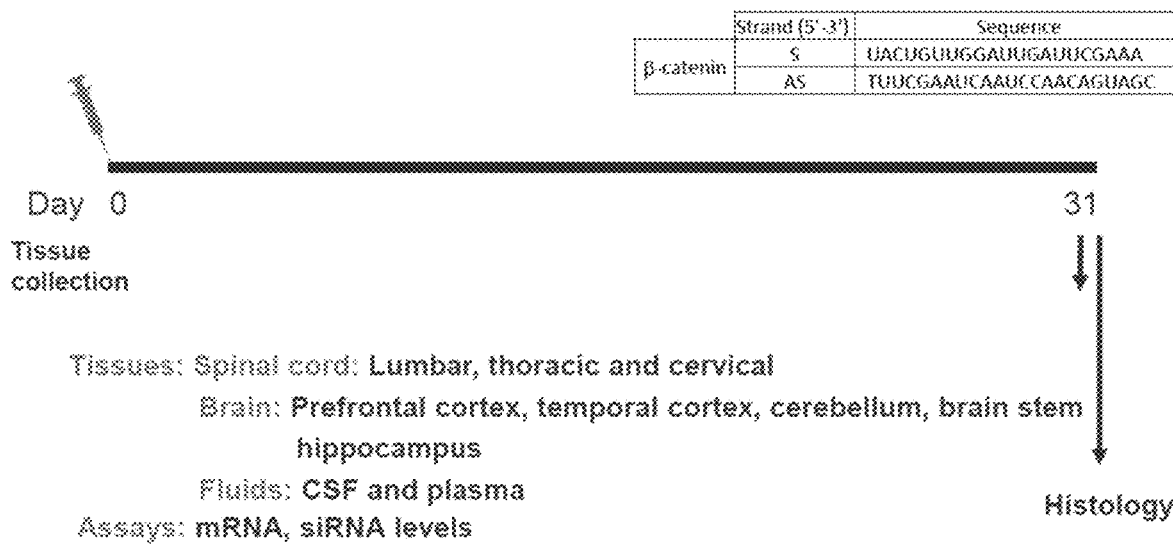
FIG. 28 is a scheme showing The protocol and siRNA duplexes used for intrathecal injection in the CNS study (FIG. 28 discloses SEQ ID NOS 153-154, respectively, in order). Beta-catenin gene-silencing in non-human primates was studied with siRNA conjugates listed in the table shown in FIG. 28, after a single intrathecal injection at 72 mg bolus dose.

Beta-catenin gene-silencing in non-human primates was studied with siRNA conjugates listed in the table shown in FIG. 28, after a single intrathecal injection at 72 mg bolus dose. The results are shown in FIGS. 17-23.

Figure 17:
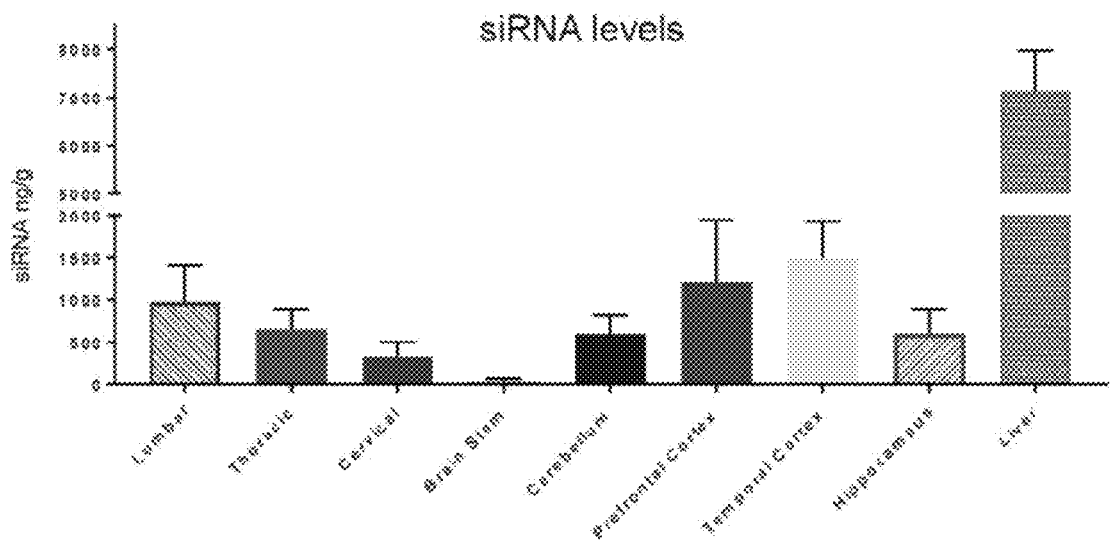
FIG. 17 shows the results of β-catenin siRNA levels following a single intrathecal (IT) dosing of an exemplary siRNA duplex in various regions of non-human primate (NHP) at Day 31.
Figure 18:
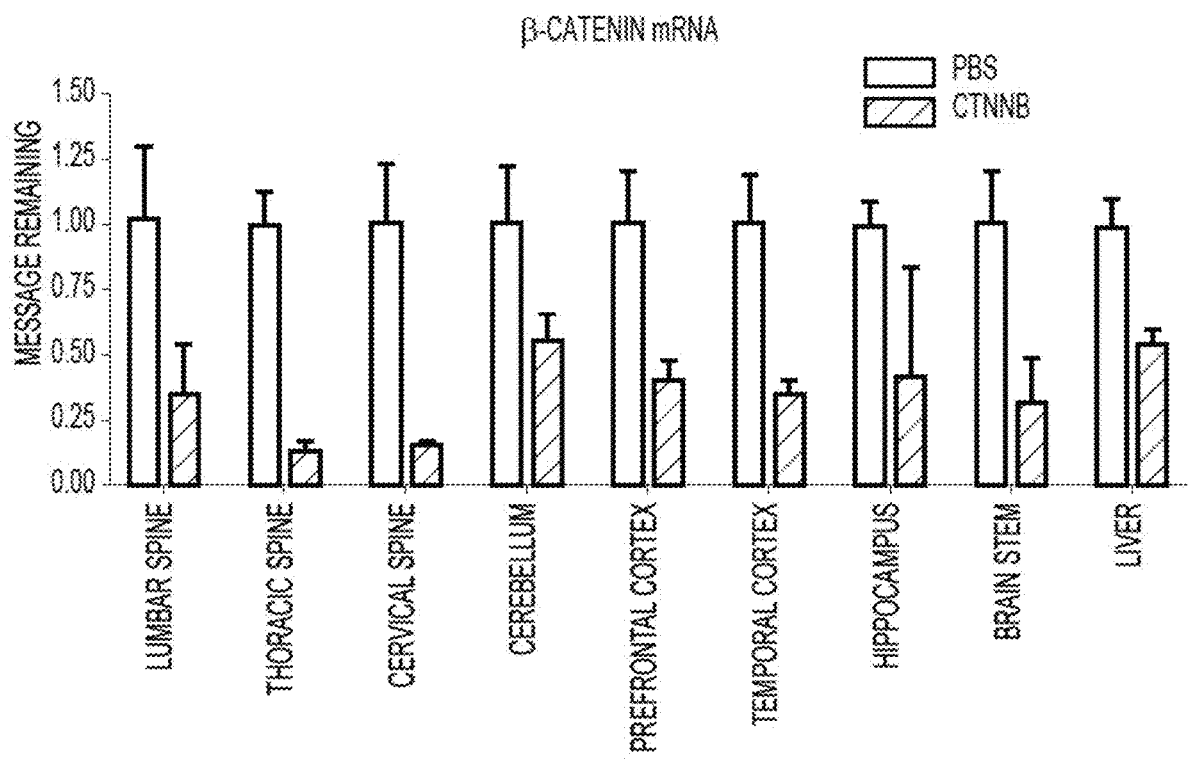
FIG. 18 shows the results of robust gene silencing of β-catenin mRNA in various tissues, at Day 31.
Figure 19:
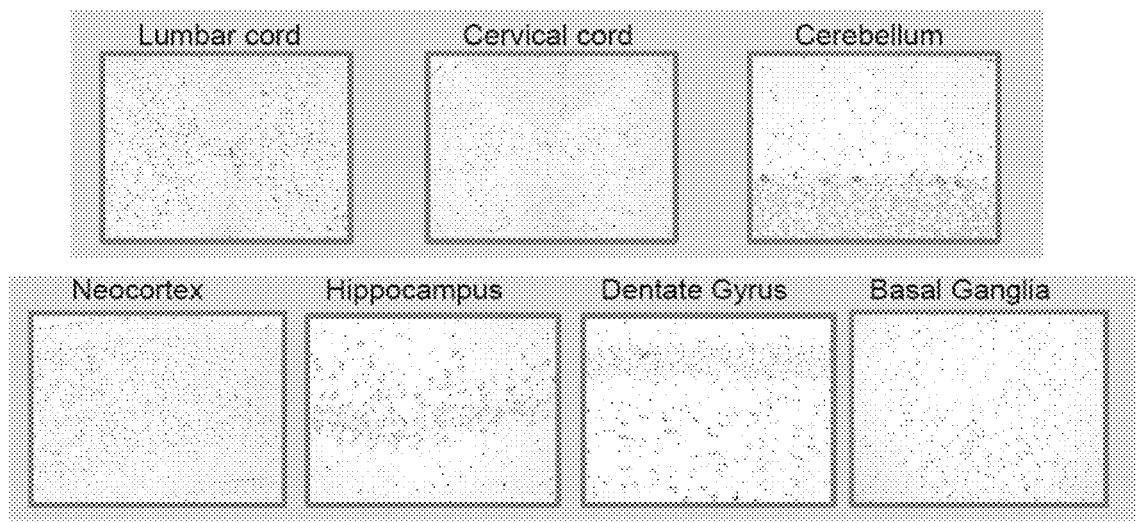
FIG. 19 shows pictures illustrating siRNAs distributed throughout the CNS in NHP, following the single IT dosing.
Figure 20:
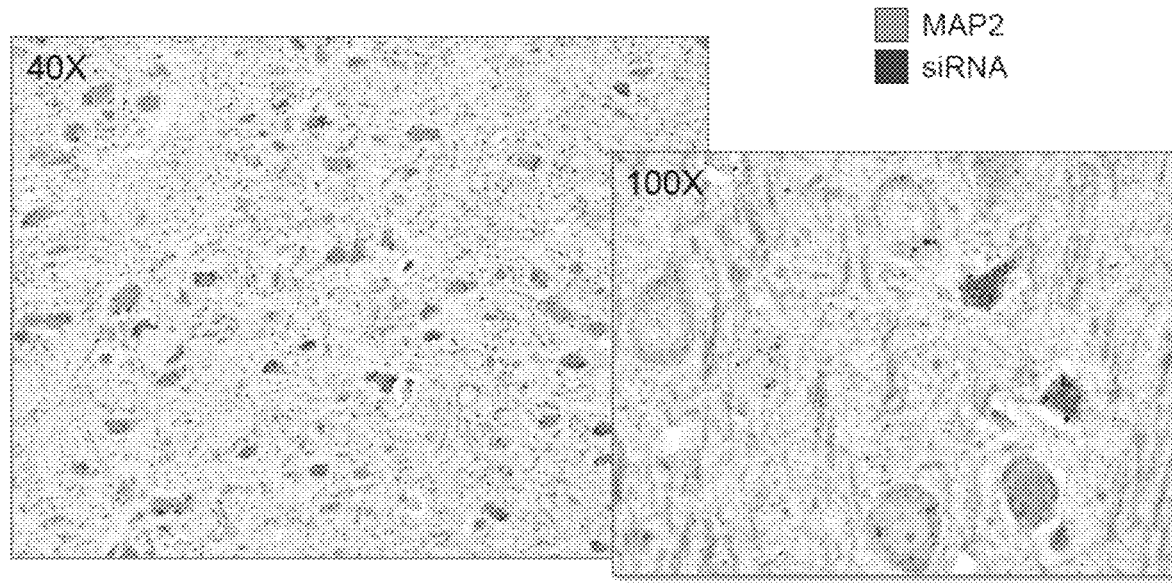
FIG. 20 shows pictures illustrating the siRNA conjugates localized to neurons, following the single IT dosing. MAP2 is a neuronal marker.
Figure 21:
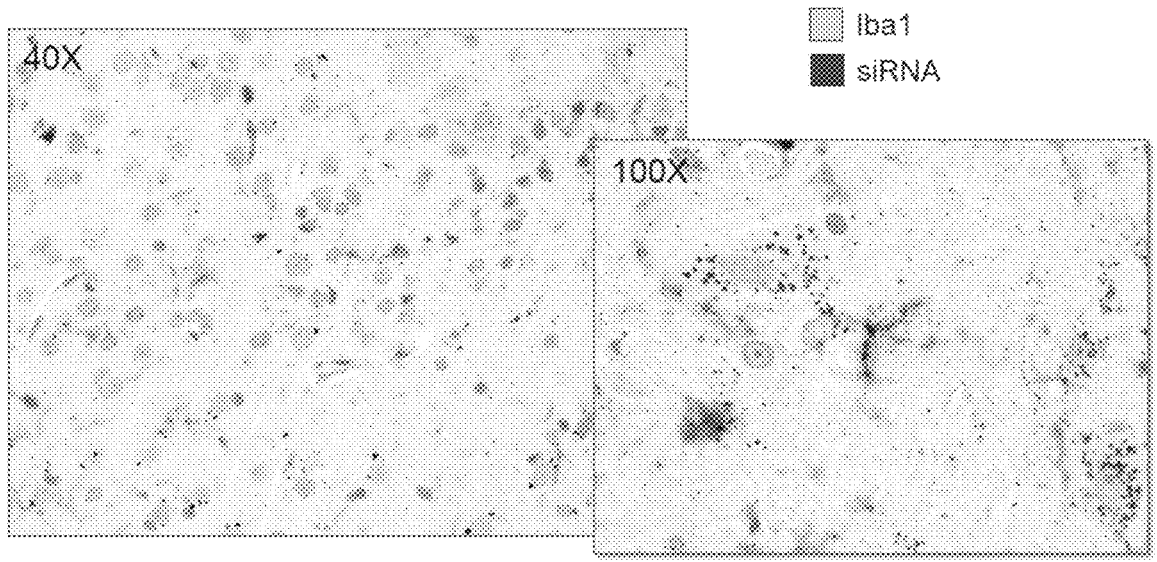
FIG. 21 shows pictures illustrating the siRNA conjugates localized to microglia, following the single IT dosing. Iba1 is a microglia marker.
Figure 22:
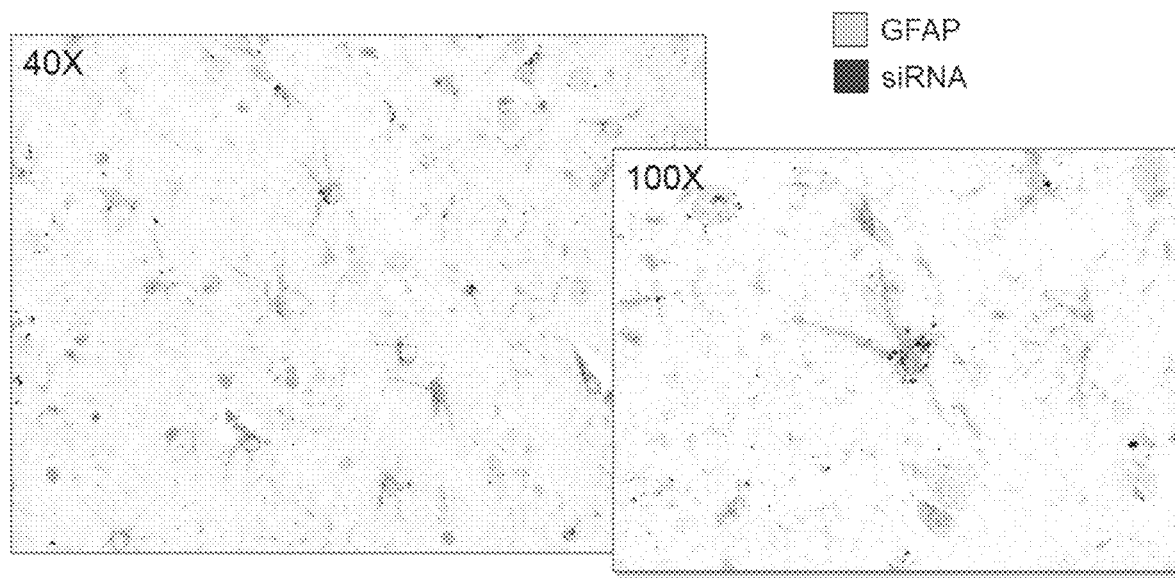
FIG. 22 shows pictures illustrating the siRNA conjugates localized to astrocytes, following the single IT dosing.
Figure 23:
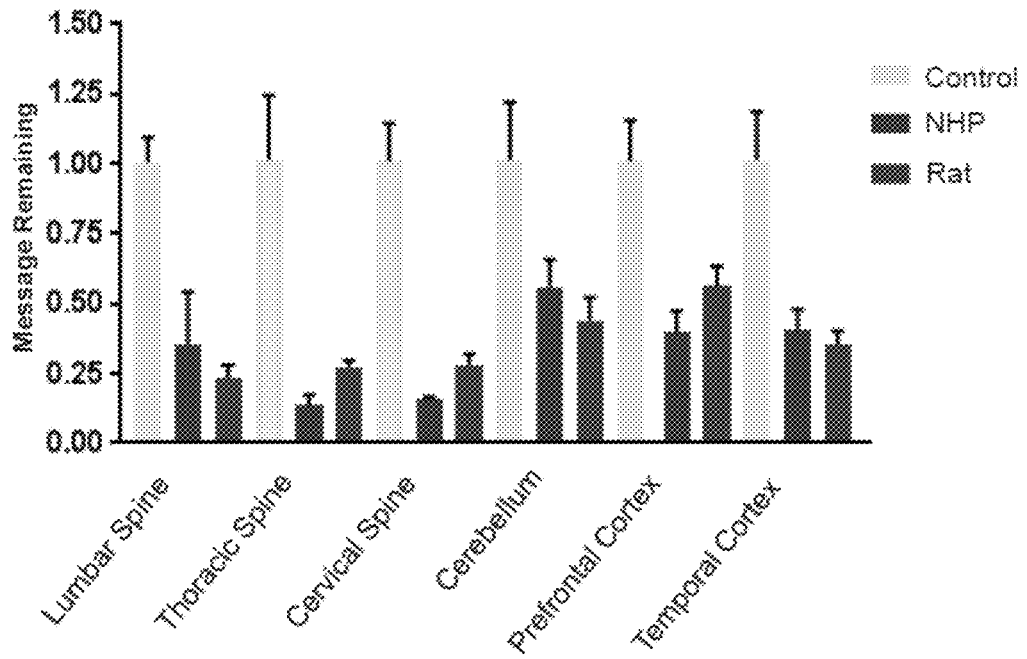
FIG. 23 shows a graph comparing the gene silencing activity observed in rats and NHP at compartment scaled dose.

FIG. 17 shows the β-catenin siRNA levels in various spinal cord and brain regions of non-human primate (NHP) at Day 31, following a single intrathecal (IT) dosing of exemplary siRNA duplexes. The figure illustrates that, at the Day-31 time point, significant siRNA levels were still present across all tissues tested, although siRNA uptake varies between various CNS regions, and the siRNA was also seen in liver. FIG. 18 shows the results of silencing of β-catenin mRNA following a single intrathecal dosing of exemplary siRNA duplexes in NHP at Day 31. As shown in the figure, the siRNA conjugate targeting β-catenin produced robust knockdown across CNS—throughout the spinal cord and brain regions—at the 31-day time point. FIG. 19 shows images illustrating the distribution of the β-catenin siRNA throughout the CNS in non-human primate following the single IT dosing. FIG. 20 shows images illustrating the siRNA uptake in neurons. As shown in the figure, MAP2 is a neuronal marker, and β-catenin (CTNNB) siRNA was probed with siRNA antibody. FIG. 21 shows images illustrating the siRNA conjugates localized to microglia following the single IT dosing. As shown in the figure, Iba1 is a microglia marker, and β-catenin (CTNNB) siRNA was probed with siRNA antibody. FIG. 22 shows images illustrating the siRNA conjugates localized to astrocytes following the single IT dosing. As shown in the figure, GFAP is a astrocyte marker, and β-catenin (CTNNB) siRNA was probed with siRNA antibody. FIG. 23 compares the gene silencing activity observed in rats and NHP at compartment scaled dose.

In summary, durable silencing of target mRNA was observed across the CNS of rat and NHP following IT administration. Silencing extended through the end of the study. Further optimized designs of the siRNA with different chemistry brought about greater than 10-fold improved potency. Tissue uptake was observed in all CNS tissues examined with drug levels in the ng/g to mg/g range. In both rat and NHP studies, intrathecal administration of the novel siRNA conjugates was found to be generally well tolerated.

Example 19: Internal Conjugation of Lipophiles to siRNA

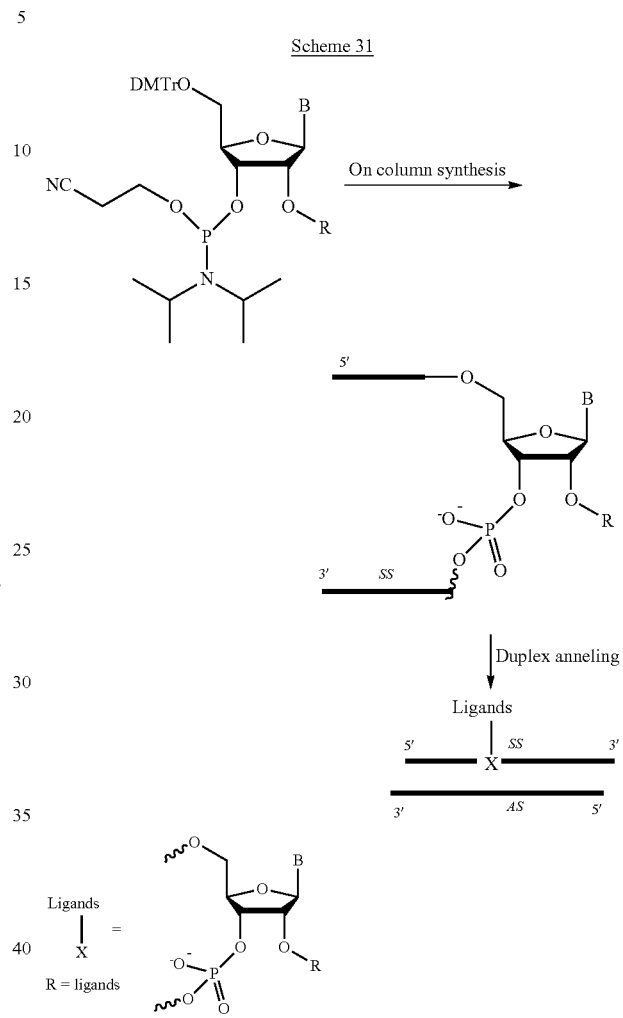

Scheme 31

Scheme 31 illustrates a synthetic protocol for internal conjugation of lipophiles to siRNA duplexes. In Scheme 31, the lipophile moiety, R, may be $C_6$-$C_{30}$ alcohols (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc).

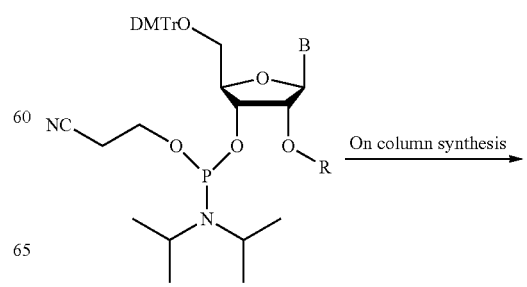

Scheme 32

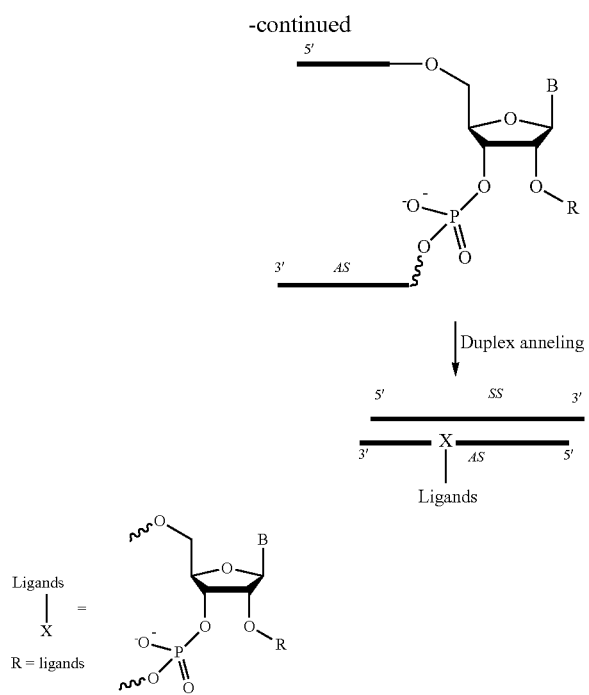

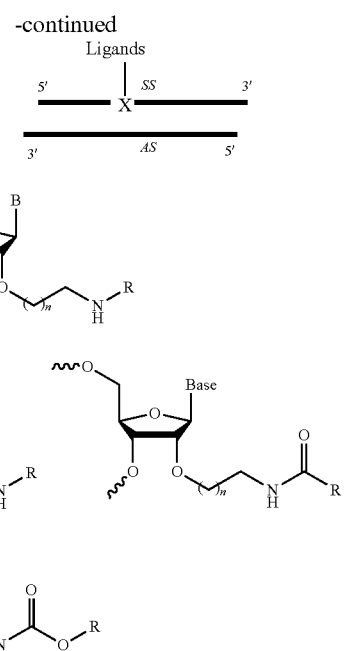

Scheme 32 illustrates an alternative synthetic protocol for internal conjugation of lipophiles to siRNA duplexes. In Scheme 32, the lipophile moiety, R, may be $C_6$-$C_{30}$ alcohols (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

Scheme 33 illustrates a protocol for post-synthetic, internal conjugation of lipophiles to siRNA duplexes. In Scheme 33, R or COR=$C_6$-$C_{30}$ acid (e.g., hexanoic acid, heptanoic acid, octanoic acid, nonanoic acid, decanoic acid, undecanoic acid, dodcanoic acid, tridecanoic acid, tetradecanoic acid, pentadecanoic acid, hexadecanoic acid, heptadecanoic acid, octadecanoic acid, oleic acid, linoleic acid, arachidonic acid, cis-4,7,10,13,16,19-docosahexanoic acid, vitamin A, vitamin E, cholesterol etc. COOR=$C_6$-$C_{30}$ alcohols (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

Example 20: Post-Synthetic Conjugation of Lipophilic Moieties to siRNA

Scheme 33

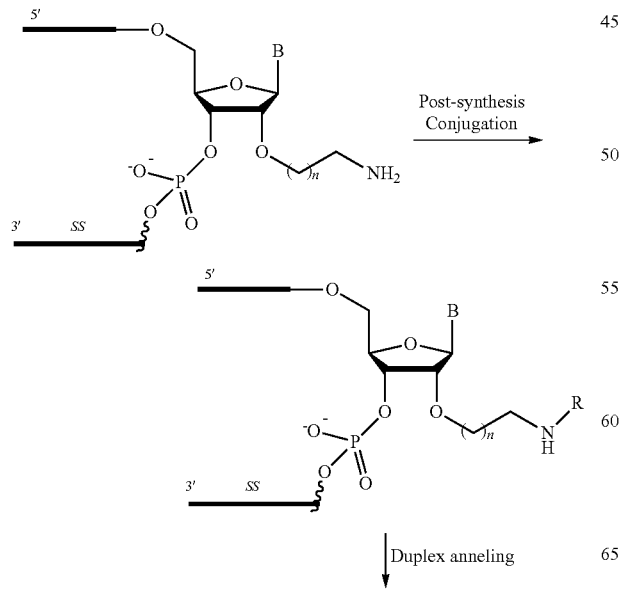

Scheme 34

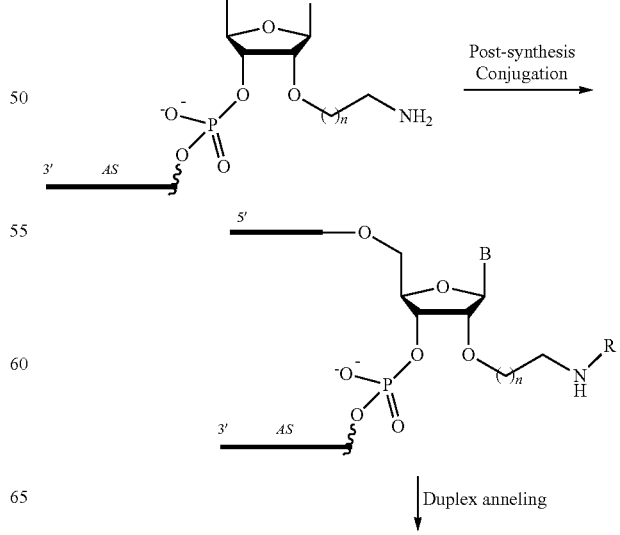

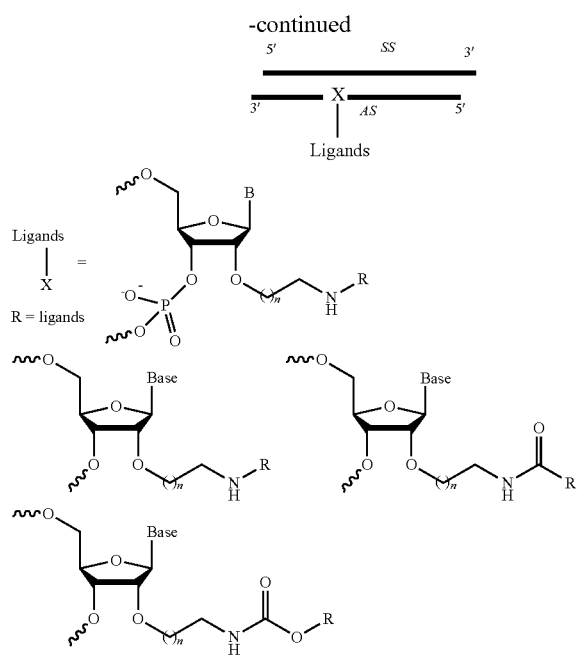

Scheme 34 illustrates an alternative protocol for post-synthetic, internal conjugation of lipophiles to siRNA duplexes. In Scheme 34, R, COR, or COOR=$C_6$-$C_{30}$ acid (e.g., hexanoic acid, heptanoic acid, octanoic acid, nonanoic acid, decanoic acid, undecanoic acid, dodcanoic acid, tridecanoic acid, tetradecanoic acid, pentadecanoic acid, hexadecanoic acid, heptadecanoic acid, octadecanoic acid, oleic acid, linoleic acid, arachidonic acid, cis-4,7,10,13,16,19-docosahexanoic acid, vitamin A, vitamin E, cholesterol etc.). COOR=$C_6$-$C_{30}$ alcohols (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

Example 21: SAR of Internal Lipid Conjugates in Mice

The structure activity relationships of siRNAs with internal conjugation of lipophilic were studied in mice. The sequences in this example are shown in Table 7 below.

TABLE 7

| DuplexName | SEQ ID NO: | Strand | OligoSeq (5'-3') | Ligand/N1 at 5' end of antisense strand |
|---|---|---|---|---|
| AD-307571 | 159 | sense | asascag(Uhd)GfuUfCfUfugcucuausasa | C16 (Uhd) |
| | 160 | antis | VPuUfauaGfagcaagaAfcAfcuguususu | |
| AD-397368 | 161 | sense | asascag(Utd)GfuUfCfUfugcucuausasa | C14 (Utd) |
| | 160 | antis | VPuUfauaGfagcaagaAfcAfcuguususu | |
| AD-397370 | 162 | sense | asascag(Udo)GfuUfCfUfugcucuausasa | C12 (Udo) |
| | 160 | antis | VPuUfauaGfagcaagaAfcAfcuguususu | |
| AD-397371 | 163 | sense | asascag(Ude)GfuUfCfUfugcucuausasa | C10 (Ude) |
| | 160 | antis | VPuUfauaGfagcaagaAfcAfcuguususu | |
| AD-397369 | 164 | sense | asascag(Uol)GfuUfCfUfugcucuausasa | Oleyl (C18:1) (Uol) |
| | 160 | antis | VPuUfauaGfagcaagaAfcAfcuguususu | |
| AD-418424 | 165 | sense | asascag Y84GfuUfCfUfugcucuausasa | Oleyl (C18:1)(Y84) |
| | 160 | antis | VPuUfauaGfagcaagaAfcAfcuguususu | |
| AD-418422 | 166 | sense | asascag Y82GfuUfCfUfugcucuausasa | Arachidonic acid (Y82) |
| | 160 | antis | VPuUfauaGfagcaagaAfcAfcuguususu | |
| AD-418426 | 167 | sense | asascag Y110GfuUfCfUfugcucuausasa | Vitamin A (Y110) |
| | 160 | antis | VPuUfauaGfagcaagaAfcAfcuguususu | |
| AD-418425 | 168 | sense | asascag Y76GfuUfCfUfugcucuausasa | C10 (Y76) |
| | 160 | antis | VPuUfauaGfagcaagaAfcAfcuguususu | |
| AD-418431 | 159 | sense | asascag(Uhd)GfuUfCfUfugcucuausasa | C16/Chiral PS-2PS |
| | 169 | antis | (uRs)(UfRs)auaGfaGfCfaagaAfcAfcugu(uSs)(uSs)u | |
| AD-397372 | 159 | sense | asascag(Uhd)GfuUfCfUfugcucuausasa | C16/2'-OMe |
| | 170 | antis | usUfsauaGfagcaagaAfcAfcuguususu | |
| AD-418430 | 159 | sense | asascag(Uhd)GfuUfCfUfugcucuausasa | C16/Chiral PS-PS |
| | 171 | antis | (uRs)UfauaGfaGfCfaagaAfcAfcugu(uSs)(uSs)u | |
| AD-418428 | 159 | sense | asascag(Uhd)GfuUfCfUfugcucuausasa | C16/PO3 |
| | 172 | antis | PusUfsauaGfagcaagaAfcAfcuguususu | |
| AD-418427 | 159 | sense | asascag(Uhd)GfuUfCfUfugcucuausasa | C16/DNA |
| | 173 | antis | dTsUfsauaGfagcaagaAfcAfcuguususu | |
| AD-418429 | 159 | sense | asascag(Uhd)GfuUfCfUfugcucuausasa | C16/RNA |
| | 174 | antis | UsUfsauaGfagcaagaAfcAfcuguususu | |
| AD-421436 | 159 | sense | asascag(Uhd)GfuUfCfUfugcucuausasa | C16/2'-F |
| | 174 | antis | UfsUfsauaGfagcaagaAfcAfcuguususu | |

TABLE 7-continued
| DuplexName | SEQ ID NO: | Strand | OligoSeq (5'-3') | Ligand/N1 at 5' end of antisense strand |
|---|---|---|---|---|
| AD-421439 | 159 | sense | asascag(Uhd)GfuUfCfUfugcucuausasa | C16/Phosphate prodrug |
| | 175 | antis | (Pmds)uUfauaGfagcaagaAfcAfcuguususu | |
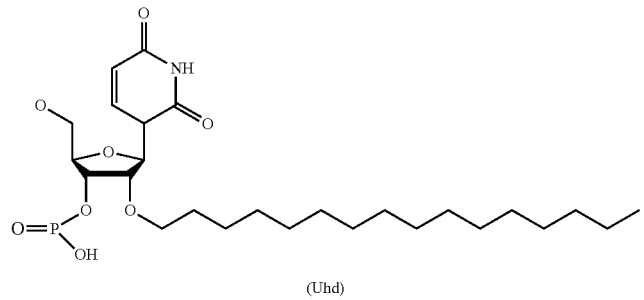
(Uhd)
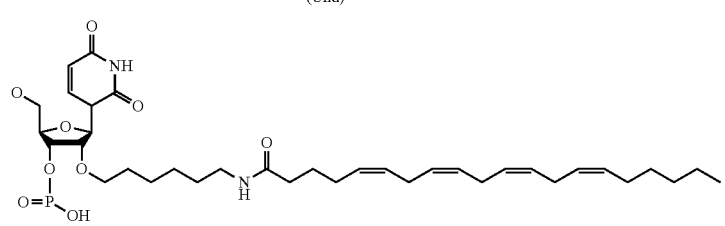
Y82
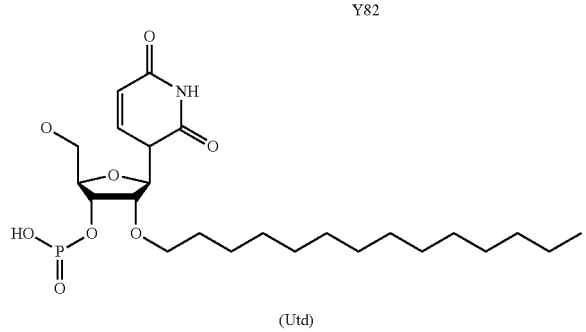
(Utd)
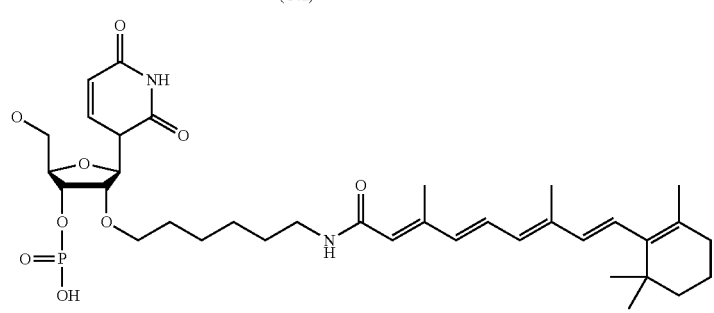
Y110
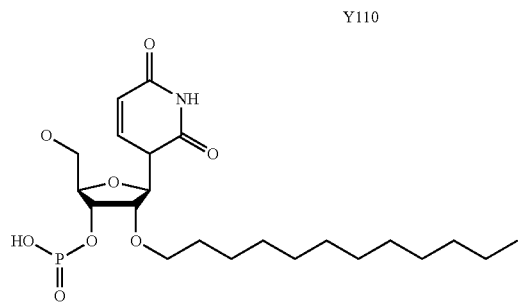
(Udo)

TABLE 7-continued
| DuplexName | SEQ ID NO: | Strand | OligoSeq (5'-3') | Ligand/N1 at 5' end of antisense strand |
|---|---|---|---|---|
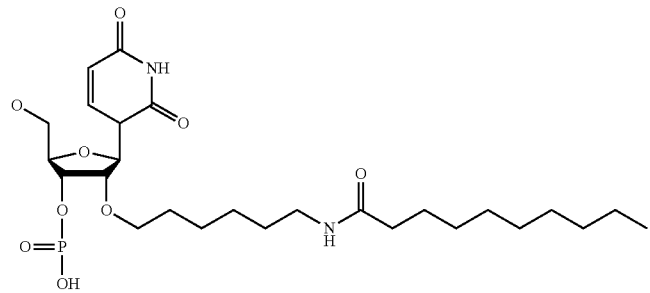
Y76
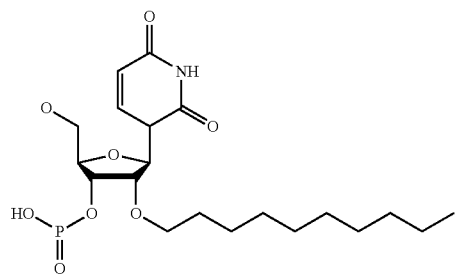
(Ude)
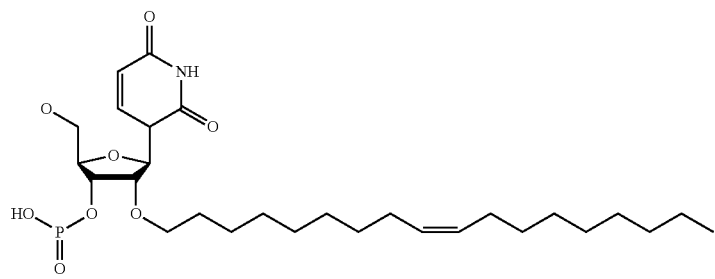
(Uol)
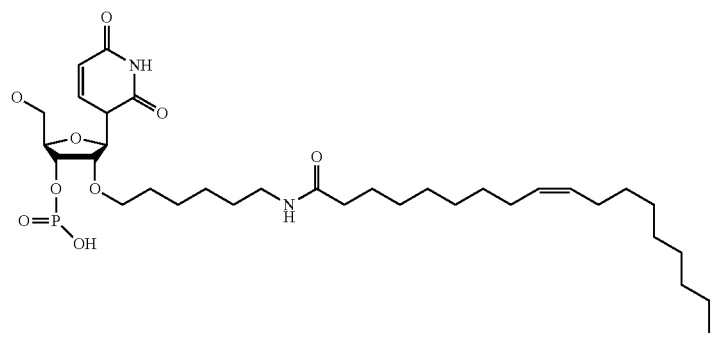
Y84

Figure 24:
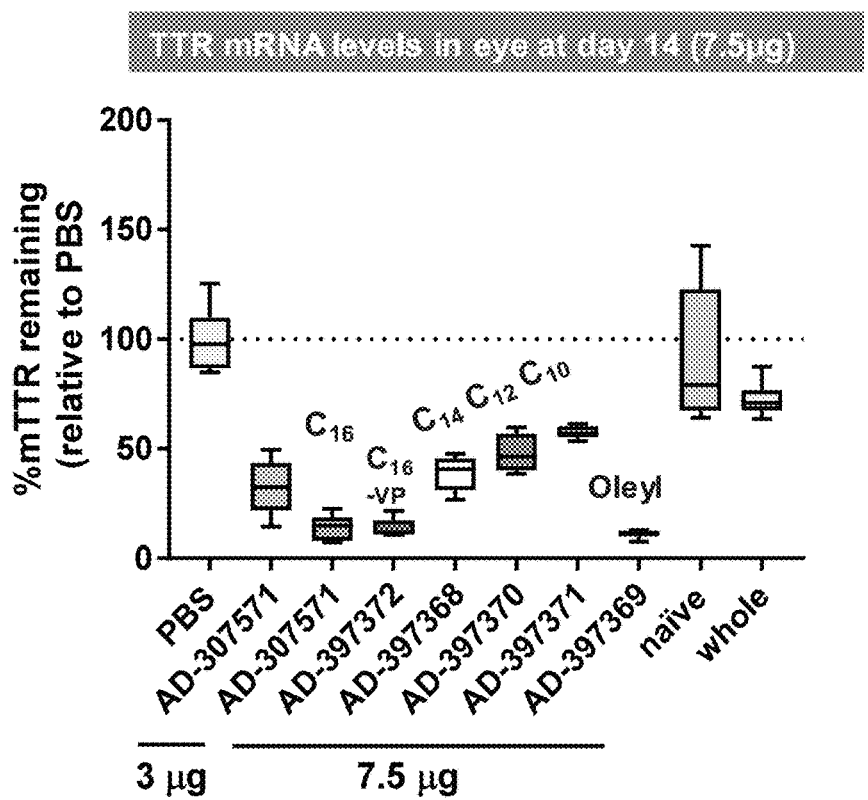
FIG. 24 shows the results of TTR mRNA levels in the eye of mice at Day 14 following administrating various exemplary siRNA duplexes shown in Table 7, at a dosage of 3 μg or 7.5 μg.

SAR of Internal Lipid Conjugates in Mice #1. FIG. 24 shows the results of TTR mRNA levels in the eye of mice at Day 14, following administrating various exemplary siRNA duplexes shown in Table 7, at a dosage of 3 µg or 7.5 µg. As shown in Table 7 above, the siRNAs are modified by conjugating a lipophilic moiety (oleyl, $C_{16}$, $C_{14}$, $C_{12}$, or $C_{10}$) at an internal position of the sense strand. As shown in FIG. 24, the TTR knockdown ability for the siRNAs with lipophilic conjugations are: oleyl $(C_{18}) \geq C_{16} > C_{14} > C_{12} > C_{10}$. This result illustrates the impact of hydrophobicity on the gene silencing activity of siRNAs.

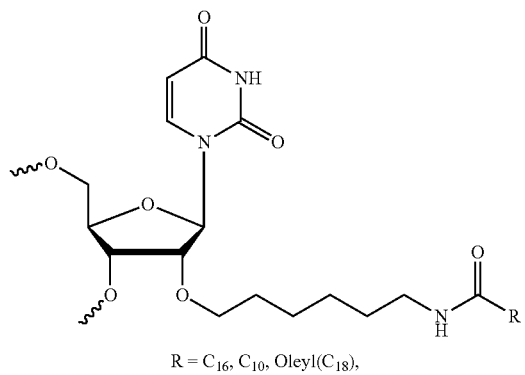

R = $C_{16}$, $C_{10}$, Oleyl($C_{18}$), Arachidonic acid, Vitamin A

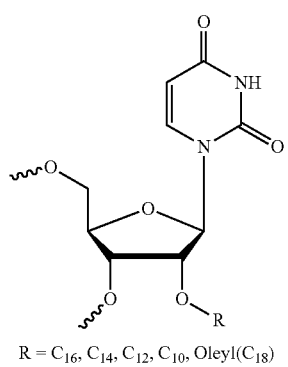

R = $C_{16}$, $C_{14}$, $C_{12}$, $C_{10}$, Oleyl($C_{18}$)

Figure 25:
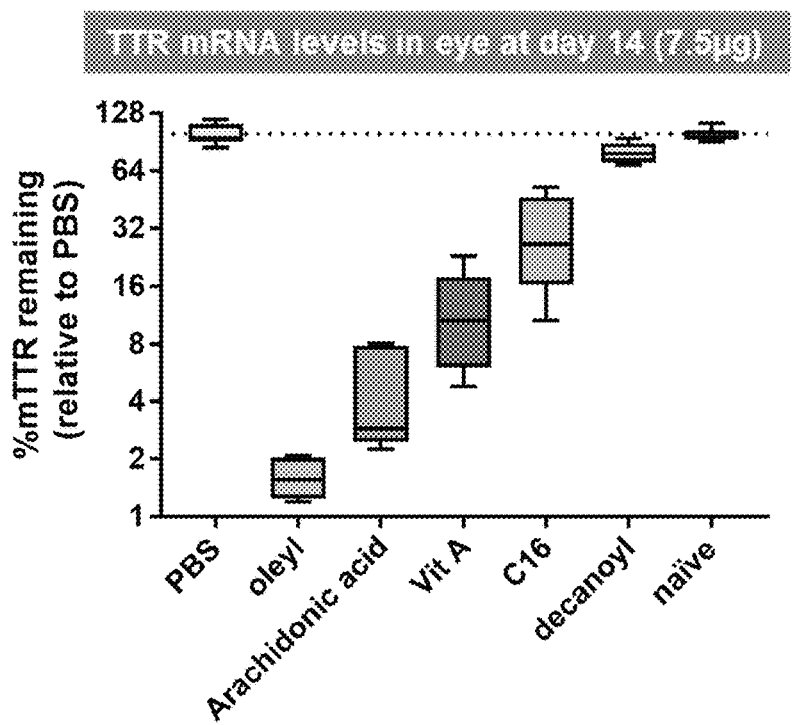
FIG. 25 shows the results of TTR mRNA levels in the eye of mice at Day 14, following administrating various exemplary siRNA duplexes shown in Table 7, at a dosage of 7.5 μg.

SAR of Internal Lipid Conjugates in Mice #2. FIG. 25 shows the results of TTR mRNA levels in the eye of mice at Day 14, following administrating various exemplary siRNA duplexes shown in Table 7, at a dosage of 7.5 µg. As shown in FIG. 25, the siRNAs conjugated with oleyl ($C_{18}$), arachidonic acid, and vitamin A conjugates had better TTR knockdown ability than the other conjugates.

R = $C_{16}$

Figure 26:
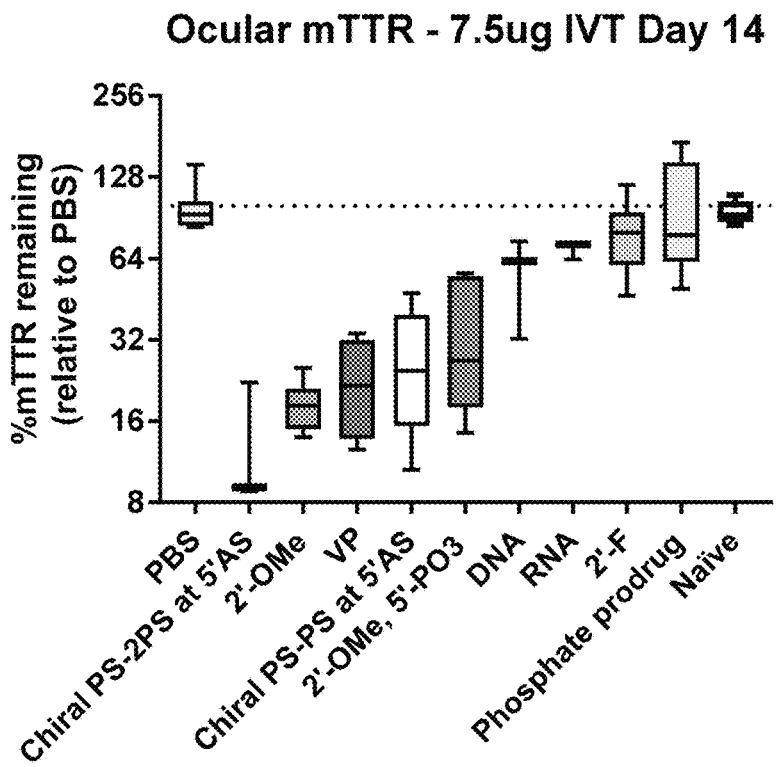
FIG. 26 shows the results of TTR mRNA levels in the eye of mice at Day 14, following an intravitreal administration of various exemplary siRNA duplexes shown in Table 7, at a dosage of 7.5 μg.

5' AS Strand SAR with Internal $C_{16}$ Conjugates in mice. FIG. 26 shows the results of TTR mRNA levels in the eye of mice at Day 14, following an intravitreal administration of various exemplary siRNA duplexes shown in Table 7, at a dosage of 7.5 µg. As shown in Table 7 above, the siRNAs are modified by conjugating a lipophilic moiety ($C_{16}$) at an internal position of the sense strand, and various modifications (e.g., 2 chiral PS; 2'-OMe; VP; 1 chiral PS; PO3; DNA; RNA; 2'-F; phosphate prodrug) at the 5' end of the antisense strand.

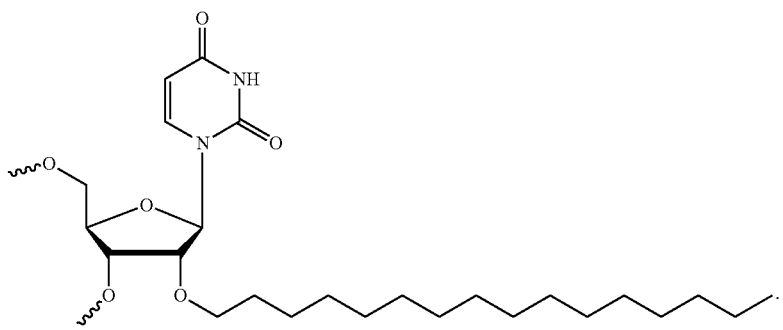

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

We claim:

1. A double-stranded iRNA agent comprising:
   an antisense strand which is complementary to a target mRNA;
   a sense strand which is complementary to said antisense strand; and
   one lipophilic moiety directly bonded to a 2'-O of a sugar moiety at an internal position of the sense strand, wherein:
   the sense and antisense strands are each independently 19 to 25 nucleotides in length and form a double-stranded region 19-21 nucleotide pairs in length, having a blunt end at the 5'-end of the antisense strand;
   the lipophilic moiety is a linear $C_{16}$ alkyl chain;
   the internal position is a position on the sense strand excluding the three terminal positions from each of the 5'-end and 3'-end of the sense strand and excluding positions 11 to 13, counting from the 3'-end of the sense strand; and
   the double-stranded iRNA agent does not comprise a N-acetylgalactosamine (GalNAc) conjugate.

2. The double-stranded iRNA agent of claim 1, wherein the internal positions exclude positions 9-12 counting from the 5'-end of the sense strand.

3. The double-stranded iRNA agent of claim 1, wherein the sense and antisense strands are each independently 21 to 23 nucleotides in length, and the internal position is one of positions 4-8 and 13-18, counting from the 5'-end of sense strand.

4. The double-stranded iRNA agent of claim 1, wherein the internal position is position 5, counting from the 5'-end of the sense strand.

5. The double-stranded iRNA agent of claim 1, wherein the internal position is position 6, counting from the 5'-end of the sense strand.

6. The double-stranded iRNA agent of claim 1, wherein the internal position is position 7, counting from the 5'-end of the sense strand.

7. The double-stranded iRNA agent of claim 1, wherein the sense strand and antisense strand are each 19 nucleotides in length, wherein the sense strand contains 2'-F modifications on the nucleotides at positions 7, 8, and 9 from the 5'-end of the sense strand.

8. The double-stranded iRNA agent of claim 7, wherein the antisense strand contains 2'-O-methyl modifications on the nucleotides at positions 11, 12, and 13 from the 5'-end of the antisense strand.

9. The double-stranded iRNA agent of claim 1, wherein the sense strand and antisense strand are each 20 nucleotides in length, wherein the sense strand contains 2'-F modifications on the nucleotides at positions 8, 9, and 10 from the 5'-end of the sense strand.

10. The double-stranded iRNA agent of claim 9, wherein the antisense strand contains 2'-O-methyl modifications on the nucleotides at positions 11, 12, and 13 from the 5'-end of the antisense strand.

11. The double-stranded iRNA agent of claim 1, wherein the sense strand and antisense strand are each 21 nucleotides in length, wherein the sense strand contains 2'-F modifications on the nucleotides at positions 9, 10, and 11 from the 5'-end of the sense strand.

12. The double-stranded iRNA agent of claim 11, wherein the antisense strand contains of 2'-O-methyl modifications on the nucleotides at positions 11, 12, and 13 from the 5'-end of the antisense strand.

13. The double-stranded iRNA agent of claim 1, wherein the sense strand is 21 nucleotides in length, and the antisense strand is 23 nucleotides in length and has a two nucleotide overhang at the 3'-end of the antisense strand, wherein:
   the sense strand contains 2'-F modifications on the nucleotides at positions 9, 10, and 11 from the 5'-end of the sense strand; and
   the antisense strand contains 2'-O-methyl modifications on the nucleotides at positions 11, 12, and 13 from the 5'-end of the antisense strand.

14. The double-stranded iRNA agent of claim 1, wherein the first base pair at the 5'-end of the antisense strand is an AU base pair.

15. The double-stranded iRNA agent of claim 1, further comprising at least one phosphorothioate or methylphosphonate internucleotide linkage.

16. The double-stranded iRNA agent of claim 15, wherein the double-stranded iRNA agent comprises at least two phosphorothioate internucleotide linkages at the first five nucleotides on the antisense strand, counting from the 5'-end of the antisense strand.

17. The double-stranded iRNA agent of claim 15, wherein the double-stranded iRNA agent comprises 8 phosphorothioate internucleotide linkages.

18. The double-stranded iRNA agent of claim 1, wherein each of the sense and antisense strands contains at least two different modifications.

19. The double-stranded iRNA agent of claim 1, wherein the double-stranded iRNA agent comprises a mismatch to the target RNA within the duplex region.

20. The double-stranded iRNA agent of claim 1, wherein each of the sense and antisense strands is independently modified with one or more modifications selected from the group consisting of an acyclic nucleotide, LNA, HNA, CeNA, 2'-methoxyethyl, 2'-O-methyl, 2'-O-allyl, 2'-C-allyl, 2'-deoxy, 2'-fluoro, 2'-O-N-methylacetamido (2'-O-NMA), a 2'-O-dimethylaminoethoxyethyl (2'-O-DMAEOE), 2'-O-aminopropyl (2'-O-AP), and 2'-ara-F.

21. The double-stranded iRNA agent of claim 20, wherein one or more modification is acyclic nucleotide modification, and the acyclic nucleotide is an UNA or a GNA.

22. The double-stranded iRNA agent of claim 1, further comprising a 2'-5' internucleotide linkage.

23. The double-stranded iRNA agent of claim 1, further comprising an overhang region at the 3'-end of the antisense strand containing two nucleotides and having a phosphorothioate or methylphosphonate internucleotide linkage between the two overhang nucleotides.

24. The double-stranded iRNA agent of claim 1, further comprising an overhang region at the 3'-end of the antisense strand and two phosphorothioate internucleotide linkages between the terminal three nucleotides at the 3'-end of the antisense strand, in which two of the three nucleotides are the overhang nucleotides, and the third is the paired nucleotide next to the overhang nucleotide.

25. The double-stranded iRNA agent of claim 1, further comprising a phosphate at the 5'-end of the antisense strand.

26. The double-stranded iRNA agent of claim 1, further comprising a phosphate mimic at the 5'-end of the antisense strand.

27. The double-stranded iRNA agent of claim 26, wherein the phosphate mimic is a 5'-vinyl phosphonate (VP).

28. The double-stranded iRNA agent of claim 1, comprising
   (a) a sense strand having:
      (i) a length of 21 nucleotides;
      (ii) 2'-OMe modifications at positions 1 to 6, 8, and 12 to 21, and 2'-F modifications at positions 7, and 9 to 11; and
      (iii) phosphorothioate internucleotide linkages between nucleotide positions 1 and 2, and between nucleotide positions 2 and 3, counting from the 5'-end of the sense strand; and
   (b) an antisense strand having:
      (i) a length of 23 nucleotides;
      (ii) (1) 2'-OMe modifications at positions 1, 3 to 5, 7, 8, 10 to 13, 15, and 17 to 23, and 2'-F modifications at positions 2, 6, 9, 14, and 16, counting from the 5'-end of the antisense strand; or
      (2) 2'-OMe modifications at positions 1, 3 to 5, 7, 10 to 13, 15, and 17 to 23, and 2'-F modifications at positions 2, 6, 8, 9, 14, and 16, counting from the 5'-end of the antisense strand; and
      (iii) phosphorothioate internucleotide linkages between nucleotide positions 1 and 2, between nucleotide positions 2 and 3, between nucleotide positions 21 and 22, and between nucleotide positions 22 and 23, counting from the 5'-end of the antisense strand;
   wherein the double-stranded iRNA agent has a two-nucleotide overhang at the 3'-end of the antisense strand, and a blunt end at the 5'-end of the antisense strand.

* * * * *

```
                               SEQUENCE LISTING

Sequence total quantity: 175
SEQ ID NO: 1           moltype = AA  length = 8
FEATURE                Location/Qualifiers
REGION                 1..8
                       note = Description of Unknown: RGD peptide sequence
source                 1..8
                       mol_type = protein
                       organism = unidentified
SEQUENCE: 1
GRGDSPKC                                                                  8

SEQ ID NO: 2           moltype = AA  length = 5
FEATURE                Location/Qualifiers
REGION                 1..5
                       note = Description of Unknown: RGD peptide sequence
source                 1..5
                       mol_type = protein
                       organism = unidentified
SEQUENCE: 2
RGDFC                                                                     5

SEQ ID NO: 3           moltype = AA  length = 29
FEATURE                Location/Qualifiers
REGION                 1..29
                       note = Description of Artificial Sequence: Synthetic peptide
source                 1..29
                       mol_type = protein
                       organism = synthetic construct
SEQUENCE: 3
AALEALAEAL EALAEALEAL AEAAAAGGC                                          29

SEQ ID NO: 4           moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 4
AALAEALAEA LAEALAEALA EALAAAAGGC                                         30

SEQ ID NO: 5           moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 5
ALEALAEALE ALAEA                                                         15

SEQ ID NO: 6           moltype = AA  length = 22
FEATURE                Location/Qualifiers
REGION                 1..22
                       note = Description of Artificial Sequence: Synthetic peptide
source                 1..22
                       mol_type = protein
                       organism = synthetic construct
SEQUENCE: 6
GLFEAIEGFI ENGWEGMIWD YG                                                 22

SEQ ID NO: 7           moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 7
GLFGAIAGFI ENGWEGMIDG WYG                                                23
```

```
SEQ ID NO: 8              moltype = AA  length = 48
FEATURE                   Location/Qualifiers
REGION                    1..48
                          note = Description of Artificial Sequence: Synthetic
                           polypeptide
source                    1..48
                          mol_type = protein
                          organism = synthetic construct
SEQUENCE: 8
GLFEAIEGFI ENGWEGMIDG WYGCGLFEAI EGFIENGWEG MIDGWYGC                 48

SEQ ID NO: 9              moltype = AA  length = 44
FEATURE                   Location/Qualifiers
REGION                    1..44
                          note = Description of Artificial Sequence: Synthetic
                           polypeptide
source                    1..44
                          mol_type = protein
                          organism = synthetic construct
SEQUENCE: 9
GLFEAIEGFI ENGWEGMIDG GCGLFEAIEG FIENGWEGMI DGGC                     44

SEQ ID NO: 10             moltype = AA  length = 35
FEATURE                   Location/Qualifiers
REGION                    1..35
                          note = Description of Artificial Sequence: Synthetic
                           polypeptide
source                    1..35
                          mol_type = protein
                          organism = synthetic construct
SEQUENCE: 10
GLFGALAEAL AEALAEHLAE ALAEALEALA AGGSC                               35

SEQ ID NO: 11             moltype = AA  length = 34
FEATURE                   Location/Qualifiers
REGION                    1..34
                          note = Description of Artificial Sequence: Synthetic
                           polypeptide
source                    1..34
                          mol_type = protein
                          organism = synthetic construct
SEQUENCE: 11
GLFEAIEGFI ENGWEGLAEA LAEALEALAA GGSC                                34

SEQ ID NO: 12             moltype = AA  length = 41
FEATURE                   Location/Qualifiers
REGION                    1..41
                          note = Description of Artificial Sequence: Synthetic
                           polypeptide
MOD_RES                   17
                          note = Norleucine
MOD_RES                   38
                          note = Norleucine
source                    1..41
                          mol_type = protein
                          organism = synthetic construct
SEQUENCE: 12
GLFEAIEGFI ENGWEGXIDG KGLFEAIEGF IENGWEGXID G                        41

SEQ ID NO: 13             moltype = AA  length = 19
FEATURE                   Location/Qualifiers
REGION                    1..19
                          note = Description of Artificial Sequence: Synthetic peptide
source                    1..19
                          mol_type = protein
                          organism = synthetic construct
SEQUENCE: 13
LFEALLELLE SLWELLLEA                                                 19

SEQ ID NO: 14             moltype = AA  length = 20
FEATURE                   Location/Qualifiers
REGION                    1..20
                          note = Description of Artificial Sequence: Synthetic peptide
source                    1..20
                          mol_type = protein
                          organism = synthetic construct
SEQUENCE: 14
GLFKALLKLL KSLWKLLLKA                                                20
```

```
SEQ ID NO: 15            moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 15
GLFRALLRLL RSLWRLLLRA                                                      20

SEQ ID NO: 16            moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 16
WEAKLAKALA KALAKHLAKA LAKALKACEA                                           30

SEQ ID NO: 17            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 17
GLFFEAIAEF IEGGWEGLIE GC                                                   22

SEQ ID NO: 18            moltype = AA  length = 26
FEATURE                  Location/Qualifiers
REGION                   1..26
                         note = Description of Artificial Sequence: Synthetic peptide
source                   1..26
                         mol_type = protein
                         organism = synthetic construct
SEQUENCE: 18
GIGAVLKVLT TGLPALISWI KRKRQQ                                               26

SEQ ID NO: 19            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 19
HHHHHWYG                                                                   8

SEQ ID NO: 20            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 20
CHKKKKKKHC                                                                 10

SEQ ID NO: 21            moltype = AA  length = 16
FEATURE                  Location/Qualifiers
source                   1..16
                         mol_type = protein
                         organism = Drosophila sp.
SEQUENCE: 21
RQIKIWFQNR RMKWKK                                                          16

SEQ ID NO: 22            moltype = AA  length = 14
FEATURE                  Location/Qualifiers
source                   1..14
                         mol_type = protein
                         organism = Human immunodeficiency virus
SEQUENCE: 22
GRKKRRQRRR PPQC                                                            14

SEQ ID NO: 23            moltype = AA  length = 27
FEATURE                  Location/Qualifiers
```

```
REGION                  1..27
                        note = Description of Unknown: Signal sequence based peptide
source                  1..27
                        mol_type = protein
                        organism = unidentified
SEQUENCE: 23
GALFLGWLGA AGSTMGAWSQ PKKKRKV                                           27

SEQ ID NO: 24           moltype = AA   length = 18
FEATURE                 Location/Qualifiers
source                  1..18
                        mol_type = protein
                        organism = Mus sp.
SEQUENCE: 24
LLIILRRRIR KQAHAHSK                                                     18

SEQ ID NO: 25           moltype = AA   length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 25
GWTLNSAGYL LKINLKALAA LAKKIL                                            26

SEQ ID NO: 26           moltype = AA   length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 26
KLALKLALKA LKAALKLA                                                     18

SEQ ID NO: 27           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 27
RRRRRRRRR                                                                9

SEQ ID NO: 28           moltype = AA   length = 10
FEATURE                 Location/Qualifiers
REGION                  1..10
                        note = Description of Unknown: Bacterial cell wall
                         permeating peptide
source                  1..10
                        mol_type = protein
                        organism = unidentified
SEQUENCE: 28
KFFKFFKFFK                                                              10

SEQ ID NO: 29           moltype = AA   length = 37
FEATURE                 Location/Qualifiers
REGION                  1..37
                        note = Description of Unknown: LL37 sequence
source                  1..37
                        mol_type = protein
                        organism = unidentified
SEQUENCE: 29
LLGDFFRKSK EKIGKEFKRI VQRIKDFLRN LVPRTES                                37

SEQ ID NO: 30           moltype = AA   length = 31
FEATURE                 Location/Qualifiers
REGION                  1..31
                        note = Description of Unknown: Cecropin P1 sequence
source                  1..31
                        mol_type = protein
                        organism = unidentified
SEQUENCE: 30
SWLSKTAKKL ENSAKKRISE GIAIAIQGGP R                                      31

SEQ ID NO: 31           moltype = AA   length = 30
FEATURE                 Location/Qualifiers
```

| | |
|---|---|
| REGION | 1..30<br>note = Description of Unknown: Alpha-defensin sequence |
| source | 1..30<br>mol_type = protein<br>organism = unidentified |

SEQUENCE: 31
ACYCRIPACI AGERRYGTCI YQGRLWAFCC                                            30

| | |
|---|---|
| SEQ ID NO: 32 | moltype = AA  length = 36 |
| FEATURE | Location/Qualifiers |
| REGION | 1..36<br>note = Description of Unknown: Beta-defensin sequence |
| source | 1..36<br>mol_type = protein<br>organism = unidentified |

SEQUENCE: 32
DHYNCVSSGG QCLYSACPIF TKIQGTCYRG KAKCCK                                     36

| | |
|---|---|
| SEQ ID NO: 33 | moltype = AA  length = 42 |
| FEATURE | Location/Qualifiers |
| REGION | 1..42<br>note = Description of Unknown: PR-39 sequence |
| source | 1..42<br>mol_type = protein<br>organism = unidentified |

SEQUENCE: 33
RRRPRPPYLP RPRPPPFFPP RLPPRIPPGF PPRFPPRFPG KR                              42

| | |
|---|---|
| SEQ ID NO: 34 | moltype = AA  length = 13 |
| FEATURE | Location/Qualifiers |
| REGION | 1..13<br>note = Description of Unknown: Indolicidin sequence |
| source | 1..13<br>mol_type = protein<br>organism = unidentified |

SEQUENCE: 34
ILPWKWPWWP WRR                                                             13

| | |
|---|---|
| SEQ ID NO: 35 | moltype = AA  length = 16 |
| FEATURE | Location/Qualifiers |
| REGION | 1..16<br>note = Description of Unknown: RFGF peptide sequence |
| source | 1..16<br>mol_type = protein<br>organism = unidentified |

SEQUENCE: 35
AAVALLPAVL LALLAP                                                          16

| | |
|---|---|
| SEQ ID NO: 36 | moltype = AA  length = 11 |
| FEATURE | Location/Qualifiers |
| REGION | 1..11<br>note = Description of Unknown: RFGF peptide analogue<br>sequence |
| source | 1..11<br>mol_type = protein<br>organism = unidentified |

SEQUENCE: 36
AALLPVLLAA P                                                               11

| | |
|---|---|
| SEQ ID NO: 37 | moltype = AA  length = 12 |
| FEATURE | Location/Qualifiers |
| REGION | 1..12<br>note = Description of Unknown: Bactenecin sequence |
| source | 1..12<br>mol_type = protein<br>organism = unidentified |

SEQUENCE: 37
RKCRIVVIRV CR                                                              12

| | |
|---|---|
| SEQ ID NO: 38 | moltype = DNA  length = 23 |
| FEATURE | Location/Qualifiers |
| source | 1..23<br>mol_type = other DNA<br>organism = synthetic construct |
| modified_base | 1<br>mod_base = OTHER<br>note = 2'-O-methyluridine-3'-phosphorothioate |
| modified_base | 2<br>mod_base = OTHER |

|                 |                                                                                                      |
|-----------------|------------------------------------------------------------------------------------------------------|
| | note = 2'-O-methyladenosine-3'-phosphorothioate |
| modified_base | 3 |
| | mod_base = OTHER |
| | note = 2'-O-methylcytidine-3'-phosphate |
| modified_base | 4 |
| | mod_base = OTHER |
| | note = 2'-O-methyluridine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-O-methyluridine-3'-phosphate |
| modified_base | 7 |
| | mod_base = OTHER |
| | note = 2'-deoxy-2'-fluorouridine-3'-phosphate |
| modified_base | 8 |
| | mod_base = OTHER |
| | note = 2'-O-methylguanosine-3'-phosphate |
| modified_base | 9 |
| | mod_base = OTHER |
| | note = 2'-deoxy-2'-fluoroguanosine-3'-phosphate |
| modified_base | 10 |
| | mod_base = OTHER |
| | note = 2'-deoxy-2'-fluoroadenosine-3'-phosphate |
| modified_base | 11 |
| | mod_base = OTHER |
| | note = 2'-deoxy-2'-fluorouridine-3'-phosphate |
| modified_base | 12 |
| | mod_base = OTHER |
| | note = 2'-O-methyluridine-3'-phosphate |
| modified_base | 13 |
| | mod_base = OTHER |
| | note = 2'-O-methylguanosine-3'-phosphate |
| modified_base | 14 |
| | mod_base = OTHER |
| | note = 2'-O-methyladenosine-3'-phosphate |
| modified_base | 15 |
| | mod_base = OTHER |
| | note = 2'-O-methyluridine-3'-phosphate |
| modified_base | 16 |
| | mod_base = OTHER |
| | note = 2'-O-methyluridine-3'-phosphate |
| modified_base | 17 |
| | mod_base = OTHER |
| | note = 2'-O-methylcytidine-3'-phosphate |
| modified_base | 18 |
| | mod_base = OTHER |
| | note = 2'-O-methylguanosine-3'-phosphate |
| modified_base | 19 |
| | mod_base = OTHER |
| | note = 2'-O-methyladenosine-3'-phosphate |
| modified_base | 20 |
| | mod_base = OTHER |
| | note = 2'-O-methyladenosine-3'-phosphorothioate |
| modified_base | 21 |
| | mod_base = OTHER |
| | note = 2'-O-methyladenosine-3'-phosphate |
| modified_base | 23 |
| | mod_base = OTHER |
| | note = 2'-deoxythymidine-3'-phosphate |
| | ((2S,4R)-N-(1-oxo-6-((3beta-cholest-5-en-3-yl)oxcarboxamido |
| | )hexyl)-4-hydroxypyrrolidin-2-yl)methyl ester |
| misc_feature | 1..21 |
| | note = RNA |
| misc_feature | 22..23 |
| | note = DNA |
| SEQUENCE: 38 | |
| tactgttgga ttgattcgaa att                              23 |

| SEQ ID NO: 39 | moltype = RNA   length = 23 |
| FEATURE | Location/Qualifiers |
| source | 1..23 |
| | mol_type = other RNA |
| | organism = synthetic construct |
| modified_base | 1 |
| | mod_base = OTHER |
| | note = |
| | 2'-O-(N-methylacetamide)thymidine-3'-phosphorothioate |

|   |   |
|---|---|
| | 5'-(E)-Vinylphosphonate |
| modified_base | 2 |
| | mod_base = OTHER |
| | note = 2'-deoxy-2'-fluorouridine-3'-phosphorothioate |
| modified_base | 3 |
| | mod_base = OTHER |
| | note = 2'-O-methyluridine-3'-phosphate |
| modified_base | 4 |
| | mod_base = OTHER |
| | note = 2'-O-methylcytidine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-deoxy-2'-fluoroadenosine-3'-phosphate |
| modified_base | 7 |
| | mod_base = OTHER |
| | note = 2'-O-methyladenosine-3'-phosphate |
| modified_base | 8 |
| | mod_base = OTHER |
| | note = 2'-deoxy-2'-fluorouridine-3'-phosphate |
| modified_base | 9 |
| | mod_base = OTHER |
| | note = 2'-deoxy-2'-fluorocytidine-3'-phosphate |
| modified_base | 10 |
| | mod_base = OTHER |
| | note = 2'-O-methyladenosine-3'-phosphate |
| modified_base | 11 |
| | mod_base = OTHER |
| | note = 2'-O-methyladenosine-3'-phosphate |
| modified_base | 12 |
| | mod_base = OTHER |
| | note = 2'-O-methyluridine-3'-phosphate |
| modified_base | 13 |
| | mod_base = OTHER |
| | note = 2'-O-methylcytidine-3'-phosphate |
| modified_base | 14 |
| | mod_base = OTHER |
| | note = 2'-deoxy-2'-fluorocytidine-3'-phosphate |
| modified_base | 15 |
| | mod_base = OTHER |
| | note = 2'-O-methyladenosine-3'-phosphate |
| modified_base | 16 |
| | mod_base = OTHER |
| | note = 2'-deoxy-2'-fluoroadenosine-3'-phosphate |
| modified_base | 17 |
| | mod_base = OTHER |
| | note = 2'-O-methylcytidine-3'-phosphate |
| modified_base | 18 |
| | mod_base = OTHER |
| | note = 2'-O-methyladenosine-3'-phosphate |
| modified_base | 19 |
| | mod_base = OTHER |
| | note = 2'-O-methylguanosine-3'-phosphate |
| modified_base | 20 |
| | mod_base = OTHER |
| | note = 2'-O-methyluridine-3'-phosphate |
| modified_base | 21 |
| | mod_base = OTHER |
| | note = 2'-O-methyladenosine-3'-phosphorothioate |
| modified_base | 22 |
| | mod_base = OTHER |
| | note = 2'-O-methylguanosine-3'-phosphorothioate |
| modified_base | 23 |
| | mod_base = OTHER |
| | note = 2'-O-methylcytidine |
| SEQUENCE: 39 | |
| tttcgaatca atccaacagt agc | 23 |
| | |
| SEQ ID NO: 40 | moltype = RNA  length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-O-methyluridine-3'-phosphorothioate |
| modified_base | 2 |

|  | mod_base = OTHER |
|---|---|
|  | note = 2'-O-methyladenosine-3'-phosphorothioate |
| modified_base | 3 |
|  | mod_base = OTHER |
|  | note = 2'-O-methylcytidine-3'-phosphate |
| modified_base | 4 |
|  | mod_base = OTHER |
|  | note = 2'-O-methyluridine-3'-phosphate |
| modified_base | 5 |
|  | mod_base = OTHER |
|  | note = 2'-O-methylguanosine-3'-phosphate |
| modified_base | 6 |
|  | mod_base = OTHER |
|  | note = 2'-O-methyluridine-3'-phosphate |
| modified_base | 7 |
|  | mod_base = OTHER |
|  | note = 2'-deoxy-2'-fluorouridine-3'-phosphate |
| modified_base | 8 |
|  | mod_base = OTHER |
|  | note = 2'-O-methylguanosine-3'-phosphate |
| modified_base | 9 |
|  | mod_base = OTHER |
|  | note = 2'-deoxy-2'-fluoroguanosine-3'-phosphate |
| modified_base | 10 |
|  | mod_base = OTHER |
|  | note = 2'-deoxy-2'-fluoroadenosine-3'-phosphate |
| modified_base | 11 |
|  | mod_base = OTHER |
|  | note = 2'-deoxy-2'-fluorouridine-3'-phosphate |
| modified_base | 12 |
|  | mod_base = OTHER |
|  | note = 2'-O-methyluridine-3'-phosphate |
| modified_base | 13 |
|  | mod_base = OTHER |
|  | note = 2'-O-methylguanosine-3'-phosphate |
| modified_base | 14 |
|  | mod_base = OTHER |
|  | note = 2'-O-methyladenosine-3'-phosphate |
| modified_base | 15 |
|  | mod_base = OTHER |
|  | note = 2'-O-methyluridine-3'-phosphate |
| modified_base | 16 |
|  | mod_base = OTHER |
|  | note = 2'-O-methyluridine-3'-phosphate |
| modified_base | 17 |
|  | mod_base = OTHER |
|  | note = 2'-O-methylcytidine-3'-phosphate |
| modified_base | 18 |
|  | mod_base = OTHER |
|  | note = 2'-O-methylguanosine-3'-phosphate |
| modified_base | 19 |
|  | mod_base = OTHER |
|  | note = 2'-O-methyladenosine-3'-phosphate |
| modified_base | 20 |
|  | mod_base = OTHER |
|  | note = 2'-O-methyladenosine-3'-phosphate |
| modified_base | 21 |
|  | mod_base = OTHER |
|  | note = 2'-O-methyladenosine-3'-phosphate (4R-((hydroxy(N-(6-((6-((2S-(4-isobutylphenyl)-propanoyl)amino)hexanoyl)amino)hexanoyl)-4R-hydroxypyrrolidin-2S-ylmethoxy)phosphoryl)oxy)-N-(6-((6-((2S-(4-isobutylphenyl)-propanoyl)amino)hexanoyl)amino)hexanoyl)-pyrrolidin-2S-yl)methyl ester |
| SEQUENCE: 40 |  |
| tactgttgga ttgattcgaa a | 21 |
|  |  |
| SEQ ID NO: 41 | moltype = RNA length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-O-methyladenosine-3'-phosphorothioate |
| modified_base | 3 |
|  | mod_base = OTHER |

```
                        note = 2'-O-methylcytidine-3'-phosphate
modified_base           4
                        mod_base = OTHER
                        note = 2'-O-methyluridine-3'-phosphate
modified_base           5
                        mod_base = OTHER
                        note = 2'-O-methylguanosine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluorouridine-3'-phosphate
modified_base           8
                        mod_base = OTHER
                        note = 2'-O-methylguanosine-3'-phosphate
modified_base           9
                        mod_base = OTHER
                        note = 2'-deoxy-2'-fluoroguanosine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methyladenosine-3'-phosphate
modified_base           15
                        mod_base = OTHER
                        note = 2'-O-methyluridine-3'-phosphate
modified_base           16
                        mod_base = OTHER
                        note = 2'-O-methyluridine-3'-phosphate
modified_base           17
                        mod_base = OTHER
                        note = 2'-O-methylcytidine-3'-phosphate
modified_base           18
                        mod_base = OTHER
                        note = 2'-O-methylguanosine-3'-phosphate
modified_base           19
                        mod_base = OTHER
                        note = 2'-O-methyladenosine-3'-phosphate
modified_base           20
                        mod_base = OTHER
                        note = 2'-O-methyladenosine-3'-phosphate
modified_base           21
                        mod_base = OTHER
                        note = 2'-O-methyladenosine-3'-phosphate
                        ((2S,4R)-N-(6-(hexadecanoylamino)caproyl)-4-hydroxypyrrolid
                        in-2-yl)methyl ester
SEQUENCE: 41
tactgttgga ttgattcgaa a                                              21

SEQ ID NO: 42           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyluridine-3'-phosphate
modified_base           5
                        mod_base = OTHER
```

```
                        note = 2'-O-methylguanosine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluorouridine-3'-phosphate
modified_base           8
                        mod_base = OTHER
                        note = 2'-O-methylguanosine-3'-phosphate
modified_base           9
                        mod_base = OTHER
                        note = 2'-deoxy-2'-fluoroguanosine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methyladenosine-3'-phosphate
modified_base           15
                        mod_base = OTHER
                        note = 2'-O-methyluridine-3'-phosphate
modified_base           16
                        mod_base = OTHER
                        note = 2'-O-methyluridine-3'-phosphate
modified_base           17
                        mod_base = OTHER
                        note = 2'-O-methylcytidine-3'-phosphate
modified_base           18
                        mod_base = OTHER
                        note = 2'-O-methylguanosine-3'-phosphate
modified_base           19
                        mod_base = OTHER
                        note = 2'-O-methyladenosine-3'-phosphate
modified_base           20
                        mod_base = OTHER
                        note = 2'-O-methyladenosine-3'-phosphate
modified_base           21
                        mod_base = OTHER
                        note = 2'-O-methyladenosine-3'-phosphate
                        ((2S,4R)-N-(6-(dodecanoylamino)caproyl)-4-hydroxypyrrolidin
                        -2-yl)methyl ester
SEQUENCE: 42
tactgttgga ttgattcgaa a                                              21

SEQ ID NO: 43           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyluridine-3'-phosphate
modified_base           5
                        mod_base = OTHER
                        note = 2'-O-methylguanosine-3'-phosphate
modified_base           6
                        mod_base = OTHER
                        note = 2'-O-methyluridine-3'-phosphate
modified_base           7
                        mod_base = OTHER
```

```
                          note = 2'-deoxy-2'-fluorouridine-3'-phosphate
modified_base             8
                          mod_base = OTHER
                          note = 2'-O-methylguanosine-3'-phosphate
modified_base             9
                          mod_base = OTHER
                          note = 2'-deoxy-2'-fluoroguanosine-3'-phosphate
modified_base             10
                          mod_base = OTHER
                          note = 2'-deoxy-2'-fluoroadenosine-3'-phosphate
modified_base             11
                          mod_base = OTHER
                          note = 2'-deoxy-2'-fluorouridine-3'-phosphate
modified_base             12
                          mod_base = OTHER
                          note = 2'-O-methyluridine-3'-phosphate
modified_base             13
                          mod_base = OTHER
                          note = 2'-O-methylguanosine-3'-phosphate
modified_base             14
                          mod_base = OTHER
                          note = 2'-O-methyladenosine-3'-phosphate
modified_base             15
                          mod_base = OTHER
                          note = 2'-O-methyluridine-3'-phosphate
modified_base             16
                          mod_base = OTHER
                          note = 2'-O-methyluridine-3'-phosphate
modified_base             17
                          mod_base = OTHER
                          note = 2'-O-methylcytidine-3'-phosphate
modified_base             18
                          mod_base = OTHER
                          note = 2'-O-methylguanosine-3'-phosphate
modified_base             19
                          mod_base = OTHER
                          note = 2'-O-methyladenosine-3'-phosphate
modified_base             20
                          mod_base = OTHER
                          note = 2'-O-methyladenosine-3'-phosphate
modified_base             21
                          mod_base = OTHER
                          note = 2'-O-methyladenosine-3'-phosphate
                           ((2S,4R)-N-(6-octadecan-9Z,12Z-dien-1-oylaminocaproyl)-4-hy
                           droxypyrrolidin-2-yl)methyl ester
SEQUENCE: 43
tactgttgga ttgattcgaa a                                             21

SEQ ID NO: 44             moltype = RNA  length = 21
FEATURE                   Location/Qualifiers
source                    1..21
                          mol_type = other RNA
                          organism = synthetic construct
modified_base             1
                          mod_base = OTHER
                          note = 2'-O-methyluridine-3'-phosphorothioate
modified_base             2
                          mod_base = OTHER
                          note = 2'-O-methyladenosine-3'-phosphorothioate
modified_base             3
                          mod_base = OTHER
                          note = 2'-O-methylcytidine-3'-phosphate
modified_base             4
                          mod_base = OTHER
                          note = 2'-O-methyluridine-3'-phosphate
modified_base             5
                          mod_base = OTHER
                          note = 2'-O-methylguanosine-3'-phosphate
modified_base             6
                          mod_base = OTHER
                          note = 2'-O-methyluridine-3'-phosphate
modified_base             7
                          mod_base = OTHER
                          note = 2'-deoxy-2'-fluorouridine-3'-phosphate
modified_base             8
                          mod_base = OTHER
                          note = 2'-O-methylguanosine-3'-phosphate
modified_base             9
                          mod_base = OTHER
```

```
                         note = 2'-deoxy-2'-fluoroguanosine-3'-phosphate
modified_base            10
                         mod_base = OTHER
                         note = 2'-deoxy-2'-fluoroadenosine-3'-phosphate
modified_base            11
                         mod_base = OTHER
                         note = 2'-deoxy-2'-fluorouridine-3'-phosphate
modified_base            12
                         mod_base = OTHER
                         note = 2'-O-methyluridine-3'-phosphate
modified_base            13
                         mod_base = OTHER
                         note = 2'-O-methylguanosine-3'-phosphate
modified_base            14
                         mod_base = OTHER
                         note = 2'-O-methyladenosine-3'-phosphate
modified_base            15
                         mod_base = OTHER
                         note = 2'-O-methyluridine-3'-phosphate
modified_base            16
                         mod_base = OTHER
                         note = 2'-O-methyluridine-3'-phosphate
modified_base            17
                         mod_base = OTHER
                         note = 2'-O-methylcytidine-3'-phosphate
modified_base            18
                         mod_base = OTHER
                         note = 2'-O-methylguanosine-3'-phosphate
modified_base            19
                         mod_base = OTHER
                         note = 2'-O-methyladenosine-3'-phosphate
modified_base            20
                         mod_base = OTHER
                         note = 2'-O-methyladenosine-3'-phosphate
modified_base            21
                         mod_base = OTHER
                         note = 2'-O-methyladenosine-3'-phosphate
                         ((2S,4R)-N-(6-(stearoylamino)caproyl)-4-hydroxypyrrolidin-2
                         -yl)methyl ester
SEQUENCE: 44
tactgttgga ttgattcgaa a                                                   21

SEQ ID NO: 45           moltype = RNA   length = 21
FEATURE                 Location/Qualifiers
source                  1..21
                         mol_type = other RNA
                         organism = synthetic construct
modified_base            1
                         mod_base = OTHER
                         note = 2'-O-methyluridine-3'-phosphorothioate
modified_base            2
                         mod_base = OTHER
                         note = 2'-O-methyladenosine-3'-phosphorothioate
modified_base            3
                         mod_base = OTHER
                         note = 2'-O-methylcytidine-3'-phosphate
modified_base            4
                         mod_base = OTHER
                         note = 2'-O-methyluridine-3'-phosphate
modified_base            5
                         mod_base = OTHER
                         note = 2'-O-methylguanosine-3'-phosphate
modified_base            6
                         mod_base = OTHER
                         note = 2'-O-methyluridine-3'-phosphate
modified_base            7
                         mod_base = OTHER
                         note = 2'-deoxy-2'-fluorouridine-3'-phosphate
modified_base            8
                         mod_base = OTHER
                         note = 2'-O-methylguanosine-3'-phosphate
modified_base            9
                         mod_base = OTHER
                         note = 2'-deoxy-2'-fluoroguanosine-3'-phosphate
modified_base            10
                         mod_base = OTHER
                         note = 2'-deoxy-2'-fluoroadenosine-3'-phosphate
modified_base            11
                         mod_base = OTHER
```

```
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methyladenosine-3'-phosphate
modified_base           15
                        mod_base = OTHER
                        note = 2'-O-methyluridine-3'-phosphate
modified_base           16
                        mod_base = OTHER
                        note = 2'-O-methyluridine-3'-phosphate
modified_base           17
                        mod_base = OTHER
                        note = 2'-O-methylcytidine-3'-phosphate
modified_base           18
                        mod_base = OTHER
                        note = 2'-O-methylguanosine-3'-phosphate
modified_base           19
                        mod_base = OTHER
                        note = 2'-O-methyladenosine-3'-phosphate
modified_base           20
                        mod_base = OTHER
                        note = 2'-O-methyladenosine-3'-phosphate
modified_base           21
                        mod_base = OTHER
                        note = 2'-O-methyladenosine-3'-phosphate
                        ((2S,4R)-N-(1-oxo-6-((3beta-cholest-5-en-3-yl)oxcarboxamido
                        )hexyl)-4-hydroxypyrrolidin-2-yl)methyl ester
SEQUENCE: 45
tactgttgga ttgattcgaa a                                              21

SEQ ID NO: 46           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyluridine-3'-phosphate
modified_base           5
                        mod_base = OTHER
                        note = 2'-O-methylguanosine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluorouridine-3'-phosphate
modified_base           8
                        mod_base = OTHER
                        note = 2'-O-methylguanosine-3'-phosphate
modified_base           9
                        mod_base = OTHER
                        note = 2'-deoxy-2'-fluoroguanosine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
```

| | |
|---|---|
| | note = 2'-O-methylguanosine-3'-phosphate |
| modified_base | 14 |
| | mod_base = OTHER |
| | note = 2'-O-methyladenosine-3'-phosphate |
| modified_base | 15 |
| | mod_base = OTHER |
| | note = 2'-O-methyluridine-3'-phosphate |
| modified_base | 16 |
| | mod_base = OTHER |
| | note = 2'-O-methyluridine-3'-phosphate |
| modified_base | 17 |
| | mod_base = OTHER |
| | note = 2'-O-methylcytidine-3'-phosphate |
| modified_base | 18 |
| | mod_base = OTHER |
| | note = 2'-O-methylguanosine-3'-phosphate |
| modified_base | 19 |
| | mod_base = OTHER |
| | note = 2'-O-methyladenosine-3'-phosphate |
| modified_base | 20 |
| | mod_base = OTHER |
| | note = 2'-O-methyladenosine-3'-phosphate |
| modified_base | 21 |
| | mod_base = OTHER |
| | note = 2'-O-methyladenosine-3'-phosphate ((2S,4R)-N-(6-aminocaproyl)-4-hydroxypyrrolidin-2-yl)methyl ester |
| SEQUENCE: 46 | |
| tactgttgga ttgattcgaa a | 21 |
| | |
| SEQ ID NO: 47 | moltype = RNA  length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-O-methyluridine-3'-phosphorothioate |
| modified_base | 2 |
| | mod_base = OTHER |
| | note = 2'-O-methyladenosine-3'-phosphorothioate |
| modified_base | 3 |
| | mod_base = OTHER |
| | note = 2'-O-methylcytidine-3'-phosphate |
| modified_base | 4 |
| | mod_base = OTHER |
| | note = 2'-O-methyluridine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-O-methyluridine-3'-phosphate |
| modified_base | 7 |
| | mod_base = OTHER |
| | note = 2'-deoxy-2'-fluorouridine-3'-phosphate |
| modified_base | 8 |
| | mod_base = OTHER |
| | note = 2'-O-methylguanosine-3'-phosphate |
| modified_base | 9 |
| | mod_base = OTHER |
| | note = 2'-deoxy-2'-fluoroguanosine-3'-phosphate |
| modified_base | 10 |
| | mod_base = OTHER |
| | note = 2'-deoxy-2'-fluoroadenosine-3'-phosphate |
| modified_base | 11 |
| | mod_base = OTHER |
| | note = 2'-deoxy-2'-fluorouridine-3'-phosphate |
| modified_base | 12 |
| | mod_base = OTHER |
| | note = 2'-O-methyluridine-3'-phosphate |
| modified_base | 13 |
| | mod_base = OTHER |
| | note = 2'-O-methylguanosine-3'-phosphate |
| modified_base | 14 |
| | mod_base = OTHER |
| | note = 2'-O-methyladenosine-3'-phosphate |
| modified_base | 15 |
| | mod_base = OTHER |

|               | note = 2'-O-methyluridine-3'-phosphate |
| modified_base | 16 |
|               | mod_base = OTHER |
|               | note = 2'-O-methyluridine-3'-phosphate |
| modified_base | 17 |
|               | mod_base = OTHER |
|               | note = 2'-O-methylcytidine-3'-phosphate |
| modified_base | 18 |
|               | mod_base = OTHER |
|               | note = 2'-O-methylguanosine-3'-phosphate |
| modified_base | 19 |
|               | mod_base = OTHER |
|               | note = 2'-O-methyladenosine-3'-phosphate |
| modified_base | 20 |
|               | mod_base = OTHER |
|               | note = 2'-O-methyladenosine-3'-phosphate |
| modified_base | 21 |
|               | mod_base = OTHER |
|               | note = 2'-O-methyladenosine-3'-phosphate |
|               | ((2S,4R)-N-(6-(docosa-4E,7E,10E,13E,16E,19E-hexaen-1-oylami |
|               | no)caproyl)-4-hydroxypyrrolidin-2-yl)methyl ester |

SEQUENCE: 47
tactgttgga ttgattcgaa a                                            21

| SEQ ID NO: 48 | moltype = RNA  length = 21 |
| FEATURE       | Location/Qualifiers |
| source        | 1..21 |
|               | mol_type = other RNA |
|               | organism = synthetic construct |
| modified_base | 1 |
|               | mod_base = OTHER |
|               | note = 2'-O-methyluridine-3'-phosphorothioate |
| modified_base | 2 |
|               | mod_base = OTHER |
|               | note = 2'-O-methyladenosine-3'-phosphorothioate |
| modified_base | 3 |
|               | mod_base = OTHER |
|               | note = 2'-O-methylcytidine-3'-phosphate |
| modified_base | 4 |
|               | mod_base = OTHER |
|               | note = 2'-O-methyluridine-3'-phosphate |
| modified_base | 5 |
|               | mod_base = OTHER |
|               | note = 2'-O-methylguanosine-3'-phosphate |
| modified_base | 6 |
|               | mod_base = OTHER |
|               | note = 2'-O-methyluridine-3'-phosphate |
| modified_base | 7 |
|               | mod_base = OTHER |
|               | note = 2'-deoxy-2'-fluorouridine-3'-phosphate |
| modified_base | 8 |
|               | mod_base = OTHER |
|               | note = 2'-O-methylguanosine-3'-phosphate |
| modified_base | 9 |
|               | mod_base = OTHER |
|               | note = 2'-deoxy-2'-fluoroguanosine-3'-phosphate |
| modified_base | 10 |
|               | mod_base = OTHER |
|               | note = 2'-deoxy-2'-fluoroadenosine-3'-phosphate |
| modified_base | 11 |
|               | mod_base = OTHER |
|               | note = 2'-deoxy-2'-fluorouridine-3'-phosphate |
| modified_base | 12 |
|               | mod_base = OTHER |
|               | note = 2'-O-methyluridine-3'-phosphate |
| modified_base | 13 |
|               | mod_base = OTHER |
|               | note = 2'-O-methylguanosine-3'-phosphate |
| modified_base | 14 |
|               | mod_base = OTHER |
|               | note = 2'-O-methyladenosine-3'-phosphate |
| modified_base | 15 |
|               | mod_base = OTHER |
|               | note = 2'-O-methyluridine-3'-phosphate |
| modified_base | 16 |
|               | mod_base = OTHER |
|               | note = 2'-O-hexadecyl-uridine-3'-phosphate |
| modified_base | 17 |
|               | mod_base = OTHER |

```
                              note = 2'-O-methylcytidine-3'-phosphate
modified_base                 18
                              mod_base = OTHER
                              note = 2'-O-methylguanosine-3'-phosphate
modified_base                 19
                              mod_base = OTHER
                              note = 2'-O-methyladenosine-3'-phosphorothioate
modified_base                 20
                              mod_base = OTHER
                              note = 2'-O-methyladenosine-3'-phosphorothioate
modified_base                 21
                              mod_base = OTHER
                              note = 2'-O-methyladenosine
SEQUENCE: 48
tactgttgga ttgattcgaa a                                                  21

SEQ ID NO: 49                 moltype = RNA   length = 21
FEATURE                       Location/Qualifiers
source                        1..21
                              mol_type = other RNA
                              organism = synthetic construct
modified_base                 1
                              mod_base = OTHER
                              note = 2'-O-methyluridine-3'-phosphorothioate
modified_base                 2
                              mod_base = OTHER
                              note = 2'-O-methyladenosine-3'-phosphorothioate
modified_base                 3
                              mod_base = OTHER
                              note = 2'-O-methylcytidine-3'-phosphate
modified_base                 4
                              mod_base = OTHER
                              note = 2'-O-methyluridine-3'-phosphate
modified_base                 5
                              mod_base = OTHER
                              note = 2'-O-methylguanosine-3'-phosphate
modified_base                 6
                              mod_base = OTHER
                              note = 2'-O-methyluridine-3'-phosphate
modified_base                 7
                              mod_base = OTHER
                              note = 2'-deoxy-2'-fluorouridine-3'-phosphate
modified_base                 8
                              mod_base = OTHER
                              note = 2'-O-methylguanosine-3'-phosphate
modified_base                 9
                              mod_base = OTHER
                              note = 2'-deoxy-2'-fluoroguanosine-3'-phosphate
modified_base                 10
                              mod_base = OTHER
                              note = 2'-deoxy-2'-fluoroadenosine-3'-phosphate
modified_base                 11
                              mod_base = OTHER
                              note = 2'-deoxy-2'-fluorouridine-3'-phosphate
modified_base                 12
                              mod_base = OTHER
                              note = 2'-O-methyluridine-3'-phosphate
modified_base                 13
                              mod_base = OTHER
                              note = 2'-O-methylguanosine-3'-phosphate
modified_base                 14
                              mod_base = OTHER
                              note = 2'-O-methyladenosine-3'-phosphate
modified_base                 15
                              mod_base = OTHER
                              note = 2'-O-methyluridine-3'-phosphate
modified_base                 16
                              mod_base = OTHER
                              note = 2'-O-methyluridine-3'-phosphate
modified_base                 17
                              mod_base = OTHER
                              note = 2'-O-methylcytidine-3'-phosphate
modified_base                 18
                              mod_base = OTHER
                              note = 2'-O-methylguanosine-3'-phosphate
modified_base                 19
                              mod_base = OTHER
                              note = 2'-O-methyladenosine-3'-phosphate
modified_base                 20
```

```
                        mod_base = OTHER
                        note = 2'-O-methyladenosine-3'-phosphate
modified_base           21
                        mod_base = OTHER
                        note = 2'-O-methyladenosine-3'-phosphate
                        ((2S,4R)-N-(6-((2-([ole-1-yloxy]methyl)-2-(ole-1-yloxy)ethy
                        l)oxycarbonylamino)-hexanoyl)-4-hydroxypyrrolidin-2-yl)meth
                        yl ester
SEQUENCE: 49
tactgttgga ttgattcgaa a                                                21

SEQ ID NO: 50           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylcytidine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methyluridine-3'-phosphate
modified_base           4
                        mod_base = OTHER
                        note = 2'-O-methyluridine-3'-phosphate
modified_base           5
                        mod_base = OTHER
                        note = 2'-O-methyluridine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluoroadenosine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluorocytidine-3'-phosphate
modified_base           12
                        mod_base = OTHER
                        note = 2'-O-methyluridine-3'-phosphate
modified_base           13
                        mod_base = OTHER
                        note = 2'-O-methylcytidine-3'-phosphate
modified_base           14
                        mod_base = OTHER
                        note = 2'-O-methyladenosine-3'-phosphate
modified_base           15
                        mod_base = OTHER
                        note = 2'-O-methylcytidine-3'-phosphate
modified_base           16
                        mod_base = OTHER
                        note = 2'-O-methyluridine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methyladenosine-3'-phosphate
modified_base           20
                        mod_base = OTHER
                        note = 2'-O-methyladenosine-3'-phosphate
modified_base           21
                        mod_base = OTHER
                        note = 2'-O-methyladenosine-3'-phosphate
```

((2S,4R)-1-[29-[[2-(acetylamino)-2-deoxy-beta-D-galactopyra
                         nosyl]oxy]-14,14-bis[[3-[[3-[[5-[[2-(acetylamino)-2-deoxy-b
                         eta-D-galactopyranosyl]oxy]-1-oxopentyl]amino]propyl]amino]
                         -3-oxopropoxy]methyl]-1,12,19,25-tetraoxo-16-oxa-13,20,24-t
                         riazanonacos-1-yl]-4-hydroxy-2-pyrrolidinyl)methyl ester
SEQUENCE: 50
cattttaatc ctcactctaa a                                                    21

SEQ ID NO: 51            moltype = RNA  length = 23
FEATURE                  Location/Qualifiers
source                   1..23
                         mol_type = other RNA
                         organism = synthetic construct
modified_base            1
                         mod_base = OTHER
                         note = 2'-O-methyluridine-3'-phosphorothioate
modified_base            2
                         mod_base = OTHER
                         note = 2'-deoxy-2'-fluorouridine-3'-phosphorothioate
modified_base            3
                         mod_base = OTHER
                         note = 2'-O-methyluridine-3'-phosphate
modified_base            4
                         mod_base = OTHER
                         note = 2'-O-methyladenosine-3'-phosphate
modified_base            5
                         mod_base = OTHER
                         note = 2'-O-methylguanosine-3'-phosphate
modified_base            6
                         mod_base = OTHER
                         note = 2'-deoxy-2'-fluoroadenosine-3'-phosphate
modified_base            7
                         mod_base = OTHER
                         note = 2'-O-methylguanosine-3'-phosphate
modified_base            8
                         mod_base = OTHER
                         note = 2'-deoxy-2'-fluorouridine-3'-phosphate
modified_base            9
                         mod_base = OTHER
                         note = 2'-deoxy-2'-fluoroguanosine-3'-phosphate
modified_base            10
                         mod_base = OTHER
                         note = 2'-O-methyladenosine-3'-phosphate
modified_base            11
                         mod_base = OTHER
                         note = 2'-O-methylguanosine-3'-phosphate
modified_base            12
                         mod_base = OTHER
                         note = 2'-O-methylguanosine-3'-phosphate
modified_base            13
                         mod_base = OTHER
                         note = 2'-O-methyladenosine-3'-phosphate
modified_base            14
                         mod_base = OTHER
                         note = 2'-deoxy-2'-fluorouridine-3'-phosphate
modified_base            15
                         mod_base = OTHER
                         note = 2'-O-methyluridine-3'-phosphate
modified_base            16
                         mod_base = OTHER
                         note = 2'-deoxy-2'-fluoroadenosine-3'-phosphate
modified_base            17
                         mod_base = OTHER
                         note = 2'-O-methyladenosine-3'-phosphate
modified_base            18
                         mod_base = OTHER
                         note = 2'-O-methyladenosine-3'-phosphate
modified_base            19
                         mod_base = OTHER
                         note = 2'-O-methyladenosine-3'-phosphate
modified_base            20
                         mod_base = OTHER
                         note = 2'-O-methyluridine-3'-phosphate
modified_base            21
                         mod_base = OTHER
                         note = 2'-O-methylguanosine-3'-phosphorothioate
modified_base            22
                         mod_base = OTHER
                         note = 2'-O-methyladenosine-3'-phosphorothioate

```
                        23
                        mod_base = OTHER
                        note = 2'-O-methylguanosine
SEQUENCE: 51
tttagagtga ggattaaaat gag                                               23

SEQ ID NO: 52           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylcytidine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methyluridine-3'-phosphate
modified_base           4
                        mod_base = OTHER
                        note = 2'-O-methyluridine-3'-phosphate
modified_base           5
                        mod_base = OTHER
                        note = 2'-O-methyluridine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluoroadenosine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluorocytidine-3'-phosphate
modified_base           12
                        mod_base = OTHER
                        note = 2'-O-methyluridine-3'-phosphate
modified_base           13
                        mod_base = OTHER
                        note = 2'-O-methylcytidine-3'-phosphate
modified_base           14
                        mod_base = OTHER
                        note = 2'-O-methyladenosine-3'-phosphate
modified_base           15
                        mod_base = OTHER
                        note = 2'-O-methylcytidine-3'-phosphate
modified_base           16
                        mod_base = OTHER
                        note = 2'-O-methyluridine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methyladenosine-3'-phosphate
modified_base           20
                        mod_base = OTHER
                        note = 2'-O-methyladenosine-3'-phosphate
modified_base           21
                        mod_base = OTHER
                        note = 2'-O-methyladenosine-3'-phosphate
                        ((2S,4R)-N-(1-oxo-6-((3beta-cholest-5-en-3-yl)oxcarboxamido
                        )hexyl)-4-hydroxypyrrolidin-2-yl)methyl ester
SEQUENCE: 52
cattttaatc ctcactctaa a                                                 21
```

-continued

| | |
|---|---|
| SEQ ID NO: 53 | moltype = RNA length = 21 |
| FEATURE | Location/Qualifiers |
| source | 1..21<br>mol_type = other RNA<br>organism = synthetic construct |
| modified_base | 1<br>mod_base = OTHER<br>note = 2'-O-methylcytidine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyluridine-3'-phosphate |
| modified_base | 4<br>mod_base = OTHER<br>note = 2'-O-methyluridine-3'-phosphate |
| modified_base | 5<br>mod_base = OTHER<br>note = 2'-O-methyluridine-3'-phosphate |
| modified_base | 6<br>mod_base = OTHER<br>note = 2'-O-hexadecyl-uridine-3'-phosphate |
| modified_base | 7<br>mod_base = OTHER<br>note = 2'-deoxy-2'-fluoroadenosine-3'-phosphate |
| modified_base | 8<br>mod_base = OTHER<br>note = 2'-O-methyladenosine-3'-phosphate |
| modified_base | 9<br>mod_base = OTHER<br>note = 2'-deoxy-2'-fluorouridine-3'-phosphate |
| modified_base | 10<br>mod_base = OTHER<br>note = 2'-deoxy-2'-fluorocytidine-3'-phosphate |
| modified_base | 11<br>mod_base = OTHER<br>note = 2'-deoxy-2'-fluorocytidine-3'-phosphate |
| modified_base | 12<br>mod_base = OTHER<br>note = 2'-O-methyluridine-3'-phosphate |
| modified_base | 13<br>mod_base = OTHER<br>note = 2'-O-methylcytidine-3'-phosphate |
| modified_base | 14<br>mod_base = OTHER<br>note = 2'-O-methyladenosine-3'-phosphate |
| modified_base | 15<br>mod_base = OTHER<br>note = 2'-O-methylcytidine-3'-phosphate |
| modified_base | 16<br>mod_base = OTHER<br>note = 2'-O-methyluridine-3'-phosphate |
| modified_base | 17<br>mod_base = OTHER<br>note = 2'-O-methylcytidine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyladenosine-3'-phosphate |
| modified_base | 20<br>mod_base = OTHER<br>note = 2'-O-methyladenosine-3'-phosphate |
| modified_base | 21<br>mod_base = OTHER<br>note = 2'-O-methyladenosine |
| SEQUENCE: 53 | |
| cattttaatc ctcactctaa a | 21 |
| | |
| SEQ ID NO: 54 | moltype = RNA length = 21 |
| FEATURE | Location/Qualifiers |
| source | 1..21<br>mol_type = other RNA<br>organism = synthetic construct |
| modified_base | 1<br>mod_base = OTHER<br>note = 2'-O-methylcytidine-3'-phosphorothioate |

-continued

```
modified_base      2
                   mod_base = OTHER
                   note = 2'-O-methyladenosine-3'-phosphorothioate
modified_base      3
                   mod_base = OTHER
                   note = 2'-O-methyluridine-3'-phosphate
modified_base      4
                   mod_base = OTHER
                   note = 2'-O-methyluridine-3'-phosphate
modified_base      5
                   mod_base = OTHER
                   note = 2'-O-methyluridine-3'-phosphate
modified_base      6
                   mod_base = OTHER
                   note = 2'-O-methyluridine-3'-phosphate
modified_base      7
                   mod_base = OTHER
                   note = 2'-deoxy-2'-fluoroadenosine-3'-phosphate
modified_base      8
                   mod_base = OTHER
                   note = 2'-O-methyladenosine-3'-phosphate
modified_base      9
                   mod_base = OTHER
                   note = 2'-deoxy-2'-fluorouridine-3'-phosphate
modified_base      10
                   mod_base = OTHER
                   note = 2'-deoxy-2'-fluorocytidine-3'-phosphate
modified_base      11
                   mod_base = OTHER
                   note = 2'-deoxy-2'-fluorocytidine-3'-phosphate
modified_base      12
                   mod_base = OTHER
                   note = 2'-O-methyluridine-3'-phosphate
modified_base      13
                   mod_base = OTHER
                   note = 2'-O-methylcytidine-3'-phosphate
modified_base      14
                   mod_base = OTHER
                   note = 2'-O-methyladenosine-3'-phosphate
modified_base      15
                   mod_base = OTHER
                   note = 2'-O-methylcytidine-3'-phosphate
modified_base      16
                   mod_base = OTHER
                   note = 2'-O-methyluridine-3'-phosphate
modified_base      17
                   mod_base = OTHER
                   note = 2'-O-methylcytidine-3'-phosphate
modified_base      18
                   mod_base = OTHER
                   note = 2'-O-methyluridine-3'-phosphate
modified_base      19
                   mod_base = OTHER
                   note = 2'-O-methyladenosine-3'-phosphate
modified_base      20
                   mod_base = OTHER
                   note = 2'-O-methyladenosine-3'-phosphate
modified_base      21
                   mod_base = OTHER
                   note = 2'-O-methyladenosine
SEQUENCE: 54
cattttaatc ctcactctaa a                                              21

SEQ ID NO: 55      moltype = RNA   length = 21
FEATURE            Location/Qualifiers
source             1..21
                   mol_type = other RNA
                   organism = synthetic construct
modified_base      1
                   mod_base = OTHER
                   note = 2'-O-methylguanosine-3'-phosphorothioate
modified_base      2
                   mod_base = OTHER
                   note = 2'-O-methyladenosine-3'-phosphorothioate
modified_base      3
                   mod_base = OTHER
                   note = 2'-O-methyladenosine-3'-phosphate
modified_base      4
                   mod_base = OTHER
```

| | | |
|---|---|---|
| modified_base | | note = 2'-O-methyladenosine-3'-phosphate |
| | 5 | |
| | | mod_base = OTHER |
| | | note = 2'-O-methylcytidine-3'-phosphate |
| modified_base | 6 | |
| | | mod_base = OTHER |
| | | note = 2'-O-methyluridine-3'-phosphate |
| modified_base | 7 | |
| | | mod_base = OTHER |
| | | note = 2'-deoxy-2'-fluorocytidine-3'-phosphate |
| modified_base | 8 | |
| | | mod_base = OTHER |
| | | note = 2'-O-methyladenosine-3'-phosphate |
| modified_base | 9 | |
| | | mod_base = OTHER |
| | | note = 2'-deoxy-2'-fluoroadenosine-3'-phosphate |
| modified_base | 10 | |
| | | mod_base = OTHER |
| | | note = 2'-deoxy-2'-fluorouridine-3'-phosphate |
| modified_base | 11 | |
| | | mod_base = OTHER |
| | | note = 2'-deoxy-2'-fluoroadenosine-3'-phosphate |
| modified_base | 12 | |
| | | mod_base = OTHER |
| | | note = 2'-O-methyladenosine-3'-phosphate |
| modified_base | 13 | |
| | | mod_base = OTHER |
| | | note = 2'-O-methyladenosine-3'-phosphate |
| modified_base | 14 | |
| | | mod_base = OTHER |
| | | note = 2'-O-methylguanosine-3'-phosphate |
| modified_base | 15 | |
| | | mod_base = OTHER |
| | | note = 2'-O-hexadecyl-uridine-3'-phosphate |
| modified_base | 16 | |
| | | mod_base = OTHER |
| | | note = 2'-O-methylguanosine-3'-phosphate |
| modified_base | 17 | |
| | | mod_base = OTHER |
| | | note = 2'-O-methylcytidine-3'-phosphate |
| modified_base | 18 | |
| | | mod_base = OTHER |
| | | note = 2'-O-methyluridine-3'-phosphate |
| modified_base | 19 | |
| | | mod_base = OTHER |
| | | note = 2'-O-methyluridine-3'-phosphate |
| modified_base | 20 | |
| | | mod_base = OTHER |
| | | note = 2'-O-methyluridine-3'-phosphate |
| modified_base | 21 | |
| | | mod_base = OTHER |
| | | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 55 | | |
| gaaactcaat aaagtgcttt a | | 21 |
| | | |
| SEQ ID NO: 56 | moltype = RNA length = 23 | |
| FEATURE | Location/Qualifiers | |
| source | 1..23 | |
| | | mol_type = other RNA |
| | | organism = synthetic construct |
| modified_base | 1 | |
| | | mod_base = OTHER |
| | | note = 2'-O-methyluridine-3'-phosphorothioate |
| modified_base | 2 | |
| | | mod_base = OTHER |
| | | note = 2'-deoxy-2'-fluoroadenosine-3'-phosphorothioate |
| modified_base | 3 | |
| | | mod_base = OTHER |
| | | note = 2'-O-methyladenosine-3'-phosphate |
| modified_base | 4 | |
| | | mod_base = OTHER |
| | | note = 2'-O-methyladenosine-3'-phosphate |
| modified_base | 5 | |
| | | mod_base = OTHER |

```
modified_base       note = 2'-O-methylguanosine-3'-phosphate
                    6
                    mod_base = OTHER
                    note = 2'-deoxy-2'-fluorocytidine-3'-phosphate
modified_base       7
                    mod_base = OTHER
                    note = 2'-O-methyladenosine-3'-phosphate
modified_base       8
                    mod_base = OTHER
                    note = 2'-O-methylcytidine-3'-phosphate
modified_base       9
                    mod_base = OTHER
                    note = 2'-O-methyluridine-3'-phosphate
modified_base       10
                    mod_base = OTHER
                    note = 2'-O-methyluridine-3'-phosphate
modified_base       11
                    mod_base = OTHER
                    note = 2'-O-methyluridine-3'-phosphate
modified_base       12
                    mod_base = OTHER
                    note = 2'-O-methyladenosine-3'-phosphate
modified_base       13
                    mod_base = OTHER
                    note = 2'-O-methyluridine-3'-phosphate
modified_base       14
                    mod_base = OTHER
                    note = 2'-deoxy-2'-fluorouridine-3'-phosphate
modified_base       15
                    mod_base = OTHER
                    note = 2'-O-methylguanosine-3'-phosphate
modified_base       16
                    mod_base = OTHER
                    note = 2'-deoxy-2'-fluoroadenosine-3'-phosphate
modified_base       17
                    mod_base = OTHER
                    note = 2'-O-methylguanosine-3'-phosphate
modified_base       18
                    mod_base = OTHER
                    note = 2'-O-methyluridine-3'-phosphate
modified_base       19
                    mod_base = OTHER
                    note = 2'-O-methyluridine-3'-phosphate
modified_base       20
                    mod_base = OTHER
                    note = 2'-O-methyluridine-3'-phosphate
modified_base       21
                    mod_base = OTHER
                    note = 2'-O-methylcytidine-3'-phosphorothioate
modified_base       22
                    mod_base = OTHER
                    note = 2'-O-methyluridine-3'-phosphorothioate
modified_base       23
                    mod_base = OTHER
                    note = 2'-O-methylguanosine
SEQUENCE: 56
taaagcactt tattgagttt ctg                                               23

SEQ ID NO: 57       moltype = RNA   length = 21
FEATURE             Location/Qualifiers
source              1..21
                    mol_type = other RNA
                    organism = synthetic construct
modified_base       1
                    mod_base = OTHER
                    note = 2'-O-methylguanosine-3'-phosphorothioate
modified_base       2
                    mod_base = OTHER
                    note = 2'-O-methyladenosine-3'-phosphorothioate
modified_base       3
                    mod_base = OTHER
                    note = 2'-O-methyladenosine-3'-phosphate
modified_base       4
                    mod_base = OTHER
                    note = 2'-O-methyladenosine-3'-phosphate
modified_base       5
                    mod_base = OTHER
                    note = 2'-O-methylcytidine-3'-phosphate
modified_base       6
```

| | | |
|---|---|---|
| | | mod_base = OTHER |
| | | note = 2'-O-hexadecyl-uridine-3'-phosphate |
| modified_base | 7 | |
| | | mod_base = OTHER |
| | | note = 2'-deoxy-2'-fluorocytidine-3'-phosphate |
| modified_base | 8 | |
| | | mod_base = OTHER |
| | | note = 2'-O-methyladenosine-3'-phosphate |
| modified_base | 9 | |
| | | mod_base = OTHER |
| | | note = 2'-deoxy-2'-fluoroadenosine-3'-phosphate |
| modified_base | 10 | |
| | | mod_base = OTHER |
| | | note = 2'-deoxy-2'-fluorouridine-3'-phosphate |
| modified_base | 11 | |
| | | mod_base = OTHER |
| | | note = 2'-deoxy-2'-fluoroadenosine-3'-phosphate |
| modified_base | 12 | |
| | | mod_base = OTHER |
| | | note = 2'-O-methyladenosine-3'-phosphate |
| modified_base | 13 | |
| | | mod_base = OTHER |
| | | note = 2'-O-methyladenosine-3'-phosphate |
| modified_base | 14 | |
| | | mod_base = OTHER |
| | | note = 2'-O-methylguanosine-3'-phosphate |
| modified_base | 15 | |
| | | mod_base = OTHER |
| | | note = 2'-O-methyluridine-3'-phosphate |
| modified_base | 16 | |
| | | mod_base = OTHER |
| | | note = 2'-O-methylguanosine-3'-phosphate |
| modified_base | 17 | |
| | | mod_base = OTHER |
| | | note = 2'-O-methylcytidine-3'-phosphate |
| modified_base | 18 | |
| | | mod_base = OTHER |
| | | note = 2'-O-methyluridine-3'-phosphate |
| modified_base | 19 | |
| | | mod_base = OTHER |
| | | note = 2'-O-methyluridine-3'-phosphate |
| modified_base | 20 | |
| | | mod_base = OTHER |
| | | note = 2'-O-methyluridine-3'-phosphate |
| modified_base | 21 | |
| | | mod_base = OTHER |
| | | note = 2'-O-methyladenosine-3'-phosphate |
| | | ((2S,4R)-1-[29-[[2-(acetylamino)-2-deoxy-beta-D-galactopyra |
| | | nosyl]oxy]-14,14-bis[[3-[[3-[[5-[[2-(acetylamino)-2-deoxy-b |
| | | eta-D-galactopyranosyl]oxy]-1-oxopentyl]amino]propyl]amino] |
| | | -3-oxopropoxy]methyl]-1,12,19,25-tetraoxo-16-oxa-13,20,24-t |
| | | riazanonacos-1-yl]-4-hydroxy-2-pyrrolidinyl)methyl ester |
| SEQUENCE: 57 | | |
| gaaactcaat aaagtgcttt a | | 21 |
| | | |
| SEQ ID NO: 58 | moltype = RNA   length = 21 | |
| FEATURE | Location/Qualifiers | |
| source | 1..21 | |
| | | mol_type = other RNA |
| | | organism = synthetic construct |
| modified_base | 1 | |
| | | mod_base = OTHER |
| | | note = 2'-O-methylguanosine-3'-phosphorothioate |
| modified_base | 2 | |
| | | mod_base = OTHER |
| | | note = 2'-O-methyladenosine-3'-phosphorothioate |
| modified_base | 3 | |
| | | mod_base = OTHER |
| | | note = 2'-O-methyladenosine-3'-phosphate |
| modified_base | 4 | |
| | | mod_base = OTHER |
| | | note = 2'-O-methyladenosine-3'-phosphate |
| modified_base | 5 | |
| | | mod_base = OTHER |
| | | note = 2'-O-methylcytidine-3'-phosphate |
| modified_base | 6 | |
| | | mod_base = OTHER |
| | | note = 2'-O-methyluridine-3'-phosphate |
| modified_base | 7 | |

|     |     |
| --- | --- |
|  | mod_base = OTHER |
|  | note = 2'-deoxy-2'-fluorocytidine-3'-phosphate |
| modified_base | 8 |
|  | mod_base = OTHER |
|  | note = 2'-O-methyladenosine-3'-phosphate |
| modified_base | 9 |
|  | mod_base = OTHER |
|  | note = 2'-deoxy-2'-fluoroadenosine-3'-phosphate |
| modified_base | 10 |
|  | mod_base = OTHER |
|  | note = 2'-deoxy-2'-fluorouridine-3'-phosphate |
| modified_base | 11 |
|  | mod_base = OTHER |
|  | note = 2'-deoxy-2'-fluoroadenosine-3'-phosphate |
| modified_base | 12 |
|  | mod_base = OTHER |
|  | note = 2'-O-methyladenosine-3'-phosphate |
| modified_base | 13 |
|  | mod_base = OTHER |
|  | note = 2'-O-methyladenosine-3'-phosphate |
| modified_base | 14 |
|  | mod_base = OTHER |
|  | note = 2'-O-methylguanosine-3'-phosphate |
| modified_base | 15 |
|  | mod_base = OTHER |
|  | note = 2'-O-methyluridine-3'-phosphate |
| modified_base | 16 |
|  | mod_base = OTHER |
|  | note = 2'-O-methylguanosine-3'-phosphate |
| modified_base | 17 |
|  | mod_base = OTHER |
|  | note = 2'-O-methylcytidine-3'-phosphate |
| modified_base | 18 |
|  | mod_base = OTHER |
|  | note = 2'-O-methyluridine-3'-phosphate |
| modified_base | 19 |
|  | mod_base = OTHER |
|  | note = 2'-O-methyluridine-3'-phosphate |
| modified_base | 20 |
|  | mod_base = OTHER |
|  | note = 2'-O-methyluridine-3'-phosphate |
| modified_base | 21 |
|  | mod_base = OTHER |
|  | note = 2'-O-methyladenosine-3'-phosphate |
|  | ((2S,4R)-1-[29-[[2-(acetylamino)-2-deoxy-beta-D-galactopyra |
|  | nosyl]oxy]-14,14-bis[[3-[[3-[[5-[[2-(acetylamino)-2-deoxy-b |
|  | eta-D-galactopyranosyl]oxy]-1-oxopentyl]amino]propyl]amino] |
|  | -3-oxopropoxy]methyl]-1,12,19,25-tetraoxo-16-oxa-13,20,24-t |
|  | riazanonacos-1-yl]-4-hydroxy-2-pyrrolidinyl)methyl ester |
| SEQUENCE: 58 |  |
| gaaactcaat aaagtgcttt a | 21 |
|  |  |
| SEQ ID NO: 59 | moltype = RNA  length = 23 |
| FEATURE | Location/Qualifiers |
| source | 1..23 |
|  | mol_type = other RNA |
|  | organism = synthetic construct |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-deoxy-2'-fluoroadenosine-3'-phosphorothioate |
| modified_base | 3 |
|  | mod_base = OTHER |
|  | note = 2'-O-methyladenosine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methylguanosine-3'-phosphate |
| modified_base | 6 |
|  | mod_base = OTHER |
|  | note = 2'-deoxy-2'-fluorocytidine-3'-phosphate |
| modified_base | 7 |
|  | mod_base = OTHER |
|  | note = 2'-O-methyladenosine-3'-phosphate |
| modified_base | 8 |

|  |  |
|---|---|
|  | mod_base = OTHER |
|  | note = 2'-O-methylcytidine-3'-phosphate |
| modified_base | 9 |
|  | mod_base = OTHER |
|  | note = 2'-O-methyluridine-3'-phosphate |
| modified_base | 10 |
|  | mod_base = OTHER |
|  | note = 2'-O-methyluridine-3'-phosphate |
| modified_base | 11 |
|  | mod_base = OTHER |
|  | note = 2'-O-methyluridine-3'-phosphate |
| modified_base | 12 |
|  | mod_base = OTHER |
|  | note = 2'-O-methyladenosine-3'-phosphate |
| modified_base | 13 |
|  | mod_base = OTHER |
|  | note = 2'-O-methyluridine-3'-phosphate |
| modified_base | 14 |
|  | mod_base = OTHER |
|  | note = 2'-deoxy-2'-fluorouridine-3'-phosphate |
| modified_base | 15 |
|  | mod_base = OTHER |
|  | note = 2'-O-hexadecyl-guanosine-3'-phosphate |
| modified_base | 16 |
|  | mod_base = OTHER |
|  | note = 2'-deoxy-2'-fluoroadenosine-3'-phosphate |
| modified_base | 17 |
|  | mod_base = OTHER |
|  | note = 2'-O-methylguanosine-3'-phosphate |
| modified_base | 18 |
|  | mod_base = OTHER |
|  | note = 2'-O-methyluridine-3'-phosphate |
| modified_base | 19 |
|  | mod_base = OTHER |
|  | note = 2'-O-methyluridine-3'-phosphate |
| modified_base | 20 |
|  | mod_base = OTHER |
|  | note = 2'-O-methyluridine-3'-phosphate |
| modified_base | 21 |
|  | mod_base = OTHER |
|  | note = 2'-O-methylcytidine-3'-phosphorothioate |
| modified_base | 22 |
|  | mod_base = OTHER |
|  | note = 2'-O-methyluridine-3'-phosphorothioate |
| modified_base | 23 |
|  | mod_base = OTHER |
|  | note = 2'-O-methylguanosine |
| SEQUENCE: 59 |  |
| taaagcactt tattgagttt ctg | 23 |
|  |  |
| SEQ ID NO: 60 | moltype = RNA  length = 23 |
| FEATURE | Location/Qualifiers |
| source | 1..23 |
|  | mol_type = other RNA |
|  | organism = synthetic construct |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-deoxy-2'-fluoroadenosine-3'-phosphorothioate |
| modified_base | 3 |
|  | mod_base = OTHER |
|  | note = 2'-O-methyladenosine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methylguanosine-3'-phosphate |
| modified_base | 6 |
|  | mod_base = OTHER |
|  | note = 2'-deoxy-2'-fluorocytidine-3'-phosphate |
| modified_base | 7 |
|  | mod_base = OTHER |
|  | note = 2'-O-methyladenosine-3'-phosphate |
| modified_base | 8 |
|  | mod_base = OTHER |
|  | note = 2'-O-methylcytidine-3'-phosphate |

| | |
|---|---|
| modified_base | 9<br>mod_base = OTHER<br>note = 2'-O-methyluridine-3'-phosphate |
| modified_base | 10<br>mod_base = OTHER<br>note = 2'-O-methyluridine-3'-phosphate |
| modified_base | 11<br>mod_base = OTHER<br>note = 2'-O-methyluridine-3'-phosphate |
| modified_base | 12<br>mod_base = OTHER<br>note = 2'-O-methyladenosine-3'-phosphate |
| modified_base | 13<br>mod_base = OTHER<br>note = 2'-O-methyluridine-3'-phosphate |
| modified_base | 14<br>mod_base = OTHER<br>note = 2'-deoxy-2'-fluorouridine-3'-phosphate |
| modified_base | 15<br>mod_base = OTHER<br>note = 2'-O-methylguanosine-3'-phosphate |
| modified_base | 16<br>mod_base = OTHER<br>note = 2'-deoxy-2'-fluoroadenosine-3'-phosphate |
| modified_base | 17<br>mod_base = OTHER<br>note = 2'-O-hexadecyl-guanosine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methylcytidine-3'-phosphorothioate |
| modified_base | 22<br>mod_base = OTHER<br>note = 2'-O-methyluridine-3'-phosphorothioate |
| modified_base | 23<br>mod_base = OTHER<br>note = 2'-O-methylguanosine |
| SEQUENCE: 60 | |
| taaagcactt tattgagttt ctg | 23 |
| SEQ ID NO: 61<br>FEATURE<br>source | moltype = RNA  length = 21<br>Location/Qualifiers<br>1..21<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylcytidine-3'-phosphate |
| modified_base | 6<br>mod_base = OTHER<br>note = 2'-O-methyluridine-3'-phosphate |
| modified_base | 7<br>mod_base = OTHER<br>note = 2'-deoxy-2'-fluorocytidine-3'-phosphate |
| modified_base | 8<br>mod_base = OTHER<br>note = 2'-O-methyladenosine-3'-phosphate |
| modified_base | 9<br>mod_base = OTHER |

|  |  |
|---|---|
| modified_base | 10<br>mod_base = OTHER<br>note = 2'-deoxy-2'-fluoroadenosine-3'-phosphate |
| modified_base | 11<br>mod_base = OTHER<br>note = 2'-deoxy-2'-fluorouridine-3'-phosphate |
| modified_base | 12<br>mod_base = OTHER<br>note = 2'-deoxy-2'-fluoroadenosine-3'-phosphate |
| modified_base | 13<br>mod_base = OTHER<br>note = 2'-O-methyladenosine-3'-phosphate |
| modified_base | 14<br>mod_base = OTHER<br>note = 2'-O-methyladenosine-3'-phosphate |
| modified_base | 15<br>mod_base = OTHER<br>note = 2'-O-methylguanosine-3'-phosphate |
| modified_base | 16<br>mod_base = OTHER<br>note = 2'-O-methyluridine-3'-phosphate |
| modified_base | 17<br>mod_base = OTHER<br>note = 2'-O-methylguanosine-3'-phosphate |
| modified_base | 18<br>mod_base = OTHER<br>note = 2'-O-hexadecyl-cytidine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 61 | |
| gaaactcaat aaagtgcttt a | 21 |
| SEQ ID NO: 62<br>FEATURE<br>source | moltype = RNA  length = 21<br>Location/Qualifiers<br>1..21<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylcytidine-3'-phosphate |
| modified_base | 6<br>mod_base = OTHER<br>note = 2'-O-methyluridine-3'-phosphate |
| modified_base | 7<br>mod_base = OTHER<br>note = 2'-deoxy-2'-fluorocytidine-3'-phosphate |
| modified_base | 8<br>mod_base = OTHER<br>note = 2'-O-methyladenosine-3'-phosphate |
| modified_base | 9<br>mod_base = OTHER<br>note = 2'-deoxy-2'-fluoroadenosine-3'-phosphate |
| modified_base | 10<br>mod_base = OTHER |

|                | | |
|---|---|---|
| | | note = 2'-deoxy-2'-fluorouridine-3'-phosphate |
| modified_base | 11 | |
| | | mod_base = OTHER |
| | | note = 2'-deoxy-2'-fluoroadenosine-3'-phosphate |
| modified_base | 12 | |
| | | mod_base = OTHER |
| | | note = 2'-O-methyladenosine-3'-phosphate |
| modified_base | 13 | |
| | | mod_base = OTHER |
| | | note = 2'-O-hexadecyl-adenosine-3'-phosphate |
| modified_base | 14 | |
| | | mod_base = OTHER |
| | | note = 2'-O-methylguanosine-3'-phosphate |
| modified_base | 15 | |
| | | mod_base = OTHER |
| | | note = 2'-O-methyluridine-3'-phosphate |
| modified_base | 16 | |
| | | mod_base = OTHER |
| | | note = 2'-O-methylguanosine-3'-phosphate |
| modified_base | 17 | |
| | | mod_base = OTHER |
| | | note = 2'-O-methylcytidine-3'-phosphate |
| modified_base | 18 | |
| | | mod_base = OTHER |
| | | note = 2'-O-methyluridine-3'-phosphate |
| modified_base | 19 | |
| | | mod_base = OTHER |
| | | note = 2'-O-methyluridine-3'-phosphate |
| modified_base | 20 | |
| | | mod_base = OTHER |
| | | note = 2'-O-methyluridine-3'-phosphate |
| modified_base | 21 | |
| | | mod_base = OTHER |
| | | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 62 | | |
| gaaactcaat aaagtgcttt a | | 21 |
| | | |
| SEQ ID NO: 63 | moltype = RNA   length = 21 | |
| FEATURE | Location/Qualifiers | |
| source | 1..21 | |
| | mol_type = other RNA | |
| | organism = synthetic construct | |
| modified_base | 1 | |
| | | mod_base = OTHER |
| | | note = 2'-O-methylguanosine-3'-phosphorothioate |
| modified_base | 2 | |
| | | mod_base = OTHER |
| | | note = 2'-O-methyladenosine-3'-phosphorothioate |
| modified_base | 3 | |
| | | mod_base = OTHER |
| | | note = 2'-O-methyladenosine-3'-phosphate |
| modified_base | 4 | |
| | | mod_base = OTHER |
| | | note = 2'-O-methyladenosine-3'-phosphate |
| modified_base | 5 | |
| | | mod_base = OTHER |
| | | note = 2'-O-methylcytidine-3'-phosphate |
| modified_base | 6 | |
| | | mod_base = OTHER |
| | | note = 2'-O-methyluridine-3'-phosphate |
| modified_base | 7 | |
| | | mod_base = OTHER |
| | | note = 2'-deoxy-2'-fluorocytidine-3'-phosphate |
| modified_base | 8 | |
| | | mod_base = OTHER |
| | | note = 2'-O-methyladenosine-3'-phosphate |
| modified_base | 9 | |
| | | mod_base = OTHER |
| | | note = 2'-deoxy-2'-fluoroadenosine-3'-phosphate |
| modified_base | 10 | |
| | | mod_base = OTHER |
| | | note = 2'-deoxy-2'-fluorouridine-3'-phosphate |
| modified_base | 11 | |
| | | mod_base = OTHER |

```
modified_base            note = 2'-deoxy-2'-fluoroadenosine-3'-phosphate
                         12
                         mod_base = OTHER
                         note = 2'-O-methyladenosine-3'-phosphate
modified_base            13
                         mod_base = OTHER
                         note = 2'-O-methyladenosine-3'-phosphate
modified_base            14
                         mod_base = OTHER
                         note = 2'-O-hexadecyl-guanosine-3'-phosphate
modified_base            15
                         mod_base = OTHER
                         note = 2'-O-methyluridine-3'-phosphate
modified_base            16
                         mod_base = OTHER
                         note = 2'-O-methylguanosine-3'-phosphate
modified_base            17
                         mod_base = OTHER
                         note = 2'-O-methylcytidine-3'-phosphate
modified_base            18
                         mod_base = OTHER
                         note = 2'-O-methyluridine-3'-phosphate
modified_base            19
                         mod_base = OTHER
                         note = 2'-O-methyluridine-3'-phosphate
modified_base            20
                         mod_base = OTHER
                         note = 2'-O-methyluridine-3'-phosphate
modified_base            21
                         mod_base = OTHER
                         note = 2'-O-methyladenosine-3'-phosphate
                         ((2S,4R)-1-[29-[[2-(acetylamino)-2-deoxy-beta-D-galactopyra
                         nosyl]oxy]-14,14-bis[[3-[[3-[[5-[[2-(acetylamino)-2-deoxy-b
                         eta-D-galactopyranosyl]oxy]-1-oxopentyl]amino]propyl]amino]
                         -3-oxopropoxy]methyl]-1,12,19,25-tetraoxo-16-oxa-13,20,24-t
                         riazanonacos-1-yl]-4-hydroxy-2-pyrrolidinyl)methyl ester
SEQUENCE: 63
gaaactcaat aaagtgcttt a                                                  21

SEQ ID NO: 64            moltype = RNA   length = 21
FEATURE                  Location/Qualifiers
source                   1..21
                         mol_type = other RNA
                         organism = synthetic construct
modified_base            1
                         mod_base = OTHER
                         note = 2'-O-methylguanosine-3'-phosphorothioate
modified_base            2
                         mod_base = OTHER
                         note = 2'-O-methyladenosine-3'-phosphorothioate
modified_base            3
                         mod_base = OTHER
                         note = 2'-O-methyladenosine-3'-phosphate
modified_base            4
                         mod_base = OTHER
                         note = 2'-O-methyladenosine-3'-phosphate
modified_base            5
                         mod_base = OTHER
                         note = 2'-O-methylcytidine-3'-phosphate
modified_base            6
                         mod_base = OTHER
                         note = 2'-O-methyluridine-3'-phosphate
modified_base            7
                         mod_base = OTHER
                         note = 2'-O-hexadecyl-cytidine-3'-phosphate
modified_base            8
                         mod_base = OTHER
                         note = 2'-O-methyladenosine-3'-phosphate
modified_base            9
                         mod_base = OTHER
                         note = 2'-deoxy-2'-fluoroadenosine-3'-phosphate
modified_base            10
                         mod_base = OTHER
                         note = 2'-deoxy-2'-fluorouridine-3'-phosphate
modified_base            11
                         mod_base = OTHER
                         note = 2'-deoxy-2'-fluoroadenosine-3'-phosphate
modified_base            12
                         mod_base = OTHER
```

```
                         note = 2'-O-methyladenosine-3'-phosphate
modified_base            13
                         mod_base = OTHER
                         note = 2'-O-methyladenosine-3'-phosphate
modified_base            14
                         mod_base = OTHER
                         note = 2'-O-methylguanosine-3'-phosphate
modified_base            15
                         mod_base = OTHER
                         note = 2'-O-methyluridine-3'-phosphate
modified_base            16
                         mod_base = OTHER
                         note = 2'-O-methylguanosine-3'-phosphate
modified_base            17
                         mod_base = OTHER
                         note = 2'-O-methylcytidine-3'-phosphate
modified_base            18
                         mod_base = OTHER
                         note = 2'-O-methyluridine-3'-phosphate
modified_base            19
                         mod_base = OTHER
                         note = 2'-O-methyluridine-3'-phosphate
modified_base            20
                         mod_base = OTHER
                         note = 2'-O-methyluridine-3'-phosphate
modified_base            21
                         mod_base = OTHER
                         note = 2'-O-methyladenosine-3'-phosphate
                         ((2S,4R)-1-[29-[[2-(acetylamino)-2-deoxy-beta-D-galactopyra
                         nosyl]oxy]-14,14-bis[[3-[[3-[[5-[[2-(acetylamino)-2-deoxy-b
                         eta-D-galactopyranosyl]oxy]-1-oxopentyl]amino]propyl]amino]
                         -3-oxopropoxy]methyl]-1,12,19,25-tetraoxo-16-oxa-13,20,24-t
                         riazanonacos-1-yl]-4-hydroxy-2-pyrrolidinyl)methyl ester
SEQUENCE: 64
gaaactcaat aaagtgcttt a                                                   21

SEQ ID NO: 65            moltype = RNA   length = 21
FEATURE                  Location/Qualifiers
source                   1..21
                         mol_type = other RNA
                         organism = synthetic construct
modified_base            1
                         mod_base = OTHER
                         note = 2'-O-methylguanosine-3'-phosphorothioate
modified_base            2
                         mod_base = OTHER
                         note = 2'-O-methyladenosine-3'-phosphorothioate
modified_base            3
                         mod_base = OTHER
                         note = 2'-O-methyladenosine-3'-phosphate
modified_base            4
                         mod_base = OTHER
                         note = 2'-O-methyladenosine-3'-phosphate
modified_base            5
                         mod_base = OTHER
                         note = 2'-O-methylcytidine-3'-phosphate
modified_base            6
                         mod_base = OTHER
                         note = 2'-O-methyluridine-3'-phosphate
modified_base            7
                         mod_base = OTHER
                         note = 2'-deoxy-2'-fluorocytidine-3'-phosphate
modified_base            8
                         mod_base = OTHER
                         note = 2'-O-hexadecyl-adenosine-3'-phosphate
modified_base            9
                         mod_base = OTHER
                         note = 2'-deoxy-2'-fluoroadenosine-3'-phosphate
modified_base            10
                         mod_base = OTHER
                         note = 2'-deoxy-2'-fluorouridine-3'-phosphate
modified_base            11
                         mod_base = OTHER
                         note = 2'-deoxy-2'-fluoroadenosine-3'-phosphate
modified_base            12
                         mod_base = OTHER
                         note = 2'-O-methyladenosine-3'-phosphate
modified_base            13
                         mod_base = OTHER
```

|                  | note = 2'-O-methyladenosine-3'-phosphate |
| --- | --- |
| modified_base    | 14 |
|                  | mod_base = OTHER |
|                  | note = 2'-O-methylguanosine-3'-phosphate |
| modified_base    | 15 |
|                  | mod_base = OTHER |
|                  | note = 2'-O-methyluridine-3'-phosphate |
| modified_base    | 16 |
|                  | mod_base = OTHER |
|                  | note = 2'-O-methylguanosine-3'-phosphate |
| modified_base    | 17 |
|                  | mod_base = OTHER |
|                  | note = 2'-O-methylcytidine-3'-phosphate |
| modified_base    | 18 |
|                  | mod_base = OTHER |
|                  | note = 2'-O-methyluridine-3'-phosphate |
| modified_base    | 19 |
|                  | mod_base = OTHER |
|                  | note = 2'-O-methyluridine-3'-phosphate |
| modified_base    | 20 |
|                  | mod_base = OTHER |
|                  | note = 2'-O-methyluridine-3'-phosphate |
| modified_base    | 21 |
|                  | mod_base = OTHER |
|                  | note = 2'-O-methyladenosine-3'-phosphate ((2S,4R)-1-[29-[[2-(acetylamino)-2-deoxy-beta-D-galactopyra nosyl]oxy]-14,14-bis[[3-[[3-[[5-[[2-(acetylamino)-2-deoxy-b eta-D-galactopyranosyl]oxy]-1-oxopentyl]amino]propyl]amino] -3-oxopropoxy]methyl]-1,12,19,25-tetraoxo-16-oxa-13,20,24-t riazanonacos-1-yl]-4-hydroxy-2-pyrrolidinyl)methyl ester |
| SEQUENCE: 65 | |
| gaaactcaat aaagtgcttt a | 21 |
| | |
| SEQ ID NO: 66    | moltype = RNA   length = 23 |
| FEATURE          | Location/Qualifiers |
| source           | 1..23 |
|                  | mol_type = other RNA |
|                  | organism = synthetic construct |
| modified_base    | 1 |
|                  | mod_base = OTHER |
|                  | note = 2'-O-methyluridine-3'-phosphorothioate |
| modified_base    | 2 |
|                  | mod_base = OTHER |
|                  | note = 2'-deoxy-2'-fluoroadenosine-3'-phosphorothioate |
| modified_base    | 3 |
|                  | mod_base = OTHER |
|                  | note = 2'-O-methyladenosine-3'-phosphate |
| modified_base    | 4 |
|                  | mod_base = OTHER |
|                  | note = 2'-O-methyladenosine-3'-phosphate |
| modified_base    | 5 |
|                  | mod_base = OTHER |
|                  | note = 2'-O-methylguanosine-3'-phosphate |
| modified_base    | 6 |
|                  | mod_base = OTHER |
|                  | note = 2'-deoxy-2'-fluorocytidine-3'-phosphate |
| modified_base    | 7 |
|                  | mod_base = OTHER |
|                  | note = 2'-O-methyladenosine-3'-phosphate |
| modified_base    | 8 |
|                  | mod_base = OTHER |
|                  | note = 2'-O-hexadecyl-cytidine-3'-phosphate |
| modified_base    | 9 |
|                  | mod_base = OTHER |
|                  | note = 2'-O-methyluridine-3'-phosphate |
| modified_base    | 10 |
|                  | mod_base = OTHER |
|                  | note = 2'-O-methyluridine-3'-phosphate |
| modified_base    | 11 |
|                  | mod_base = OTHER |
|                  | note = 2'-O-methyluridine-3'-phosphate |
| modified_base    | 12 |
|                  | mod_base = OTHER |
|                  | note = 2'-O-methyladenosine-3'-phosphate |
| modified_base    | 13 |
|                  | mod_base = OTHER |
|                  | note = 2'-O-methyluridine-3'-phosphate |
| modified_base    | 14 |
|                  | mod_base = OTHER |

```
                            note = 2'-deoxy-2'-fluorouridine-3'-phosphate
modified_base               15
                            mod_base = OTHER
                            note = 2'-O-methylguanosine-3'-phosphate
modified_base               16
                            mod_base = OTHER
                            note = 2'-deoxy-2'-fluoroadenosine-3'-phosphate
modified_base               17
                            mod_base = OTHER
                            note = 2'-O-methylguanosine-3'-phosphate
modified_base               18
                            mod_base = OTHER
                            note = 2'-O-methyluridine-3'-phosphate
modified_base               19
                            mod_base = OTHER
                            note = 2'-O-methyluridine-3'-phosphate
modified_base               20
                            mod_base = OTHER
                            note = 2'-O-methyluridine-3'-phosphate
modified_base               21
                            mod_base = OTHER
                            note = 2'-O-methylcytidine-3'-phosphorothioate
modified_base               22
                            mod_base = OTHER
                            note = 2'-O-methyluridine-3'-phosphorothioate
modified_base               23
                            mod_base = OTHER
                            note = 2'-O-methylguanosine
SEQUENCE: 66
taaagcactt tattgagttt ctg                                              23

SEQ ID NO: 67               moltype = RNA   length = 21
FEATURE                     Location/Qualifiers
source                      1..21
                            mol_type = other RNA
                            organism = synthetic construct
modified_base               1
                            mod_base = OTHER
                            note = 2'-O-methylguanosine-3'-phosphorothioate
modified_base               2
                            mod_base = OTHER
                            note = 2'-O-methyladenosine-3'-phosphorothioate
modified_base               3
                            mod_base = OTHER
                            note = 2'-O-methyladenosine-3'-phosphate
modified_base               4
                            mod_base = OTHER
                            note = 2'-O-methyladenosine-3'-phosphate
modified_base               5
                            mod_base = OTHER
                            note = 2'-O-methylcytidine-3'-phosphate
modified_base               6
                            mod_base = OTHER
                            note = 2'-O-methyluridine-3'-phosphate
modified_base               7
                            mod_base = OTHER
                            note = 2'-deoxy-2'-fluorocytidine-3'-phosphate
modified_base               8
                            mod_base = OTHER
                            note = 2'-O-methyladenosine-3'-phosphate
modified_base               9
                            mod_base = OTHER
                            note = 2'-deoxy-2'-fluoroadenosine-3'-phosphate
modified_base               10
                            mod_base = OTHER
                            note = 2'-deoxy-2'-fluorouridine-3'-phosphate
modified_base               11
                            mod_base = OTHER
                            note = 2'-deoxy-2'-fluoroadenosine-3'-phosphate
modified_base               12
                            mod_base = OTHER
                            note = 2'-O-methyladenosine-3'-phosphate
modified_base               13
                            mod_base = OTHER
                            note = 2'-O-methyladenosine-3'-phosphate
modified_base               14
                            mod_base = OTHER
                            note = 2'-O-methylguanosine-3'-phosphate
modified_base               15
```

```
                          mod_base = OTHER
                          note = 2'-O-methyluridine-3'-phosphate
modified_base             16
                          mod_base = OTHER
                          note = 2'-O-methylguanosine-3'-phosphate
modified_base             17
                          mod_base = OTHER
                          note = 2'-O-methylcytidine-3'-phosphate
modified_base             18
                          mod_base = OTHER
                          note = 2'-O-hexadecyl-uridine-3'-phosphate
modified_base             19
                          mod_base = OTHER
                          note = 2'-O-methyluridine-3'-phosphate
modified_base             20
                          mod_base = OTHER
                          note = 2'-O-methyluridine-3'-phosphate
modified_base             21
                          mod_base = OTHER
                          note = 2'-O-methyladenosine-3'-phosphate
                           ((2S,4R)-1-[29-[[2-(acetylamino)-2-deoxy-beta-D-galactopyra
                          nosyl]oxy]-14,14-bis[[3-[[3-[[5-[[2-(acetylamino)-2-deoxy-b
                          eta-D-galactopyranosyl]oxy]-1-oxopentyl]amino]propyl]amino]
                          -3-oxopropoxy]methyl]-1,12,19,25-tetraoxo-16-oxa-13,20,24-t
                          riazanonacos-1-yl]-4-hydroxy-2-pyrrolidinyl)methyl ester
SEQUENCE: 67
gaaactcaat aaagtgcttt a                                                            21

SEQ ID NO: 68             moltype = RNA   length = 21
FEATURE                   Location/Qualifiers
source                    1..21
                          mol_type = other RNA
                          organism = synthetic construct
modified_base             1
                          mod_base = OTHER
                          note = 2'-O-methylguanosine-3'-phosphorothioate
modified_base             2
                          mod_base = OTHER
                          note = 2'-O-methyladenosine-3'-phosphorothioate
modified_base             3
                          mod_base = OTHER
                          note = 2'-O-methyladenosine-3'-phosphate
modified_base             4
                          mod_base = OTHER
                          note = 2'-O-methyladenosine-3'-phosphate
modified_base             5
                          mod_base = OTHER
                          note = 2'-O-methylcytidine-3'-phosphate
modified_base             6
                          mod_base = OTHER
                          note = 2'-O-methyluridine-3'-phosphate
modified_base             7
                          mod_base = OTHER
                          note = 2'-deoxy-2'-fluorocytidine-3'-phosphate
modified_base             8
                          mod_base = OTHER
                          note = 2'-O-methyladenosine-3'-phosphate
modified_base             9
                          mod_base = OTHER
                          note = 2'-deoxy-2'-fluoroadenosine-3'-phosphate
modified_base             10
                          mod_base = OTHER
                          note = 2'-deoxy-2'-fluorouridine-3'-phosphate
modified_base             11
                          mod_base = OTHER
                          note = 2'-deoxy-2'-fluoroadenosine-3'-phosphate
modified_base             12
                          mod_base = OTHER
                          note = 2'-O-methyladenosine-3'-phosphate
modified_base             13
                          mod_base = OTHER
                          note = 2'-O-methyladenosine-3'-phosphate
modified_base             14
                          mod_base = OTHER
                          note = 2'-O-methylguanosine-3'-phosphate
modified_base             15
                          mod_base = OTHER
                          note = 2'-O-methyluridine-3'-phosphate
modified_base             16
```

```
                        mod_base = OTHER
                        note = 2'-O-hexadecyl-guanosine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methyladenosine-3'-phosphate
                        ((2S,4R)-1-[29-[[2-(acetylamino)-2-deoxy-beta-D-galactopyra
                        nosyl]oxy]-14,14-bis[[3-[[3-[[5-[[2-(acetylamino)-2-deoxy-b
                        eta-D-galactopyranosyl]oxy]-1-oxopentyl]amino]propyl]amino]
                        -3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 68
gaaactcaat aaagtgcttt a                                         21

SEQ ID NO: 69           moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-hexadecyl-uridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
```

```
                        mod_base = OTHER
                        note = 2'-O-methylguanosine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methyluridine-3'-phosphorothioate
modified_base           23
                        mod_base = OTHER
                        note = 2'-O-methylguanosine
SEQUENCE: 69
taaagcactt tattgagttt ctg                                              23

SEQ ID NO: 70           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methyladenosine-3'-phosphate
modified_base           4
                        mod_base = OTHER
                        note = 2'-O-methylcytidine-3'-phosphate
modified_base           5
                        mod_base = OTHER
                        note = 2'-O-methyluridine-3'-phosphate
modified_base           6
                        mod_base = OTHER
                        note = 2'-O-methylcytidine-3'-phosphate
modified_base           7
                        mod_base = OTHER
                        note = 2'-deoxy-2'-fluoroadenosine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyladenosine-3'-phosphate
modified_base           13
                        mod_base = OTHER
                        note = 2'-O-methylguanosine-3'-phosphate
modified_base           14
                        mod_base = OTHER
                        note = 2'-O-methyluridine-3'-phosphate
modified_base           15
                        mod_base = OTHER
                        note = 2'-O-hexadecyl-guanosine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
```

| | |
|---|---|
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-methylguanosine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 70 | |

```
gaactcaata aagtgctttg a                                              21
```

| | |
|---|---|
| SEQ ID NO: 71<br>FEATURE<br>source | moltype = RNA  length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate |
| modified_base | 2<br>mod_base = OTHER<br>note = 2'-deoxy-2'-fluorocytidine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methyladenosine-3'-phosphate |
| modified_base | 6<br>mod_base = OTHER<br>note = 2'-deoxy-2'-fluoroguanosine-3'-phosphate |
| modified_base | 7<br>mod_base = OTHER<br>note = 2'-O-methylcytidine-3'-phosphate |
| modified_base | 8<br>mod_base = OTHER<br>note = 2'-deoxy-2'-fluoroadenosine-3'-phosphate |
| modified_base | 9<br>mod_base = OTHER<br>note = 2'-deoxy-2'-fluorocytidine-3'-phosphate |
| modified_base | 10<br>mod_base = OTHER<br>note = 2'-O-methyluridine-3'-phosphate |
| modified_base | 11<br>mod_base = OTHER<br>note = 2'-O-methyluridine-3'-phosphate |
| modified_base | 12<br>mod_base = OTHER<br>note = 2'-O-methyluridine-3'-phosphate |
| modified_base | 13<br>mod_base = OTHER<br>note = 2'-O-methyladenosine-3'-phosphate |
| modified_base | 14<br>mod_base = OTHER<br>note = 2'-deoxy-2'-fluorouridine-3'-phosphate |
| modified_base | 15<br>mod_base = OTHER<br>note = 2'-O-methyluridine-3'-phosphate |
| modified_base | 16<br>mod_base = OTHER<br>note = 2'-deoxy-2'-fluoroguanosine-3'-phosphate |
| modified_base | 17<br>mod_base = OTHER<br>note = 2'-O-methyladenosine-3'-phosphate |
| modified_base | 18<br>mod_base = OTHER<br>note = 2'-O-methylguanosine-3'-phosphate |

```
                          -continued modified_base             19
                          mod_base = OTHER
                          note = 2'-O-methyluridine-3'-phosphate
modified_base             20
                          mod_base = OTHER
                          note = 2'-O-methyluridine-3'-phosphate
modified_base             21
                          mod_base = OTHER
                          note = 2'-O-methylcytidine-3'-phosphorothioate
modified_base             22
                          mod_base = OTHER
                          note = 2'-O-methylcytidine-3'-phosphorothioate
modified_base             23
                          mod_base = OTHER
                          note = 2'-O-methyluridine
SEQUENCE: 71
tcaaagcact ttattgagtt cct                                         23

SEQ ID NO: 72             moltype = RNA  length = 21
FEATURE                   Location/Qualifiers
source                    1..21
                          mol_type = other RNA
                          organism = synthetic construct
modified_base             1
                          mod_base = OTHER
                          note = 2'-O-methylguanosine-3'-phosphorothioate
modified_base             2
                          mod_base = OTHER
                          note = 2'-O-hexadecyl-adenosine-3'-phosphorothioate
modified_base             3
                          mod_base = OTHER
                          note = 2'-O-methyladenosine-3'-phosphate
modified_base             4
                          mod_base = OTHER
                          note = 2'-O-methylcytidine-3'-phosphate
modified_base             5
                          mod_base = OTHER
                          note = 2'-O-methyluridine-3'-phosphate
modified_base             6
                          mod_base = OTHER
                          note = 2'-O-methylcytidine-3'-phosphate
modified_base             7
                          mod_base = OTHER
                          note = 2'-deoxy-2'-fluoroadenosine-3'-phosphate
modified_base             8
                          mod_base = OTHER
                          note = 2'-O-methyladenosine-3'-phosphate
modified_base             9
                          mod_base = OTHER
                          note = 2'-deoxy-2'-fluorouridine-3'-phosphate
modified_base             10
                          mod_base = OTHER
                          note = 2'-deoxy-2'-fluoroadenosine-3'-phosphate
modified_base             11
                          mod_base = OTHER
                          note = 2'-deoxy-2'-fluoroadenosine-3'-phosphate
modified_base             12
                          mod_base = OTHER
                          note = 2'-O-methyladenosine-3'-phosphate
modified_base             13
                          mod_base = OTHER
                          note = 2'-O-methylguanosine-3'-phosphate
modified_base             14
                          mod_base = OTHER
                          note = 2'-O-methyluridine-3'-phosphate
modified_base             15
                          mod_base = OTHER
                          note = 2'-O-methylguanosine-3'-phosphate
modified_base             16
                          mod_base = OTHER
                          note = 2'-O-methylcytidine-3'-phosphate
modified_base             17
                          mod_base = OTHER
                          note = 2'-O-methyluridine-3'-phosphate
modified_base             18
                          mod_base = OTHER
                          note = 2'-O-methyluridine-3'-phosphate
modified_base             19
                          mod_base = OTHER
```

-continued

```
                         note = 2'-O-methyluridine-3'-phosphate
modified_base            20
                         mod_base = OTHER
                         note = 2'-O-methylguanosine-3'-phosphate
modified_base            21
                         mod_base = OTHER
                         note = 2'-O-methyladenosine-3'-phosphate
                         ((2S,4R)-1-[29-[[2-(acetylamino)-2-deoxy-beta-D-galactopyra
                         nosyl]oxy]-14,14-bis[[3-[[3-[[5-[[2-(acetylamino)-2-deoxy-b
                         eta-D-galactopyranosyl]oxy]-1-oxopentyl]amino]propyl]amino]
                         -3-oxopropoxy]methyl]-1,12,19,25-tetraoxo-16-oxa-13,20,24-t
                         riazanonacos-1-yl]-4-hydroxy-2-pyrrolidinyl)methyl ester
SEQUENCE: 72
gaactcaata aagtgctttg a                                              21

SEQ ID NO: 73            moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methylguanosine-3'-phosphorothioate
modified_base            2
                         mod_base = OTHER
                         note = 2'-O-methyladenosine-3'-phosphorothioate
modified_base            3
                         mod_base = OTHER
                         note = 2'-O-methyladenosine-3'-phosphate
modified_base            4
                         mod_base = OTHER
                         note = 2'-O-methylcytidine-3'-phosphate
modified_base            5
                         mod_base = OTHER
                         note = 2'-O-methyluridine-3'-phosphate
modified_base            6
                         mod_base = OTHER
                         note = 2'-O-methylcytidine-3'-phosphate
modified_base            7
                         mod_base = OTHER
                         note = 2'-deoxy-2'-fluoroadenosine-3'-phosphate
modified_base            8
                         mod_base = OTHER
                         note = 2'-O-methyladenosine-3'-phosphate
modified_base            9
                         mod_base = OTHER
                         note = 2'-deoxy-2'-fluorouridine-3'-phosphate
modified_base            10
                         mod_base = OTHER
                         note = 2'-deoxy-2'-fluoroadenosine-3'-phosphate
modified_base            11
                         mod_base = OTHER
                         note = 2'-deoxy-2'-fluoroadenosine-3'-phosphate
modified_base            12
                         mod_base = OTHER
                         note = 2'-O-methyladenosine-3'-phosphate
modified_base            13
                         mod_base = OTHER
                         note = 2'-O-methylguanosine-3'-phosphate
modified_base            14
                         mod_base = OTHER
                         note = 2'-O-hexadecyl-uridine-3'-phosphate
modified_base            15
                         mod_base = OTHER
                         note = 2'-O-methylguanosine-3'-phosphate
modified_base            16
                         mod_base = OTHER
                         note = 2'-O-methylcytidine-3'-phosphate
modified_base            17
                         mod_base = OTHER
                         note = 2'-O-methyluridine-3'-phosphate
modified_base            18
                         mod_base = OTHER
                         note = 2'-O-methyluridine-3'-phosphate
modified_base            19
                         mod_base = OTHER
                         note = 2'-O-methyluridine-3'-phosphate
modified_base            20
                         mod_base = OTHER
```

```
                    note = 2'-O-methylguanosine-3'-phosphate
modified_base       21
                    mod_base = OTHER
                    note = 2'-O-methyladenosine-3'-phosphate
                    ((2S,4R)-1-[29-[[2-(acetylamino)-2-deoxy-beta-D-galactopyra
                    nosyl]oxy]-14,14-bis[[3-[[3-[[5-[[2-(acetylamino)-2-deoxy-b
                    eta-D-galactopyranosyl]oxy]-1-oxopentyl]amino]propyl]amino]
                    -3-oxopropoxy]methyl]-1,12,19,25-tetraoxo-16-oxa-13,20,24-t
                    riazanonacos-1-yl]-4-hydroxy-2-pyrrolidinyl)methyl ester
SEQUENCE: 73
gaactcaata aagtgctttg a                                                    21

SEQ ID NO: 74       moltype = RNA  length = 23
FEATURE             Location/Qualifiers
source              1..23
                    mol_type = other RNA
                    organism = synthetic construct
modified_base       1
                    mod_base = OTHER
                    note = 2'-O-methyluridine-3'-phosphorothioate
modified_base       2
                    mod_base = OTHER
                    note = 2'-deoxy-2'-fluoroadenosine-3'-phosphorothioate
modified_base       3
                    mod_base = OTHER
                    note = 2'-O-methyladenosine-3'-phosphate
modified_base       4
                    mod_base = OTHER
                    note = 2'-O-methyladenosine-3'-phosphate
modified_base       5
                    mod_base = OTHER
                    note = 2'-O-methylguanosine-3'-phosphate
modified_base       6
                    mod_base = OTHER
                    note = 2'-deoxy-2'-fluorocytidine-3'-phosphate
modified_base       7
                    mod_base = OTHER
                    note = 2'-O-methyladenosine-3'-phosphate
modified_base       8
                    mod_base = OTHER
                    note = 2'-O-methylcytidine-3'-phosphate
modified_base       9
                    mod_base = OTHER
                    note = 2'-O-methyluridine-3'-phosphate
modified_base       10
                    mod_base = OTHER
                    note = 2'-O-methyluridine-3'-phosphate
modified_base       11
                    mod_base = OTHER
                    note = 2'-O-methyluridine-3'-phosphate
modified_base       12
                    mod_base = OTHER
                    note = 2'-O-methyladenosine-3'-phosphate
modified_base       13
                    mod_base = OTHER
                    note = 2'-O-methyluridine-3'-phosphate
modified_base       14
                    mod_base = OTHER
                    note = 2'-deoxy-2'-fluorouridine-3'-phosphate
modified_base       15
                    mod_base = OTHER
                    note = 2'-O-methylguanosine-3'-phosphate
modified_base       16
                    mod_base = OTHER
                    note = 2'-deoxy-2'-fluoroadenosine-3'-phosphate
modified_base       17
                    mod_base = OTHER
                    note = 2'-O-methylguanosine-3'-phosphate
modified_base       18
                    mod_base = OTHER
                    note = 2'-O-methyluridine-3'-phosphate
modified_base       19
                    mod_base = OTHER
                    note = 2'-O-methyluridine-3'-phosphate
modified_base       20
                    mod_base = OTHER
                    note = 2'-O-hexadecyl-uridine-3'-phosphate
modified_base       21
                    mod_base = OTHER
```

```
                        note = 2'-O-methylcytidine-3'-phosphorothioate
modified_base           22
                        mod_base = OTHER
                        note = 2'-O-methyluridine-3'-phosphorothioate
modified_base           23
                        mod_base = OTHER
                        note = 2'-O-methylguanosine
SEQUENCE: 74
taaagcactt tattgagttt ctg                                             23

SEQ ID NO: 75           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphorothioate
modified_base           2
                        mod_base = OTHER
                        note = 2'-O-hexadecyl-adenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylcytidine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluorocytidine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluoroadenosine-3'-phosphate
modified_base           10
                        mod_base = OTHER
                        note = 2'-deoxy-2'-fluorouridine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyladenosine-3'-phosphate
modified_base           13
                        mod_base = OTHER
                        note = 2'-O-methyladenosine-3'-phosphate
modified_base           14
                        mod_base = OTHER
                        note = 2'-O-methylguanosine-3'-phosphate
modified_base           15
                        mod_base = OTHER
                        note = 2'-O-methyluridine-3'-phosphate
modified_base           16
                        mod_base = OTHER
                        note = 2'-O-methylguanosine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methyladenosine-3'-phosphate
                        ((2S,4R)-1-[29-[[2-(acetylamino)-2-deoxy-beta-D-galactopyra
```

-continued nosyl]oxy]-14,14-bis[[3-[[3-[[5-[[2-(acetylamino)-2-deoxy-b
eta-D-galactopyranosyl]oxy]-1-oxopentyl]amino]propyl]amino]
-3-oxopropoxy]methyl]-1,12,19,25-tetraoxo-16-oxa-13,20,24-t
riazanonacos-1-yl]-4-hydroxy-2-pyrrolidinyl)methyl ester

```
SEQUENCE: 75
gaaactcaat aaagtgcttt a                                    21

SEQ ID NO: 76         moltype = RNA  length = 21
FEATURE               Location/Qualifiers
source                1..21
                      mol_type = other RNA
                      organism = synthetic construct
modified_base         1
                      mod_base = OTHER
                      note = 2'-O-methylguanosine-3'-phosphorothioate
modified_base         2
                      mod_base = OTHER
                      note = 2'-O-methyladenosine-3'-phosphorothioate
modified_base         3
                      mod_base = OTHER
                      note = 2'-O-methyladenosine-3'-phosphate
modified_base         4
                      mod_base = OTHER
                      note = 2'-O-methylcytidine-3'-phosphate
modified_base         5
                      mod_base = OTHER
                      note = 2'-O-methyluridine-3'-phosphate
modified_base         6
                      mod_base = OTHER
                      note = 2'-O-methylcytidine-3'-phosphate
modified_base         7
                      mod_base = OTHER
                      note = 2'-deoxy-2'-fluoroadenosine-3'-phosphate
modified_base         8
                      mod_base = OTHER
                      note = 2'-O-methyladenosine-3'-phosphate
modified_base         9
                      mod_base = OTHER
                      note = 2'-deoxy-2'-fluorouridine-3'-phosphate
modified_base         10
                      mod_base = OTHER
                      note = 2'-deoxy-2'-fluoroadenosine-3'-phosphate
modified_base         11
                      mod_base = OTHER
                      note = 2'-deoxy-2'-fluoroadenosine-3'-phosphate
modified_base         12
                      mod_base = OTHER
                      note = 2'-O-methyladenosine-3'-phosphate
modified_base         13
                      mod_base = OTHER
                      note = 2'-O-methylguanosine-3'-phosphate
modified_base         14
                      mod_base = OTHER
                      note = 2'-O-methyluridine-3'-phosphate
modified_base         15
                      mod_base = OTHER
                      note = 2'-O-methylguanosine-3'-phosphate
modified_base         16
                      mod_base = OTHER
                      note = 2'-O-hexadecyl-cytidine-3'-phosphate
modified_base         17
                      mod_base = OTHER
                      note = 2'-O-methyluridine-3'-phosphate
modified_base         18
                      mod_base = OTHER
                      note = 2'-O-methyluridine-3'-phosphate
modified_base         19
                      mod_base = OTHER
                      note = 2'-O-methyluridine-3'-phosphate
modified_base         20
                      mod_base = OTHER
                      note = 2'-O-methylguanosine-3'-phosphate
modified_base         21
                      mod_base = OTHER
                      note = 2'-O-methyladenosine-3'-phosphate
                       ((2S,4R)-1-[29-[[2-(acetylamino)-2-deoxy-beta-D-galactopyra
                       nosyl]oxy]-14,14-bis[[3-[[3-[[5-[[2-(acetylamino)-2-deoxy-b
                       eta-D-galactopyranosyl]oxy]-1-oxopentyl]amino]propyl]amino]
                       -3-oxopropoxy]methyl]-1,12,19,25-tetraoxo-16-oxa-13,20,24-t
``` riazanonacos-1-yl]-4-hydroxy-2-pyrrolidinyl)methyl ester

SEQUENCE: 76
gaactcaata aagtgctttg a                                                           21

| | |
|---|---|
| SEQ ID NO: 77 | moltype = RNA length = 23 |
| FEATURE | Location/Qualifiers |
| source | 1..23 |
| | mol_type = other RNA |
| | organism = synthetic construct |
| modified_base | 1 |
| | mod_base = OTHER |
| | note = 2'-O-methyluridine-3'-phosphorothioate |
| modified_base | 2 |
| | mod_base = OTHER |
| | note = 2'-deoxy-2'-fluoroadenosine-3'-phosphorothioate |
| modified_base | 3 |
| | mod_base = OTHER |
| | note = 2'-O-methyladenosine-3'-phosphate |
| modified_base | 4 |
| | mod_base = OTHER |
| | note = 2'-O-methyladenosine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-deoxy-2'-fluorocytidine-3'-phosphate |
| modified_base | 7 |
| | mod_base = OTHER |
| | note = 2'-O-hexadecyl-adenosine-3'-phosphate |
| modified_base | 8 |
| | mod_base = OTHER |
| | note = 2'-O-methylcytidine-3'-phosphate |
| modified_base | 9 |
| | mod_base = OTHER |
| | note = 2'-O-methyluridine-3'-phosphate |
| modified_base | 10 |
| | mod_base = OTHER |
| | note = 2'-O-methyluridine-3'-phosphate |
| modified_base | 11 |
| | mod_base = OTHER |
| | note = 2'-O-methyluridine-3'-phosphate |
| modified_base | 12 |
| | mod_base = OTHER |
| | note = 2'-O-methyladenosine-3'-phosphate |
| modified_base | 13 |
| | mod_base = OTHER |
| | note = 2'-O-methyluridine-3'-phosphate |
| modified_base | 14 |
| | mod_base = OTHER |
| | note = 2'-deoxy-2'-fluorouridine-3'-phosphate |
| modified_base | 15 |
| | mod_base = OTHER |
| | note = 2'-O-methylguanosine-3'-phosphate |
| modified_base | 16 |
| | mod_base = OTHER |
| | note = 2'-deoxy-2'-fluoroadenosine-3'-phosphate |
| modified_base | 17 |
| | mod_base = OTHER |
| | note = 2'-O-methylguanosine-3'-phosphate |
| modified_base | 18 |
| | mod_base = OTHER |
| | note = 2'-O-methyluridine-3'-phosphate |
| modified_base | 19 |
| | mod_base = OTHER |
| | note = 2'-O-methyluridine-3'-phosphate |
| modified_base | 20 |
| | mod_base = OTHER |
| | note = 2'-O-methyluridine-3'-phosphate |
| modified_base | 21 |
| | mod_base = OTHER |
| | note = 2'-O-methylcytidine-3'-phosphorothioate |
| modified_base | 22 |
| | mod_base = OTHER |
| | note = 2'-O-methyluridine-3'-phosphorothioate |
| modified_base | 23 |
| | mod_base = OTHER |
| | note = 2'-O-methylguanosine |

SEQUENCE: 77

```
taaagcactt tattgagttt ctg                                              23

SEQ ID NO: 78          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylguanosine-3'-phosphorothioate
modified_base          2
                       mod_base = OTHER
                       note = 2'-O-methyladenosine-3'-phosphorothioate
modified_base          3
                       mod_base = OTHER
                       note = 2'-O-methyladenosine-3'-phosphate
modified_base          4
                       mod_base = OTHER
                       note = 2'-O-methylcytidine-3'-phosphate
modified_base          5
                       mod_base = OTHER
                       note = 2'-O-methyluridine-3'-phosphate
modified_base          6
                       mod_base = OTHER
                       note = 2'-O-hexadecyl-cytidine-3'-phosphate
modified_base          7
                       mod_base = OTHER
                       note = 2'-deoxy-2'-fluoroadenosine-3'-phosphate
modified_base          8
                       mod_base = OTHER
                       note = 2'-O-methyladenosine-3'-phosphate
modified_base          9
                       mod_base = OTHER
                       note = 2'-deoxy-2'-fluorouridine-3'-phosphate
modified_base          10
                       mod_base = OTHER
                       note = 2'-deoxy-2'-fluoroadenosine-3'-phosphate
modified_base          11
                       mod_base = OTHER
                       note = 2'-deoxy-2'-fluoroadenosine-3'-phosphate
modified_base          12
                       mod_base = OTHER
                       note = 2'-O-methyladenosine-3'-phosphate
modified_base          13
                       mod_base = OTHER
                       note = 2'-O-methylguanosine-3'-phosphate
modified_base          14
                       mod_base = OTHER
                       note = 2'-O-methyluridine-3'-phosphate
modified_base          15
                       mod_base = OTHER
                       note = 2'-O-methylguanosine-3'-phosphate
modified_base          16
                       mod_base = OTHER
                       note = 2'-O-methylcytidine-3'-phosphate
modified_base          17
                       mod_base = OTHER
                       note = 2'-O-methyluridine-3'-phosphate
modified_base          18
                       mod_base = OTHER
                       note = 2'-O-methyluridine-3'-phosphate
modified_base          19
                       mod_base = OTHER
                       note = 2'-O-methyluridine-3'-phosphate
modified_base          20
                       mod_base = OTHER
                       note = 2'-O-methylguanosine-3'-phosphate
modified_base          21
                       mod_base = OTHER
                       note = 2'-O-methyladenosine-3'-phosphate
                        ((2S,4R)-1-[29-[[2-(acetylamino)-2-deoxy-beta-D-galactopyra
                        nosyl]oxy]-14,14-bis[[3-[[3-[[5-[[2-(acetylamino)-2-deoxy-b
                        eta-D-galactopyranosyl]oxy]-1-oxopentyl]amino]propyl]amino]
                        -3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 78
gaactcaata aagtgctttg a                                                21

SEQ ID NO: 79          moltype = RNA  length = 21
```

| FEATURE | Location/Qualifiers |
|---|---|
| source | 1..21 |
| | mol_type = other RNA |
| | organism = synthetic construct |
| modified_base | 1 |
| | mod_base = OTHER |
| | note = 2'-O-methylguanosine-3'-phosphorothioate |
| modified_base | 2 |
| | mod_base = OTHER |
| | note = 2'-O-methyladenosine-3'-phosphorothioate |
| modified_base | 3 |
| | mod_base = OTHER |
| | note = 2'-O-hexadecyl-adenosine-3'-phosphate |
| modified_base | 4 |
| | mod_base = OTHER |
| | note = 2'-O-methyladenosine-3'-phosphate |
| modified_base | 5 |
| | mod_base = OTHER |
| | note = 2'-O-methylcytidine-3'-phosphate |
| modified_base | 6 |
| | mod_base = OTHER |
| | note = 2'-O-methyluridine-3'-phosphate |
| modified_base | 7 |
| | mod_base = OTHER |
| | note = 2'-deoxy-2'-fluorocytidine-3'-phosphate |
| modified_base | 8 |
| | mod_base = OTHER |
| | note = 2'-O-methyladenosine-3'-phosphate |
| modified_base | 9 |
| | mod_base = OTHER |
| | note = 2'-deoxy-2'-fluoroadenosine-3'-phosphate |
| modified_base | 10 |
| | mod_base = OTHER |
| | note = 2'-deoxy-2'-fluorouridine-3'-phosphate |
| modified_base | 11 |
| | mod_base = OTHER |
| | note = 2'-deoxy-2'-fluoroadenosine-3'-phosphate |
| modified_base | 12 |
| | mod_base = OTHER |
| | note = 2'-O-methyladenosine-3'-phosphate |
| modified_base | 13 |
| | mod_base = OTHER |
| | note = 2'-O-methyladenosine-3'-phosphate |
| modified_base | 14 |
| | mod_base = OTHER |
| | note = 2'-O-methylguanosine-3'-phosphate |
| modified_base | 15 |
| | mod_base = OTHER |
| | note = 2'-O-methyluridine-3'-phosphate |
| modified_base | 16 |
| | mod_base = OTHER |
| | note = 2'-O-methylguanosine-3'-phosphate |
| modified_base | 17 |
| | mod_base = OTHER |
| | note = 2'-O-methylcytidine-3'-phosphate |
| modified_base | 18 |
| | mod_base = OTHER |
| | note = 2'-O-methyluridine-3'-phosphate |
| modified_base | 19 |
| | mod_base = OTHER |
| | note = 2'-O-methyluridine-3'-phosphate |
| modified_base | 20 |
| | mod_base = OTHER |
| | note = 2'-O-methyluridine-3'-phosphate |
| modified_base | 21 |
| | mod_base = OTHER |
| | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 79 | |
| gaaactcaat aaagtgcttt a | 21 |
| | |
| SEQ ID NO: 80 | moltype = RNA   length = 21 |
| FEATURE | Location/Qualifiers |
| source | 1..21 |
| | mol_type = other RNA |

|   |   |
|---|---|
|   | organism = synthetic construct |
| modified_base | 1 |
|   | mod_base = OTHER |
|   | note = 2'-O-methylguanosine-3'-phosphorothioate |
| modified_base | 2 |
|   | mod_base = OTHER |
|   | note = 2'-O-methyladenosine-3'-phosphorothioate |
| modified_base | 3 |
|   | mod_base = OTHER |
|   | note = 2'-O-methyladenosine-3'-phosphate |
| modified_base | 4 |
|   | mod_base = OTHER |
|   | note = 2'-O-methylcytidine-3'-phosphate |
| modified_base | 5 |
|   | mod_base = OTHER |
|   | note = 2'-O-methyluridine-3'-phosphate |
| modified_base | 6 |
|   | mod_base = OTHER |
|   | note = 2'-O-methylcytidine-3'-phosphate |
| modified_base | 7 |
|   | mod_base = OTHER |
|   | note = 2'-deoxy-2'-fluoroadenosine-3'-phosphate |
| modified_base | 8 |
|   | mod_base = OTHER |
|   | note = 2'-O-methyladenosine-3'-phosphate |
| modified_base | 9 |
|   | mod_base = OTHER |
|   | note = 2'-deoxy-2'-fluorouridine-3'-phosphate |
| modified_base | 10 |
|   | mod_base = OTHER |
|   | note = 2'-deoxy-2'-fluoroadenosine-3'-phosphate |
| modified_base | 11 |
|   | mod_base = OTHER |
|   | note = 2'-deoxy-2'-fluoroadenosine-3'-phosphate |
| modified_base | 12 |
|   | mod_base = OTHER |
|   | note = 2'-O-methyladenosine-3'-phosphate |
| modified_base | 13 |
|   | mod_base = OTHER |
|   | note = 2'-O-methylguanosine-3'-phosphate |
| modified_base | 14 |
|   | mod_base = OTHER |
|   | note = 2'-O-methyluridine-3'-phosphate |
| modified_base | 15 |
|   | mod_base = OTHER |
|   | note = 2'-O-methylguanosine-3'-phosphate |
| modified_base | 16 |
|   | mod_base = OTHER |
|   | note = 2'-O-methylcytidine-3'-phosphate |
| modified_base | 17 |
|   | mod_base = OTHER |
|   | note = 2'-O-methyluridine-3'-phosphate |
| modified_base | 18 |
|   | mod_base = OTHER |
|   | note = 2'-O-methyluridine-3'-phosphate |
| modified_base | 19 |
|   | mod_base = OTHER |
|   | note = 2'-O-methyluridine-3'-phosphate |
| modified_base | 20 |
|   | mod_base = OTHER |
|   | note = 2'-O-methylguanosine-3'-phosphate |
| modified_base | 21 |
|   | mod_base = OTHER |
|   | note = 2'-O-methyladenosine-3'-phosphate |
|   | ((2S,4R)-1-[29-[[2-(acetylamino)-2-deoxy-beta-D-galactopyra |
|   | nosyl]oxy]-14,14-bis[[3-[[3-[[5-[[2-(acetylamino)-2-deoxy-b |
|   | eta-D-galactopyranosyl]oxy]-1-oxopentyl]amino]propyl]amino] |
|   | -3-oxopropoxy]methyl]-1,12,19,25-tetraoxo-16-oxa-13,20,24-t |
|   | riazanonacos-1-yl]-4-hydroxy-2-pyrrolidinyl)methyl ester |
| SEQUENCE: 80 |   |
| gaactcaata aagtgctttg a | 21 |
|   |   |
| SEQ ID NO: 81 | moltype = RNA length = 23 |
| FEATURE | Location/Qualifiers |
| source | 1..23 |
|   | mol_type = other RNA |
|   | organism = synthetic construct |
| modified_base | 1 |
|   | mod_base = OTHER |

| | | |
|---|---|---|
| modified_base | | note = 2'-O-methyluridine-3'-phosphorothioate |
| | 2 | |
| | | mod_base = OTHER |
| | | note = 2'-deoxy-2'-fluorocytidine-3'-phosphorothioate |
| modified_base | 3 | |
| | | mod_base = OTHER |
| | | note = 2'-O-methyladenosine-3'-phosphate |
| modified_base | 4 | |
| | | mod_base = OTHER |
| | | note = 2'-O-methyladenosine-3'-phosphate |
| modified_base | 5 | |
| | | mod_base = OTHER |
| | | note = 2'-O-methyladenosine-3'-phosphate |
| modified_base | 6 | |
| | | mod_base = OTHER |
| | | note = 2'-deoxy-2'-fluoroguanosine-3'-phosphate |
| modified_base | 7 | |
| | | mod_base = OTHER |
| | | note = 2'-O-methylcytidine-3'-phosphate |
| modified_base | 8 | |
| | | mod_base = OTHER |
| | | note = 2'-deoxy-2'-fluoroadenosine-3'-phosphate |
| modified_base | 9 | |
| | | mod_base = OTHER |
| | | note = 2'-O-hexadecyl-cytidine-3'-phosphate |
| modified_base | 10 | |
| | | mod_base = OTHER |
| | | note = 2'-O-methyluridine-3'-phosphate |
| modified_base | 11 | |
| | | mod_base = OTHER |
| | | note = 2'-O-methyluridine-3'-phosphate |
| modified_base | 12 | |
| | | mod_base = OTHER |
| | | note = 2'-O-methyluridine-3'-phosphate |
| modified_base | 13 | |
| | | mod_base = OTHER |
| | | note = 2'-O-methyladenosine-3'-phosphate |
| modified_base | 14 | |
| | | mod_base = OTHER |
| | | note = 2'-deoxy-2'-fluorouridine-3'-phosphate |
| modified_base | 15 | |
| | | mod_base = OTHER |
| | | note = 2'-O-methyluridine-3'-phosphate |
| modified_base | 16 | |
| | | mod_base = OTHER |
| | | note = 2'-deoxy-2'-fluoroguanosine-3'-phosphate |
| modified_base | 17 | |
| | | mod_base = OTHER |
| | | note = 2'-O-methyladenosine-3'-phosphate |
| modified_base | 18 | |
| | | mod_base = OTHER |
| | | note = 2'-O-methylguanosine-3'-phosphate |
| modified_base | 19 | |
| | | mod_base = OTHER |
| | | note = 2'-O-methyluridine-3'-phosphate |
| modified_base | 20 | |
| | | mod_base = OTHER |
| | | note = 2'-O-methyluridine-3'-phosphate |
| modified_base | 21 | |
| | | mod_base = OTHER |
| | | note = 2'-O-methylcytidine-3'-phosphorothioate |
| modified_base | 22 | |
| | | mod_base = OTHER |
| | | note = 2'-O-methylcytidine-3'-phosphorothioate |
| modified_base | 23 | |
| | | mod_base = OTHER |
| | | note = 2'-O-methyluridine |
| SEQUENCE: 81 | | |
| tcaaagcact ttattgagtt cct | | 23 |
| | | |
| SEQ ID NO: 82 | moltype = RNA   length = 21 | |
| FEATURE | Location/Qualifiers | |
| source | 1..21 | |
| | | mol_type = other RNA |
| | | organism = synthetic construct |
| modified_base | 1 | |
| | | mod_base = OTHER |
| | | note = 2'-O-methylguanosine-3'-phosphorothioate |
| modified_base | 2 | |

|  |  |
|---|---|
| modified_base | mod_base = OTHER<br>note = 2'-O-methyladenosine-3'-phosphorothioate<br>3 |
| modified_base | mod_base = OTHER<br>note = 2'-O-methyladenosine-3'-phosphate<br>4 |
| modified_base | mod_base = OTHER<br>note = 2'-O-methylcytidine-3'-phosphate<br>5 |
| modified_base | mod_base = OTHER<br>note = 2'-O-methyluridine-3'-phosphate<br>6 |
| modified_base | mod_base = OTHER<br>note = 2'-O-methylcytidine-3'-phosphate<br>7 |
| modified_base | mod_base = OTHER<br>note = 2'-O-hexadecyl-adenosine-3'-phosphate<br>8 |
| modified_base | mod_base = OTHER<br>note = 2'-O-methyladenosine-3'-phosphate<br>9 |
| modified_base | mod_base = OTHER<br>note = 2'-deoxy-2'-fluorouridine-3'-phosphate<br>10 |
| modified_base | mod_base = OTHER<br>note = 2'-deoxy-2'-fluoroadenosine-3'-phosphate<br>11 |
| modified_base | mod_base = OTHER<br>note = 2'-deoxy-2'-fluoroadenosine-3'-phosphate<br>12 |
| modified_base | mod_base = OTHER<br>note = 2'-O-methyladenosine-3'-phosphate<br>13 |
| modified_base | mod_base = OTHER<br>note = 2'-O-methylguanosine-3'-phosphate<br>14 |
| modified_base | mod_base = OTHER<br>note = 2'-O-methyluridine-3'-phosphate<br>15 |
| modified_base | mod_base = OTHER<br>note = 2'-O-methylguanosine-3'-phosphate<br>16 |
| modified_base | mod_base = OTHER<br>note = 2'-O-methylcytidine-3'-phosphate<br>17 |
| modified_base | mod_base = OTHER<br>note = 2'-O-methyluridine-3'-phosphate<br>18 |
| modified_base | mod_base = OTHER<br>note = 2'-O-methyluridine-3'-phosphate<br>19 |
| modified_base | mod_base = OTHER<br>note = 2'-O-methyluridine-3'-phosphate<br>20 |
| modified_base | mod_base = OTHER<br>note = 2'-O-methylguanosine-3'-phosphate<br>21 |
| modified_base | mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 82 | |
| gaactcaata aagtgctttg a | 21 |
| SEQ ID NO: 83<br>FEATURE<br>source | moltype = RNA length = 21<br>Location/Qualifiers<br>1..21<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3 |

|                | mod_base = OTHER |
|                | note = 2'-O-methyladenosine-3'-phosphate |
| modified_base  | 4 |
|                | mod_base = OTHER |
|                | note = 2'-O-hexadecyl-adenosine-3'-phosphate |
| modified_base  | 5 |
|                | mod_base = OTHER |
|                | note = 2'-O-methylcytidine-3'-phosphate |
| modified_base  | 6 |
|                | mod_base = OTHER |
|                | note = 2'-O-methyluridine-3'-phosphate |
| modified_base  | 7 |
|                | mod_base = OTHER |
|                | note = 2'-deoxy-2'-fluorocytidine-3'-phosphate |
| modified_base  | 8 |
|                | mod_base = OTHER |
|                | note = 2'-O-methyladenosine-3'-phosphate |
| modified_base  | 9 |
|                | mod_base = OTHER |
|                | note = 2'-deoxy-2'-fluoroadenosine-3'-phosphate |
| modified_base  | 10 |
|                | mod_base = OTHER |
|                | note = 2'-deoxy-2'-fluorouridine-3'-phosphate |
| modified_base  | 11 |
|                | mod_base = OTHER |
|                | note = 2'-deoxy-2'-fluoroadenosine-3'-phosphate |
| modified_base  | 12 |
|                | mod_base = OTHER |
|                | note = 2'-O-methyladenosine-3'-phosphate |
| modified_base  | 13 |
|                | mod_base = OTHER |
|                | note = 2'-O-methyladenosine-3'-phosphate |
| modified_base  | 14 |
|                | mod_base = OTHER |
|                | note = 2'-O-methylguanosine-3'-phosphate |
| modified_base  | 15 |
|                | mod_base = OTHER |
|                | note = 2'-O-methyluridine-3'-phosphate |
| modified_base  | 16 |
|                | mod_base = OTHER |
|                | note = 2'-O-methylguanosine-3'-phosphate |
| modified_base  | 17 |
|                | mod_base = OTHER |
|                | note = 2'-O-methylcytidine-3'-phosphate |
| modified_base  | 18 |
|                | mod_base = OTHER |
|                | note = 2'-O-methyluridine-3'-phosphate |
| modified_base  | 19 |
|                | mod_base = OTHER |
|                | note = 2'-O-methyluridine-3'-phosphate |
| modified_base  | 20 |
|                | mod_base = OTHER |
|                | note = 2'-O-methyluridine-3'-phosphate |
| modified_base  | 21 |
|                | mod_base = OTHER |
|                | note = 2'-O-methyladenosine-3'-phosphate |
|                | ((2S,4R)-1-[29-[[2-(acetylamino)-2-deoxy-beta-D-galactopyra |
|                | nosyl]oxy]-14,14-bis[[3-[[3-[[5-[[2-(acetylamino)-2-deoxy-b |
|                | eta-D-galactopyranosyl]oxy]-1-oxopentyl]amino]propyl]amino] |
|                | -3-oxopropoxy]methyl]-1,12,19,25-tetraoxo-16-oxa-13,20,24-t |
|                | riazanonacos-1-yl]-4-hydroxy-2-pyrrolidinyl)methyl ester |
| SEQUENCE: 83   |   |
| gaaactcaat aaagtgcttt a | 21 |

| SEQ ID NO: 84  | moltype = RNA   length = 23 |
| FEATURE        | Location/Qualifiers |
| source         | 1..23 |
|                | mol_type = other RNA |
|                | organism = synthetic construct |
| modified_base  | 1 |
|                | mod_base = OTHER |
|                | note = 2'-O-methyluridine-3'-phosphorothioate |
| modified_base  | 2 |
|                | mod_base = OTHER |
|                | note = 2'-deoxy-2'-fluorocytidine-3'-phosphorothioate |
| modified_base  | 3 |
|                | mod_base = OTHER |
|                | note = 2'-O-methyladenosine-3'-phosphate |
| modified_base  | 4 |

|  |  |  |
|---|---|---|
|  | mod_base | = OTHER |
|  | note | = 2'-O-methyladenosine-3'-phosphate |
| modified_base | 5 |  |
|  | mod_base | = OTHER |
|  | note | = 2'-O-methyladenosine-3'-phosphate |
| modified_base | 6 |  |
|  | mod_base | = OTHER |
|  | note | = 2'-deoxy-2'-fluoroguanosine-3'-phosphate |
| modified_base | 7 |  |
|  | mod_base | = OTHER |
|  | note | = 2'-O-methylcytidine-3'-phosphate |
| modified_base | 8 |  |
|  | mod_base | = OTHER |
|  | note | = 2'-deoxy-2'-fluoroadenosine-3'-phosphate |
| modified_base | 9 |  |
|  | mod_base | = OTHER |
|  | note | = 2'-deoxy-2'-fluorocytidine-3'-phosphate |
| modified_base | 10 |  |
|  | mod_base | = OTHER |
|  | note | = 2'-O-methyluridine-3'-phosphate |
| modified_base | 11 |  |
|  | mod_base | = OTHER |
|  | note | = 2'-O-methyluridine-3'-phosphate |
| modified_base | 12 |  |
|  | mod_base | = OTHER |
|  | note | = 2'-O-methyluridine-3'-phosphate |
| modified_base | 13 |  |
|  | mod_base | = OTHER |
|  | note | = 2'-O-methyladenosine-3'-phosphate |
| modified_base | 14 |  |
|  | mod_base | = OTHER |
|  | note | = 2'-deoxy-2'-fluorouridine-3'-phosphate |
| modified_base | 15 |  |
|  | mod_base | = OTHER |
|  | note | = 2'-O-methyluridine-3'-phosphate |
| modified_base | 16 |  |
|  | mod_base | = OTHER |
|  | note | = 2'-O-hexadecyl-guanosine-3'-phosphate |
| modified_base | 17 |  |
|  | mod_base | = OTHER |
|  | note | = 2'-O-methyladenosine-3'-phosphate |
| modified_base | 18 |  |
|  | mod_base | = OTHER |
|  | note | = 2'-O-methylguanosine-3'-phosphate |
| modified_base | 19 |  |
|  | mod_base | = OTHER |
|  | note | = 2'-O-methyluridine-3'-phosphate |
| modified_base | 20 |  |
|  | mod_base | = OTHER |
|  | note | = 2'-O-methyluridine-3'-phosphate |
| modified_base | 21 |  |
|  | mod_base | = OTHER |
|  | note | = 2'-O-methylcytidine-3'-phosphorothioate |
| modified_base | 22 |  |
|  | mod_base | = OTHER |
|  | note | = 2'-O-methylcytidine-3'-phosphorothioate |
| modified_base | 23 |  |
|  | mod_base | = OTHER |
|  | note | = 2'-O-methyluridine |
| SEQUENCE: 84 |  |  |
| tcaaagcact ttattgagtt cct |  | 23 |
| SEQ ID NO: 85 | moltype = RNA   length = 23 |  |
| FEATURE | Location/Qualifiers |  |
| source | 1..23 |  |
|  | mol_type = other RNA |  |
|  | organism = synthetic construct |  |
| modified_base | 1 |  |
|  | mod_base | = OTHER |
|  | note | = 2'-O-methyluridine-3'-phosphorothioate |
| modified_base | 2 |  |
|  | mod_base | = OTHER |
|  | note | = 2'-deoxy-2'-fluorocytidine-3'-phosphorothioate |
| modified_base | 3 |  |
|  | mod_base | = OTHER |
|  | note | = 2'-O-methyladenosine-3'-phosphate |
| modified_base | 4 |  |
|  | mod_base | = OTHER |
|  | note | = 2'-O-methyladenosine-3'-phosphate |

| | |
|---|---|
| modified_base | 5<br>mod_base = OTHER<br>note = 2'-O-methyladenosine-3'-phosphate |
| modified_base | 6<br>mod_base = OTHER<br>note = 2'-deoxy-2'-fluoroguanosine-3'-phosphate |
| modified_base | 7<br>mod_base = OTHER<br>note = 2'-O-hexadecyl-cytidine-3'-phosphate |
| modified_base | 8<br>mod_base = OTHER<br>note = 2'-deoxy-2'-fluoroadenosine-3'-phosphate |
| modified_base | 9<br>mod_base = OTHER<br>note = 2'-deoxy-2'-fluorocytidine-3'-phosphate |
| modified_base | 10<br>mod_base = OTHER<br>note = 2'-O-methyluridine-3'-phosphate |
| modified_base | 11<br>mod_base = OTHER<br>note = 2'-O-methyluridine-3'-phosphate |
| modified_base | 12<br>mod_base = OTHER<br>note = 2'-O-methyluridine-3'-phosphate |
| modified_base | 13<br>mod_base = OTHER<br>note = 2'-O-methyladenosine-3'-phosphate |
| modified_base | 14<br>mod_base = OTHER<br>note = 2'-deoxy-2'-fluorouridine-3'-phosphate |
| modified_base | 15<br>mod_base = OTHER<br>note = 2'-O-methyluridine-3'-phosphate |
| modified_base | 16<br>mod_base = OTHER<br>note = 2'-deoxy-2'-fluoroguanosine-3'-phosphate |
| modified_base | 17<br>mod_base = OTHER<br>note = 2'-O-methyladenosine-3'-phosphate |
| modified_base | 18<br>mod_base = OTHER<br>note = 2'-O-methylguanosine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methylcytidine-3'-phosphorothioate |
| modified_base | 22<br>mod_base = OTHER<br>note = 2'-O-methylcytidine-3'-phosphorothioate |
| modified_base | 23<br>mod_base = OTHER<br>note = 2'-O-methyluridine |
| SEQUENCE: 85 | |
| tcaaagcact ttattgagtt cct | 23 |
| | |
| SEQ ID NO: 86<br>FEATURE<br>source | moltype = RNA   length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate |
| modified_base | 2<br>mod_base = OTHER<br>note = 2'-deoxy-2'-fluorocytidine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER |

|                    |                                                                |
|--------------------|----------------------------------------------------------------|
|                    | note = 2'-O-methyladenosine-3'-phosphate                       |
| modified_base      | 6                                                              |
|                    | mod_base = OTHER                                               |
|                    | note = 2'-O-hexadecyl-guanosine-3'-phosphate                   |
| modified_base      | 7                                                              |
|                    | mod_base = OTHER                                               |
|                    | note = 2'-O-methylcytidine-3'-phosphate                        |
| modified_base      | 8                                                              |
|                    | mod_base = OTHER                                               |
|                    | note = 2'-deoxy-2'-fluoroadenosine-3'-phosphate                |
| modified_base      | 9                                                              |
|                    | mod_base = OTHER                                               |
|                    | note = 2'-deoxy-2'-fluorocytidine-3'-phosphate                 |
| modified_base      | 10                                                             |
|                    | mod_base = OTHER                                               |
|                    | note = 2'-O-methyluridine-3'-phosphate                         |
| modified_base      | 11                                                             |
|                    | mod_base = OTHER                                               |
|                    | note = 2'-O-methyluridine-3'-phosphate                         |
| modified_base      | 12                                                             |
|                    | mod_base = OTHER                                               |
|                    | note = 2'-O-methyluridine-3'-phosphate                         |
| modified_base      | 13                                                             |
|                    | mod_base = OTHER                                               |
|                    | note = 2'-O-methyladenosine-3'-phosphate                       |
| modified_base      | 14                                                             |
|                    | mod_base = OTHER                                               |
|                    | note = 2'-deoxy-2'-fluorouridine-3'-phosphate                  |
| modified_base      | 15                                                             |
|                    | mod_base = OTHER                                               |
|                    | note = 2'-O-methyluridine-3'-phosphate                         |
| modified_base      | 16                                                             |
|                    | mod_base = OTHER                                               |
|                    | note = 2'-deoxy-2'-fluoroguanosine-3'-phosphate                |
| modified_base      | 17                                                             |
|                    | mod_base = OTHER                                               |
|                    | note = 2'-O-methyladenosine-3'-phosphate                       |
| modified_base      | 18                                                             |
|                    | mod_base = OTHER                                               |
|                    | note = 2'-O-methylguanosine-3'-phosphate                       |
| modified_base      | 19                                                             |
|                    | mod_base = OTHER                                               |
|                    | note = 2'-O-methyluridine-3'-phosphate                         |
| modified_base      | 20                                                             |
|                    | mod_base = OTHER                                               |
|                    | note = 2'-O-methyluridine-3'-phosphate                         |
| modified_base      | 21                                                             |
|                    | mod_base = OTHER                                               |
|                    | note = 2'-O-methylcytidine-3'-phosphorothioate                 |
| modified_base      | 22                                                             |
|                    | mod_base = OTHER                                               |
|                    | note = 2'-O-methylcytidine-3'-phosphorothioate                 |
| modified_base      | 23                                                             |
|                    | mod_base = OTHER                                               |
|                    | note = 2'-O-methyluridine                                      |
| SEQUENCE: 86       |                                                                |
| tcaaagcact ttattgagtt cct                                                           23 |
|                    |                                                                |
| SEQ ID NO: 87      | moltype = RNA   length = 21                                    |
| FEATURE            | Location/Qualifiers                                            |
| source             | 1..21                                                          |
|                    | mol_type = other RNA                                           |
|                    | organism = synthetic construct                                 |
| modified_base      | 1                                                              |
|                    | mod_base = OTHER                                               |
|                    | note = 2'-O-methylguanosine-3'-phosphorothioate                |
| modified_base      | 2                                                              |
|                    | mod_base = OTHER                                               |
|                    | note = 2'-O-methyladenosine-3'-phosphorothioate                |
| modified_base      | 3                                                              |
|                    | mod_base = OTHER                                               |
|                    | note = 2'-O-methyladenosine-3'-phosphate                       |
| modified_base      | 4                                                              |
|                    | mod_base = OTHER                                               |
|                    | note = 2'-O-methyladenosine-3'-phosphate                       |
| modified_base      | 5                                                              |
|                    | mod_base = OTHER                                               |
|                    | note = 2'-O-methylcytidine-3'-phosphate                        |
| modified_base      | 6                                                              |

```
                        mod_base = OTHER
                        note = 2'-O-methyluridine-3'-phosphate
modified_base           7
                        mod_base = OTHER
                        note = 2'-deoxy-2'-fluorocytidine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluoroadenosine-3'-phosphate
modified_base           10
                        mod_base = OTHER
                        note = 2'-deoxy-2'-fluorouridine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyladenosine-3'-phosphate
modified_base           13
                        mod_base = OTHER
                        note = 2'-O-methyladenosine-3'-phosphate
modified_base           14
                        mod_base = OTHER
                        note = 2'-O-methylguanosine-3'-phosphate
modified_base           15
                        mod_base = OTHER
                        note = 2'-O-methyluridine-3'-phosphate
modified_base           16
                        mod_base = OTHER
                        note = 2'-O-methylguanosine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-hexadecyl-uridine-3'-phosphate
modified_base           21
                        mod_base = OTHER
                        note = 2'-O-methyladenosine-3'-phosphate
                        ((2S,4R)-1-[29-[[2-(acetylamino)-2-deoxy-beta-D-galactopyra
                        nosyl]oxy]-14,14-bis[[3-[[3-[[5-[[2-(acetylamino)-2-deoxy-b
                        eta-D-galactopyranosyl]oxy]-1-oxopentyl]amino]propyl]amino]
                        -3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 87
gaaactcaat aaagtgcttt a                                                    21

SEQ ID NO: 88           moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
```

| | | |
|---|---|---|
| | | mod_base = OTHER |
| | | note = 2'-O-methyladenosine-3'-phosphate |
| modified_base | 8 | |
| | | mod_base = OTHER |
| | | note = 2'-O-methylcytidine-3'-phosphate |
| modified_base | 9 | |
| | | mod_base = OTHER |
| | | note = 2'-O-methyluridine-3'-phosphate |
| modified_base | 10 | |
| | | mod_base = OTHER |
| | | note = 2'-O-hexadecyl-uridine-3'-phosphate |
| modified_base | 11 | |
| | | mod_base = OTHER |
| | | note = 2'-O-methyluridine-3'-phosphate |
| modified_base | 12 | |
| | | mod_base = OTHER |
| | | note = 2'-O-methyladenosine-3'-phosphate |
| modified_base | 13 | |
| | | mod_base = OTHER |
| | | note = 2'-O-methyluridine-3'-phosphate |
| modified_base | 14 | |
| | | mod_base = OTHER |
| | | note = 2'-deoxy-2'-fluorouridine-3'-phosphate |
| modified_base | 15 | |
| | | mod_base = OTHER |
| | | note = 2'-O-methylguanosine-3'-phosphate |
| modified_base | 16 | |
| | | mod_base = OTHER |
| | | note = 2'-deoxy-2'-fluoroadenosine-3'-phosphate |
| modified_base | 17 | |
| | | mod_base = OTHER |
| | | note = 2'-O-methylguanosine-3'-phosphate |
| modified_base | 18 | |
| | | mod_base = OTHER |
| | | note = 2'-O-methyluridine-3'-phosphate |
| modified_base | 19 | |
| | | mod_base = OTHER |
| | | note = 2'-O-methyluridine-3'-phosphate |
| modified_base | 20 | |
| | | mod_base = OTHER |
| | | note = 2'-O-methyluridine-3'-phosphate |
| modified_base | 21 | |
| | | mod_base = OTHER |
| | | note = 2'-O-methylcytidine-3'-phosphorothioate |
| modified_base | 22 | |
| | | mod_base = OTHER |
| | | note = 2'-O-methyluridine-3'-phosphorothioate |
| modified_base | 23 | |
| | | mod_base = OTHER |
| | | note = 2'-O-methylguanosine |
| SEQUENCE: 88 | | |
| taaagcactt tattgagttt ctg | | 23 |
| | | |
| SEQ ID NO: 89 | moltype = RNA   length = 23 | |
| FEATURE | Location/Qualifiers | |
| source | 1..23 | |
| | | mol_type = other RNA |
| | | organism = synthetic construct |
| modified_base | 1 | |
| | | mod_base = OTHER |
| | | note = 2'-O-methyluridine-3'-phosphorothioate |
| modified_base | 2 | |
| | | mod_base = OTHER |
| | | note = 2'-deoxy-2'-fluorocytidine-3'-phosphorothioate |
| modified_base | 3 | |
| | | mod_base = OTHER |
| | | note = 2'-O-methyladenosine-3'-phosphate |
| modified_base | 4 | |
| | | mod_base = OTHER |
| | | note = 2'-O-methyladenosine-3'-phosphate |
| modified_base | 5 | |
| | | mod_base = OTHER |
| | | note = 2'-O-methyladenosine-3'-phosphate |
| modified_base | 6 | |
| | | mod_base = OTHER |
| | | note = 2'-deoxy-2'-fluoroguanosine-3'-phosphate |
| modified_base | 7 | |
| | | mod_base = OTHER |
| | | note = 2'-O-methylcytidine-3'-phosphate |

| | |
|---|---|
| modified_base | 8<br>mod_base = OTHER<br>note = 2'-deoxy-2'-fluoroadenosine-3'-phosphate |
| modified_base | 9<br>mod_base = OTHER<br>note = 2'-deoxy-2'-fluorocytidine-3'-phosphate |
| modified_base | 10<br>mod_base = OTHER<br>note = 2'-O-methyluridine-3'-phosphate |
| modified_base | 11<br>mod_base = OTHER<br>note = 2'-O-methyluridine-3'-phosphate |
| modified_base | 12<br>mod_base = OTHER<br>note = 2'-O-methyluridine-3'-phosphate |
| modified_base | 13<br>mod_base = OTHER<br>note = 2'-O-methyladenosine-3'-phosphate |
| modified_base | 14<br>mod_base = OTHER<br>note = 2'-deoxy-2'-fluorouridine-3'-phosphate |
| modified_base | 15<br>mod_base = OTHER<br>note = 2'-O-methyluridine-3'-phosphate |
| modified_base | 16<br>mod_base = OTHER<br>note = 2'-deoxy-2'-fluoroguanosine-3'-phosphate |
| modified_base | 17<br>mod_base = OTHER<br>note = 2'-O-hexadecyl-adenosine-3'-phosphate |
| modified_base | 18<br>mod_base = OTHER<br>note = 2'-O-methylguanosine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methylcytidine-3'-phosphorothioate |
| modified_base | 22<br>mod_base = OTHER<br>note = 2'-O-methylcytidine-3'-phosphorothioate |
| modified_base | 23<br>mod_base = OTHER<br>note = 2'-O-methyluridine |
| SEQUENCE: 89 | |
| tcaaagcact ttattgagtt cct | 23 |
| SEQ ID NO: 90<br>FEATURE<br>source | moltype = RNA length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate |
| modified_base | 2<br>mod_base = OTHER<br>note = 2'-deoxy-2'-fluorocytidine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methyladenosine-3'-phosphate |
| modified_base | 6<br>mod_base = OTHER<br>note = 2'-deoxy-2'-fluoroguanosine-3'-phosphate |
| modified_base | 7<br>mod_base = OTHER<br>note = 2'-O-methylcytidine-3'-phosphate |
| modified_base | 8<br>mod_base = OTHER |

-continued

```
                              note = 2'-deoxy-2'-fluoroadenosine-3'-phosphate
modified_base                 9
                              mod_base = OTHER
                              note = 2'-deoxy-2'-fluorocytidine-3'-phosphate
modified_base                 10
                              mod_base = OTHER
                              note = 2'-O-methyluridine-3'-phosphate
modified_base                 11
                              mod_base = OTHER
                              note = 2'-O-methyluridine-3'-phosphate
modified_base                 12
                              mod_base = OTHER
                              note = 2'-O-methyluridine-3'-phosphate
modified_base                 13
                              mod_base = OTHER
                              note = 2'-O-methyladenosine-3'-phosphate
modified_base                 14
                              mod_base = OTHER
                              note = 2'-deoxy-2'-fluorouridine-3'-phosphate
modified_base                 15
                              mod_base = OTHER
                              note = 2'-O-methyluridine-3'-phosphate
modified_base                 16
                              mod_base = OTHER
                              note = 2'-deoxy-2'-fluoroguanosine-3'-phosphate
modified_base                 17
                              mod_base = OTHER
                              note = 2'-O-methyladenosine-3'-phosphate
modified_base                 18
                              mod_base = OTHER
                              note = 2'-O-hexadecyl-guanosine-3'-phosphate
modified_base                 19
                              mod_base = OTHER
                              note = 2'-O-methyluridine-3'-phosphate
modified_base                 20
                              mod_base = OTHER
                              note = 2'-O-methyluridine-3'-phosphate
modified_base                 21
                              mod_base = OTHER
                              note = 2'-O-methylcytidine-3'-phosphorothioate
modified_base                 22
                              mod_base = OTHER
                              note = 2'-O-methylcytidine-3'-phosphorothioate
modified_base                 23
                              mod_base = OTHER
                              note = 2'-O-methyluridine
SEQUENCE: 90
tcaaagcact ttattgagtt cct                                                 23

SEQ ID NO: 91                 moltype = RNA   length = 23
FEATURE                       Location/Qualifiers
source                        1..23
                              mol_type = other RNA
                              organism = synthetic construct
modified_base                 1
                              mod_base = OTHER
                              note = 2'-O-methyluridine-3'-phosphorothioate
modified_base                 2
                              mod_base = OTHER
                              note = 2'-deoxy-2'-fluorocytidine-3'-phosphorothioate
modified_base                 3
                              mod_base = OTHER
                              note = 2'-O-methyladenosine-3'-phosphate
modified_base                 4
                              mod_base = OTHER
                              note = 2'-O-methyladenosine-3'-phosphate
modified_base                 5
                              mod_base = OTHER
                              note = 2'-O-methyladenosine-3'-phosphate
modified_base                 6
                              mod_base = OTHER
                              note = 2'-deoxy-2'-fluoroguanosine-3'-phosphate
modified_base                 7
                              mod_base = OTHER
                              note = 2'-O-methylcytidine-3'-phosphate
modified_base                 8
                              mod_base = OTHER
                              note = 2'-deoxy-2'-fluoroadenosine-3'-phosphate
modified_base                 9
```

-continued

|  |  |
|---|---|
|  | mod_base = OTHER<br>note = 2'-deoxy-2'-fluorocytidine-3'-phosphate |
| modified_base | 10<br>mod_base = OTHER<br>note = 2'-O-hexadecyl-uridine-3'-phosphate |
| modified_base | 11<br>mod_base = OTHER<br>note = 2'-O-methyluridine-3'-phosphate |
| modified_base | 12<br>mod_base = OTHER<br>note = 2'-O-methyluridine-3'-phosphate |
| modified_base | 13<br>mod_base = OTHER<br>note = 2'-O-methyladenosine-3'-phosphate |
| modified_base | 14<br>mod_base = OTHER<br>note = 2'-deoxy-2'-fluorouridine-3'-phosphate |
| modified_base | 15<br>mod_base = OTHER<br>note = 2'-O-methyluridine-3'-phosphate |
| modified_base | 16<br>mod_base = OTHER<br>note = 2'-deoxy-2'-fluoroguanosine-3'-phosphate |
| modified_base | 17<br>mod_base = OTHER<br>note = 2'-O-methyladenosine-3'-phosphate |
| modified_base | 18<br>mod_base = OTHER<br>note = 2'-O-methylguanosine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methylcytidine-3'-phosphorothioate |
| modified_base | 22<br>mod_base = OTHER<br>note = 2'-O-methylcytidine-3'-phosphorothioate |
| modified_base | 23<br>mod_base = OTHER<br>note = 2'-O-methyluridine |

SEQUENCE: 91
tcaaagcact ttattgagtt cct                                          23

| SEQ ID NO: 92 | moltype = RNA  length = 21 |
|---|---|
| FEATURE | Location/Qualifiers |
| source | 1..21<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methylcytidine-3'-phosphate |
| modified_base | 5<br>mod_base = OTHER<br>note = 2'-O-methyluridine-3'-phosphate |
| modified_base | 6<br>mod_base = OTHER<br>note = 2'-O-methylcytidine-3'-phosphate |
| modified_base | 7<br>mod_base = OTHER<br>note = 2'-deoxy-2'-fluoroadenosine-3'-phosphate |
| modified_base | 8<br>mod_base = OTHER<br>note = 2'-O-methyladenosine-3'-phosphate |
| modified_base | 9<br>mod_base = OTHER<br>note = 2'-deoxy-2'-fluorouridine-3'-phosphate |

```
modified_base       10
                    mod_base = OTHER
                    note = 2'-deoxy-2'-fluoroadenosine-3'-phosphate
modified_base       11
                    mod_base = OTHER
                    note = 2'-deoxy-2'-fluoroadenosine-3'-phosphate
modified_base       12
                    mod_base = OTHER
                    note = 2'-O-methyladenosine-3'-phosphate
modified_base       13
                    mod_base = OTHER
                    note = 2'-O-hexadecyl-guanosine-3'-phosphate
modified_base       14
                    mod_base = OTHER
                    note = 2'-O-methyluridine-3'-phosphate
modified_base       15
                    mod_base = OTHER
                    note = 2'-O-methylguanosine-3'-phosphate
modified_base       16
                    mod_base = OTHER
                    note = 2'-O-methylcytidine-3'-phosphate
modified_base       17
                    mod_base = OTHER
                    note = 2'-O-methyluridine-3'-phosphate
modified_base       18
                    mod_base = OTHER
                    note = 2'-O-methyluridine-3'-phosphate
modified_base       19
                    mod_base = OTHER
                    note = 2'-O-methyluridine-3'-phosphate
modified_base       20
                    mod_base = OTHER
                    note = 2'-O-methylguanosine-3'-phosphate
modified_base       21
                    mod_base = OTHER
                    note = 2'-O-methyladenosine-3'-phosphate
                     ((2S,4R)-1-[29-[[2-(acetylamino)-2-deoxy-beta-D-galactopyra
                     nosyl]oxy]-14,14-bis[[3-[[3-[[5-[[2-(acetylamino)-2-deoxy-b
                     eta-D-galactopyranosyl]oxy]-1-oxopentyl]amino]propyl]amino]
                     -3-oxopropoxy]methyl]-1,12,19,25-tetraoxo-16-oxa-13,20,24-t
                     riazanonacos-1-yl]-4-hydroxy-2-pyrrolidinyl)methyl ester
SEQUENCE: 92
gaactcaata aagtgctttg a                                                  21

SEQ ID NO: 93       moltype = RNA   length = 21
FEATURE             Location/Qualifiers
source              1..21
                    mol_type = other RNA
                    organism = synthetic construct
modified_base       1
                    mod_base = OTHER
                    note = 2'-O-methylguanosine-3'-phosphorothioate
modified_base       2
                    mod_base = OTHER
                    note = 2'-O-methyladenosine-3'-phosphorothioate
modified_base       3
                    mod_base = OTHER
                    note = 2'-O-methyladenosine-3'-phosphate
modified_base       4
                    mod_base = OTHER
                    note = 2'-O-methylcytidine-3'-phosphate
modified_base       5
                    mod_base = OTHER
                    note = 2'-O-hexadecyl-uridine-3'-phosphate
modified_base       6
                    mod_base = OTHER
                    note = 2'-O-methylcytidine-3'-phosphate
modified_base       7
                    mod_base = OTHER
                    note = 2'-deoxy-2'-fluoroadenosine-3'-phosphate
modified_base       8
                    mod_base = OTHER
                    note = 2'-O-methyladenosine-3'-phosphate
modified_base       9
                    mod_base = OTHER
                    note = 2'-deoxy-2'-fluorouridine-3'-phosphate
modified_base       10
                    mod_base = OTHER
                    note = 2'-deoxy-2'-fluoroadenosine-3'-phosphate
```

| | |
|---|---|
| modified_base | 11<br>mod_base = OTHER<br>note = 2'-deoxy-2'-fluoroadenosine-3'-phosphate |
| modified_base | 12<br>mod_base = OTHER<br>note = 2'-O-methyladenosine-3'-phosphate |
| modified_base | 13<br>mod_base = OTHER<br>note = 2'-O-methylguanosine-3'-phosphate |
| modified_base | 14<br>mod_base = OTHER<br>note = 2'-O-methyluridine-3'-phosphate |
| modified_base | 15<br>mod_base = OTHER<br>note = 2'-O-methylguanosine-3'-phosphate |
| modified_base | 16<br>mod_base = OTHER<br>note = 2'-O-methylcytidine-3'-phosphate |
| modified_base | 17<br>mod_base = OTHER<br>note = 2'-O-methyluridine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-methylguanosine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 93 | |
| gaactcaata aagtgctttg a | 21 |
| | |
| SEQ ID NO: 94<br>FEATURE<br>source | moltype = RNA  length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate |
| modified_base | 2<br>mod_base = OTHER<br>note = 2'-deoxy-2'-fluoroadenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylguanosine-3'-phosphate |
| modified_base | 6<br>mod_base = OTHER<br>note = 2'-deoxy-2'-fluorocytidine-3'-phosphate |
| modified_base | 7<br>mod_base = OTHER<br>note = 2'-O-methyladenosine-3'-phosphate |
| modified_base | 8<br>mod_base = OTHER<br>note = 2'-O-methylcytidine-3'-phosphate |
| modified_base | 9<br>mod_base = OTHER<br>note = 2'-O-methyluridine-3'-phosphate |
| modified_base | 10<br>mod_base = OTHER<br>note = 2'-O-methyluridine-3'-phosphate |
| modified_base | 11<br>mod_base = OTHER<br>note = 2'-O-methyluridine-3'-phosphate |

```
modified_base      12
                   mod_base = OTHER
                   note = 2'-O-methyladenosine-3'-phosphate
modified_base      13
                   mod_base = OTHER
                   note = 2'-O-methyluridine-3'-phosphate
modified_base      14
                   mod_base = OTHER
                   note = 2'-deoxy-2'-fluorouridine-3'-phosphate
modified_base      15
                   mod_base = OTHER
                   note = 2'-O-methylguanosine-3'-phosphate
modified_base      16
                   mod_base = OTHER
                   note = 2'-deoxy-2'-fluoroadenosine-3'-phosphate
modified_base      17
                   mod_base = OTHER
                   note = 2'-O-methylguanosine-3'-phosphate
modified_base      18
                   mod_base = OTHER
                   note = 2'-O-methyluridine-3'-phosphate
modified_base      19
                   mod_base = OTHER
                   note = 2'-O-methyluridine-3'-phosphate
modified_base      20
                   mod_base = OTHER
                   note = 2'-O-methyluridine-3'-phosphate
modified_base      21
                   mod_base = OTHER
                   note = 2'-O-hexadecyl-cytidine-3'-phosphorothioate
modified_base      22
                   mod_base = OTHER
                   note = 2'-O-methyluridine-3'-phosphorothioate
modified_base      23
                   mod_base = OTHER
                   note = 2'-O-methylguanosine
SEQUENCE: 94
taaagcactt tattgagttt ctg                                              23

SEQ ID NO: 95      moltype = RNA   length = 21
FEATURE            Location/Qualifiers
source             1..21
                   mol_type = other RNA
                   organism = synthetic construct
modified_base      1
                   mod_base = OTHER
                   note = 2'-O-methylguanosine-3'-phosphorothioate
modified_base      2
                   mod_base = OTHER
                   note = 2'-O-methyladenosine-3'-phosphorothioate
modified_base      3
                   mod_base = OTHER
                   note = 2'-O-methyladenosine-3'-phosphate
modified_base      4
                   mod_base = OTHER
                   note = 2'-O-methyladenosine-3'-phosphate
modified_base      5
                   mod_base = OTHER
                   note = 2'-O-methylcytidine-3'-phosphate
modified_base      6
                   mod_base = OTHER
                   note = 2'-O-methyluridine-3'-phosphate
modified_base      7
                   mod_base = OTHER
                   note = 2'-deoxy-2'-fluorocytidine-3'-phosphate
modified_base      8
                   mod_base = OTHER
                   note = 2'-O-methyladenosine-3'-phosphate
modified_base      9
                   mod_base = OTHER
                   note = 2'-deoxy-2'-fluoroadenosine-3'-phosphate
modified_base      10
                   mod_base = OTHER
                   note = 2'-deoxy-2'-fluorouridine-3'-phosphate
modified_base      11
                   mod_base = OTHER
                   note = 2'-deoxy-2'-fluoroadenosine-3'-phosphate
modified_base      12
                   mod_base = OTHER
```

```
                              note = 2'-O-methyladenosine-3'-phosphate
modified_base                 13
                              mod_base = OTHER
                              note = 2'-O-methyladenosine-3'-phosphate
modified_base                 14
                              mod_base = OTHER
                              note = 2'-O-methylguanosine-3'-phosphate
modified_base                 15
                              mod_base = OTHER
                              note = 2'-O-methyluridine-3'-phosphate
modified_base                 16
                              mod_base = OTHER
                              note = 2'-O-methylguanosine-3'-phosphate
modified_base                 17
                              mod_base = OTHER
                              note = 2'-O-methylcytidine-3'-phosphate
modified_base                 18
                              mod_base = OTHER
                              note = 2'-O-methyluridine-3'-phosphate
modified_base                 19
                              mod_base = OTHER
                              note = 2'-O-hexadecyl-uridine-3'-phosphate
modified_base                 20
                              mod_base = OTHER
                              note = 2'-O-methyluridine-3'-phosphate
modified_base                 21
                              mod_base = OTHER
                              note = 2'-O-methyladenosine-3'-phosphate
                               ((2S,4R)-1-[29-[[2-(acetylamino)-2-deoxy-beta-D-galactopyra
                               nosyl]oxy]-14,14-bis[[3-[[3-[[5-[[2-(acetylamino)-2-deoxy-b
                               eta-D-galactopyranosyl]oxy]-1-oxopentyl]amino]propyl]amino]
                               -3-oxopropoxy]methyl]-1,12,19,25-tetraoxo-16-oxa-13,20,24-t
                               riazanonacos-1-yl]-4-hydroxy-2-pyrrolidinyl)methyl ester
SEQUENCE: 95
gaaactcaat aaagtgcttt a                                                       21

SEQ ID NO: 96                 moltype = RNA   length = 23
FEATURE                       Location/Qualifiers
source                        1..23
                              mol_type = other RNA
                              organism = synthetic construct
modified_base                 1
                              mod_base = OTHER
                              note = 2'-O-methyluridine-3'-phosphorothioate
modified_base                 2
                              mod_base = OTHER
                              note = 2'-deoxy-2'-fluoroadenosine-3'-phosphorothioate
modified_base                 3
                              mod_base = OTHER
                              note = 2'-O-methyladenosine-3'-phosphate
modified_base                 4
                              mod_base = OTHER
                              note = 2'-O-methyladenosine-3'-phosphate
modified_base                 5
                              mod_base = OTHER
                              note = 2'-O-methylguanosine-3'-phosphate
modified_base                 6
                              mod_base = OTHER
                              note = 2'-deoxy-2'-fluorocytidine-3'-phosphate
modified_base                 7
                              mod_base = OTHER
                              note = 2'-O-methyladenosine-3'-phosphate
modified_base                 8
                              mod_base = OTHER
                              note = 2'-O-methylcytidine-3'-phosphate
modified_base                 9
                              mod_base = OTHER
                              note = 2'-O-methyluridine-3'-phosphate
modified_base                 10
                              mod_base = OTHER
                              note = 2'-O-methyluridine-3'-phosphate
modified_base                 11
                              mod_base = OTHER
                              note = 2'-O-methyluridine-3'-phosphate
modified_base                 12
                              mod_base = OTHER
                              note = 2'-O-methyladenosine-3'-phosphate
modified_base                 13
                              mod_base = OTHER
```

```
                         note = 2'-O-methyluridine-3'-phosphate
modified_base            14
                         mod_base = OTHER
                         note = 2'-deoxy-2'-fluorouridine-3'-phosphate
modified_base            15
                         mod_base = OTHER
                         note = 2'-O-methylguanosine-3'-phosphate
modified_base            16
                         mod_base = OTHER
                         note = 2'-O-hexadecyl-adenosine-3'-phosphate
modified_base            17
                         mod_base = OTHER
                         note = 2'-O-methylguanosine-3'-phosphate
modified_base            18
                         mod_base = OTHER
                         note = 2'-O-methyluridine-3'-phosphate
modified_base            19
                         mod_base = OTHER
                         note = 2'-O-methyluridine-3'-phosphate
modified_base            20
                         mod_base = OTHER
                         note = 2'-O-methyluridine-3'-phosphate
modified_base            21
                         mod_base = OTHER
                         note = 2'-O-methylcytidine-3'-phosphorothioate
modified_base            22
                         mod_base = OTHER
                         note = 2'-O-methyluridine-3'-phosphorothioate
modified_base            23
                         mod_base = OTHER
                         note = 2'-O-methylguanosine
SEQUENCE: 96
taaagcactt tattgagttt ctg                                              23

SEQ ID NO: 97            moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methylguanosine-3'-phosphorothioate
modified_base            2
                         mod_base = OTHER
                         note = 2'-O-methyladenosine-3'-phosphorothioate
modified_base            3
                         mod_base = OTHER
                         note = 2'-O-methyladenosine-3'-phosphate
modified_base            4
                         mod_base = OTHER
                         note = 2'-O-hexadecyl-cytidine-3'-phosphate
modified_base            5
                         mod_base = OTHER
                         note = 2'-O-methyluridine-3'-phosphate
modified_base            6
                         mod_base = OTHER
                         note = 2'-O-methylcytidine-3'-phosphate
modified_base            7
                         mod_base = OTHER
                         note = 2'-deoxy-2'-fluoroadenosine-3'-phosphate
modified_base            8
                         mod_base = OTHER
                         note = 2'-O-methyladenosine-3'-phosphate
modified_base            9
                         mod_base = OTHER
                         note = 2'-deoxy-2'-fluorouridine-3'-phosphate
modified_base            10
                         mod_base = OTHER
                         note = 2'-deoxy-2'-fluoroadenosine-3'-phosphate
modified_base            11
                         mod_base = OTHER
                         note = 2'-deoxy-2'-fluoroadenosine-3'-phosphate
modified_base            12
                         mod_base = OTHER
                         note = 2'-O-methyladenosine-3'-phosphate
modified_base            13
                         mod_base = OTHER
                         note = 2'-O-methylguanosine-3'-phosphate
modified_base            14
```

|                | -continued |
|---|---|
|                | mod_base = OTHER |
|                | note = 2'-O-methyluridine-3'-phosphate |
| modified_base  | 15 |
|                | mod_base = OTHER |
|                | note = 2'-O-methylguanosine-3'-phosphate |
| modified_base  | 16 |
|                | mod_base = OTHER |
|                | note = 2'-O-methylcytidine-3'-phosphate |
| modified_base  | 17 |
|                | mod_base = OTHER |
|                | note = 2'-O-methyluridine-3'-phosphate |
| modified_base  | 18 |
|                | mod_base = OTHER |
|                | note = 2'-O-methyluridine-3'-phosphate |
| modified_base  | 19 |
|                | mod_base = OTHER |
|                | note = 2'-O-methyluridine-3'-phosphate |
| modified_base  | 20 |
|                | mod_base = OTHER |
|                | note = 2'-O-methylguanosine-3'-phosphate |
| modified_base  | 21 |
|                | mod_base = OTHER |
|                | note = 2'-O-methyladenosine-3'-phosphate |
|                | ((2S,4R)-1-[29-[[2-(acetylamino)-2-deoxy-beta-D-galactopyra |
|                | nosyl]oxy]-14,14-bis[[3-[[3-[[5-[[2-(acetylamino)-2-deoxy-b |
|                | eta-D-galactopyranosyl]oxy]-1-oxopentyl]amino]propyl]amino] |
|                | -3-oxopropoxy]methyl]-1,12,19,25-tetraoxo-16-oxa-13,20,24-t |
|                | riazanonacos-1-yl]-4-hydroxy-2-pyrrolidinyl)methyl ester |
| SEQUENCE: 97   | |
| gaactcaata aagtgctttg a                              21 |

| SEQ ID NO: 98  | moltype = RNA  length = 21 |
| FEATURE        | Location/Qualifiers |
| source         | 1..21 |
|                | mol_type = other RNA |
|                | organism = synthetic construct |
| modified_base  | 1 |
|                | mod_base = OTHER |
|                | note = 2'-O-methylguanosine-3'-phosphorothioate |
| modified_base  | 2 |
|                | mod_base = OTHER |
|                | note = 2'-O-methyladenosine-3'-phosphorothioate |
| modified_base  | 3 |
|                | mod_base = OTHER |
|                | note = 2'-O-methyladenosine-3'-phosphate |
| modified_base  | 4 |
|                | mod_base = OTHER |
|                | note = 2'-O-methylcytidine-3'-phosphate |
| modified_base  | 5 |
|                | mod_base = OTHER |
|                | note = 2'-O-methyluridine-3'-phosphate |
| modified_base  | 6 |
|                | mod_base = OTHER |
|                | note = 2'-O-methylcytidine-3'-phosphate |
| modified_base  | 7 |
|                | mod_base = OTHER |
|                | note = 2'-deoxy-2'-fluoroadenosine-3'-phosphate |
| modified_base  | 8 |
|                | mod_base = OTHER |
|                | note = 2'-O-methyladenosine-3'-phosphate |
| modified_base  | 9 |
|                | mod_base = OTHER |
|                | note = 2'-deoxy-2'-fluorouridine-3'-phosphate |
| modified_base  | 10 |
|                | mod_base = OTHER |
|                | note = 2'-deoxy-2'-fluoroadenosine-3'-phosphate |
| modified_base  | 11 |
|                | mod_base = OTHER |
|                | note = 2'-deoxy-2'-fluoroadenosine-3'-phosphate |
| modified_base  | 12 |
|                | mod_base = OTHER |
|                | note = 2'-O-methyladenosine-3'-phosphate |
| modified_base  | 13 |
|                | mod_base = OTHER |
|                | note = 2'-O-methylguanosine-3'-phosphate |
| modified_base  | 14 |
|                | mod_base = OTHER |
|                | note = 2'-O-methyluridine-3'-phosphate |
| modified_base  | 15 |

```
                            mod_base = OTHER
                            note = 2'-O-methylguanosine-3'-phosphate
modified_base               16
                            mod_base = OTHER
                            note = 2'-O-methylcytidine-3'-phosphate
modified_base               17
                            mod_base = OTHER
                            note = 2'-O-hexadecyl-uridine-3'-phosphate
modified_base               18
                            mod_base = OTHER
                            note = 2'-O-methyluridine-3'-phosphate
modified_base               19
                            mod_base = OTHER
                            note = 2'-O-methyluridine-3'-phosphate
modified_base               20
                            mod_base = OTHER
                            note = 2'-O-methylguanosine-3'-phosphate
modified_base               21
                            mod_base = OTHER
                            note = 2'-O-methyladenosine-3'-phosphate
                             ((2S,4R)-1-[29-[[2-(acetylamino)-2-deoxy-beta-D-galactopyra
                            nosyl]oxy]-14,14-bis[[3-[[3-[[5-[[2-(acetylamino)-2-deoxy-b
                            eta-D-galactopyranosyl]oxy]-1-oxopentyl]amino]propyl]amino]
                            -3-oxopropoxy]methyl]-1,12,19,25-tetraoxo-16-oxa-13,20,24-t
                            riazanonacos-1-yl]-4-hydroxy-2-pyrrolidinyl)methyl ester
SEQUENCE: 98
gaactcaata aagtgctttg a                                                 21

SEQ ID NO: 99               moltype = RNA  length = 23
FEATURE                     Location/Qualifiers
source                      1..23
                            mol_type = other RNA
                            organism = synthetic construct
modified_base               1
                            mod_base = OTHER
                            note = 2'-O-methyluridine-3'-phosphorothioate
modified_base               2
                            mod_base = OTHER
                            note = 2'-deoxy-2'-fluorocytidine-3'-phosphorothioate
modified_base               3
                            mod_base = OTHER
                            note = 2'-O-methyladenosine-3'-phosphate
modified_base               4
                            mod_base = OTHER
                            note = 2'-O-methyladenosine-3'-phosphate
modified_base               5
                            mod_base = OTHER
                            note = 2'-O-methyladenosine-3'-phosphate
modified_base               6
                            mod_base = OTHER
                            note = 2'-deoxy-2'-fluoroguanosine-3'-phosphate
modified_base               7
                            mod_base = OTHER
                            note = 2'-O-methylcytidine-3'-phosphate
modified_base               8
                            mod_base = OTHER
                            note = 2'-O-hexadecyl-adenosine-3'-phosphate
modified_base               9
                            mod_base = OTHER
                            note = 2'-deoxy-2'-fluorocytidine-3'-phosphate
modified_base               10
                            mod_base = OTHER
                            note = 2'-O-methyluridine-3'-phosphate
modified_base               11
                            mod_base = OTHER
                            note = 2'-O-methyluridine-3'-phosphate
modified_base               12
                            mod_base = OTHER
                            note = 2'-O-methyluridine-3'-phosphate
modified_base               13
                            mod_base = OTHER
                            note = 2'-O-methyladenosine-3'-phosphate
modified_base               14
                            mod_base = OTHER
                            note = 2'-deoxy-2'-fluorouridine-3'-phosphate
modified_base               15
                            mod_base = OTHER
                            note = 2'-O-methyluridine-3'-phosphate
modified_base               16
```

```
                        mod_base = OTHER
                        note = 2'-deoxy-2'-fluoroguanosine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methyluridine
SEQUENCE: 99
tcaaagcact ttattgagtt cct                                               23

SEQ ID NO: 100          moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-O-hexadecyl-cytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
```

```
modified_base          17
                       mod_base = OTHER
                       note = 2'-O-methylguanosine-3'-phosphate
modified_base          18
                       mod_base = OTHER
                       note = 2'-O-methyluridine-3'-phosphate
modified_base          19
                       mod_base = OTHER
                       note = 2'-O-methyluridine-3'-phosphate
modified_base          20
                       mod_base = OTHER
                       note = 2'-O-methyluridine-3'-phosphate
modified_base          21
                       mod_base = OTHER
                       note = 2'-O-methylcytidine-3'-phosphorothioate
modified_base          22
                       mod_base = OTHER
                       note = 2'-O-methyluridine-3'-phosphorothioate
modified_base          23
                       mod_base = OTHER
                       note = 2'-O-methylguanosine
SEQUENCE: 100
taaagcactt tattgagttt ctg                                          23

SEQ ID NO: 101         moltype = RNA   length = 21
FEATURE                Location/Qualifiers
source                 1..21
                       mol_type = other RNA
                       organism = synthetic construct
modified_base          1
                       mod_base = OTHER
                       note = 2'-O-methylguanosine-3'-phosphorothioate
modified_base          2
                       mod_base = OTHER
                       note = 2'-O-methyladenosine-3'-phosphorothioate
modified_base          3
                       mod_base = OTHER
                       note = 2'-O-methyladenosine-3'-phosphate
modified_base          4
                       mod_base = OTHER
                       note = 2'-O-methylcytidine-3'-phosphate
modified_base          5
                       mod_base = OTHER
                       note = 2'-O-methyluridine-3'-phosphate
modified_base          6
                       mod_base = OTHER
                       note = 2'-O-methylcytidine-3'-phosphate
modified_base          7
                       mod_base = OTHER
                       note = 2'-deoxy-2'-fluoroadenosine-3'-phosphate
modified_base          8
                       mod_base = OTHER
                       note = 2'-O-hexadecyl-adenosine-3'-phosphate
modified_base          9
                       mod_base = OTHER
                       note = 2'-deoxy-2'-fluorouridine-3'-phosphate
modified_base          10
                       mod_base = OTHER
                       note = 2'-deoxy-2'-fluoroadenosine-3'-phosphate
modified_base          11
                       mod_base = OTHER
                       note = 2'-deoxy-2'-fluoroadenosine-3'-phosphate
modified_base          12
                       mod_base = OTHER
                       note = 2'-O-methyladenosine-3'-phosphate
modified_base          13
                       mod_base = OTHER
                       note = 2'-O-methylguanosine-3'-phosphate
modified_base          14
                       mod_base = OTHER
                       note = 2'-O-methyluridine-3'-phosphate
modified_base          15
                       mod_base = OTHER
                       note = 2'-O-methylguanosine-3'-phosphate
modified_base          16
                       mod_base = OTHER
                       note = 2'-O-methylcytidine-3'-phosphate
modified_base          17
                       mod_base = OTHER
```

```
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methylguanosine-3'-phosphate
modified_base           21
                        mod_base = OTHER
                        note = 2'-O-methyladenosine-3'-phosphate
                        ((2S,4R)-1-[29-[[2-(acetylamino)-2-deoxy-beta-D-galactopyra
                        nosyl]oxy]-14,14-bis[[3-[[3-[[5-[[2-(acetylamino)-2-deoxy-b
                        eta-D-galactopyranosyl]oxy]-1-oxopentyl]amino]propyl]amino]
                        -3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 101
gaactcaata aagtgctttg a                                                  21

SEQ ID NO: 102          moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylguanosine-3'-phosphate
modified_base           18
                        mod_base = OTHER
```

```
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-hexadecyl-uridine-3'-phosphorothioate
modified_base           23
                        mod_base = OTHER
                        note = 2'-O-methylguanosine
SEQUENCE: 102
taaagcactt tattgagttt ctg                                          23

SEQ ID NO: 103          moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-hexadecyl-adenosine-3'-phosphate
modified_base           4
                        mod_base = OTHER
                        note = 2'-O-methylcytidine-3'-phosphate
modified_base           5
                        mod_base = OTHER
                        note = 2'-O-methyluridine-3'-phosphate
modified_base           6
                        mod_base = OTHER
                        note = 2'-O-methylcytidine-3'-phosphate
modified_base           7
                        mod_base = OTHER
                        note = 2'-deoxy-2'-fluoroadenosine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyladenosine-3'-phosphate
modified_base           13
                        mod_base = OTHER
                        note = 2'-O-methylguanosine-3'-phosphate
modified_base           14
                        mod_base = OTHER
                        note = 2'-O-methyluridine-3'-phosphate
modified_base           15
                        mod_base = OTHER
                        note = 2'-O-methylguanosine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
```

```
                    mod_base = OTHER
                    note = 2'-O-methyluridine-3'-phosphate
modified_base       20
                    mod_base = OTHER
                    note = 2'-O-methylguanosine-3'-phosphate
modified_base       21
                    mod_base = OTHER
                    note = 2'-O-methyladenosine-3'-phosphate
                    ((2S,4R)-1-[29-[[2-(acetylamino)-2-deoxy-beta-D-galactopyra
                    nosyl]oxy]-14,14-bis[[3-[[3-[[5-[[2-(acetylamino)-2-deoxy-b
                    eta-D-galactopyranosyl]oxy]-1-oxopentyl]amino]propyl]amino]
                    -3-oxopropoxy]methyl]-1,12,19,25-tetraoxo-16-oxa-13,20,24-t
                    riazanonacos-1-yl]-4-hydroxy-2-pyrrolidinyl)methyl ester
SEQUENCE: 103
gaactcaata aagtgctttg a                                                     21

SEQ ID NO: 104      moltype = RNA   length = 23
FEATURE             Location/Qualifiers
source              1..23
                    mol_type = other RNA
                    organism = synthetic construct
modified_base       1
                    mod_base = OTHER
                    note = 2'-O-methyluridine-3'-phosphorothioate
modified_base       2
                    mod_base = OTHER
                    note = 2'-deoxy-2'-fluorocytidine-3'-phosphorothioate
modified_base       3
                    mod_base = OTHER
                    note = 2'-O-methyladenosine-3'-phosphate
modified_base       4
                    mod_base = OTHER
                    note = 2'-O-methyladenosine-3'-phosphate
modified_base       5
                    mod_base = OTHER
                    note = 2'-O-methyladenosine-3'-phosphate
modified_base       6
                    mod_base = OTHER
                    note = 2'-deoxy-2'-fluoroguanosine-3'-phosphate
modified_base       7
                    mod_base = OTHER
                    note = 2'-O-methylcytidine-3'-phosphate
modified_base       8
                    mod_base = OTHER
                    note = 2'-deoxy-2'-fluoroadenosine-3'-phosphate
modified_base       9
                    mod_base = OTHER
                    note = 2'-deoxy-2'-fluorocytidine-3'-phosphate
modified_base       10
                    mod_base = OTHER
                    note = 2'-O-methyluridine-3'-phosphate
modified_base       11
                    mod_base = OTHER
                    note = 2'-O-methyluridine-3'-phosphate
modified_base       12
                    mod_base = OTHER
                    note = 2'-O-methyluridine-3'-phosphate
modified_base       13
                    mod_base = OTHER
                    note = 2'-O-methyladenosine-3'-phosphate
modified_base       14
                    mod_base = OTHER
                    note = 2'-deoxy-2'-fluorouridine-3'-phosphate
modified_base       15
                    mod_base = OTHER
                    note = 2'-O-hexadecyl-uridine-3'-phosphate
modified_base       16
                    mod_base = OTHER
                    note = 2'-deoxy-2'-fluoroguanosine-3'-phosphate
modified_base       17
                    mod_base = OTHER
                    note = 2'-O-methyladenosine-3'-phosphate
modified_base       18
                    mod_base = OTHER
                    note = 2'-O-methylguanosine-3'-phosphate
modified_base       19
                    mod_base = OTHER
                    note = 2'-O-methyluridine-3'-phosphate
modified_base       20
```

```
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methyluridine
SEQUENCE: 104
tcaaagcact ttattgagtt cct                                              23

SEQ ID NO: 105          moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylguanosine-3'-phosphate
modified_base           18
                        mod_base = OTHER
                        note = 2'-O-methyluridine-3'-phosphate
modified_base           19
                        mod_base = OTHER
                        note = 2'-O-hexadecyl-uridine-3'-phosphate
modified_base           20
                        mod_base = OTHER
                        note = 2'-O-methyluridine-3'-phosphate
```

```
modified_base          21
                       mod_base = OTHER
                       note = 2'-O-methylcytidine-3'-phosphorothioate
modified_base          22
                       mod_base = OTHER
                       note = 2'-O-methyluridine-3'-phosphorothioate
modified_base          23
                       mod_base = OTHER
                       note = 2'-O-methylguanosine
SEQUENCE: 105
taaagcactt tattgagttt ctg                                              23

SEQ ID NO: 106         moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methyluridine-3'-phosphorothioate
modified_base          2
                       mod_base = OTHER
                       note = 2'-deoxy-2'-fluoroadenosine-3'-phosphorothioate
modified_base          3
                       mod_base = OTHER
                       note = 2'-O-methyladenosine-3'-phosphate
modified_base          4
                       mod_base = OTHER
                       note = 2'-O-methyladenosine-3'-phosphate
modified_base          5
                       mod_base = OTHER
                       note = 2'-O-methylguanosine-3'-phosphate
modified_base          6
                       mod_base = OTHER
                       note = 2'-deoxy-2'-fluorocytidine-3'-phosphate
modified_base          7
                       mod_base = OTHER
                       note = 2'-O-methyladenosine-3'-phosphate
modified_base          8
                       mod_base = OTHER
                       note = 2'-O-methylcytidine-3'-phosphate
modified_base          9
                       mod_base = OTHER
                       note = 2'-O-methyluridine-3'-phosphate
modified_base          10
                       mod_base = OTHER
                       note = 2'-O-methyluridine-3'-phosphate
modified_base          11
                       mod_base = OTHER
                       note = 2'-O-methyluridine-3'-phosphate
modified_base          12
                       mod_base = OTHER
                       note = 2'-O-methyladenosine-3'-phosphate
modified_base          13
                       mod_base = OTHER
                       note = 2'-O-methyluridine-3'-phosphate
modified_base          14
                       mod_base = OTHER
                       note = 2'-deoxy-2'-fluorouridine-3'-phosphate
modified_base          15
                       mod_base = OTHER
                       note = 2'-O-methylguanosine-3'-phosphate
modified_base          16
                       mod_base = OTHER
                       note = 2'-deoxy-2'-fluoroadenosine-3'-phosphate
modified_base          17
                       mod_base = OTHER
                       note = 2'-O-methylguanosine-3'-phosphate
modified_base          18
                       mod_base = OTHER
                       note = 2'-O-methyluridine-3'-phosphate
modified_base          19
                       mod_base = OTHER
                       note = 2'-O-methyluridine-3'-phosphate
modified_base          20
                       mod_base = OTHER
                       note = 2'-O-methyluridine-3'-phosphate
modified_base          21
                       mod_base = OTHER
```

```
                    note = 2'-O-methylcytidine-3'-phosphorothioate
modified_base       22
                    mod_base = OTHER
                    note = 2'-O-methyluridine-3'-phosphorothioate
modified_base       23
                    mod_base = OTHER
                    note = 2'-O-hexadecyl-guanosine
SEQUENCE: 106
taaagcactt tattgagttt ctg                                                   23

SEQ ID NO: 107      moltype = RNA   length = 23
FEATURE             Location/Qualifiers
source              1..23
                    mol_type = other RNA
                    organism = synthetic construct
modified_base       1
                    mod_base = OTHER
                    note = 2'-O-methyluridine-3'-phosphorothioate
modified_base       2
                    mod_base = OTHER
                    note = 2'-deoxy-2'-fluorocytidine-3'-phosphorothioate
modified_base       3
                    mod_base = OTHER
                    note = 2'-O-methyladenosine-3'-phosphate
modified_base       4
                    mod_base = OTHER
                    note = 2'-O-methyladenosine-3'-phosphate
modified_base       5
                    mod_base = OTHER
                    note = 2'-O-methyladenosine-3'-phosphate
modified_base       6
                    mod_base = OTHER
                    note = 2'-deoxy-2'-fluoroguanosine-3'-phosphate
modified_base       7
                    mod_base = OTHER
                    note = 2'-O-methylcytidine-3'-phosphate
modified_base       8
                    mod_base = OTHER
                    note = 2'-deoxy-2'-fluoroadenosine-3'-phosphate
modified_base       9
                    mod_base = OTHER
                    note = 2'-deoxy-2'-fluorocytidine-3'-phosphate
modified_base       10
                    mod_base = OTHER
                    note = 2'-O-methyluridine-3'-phosphate
modified_base       11
                    mod_base = OTHER
                    note = 2'-O-methyluridine-3'-phosphate
modified_base       12
                    mod_base = OTHER
                    note = 2'-O-methyluridine-3'-phosphate
modified_base       13
                    mod_base = OTHER
                    note = 2'-O-methyladenosine-3'-phosphate
modified_base       14
                    mod_base = OTHER
                    note = 2'-deoxy-2'-fluorouridine-3'-phosphate
modified_base       15
                    mod_base = OTHER
                    note = 2'-O-methyluridine-3'-phosphate
modified_base       16
                    mod_base = OTHER
                    note = 2'-deoxy-2'-fluoroguanosine-3'-phosphate
modified_base       17
                    mod_base = OTHER
                    note = 2'-O-methyladenosine-3'-phosphate
modified_base       18
                    mod_base = OTHER
                    note = 2'-O-methylguanosine-3'-phosphate
modified_base       19
                    mod_base = OTHER
                    note = 2'-O-hexadecyl-uridine-3'-phosphate
modified_base       20
                    mod_base = OTHER
                    note = 2'-O-methyluridine-3'-phosphate
modified_base       21
                    mod_base = OTHER
                    note = 2'-O-methylcytidine-3'-phosphorothioate
modified_base       22
```

|                | mod_base = OTHER |
|                | note = 2'-O-methylcytidine-3'-phosphorothioate |
| modified_base  | 23 |
|                | mod_base = OTHER |
|                | note = 2'-O-methyluridine |

SEQUENCE: 107
tcaaagcact ttattgagtt cct        23

| SEQ ID NO: 108 | moltype = RNA  length = 21 |
| FEATURE        | Location/Qualifiers |
| source         | 1..21 |
|                | mol_type = other RNA |
|                | organism = synthetic construct |
| modified_base  | 1 |
|                | mod_base = OTHER |
|                | note = 2'-O-methylguanosine-3'-phosphorothioate |
| modified_base  | 2 |
|                | mod_base = OTHER |
|                | note = 2'-O-methyladenosine-3'-phosphorothioate |
| modified_base  | 3 |
|                | mod_base = OTHER |
|                | note = 2'-O-methyladenosine-3'-phosphate |
| modified_base  | 4 |
|                | mod_base = OTHER |
|                | note = 2'-O-methyladenosine-3'-phosphate |
| modified_base  | 5 |
|                | mod_base = OTHER |
|                | note = 2'-O-methylcytidine-3'-phosphate |
| modified_base  | 6 |
|                | mod_base = OTHER |
|                | note = 2'-O-methyluridine-3'-phosphate |
| modified_base  | 7 |
|                | mod_base = OTHER |
|                | note = 2'-deoxy-2'-fluorocytidine-3'-phosphate |
| modified_base  | 8 |
|                | mod_base = OTHER |
|                | note = 2'-O-methyladenosine-3'-phosphate |
| modified_base  | 9 |
|                | mod_base = OTHER |
|                | note = 2'-deoxy-2'-fluoroadenosine-3'-phosphate |
| modified_base  | 10 |
|                | mod_base = OTHER |
|                | note = 2'-deoxy-2'-fluorouridine-3'-phosphate |
| modified_base  | 11 |
|                | mod_base = OTHER |
|                | note = 2'-deoxy-2'-fluoroadenosine-3'-phosphate |
| modified_base  | 12 |
|                | mod_base = OTHER |
|                | note = 2'-O-methyladenosine-3'-phosphate |
| modified_base  | 13 |
|                | mod_base = OTHER |
|                | note = 2'-O-methyladenosine-3'-phosphate |
| modified_base  | 14 |
|                | mod_base = OTHER |
|                | note = 2'-O-methylguanosine-3'-phosphate |
| modified_base  | 15 |
|                | mod_base = OTHER |
|                | note = 2'-O-methyluridine-3'-phosphate |
| modified_base  | 16 |
|                | mod_base = OTHER |
|                | note = 2'-O-methylguanosine-3'-phosphate |
| modified_base  | 17 |
|                | mod_base = OTHER |
|                | note = 2'-O-methylcytidine-3'-phosphate |
| modified_base  | 18 |
|                | mod_base = OTHER |
|                | note = 2'-O-methyluridine-3'-phosphate |
| modified_base  | 19 |
|                | mod_base = OTHER |
|                | note = 2'-O-methyluridine-3'-phosphate |
| modified_base  | 20 |
|                | mod_base = OTHER |
|                | note = 2'-O-methyluridine-3'-phosphate |
| modified_base  | 21 |
|                | mod_base = OTHER |
|                | note = 2'-O-hexadecyl-adenosine-3'-phosphate |
|                | ((2S,4R)-1-[29-[[2-(acetylamino)-2-deoxy-beta-D-galactopyra |
|                | nosyl]oxy]-14,14-bis[[3-[[3-[[5-[[2-(acetylamino)-2-deoxy-b |
|                | eta-D-galactopyranosyl]oxy]-1-oxopentyl]amino]propyl]amino] |

-3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 108
gaaactcaat aaagtgcttt a                                                     21

SEQ ID NO: 109          moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylguanosine-3'-phosphate
modified_base           18
                        mod_base = OTHER
                        note = 2'-O-hexadecyl-uridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methyluridine-3'-phosphorothioate
modified_base           23
                        mod_base = OTHER
                        note = 2'-O-methylguanosine

```
SEQUENCE: 109
taaagcactt tattgagttt ctg                                              23

SEQ ID NO: 110           moltype = RNA   length = 21
FEATURE                  Location/Qualifiers
source                   1..21
                         mol_type = other RNA
                         organism = synthetic construct
modified_base            1
                         mod_base = OTHER
                         note = 2'-O-methylguanosine-3'-phosphorothioate
modified_base            2
                         mod_base = OTHER
                         note = 2'-O-methyladenosine-3'-phosphorothioate
modified_base            3
                         mod_base = OTHER
                         note = 2'-O-methyladenosine-3'-phosphate
modified_base            4
                         mod_base = OTHER
                         note = 2'-O-methyladenosine-3'-phosphate
modified_base            5
                         mod_base = OTHER
                         note = 2'-O-methylcytidine-3'-phosphate
modified_base            6
                         mod_base = OTHER
                         note = 2'-O-methyluridine-3'-phosphate
modified_base            7
                         mod_base = OTHER
                         note = 2'-deoxy-2'-fluorocytidine-3'-phosphate
modified_base            8
                         mod_base = OTHER
                         note = 2'-O-methyladenosine-3'-phosphate
modified_base            9
                         mod_base = OTHER
                         note = 2'-deoxy-2'-fluoroadenosine-3'-phosphate
modified_base            10
                         mod_base = OTHER
                         note = 2'-deoxy-2'-fluorouridine-3'-phosphate
modified_base            11
                         mod_base = OTHER
                         note = 2'-deoxy-2'-fluoroadenosine-3'-phosphate
modified_base            12
                         mod_base = OTHER
                         note = 2'-O-hexadecyl-adenosine-3'-phosphate
modified_base            13
                         mod_base = OTHER
                         note = 2'-O-methyladenosine-3'-phosphate
modified_base            14
                         mod_base = OTHER
                         note = 2'-O-methylguanosine-3'-phosphate
modified_base            15
                         mod_base = OTHER
                         note = 2'-O-methyluridine-3'-phosphate
modified_base            16
                         mod_base = OTHER
                         note = 2'-O-methylguanosine-3'-phosphate
modified_base            17
                         mod_base = OTHER
                         note = 2'-O-methylcytidine-3'-phosphate
modified_base            18
                         mod_base = OTHER
                         note = 2'-O-methyluridine-3'-phosphate
modified_base            19
                         mod_base = OTHER
                         note = 2'-O-methyluridine-3'-phosphate
modified_base            20
                         mod_base = OTHER
                         note = 2'-O-methyluridine-3'-phosphate
modified_base            21
                         mod_base = OTHER
                         note = 2'-O-methyladenosine-3'-phosphate
                         ((2S,4R)-1-[29-[[2-(acetylamino)-2-deoxy-beta-D-galactopyra
                         nosyl]oxy]-14,14-bis[[3-[[3-[[5-[[2-(acetylamino)-2-deoxy-b
                         eta-D-galactopyranosyl]oxy]-1-oxopentyl]amino]propyl]amino]
                         -3-oxopropoxy]methyl]-1,12,19,25-tetraoxo-16-oxa-13,20,24-t
                         riazanonacos-1-yl]-4-hydroxy-2-pyrrolidinyl)methyl ester
SEQUENCE: 110
gaaactcaat aaagtgcttt a                                                21
```

-continued

```
SEQ ID NO: 111            moltype = RNA   length = 23
FEATURE                   Location/Qualifiers
source                    1..23
                          mol_type = other RNA
                          organism = synthetic construct
modified_base             1
                          mod_base = OTHER
                          note = 2'-O-methyluridine-3'-phosphorothioate
modified_base             2
                          mod_base = OTHER
                          note = 2'-deoxy-2'-fluorocytidine-3'-phosphorothioate
modified_base             3
                          mod_base = OTHER
                          note = 2'-O-methyladenosine-3'-phosphate
modified_base             4
                          mod_base = OTHER
                          note = 2'-O-methyladenosine-3'-phosphate
modified_base             5
                          mod_base = OTHER
                          note = 2'-O-methyladenosine-3'-phosphate
modified_base             6
                          mod_base = OTHER
                          note = 2'-deoxy-2'-fluoroguanosine-3'-phosphate
modified_base             7
                          mod_base = OTHER
                          note = 2'-O-methylcytidine-3'-phosphate
modified_base             8
                          mod_base = OTHER
                          note = 2'-deoxy-2'-fluoroadenosine-3'-phosphate
modified_base             9
                          mod_base = OTHER
                          note = 2'-deoxy-2'-fluorocytidine-3'-phosphate
modified_base             10
                          mod_base = OTHER
                          note = 2'-O-methyluridine-3'-phosphate
modified_base             11
                          mod_base = OTHER
                          note = 2'-O-methyluridine-3'-phosphate
modified_base             12
                          mod_base = OTHER
                          note = 2'-O-methyluridine-3'-phosphate
modified_base             13
                          mod_base = OTHER
                          note = 2'-O-methyladenosine-3'-phosphate
modified_base             14
                          mod_base = OTHER
                          note = 2'-deoxy-2'-fluorouridine-3'-phosphate
modified_base             15
                          mod_base = OTHER
                          note = 2'-O-methyluridine-3'-phosphate
modified_base             16
                          mod_base = OTHER
                          note = 2'-deoxy-2'-fluoroguanosine-3'-phosphate
modified_base             17
                          mod_base = OTHER
                          note = 2'-O-methyladenosine-3'-phosphate
modified_base             18
                          mod_base = OTHER
                          note = 2'-O-methylguanosine-3'-phosphate
modified_base             19
                          mod_base = OTHER
                          note = 2'-O-methyluridine-3'-phosphate
modified_base             20
                          mod_base = OTHER
                          note = 2'-O-hexadecyl-uridine-3'-phosphate
modified_base             21
                          mod_base = OTHER
                          note = 2'-O-methylcytidine-3'-phosphorothioate
modified_base             22
                          mod_base = OTHER
                          note = 2'-O-methylcytidine-3'-phosphorothioate
modified_base             23
                          mod_base = OTHER
                          note = 2'-O-methyluridine
SEQUENCE: 111
tcaaagcact ttattgagtt cct                                            23

SEQ ID NO: 112            moltype = RNA   length = 22
FEATURE                   Location/Qualifiers
```

| | |
|---|---|
| source | 1..22<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-hexadecyl-cytidine-3'-phosphate |
| modified_base | 6<br>mod_base = OTHER<br>note = 2'-O-methylcytidine-3'-phosphate |
| modified_base | 7<br>mod_base = OTHER<br>note = 2'-O-methyluridine-3'-phosphate |
| modified_base | 8<br>mod_base = OTHER<br>note = 2'-deoxy-2'-fluorocytidine-3'-phosphate |
| modified_base | 9<br>mod_base = OTHER<br>note = 2'-O-methyladenosine-3'-phosphate |
| modified_base | 10<br>mod_base = OTHER<br>note = 2'-deoxy-2'-fluoroadenosine-3'-phosphate |
| modified_base | 11<br>mod_base = OTHER<br>note = 2'-deoxy-2'-fluorouridine-3'-phosphate |
| modified_base | 12<br>mod_base = OTHER<br>note = 2'-deoxy-2'-fluoroadenosine-3'-phosphate |
| modified_base | 13<br>mod_base = OTHER<br>note = 2'-O-methyladenosine-3'-phosphate |
| modified_base | 14<br>mod_base = OTHER<br>note = 2'-O-methyladenosine-3'-phosphate |
| modified_base | 15<br>mod_base = OTHER<br>note = 2'-O-methylguanosine-3'-phosphate |
| modified_base | 16<br>mod_base = OTHER<br>note = 2'-O-methyluridine-3'-phosphate |
| modified_base | 17<br>mod_base = OTHER<br>note = 2'-O-methylguanosine-3'-phosphate |
| modified_base | 18<br>mod_base = OTHER<br>note = 2'-O-methylcytidine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methyluridine-3'-phosphate |
| modified_base | 22<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 112 | | gaaacctcaa taaagtgctt ta                                              22

| | |
|---|---|
| SEQ ID NO: 113<br>FEATURE | moltype = RNA   length = 21<br>Location/Qualifiers |

| | | |
|---|---|---|
| source | | 1..21<br>mol_type = other RNA<br>organism = synthetic construct |
| modified_base | | 1<br>mod_base = OTHER<br>note = 2'-O-methylguanosine-3'-phosphorothioate |
| modified_base | | 2<br>mod_base = OTHER<br>note = 2'-O-methyladenosine-3'-phosphorothioate |
| modified_base | | 3<br>mod_base = OTHER<br>note = 2'-O-methyladenosine-3'-phosphate |
| modified_base | | 4<br>mod_base = OTHER<br>note = 2'-O-methylcytidine-3'-phosphate |
| modified_base | | 5<br>mod_base = OTHER<br>note = 2'-O-methyluridine-3'-phosphate |
| modified_base | | 6<br>mod_base = OTHER<br>note = 2'-O-methylcytidine-3'-phosphate |
| modified_base | | 7<br>mod_base = OTHER<br>note = 2'-deoxy-2'-fluoroadenosine-3'-phosphate |
| modified_base | | 8<br>mod_base = OTHER<br>note = 2'-O-methyladenosine-3'-phosphate |
| modified_base | | 9<br>mod_base = OTHER<br>note = 2'-deoxy-2'-fluorouridine-3'-phosphate |
| modified_base | | 10<br>mod_base = OTHER<br>note = 2'-deoxy-2'-fluoroadenosine-3'-phosphate |
| modified_base | | 11<br>mod_base = OTHER<br>note = 2'-deoxy-2'-fluoroadenosine-3'-phosphate |
| modified_base | | 12<br>mod_base = OTHER<br>note = 2'-O-methyladenosine-3'-phosphate |
| modified_base | | 13<br>mod_base = OTHER<br>note = 2'-O-methylguanosine-3'-phosphate |
| modified_base | | 14<br>mod_base = OTHER<br>note = 2'-O-methyluridine-3'-phosphate |
| modified_base | | 15<br>mod_base = OTHER<br>note = 2'-O-methylguanosine-3'-phosphate |
| modified_base | | 16<br>mod_base = OTHER<br>note = 2'-O-methylcytidine-3'-phosphate |
| modified_base | | 17<br>mod_base = OTHER<br>note = 2'-O-methyluridine-3'-phosphate |
| modified_base | | 18<br>mod_base = OTHER<br>note = 2'-O-methyluridine-3'-phosphate |
| modified_base | | 19<br>mod_base = OTHER<br>note = 2'-O-hexadecyl-uridine-3'-phosphate |
| modified_base | | 20<br>mod_base = OTHER<br>note = 2'-O-methylguanosine-3'-phosphate |
| modified_base | | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 113 | | |
| gaactcaata aagtgctttg a | | 21 |
| | | |
| SEQ ID NO: 114 | | moltype = RNA   length = 21 |
| FEATURE | | Location/Qualifiers |
| source | | 1..21<br>mol_type = other RNA<br>organism = synthetic construct |

| | |
|---|---|
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methylcytidine-3'-phosphate |
| modified_base | 5<br>mod_base = OTHER<br>note = 2'-O-methyluridine-3'-phosphate |
| modified_base | 6<br>mod_base = OTHER<br>note = 2'-O-methylcytidine-3'-phosphate |
| modified_base | 7<br>mod_base = OTHER<br>note = 2'-deoxy-2'-fluoroadenosine-3'-phosphate |
| modified_base | 8<br>mod_base = OTHER<br>note = 2'-O-methyladenosine-3'-phosphate |
| modified_base | 9<br>mod_base = OTHER<br>note = 2'-deoxy-2'-fluorouridine-3'-phosphate |
| modified_base | 10<br>mod_base = OTHER<br>note = 2'-deoxy-2'-fluoroadenosine-3'-phosphate |
| modified_base | 11<br>mod_base = OTHER<br>note = 2'-deoxy-2'-fluoroadenosine-3'-phosphate |
| modified_base | 12<br>mod_base = OTHER<br>note = 2'-O-methyladenosine-3'-phosphate |
| modified_base | 13<br>mod_base = OTHER<br>note = 2'-O-methylguanosine-3'-phosphate |
| modified_base | 14<br>mod_base = OTHER<br>note = 2'-O-methyluridine-3'-phosphate |
| modified_base | 15<br>mod_base = OTHER<br>note = 2'-O-methylguanosine-3'-phosphate |
| modified_base | 16<br>mod_base = OTHER<br>note = 2'-O-methylcytidine-3'-phosphate |
| modified_base | 17<br>mod_base = OTHER<br>note = 2'-O-methyluridine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-hexadecyl-guanosine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 114 | |
| gaactcaata aagtgctttg a | 21 |
| SEQ ID NO: 115<br>FEATURE<br>source | moltype = RNA length = 21<br>Location/Qualifiers<br>1..21<br>mol_type = other RNA<br>organism = synthetic construct |
| modified_base | 1<br>mod_base = OTHER<br>note = 2'-O-hexadecyl-guanosine-3'-phosphorothioate |

| | |
|---|---|
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylcytidine-3'-phosphate |
| modified_base | 6<br>mod_base = OTHER<br>note = 2'-O-methyluridine-3'-phosphate |
| modified_base | 7<br>mod_base = OTHER<br>note = 2'-deoxy-2'-fluorocytidine-3'-phosphate |
| modified_base | 8<br>mod_base = OTHER<br>note = 2'-O-methyladenosine-3'-phosphate |
| modified_base | 9<br>mod_base = OTHER<br>note = 2'-deoxy-2'-fluoroadenosine-3'-phosphate |
| modified_base | 10<br>mod_base = OTHER<br>note = 2'-deoxy-2'-fluorouridine-3'-phosphate |
| modified_base | 11<br>mod_base = OTHER<br>note = 2'-deoxy-2'-fluoroadenosine-3'-phosphate |
| modified_base | 12<br>mod_base = OTHER<br>note = 2'-O-methyladenosine-3'-phosphate |
| modified_base | 13<br>mod_base = OTHER<br>note = 2'-O-methyladenosine-3'-phosphate |
| modified_base | 14<br>mod_base = OTHER<br>note = 2'-O-methylguanosine-3'-phosphate |
| modified_base | 15<br>mod_base = OTHER<br>note = 2'-O-methyluridine-3'-phosphate |
| modified_base | 16<br>mod_base = OTHER<br>note = 2'-O-methylguanosine-3'-phosphate |
| modified_base | 17<br>mod_base = OTHER<br>note = 2'-O-methylcytidine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 115 | |
| gaaactcaat aaagtgcttt a | 21 |
| | |
| SEQ ID NO: 116 | moltype = RNA length = 21 |
| FEATURE | Location/Qualifiers |
| source | 1..21<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |

| | | |
|---|---|---|
| modified_base | 3 | |
| | mod_base = OTHER | |
| | note = 2'-O-methyladenosine-3'-phosphate | |
| modified_base | 4 | |
| | mod_base = OTHER | |
| | note = 2'-O-methylcytidine-3'-phosphate | |
| modified_base | 5 | |
| | mod_base = OTHER | |
| | note = 2'-O-methyluridine-3'-phosphate | |
| modified_base | 6 | |
| | mod_base = OTHER | |
| | note = 2'-O-methylcytidine-3'-phosphate | |
| modified_base | 7 | |
| | mod_base = OTHER | |
| | note = 2'-deoxy-2'-fluoroadenosine-3'-phosphate | |
| modified_base | 8 | |
| | mod_base = OTHER | |
| | note = 2'-O-methyladenosine-3'-phosphate | |
| modified_base | 9 | |
| | mod_base = OTHER | |
| | note = 2'-deoxy-2'-fluorouridine-3'-phosphate | |
| modified_base | 10 | |
| | mod_base = OTHER | |
| | note = 2'-deoxy-2'-fluoroadenosine-3'-phosphate | |
| modified_base | 11 | |
| | mod_base = OTHER | |
| | note = 2'-deoxy-2'-fluoroadenosine-3'-phosphate | |
| modified_base | 12 | |
| | mod_base = OTHER | |
| | note = 2'-O-hexadecyl-adenosine-3'-phosphate | |
| modified_base | 13 | |
| | mod_base = OTHER | |
| | note = 2'-O-methylguanosine-3'-phosphate | |
| modified_base | 14 | |
| | mod_base = OTHER | |
| | note = 2'-O-methyluridine-3'-phosphate | |
| modified_base | 15 | |
| | mod_base = OTHER | |
| | note = 2'-O-methylguanosine-3'-phosphate | |
| modified_base | 16 | |
| | mod_base = OTHER | |
| | note = 2'-O-methylcytidine-3'-phosphate | |
| modified_base | 17 | |
| | mod_base = OTHER | |
| | note = 2'-O-methyluridine-3'-phosphate | |
| modified_base | 18 | |
| | mod_base = OTHER | |
| | note = 2'-O-methyluridine-3'-phosphate | |
| modified_base | 19 | |
| | mod_base = OTHER | |
| | note = 2'-O-methyluridine-3'-phosphate | |
| modified_base | 20 | |
| | mod_base = OTHER | |
| | note = 2'-O-methylguanosine-3'-phosphate | |
| modified_base | 21 | |
| | mod_base = OTHER | |
| | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester | |
| SEQUENCE: 116 | | |
| gaactcaata aagtgctttg a | | 21 |
| | | |
| SEQ ID NO: 117 | moltype = RNA  length = 23 | |
| FEATURE | Location/Qualifiers | |
| source | 1..23 | |
| | mol_type = other RNA | |
| | organism = synthetic construct | |
| modified_base | 1 | |
| | mod_base = OTHER | |
| | note = 2'-O-methyluridine-3'-phosphorothioate | |
| modified_base | 2 | |
| | mod_base = OTHER | |
| | note = 2'-deoxy-2'-fluorocytidine-3'-phosphorothioate | |
| modified_base | 3 | |
| | mod_base = OTHER | |
| | note = 2'-O-methyladenosine-3'-phosphate | |

| | | |
|---|---|---|
| modified_base | 4 | |
| | mod_base = OTHER | |
| | note = 2'-O-methyladenosine-3'-phosphate | |
| modified_base | 5 | |
| | mod_base = OTHER | |
| | note = 2'-O-hexadecyl-adenosine-3'-phosphate | |
| modified_base | 6 | |
| | mod_base = OTHER | |
| | note = 2'-deoxy-2'-fluoroguanosine-3'-phosphate | |
| modified_base | 7 | |
| | mod_base = OTHER | |
| | note = 2'-O-methylcytidine-3'-phosphate | |
| modified_base | 8 | |
| | mod_base = OTHER | |
| | note = 2'-deoxy-2'-fluoroadenosine-3'-phosphate | |
| modified_base | 9 | |
| | mod_base = OTHER | |
| | note = 2'-deoxy-2'-fluorocytidine-3'-phosphate | |
| modified_base | 10 | |
| | mod_base = OTHER | |
| | note = 2'-O-methyluridine-3'-phosphate | |
| modified_base | 11 | |
| | mod_base = OTHER | |
| | note = 2'-O-methyluridine-3'-phosphate | |
| modified_base | 12 | |
| | mod_base = OTHER | |
| | note = 2'-O-methyluridine-3'-phosphate | |
| modified_base | 13 | |
| | mod_base = OTHER | |
| | note = 2'-O-methyladenosine-3'-phosphate | |
| modified_base | 14 | |
| | mod_base = OTHER | |
| | note = 2'-deoxy-2'-fluorouridine-3'-phosphate | |
| modified_base | 15 | |
| | mod_base = OTHER | |
| | note = 2'-O-methyluridine-3'-phosphate | |
| modified_base | 16 | |
| | mod_base = OTHER | |
| | note = 2'-deoxy-2'-fluoroguanosine-3'-phosphate | |
| modified_base | 17 | |
| | mod_base = OTHER | |
| | note = 2'-O-methyladenosine-3'-phosphate | |
| modified_base | 18 | |
| | mod_base = OTHER | |
| | note = 2'-O-methylguanosine-3'-phosphate | |
| modified_base | 19 | |
| | mod_base = OTHER | |
| | note = 2'-O-methyluridine-3'-phosphate | |
| modified_base | 20 | |
| | mod_base = OTHER | |
| | note = 2'-O-methyluridine-3'-phosphate | |
| modified_base | 21 | |
| | mod_base = OTHER | |
| | note = 2'-O-methylcytidine-3'-phosphorothioate | |
| modified_base | 22 | |
| | mod_base = OTHER | |
| | note = 2'-O-methylcytidine-3'-phosphorothioate | |
| modified_base | 23 | |
| | mod_base = OTHER | |
| | note = 2'-O-methyluridine | |
| SEQUENCE: 117 | | |
| tcaaagcact ttattgagtt cct | | 23 |
| | | |
| SEQ ID NO: 118 | moltype = RNA  length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-O-methylguanosine-3'-phosphorothioate | |
| modified_base | 2 | |
| | mod_base = OTHER | |
| | note = 2'-O-methyladenosine-3'-phosphorothioate | |
| modified_base | 3 | |
| | mod_base = OTHER | |
| | note = 2'-O-methyladenosine-3'-phosphate | |
| modified_base | 4 | |
| | mod_base = OTHER | |

|               | note = 2'-O-methylcytidine-3'-phosphate |
| modified_base | 5 |
|               | mod_base = OTHER |
|               | note = 2'-O-methyluridine-3'-phosphate |
| modified_base | 6 |
|               | mod_base = OTHER |
|               | note = 2'-O-methylcytidine-3'-phosphate |
| modified_base | 7 |
|               | mod_base = OTHER |
|               | note = 2'-deoxy-2'-fluoroadenosine-3'-phosphate |
| modified_base | 8 |
|               | mod_base = OTHER |
|               | note = 2'-O-methyladenosine-3'-phosphate |
| modified_base | 9 |
|               | mod_base = OTHER |
|               | note = 2'-deoxy-2'-fluorouridine-3'-phosphate |
| modified_base | 10 |
|               | mod_base = OTHER |
|               | note = 2'-deoxy-2'-fluoroadenosine-3'-phosphate |
| modified_base | 11 |
|               | mod_base = OTHER |
|               | note = 2'-deoxy-2'-fluoroadenosine-3'-phosphate |
| modified_base | 12 |
|               | mod_base = OTHER |
|               | note = 2'-O-methyladenosine-3'-phosphate |
| modified_base | 13 |
|               | mod_base = OTHER |
|               | note = 2'-O-methylguanosine-3'-phosphate |
| modified_base | 14 |
|               | mod_base = OTHER |
|               | note = 2'-O-methyluridine-3'-phosphate |
| modified_base | 15 |
|               | mod_base = OTHER |
|               | note = 2'-O-methylguanosine-3'-phosphate |
| modified_base | 16 |
|               | mod_base = OTHER |
|               | note = 2'-O-methylcytidine-3'-phosphate |
| modified_base | 17 |
|               | mod_base = OTHER |
|               | note = 2'-O-methyluridine-3'-phosphate |
| modified_base | 18 |
|               | mod_base = OTHER |
|               | note = 2'-O-hexadecyl-uridine-3'-phosphate |
| modified_base | 19 |
|               | mod_base = OTHER |
|               | note = 2'-O-methyluridine-3'-phosphate |
| modified_base | 20 |
|               | mod_base = OTHER |
|               | note = 2'-O-methylguanosine-3'-phosphate |
| modified_base | 21 |
|               | mod_base = OTHER |
|               | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 118 |  | gaactcaata aagtgctttg a                                                21

| SEQ ID NO: 119 | moltype = RNA  length = 23 |
| FEATURE       | Location/Qualifiers |
| source        | 1..23 |
|               | mol_type = other RNA |
|               | organism = synthetic construct |
| modified_base | 1 |
|               | mod_base = OTHER |
|               | note = 2'-O-methyluridine-3'-phosphorothioate |
| modified_base | 2 |
|               | mod_base = OTHER |
|               | note = 2'-deoxy-2'-fluorocytidine-3'-phosphorothioate |
| modified_base | 3 |
|               | mod_base = OTHER |
|               | note = 2'-O-methyladenosine-3'-phosphate |
| modified_base | 4 |
|               | mod_base = OTHER |
|               | note = 2'-O-methyladenosine-3'-phosphate |
| modified_base | 5 |
|               | mod_base = OTHER |

```
                        note = 2'-O-methyladenosine-3'-phosphate
modified_base           6
                        mod_base = OTHER
                        note = 2'-deoxy-2'-fluoroguanosine-3'-phosphate
modified_base           7
                        mod_base = OTHER
                        note = 2'-O-methylcytidine-3'-phosphate
modified_base           8
                        mod_base = OTHER
                        note = 2'-deoxy-2'-fluoroadenosine-3'-phosphate
modified_base           9
                        mod_base = OTHER
                        note = 2'-deoxy-2'-fluorocytidine-3'-phosphate
modified_base           10
                        mod_base = OTHER
                        note = 2'-O-methyluridine-3'-phosphate
modified_base           11
                        mod_base = OTHER
                        note = 2'-O-hexadecyl-uridine-3'-phosphate
modified_base           12
                        mod_base = OTHER
                        note = 2'-O-methyluridine-3'-phosphate
modified_base           13
                        mod_base = OTHER
                        note = 2'-O-methyladenosine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methyluridine-3'-phosphate
modified_base           16
                        mod_base = OTHER
                        note = 2'-deoxy-2'-fluoroguanosine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methyluridine
SEQUENCE: 119
tcaaagcact ttattgagtt cct                                            23

SEQ ID NO: 120          moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluorocytidine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methyladenosine-3'-phosphate
modified_base           6
```

|  |  |
|---|---|
| | mod_base = OTHER |
| | note = 2'-deoxy-2'-fluoroguanosine-3'-phosphate |
| modified_base | 7 |
| | mod_base = OTHER |
| | note = 2'-O-methylcytidine-3'-phosphate |
| modified_base | 8 |
| | mod_base = OTHER |
| | note = 2'-deoxy-2'-fluoroadenosine-3'-phosphate |
| modified_base | 9 |
| | mod_base = OTHER |
| | note = 2'-deoxy-2'-fluorocytidine-3'-phosphate |
| modified_base | 10 |
| | mod_base = OTHER |
| | note = 2'-O-methyluridine-3'-phosphate |
| modified_base | 11 |
| | mod_base = OTHER |
| | note = 2'-O-methyluridine-3'-phosphate |
| modified_base | 12 |
| | mod_base = OTHER |
| | note = 2'-O-methyluridine-3'-phosphate |
| modified_base | 13 |
| | mod_base = OTHER |
| | note = 2'-O-methyladenosine-3'-phosphate |
| modified_base | 14 |
| | mod_base = OTHER |
| | note = 2'-deoxy-2'-fluorouridine-3'-phosphate |
| modified_base | 15 |
| | mod_base = OTHER |
| | note = 2'-O-methyluridine-3'-phosphate |
| modified_base | 16 |
| | mod_base = OTHER |
| | note = 2'-deoxy-2'-fluoroguanosine-3'-phosphate |
| modified_base | 17 |
| | mod_base = OTHER |
| | note = 2'-O-methyladenosine-3'-phosphate |
| modified_base | 18 |
| | mod_base = OTHER |
| | note = 2'-O-methylguanosine-3'-phosphate |
| modified_base | 19 |
| | mod_base = OTHER |
| | note = 2'-O-methyluridine-3'-phosphate |
| modified_base | 20 |
| | mod_base = OTHER |
| | note = 2'-O-methyluridine-3'-phosphate |
| modified_base | 21 |
| | mod_base = OTHER |
| | note = 2'-O-methylcytidine-3'-phosphorothioate |
| modified_base | 22 |
| | mod_base = OTHER |
| | note = 2'-O-methylcytidine-3'-phosphorothioate |
| modified_base | 23 |
| | mod_base = OTHER |
| | note = 2'-O-hexadecyl-uridine |
| SEQUENCE: 120 | |
| tcaaagcact ttattgagtt cct | 23 |
| | |
| SEQ ID NO: 121 | moltype = RNA   length = 23 |
| FEATURE | Location/Qualifiers |
| source | 1..23 |
| | mol_type = other RNA |
| | organism = synthetic construct |
| modified_base | 1 |
| | mod_base = OTHER |
| | note = 2'-O-methyluridine-3'-phosphorothioate |
| modified_base | 2 |
| | mod_base = OTHER |
| | note = 2'-deoxy-2'-fluoroadenosine-3'-phosphorothioate |
| modified_base | 3 |
| | mod_base = OTHER |
| | note = 2'-O-methyladenosine-3'-phosphate |
| modified_base | 4 |
| | mod_base = OTHER |
| | note = 2'-O-hexadecyl-adenosine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-deoxy-2'-fluorocytidine-3'-phosphate |

```
modified_base      7
                   mod_base = OTHER
                   note = 2'-O-methyladenosine-3'-phosphate
modified_base      8
                   mod_base = OTHER
                   note = 2'-O-methylcytidine-3'-phosphate
modified_base      9
                   mod_base = OTHER
                   note = 2'-O-methyluridine-3'-phosphate
modified_base      10
                   mod_base = OTHER
                   note = 2'-O-methyluridine-3'-phosphate
modified_base      11
                   mod_base = OTHER
                   note = 2'-O-methyluridine-3'-phosphate
modified_base      12
                   mod_base = OTHER
                   note = 2'-O-methyladenosine-3'-phosphate
modified_base      13
                   mod_base = OTHER
                   note = 2'-O-methyluridine-3'-phosphate
modified_base      14
                   mod_base = OTHER
                   note = 2'-deoxy-2'-fluorouridine-3'-phosphate
modified_base      15
                   mod_base = OTHER
                   note = 2'-O-methylguanosine-3'-phosphate
modified_base      16
                   mod_base = OTHER
                   note = 2'-deoxy-2'-fluoroadenosine-3'-phosphate
modified_base      17
                   mod_base = OTHER
                   note = 2'-O-methylguanosine-3'-phosphate
modified_base      18
                   mod_base = OTHER
                   note = 2'-O-methyluridine-3'-phosphate
modified_base      19
                   mod_base = OTHER
                   note = 2'-O-methyluridine-3'-phosphate
modified_base      20
                   mod_base = OTHER
                   note = 2'-O-methyluridine-3'-phosphate
modified_base      21
                   mod_base = OTHER
                   note = 2'-O-methylcytidine-3'-phosphorothioate
modified_base      22
                   mod_base = OTHER
                   note = 2'-O-methyluridine-3'-phosphorothioate
modified_base      23
                   mod_base = OTHER
                   note = 2'-O-methylguanosine
SEQUENCE: 121
taaagcactt tattgagttt ctg                                            23

SEQ ID NO: 122     moltype = RNA   length = 23
FEATURE            Location/Qualifiers
source             1..23
                   mol_type = other RNA
                   organism = synthetic construct
modified_base      1
                   mod_base = OTHER
                   note = 2'-O-methyluridine-3'-phosphorothioate
modified_base      2
                   mod_base = OTHER
                   note = 2'-deoxy-2'-fluorocytidine-3'-phosphorothioate
modified_base      3
                   mod_base = OTHER
                   note = 2'-O-methyladenosine-3'-phosphate
modified_base      4
                   mod_base = OTHER
                   note = 2'-O-methyladenosine-3'-phosphate
modified_base      5
                   mod_base = OTHER
                   note = 2'-O-methyladenosine-3'-phosphate
modified_base      6
                   mod_base = OTHER
                   note = 2'-deoxy-2'-fluoroguanosine-3'-phosphate
modified_base      7
                   mod_base = OTHER
```

|  |  |
|---|---|
| modified_base | 8 |
|  | mod_base = OTHER |
|  | note = 2'-O-methylcytidine-3'-phosphate |
| modified_base | 9 |
|  | mod_base = OTHER |
|  | note = 2'-deoxy-2'-fluoroadenosine-3'-phosphate |
| modified_base | 10 |
|  | mod_base = OTHER |
|  | note = 2'-deoxy-2'-fluorocytidine-3'-phosphate |
| modified_base | 11 |
|  | mod_base = OTHER |
|  | note = 2'-O-methyluridine-3'-phosphate |
| modified_base | 12 |
|  | mod_base = OTHER |
|  | note = 2'-O-methyluridine-3'-phosphate |
| modified_base | 13 |
|  | mod_base = OTHER |
|  | note = 2'-O-methyluridine-3'-phosphate |
| modified_base | 14 |
|  | mod_base = OTHER |
|  | note = 2'-O-methyladenosine-3'-phosphate |
| modified_base | 15 |
|  | mod_base = OTHER |
|  | note = 2'-deoxy-2'-fluorouridine-3'-phosphate |
| modified_base | 16 |
|  | mod_base = OTHER |
|  | note = 2'-O-methyluridine-3'-phosphate |
| modified_base | 17 |
|  | mod_base = OTHER |
|  | note = 2'-deoxy-2'-fluoroguanosine-3'-phosphate |
| modified_base | 18 |
|  | mod_base = OTHER |
|  | note = 2'-O-methyladenosine-3'-phosphate |
| modified_base | 19 |
|  | mod_base = OTHER |
|  | note = 2'-O-methylguanosine-3'-phosphate |
| modified_base | 20 |
|  | mod_base = OTHER |
|  | note = 2'-O-methyluridine-3'-phosphate |
| modified_base | 21 |
|  | mod_base = OTHER |
|  | note = 2'-O-methyluridine-3'-phosphate |
| modified_base | 22 |
|  | mod_base = OTHER |
|  | note = 2'-O-methylcytidine-3'-phosphorothioate |
| modified_base | 23 |
|  | mod_base = OTHER |
|  | note = 2'-O-hexadecyl-cytidine-3'-phosphorothioate |
|  | mod_base = OTHER |
|  | note = 2'-O-methyluridine |
| SEQUENCE: 122 |  |
| tcaaagcact ttattgagtt cct | 23 |
|  |  |
| SEQ ID NO: 123 | moltype = RNA length = 23 |
| FEATURE | Location/Qualifiers |
| source | 1..23 |
|  | mol_type = other RNA |
|  | organism = synthetic construct |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-deoxy-2'-fluorocytidine-3'-phosphorothioate |
| modified_base | 3 |
|  | mod_base = OTHER |
|  | note = 2'-O-methyladenosine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methyladenosine-3'-phosphate |
| modified_base | 6 |
|  | mod_base = OTHER |
|  | note = 2'-deoxy-2'-fluoroguanosine-3'-phosphate |
| modified_base | 7 |
|  | mod_base = OTHER |
|  | note = 2'-O-methylcytidine-3'-phosphate |
| modified_base | 8 |

|  | mod_base = OTHER |
|  | note = 2'-deoxy-2'-fluoroadenosine-3'-phosphate |
| modified_base | 9 |
|  | mod_base = OTHER |
|  | note = 2'-deoxy-2'-fluorocytidine-3'-phosphate |
| modified_base | 10 |
|  | mod_base = OTHER |
|  | note = 2'-O-methyluridine-3'-phosphate |
| modified_base | 11 |
|  | mod_base = OTHER |
|  | note = 2'-O-methyluridine-3'-phosphate |
| modified_base | 12 |
|  | mod_base = OTHER |
|  | note = 2'-O-methyluridine-3'-phosphate |
| modified_base | 13 |
|  | mod_base = OTHER |
|  | note = 2'-O-methyladenosine-3'-phosphate |
| modified_base | 14 |
|  | mod_base = OTHER |
|  | note = 2'-deoxy-2'-fluorouridine-3'-phosphate |
| modified_base | 15 |
|  | mod_base = OTHER |
|  | note = 2'-O-methyluridine-3'-phosphate |
| modified_base | 16 |
|  | mod_base = OTHER |
|  | note = 2'-deoxy-2'-fluoroguanosine-3'-phosphate |
| modified_base | 17 |
|  | mod_base = OTHER |
|  | note = 2'-O-methyladenosine-3'-phosphate |
| modified_base | 18 |
|  | mod_base = OTHER |
|  | note = 2'-O-methylguanosine-3'-phosphate |
| modified_base | 19 |
|  | mod_base = OTHER |
|  | note = 2'-O-methyluridine-3'-phosphate |
| modified_base | 20 |
|  | mod_base = OTHER |
|  | note = 2'-O-methyluridine-3'-phosphate |
| modified_base | 21 |
|  | mod_base = OTHER |
|  | note = 2'-O-hexadecyl-cytidine-3'-phosphorothioate |
| modified_base | 22 |
|  | mod_base = OTHER |
|  | note = 2'-O-methylcytidine-3'-phosphorothioate |
| modified_base | 23 |
|  | mod_base = OTHER |
|  | note = 2'-O-methyluridine |
| SEQUENCE: 123 |  |
| tcaaagcact ttattgagtt cct | 23 |

| SEQ ID NO: 124 | moltype = RNA  length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-O-methylguanosine-3'-phosphorothioate |
| modified_base | 2 |
|  | mod_base = OTHER |
|  | note = 2'-O-methyladenosine-3'-phosphorothioate |
| modified_base | 3 |
|  | mod_base = OTHER |
|  | note = 2'-O-methyladenosine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methylcytidine-3'-phosphate |
| modified_base | 6 |
|  | mod_base = OTHER |
|  | note = 2'-O-methyluridine-3'-phosphate |
| modified_base | 7 |
|  | mod_base = OTHER |
|  | note = 2'-deoxy-2'-fluorocytidine-3'-phosphate |
| modified_base | 8 |
|  | mod_base = OTHER |
|  | note = 2'-O-methyladenosine-3'-phosphate |

| | | |
|---|---|---|
| modified_base | | 9 |
| | | mod_base = OTHER |
| | | note = 2'-O-hexadecyl-adenosine-3'-phosphate |
| modified_base | | 10 |
| | | mod_base = OTHER |
| | | note = 2'-deoxy-2'-fluorouridine-3'-phosphate |
| modified_base | | 11 |
| | | mod_base = OTHER |
| | | note = 2'-deoxy-2'-fluoroadenosine-3'-phosphate |
| modified_base | | 12 |
| | | mod_base = OTHER |
| | | note = 2'-O-methyladenosine-3'-phosphate |
| modified_base | | 13 |
| | | mod_base = OTHER |
| | | note = 2'-O-methyladenosine-3'-phosphate |
| modified_base | | 14 |
| | | mod_base = OTHER |
| | | note = 2'-O-methylguanosine-3'-phosphate |
| modified_base | | 15 |
| | | mod_base = OTHER |
| | | note = 2'-O-methyluridine-3'-phosphate |
| modified_base | | 16 |
| | | mod_base = OTHER |
| | | note = 2'-O-methylguanosine-3'-phosphate |
| modified_base | | 17 |
| | | mod_base = OTHER |
| | | note = 2'-O-methylcytidine-3'-phosphate |
| modified_base | | 18 |
| | | mod_base = OTHER |
| | | note = 2'-O-methyluridine-3'-phosphate |
| modified_base | | 19 |
| | | mod_base = OTHER |
| | | note = 2'-O-methyluridine-3'-phosphate |
| modified_base | | 20 |
| | | mod_base = OTHER |
| | | note = 2'-O-methyluridine-3'-phosphate |
| modified_base | | 21 |
| | | mod_base = OTHER |
| | | note = 2'-O-methyladenosine-3'-phosphate |
| | | ((2S,4R)-1-[29-[[2-(acetylamino)-2-deoxy-beta-D-galactopyra |
| | | nosyl]oxy]-14,14-bis[[3-[[3-[[5-[[2-(acetylamino)-2-deoxy-b |
| | | eta-D-galactopyranosyl]oxy]-1-oxopentyl]amino]propyl]amino] |
| | | -3-oxopropoxy]methyl]-1,12,19,25-tetraoxo-16-oxa-13,20,24-t |
| | | riazanonacos-1-yl]-4-hydroxy-2-pyrrolidinyl)methyl ester |
| SEQUENCE: 124 | | |
| gaaactcaat aaagtgcttt a | | 21 |
| | | |
| SEQ ID NO: 125 | moltype = RNA length = 21 | |
| FEATURE | Location/Qualifiers | |
| source | 1..21 | |
| | mol_type = other RNA | |
| | organism = synthetic construct | |
| modified_base | | 1 |
| | | mod_base = OTHER |
| | | note = 2'-O-methylguanosine-3'-phosphorothioate |
| modified_base | | 2 |
| | | mod_base = OTHER |
| | | note = 2'-O-methyladenosine-3'-phosphorothioate |
| modified_base | | 3 |
| | | mod_base = OTHER |
| | | note = 2'-O-methyladenosine-3'-phosphate |
| modified_base | | 4 |
| | | mod_base = OTHER |
| | | note = 2'-O-methylcytidine-3'-phosphate |
| modified_base | | 5 |
| | | mod_base = OTHER |
| | | note = 2'-O-methyluridine-3'-phosphate |
| modified_base | | 6 |
| | | mod_base = OTHER |
| | | note = 2'-O-methylcytidine-3'-phosphate |
| modified_base | | 7 |
| | | mod_base = OTHER |
| | | note = 2'-deoxy-2'-fluoroadenosine-3'-phosphate |
| modified_base | | 8 |
| | | mod_base = OTHER |
| | | note = 2'-O-methyladenosine-3'-phosphate |
| modified_base | | 9 |
| | | mod_base = OTHER |
| | | note = 2'-deoxy-2'-fluorouridine-3'-phosphate |

| | | |
|---|---|---|
| modified_base | 10 | |
| | mod_base = OTHER | |
| | note = 2'-deoxy-2'-fluoroadenosine-3'-phosphate | |
| modified_base | 11 | |
| | mod_base = OTHER | |
| | note = 2'-deoxy-2'-fluoroadenosine-3'-phosphate | |
| modified_base | 12 | |
| | mod_base = OTHER | |
| | note = 2'-O-methyladenosine-3'-phosphate | |
| modified_base | 13 | |
| | mod_base = OTHER | |
| | note = 2'-O-methylguanosine-3'-phosphate | |
| modified_base | 14 | |
| | mod_base = OTHER | |
| | note = 2'-O-methyluridine-3'-phosphate | |
| modified_base | 15 | |
| | mod_base = OTHER | |
| | note = 2'-O-methylguanosine-3'-phosphate | |
| modified_base | 16 | |
| | mod_base = OTHER | |
| | note = 2'-O-methylcytidine-3'-phosphate | |
| modified_base | 17 | |
| | mod_base = OTHER | |
| | note = 2'-O-methyluridine-3'-phosphate | |
| modified_base | 18 | |
| | mod_base = OTHER | |
| | note = 2'-O-methyluridine-3'-phosphate | |
| modified_base | 19 | |
| | mod_base = OTHER | |
| | note = 2'-O-methyluridine-3'-phosphate | |
| modified_base | 20 | |
| | mod_base = OTHER | |
| | note = 2'-O-methylguanosine-3'-phosphate | |
| modified_base | 21 | |
| | mod_base = OTHER | |
| | note = 2'-O-hexadecyl-adenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester | |
| SEQUENCE: 125 | | |
| gaactcaata aagtgctttg a | | 21 |
| SEQ ID NO: 126 | moltype = RNA   length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-O-methylguanosine-3'-phosphorothioate | |
| modified_base | 2 | |
| | mod_base = OTHER | |
| | note = 2'-O-methyladenosine-3'-phosphorothioate | |
| modified_base | 3 | |
| | mod_base = OTHER | |
| | note = 2'-O-methyladenosine-3'-phosphate | |
| modified_base | 4 | |
| | mod_base = OTHER | |
| | note = 2'-O-methyladenosine-3'-phosphate | |
| modified_base | 5 | |
| | mod_base = OTHER | |
| | note = 2'-O-methylcytidine-3'-phosphate | |
| modified_base | 6 | |
| | mod_base = OTHER | |
| | note = 2'-O-methyluridine-3'-phosphate | |
| modified_base | 7 | |
| | mod_base = OTHER | |
| | note = 2'-deoxy-2'-fluorocytidine-3'-phosphate | |
| modified_base | 8 | |
| | mod_base = OTHER | |
| | note = 2'-O-methyladenosine-3'-phosphate | |
| modified_base | 9 | |
| | mod_base = OTHER | |
| | note = 2'-deoxy-2'-fluoroadenosine-3'-phosphate | |
| modified_base | 10 | |
| | mod_base = OTHER | |
| | note = 2'-deoxy-2'-fluorouridine-3'-phosphate | |

| | | |
|---|---|---|
| modified_base | | 11 |
| | | mod_base = OTHER |
| | | note = 2'-O-hexadecyl-adenosine-3'-phosphate |
| modified_base | | 12 |
| | | mod_base = OTHER |
| | | note = 2'-O-methyladenosine-3'-phosphate |
| modified_base | | 13 |
| | | mod_base = OTHER |
| | | note = 2'-O-methyladenosine-3'-phosphate |
| modified_base | | 14 |
| | | mod_base = OTHER |
| | | note = 2'-O-methylguanosine-3'-phosphate |
| modified_base | | 15 |
| | | mod_base = OTHER |
| | | note = 2'-O-methyluridine-3'-phosphate |
| modified_base | | 16 |
| | | mod_base = OTHER |
| | | note = 2'-O-methylguanosine-3'-phosphate |
| modified_base | | 17 |
| | | mod_base = OTHER |
| | | note = 2'-O-methylcytidine-3'-phosphate |
| modified_base | | 18 |
| | | mod_base = OTHER |
| | | note = 2'-O-methyluridine-3'-phosphate |
| modified_base | | 19 |
| | | mod_base = OTHER |
| | | note = 2'-O-methyluridine-3'-phosphate |
| modified_base | | 20 |
| | | mod_base = OTHER |
| | | note = 2'-O-methyluridine-3'-phosphate |
| modified_base | | 21 |
| | | mod_base = OTHER |
| | | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 126 | | |
| gaaactcaat aaagtgcttt a | | 21 |
| | | |
| SEQ ID NO: 127 | moltype = RNA length = 21 | |
| FEATURE | Location/Qualifiers | |
| source | 1..21 | |
| | mol_type = other RNA | |
| | organism = synthetic construct | |
| modified_base | | 1 |
| | | mod_base = OTHER |
| | | note = 2'-O-hexadecyl-guanosine-3'-phosphorothioate |
| modified_base | | 2 |
| | | mod_base = OTHER |
| | | note = 2'-O-methyladenosine-3'-phosphorothioate |
| modified_base | | 3 |
| | | mod_base = OTHER |
| | | note = 2'-O-methyladenosine-3'-phosphate |
| modified_base | | 4 |
| | | mod_base = OTHER |
| | | note = 2'-O-methylcytidine-3'-phosphate |
| modified_base | | 5 |
| | | mod_base = OTHER |
| | | note = 2'-O-methyluridine-3'-phosphate |
| modified_base | | 6 |
| | | mod_base = OTHER |
| | | note = 2'-O-methylcytidine-3'-phosphate |
| modified_base | | 7 |
| | | mod_base = OTHER |
| | | note = 2'-deoxy-2'-fluoroadenosine-3'-phosphate |
| modified_base | | 8 |
| | | mod_base = OTHER |
| | | note = 2'-O-methyladenosine-3'-phosphate |
| modified_base | | 9 |
| | | mod_base = OTHER |
| | | note = 2'-deoxy-2'-fluorouridine-3'-phosphate |
| modified_base | | 10 |
| | | mod_base = OTHER |
| | | note = 2'-deoxy-2'-fluoroadenosine-3'-phosphate |
| modified_base | | 11 |
| | | mod_base = OTHER |
| | | note = 2'-deoxy-2'-fluoroadenosine-3'-phosphate |

| | |
|---|---|
| modified_base | 12<br>mod_base = OTHER<br>note = 2'-O-methyladenosine-3'-phosphate |
| modified_base | 13<br>mod_base = OTHER<br>note = 2'-O-methylguanosine-3'-phosphate |
| modified_base | 14<br>mod_base = OTHER<br>note = 2'-O-methyluridine-3'-phosphate |
| modified_base | 15<br>mod_base = OTHER<br>note = 2'-O-methylguanosine-3'-phosphate |
| modified_base | 16<br>mod_base = OTHER<br>note = 2'-O-methylcytidine-3'-phosphate |
| modified_base | 17<br>mod_base = OTHER<br>note = 2'-O-methyluridine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-methylguanosine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 127 | |
| gaactcaata aagtgctttg a | 21 |
| SEQ ID NO: 128<br>FEATURE<br>source | moltype = RNA   length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate |
| modified_base | 2<br>mod_base = OTHER<br>note = 2'-deoxy-2'-fluoroadenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylguanosine-3'-phosphate |
| modified_base | 6<br>mod_base = OTHER<br>note = 2'-deoxy-2'-fluorocytidine-3'-phosphate |
| modified_base | 7<br>mod_base = OTHER<br>note = 2'-O-methyladenosine-3'-phosphate |
| modified_base | 8<br>mod_base = OTHER<br>note = 2'-O-methylcytidine-3'-phosphate |
| modified_base | 9<br>mod_base = OTHER<br>note = 2'-O-methyluridine-3'-phosphate |
| modified_base | 10<br>mod_base = OTHER<br>note = 2'-O-methyluridine-3'-phosphate |
| modified_base | 11<br>mod_base = OTHER<br>note = 2'-O-hexadecyl-uridine-3'-phosphate |
| modified_base | 12<br>mod_base = OTHER<br>note = 2'-O-methyladenosine-3'-phosphate |

| | |
|---|---|
| modified_base | 13<br>mod_base = OTHER<br>note = 2'-O-methyluridine-3'-phosphate |
| modified_base | 14<br>mod_base = OTHER<br>note = 2'-deoxy-2'-fluorouridine-3'-phosphate |
| modified_base | 15<br>mod_base = OTHER<br>note = 2'-O-methylguanosine-3'-phosphate |
| modified_base | 16<br>mod_base = OTHER<br>note = 2'-deoxy-2'-fluoroadenosine-3'-phosphate |
| modified_base | 17<br>mod_base = OTHER<br>note = 2'-O-methylguanosine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methylcytidine-3'-phosphorothioate |
| modified_base | 22<br>mod_base = OTHER<br>note = 2'-O-methyluridine-3'-phosphorothioate |
| modified_base | 23<br>mod_base = OTHER<br>note = 2'-O-methylguanosine |

SEQUENCE: 128
taaagcactt tattgagttt ctg                     23

| | |
|---|---|
| SEQ ID NO: 129<br>FEATURE<br>source | moltype = RNA  length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate |
| modified_base | 2<br>mod_base = OTHER<br>note = 2'-deoxy-2'-fluoroadenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methyladenosine-3'-phosphate |
| modified_base | 5<br>mod_base = OTHER<br>note = 2'-O-hexadecyl-guanosine-3'-phosphate |
| modified_base | 6<br>mod_base = OTHER<br>note = 2'-deoxy-2'-fluorocytidine-3'-phosphate |
| modified_base | 7<br>mod_base = OTHER<br>note = 2'-O-methyladenosine-3'-phosphate |
| modified_base | 8<br>mod_base = OTHER<br>note = 2'-O-methylcytidine-3'-phosphate |
| modified_base | 9<br>mod_base = OTHER<br>note = 2'-O-methyluridine-3'-phosphate |
| modified_base | 10<br>mod_base = OTHER<br>note = 2'-O-methyluridine-3'-phosphate |
| modified_base | 11<br>mod_base = OTHER<br>note = 2'-O-methyluridine-3'-phosphate |
| modified_base | 12<br>mod_base = OTHER<br>note = 2'-O-methyladenosine-3'-phosphate |
| modified_base | 13<br>mod_base = OTHER |

```
                           note = 2'-O-methyluridine-3'-phosphate
modified_base              14
                           mod_base = OTHER
                           note = 2'-deoxy-2'-fluorouridine-3'-phosphate
modified_base              15
                           mod_base = OTHER
                           note = 2'-O-methylguanosine-3'-phosphate
modified_base              16
                           mod_base = OTHER
                           note = 2'-deoxy-2'-fluoroadenosine-3'-phosphate
modified_base              17
                           mod_base = OTHER
                           note = 2'-O-methylguanosine-3'-phosphate
modified_base              18
                           mod_base = OTHER
                           note = 2'-O-methyluridine-3'-phosphate
modified_base              19
                           mod_base = OTHER
                           note = 2'-O-methyluridine-3'-phosphate
modified_base              20
                           mod_base = OTHER
                           note = 2'-O-methyluridine-3'-phosphate
modified_base              21
                           mod_base = OTHER
                           note = 2'-O-methylcytidine-3'-phosphorothioate
modified_base              22
                           mod_base = OTHER
                           note = 2'-O-methyluridine-3'-phosphorothioate
modified_base              23
                           mod_base = OTHER
                           note = 2'-O-methylguanosine
SEQUENCE: 129
taaagcactt tattgagttt ctg                                              23

SEQ ID NO: 130             moltype = RNA   length = 23
FEATURE                    Location/Qualifiers
source                     1..23
                           mol_type = other RNA
                           organism = synthetic construct
modified_base              1
                           mod_base = OTHER
                           note = 2'-O-methyluridine-3'-phosphorothioate
modified_base              2
                           mod_base = OTHER
                           note = 2'-deoxy-2'-fluoroadenosine-3'-phosphorothioate
modified_base              3
                           mod_base = OTHER
                           note = 2'-O-hexadecyl-adenosine-3'-phosphate
modified_base              4
                           mod_base = OTHER
                           note = 2'-O-methyladenosine-3'-phosphate
modified_base              5
                           mod_base = OTHER
                           note = 2'-O-methylguanosine-3'-phosphate
modified_base              6
                           mod_base = OTHER
                           note = 2'-deoxy-2'-fluorocytidine-3'-phosphate
modified_base              7
                           mod_base = OTHER
                           note = 2'-O-methyladenosine-3'-phosphate
modified_base              8
                           mod_base = OTHER
                           note = 2'-O-methylcytidine-3'-phosphate
modified_base              9
                           mod_base = OTHER
                           note = 2'-O-methyluridine-3'-phosphate
modified_base              10
                           mod_base = OTHER
                           note = 2'-O-methyluridine-3'-phosphate
modified_base              11
                           mod_base = OTHER
                           note = 2'-O-methyluridine-3'-phosphate
modified_base              12
                           mod_base = OTHER
                           note = 2'-O-methyladenosine-3'-phosphate
modified_base              13
                           mod_base = OTHER
                           note = 2'-O-methyluridine-3'-phosphate
modified_base              14
```

```
                            mod_base = OTHER
                            note = 2'-deoxy-2'-fluorouridine-3'-phosphate
modified_base               15
                            mod_base = OTHER
                            note = 2'-O-methylguanosine-3'-phosphate
modified_base               16
                            mod_base = OTHER
                            note = 2'-deoxy-2'-fluoroadenosine-3'-phosphate
modified_base               17
                            mod_base = OTHER
                            note = 2'-O-methylguanosine-3'-phosphate
modified_base               18
                            mod_base = OTHER
                            note = 2'-O-methyluridine-3'-phosphate
modified_base               19
                            mod_base = OTHER
                            note = 2'-O-methyluridine-3'-phosphate
modified_base               20
                            mod_base = OTHER
                            note = 2'-O-methyluridine-3'-phosphate
modified_base               21
                            mod_base = OTHER
                            note = 2'-O-methylcytidine-3'-phosphorothioate
modified_base               22
                            mod_base = OTHER
                            note = 2'-O-methyluridine-3'-phosphorothioate
modified_base               23
                            mod_base = OTHER
                            note = 2'-O-methylguanosine
SEQUENCE: 130
taaagcactt tattgagttt ctg                                                    23

SEQ ID NO: 131              moltype = RNA   length = 23
FEATURE                     Location/Qualifiers
source                      1..23
                            mol_type = other RNA
                            organism = synthetic construct
modified_base               1
                            mod_base = OTHER
                            note = 2'-O-methyluridine-3'-phosphorothioate
modified_base               2
                            mod_base = OTHER
                            note = 2'-deoxy-2'-fluorocytidine-3'-phosphorothioate
modified_base               3
                            mod_base = OTHER
                            note = 2'-O-methyladenosine-3'-phosphate
modified_base               4
                            mod_base = OTHER
                            note = 2'-O-hexadecyl-adenosine-3'-phosphate
modified_base               5
                            mod_base = OTHER
                            note = 2'-O-methyladenosine-3'-phosphate
modified_base               6
                            mod_base = OTHER
                            note = 2'-deoxy-2'-fluoroguanosine-3'-phosphate
modified_base               7
                            mod_base = OTHER
                            note = 2'-O-methylcytidine-3'-phosphate
modified_base               8
                            mod_base = OTHER
                            note = 2'-deoxy-2'-fluoroadenosine-3'-phosphate
modified_base               9
                            mod_base = OTHER
                            note = 2'-deoxy-2'-fluorocytidine-3'-phosphate
modified_base               10
                            mod_base = OTHER
                            note = 2'-O-methyluridine-3'-phosphate
modified_base               11
                            mod_base = OTHER
                            note = 2'-O-methyluridine-3'-phosphate
modified_base               12
                            mod_base = OTHER
                            note = 2'-O-methyluridine-3'-phosphate
modified_base               13
                            mod_base = OTHER
                            note = 2'-O-methyladenosine-3'-phosphate
modified_base               14
                            mod_base = OTHER
                            note = 2'-deoxy-2'-fluorouridine-3'-phosphate
```

| | |
|---|---|
| modified_base | 15<br>mod_base = OTHER<br>note = 2'-O-methyluridine-3'-phosphate |
| modified_base | 16<br>mod_base = OTHER<br>note = 2'-deoxy-2'-fluoroguanosine-3'-phosphate |
| modified_base | 17<br>mod_base = OTHER<br>note = 2'-O-methyladenosine-3'-phosphate |
| modified_base | 18<br>mod_base = OTHER<br>note = 2'-O-methylguanosine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyluridine-3'-phosphate |
| modified_base | 21<br>mod_base = OTHER<br>note = 2'-O-methylcytidine-3'-phosphorothioate |
| modified_base | 22<br>mod_base = OTHER<br>note = 2'-O-methylcytidine-3'-phosphorothioate |
| modified_base | 23<br>mod_base = OTHER<br>note = 2'-O-methyluridine |
| SEQUENCE: 131 | |
| tcaaagcact ttattgagtt cct | 23 |
| SEQ ID NO: 132<br>FEATURE<br>source | moltype = RNA  length = 21<br>Location/Qualifiers<br>1..21<br>mol_type = other RNA<br>organism = synthetic construct |
| modified_base | 1<br>mod_base = OTHER<br>note = 2'-O-methylguanosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methyladenosine-3'-phosphate |
| modified_base | 4<br>mod_base = OTHER<br>note = 2'-O-methylcytidine-3'-phosphate |
| modified_base | 5<br>mod_base = OTHER<br>note = 2'-O-methyluridine-3'-phosphate |
| modified_base | 6<br>mod_base = OTHER<br>note = 2'-O-methylcytidine-3'-phosphate |
| modified_base | 7<br>mod_base = OTHER<br>note = 2'-deoxy-2'-fluoroadenosine-3'-phosphate |
| modified_base | 8<br>mod_base = OTHER<br>note = 2'-O-methyladenosine-3'-phosphate |
| modified_base | 9<br>mod_base = OTHER<br>note = 2'-deoxy-2'-fluorouridine-3'-phosphate |
| modified_base | 10<br>mod_base = OTHER<br>note = 2'-deoxy-2'-fluoroadenosine-3'-phosphate |
| modified_base | 11<br>mod_base = OTHER<br>note = 2'-O-hexadecyl-adenosine-3'-phosphate |
| modified_base | 12<br>mod_base = OTHER<br>note = 2'-O-methyladenosine-3'-phosphate |
| modified_base | 13<br>mod_base = OTHER<br>note = 2'-O-methylguanosine-3'-phosphate |
| modified_base | 14<br>mod_base = OTHER<br>note = 2'-O-methyluridine-3'-phosphate |
| modified_base | 15<br>mod_base = OTHER |

```
                        note = 2'-O-methylguanosine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methylguanosine-3'-phosphate
modified_base           21
                        mod_base = OTHER
                        note = 2'-O-methyladenosine-3'-phosphate
                        ((2S,4R)-1-[29-[[2-(acetylamino)-2-deoxy-beta-D-galactopyra
                        nosyl]oxy]-14,14-bis[[3-[[3-[[5-[[2-(acetylamino)-2-deoxy-b
                        eta-D-galactopyranosyl]oxy]-1-oxopentyl]amino]propyl]amino]
                        -3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 132
gaactcaata aagtgctttg a                                              21

SEQ ID NO: 133          moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluorocytidine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methyladenosine-3'-phosphate
modified_base           6
                        mod_base = OTHER
                        note = 2'-deoxy-2'-fluoroguanosine-3'-phosphate
modified_base           7
                        mod_base = OTHER
                        note = 2'-O-methylcytidine-3'-phosphate
modified_base           8
                        mod_base = OTHER
                        note = 2'-deoxy-2'-fluoroadenosine-3'-phosphate
modified_base           9
                        mod_base = OTHER
                        note = 2'-deoxy-2'-fluorocytidine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyluridine-3'-phosphate
modified_base           13
                        mod_base = OTHER
                        note = 2'-O-methyladenosine-3'-phosphate
modified_base           14
                        mod_base = OTHER
                        note = 2'-O-hexadecyl-uridine-3'-phosphate
modified_base           15
                        mod_base = OTHER
                        note = 2'-O-methyluridine-3'-phosphate
modified_base           16
                        mod_base = OTHER
```

```
                        note = 2'-deoxy-2'-fluoroguanosine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methyluridine
SEQUENCE: 133
tcaaagcact ttattgagtt cct                                              23

SEQ ID NO: 134          moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylcytidine-3'-phosphate
modified_base           6
                        mod_base = OTHER
                        note = 2'-O-methyluridine-3'-phosphate
modified_base           7
                        mod_base = OTHER
                        note = 2'-deoxy-2'-fluorocytidine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluoroadenosine-3'-phosphate
modified_base           10
                        mod_base = OTHER
                        note = 2'-O-hexadecyl-uridine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyladenosine-3'-phosphate
modified_base           13
                        mod_base = OTHER
                        note = 2'-O-methyladenosine-3'-phosphate
modified_base           14
                        mod_base = OTHER
                        note = 2'-O-methylguanosine-3'-phosphate
modified_base           15
                        mod_base = OTHER
                        note = 2'-O-methyluridine-3'-phosphate
modified_base           16
                        mod_base = OTHER
                        note = 2'-O-methylguanosine-3'-phosphate
modified_base           17
```

```
                           mod_base = OTHER
                           note = 2'-O-methylcytidine-3'-phosphate
modified_base              18
                           mod_base = OTHER
                           note = 2'-O-methyluridine-3'-phosphate
modified_base              19
                           mod_base = OTHER
                           note = 2'-O-methyluridine-3'-phosphate
modified_base              20
                           mod_base = OTHER
                           note = 2'-O-methyluridine-3'-phosphate
modified_base              21
                           mod_base = OTHER
                           note = 2'-O-methyladenosine-3'-phosphate
                            ((2S,4R)-1-[29-[[2-(acetylamino)-2-deoxy-beta-D-galactopyra
                            nosyl]oxy]-14,14-bis[[3-[[3-[[5-[[2-(acetylamino)-2-deoxy-b
                            eta-D-galactopyranosyl]oxy]-1-oxopentyl]amino]propyl]amino]
                            -3-oxopropoxy]methyl]-1,12,19,25-tetraoxo-16-oxa-13,20,24-t
                            riazanonacos-1-yl]-4-hydroxy-2-pyrrolidinyl)methyl ester
SEQUENCE: 134
gaaactcaat aaagtgcttt a                                                         21

SEQ ID NO: 135             moltype = RNA   length = 23
FEATURE                    Location/Qualifiers
source                     1..23
                           mol_type = other RNA
                           organism = synthetic construct
modified_base              1
                           mod_base = OTHER
                           note = 2'-O-hexadecyl-uridine-3'-phosphorothioate
modified_base              2
                           mod_base = OTHER
                           note = 2'-deoxy-2'-fluoroadenosine-3'-phosphorothioate
modified_base              3
                           mod_base = OTHER
                           note = 2'-O-methyladenosine-3'-phosphate
modified_base              4
                           mod_base = OTHER
                           note = 2'-O-methyladenosine-3'-phosphate
modified_base              5
                           mod_base = OTHER
                           note = 2'-O-methylguanosine-3'-phosphate
modified_base              6
                           mod_base = OTHER
                           note = 2'-deoxy-2'-fluorocytidine-3'-phosphate
modified_base              7
                           mod_base = OTHER
                           note = 2'-O-methyladenosine-3'-phosphate
modified_base              8
                           mod_base = OTHER
                           note = 2'-O-methylcytidine-3'-phosphate
modified_base              9
                           mod_base = OTHER
                           note = 2'-O-methyluridine-3'-phosphate
modified_base              10
                           mod_base = OTHER
                           note = 2'-O-methyluridine-3'-phosphate
modified_base              11
                           mod_base = OTHER
                           note = 2'-O-methyluridine-3'-phosphate
modified_base              12
                           mod_base = OTHER
                           note = 2'-O-methyladenosine-3'-phosphate
modified_base              13
                           mod_base = OTHER
                           note = 2'-O-methyluridine-3'-phosphate
modified_base              14
                           mod_base = OTHER
                           note = 2'-deoxy-2'-fluorouridine-3'-phosphate
modified_base              15
                           mod_base = OTHER
                           note = 2'-O-methylguanosine-3'-phosphate
modified_base              16
                           mod_base = OTHER
                           note = 2'-deoxy-2'-fluoroadenosine-3'-phosphate
modified_base              17
                           mod_base = OTHER
                           note = 2'-O-methylguanosine-3'-phosphate
modified_base              18
```

```
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methyluridine-3'-phosphorothioate
modified_base           23
                        mod_base = OTHER
                        note = 2'-O-methylguanosine
SEQUENCE: 135
taaagcactt tattgagttt ctg                                              23

SEQ ID NO: 136          moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-hexadecyl-adenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylguanosine-3'-phosphate
modified_base           18
                        mod_base = OTHER
                        note = 2'-O-methyluridine-3'-phosphate
```

```
modified_base        19
                     mod_base = OTHER
                     note = 2'-O-methyluridine-3'-phosphate
modified_base        20
                     mod_base = OTHER
                     note = 2'-O-methyluridine-3'-phosphate
modified_base        21
                     mod_base = OTHER
                     note = 2'-O-methylcytidine-3'-phosphorothioate
modified_base        22
                     mod_base = OTHER
                     note = 2'-O-methyluridine-3'-phosphorothioate
modified_base        23
                     mod_base = OTHER
                     note = 2'-O-methylguanosine
SEQUENCE: 136
taaagcactt tattgagttt ctg                                              23

SEQ ID NO: 137       moltype = RNA   length = 23
FEATURE              Location/Qualifiers
source               1..23
                     mol_type = other RNA
                     organism = synthetic construct
modified_base        1
                     mod_base = OTHER
                     note = 2'-O-methyluridine-3'-phosphorothioate
modified_base        2
                     mod_base = OTHER
                     note = 2'-deoxy-2'-fluorocytidine-3'-phosphorothioate
modified_base        3
                     mod_base = OTHER
                     note = 2'-O-methyladenosine-3'-phosphate
modified_base        4
                     mod_base = OTHER
                     note = 2'-O-methyladenosine-3'-phosphate
modified_base        5
                     mod_base = OTHER
                     note = 2'-O-methyladenosine-3'-phosphate
modified_base        6
                     mod_base = OTHER
                     note = 2'-deoxy-2'-fluoroguanosine-3'-phosphate
modified_base        7
                     mod_base = OTHER
                     note = 2'-O-methylcytidine-3'-phosphate
modified_base        8
                     mod_base = OTHER
                     note = 2'-deoxy-2'-fluoroadenosine-3'-phosphate
modified_base        9
                     mod_base = OTHER
                     note = 2'-deoxy-2'-fluorocytidine-3'-phosphate
modified_base        10
                     mod_base = OTHER
                     note = 2'-O-methyluridine-3'-phosphate
modified_base        11
                     mod_base = OTHER
                     note = 2'-O-methyluridine-3'-phosphate
modified_base        12
                     mod_base = OTHER
                     note = 2'-O-hexadecyl-uridine-3'-phosphate
modified_base        13
                     mod_base = OTHER
                     note = 2'-O-methyladenosine-3'-phosphate
modified_base        14
                     mod_base = OTHER
                     note = 2'-deoxy-2'-fluorouridine-3'-phosphate
modified_base        15
                     mod_base = OTHER
                     note = 2'-O-methyluridine-3'-phosphate
modified_base        16
                     mod_base = OTHER
                     note = 2'-deoxy-2'-fluoroguanosine-3'-phosphate
modified_base        17
                     mod_base = OTHER
                     note = 2'-O-methyladenosine-3'-phosphate
modified_base        18
                     mod_base = OTHER
                     note = 2'-O-methylguanosine-3'-phosphate
modified_base        19
                     mod_base = OTHER
```

```
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methyluridine
SEQUENCE: 137
tcaaagcact ttattgagtt cct                                             23

SEQ ID NO: 138          moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-O-hexadecyl-cytidine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methyladenosine-3'-phosphate
modified_base           6
                        mod_base = OTHER
                        note = 2'-deoxy-2'-fluoroguanosine-3'-phosphate
modified_base           7
                        mod_base = OTHER
                        note = 2'-O-methylcytidine-3'-phosphate
modified_base           8
                        mod_base = OTHER
                        note = 2'-deoxy-2'-fluoroadenosine-3'-phosphate
modified_base           9
                        mod_base = OTHER
                        note = 2'-deoxy-2'-fluorocytidine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyluridine-3'-phosphate
modified_base           13
                        mod_base = OTHER
                        note = 2'-O-methyladenosine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methyluridine-3'-phosphate
modified_base           16
                        mod_base = OTHER
                        note = 2'-deoxy-2'-fluoroguanosine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
                        note = 2'-O-methyluridine-3'-phosphate
modified_base           20
```

|                | mod_base = OTHER |
|---|---|
|                | note = 2'-O-methyluridine-3'-phosphate |
| modified_base  | 21 |
|                | mod_base = OTHER |
|                | note = 2'-O-methylcytidine-3'-phosphorothioate |
| modified_base  | 22 |
|                | mod_base = OTHER |
|                | note = 2'-O-methylcytidine-3'-phosphorothioate |
| modified_base  | 23 |
|                | mod_base = OTHER |
|                | note = 2'-O-methyluridine |
| SEQUENCE: 138 | |
| tcaaagcact ttattgagtt cct | 23 |
| | |
| SEQ ID NO: 139 | moltype = RNA  length = 23 |
| FEATURE | Location/Qualifiers |
| source | 1..23 |
|  | mol_type = other RNA |
|  | organism = synthetic construct |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-deoxy-2'-fluoroadenosine-3'-phosphorothioate |
| modified_base | 3 |
|  | mod_base = OTHER |
|  | note = 2'-O-methyladenosine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methylguanosine-3'-phosphate |
| modified_base | 6 |
|  | mod_base = OTHER |
|  | note = 2'-deoxy-2'-fluorocytidine-3'-phosphate |
| modified_base | 7 |
|  | mod_base = OTHER |
|  | note = 2'-O-methyladenosine-3'-phosphate |
| modified_base | 8 |
|  | mod_base = OTHER |
|  | note = 2'-O-methylcytidine-3'-phosphate |
| modified_base | 9 |
|  | mod_base = OTHER |
|  | note = 2'-O-methyluridine-3'-phosphate |
| modified_base | 10 |
|  | mod_base = OTHER |
|  | note = 2'-O-methyluridine-3'-phosphate |
| modified_base | 11 |
|  | mod_base = OTHER |
|  | note = 2'-O-methyluridine-3'-phosphate |
| modified_base | 12 |
|  | mod_base = OTHER |
|  | note = 2'-O-methyladenosine-3'-phosphate |
| modified_base | 13 |
|  | mod_base = OTHER |
|  | note = 2'-O-methyluridine-3'-phosphate |
| modified_base | 14 |
|  | mod_base = OTHER |
|  | note = 2'-O-hexadecyl-uridine-3'-phosphate |
| modified_base | 15 |
|  | mod_base = OTHER |
|  | note = 2'-O-methylguanosine-3'-phosphate |
| modified_base | 16 |
|  | mod_base = OTHER |
|  | note = 2'-deoxy-2'-fluoroadenosine-3'-phosphate |
| modified_base | 17 |
|  | mod_base = OTHER |
|  | note = 2'-O-methylguanosine-3'-phosphate |
| modified_base | 18 |
|  | mod_base = OTHER |
|  | note = 2'-O-methyluridine-3'-phosphate |
| modified_base | 19 |
|  | mod_base = OTHER |
|  | note = 2'-O-methyluridine-3'-phosphate |
| modified_base | 20 |
|  | mod_base = OTHER |
|  | note = 2'-O-methyluridine-3'-phosphate |

```
modified_base         21
                      mod_base = OTHER
                      note = 2'-O-methylcytidine-3'-phosphorothioate
modified_base         22
                      mod_base = OTHER
                      note = 2'-O-methyluridine-3'-phosphorothioate
modified_base         23
                      mod_base = OTHER
                      note = 2'-O-methylguanosine
SEQUENCE: 139
taaagcactt tattgagttt ctg                                         23

SEQ ID NO: 140        moltype = RNA  length = 21
FEATURE               Location/Qualifiers
source                1..21
                      mol_type = other RNA
                      organism = synthetic construct
modified_base         1
                      mod_base = OTHER
                      note = 2'-O-methylguanosine-3'-phosphorothioate
modified_base         2
                      mod_base = OTHER
                      note = 2'-O-methyladenosine-3'-phosphorothioate
modified_base         3
                      mod_base = OTHER
                      note = 2'-O-methyladenosine-3'-phosphate
modified_base         4
                      mod_base = OTHER
                      note = 2'-O-methylcytidine-3'-phosphate
modified_base         5
                      mod_base = OTHER
                      note = 2'-O-methyluridine-3'-phosphate
modified_base         6
                      mod_base = OTHER
                      note = 2'-O-methylcytidine-3'-phosphate
modified_base         7
                      mod_base = OTHER
                      note = 2'-deoxy-2'-fluoroadenosine-3'-phosphate
modified_base         8
                      mod_base = OTHER
                      note = 2'-O-methyladenosine-3'-phosphate
modified_base         9
                      mod_base = OTHER
                      note = 2'-deoxy-2'-fluorouridine-3'-phosphate
modified_base         10
                      mod_base = OTHER
                      note = 2'-O-hexadecyl-adenosine-3'-phosphate
modified_base         11
                      mod_base = OTHER
                      note = 2'-deoxy-2'-fluoroadenosine-3'-phosphate
modified_base         12
                      mod_base = OTHER
                      note = 2'-O-methyladenosine-3'-phosphate
modified_base         13
                      mod_base = OTHER
                      note = 2'-O-methylguanosine-3'-phosphate
modified_base         14
                      mod_base = OTHER
                      note = 2'-O-methyluridine-3'-phosphate
modified_base         15
                      mod_base = OTHER
                      note = 2'-O-methylguanosine-3'-phosphate
modified_base         16
                      mod_base = OTHER
                      note = 2'-O-methylcytidine-3'-phosphate
modified_base         17
                      mod_base = OTHER
                      note = 2'-O-methyluridine-3'-phosphate
modified_base         18
                      mod_base = OTHER
                      note = 2'-O-methyluridine-3'-phosphate
modified_base         19
                      mod_base = OTHER
                      note = 2'-O-methyluridine-3'-phosphate
modified_base         20
                      mod_base = OTHER
                      note = 2'-O-methylguanosine-3'-phosphate
modified_base         21
                      mod_base = OTHER
```

-continued

```
                           note = 2'-O-methyladenosine-3'-phosphate
                           ((2S,4R)-1-[29-[[2-(acetylamino)-2-deoxy-beta-D-galactopyra
                           nosyl]oxy]-14,14-bis[[3-[[3-[[5-[[2-(acetylamino)-2-deoxy-b
                           eta-D-galactopyranosyl]oxy]-1-oxopentyl]amino]propyl]amino]
                           -3-oxopropoxy]methyl]-1,12,19,25-tetraoxo-16-oxa-13,20,24-t
                           riazanonacos-1-yl]-4-hydroxy-2-pyrrolidinyl)methyl ester
SEQUENCE: 140
gaactcaata aagtgctttg a                                                  21

SEQ ID NO: 141             moltype = RNA   length = 23
FEATURE                    Location/Qualifiers
source                     1..23
                           mol_type = other RNA
                           organism = synthetic construct
modified_base              1
                           mod_base = OTHER
                           note = 2'-O-methyluridine-3'-phosphorothioate
modified_base              2
                           mod_base = OTHER
                           note = 2'-deoxy-2'-fluorocytidine-3'-phosphorothioate
modified_base              3
                           mod_base = OTHER
                           note = 2'-O-methyladenosine-3'-phosphate
modified_base              4
                           mod_base = OTHER
                           note = 2'-O-methyladenosine-3'-phosphate
modified_base              5
                           mod_base = OTHER
                           note = 2'-O-methyladenosine-3'-phosphate
modified_base              6
                           mod_base = OTHER
                           note = 2'-deoxy-2'-fluoroguanosine-3'-phosphate
modified_base              7
                           mod_base = OTHER
                           note = 2'-O-methylcytidine-3'-phosphate
modified_base              8
                           mod_base = OTHER
                           note = 2'-deoxy-2'-fluoroadenosine-3'-phosphate
modified_base              9
                           mod_base = OTHER
                           note = 2'-deoxy-2'-fluorocytidine-3'-phosphate
modified_base              10
                           mod_base = OTHER
                           note = 2'-O-methyluridine-3'-phosphate
modified_base              11
                           mod_base = OTHER
                           note = 2'-O-methyluridine-3'-phosphate
modified_base              12
                           mod_base = OTHER
                           note = 2'-O-methyluridine-3'-phosphate
modified_base              13
                           mod_base = OTHER
                           note = 2'-O-hexadecyl-adenosine-3'-phosphate
modified_base              14
                           mod_base = OTHER
                           note = 2'-deoxy-2'-fluorouridine-3'-phosphate
modified_base              15
                           mod_base = OTHER
                           note = 2'-O-methyluridine-3'-phosphate
modified_base              16
                           mod_base = OTHER
                           note = 2'-deoxy-2'-fluoroguanosine-3'-phosphate
modified_base              17
                           mod_base = OTHER
                           note = 2'-O-methyladenosine-3'-phosphate
modified_base              18
                           mod_base = OTHER
                           note = 2'-O-methylguanosine-3'-phosphate
modified_base              19
                           mod_base = OTHER
                           note = 2'-O-methyluridine-3'-phosphate
modified_base              20
                           mod_base = OTHER
                           note = 2'-O-methyluridine-3'-phosphate
modified_base              21
                           mod_base = OTHER
                           note = 2'-O-methylcytidine-3'-phosphorothioate
modified_base              22
                           mod_base = OTHER
```

```
                        note = 2'-O-methylcytidine-3'-phosphorothioate
modified_base           23
                        mod_base = OTHER
                        note = 2'-O-methyluridine
SEQUENCE: 141
tcaaagcact ttattgagtt cct                                              23

SEQ ID NO: 142          moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-deoxy-2'-fluoroadenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-hexadecyl-uridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylguanosine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methyluridine-3'-phosphorothioate
modified_base           23
```

|  |  |
|---|---|
|  | mod_base = OTHER |
|  | note = 2'-O-methylguanosine |
| SEQUENCE: 142 |  |
| taaagcactt tattgagttt ctg | 23 |

|  |  |
|---|---|
| SEQ ID NO: 143 | moltype = RNA   length = 24 |
| FEATURE | Location/Qualifiers |
| source | 1..24 |
|  | mol_type = other RNA |
|  | organism = synthetic construct |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-deoxy-2'-fluorocytidine-3'-phosphorothioate |
| modified_base | 3 |
|  | mod_base = OTHER |
|  | note = 2'-O-hexadecyl-adenosine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methyladenosine-3'-phosphate |
| modified_base | 6 |
|  | mod_base = OTHER |
|  | note = 2'-O-methyladenosine-3'-phosphate |
| modified_base | 7 |
|  | mod_base = OTHER |
|  | note = 2'-deoxy-2'-fluoroguanosine-3'-phosphate |
| modified_base | 8 |
|  | mod_base = OTHER |
|  | note = 2'-O-methylcytidine-3'-phosphate |
| modified_base | 9 |
|  | mod_base = OTHER |
|  | note = 2'-deoxy-2'-fluoroadenosine-3'-phosphate |
| modified_base | 10 |
|  | mod_base = OTHER |
|  | note = 2'-deoxy-2'-fluorocytidine-3'-phosphate |
| modified_base | 11 |
|  | mod_base = OTHER |
|  | note = 2'-O-methyluridine-3'-phosphate |
| modified_base | 12 |
|  | mod_base = OTHER |
|  | note = 2'-O-methyluridine-3'-phosphate |
| modified_base | 13 |
|  | mod_base = OTHER |
|  | note = 2'-O-methyluridine-3'-phosphate |
| modified_base | 14 |
|  | mod_base = OTHER |
|  | note = 2'-O-methyladenosine-3'-phosphate |
| modified_base | 15 |
|  | mod_base = OTHER |
|  | note = 2'-deoxy-2'-fluorouridine-3'-phosphate |
| modified_base | 16 |
|  | mod_base = OTHER |
|  | note = 2'-O-methyluridine-3'-phosphate |
| modified_base | 17 |
|  | mod_base = OTHER |
|  | note = 2'-deoxy-2'-fluoroguanosine-3'-phosphate |
| modified_base | 18 |
|  | mod_base = OTHER |
|  | note = 2'-O-methyladenosine-3'-phosphate |
| modified_base | 19 |
|  | mod_base = OTHER |
|  | note = 2'-O-methylguanosine-3'-phosphate |
| modified_base | 20 |
|  | mod_base = OTHER |
|  | note = 2'-O-methyluridine-3'-phosphate |
| modified_base | 21 |
|  | mod_base = OTHER |
|  | note = 2'-O-methyluridine-3'-phosphate |
| modified_base | 22 |
|  | mod_base = OTHER |
|  | note = 2'-O-methylcytidine-3'-phosphorothioate |
| modified_base | 23 |
|  | mod_base = OTHER |
|  | note = 2'-O-methylcytidine-3'-phosphorothioate |

| | | |
|---|---|---|
| | 24 | |
| | mod_base = OTHER | |
| | note = 2'-O-methyluridine | |
| SEQUENCE: 143 | | |
| tcaaaagcac tttattgagt tcct | | 24 |

| | | |
|---|---|---|
| SEQ ID NO: 144 | moltype = RNA  length = 23 | |
| FEATURE | Location/Qualifiers | |
| source | 1..23 | |
| | mol_type = other RNA | |
| | organism = synthetic construct | |
| modified_base | 1 | |
| | mod_base = OTHER | |
| | note = 2'-O-hexadecyl-uridine-3'-phosphorothioate | |
| modified_base | 2 | |
| | mod_base = OTHER | |
| | note = 2'-deoxy-2'-fluorocytidine-3'-phosphorothioate | |
| modified_base | 3 | |
| | mod_base = OTHER | |
| | note = 2'-O-methyladenosine-3'-phosphate | |
| modified_base | 4 | |
| | mod_base = OTHER | |
| | note = 2'-O-methyladenosine-3'-phosphate | |
| modified_base | 5 | |
| | mod_base = OTHER | |
| | note = 2'-O-methyladenosine-3'-phosphate | |
| modified_base | 6 | |
| | mod_base = OTHER | |
| | note = 2'-deoxy-2'-fluoroguanosine-3'-phosphate | |
| modified_base | 7 | |
| | mod_base = OTHER | |
| | note = 2'-O-methylcytidine-3'-phosphate | |
| modified_base | 8 | |
| | mod_base = OTHER | |
| | note = 2'-deoxy-2'-fluoroadenosine-3'-phosphate | |
| modified_base | 9 | |
| | mod_base = OTHER | |
| | note = 2'-deoxy-2'-fluorocytidine-3'-phosphate | |
| modified_base | 10 | |
| | mod_base = OTHER | |
| | note = 2'-O-methyluridine-3'-phosphate | |
| modified_base | 11 | |
| | mod_base = OTHER | |
| | note = 2'-O-methyluridine-3'-phosphate | |
| modified_base | 12 | |
| | mod_base = OTHER | |
| | note = 2'-O-methyluridine-3'-phosphate | |
| modified_base | 13 | |
| | mod_base = OTHER | |
| | note = 2'-O-methyladenosine-3'-phosphate | |
| modified_base | 14 | |
| | mod_base = OTHER | |
| | note = 2'-deoxy-2'-fluorouridine-3'-phosphate | |
| modified_base | 15 | |
| | mod_base = OTHER | |
| | note = 2'-O-methyluridine-3'-phosphate | |
| modified_base | 16 | |
| | mod_base = OTHER | |
| | note = 2'-deoxy-2'-fluoroguanosine-3'-phosphate | |
| modified_base | 17 | |
| | mod_base = OTHER | |
| | note = 2'-O-methyladenosine-3'-phosphate | |
| modified_base | 18 | |
| | mod_base = OTHER | |
| | note = 2'-O-methylguanosine-3'-phosphate | |
| modified_base | 19 | |
| | mod_base = OTHER | |
| | note = 2'-O-methyluridine-3'-phosphate | |
| modified_base | 20 | |
| | mod_base = OTHER | |
| | note = 2'-O-methyluridine-3'-phosphate | |
| modified_base | 21 | |
| | mod_base = OTHER | |
| | note = 2'-O-methylcytidine-3'-phosphorothioate | |
| modified_base | 22 | |
| | mod_base = OTHER | |
| | note = 2'-O-methylcytidine-3'-phosphorothioate | |
| modified_base | 23 | |
| | mod_base = OTHER | |

```
                        note = 2'-O-methyluridine
SEQUENCE: 144
tcaaagcact ttattgagtt cct                                           23

SEQ ID NO: 145          moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methyladenosine-3'-phosphate
modified_base           4
                        mod_base = OTHER
                        note = 2'-O-methylcytidine-3'-phosphate
modified_base           5
                        mod_base = OTHER
                        note = 2'-O-methyluridine-3'-phosphate
modified_base           6
                        mod_base = OTHER
                        note = 2'-O-methylcytidine-3'-phosphate
modified_base           7
                        mod_base = OTHER
                        note = 2'-deoxy-2'-fluoroadenosine-3'-phosphate
modified_base           8
                        mod_base = OTHER
                        note = 2'-O-methyladenosine-3'-phosphate
modified_base           9
                        mod_base = OTHER
                        note = 2'-O-hexadecyl-uridine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyladenosine-3'-phosphate
modified_base           13
                        mod_base = OTHER
                        note = 2'-O-methylguanosine-3'-phosphate
modified_base           14
                        mod_base = OTHER
                        note = 2'-O-methyluridine-3'-phosphate
modified_base           15
                        mod_base = OTHER
                        note = 2'-O-methylguanosine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methylguanosine-3'-phosphate
modified_base           21
                        mod_base = OTHER
                        note = 2'-O-methyladenosine-3'-phosphate
                        ((2S,4R)-1-[29-[[2-(acetylamino)-2-deoxy-beta-D-galactopyra
                        nosyl]oxy]-14,14-bis[[3-[[3-[[5-[[2-(acetylamino)-2-deoxy-b
                        eta-D-galactopyranosyl]oxy]-1-oxopentyl]amino]propyl]amino]
                        -3-oxopropoxy]methyl]-1,12,19,25-tetraoxo-16-oxa-13,20,24-t
                        riazanonacos-1-yl]-4-hydroxy-2-pyrrolidinyl)methyl ester
SEQUENCE: 145
gaactcaata aagtgctttg a                                             21
```

```
SEQ ID NO: 146          moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
modified_base           2
                        mod_base = OTHER
                        note = 2'-O-hexadecyl-adenosine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-deoxy-2'-fluorocytidine-3'-phosphate
modified_base           7
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methyladenosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylguanosine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methylcytidine-3'-phosphorothioate
modified_base           22
                        mod_base = OTHER
                        note = 2'-O-methyluridine-3'-phosphorothioate
modified_base           23
                        mod_base = OTHER
                        note = 2'-O-methylguanosine
SEQUENCE: 146
taaagcactt tattgagttt ctg                                             23

SEQ ID NO: 147          moltype = RNA  length = 21
```

| FEATURE | Location/Qualifiers |
|---|---|
| source | 1..21 |
| | mol_type = other RNA |
| | organism = synthetic construct |
| modified_base | 1 |
| | mod_base = OTHER |
| | note = 2'-O-methyladenosine-3'-phosphorothioate |
| modified_base | 2 |
| | mod_base = OTHER |
| | note = 2'-O-methyladenosine-3'-phosphorothioate |
| modified_base | 3 |
| | mod_base = OTHER |
| | note = 2'-O-methylcytidine-3'-phosphate |
| modified_base | 4 |
| | mod_base = OTHER |
| | note = 2'-O-methyladenosine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-O-methyluridine-3'-phosphate |
| modified_base | 7 |
| | mod_base = OTHER |
| | note = 2'-deoxy-2'-fluoroguanosine-3'-phosphate |
| modified_base | 8 |
| | mod_base = OTHER |
| | note = 2'-O-methyluridine-3'-phosphate |
| modified_base | 9 |
| | mod_base = OTHER |
| | note = 2'-deoxy-2'-fluorouridine-3'-phosphate |
| modified_base | 10 |
| | mod_base = OTHER |
| | note = 2'-deoxy-2'-fluorocytidine-3'-phosphate |
| modified_base | 11 |
| | mod_base = OTHER |
| | note = 2'-deoxy-2'-fluorouridine-3'-phosphate |
| modified_base | 12 |
| | mod_base = OTHER |
| | note = 2'-O-methyluridine-3'-phosphate |
| modified_base | 13 |
| | mod_base = OTHER |
| | note = 2'-O-methylguanosine-3'-phosphate |
| modified_base | 14 |
| | mod_base = OTHER |
| | note = 2'-O-methylcytidine-3'-phosphate |
| modified_base | 15 |
| | mod_base = OTHER |
| | note = 2'-O-methyluridine-3'-phosphate |
| modified_base | 16 |
| | mod_base = OTHER |
| | note = 2'-O-methylcytidine-3'-phosphate |
| modified_base | 17 |
| | mod_base = OTHER |
| | note = 2'-O-methyluridine-3'-phosphate |
| modified_base | 18 |
| | mod_base = OTHER |
| | note = 2'-O-methyladenosine-3'-phosphate |
| modified_base | 19 |
| | mod_base = OTHER |
| | note = 2'-O-methyluridine-3'-phosphate |
| modified_base | 20 |
| | mod_base = OTHER |
| | note = 2'-O-methyladenosine-3'-phosphate |
| modified_base | 21 |
| | mod_base = OTHER |
| | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 147 | |
| aacagtgttc ttgctctata a | 21 |

| SEQ ID NO: 148 | moltype = RNA  length = 23 |
|---|---|
| FEATURE | Location/Qualifiers |
| source | 1..23 |
| | mol_type = other RNA |

|  | organism = synthetic construct |
| --- | --- |
| modified_base | 1 |
|  | mod_base = OTHER |
|  | note = 2'-O-methyluridine-3'-phosphorothioate |
| modified_base | 2 |
|  | mod_base = OTHER |
|  | note = 2'-deoxy-2'-fluorouridine-3'-phosphorothioate |
| modified_base | 3 |
|  | mod_base = OTHER |
|  | note = 2'-O-methyladenosine-3'-phosphate |
| modified_base | 4 |
|  | mod_base = OTHER |
|  | note = 2'-O-methyluridine-3'-phosphate |
| modified_base | 5 |
|  | mod_base = OTHER |
|  | note = 2'-O-methyladenosine-3'-phosphate |
| modified_base | 6 |
|  | mod_base = OTHER |
|  | note = 2'-deoxy-2'-fluoroguanosine-3'-phosphate |
| modified_base | 7 |
|  | mod_base = OTHER |
|  | note = 2'-O-methyladenosine-3'-phosphate |
| modified_base | 8 |
|  | mod_base = OTHER |
|  | note = 2'-deoxy-2'-fluoroguanosine-3'-phosphate |
| modified_base | 9 |
|  | mod_base = OTHER |
|  | note = 2'-deoxy-2'-fluorocytidine-3'-phosphate |
| modified_base | 10 |
|  | mod_base = OTHER |
|  | note = 2'-O-methyladenosine-3'-phosphate |
| modified_base | 11 |
|  | mod_base = OTHER |
|  | note = 2'-O-methyladenosine-3'-phosphate |
| modified_base | 12 |
|  | mod_base = OTHER |
|  | note = 2'-O-methylguanosine-3'-phosphate |
| modified_base | 13 |
|  | mod_base = OTHER |
|  | note = 2'-O-methyladenosine-3'-phosphate |
| modified_base | 14 |
|  | mod_base = OTHER |
|  | note = 2'-deoxy-2'-fluoroadenosine-3'-phosphate |
| modified_base | 15 |
|  | mod_base = OTHER |
|  | note = 2'-O-methylcytidine-3'-phosphate |
| modified_base | 16 |
|  | mod_base = OTHER |
|  | note = 2'-deoxy-2'-fluoroadenosine-3'-phosphate |
| modified_base | 17 |
|  | mod_base = OTHER |
|  | note = 2'-O-methylcytidine-3'-phosphate |
| modified_base | 18 |
|  | mod_base = OTHER |
|  | note = 2'-O-methyluridine-3'-phosphate |
| modified_base | 19 |
|  | mod_base = OTHER |
|  | note = 2'-O-methylguanosine-3'-phosphate |
| modified_base | 20 |
|  | mod_base = OTHER |
|  | note = 2'-O-methyluridine-3'-phosphate |
| modified_base | 21 |
|  | mod_base = OTHER |
|  | note = 2'-O-methyluridine-3'-phosphorothioate |
| modified_base | 22 |
|  | mod_base = OTHER |
|  | note = 2'-O-methyluridine-3'-phosphorothioate |
| modified_base | 23 |
|  | mod_base = OTHER |
|  | note = 2'-O-methyluridine |
| SEQUENCE: 148 |  |
| ttatagagca agaacactgt ttt | 23 |
|  |  |
| SEQ ID NO: 149 | moltype = RNA  length = 21 |
| FEATURE | Location/Qualifiers |
| source | 1..21 |
|  | mol_type = other RNA |
|  | organism = synthetic construct |
| modified_base | 1 |

|  |  |
|---|---|
|  | mod_base = OTHER |
|  | note = 2'-O-methyladenosine-3'-phosphorothioate 5'-(1-(6-(cholester-3-yloxycarboxamido)caproyl)-prolinol-4-yl) phosphate |
| modified_base | 2 |
|  | mod_base = OTHER |
|  | note = 2'-O-methyladenosine-3'-phosphorothioate |
| modified_base | 3 |
|  | mod_base = OTHER |
|  | note = 2'-O-methylcytidine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methylguanosine-3'-phosphate |
| modified_base | 6 |
|  | mod_base = OTHER |
|  | note = 2'-O-methyluridine-3'-phosphate |
| modified_base | 7 |
|  | mod_base = OTHER |
|  | note = 2'-deoxy-2'-fluoroguanosine-3'-phosphate |
| modified_base | 8 |
|  | mod_base = OTHER |
|  | note = 2'-O-methyluridine-3'-phosphate |
| modified_base | 9 |
|  | mod_base = OTHER |
|  | note = 2'-deoxy-2'-fluorouridine-3'-phosphate |
| modified_base | 10 |
|  | mod_base = OTHER |
|  | note = 2'-deoxy-2'-fluorocytidine-3'-phosphate |
| modified_base | 11 |
|  | mod_base = OTHER |
|  | note = 2'-deoxy-2'-fluorouridine-3'-phosphate |
| modified_base | 12 |
|  | mod_base = OTHER |
|  | note = 2'-O-methyluridine-3'-phosphate |
| modified_base | 13 |
|  | mod_base = OTHER |
|  | note = 2'-O-methylguanosine-3'-phosphate |
| modified_base | 14 |
|  | mod_base = OTHER |
|  | note = 2'-O-methylcytidine-3'-phosphate |
| modified_base | 15 |
|  | mod_base = OTHER |
|  | note = 2'-O-methyluridine-3'-phosphate |
| modified_base | 16 |
|  | mod_base = OTHER |
|  | note = 2'-O-methylcytidine-3'-phosphate |
| modified_base | 17 |
|  | mod_base = OTHER |
|  | note = 2'-O-methyluridine-3'-phosphate |
| modified_base | 18 |
|  | mod_base = OTHER |
|  | note = 2'-O-methyladenosine-3'-phosphate |
| modified_base | 19 |
|  | mod_base = OTHER |
|  | note = 2'-O-methyluridine-3'-phosphate |
| modified_base | 20 |
|  | mod_base = OTHER |
|  | note = 2'-O-methyladenosine-3'-phosphate |
| modified_base | 21 |
|  | mod_base = OTHER |
|  | note = 2'-O-methyladenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| SEQUENCE: 149 |  |
| aacagtgttc ttgctctata a |  | 21 |
|  |  |
| SEQ ID NO: 150 | moltype = RNA  length = 21 |
| FEATURE | Location/Qualifiers |
| source | 1..21 |
|  | mol_type = other RNA |
|  | organism = synthetic construct |
| modified_base | 1 |
|  | mod_base = OTHER |

|  |  |
|---|---|
| modified_base | note = 2'-O-methyladenosine-3'-phosphorothioate<br>2<br>mod_base = OTHER<br>note = 2'-O-methyladenosine-3'-phosphorothioate |
| modified_base | 3<br>mod_base = OTHER<br>note = 2'-O-methylcytidine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylguanosine-3'-phosphate |
| modified_base | 6<br>mod_base = OTHER<br>note = 2'-O-hexadecyl-uridine-3'-phosphate |
| modified_base | 7<br>mod_base = OTHER<br>note = 2'-deoxy-2'-fluoroguanosine-3'-phosphate |
| modified_base | 8<br>mod_base = OTHER<br>note = 2'-O-methyluridine-3'-phosphate |
| modified_base | 9<br>mod_base = OTHER<br>note = 2'-deoxy-2'-fluorouridine-3'-phosphate |
| modified_base | 10<br>mod_base = OTHER<br>note = 2'-deoxy-2'-fluorocytidine-3'-phosphate |
| modified_base | 11<br>mod_base = OTHER<br>note = 2'-deoxy-2'-fluorouridine-3'-phosphate |
| modified_base | 12<br>mod_base = OTHER<br>note = 2'-O-methyluridine-3'-phosphate |
| modified_base | 13<br>mod_base = OTHER<br>note = 2'-O-methylguanosine-3'-phosphate |
| modified_base | 14<br>mod_base = OTHER<br>note = 2'-O-methylcytidine-3'-phosphate |
| modified_base | 15<br>mod_base = OTHER<br>note = 2'-O-methyluridine-3'-phosphate |
| modified_base | 16<br>mod_base = OTHER<br>note = 2'-O-methylcytidine-3'-phosphate |
| modified_base | 17<br>mod_base = OTHER<br>note = 2'-O-methyluridine-3'-phosphate |
| modified_base | 18<br>mod_base = OTHER<br>note = 2'-O-methyladenosine-3'-phosphate |
| modified_base | 19<br>mod_base = OTHER<br>note = 2'-O-methyluridine-3'-phosphate |
| modified_base | 20<br>mod_base = OTHER<br>note = 2'-O-methyladenosine-3'-phosphate |
| modified_base | 21<br>mod_base = OTHER<br>note = 2'-O-methyladenosine-3'-phosphate<br>((2S,4R)-1-[29-[[2-(acetylamino)-2-deoxy-beta-D-galactopyra<br>nosyl]oxy]-14,14-bis[[3-[[3-[[5-[[2-(acetylamino)-2-deoxy-b<br>eta-D-galactopyranosyl]oxy]-1-oxopentyl]amino]propyl]amino]<br>-3-oxopropoxy]methyl]-1,12,19,25-tetraoxo-16-oxa-13,20,24-t<br>riazanonacos-1-yl]-4-hydroxy-2-pyrrolidinyl)methyl ester |
| SEQUENCE: 150 | |
| aacagtgttc ttgctctata a | 21 |
| SEQ ID NO: 151<br>FEATURE<br>source | moltype = DNA  length = 21<br>Location/Qualifiers<br>1..21<br>mol_type = other DNA<br>organism = synthetic construct |
| modified_base | 1<br>mod_base = OTHER<br>note = 2'-O-methoxyethyl-5-methyluridine-3'-phosphorothioate |
| modified_base | 2<br>mod_base = OTHER |

|   |   |
|---|---|
|  | note = 2'-O-methoxyethyl-5-methylcytidine-3'-phosphorothioate |
| modified_base | 3 |
|  | mod_base = OTHER |
|  | note = 2'-O-methoxyethyl-5-methyluridine-3'-phosphorothioate |
| modified_base | 4 |
|  | mod_base = OTHER |
|  | note = 2'-O-methoxyethyl-5-methyluridine-3'-phosphorothioate |
| modified_base | 5 |
|  | mod_base = OTHER |
|  | note = 2'-O-methoxyethylguanosine-3'-phosphorothioate |
| modified_base | 6 |
|  | mod_base = OTHER |
|  | note = 2'-deoxyguanosine-3'-phosphorothioate |
| modified_base | 7 |
|  | mod_base = OTHER |
|  | note = 2'-deoxythymidine-3'-phosphorothioate |
| modified_base | 8 |
|  | mod_base = OTHER |
|  | note = 2'-deoxythymidine-3'-phosphorothioate |
| modified_base | 9 |
|  | mod_base = OTHER |
|  | note = 2'-deoxyadenosine-3'-phosphorothioate |
| modified_base | 10 |
|  | mod_base = OTHER |
|  | note = 2'-deoxy-5-methylcytidine-3'-phosphorothioate |
| modified_base | 11 |
|  | mod_base = OTHER |
|  | note = 2'-deoxyadenosine-3'-phosphorothioate |
| modified_base | 12 |
|  | mod_base = OTHER |
|  | note = 2'-deoxythymidine-3'-phosphorothioate |
| modified_base | 13 |
|  | mod_base = OTHER |
|  | note = 2'-deoxyguanosine-3'-phosphorothioate |
| modified_base | 14 |
|  | mod_base = OTHER |
|  | note = 2'-deoxyadenosine-3'-phosphorothioate |
| modified_base | 15 |
|  | mod_base = OTHER |
|  | note = 2'-deoxyadenosine-3'-phosphorothioate |
| modified_base | 16 |
|  | mod_base = OTHER |
|  | note = 2'-O-methoxyethyl-adenosine-3'-phosphorothioate |
| modified_base | 17 |
|  | mod_base = OTHER |
|  | note = 2'-O-methoxyethyl-5-methyluridine-3'-phosphorothioate |
| modified_base | 18 |
|  | mod_base = OTHER |
|  | note = 2'-O-methoxyethyl-5-methylcytidine-3'-phosphorothioate |
| modified_base | 19 |
|  | mod_base = OTHER |
|  | note = 2'-O-methoxyethyl-5-methylcytidine-3'-phosphorothioate |
| modified_base | 20 |
|  | mod_base = OTHER |
|  | note = 2'-O-methoxyethyl-5-methylcytidine-3'-phosphorothioate |
| modified_base | 21 |
|  | mod_base = OTHER |
|  | note = 2'-deoxyadenosine-3'-phosphate ((2S,4R)-1-[29-[[2-(acetylamino)-2-deoxy-beta-D-galactopyranosyl]oxy]-14,14-bis[[3-[[3-[[5-[[2-(acetylamino)-2-deoxy-beta-D-galactopyranosyl]oxy]-1-oxopentyl]amino]propyl]amino]-3-oxopropoxy]methyl]-1,12,19,25-tetraoxo-16-oxa-13,20,24-triazanonacos-1-yl]-4-hydroxy-2-pyrrolidinyl)methyl ester |
| misc_feature | 1..5 |
|  | note = RNA |
| misc_feature | 16..20 |
|  | note = RNA |
| misc_feature | 6..15 |
|  | note = DNA |
| misc_feature | 21 |
|  | note = DNA |
| SEQUENCE: 151 |  |
| tcttggttac atgaaatccc a | 21 |
|  |  |
| SEQ ID NO: 152 | moltype = DNA length = 21 |

-continued

| FEATURE | Location/Qualifiers |
|---|---|
| source | 1..21 |
| | mol_type = other DNA |
| | organism = synthetic construct |
| modified_base | 1 |
| | mod_base = OTHER |
| | note = 2'-O-methoxyethyl-5-methyluridine-3'-phosphorothioate |
| modified_base | 2 |
| | mod_base = OTHER |
| | note = 2'-O-methoxyethyl-5-methyluridine-3'-phosphorothioate |
| modified_base | 3 |
| | mod_base = OTHER |
| | note = 2'-O-methoxyethyl-adenosine-3'-phosphorothioate |
| modified_base | 4 |
| | mod_base = OTHER |
| | note = 2'-O-methoxyethyl-5-methyluridine-3'-phosphorothioate |
| modified_base | 5 |
| | mod_base = OTHER |
| | note = 2'-O-methoxyethyl-adenosine-3'-phosphorothioate |
| modified_base | 6 |
| | mod_base = OTHER |
| | note = 2'-deoxyguanosine-3'-phosphorothioate |
| modified_base | 7 |
| | mod_base = OTHER |
| | note = 2'-deoxyadenosine-3'-phosphorothioate |
| modified_base | 8 |
| | mod_base = OTHER |
| | note = 2'-deoxyguanosine-3'-phosphorothioate |
| modified_base | 9 |
| | mod_base = OTHER |
| | note = 2'-deoxy-5-methylcytidine-3'-phosphorothioate |
| modified_base | 10 |
| | mod_base = OTHER |
| | note = 2'-deoxyadenosine-3'-phosphorothioate |
| modified_base | 11 |
| | mod_base = OTHER |
| | note = 2'-deoxyadenosine-3'-phosphorothioate |
| modified_base | 12 |
| | mod_base = OTHER |
| | note = 2'-deoxyguanosine-3'-phosphorothioate |
| modified_base | 13 |
| | mod_base = OTHER |
| | note = 2'-deoxyadenosine-3'-phosphorothioate |
| modified_base | 14 |
| | mod_base = OTHER |
| | note = 2'-deoxyadenosine-3'-phosphorothioate |
| modified_base | 15 |
| | mod_base = OTHER |
| | note = 2'-deoxy-5-methylcytidine-3'-phosphorothioate |
| modified_base | 16 |
| | mod_base = OTHER |
| | note = 2'-O-methoxyethyl-adenosine-3'-phosphorothioate |
| modified_base | 17 |
| | mod_base = OTHER |
| | note = |
| | 2'-O-methoxyethyl-5-methylcytidine-3'-phosphorothioate |
| modified_base | 18 |
| | mod_base = OTHER |
| | note = 2'-O-methoxyethyl-5-methyluridine-3'-phosphorothioate |
| modified_base | 19 |
| | mod_base = OTHER |
| | note = 2'-O-methoxyethylguanosine-3'-phosphorothioate |
| modified_base | 20 |
| | mod_base = OTHER |
| | note = 2'-O-methoxyethyl-5-methyluridine-3'-phosphate |
| modified_base | 21 |
| | mod_base = OTHER |
| | note = 2'-deoxyadenosine-3'-phosphate |
| | ((2S,4R)-1-[29-[[2-(acetylamino)-2-deoxy-beta-D-galactopyra |
| | nosyl]oxy]-14,14-bis[[3-[[3-[[5-[[2-(acetylamino)-2-deoxy-b |
| | eta-D-galactopyranosyl]oxy]-1-oxopentyl]amino]propyl]amino] |
| | -3-oxopropoxy]methyl]-1,12,19,25-tetraoxo-16-oxa-13,20,24-t |
| | riazanonacos-1-yl]-4-hydroxy-2-pyrrolidinyl)methyl ester |
| misc_feature | 1..5 |
| | note = RNA |
| misc_feature | 16..20 |
| | note = RNA |
| misc_feature | 6..15 |
| | note = DNA |

```
                           -continued misc_feature               21
                           note = DNA
SEQUENCE: 152
ttatagagca agaacactgt a                                              21

SEQ ID NO: 153             moltype = RNA   length = 21
FEATURE                    Location/Qualifiers
source                     1..21
                           mol_type = other RNA
                           organism = synthetic construct
modified_base              1
                           mod_base = OTHER
                           note = 2'-O-methyluridine-3'-phosphate
modified_base              2
                           mod_base = OTHER
                           note = 2'-O-methyladenosine-3'-phosphate
modified_base              3
                           mod_base = OTHER
                           note = 2'-O-methylcytidine-3'-phosphate
modified_base              4
                           mod_base = OTHER
                           note = 2'-O-methyluridine-3'-phosphate
modified_base              5
                           mod_base = OTHER
                           note = 2'-O-methylguanosine-3'-phosphate
modified_base              6
                           mod_base = OTHER
                           note = 2'-O-methyluridine-3'-phosphate
modified_base              7
                           mod_base = OTHER
                           note = 2'-O-methyluridine-3'-phosphate
modified_base              8
                           mod_base = OTHER
                           note = 2'-O-methylguanosine-3'-phosphate
modified_base              9
                           mod_base = OTHER
                           note = 2'-O-methylguanosine-3'-phosphate
modified_base              10
                           mod_base = OTHER
                           note = 2'-O-methyladenosine-3'-phosphate
modified_base              11
                           mod_base = OTHER
                           note = 2'-O-methyluridine-3'-phosphate
modified_base              12
                           mod_base = OTHER
                           note = 2'-O-methyluridine-3'-phosphate
modified_base              13
                           mod_base = OTHER
                           note = 2'-O-methylguanosine-3'-phosphate
modified_base              14
                           mod_base = OTHER
                           note = 2'-O-methyladenosine-3'-phosphate
modified_base              15
                           mod_base = OTHER
                           note = 2'-O-methyluridine-3'-phosphate
modified_base              16
                           mod_base = OTHER
                           note = 2'-O-methyluridine-3'-phosphate
modified_base              17
                           mod_base = OTHER
                           note = 2'-O-methylcytidine-3'-phosphate
modified_base              18
                           mod_base = OTHER
                           note = 2'-O-methylguanosine-3'-phosphate
modified_base              19
                           mod_base = OTHER
                           note = 2'-O-methyladenosine-3'-phosphate
modified_base              20
                           mod_base = OTHER
                           note = 2'-O-methyladenosine-3'-phosphate
modified_base              21
                           mod_base = OTHER
                           note = 2'-O-methyladenosine
SEQUENCE: 153
tactgttgga ttgattcgaa a                                              21

SEQ ID NO: 154             moltype = RNA   length = 23
FEATURE                    Location/Qualifiers
source                     1..23
```

|  |  |
|---|---|
| modified_base | 1<br>mod_base = OTHER<br>note = 2'-O-methyl-5-methyluridine-3'-phosphate |
| modified_base | 2<br>mod_base = OTHER<br>note = 2'-O-methyluridine-3'-phosphate |
| modified_base | 3<br>mod_base = OTHER<br>note = 2'-O-methyluridine-3'-phosphate |
| modified_base | 4<br>mod_base = OTHER<br>note = 2'-O-methylcytidine-3'-phosphate |
| modified_base | 5<br>mod_base = OTHER<br>note = 2'-O-methylguanosine-3'-phosphate |
| modified_base | 6<br>mod_base = OTHER<br>note = 2'-O-methyladenosine-3'-phosphate |
| modified_base | 7<br>mod_base = OTHER<br>note = 2'-O-methyladenosine-3'-phosphate |
| modified_base | 8<br>mod_base = OTHER<br>note = 2'-O-methyluridine-3'-phosphate |
| modified_base | 9<br>mod_base = OTHER<br>note = 2'-O-methylcytidine-3'-phosphate |
| modified_base | 10<br>mod_base = OTHER<br>note = 2'-O-methyladenosine-3'-phosphate |
| modified_base | 11<br>mod_base = OTHER<br>note = 2'-O-methyladenosine-3'-phosphate |
| modified_base | 12<br>mod_base = OTHER<br>note = 2'-O-methyluridine-3'-phosphate |
| modified_base | 13<br>mod_base = OTHER<br>note = 2'-O-methylcytidine-3'-phosphate |
| modified_base | 14<br>mod_base = OTHER<br>note = 2'-O-methylcytidine-3'-phosphate |
| modified_base | 15<br>mod_base = OTHER<br>note = 2'-O-methyladenosine-3'-phosphate |
| modified_base | 16<br>mod_base = OTHER<br>note = 2'-O-methyladenosine-3'-phosphate |
| modified_base | 17<br>mod_base = OTHER<br>note = 2'-O-methylcytidine-3'-phosphate |
| modified_base | 18<br>mod_base = OTHER<br>note = 2'-O-methyladenosine-3'-phosphate |
| modified_base | 19<br>mod_base = OTHER<br>note = 2'-O-methylguanosine-3'-phosphate |
| modified_base | 20<br>mod_base = OTHER<br>note = 2'-O-methyluridine-3'-phosphate |
| modified_base | 21<br>mod_base = OTHER<br>note = 2'-O-methyladenosine-3'-phosphate |
| modified_base | 22<br>mod_base = OTHER<br>note = 2'-O-methylguanosine-3'-phosphate |
| modified_base | 23<br>mod_base = OTHER<br>note = 2'-O-methylcytidine |

SEQUENCE: 154
tttcgaatca atccaacagt agc                                    23

| SEQ ID NO: 155 | moltype = RNA  length = 21 |
|---|---|
| FEATURE | Location/Qualifiers |
| source | 1..21<br>mol_type = other RNA<br>organism = synthetic construct |

| | |
|---|---|
| modified_base | 1<br>mod_base = OTHER<br>note = 2'-O-methylcytidine-3'-phosphate |
| modified_base | 2<br>mod_base = OTHER<br>note = 2'-O-methyladenosine-3'-phosphate |
| modified_base | 3<br>mod_base = OTHER<br>note = 2'-O-methyluridine-3'-phosphate |
| modified_base | 4<br>mod_base = OTHER<br>note = 2'-O-methyluridine-3'-phosphate |
| modified_base | 5<br>mod_base = OTHER<br>note = 2'-O-methyluridine-3'-phosphate |
| modified_base | 6<br>mod_base = OTHER<br>note = 2'-O-methyluridine-3'-phosphate |
| modified_base | 7<br>mod_base = OTHER<br>note = 2'-O-methyladenosine-3'-phosphate |
| modified_base | 8<br>mod_base = OTHER<br>note = 2'-O-methyladenosine-3'-phosphate |
| modified_base | 9<br>mod_base = OTHER<br>note = 2'-O-methyluridine-3'-phosphate |
| modified_base | 10<br>mod_base = OTHER<br>note = 2'-O-methylcytidine-3'-phosphate |
| modified_base | 11<br>mod_base = OTHER<br>note = 2'-O-methylcytidine-3'-phosphate |
| modified_base | 12<br>mod_base = OTHER<br>note = 2'-O-methyluridine-3'-phosphate |
| modified_base | 13<br>mod_base = OTHER<br>note = 2'-O-methylcytidine-3'-phosphate |
| modified_base | 14<br>mod_base = OTHER<br>note = 2'-O-methyladenosine-3'-phosphate |
| modified_base | 15<br>mod_base = OTHER<br>note = 2'-O-methylcytidine-3'-phosphate |
| modified_base | 16<br>mod_base = OTHER<br>note = 2'-O-methyluridine-3'-phosphate |
| modified_base | 17<br>mod_base = OTHER<br>note = 2'-O-methylcytidine-3'-phosphate |
| modified_base | 18<br>mod_base = OTHER<br>note = 2'-O-methyluridine-3'-phosphate |
| modified_base | 19<br>mod_base = OTHER<br>note = 2'-O-methyladenosine-3'-phosphate |
| modified_base | 20<br>mod_base = OTHER<br>note = 2'-O-methyladenosine-3'-phosphate |
| modified_base | 21<br>mod_base = OTHER<br>note = 2'-O-methyladenosine |

SEQUENCE: 155
cattttaatc ctcactctaa a                                          21

| | |
|---|---|
| SEQ ID NO: 156<br>FEATURE<br>source | moltype = RNA  length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphate |
| modified_base | 2<br>mod_base = OTHER<br>note = 2'-O-methyluridine-3'-phosphate |
| modified_base | 3<br>mod_base = OTHER |

```
                      note = 2'-O-methyluridine-3'-phosphate
modified_base         4
                      mod_base = OTHER
                      note = 2'-O-methyladenosine-3'-phosphate
modified_base         5
                      mod_base = OTHER
                      note = 2'-O-methylguanosine-3'-phosphate
modified_base         6
                      mod_base = OTHER
                      note = 2'-O-methyladenosine-3'-phosphate
modified_base         7
                      mod_base = OTHER
                      note = 2'-O-methylguanosine-3'-phosphate
modified_base         8
                      mod_base = OTHER
                      note = 2'-O-methyluridine-3'-phosphate
modified_base         9
                      mod_base = OTHER
                      note = 2'-O-methylguanosine-3'-phosphate
modified_base         10
                      mod_base = OTHER
                      note = 2'-O-methyladenosine-3'-phosphate
modified_base         11
                      mod_base = OTHER
                      note = 2'-O-methylguanosine-3'-phosphate
modified_base         12
                      mod_base = OTHER
                      note = 2'-O-methylguanosine-3'-phosphate
modified_base         13
                      mod_base = OTHER
                      note = 2'-O-methyladenosine-3'-phosphate
modified_base         14
                      mod_base = OTHER
                      note = 2'-O-methyluridine-3'-phosphate
modified_base         15
                      mod_base = OTHER
                      note = 2'-O-methyluridine-3'-phosphate
modified_base         16
                      mod_base = OTHER
                      note = 2'-O-methyladenosine-3'-phosphate
modified_base         17
                      mod_base = OTHER
                      note = 2'-O-methyladenosine-3'-phosphate
modified_base         18
                      mod_base = OTHER
                      note = 2'-O-methyladenosine-3'-phosphate
modified_base         19
                      mod_base = OTHER
                      note = 2'-O-methyladenosine-3'-phosphate
modified_base         20
                      mod_base = OTHER
                      note = 2'-O-methyluridine-3'-phosphate
modified_base         21
                      mod_base = OTHER
                      note = 2'-O-methylguanosine-3'-phosphate
modified_base         22
                      mod_base = OTHER
                      note = 2'-O-methyladenosine-3'-phosphate
modified_base         23
                      mod_base = OTHER
                      note = 2'-O-methylguanosine
SEQUENCE: 156
tttagagtga ggattaaaat gag                                              23

SEQ ID NO: 157        moltype = RNA  length = 21
FEATURE               Location/Qualifiers
source                1..21
                      mol_type = other RNA
                      organism = synthetic construct
modified_base         1
                      mod_base = OTHER
                      note = 2'-O-methylcytidine-3'-phosphorothioate
modified_base         2
                      mod_base = OTHER
                      note = 2'-O-methyladenosine-3'-phosphorothioate
modified_base         3
                      mod_base = OTHER
                      note = 2'-O-methyluridine-3'-phosphate
modified_base         4
```

| | | |
|---|---|---|
| | | mod_base = OTHER |
| | | note = 2'-O-methyluridine-3'-phosphate |
| modified_base | 5 | |
| | | mod_base = OTHER |
| | | note = 2'-O-methyluridine-3'-phosphate |
| modified_base | 6 | |
| | | mod_base = OTHER |
| | | note = 2'-O-hexadecyl-uridine-3'-phosphate |
| modified_base | 7 | |
| | | mod_base = OTHER |
| | | note = 2'-deoxy-2'-fluoroadenosine-3'-phosphate |
| modified_base | 8 | |
| | | mod_base = OTHER |
| | | note = 2'-O-methyladenosine-3'-phosphate |
| modified_base | 9 | |
| | | mod_base = OTHER |
| | | note = 2'-deoxy-2'-fluorouridine-3'-phosphate |
| modified_base | 10 | |
| | | mod_base = OTHER |
| | | note = 2'-deoxy-2'-fluorocytidine-3'-phosphate |
| modified_base | 11 | |
| | | mod_base = OTHER |
| | | note = 2'-deoxy-2'-fluorocytidine-3'-phosphate |
| modified_base | 12 | |
| | | mod_base = OTHER |
| | | note = 2'-O-methyluridine-3'-phosphate |
| modified_base | 13 | |
| | | mod_base = OTHER |
| | | note = 2'-O-methylcytidine-3'-phosphate |
| modified_base | 14 | |
| | | mod_base = OTHER |
| | | note = 2'-O-methyladenosine-3'-phosphate |
| modified_base | 15 | |
| | | mod_base = OTHER |
| | | note = 2'-O-methylcytidine-3'-phosphate |
| modified_base | 16 | |
| | | mod_base = OTHER |
| | | note = 2'-O-methyluridine-3'-phosphate |
| modified_base | 17 | |
| | | mod_base = OTHER |
| | | note = 2'-O-methylcytidine-3'-phosphate |
| modified_base | 18 | |
| | | mod_base = OTHER |
| | | note = 2'-O-methyluridine-3'-phosphate |
| modified_base | 19 | |
| | | mod_base = OTHER |
| | | note = 2'-O-methyladenosine-3'-phosphorothioate |
| modified_base | 20 | |
| | | mod_base = OTHER |
| | | note = 2'-O-methyladenosine-3'-phosphorothioate |
| modified_base | 21 | |
| | | mod_base = OTHER |
| | | note = 2'-O-methyladenosine |

SEQUENCE: 157
cattttaatc ctcactctaa a                                              21

| | | |
|---|---|---|
| SEQ ID NO: 158 | moltype = RNA   length = 23 | |
| FEATURE | Location/Qualifiers | |
| source | 1..23 | |
| | | mol_type = other RNA |
| | | organism = synthetic construct |
| modified_base | 1 | |
| | | mod_base = OTHER |
| | | note = 2'-O-methyluridine-3'-phosphorothioate |
| | | 5'-(E)-Vinylphosphonate |
| modified_base | 2 | |
| | | mod_base = OTHER |
| | | note = 2'-deoxy-2'-fluorouridine-3'-phosphorothioate |
| modified_base | 3 | |
| | | mod_base = OTHER |
| | | note = 2'-O-methyluridine-3'-phosphate |
| modified_base | 4 | |
| | | mod_base = OTHER |
| | | note = 2'-O-methyladenosine-3'-phosphate |
| modified_base | 5 | |
| | | mod_base = OTHER |
| | | note = 2'-O-methylguanosine-3'-phosphate |
| modified_base | 6 | |
| | | mod_base = OTHER |

| | | |
|---|---|---|
| | | note = 2'-deoxy-2'-fluoroadenosine-3'-phosphate |
| modified_base | 7 | |
| | | mod_base = OTHER |
| | | note = 2'-O-methylguanosine-3'-phosphate |
| modified_base | 8 | |
| | | mod_base = OTHER |
| | | note = 2'-deoxy-2'-fluorouridine-3'-phosphate |
| modified_base | 9 | |
| | | mod_base = OTHER |
| | | note = 2'-deoxy-2'-fluoroguanosine-3'-phosphate |
| modified_base | 10 | |
| | | mod_base = OTHER |
| | | note = 2'-O-methyladenosine-3'-phosphate |
| modified_base | 11 | |
| | | mod_base = OTHER |
| | | note = 2'-O-methylguanosine-3'-phosphate |
| modified_base | 12 | |
| | | mod_base = OTHER |
| | | note = 2'-O-methylguanosine-3'-phosphate |
| modified_base | 13 | |
| | | mod_base = OTHER |
| | | note = 2'-O-methyladenosine-3'-phosphate |
| modified_base | 14 | |
| | | mod_base = OTHER |
| | | note = 2'-deoxy-2'-fluorouridine-3'-phosphate |
| modified_base | 15 | |
| | | mod_base = OTHER |
| | | note = 2'-O-methyluridine-3'-phosphate |
| modified_base | 16 | |
| | | mod_base = OTHER |
| | | note = 2'-deoxy-2'-fluoroadenosine-3'-phosphate |
| modified_base | 17 | |
| | | mod_base = OTHER |
| | | note = 2'-O-methyladenosine-3'-phosphate |
| modified_base | 18 | |
| | | mod_base = OTHER |
| | | note = 2'-O-methyladenosine-3'-phosphate |
| modified_base | 19 | |
| | | mod_base = OTHER |
| | | note = 2'-O-methyladenosine-3'-phosphate |
| modified_base | 20 | |
| | | mod_base = OTHER |
| | | note = 2'-O-methyluridine-3'-phosphate |
| modified_base | 21 | |
| | | mod_base = OTHER |
| | | note = 2'-O-methylguanosine-3'-phosphorothioate |
| modified_base | 22 | |
| | | mod_base = OTHER |
| | | note = 2'-O-methyladenosine-3'-phosphorothioate |
| modified_base | 23 | |
| | | mod_base = OTHER |
| | | note = 2'-O-methylguanosine |
| SEQUENCE: 158 | | |
| tttagagtga ggattaaaat gag | | 23 |
| | | |
| SEQ ID NO: 159 | moltype = RNA length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-O-methyladenosine-3'-phosphorothioate | |
| modified_base | 2 | |
| | mod_base = OTHER | |
| | note = 2'-O-methyladenosine-3'-phosphorothioate | |
| modified_base | 3 | |
| | mod_base = OTHER | |
| | note = 2'-O-methylcytidine-3'-phosphate | |
| modified_base | 4 | |
| | mod_base = OTHER | |
| | note = 2'-O-methyladenosine-3'-phosphate | |
| modified_base | 5 | |
| | mod_base = OTHER | |
| | note = 2'-O-methylguanosine-3'-phosphate | |
| modified_base | 6 | |
| | mod_base = OTHER | |
| | note = 2'-O-hexadecyl-uridine-3'-phosphate | |
| modified_base | 7 | |

-continued

|               |                                                                                                  |    |
|---------------|--------------------------------------------------------------------------------------------------|----|
|               | mod_base = OTHER                                                                                 |    |
|               | note = 2'-deoxy-2'-fluoroguanosine-3'-phosphate                                                  |    |
| modified_base | 8                                                                                                |    |
|               | mod_base = OTHER                                                                                 |    |
|               | note = 2'-O-methyluridine-3'-phosphate                                                           |    |
| modified_base | 9                                                                                                |    |
|               | mod_base = OTHER                                                                                 |    |
|               | note = 2'-deoxy-2'-fluorouridine-3'-phosphate                                                    |    |
| modified_base | 10                                                                                               |    |
|               | mod_base = OTHER                                                                                 |    |
|               | note = 2'-deoxy-2'-fluorocytidine-3'-phosphate                                                   |    |
| modified_base | 11                                                                                               |    |
|               | mod_base = OTHER                                                                                 |    |
|               | note = 2'-deoxy-2'-fluorouridine-3'-phosphate                                                    |    |
| modified_base | 12                                                                                               |    |
|               | mod_base = OTHER                                                                                 |    |
|               | note = 2'-O-methyluridine-3'-phosphate                                                           |    |
| modified_base | 13                                                                                               |    |
|               | mod_base = OTHER                                                                                 |    |
|               | note = 2'-O-methylguanosine-3'-phosphate                                                         |    |
| modified_base | 14                                                                                               |    |
|               | mod_base = OTHER                                                                                 |    |
|               | note = 2'-O-methylcytidine-3'-phosphate                                                          |    |
| modified_base | 15                                                                                               |    |
|               | mod_base = OTHER                                                                                 |    |
|               | note = 2'-O-methyluridine-3'-phosphate                                                           |    |
| modified_base | 16                                                                                               |    |
|               | mod_base = OTHER                                                                                 |    |
|               | note = 2'-O-methylcytidine-3'-phosphate                                                          |    |
| modified_base | 17                                                                                               |    |
|               | mod_base = OTHER                                                                                 |    |
|               | note = 2'-O-methyluridine-3'-phosphate                                                           |    |
| modified_base | 18                                                                                               |    |
|               | mod_base = OTHER                                                                                 |    |
|               | note = 2'-O-methyladenosine-3'-phosphate                                                         |    |
| modified_base | 19                                                                                               |    |
|               | mod_base = OTHER                                                                                 |    |
|               | note = 2'-O-methyluridine-3'-phosphorothioate                                                    |    |
| modified_base | 20                                                                                               |    |
|               | mod_base = OTHER                                                                                 |    |
|               | note = 2'-O-methyladenosine-3'-phosphorothioate                                                  |    |
| modified_base | 21                                                                                               |    |
|               | mod_base = OTHER                                                                                 |    |
|               | note = 2'-O-methyladenosine                                                                      |    |
| SEQUENCE: 159 |                                                                                                  |    |
| aacagtgttc ttgctctata a |                                                                                        | 21 |
|               |                                                                                                  |    |
| SEQ ID NO: 160 | moltype = RNA  length = 23                                                                      |    |
| FEATURE       | Location/Qualifiers                                                                              |    |
| source        | 1..23                                                                                            |    |
|               | mol_type = other RNA                                                                             |    |
|               | organism = synthetic construct                                                                   |    |
| modified_base | 1                                                                                                |    |
|               | mod_base = OTHER                                                                                 |    |
|               | note = 2'-O-methyluridine-3'-phosphate                                                           |    |
|               | 5'-(E)-Vinylphosphonate                                                                          |    |
| modified_base | 2                                                                                                |    |
|               | mod_base = OTHER                                                                                 |    |
|               | note = 2'-deoxy-2'-fluorouridine-3'-phosphate                                                    |    |
| modified_base | 3                                                                                                |    |
|               | mod_base = OTHER                                                                                 |    |
|               | note = 2'-O-methyladenosine-3'-phosphate                                                         |    |
| modified_base | 4                                                                                                |    |
|               | mod_base = OTHER                                                                                 |    |
|               | note = 2'-O-methyluridine-3'-phosphate                                                           |    |
| modified_base | 5                                                                                                |    |
|               | mod_base = OTHER                                                                                 |    |
|               | note = 2'-O-methyladenosine-3'-phosphate                                                         |    |
| modified_base | 6                                                                                                |    |
|               | mod_base = OTHER                                                                                 |    |
|               | note = 2'-deoxy-2'-fluoroguanosine-3'-phosphate                                                  |    |
| modified_base | 7                                                                                                |    |
|               | mod_base = OTHER                                                                                 |    |
|               | note = 2'-O-methyladenosine-3'-phosphate                                                         |    |
| modified_base | 8                                                                                                |    |
|               | mod_base = OTHER                                                                                 |    |
|               | note = 2'-O-methylguanosine-3'-phosphate                                                         |    |
| modified_base | 9                                                                                                |    |
|               | mod_base = OTHER                                                                                 |    |

```
                        note = 2'-O-methylcytidine-3'-phosphate
modified_base           10
                        mod_base = OTHER
                        note = 2'-O-methyladenosine-3'-phosphate
modified_base           11
                        mod_base = OTHER
                        note = 2'-O-methyladenosine-3'-phosphate
modified_base           12
                        mod_base = OTHER
                        note = 2'-O-methylguanosine-3'-phosphate
modified_base           13
                        mod_base = OTHER
                        note = 2'-O-methyladenosine-3'-phosphate
modified_base           14
                        mod_base = OTHER
                        note = 2'-deoxy-2'-fluoroadenosine-3'-phosphate
modified_base           15
                        mod_base = OTHER
                        note = 2'-O-methylcytidine-3'-phosphate
modified_base           16
                        mod_base = OTHER
                        note = 2'-deoxy-2'-fluoroadenosine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methylguanosine-3'-phosphate
modified_base           20
                        mod_base = OTHER
                        note = 2'-O-methyluridine-3'-phosphate
modified_base           21
                        mod_base = OTHER
                        note = 2'-O-methyluridine-3'-phosphorothioate
modified_base           22
                        mod_base = OTHER
                        note = 2'-O-methyluridine-3'-phosphorothioate
modified_base           23
                        mod_base = OTHER
                        note = 2'-O-methyluridine
SEQUENCE: 160
ttatagagca agaacactgt ttt                                               23

SEQ ID NO: 161          moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-O-tetradecyl-uridine-3'-phosphate
modified_base           7
                        mod_base = OTHER
                        note = 2'-deoxy-2'-fluoroguanosine-3'-phosphate
modified_base           8
                        mod_base = OTHER
                        note = 2'-O-methyluridine-3'-phosphate
modified_base           9
                        mod_base = OTHER
                        note = 2'-deoxy-2'-fluorouridine-3'-phosphate
modified_base           10
```

```
                        mod_base = OTHER
                        note = 2'-deoxy-2'-fluorocytidine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methylcytidine-3'-phosphate
modified_base           15
                        mod_base = OTHER
                        note = 2'-O-methyluridine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyladenosine-3'-phosphate
modified_base           19
                        mod_base = OTHER
                        note = 2'-O-methyluridine-3'-phosphorothioate
modified_base           20
                        mod_base = OTHER
                        note = 2'-O-methyladenosine-3'-phosphorothioate
modified_base           21
                        mod_base = OTHER
                        note = 2'-O-methyladenosine
SEQUENCE: 161
aacagtgttc ttgctctata a                                            21

SEQ ID NO: 162          moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-O-dodecyl-uridine-3'-phosphate
modified_base           7
                        mod_base = OTHER
                        note = 2'-deoxy-2'-fluoroguanosine-3'-phosphate
modified_base           8
                        mod_base = OTHER
                        note = 2'-O-methyluridine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
```

|  |  |
|---|---|
| modified_base | 13<br>mod_base = OTHER<br>note = 2'-O-methylguanosine-3'-phosphate |
| modified_base | 14<br>mod_base = OTHER<br>note = 2'-O-methylcytidine-3'-phosphate |
| modified_base | 15<br>mod_base = OTHER<br>note = 2'-O-methyluridine-3'-phosphate |
| modified_base | 16<br>mod_base = OTHER<br>note = 2'-O-methylcytidine-3'-phosphate |
| modified_base | 17<br>mod_base = OTHER<br>note = 2'-O-methyluridine-3'-phosphate |
| modified_base | 18<br>mod_base = OTHER<br>note = 2'-O-methyladenosine-3'-phosphate |
| modified_base | 19<br>mod_base = OTHER<br>note = 2'-O-methyluridine-3'-phosphorothioate |
| modified_base | 20<br>mod_base = OTHER<br>note = 2'-O-methyladenosine-3'-phosphorothioate |
| modified_base | 21<br>mod_base = OTHER<br>note = 2'-O-methyladenosine |
| SEQUENCE: 162 | |
| aacagtgttc ttgctctata a | 21 |
| SEQ ID NO: 163<br>FEATURE<br>source | moltype = RNA   length = 21<br>Location/Qualifiers<br>1..21<br>mol_type = other RNA<br>organism = synthetic construct |
| modified_base | 1<br>mod_base = OTHER<br>note = 2'-O-methyladenosine-3'-phosphorothioate |
| modified_base | 2<br>mod_base = OTHER<br>note = 2'-O-methyladenosine-3'-phosphorothioate |
| modified_base | 3<br>mod_base = OTHER<br>note = 2'-O-methylcytidine-3'-phosphate |
| modified_base | 4<br>mod_base = OTHER<br>note = 2'-O-methyladenosine-3'-phosphate |
| modified_base | 5<br>mod_base = OTHER<br>note = 2'-O-methylguanosine-3'-phosphate |
| modified_base | 6<br>mod_base = OTHER<br>note = 2'-O-decyl-uridine-3'-phosphate |
| modified_base | 7<br>mod_base = OTHER<br>note = 2'-deoxy-2'-fluoroguanosine-3'-phosphate |
| modified_base | 8<br>mod_base = OTHER<br>note = 2'-O-methyluridine-3'-phosphate |
| modified_base | 9<br>mod_base = OTHER<br>note = 2'-deoxy-2'-fluorouridine-3'-phosphate |
| modified_base | 10<br>mod_base = OTHER<br>note = 2'-deoxy-2'-fluorocytidine-3'-phosphate |
| modified_base | 11<br>mod_base = OTHER<br>note = 2'-deoxy-2'-fluorouridine-3'-phosphate |
| modified_base | 12<br>mod_base = OTHER<br>note = 2'-O-methyluridine-3'-phosphate |
| modified_base | 13<br>mod_base = OTHER<br>note = 2'-O-methylguanosine-3'-phosphate |
| modified_base | 14<br>mod_base = OTHER<br>note = 2'-O-methylcytidine-3'-phosphate |
| modified_base | 15<br>mod_base = OTHER |

```
                        note = 2'-O-methyluridine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyladenosine-3'-phosphate
modified_base           19
                        mod_base = OTHER
                        note = 2'-O-methyluridine-3'-phosphorothioate
modified_base           20
                        mod_base = OTHER
                        note = 2'-O-methyladenosine-3'-phosphorothioate
modified_base           21
                        mod_base = OTHER
                        note = 2'-O-methyladenosine
SEQUENCE: 163
aacagtgttc ttgctctata a                                               21

SEQ ID NO: 164          moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-O-oleyl-uridine-3'-phosphate
modified_base           7
                        mod_base = OTHER
                        note = 2'-deoxy-2'-fluoroguanosine-3'-phosphate
modified_base           8
                        mod_base = OTHER
                        note = 2'-O-methyluridine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methylcytidine-3'-phosphate
modified_base           15
                        mod_base = OTHER
                        note = 2'-O-methyluridine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
```

```
                        mod_base = OTHER
                        note = 2'-O-methyladenosine-3'-phosphate
modified_base           19
                        mod_base = OTHER
                        note = 2'-O-methyluridine-3'-phosphorothioate
modified_base           20
                        mod_base = OTHER
                        note = 2'-O-methyladenosine-3'-phosphorothioate
modified_base           21
                        mod_base = OTHER
                        note = 2'-O-methyladenosine
SEQUENCE: 164
aacagtgttc ttgctctata a                                                21

SEQ ID NO: 165          moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-O-[N-oleoyl-(6-aminohexyl)]-uridine-3'-phosphate
modified_base           7
                        mod_base = OTHER
                        note = 2'-deoxy-2'-fluoroguanosine-3'-phosphate
modified_base           8
                        mod_base = OTHER
                        note = 2'-O-methyluridine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methylcytidine-3'-phosphate
modified_base           15
                        mod_base = OTHER
                        note = 2'-O-methyluridine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyladenosine-3'-phosphate
modified_base           19
                        mod_base = OTHER
                        note = 2'-O-methyluridine-3'-phosphorothioate
modified_base           20
                        mod_base = OTHER
                        note = 2'-O-methyladenosine-3'-phosphorothioate
```

|  |  |
|---|---|
| modified_base | 21 |
|  | mod_base = OTHER |
|  | note = 2'-O-methyladenosine |using
| SEQUENCE: 165 | |
| aacagtgttc ttgctctata a | 21 |

| | |
|---|---|
| SEQ ID NO: 166 | moltype = RNA length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-O-methyladenosine-3'-phosphorothioate |
| modified_base | 2 |
|  | mod_base = OTHER |
|  | note = 2'-O-methyladenosine-3'-phosphorothioate |
| modified_base | 3 |
|  | mod_base = OTHER |
|  | note = 2'-O-methylcytidine-3'-phosphate |
| modified_base | 4 |
|  | mod_base = OTHER |
|  | note = 2'-O-methyladenosine-3'-phosphate |
| modified_base | 5 |
|  | mod_base = OTHER |
|  | note = 2'-O-methylguanosine-3'-phosphate |
| modified_base | 6 |
|  | mod_base = OTHER |
|  | note = 2'-O-[N-(5Z,8Z,11Z,14Z)-5,8,11,14-Eicosatetraenoyl-(6-amino hexyl)]-uridine-3'-phosphate |
| modified_base | 7 |
|  | mod_base = OTHER |
|  | note = 2'-deoxy-2'-fluoroguanosine-3'-phosphate |
| modified_base | 8 |
|  | mod_base = OTHER |
|  | note = 2'-O-methyluridine-3'-phosphate |
| modified_base | 9 |
|  | mod_base = OTHER |
|  | note = 2'-deoxy-2'-fluorouridine-3'-phosphate |
| modified_base | 10 |
|  | mod_base = OTHER |
|  | note = 2'-deoxy-2'-fluorocytidine-3'-phosphate |
| modified_base | 11 |
|  | mod_base = OTHER |
|  | note = 2'-deoxy-2'-fluorouridine-3'-phosphate |
| modified_base | 12 |
|  | mod_base = OTHER |
|  | note = 2'-O-methyluridine-3'-phosphate |
| modified_base | 13 |
|  | mod_base = OTHER |
|  | note = 2'-O-methylguanosine-3'-phosphate |
| modified_base | 14 |
|  | mod_base = OTHER |
|  | note = 2'-O-methylcytidine-3'-phosphate |
| modified_base | 15 |
|  | mod_base = OTHER |
|  | note = 2'-O-methyluridine-3'-phosphate |
| modified_base | 16 |
|  | mod_base = OTHER |
|  | note = 2'-O-methylcytidine-3'-phosphate |
| modified_base | 17 |
|  | mod_base = OTHER |
|  | note = 2'-O-methyluridine-3'-phosphate |
| modified_base | 18 |
|  | mod_base = OTHER |
|  | note = 2'-O-methyladenosine-3'-phosphate |
| modified_base | 19 |
|  | mod_base = OTHER |
|  | note = 2'-O-methyluridine-3'-phosphorothioate |
| modified_base | 20 |
|  | mod_base = OTHER |
|  | note = 2'-O-methyladenosine-3'-phosphorothioate |
| modified_base | 21 |
|  | mod_base = OTHER |
|  | note = 2'-O-methyladenosine |
| SEQUENCE: 166 | |
| aacagtgttc ttgctctata a | 21 |

```
SEQ ID NO: 167          moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
modified_base           2
                        mod_base = OTHER
                        note = 2'-O-methyladenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyladenosine-3'-phosphate
modified_base           5
                        mod_base = OTHER
                        note = 2'-O-methylguanosine-3'-phosphate
modified_base           6
                        mod_base = OTHER
                        note = 2'-O-[N-retinoyl-(6-aminohexyl)]-uridine-3'-phosphate
modified_base           7
                        mod_base = OTHER
                        note = 2'-deoxy-2'-fluoroguanosine-3'-phosphate
modified_base           8
                        mod_base = OTHER
                        note = 2'-O-methyluridine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methylcytidine-3'-phosphate
modified_base           15
                        mod_base = OTHER
                        note = 2'-O-methyluridine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyladenosine-3'-phosphate
modified_base           19
                        mod_base = OTHER
                        note = 2'-O-methyluridine-3'-phosphorothioate
modified_base           20
                        mod_base = OTHER
                        note = 2'-O-methyladenosine-3'-phosphorothioate
modified_base           21
                        mod_base = OTHER
                        note = 2'-O-methyladenosine
SEQUENCE: 167
aacagtgttc ttgctctata a                                                   21

SEQ ID NO: 168          moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
```

| | |
|---|---|
| modified_base | 2 |
| | mod_base = OTHER |
| | note = 2'-O-methyladenosine-3'-phosphorothioate |
| modified_base | 3 |
| | mod_base = OTHER |
| | note = 2'-O-methylcytidine-3'-phosphate |
| modified_base | 4 |
| | mod_base = OTHER |
| | note = 2'-O-methyladenosine-3'-phosphate |
| modified_base | 5 |
| | mod_base = OTHER |
| | note = 2'-O-methylguanosine-3'-phosphate |
| modified_base | 6 |
| | mod_base = OTHER |
| | note = 2'-O-[N-decanoyl-(6-aminohexyl)]-uridine-3'-phosphate |
| modified_base | 7 |
| | mod_base = OTHER |
| | note = 2'-deoxy-2'-fluoroguanosine-3'-phosphate |
| modified_base | 8 |
| | mod_base = OTHER |
| | note = 2'-O-methyluridine-3'-phosphate |
| modified_base | 9 |
| | mod_base = OTHER |
| | note = 2'-deoxy-2'-fluorouridine-3'-phosphate |
| modified_base | 10 |
| | mod_base = OTHER |
| | note = 2'-deoxy-2'-fluorocytidine-3'-phosphate |
| modified_base | 11 |
| | mod_base = OTHER |
| | note = 2'-deoxy-2'-fluorouridine-3'-phosphate |
| modified_base | 12 |
| | mod_base = OTHER |
| | note = 2'-O-methyluridine-3'-phosphate |
| modified_base | 13 |
| | mod_base = OTHER |
| | note = 2'-O-methylguanosine-3'-phosphate |
| modified_base | 14 |
| | mod_base = OTHER |
| | note = 2'-O-methylcytidine-3'-phosphate |
| modified_base | 15 |
| | mod_base = OTHER |
| | note = 2'-O-methyluridine-3'-phosphate |
| modified_base | 16 |
| | mod_base = OTHER |
| | note = 2'-O-methylcytidine-3'-phosphate |
| modified_base | 17 |
| | mod_base = OTHER |
| | note = 2'-O-methyluridine-3'-phosphate |
| modified_base | 18 |
| | mod_base = OTHER |
| | note = 2'-O-methyladenosine-3'-phosphate |
| modified_base | 19 |
| | mod_base = OTHER |
| | note = 2'-O-methyluridine-3'-phosphorothioate |
| modified_base | 20 |
| | mod_base = OTHER |
| | note = 2'-O-methyladenosine-3'-phosphorothioate |
| modified_base | 21 |
| | mod_base = OTHER |
| | note = 2'-O-methyladenosine |
| SEQUENCE: 168 | |
| aacagtgttc ttgctctata a | 21 |
| | |
| SEQ ID NO: 169 | moltype = RNA length = 23 |
| FEATURE | Location/Qualifiers |
| source | 1..23 |
| | mol_type = other RNA |
| | organism = synthetic construct |
| modified_base | 1 |
| | mod_base = OTHER |
| | note = 2'-O-methyluridine-3'-phosphorothioate (Rp isomer) |
| modified_base | 2 |
| | mod_base = OTHER |
| | note = 2'-deoxy-2'-fluorouridine-3'-phosphorothioate (Rp isomer) |
| modified_base | 3 |
| | mod_base = OTHER |
| | note = 2'-O-methyladenosine-3'-phosphate |
| modified_base | 4 |

```
                            mod_base = OTHER
                            note = 2'-O-methyluridine-3'-phosphate
modified_base               5
                            mod_base = OTHER
                            note = 2'-O-methyladenosine-3'-phosphate
modified_base               6
                            mod_base = OTHER
                            note = 2'-deoxy-2'-fluoroguanosine-3'-phosphate
modified_base               7
                            mod_base = OTHER
                            note = 2'-O-methyladenosine-3'-phosphate
modified_base               8
                            mod_base = OTHER
                            note = 2'-deoxy-2'-fluoroguanosine-3'-phosphate
modified_base               9
                            mod_base = OTHER
                            note = 2'-deoxy-2'-fluorocytidine-3'-phosphate
modified_base               10
                            mod_base = OTHER
                            note = 2'-O-methyladenosine-3'-phosphate
modified_base               11
                            mod_base = OTHER
                            note = 2'-O-methyladenosine-3'-phosphate
modified_base               12
                            mod_base = OTHER
                            note = 2'-O-methylguanosine-3'-phosphate
modified_base               13
                            mod_base = OTHER
                            note = 2'-O-methyladenosine-3'-phosphate
modified_base               14
                            mod_base = OTHER
                            note = 2'-deoxy-2'-fluoroadenosine-3'-phosphate
modified_base               15
                            mod_base = OTHER
                            note = 2'-O-methylcytidine-3'-phosphate
modified_base               16
                            mod_base = OTHER
                            note = 2'-deoxy-2'-fluoroadenosine-3'-phosphate
modified_base               17
                            mod_base = OTHER
                            note = 2'-O-methylcytidine-3'-phosphate
modified_base               18
                            mod_base = OTHER
                            note = 2'-O-methyluridine-3'-phosphate
modified_base               19
                            mod_base = OTHER
                            note = 2'-O-methylguanosine-3'-phosphate
modified_base               20
                            mod_base = OTHER
                            note = 2'-O-methyluridine-3'-phosphate
modified_base               21
                            mod_base = OTHER
                            note = 2'-O-methyluridine-3'-phosphorothioate (Sp isomer)
modified_base               22
                            mod_base = OTHER
                            note = 2'-O-methyluridine-3'-phosphorothioate (Sp isomer)
modified_base               23
                            mod_base = OTHER
                            note = 2'-O-methyluridine
SEQUENCE: 169
ttatagagca agaacactgt ttt                                                    23

SEQ ID NO: 170              molytype = RNA   length = 23
FEATURE                     Location/Qualifiers
source                      1..23
                            mol_type = other RNA
                            organism = synthetic construct
modified_base               1
                            mod_base = OTHER
                            note = 2'-O-methyluridine-3'-phosphorothioate
modified_base               2
                            mod_base = OTHER
                            note = 2'-deoxy-2'-fluorouridine-3'-phosphorothioate
modified_base               3
                            mod_base = OTHER
                            note = 2'-O-methyladenosine-3'-phosphate
modified_base               4
                            mod_base = OTHER
                            note = 2'-O-methyluridine-3'-phosphate
```

| | |
|---|---|
| modified_base | 5<br>mod_base = OTHER<br>note = 2'-O-methyladenosine-3'-phosphate |
| modified_base | 6<br>mod_base = OTHER<br>note = 2'-deoxy-2'-fluoroguanosine-3'-phosphate |
| modified_base | 7<br>mod_base = OTHER<br>note = 2'-O-methyladenosine-3'-phosphate |
| modified_base | 8<br>mod_base = OTHER<br>note = 2'-O-methylguanosine-3'-phosphate |
| modified_base | 9<br>mod_base = OTHER<br>note = 2'-O-methylcytidine-3'-phosphate |
| modified_base | 10<br>mod_base = OTHER<br>note = 2'-O-methyladenosine-3'-phosphate |
| modified_base | 11<br>mod_base = OTHER<br>note = 2'-O-methyladenosine-3'-phosphate |
| modified_base | 12<br>mod_base = OTHER<br>note = 2'-O-methylguanosine-3'-phosphate |
| modified_base | 13<br>mod_base = OTHER<br>note = 2'-O-methyladenosine-3'-phosphate |
| modified_base | 14<br>mod_base = OTHER<br>note = 2'-deoxy-2'-fluoroadenosine-3'-phosphate |
| modified_base | 15<br>mod_base = OTHER<br>note = 2'-O-methylcytidine-3'-phosphate |
| modified_base | 16<br>mod_base = OTHER<br>note = 2'-deoxy-2'-fluoroadenosine-3'-phosphate |
| modified_base | 17<br>mod_base = OTHER<br>note = 2'-O-methylcytidine-3'-phosphate |
| modified_base | 18<br>mod_base = OTHER<br>note = 2'-O-methyluridine-3'-phosphate |
| modified_base | 19<br>mod_base = OTHER<br>note = 2'-O-methylguanosine-3'-phosphate |
| modified_base | 20<br>mod_base = OTHER<br>note = 2'-O-methyluridine-3'-phosphate |
| modified_base | 21<br>mod_base = OTHER<br>note = 2'-O-methyluridine-3'-phosphorothioate |
| modified_base | 22<br>mod_base = OTHER<br>note = 2'-O-methyluridine-3'-phosphorothioate |
| modified_base | 23<br>mod_base = OTHER<br>note = 2'-O-methyluridine |
| SEQUENCE: 170 | |
| ttatagagca agaacactgt ttt | 23 |
| SEQ ID NO: 171<br>FEATURE<br>source | moltype = RNA  length = 23<br>Location/Qualifiers<br>1..23<br>mol_type = other RNA<br>organism = synthetic construct |
| modified_base | 1<br>mod_base = OTHER<br>note = 2'-O-methyluridine-3'-phosphorothioate (Rp isomer) |
| modified_base | 2<br>mod_base = OTHER<br>note = 2'-deoxy-2'-fluorouridine-3'-phosphate |
| modified_base | 3<br>mod_base = OTHER<br>note = 2'-O-methyladenosine-3'-phosphate |
| modified_base | 4<br>mod_base = OTHER<br>note = 2'-O-methyluridine-3'-phosphate |
| modified_base | 5<br>mod_base = OTHER |

```
                    note = 2'-O-methyladenosine-3'-phosphate
modified_base       6
                    mod_base = OTHER
                    note = 2'-deoxy-2'-fluoroguanosine-3'-phosphate
modified_base       7
                    mod_base = OTHER
                    note = 2'-O-methyladenosine-3'-phosphate
modified_base       8
                    mod_base = OTHER
                    note = 2'-deoxy-2'-fluoroguanosine-3'-phosphate
modified_base       9
                    mod_base = OTHER
                    note = 2'-deoxy-2'-fluorocytidine-3'-phosphate
modified_base       10
                    mod_base = OTHER
                    note = 2'-O-methyladenosine-3'-phosphate
modified_base       11
                    mod_base = OTHER
                    note = 2'-O-methyladenosine-3'-phosphate
modified_base       12
                    mod_base = OTHER
                    note = 2'-O-methylguanosine-3'-phosphate
modified_base       13
                    mod_base = OTHER
                    note = 2'-O-methyladenosine-3'-phosphate
modified_base       14
                    mod_base = OTHER
                    note = 2'-deoxy-2'-fluoroadenosine-3'-phosphate
modified_base       15
                    mod_base = OTHER
                    note = 2'-O-methylcytidine-3'-phosphate
modified_base       16
                    mod_base = OTHER
                    note = 2'-deoxy-2'-fluoroadenosine-3'-phosphate
modified_base       17
                    mod_base = OTHER
                    note = 2'-O-methylcytidine-3'-phosphate
modified_base       18
                    mod_base = OTHER
                    note = 2'-O-methyluridine-3'-phosphate
modified_base       19
                    mod_base = OTHER
                    note = 2'-O-methylguanosine-3'-phosphate
modified_base       20
                    mod_base = OTHER
                    note = 2'-O-methyluridine-3'-phosphate
modified_base       21
                    mod_base = OTHER
                    note = 2'-O-methyluridine-3'-phosphorothioate (Sp isomer)
modified_base       22
                    mod_base = OTHER
                    note = 2'-O-methyluridine-3'-phosphorothioate (Sp isomer)
modified_base       23
                    mod_base = OTHER
                    note = 2'-O-methyluridine
SEQUENCE: 171
ttatagagca agaacactgt ttt                                           23

SEQ ID NO: 172      moltype = RNA  length = 23
FEATURE             Location/Qualifiers
source              1..23
                    mol_type = other RNA
                    organism = synthetic construct
modified_base       1
                    mod_base = OTHER
                    note = 2'-O-methyluridine-3'-phosphorothioate 5'phosphate
modified_base       2
                    mod_base = OTHER
                    note = 2'-deoxy-2'-fluorouridine-3'-phosphorothioate
modified_base       3
                    mod_base = OTHER
                    note = 2'-O-methyladenosine-3'-phosphate
modified_base       4
                    mod_base = OTHER
                    note = 2'-O-methyluridine-3'-phosphate
modified_base       5
                    mod_base = OTHER
                    note = 2'-O-methyladenosine-3'-phosphate
modified_base       6
```

|                | mod_base = OTHER |
|---|---|
|                | note = 2'-deoxy-2'-fluoroguanosine-3'-phosphate |
| modified_base | 7 |
|                | mod_base = OTHER |
|                | note = 2'-O-methyladenosine-3'-phosphate |
| modified_base | 8 |
|                | mod_base = OTHER |
|                | note = 2'-O-methylguanosine-3'-phosphate |
| modified_base | 9 |
|                | mod_base = OTHER |
|                | note = 2'-O-methylcytidine-3'-phosphate |
| modified_base | 10 |
|                | mod_base = OTHER |
|                | note = 2'-O-methyladenosine-3'-phosphate |
| modified_base | 11 |
|                | mod_base = OTHER |
|                | note = 2'-O-methyladenosine-3'-phosphate |
| modified_base | 12 |
|                | mod_base = OTHER |
|                | note = 2'-O-methylguanosine-3'-phosphate |
| modified_base | 13 |
|                | mod_base = OTHER |
|                | note = 2'-O-methyladenosine-3'-phosphate |
| modified_base | 14 |
|                | mod_base = OTHER |
|                | note = 2'-deoxy-2'-fluoroadenosine-3'-phosphate |
| modified_base | 15 |
|                | mod_base = OTHER |
|                | note = 2'-O-methylcytidine-3'-phosphate |
| modified_base | 16 |
|                | mod_base = OTHER |
|                | note = 2'-deoxy-2'-fluoroadenosine-3'-phosphate |
| modified_base | 17 |
|                | mod_base = OTHER |
|                | note = 2'-O-methylcytidine-3'-phosphate |
| modified_base | 18 |
|                | mod_base = OTHER |
|                | note = 2'-O-methyluridine-3'-phosphate |
| modified_base | 19 |
|                | mod_base = OTHER |
|                | note = 2'-O-methylguanosine-3'-phosphate |
| modified_base | 20 |
|                | mod_base = OTHER |
|                | note = 2'-O-methyluridine-3'-phosphate |
| modified_base | 21 |
|                | mod_base = OTHER |
|                | note = 2'-O-methyluridine-3'-phosphorothioate |
| modified_base | 22 |
|                | mod_base = OTHER |
|                | note = 2'-O-methyluridine-3'-phosphorothioate |
| modified_base | 23 |
|                | mod_base = OTHER |
|                | note = 2'-O-methyluridine |
| SEQUENCE: 172 | |
| ttatagagca agaacactgt ttt | 23 |
| SEQ ID NO: 173 | moltype = DNA  length = 23 |
| FEATURE | Location/Qualifiers |
| source | 1..23 |
|                | mol_type = other DNA |
|                | organism = synthetic construct |
| modified_base | 1 |
|                | mod_base = OTHER |
|                | note = 2'-deoxythymidine-3'-phosphorothioate |
| modified_base | 2 |
|                | mod_base = OTHER |
|                | note = 2'-deoxy-2'-fluorouridine-3'-phosphorothioate |
| modified_base | 3 |
|                | mod_base = OTHER |
|                | note = 2'-O-methyladenosine-3'-phosphate |
| modified_base | 4 |
|                | mod_base = OTHER |
|                | note = 2'-O-methyluridine-3'-phosphate |
| modified_base | 5 |
|                | mod_base = OTHER |
|                | note = 2'-O-methyladenosine-3'-phosphate |
| modified_base | 6 |
|                | mod_base = OTHER |
|                | note = 2'-deoxy-2'-fluoroguanosine-3'-phosphate |

```
modified_base        7
                     mod_base = OTHER
                     note = 2'-O-methyladenosine-3'-phosphate
modified_base        8
                     mod_base = OTHER
                     note = 2'-O-methylguanosine-3'-phosphate
modified_base        9
                     mod_base = OTHER
                     note = 2'-O-methylcytidine-3'-phosphate
modified_base        10
                     mod_base = OTHER
                     note = 2'-O-methyladenosine-3'-phosphate
modified_base        11
                     mod_base = OTHER
                     note = 2'-O-methyladenosine-3'-phosphate
modified_base        12
                     mod_base = OTHER
                     note = 2'-O-methylguanosine-3'-phosphate
modified_base        13
                     mod_base = OTHER
                     note = 2'-O-methyladenosine-3'-phosphate
modified_base        14
                     mod_base = OTHER
                     note = 2'-deoxy-2'-fluoroadenosine-3'-phosphate
modified_base        15
                     mod_base = OTHER
                     note = 2'-O-methylcytidine-3'-phosphate
modified_base        16
                     mod_base = OTHER
                     note = 2'-deoxy-2'-fluoroadenosine-3'-phosphate
modified_base        17
                     mod_base = OTHER
                     note = 2'-O-methylcytidine-3'-phosphate
modified_base        18
                     mod_base = OTHER
                     note = 2'-O-methyluridine-3'-phosphate
modified_base        19
                     mod_base = OTHER
                     note = 2'-O-methylguanosine-3'-phosphate
modified_base        20
                     mod_base = OTHER
                     note = 2'-O-methyluridine-3'-phosphate
modified_base        21
                     mod_base = OTHER
                     note = 2'-O-methyluridine-3'-phosphorothioate
modified_base        22
                     mod_base = OTHER
                     note = 2'-O-methyluridine-3'-phosphorothioate
modified_base        23
                     mod_base = OTHER
                     note = 2'-O-methyluridine
misc_feature         2..23
                     note = RNA
SEQUENCE: 173
ttatagagca agaacactgt ttt                                            23

SEQ ID NO: 174       moltype = RNA   length = 23
FEATURE              Location/Qualifiers
source               1..23
                     mol_type = other RNA
                     organism = synthetic construct
modified_base        1
                     mod_base = OTHER
                     note = uridine-3'-phosphorothioate
modified_base        2
                     mod_base = OTHER
                     note = 2'-deoxy-2'-fluorouridine-3'-phosphorothioate
modified_base        3
                     mod_base = OTHER
                     note = 2'-O-methyladenosine-3'-phosphate
modified_base        4
                     mod_base = OTHER
                     note = 2'-O-methyluridine-3'-phosphate
modified_base        5
                     mod_base = OTHER
                     note = 2'-O-methyladenosine-3'-phosphate
modified_base        6
                     mod_base = OTHER
                     note = 2'-deoxy-2'-fluoroguanosine-3'-phosphate
```

```
modified_base        7
                     mod_base = OTHER
                     note = 2'-O-methyladenosine-3'-phosphate
modified_base        8
                     mod_base = OTHER
                     note = 2'-O-methylguanosine-3'-phosphate
modified_base        9
                     mod_base = OTHER
                     note = 2'-O-methylcytidine-3'-phosphate
modified_base        10
                     mod_base = OTHER
                     note = 2'-O-methyladenosine-3'-phosphate
modified_base        11
                     mod_base = OTHER
                     note = 2'-O-methyladenosine-3'-phosphate
modified_base        12
                     mod_base = OTHER
                     note = 2'-O-methylguanosine-3'-phosphate
modified_base        13
                     mod_base = OTHER
                     note = 2'-O-methyladenosine-3'-phosphate
modified_base        14
                     mod_base = OTHER
                     note = 2'-deoxy-2'-fluoroadenosine-3'-phosphate
modified_base        15
                     mod_base = OTHER
                     note = 2'-O-methylcytidine-3'-phosphate
modified_base        16
                     mod_base = OTHER
                     note = 2'-deoxy-2'-fluoroadenosine-3'-phosphate
modified_base        17
                     mod_base = OTHER
                     note = 2'-O-methylcytidine-3'-phosphate
modified_base        18
                     mod_base = OTHER
                     note = 2'-O-methyluridine-3'-phosphate
modified_base        19
                     mod_base = OTHER
                     note = 2'-O-methylguanosine-3'-phosphate
modified_base        20
                     mod_base = OTHER
                     note = 2'-O-methyluridine-3'-phosphate
modified_base        21
                     mod_base = OTHER
                     note = 2'-O-methyluridine-3'-phosphorothioate
modified_base        22
                     mod_base = OTHER
                     note = 2'-O-methyluridine-3'-phosphorothioate
modified_base        23
                     mod_base = OTHER
                     note = 2'-O-methyluridine
SEQUENCE: 174
ttatagagca agaacactgt ttt                                           23

SEQ ID NO: 175       moltype = RNA   length = 23
FEATURE              Location/Qualifiers
source               1..23
                     mol_type = other RNA
                     organism = synthetic construct
modified_base        1
                     mod_base = OTHER
                     note = 2'-O-methyluridine-3'-phosphate
                     5'-[((4S,5S)-5-methoxy-1,2-dithian-4-ol)-phosphorothiodiest
                     er]
modified_base        2
                     mod_base = OTHER
                     note = 2'-deoxy-2'-fluorouridine-3'-phosphate
modified_base        3
                     mod_base = OTHER
                     note = 2'-O-methyladenosine-3'-phosphate
modified_base        4
                     mod_base = OTHER
                     note = 2'-O-methyluridine-3'-phosphate
modified_base        5
                     mod_base = OTHER
                     note = 2'-O-methyladenosine-3'-phosphate
modified_base        6
                     mod_base = OTHER
                     note = 2'-deoxy-2'-fluoroguanosine-3'-phosphate
```

```
modified_base       7
                    mod_base = OTHER
                    note = 2'-O-methyladenosine-3'-phosphate
modified_base       8
                    mod_base = OTHER
                    note = 2'-O-methylguanosine-3'-phosphate
modified_base       9
                    mod_base = OTHER
                    note = 2'-O-methylcytidine-3'-phosphate
modified_base       10
                    mod_base = OTHER
                    note = 2'-O-methyladenosine-3'-phosphate
modified_base       11
                    mod_base = OTHER
                    note = 2'-O-methyladenosine-3'-phosphate
modified_base       12
                    mod_base = OTHER
                    note = 2'-O-methylguanosine-3'-phosphate
modified_base       13
                    mod_base = OTHER
                    note = 2'-O-methyladenosine-3'-phosphate
modified_base       14
                    mod_base = OTHER
                    note = 2'-deoxy-2'-fluoroadenosine-3'-phosphate
modified_base       15
                    mod_base = OTHER
                    note = 2'-O-methylcytidine-3'-phosphate
modified_base       16
                    mod_base = OTHER
                    note = 2'-deoxy-2'-fluoroadenosine-3'-phosphate
modified_base       17
                    mod_base = OTHER
                    note = 2'-O-methylcytidine-3'-phosphate
modified_base       18
                    mod_base = OTHER
                    note = 2'-O-methyluridine-3'-phosphate
modified_base       19
                    mod_base = OTHER
                    note = 2'-O-methylguanosine-3'-phosphate
modified_base       20
                    mod_base = OTHER
                    note = 2'-O-methyluridine-3'-phosphate
modified_base       21
                    mod_base = OTHER
                    note = 2'-O-methyluridine-3'-phosphorothioate
modified_base       22
                    mod_base = OTHER
                    note = 2'-O-methyluridine-3'-phosphorothioate
modified_base       23
                    mod_base = OTHER
                    note = 2'-O-methyluridine
SEQUENCE: 175
ttatagagca agaacactgt ttt                                            23
```